(12) United States Patent
Sooknanan et al.

(10) Patent No.: US 8,216,582 B2
(45) Date of Patent: Jul. 10, 2012

(54) POLYNUCLEOTIDES AND POLYPEPTIDE SEQUENCES INVOLVED IN CANCER

(75) Inventors: Roy Rabindranauth Sooknanan, Quebec (CA); Gilles Bernard Tremblay, Quebec (CA); Mario Filion, Quebec (CA)

(73) Assignee: Alethia Biotherapeutics Inc., Montreal, Quebec (CA)

( * ) Notice: Subject to any disclaimer, the term of this patent is extended or adjusted under 35 U.S.C. 154(b) by 423 days.

(21) Appl. No.: 12/305,648

(22) PCT Filed: Jun. 22, 2007

(86) PCT No.: PCT/CA2007/001134
§ 371 (c)(1),
(2), (4) Date: Nov. 6, 2009

(87) PCT Pub. No.: WO2007/147265
PCT Pub. Date: Dec. 27, 2007

(65) Prior Publication Data
US 2010/0086537 A1   Apr. 8, 2010

Related U.S. Application Data

(60) Provisional application No. 60/815,829, filed on Jun. 23, 2006, provisional application No. 60/874,471, filed on Dec. 13, 2006.

(51) Int. Cl.
*A61K 39/395* (2006.01)

(52) U.S. Cl. ............... 424/155.1; 424/130.1; 424/138.1; 424/139.1; 424/174.1; 530/350; 530/387.1; 530/387.3; 530/387.7; 530/387.9; 530/388.8

(58) Field of Classification Search .................. 530/350, 530/387.1, 387.3, 387.7, 387.9, 388.8; 424/130.1, 424/133.1, 138.1, 139.1, 155.1, 174.1
See application file for complete search history.

(56) References Cited

U.S. PATENT DOCUMENTS

| | | | |
|---|---|---|---|
| 4,745,076 A | 5/1988 | Muller et al. |
| 5,075,447 A | 12/1991 | Muller et al. |
| 5,585,279 A | 12/1996 | Davidson |
| 5,708,022 A | 1/1998 | Bastos et al. |
| 5,712,127 A | 1/1998 | Malek et al. |
| 6,288,221 B1 | 9/2001 | Grinstaff et al. |
| 6,358,953 B1 | 3/2002 | Moheno |
| 6,806,089 B1 | 10/2004 | Lakowicz et al. |
| 6,812,339 B1 | 11/2004 | Venter et al. |
| 6,962,910 B2 | 11/2005 | Brewer et al. |
| 7,030,236 B2 | 4/2006 | Jhaveri et al. |
| 7,202,234 B2 | 4/2007 | Chow et al. |
| 7,429,567 B2 | 9/2008 | Lee et al. |
| 7,439,051 B2 | 10/2008 | Sokoloff et al. |
| 7,494,788 B2 | 2/2009 | Dunker et al. |
| 7,501,485 B2 | 3/2009 | Cowsar |
| 7,521,197 B2 | 4/2009 | Savage |
| 7,531,533 B2 | 5/2009 | Shoda et al. |
| 7,550,501 B2 | 6/2009 | Chow et al. |
| 7,557,213 B2 | 7/2009 | Melikian et al. |
| 7,560,441 B2 | 7/2009 | Wolfman et al. |
| 7,585,839 B2 | 9/2009 | Larsen et al. |
| 7,618,636 B1 | 11/2009 | Masignani et al. |
| 7,628,989 B2 | 12/2009 | Jakobovits et al. |
| 7,641,905 B2 | 1/2010 | Jakobovits et al. |
| 2002/0049190 A1 | 4/2002 | Bridger et al. |
| 2002/0106678 A1 | 8/2002 | Robishaw et al. |
| 2002/0177695 A1 | 11/2002 | Grinstaff et al. |
| 2003/0065157 A1 | 4/2003 | Lasek |
| 2003/0087250 A1 | 5/2003 | Monahan et al. |
| 2003/0099974 A1 | 5/2003 | Lillie et al. |
| 2003/0124579 A1 | 7/2003 | Mack et al. |
| 2003/0170273 A1 | 9/2003 | O'Hagan et al. |
| 2003/0180767 A1 | 9/2003 | Brewer et al. |
| 2003/0219760 A1 | 11/2003 | Gordon et al. |
| 2004/0009939 A1 | 1/2004 | Chada et al. |
| 2004/0014081 A1 | 1/2004 | Alsobrook, II et al. |
| 2004/0053824 A1 | 3/2004 | Tang et al. |
| 2004/0101874 A1 | 5/2004 | Ghosh et al. |
| 2004/0172684 A1 | 9/2004 | Kovalic et al. |
| 2004/0214272 A1 | 10/2004 | La Rosa et al. |
| 2005/0053930 A1 | 3/2005 | Anderson et al. |
| 2005/0059624 A1 | 3/2005 | Hoerr et al. |
| 2005/0064481 A1 | 3/2005 | Korfhage |
| 2005/0095592 A1 | 5/2005 | Jazaeri et al. |
| 2005/0113345 A1 | 5/2005 | Chow et al. |
| 2005/0123501 A1 | 6/2005 | Lewis |
| 2005/0147621 A1 | 7/2005 | Higgins et al. |
| 2005/0153333 A1 | 7/2005 | Sooknanan |

(Continued)

FOREIGN PATENT DOCUMENTS

EP        178450 B1      4/1986

(Continued)

OTHER PUBLICATIONS

Van den Eynde et al. (J Exp Med. Dec. 20, 1999;190(12):1793-800).*
Schumacher et al.(Am. J. Hum. Genet. Jan. 2006; 78 (1): 52-62).*
Li, et al., Genebank Acc. No. AY648683; Jun. 15, 2005.
Liang, et al. Genebank Acc. No. AY436928; Mar. 15, 2004.
Van Den Eynde et al., "A new antigen recognized by cytolytic T lymphocytes on a human kidney tumor results from reverse strand transcription," *J. Exp. Med.* 190(12):1793-9 (1999).
Vogelstein et al., "Cancer genes and the pathways they control," *Nat. Med.* 10(8):789-799 (2004).
Futreal et al., "A census of human cancer genes," *Nat. Rev.* 4:177-183 (2004).

(Continued)

*Primary Examiner* — Stephen Rawlings
(74) *Attorney, Agent, or Firm* — Choate, Hall & Stewart LLP

(57) ABSTRACT

The present invention relates to polynucleotide and polypeptide sequences which are differentially expressed in cancer cells compared to normal cells. The present invention more particularly relates to the use of these sequences in the diagnosis, prognosis or treatment of cancer and in the detection of cancer cells.

15 Claims, 107 Drawing Sheets

U.S. PATENT DOCUMENTS

| | | |
|---|---|---|
| 2005/0196754 A1 | 9/2005 | Drmanac et al. |
| 2005/0214826 A1 | 9/2005 | Mor et al. |
| 2005/0214831 A1 | 9/2005 | Monahan et al. |
| 2006/0014686 A1 | 1/2006 | Wonsey et al. |
| 2006/0078941 A1 | 4/2006 | Santin |
| 2006/0084594 A1 | 4/2006 | Santin et al. |
| 2006/0188490 A1 | 8/2006 | Hoerr et al. |
| 2006/0229433 A1 | 10/2006 | De Rouge et al. |
| 2007/0060590 A1 | 3/2007 | Shoda et al. |
| 2007/0093467 A1 | 4/2007 | Zhang et al. |
| 2007/0167409 A1 | 7/2007 | Chow et al. |
| 2007/0167443 A1 | 7/2007 | Melikian et al. |
| 2007/0298093 A1 | 12/2007 | Komur et al. |
| 2007/0299068 A1 | 12/2007 | Karp et al. |
| 2008/0025944 A1 | 1/2008 | Hoerr et al. |
| 2008/0166355 A1 | 7/2008 | Moheno et al. |
| 2008/0176790 A1 | 7/2008 | DeFrees |
| 2008/0200650 A1 | 8/2008 | Emery et al. |
| 2008/0213268 A1 | 9/2008 | Watts et al. |
| 2008/0274131 A1 | 11/2008 | Kenner et al. |
| 2008/0280317 A1 | 11/2008 | Wu et al. |
| 2008/0280818 A1 | 11/2008 | DeFrees |
| 2008/0300348 A1 | 12/2008 | Haddleton et al. |
| 2008/0306007 A1 | 12/2008 | McCluskey et al. |
| 2008/0311145 A1 | 12/2008 | Campion et al. |
| 2009/0074658 A1 | 3/2009 | Lupold et al. |
| 2009/0075832 A1 | 3/2009 | Neuman et al. |
| 2009/0093621 A1 | 4/2009 | Ferrari et al. |
| 2009/0110662 A1 | 4/2009 | Breitenkamp et al. |
| 2009/0137003 A1 | 5/2009 | Tolstrup et al. |
| 2009/0169520 A1 | 7/2009 | Soreq et al. |
| 2009/0176664 A1 | 7/2009 | Chu |
| 2009/0186855 A1 | 7/2009 | Chow et al. |
| 2009/0197345 A1 | 8/2009 | Seppala |
| 2009/0203542 A1 | 8/2009 | Reichmann et al. |
| 2009/0208507 A1 | 8/2009 | Rohlff |
| 2009/0209463 A1 | 8/2009 | Nakamura et al. |
| 2009/0214467 A1 | 8/2009 | Shakhov et al. |
| 2009/0214585 A1 | 8/2009 | Ciocca et al. |
| 2009/0221032 A1 | 9/2009 | Dunker et al. |
| 2009/0226448 A1 | 9/2009 | Glucksmann et al. |
| 2009/0226451 A1 | 9/2009 | Glucksmann et al. |
| 2009/0226921 A1 | 9/2009 | Afar et al. |
| 2009/0232766 A1 | 9/2009 | Wang et al. |
| 2009/0253156 A1 | 10/2009 | Patton et al. |
| 2009/0275137 A1 | 11/2009 | Kranz et al. |
| 2009/0297401 A1 | 12/2009 | Lundstrom et al. |
| 2009/0305282 A1 | 12/2009 | Yuen et al. |
| 2009/0305962 A1 | 12/2009 | Bakker et al. |
| 2009/0311681 A1 | 12/2009 | Faure |
| 2009/0325869 A1 | 12/2009 | Theil |
| 2010/0003280 A1 | 1/2010 | O'Hagan et al. |
| 2010/0003305 A1 | 1/2010 | Pattanaik |
| 2010/0040606 A1 | 2/2010 | Lantto et al. |
| 2010/0047261 A1 | 2/2010 | Hoerr et al. |
| 2010/0055077 A1 | 3/2010 | Shakhov et al. |
| 2010/0055731 A1 | 3/2010 | Wang et al. |
| 2010/0056459 A1 | 3/2010 | Bonny |
| 2010/0086541 A1 | 4/2010 | Wu et al. |
| 2010/0105692 A1 | 4/2010 | Moheno et al. |
| 2010/0111993 A1 | 5/2010 | Tureci et al. |
| 2011/0223107 A1 | 9/2011 | Tremblay et al. |

FOREIGN PATENT DOCUMENTS

| | | |
|---|---|---|
| EP | 0636031 B1 | 2/1995 |
| EP | 0816377 | 1/1998 |
| EP | 1318835 B1 | 6/2003 |
| EP | 1422242 | 5/2004 |
| EP | 1458410 B1 | 9/2004 |
| EP | 1465933 B1 | 10/2004 |
| EP | 1547581 A1 | 6/2005 |
| EP | 1550458 A1 | 6/2005 |
| EP | 1646661 B1 | 4/2006 |
| EP | 1751179 | 2/2007 |
| EP | 1847533 A1 | 10/2007 |
| EP | 1905844 A2 | 4/2008 |
| EP | 1970383 | 9/2008 |
| EP | 1987356 | 11/2008 |
| EP | 2002036 | 12/2008 |
| EP | 2021467 | 2/2009 |
| EP | 2057465 | 5/2009 |
| EP | 2161291 A2 | 3/2010 |
| WO | WO8704523 A1 | 7/1987 |
| WO | WO9109849 A1 | 7/1991 |
| WO | WO9613510 A1 | 5/1996 |
| WO | WO9858079 A1 | 12/1998 |
| WO | WO9931513 A1 | 6/1999 |
| WO | WO-99/58546 | 11/1999 |
| WO | WO9958546 A1 * | 11/1999 |
| WO | WO0001702 A1 | 1/2000 |
| WO | WO00014515 A1 | 3/2000 |
| WO | WO0023448 A1 | 4/2000 |
| WO | WO0025788 A1 | 5/2000 |
| WO | WO0056743 A1 | 9/2000 |
| WO | WO0119798 A2 | 3/2001 |
| WO | WO0146209 A1 | 6/2001 |
| WO | WO-01/70979 | 9/2001 |
| WO | WO-01/98468 | 12/2001 |
| WO | WO-02/070539 | 9/2002 |
| WO | WO-02/086443 | 10/2002 |
| WO | WO-02/102235 | 12/2002 |
| WO | WO03043987 A2 | 5/2003 |
| WO | WO03047526 | 6/2003 |
| WO | WO03051401 A2 | 6/2003 |
| WO | WO-03/068054 | 8/2003 |
| WO | WO03075952 A1 | 9/2003 |
| WO | WO03087768 | 10/2003 |
| WO | WO-2004/030615 | 4/2004 |
| WO | WO-2004/076622 | 9/2004 |
| WO | WO2004087874 A2 | 10/2004 |
| WO | WO2004113394 A2 | 12/2004 |
| WO | WO-2005/024055 | 3/2005 |
| WO | WO2005039504 A2 | 5/2005 |
| WO | WO2005063201 A2 | 7/2005 |
| WO | WO2005063288 A1 | 7/2005 |
| WO | WO2006003352 A1 | 1/2006 |
| WO | WO2006024518 A1 | 3/2006 |
| WO | WO2006027202 A1 | 3/2006 |
| WO | WO2006029385 A2 | 3/2006 |
| WO | WO2006102097 A2 | 9/2006 |
| WO | WO2006138380 A2 | 12/2006 |
| WO | WO2007002559 A1 | 1/2007 |
| WO | WO2007002563 A1 | 1/2007 |
| WO | WO2007005249 A2 | 1/2007 |
| WO | WO2007023287 A1 | 3/2007 |
| WO | WO2007045876 A1 | 4/2007 |
| WO | WO2007059108 A2 | 5/2007 |
| WO | WO2007061853 A2 | 5/2007 |
| WO | WO2007073432 A2 | 6/2007 |
| WO | WO2007084413 A2 | 7/2007 |
| WO | WO2007104948 A2 | 9/2007 |
| WO | WO2007110755 A1 | 10/2007 |
| WO | WO2008002267 A1 | 1/2008 |
| WO | WO2008016356 | 2/2008 |
| WO | WO2008021290 | 2/2008 |
| WO | WO2008033932 A2 | 3/2008 |
| WO | WO2008052770 A2 | 5/2008 |
| WO | WO2008054793 A2 | 5/2008 |
| WO | WO2008082887 A2 | 7/2008 |
| WO | WO2008083949 A2 | 7/2008 |
| WO | WO2008104804 | 9/2008 |
| WO | WO2009004329 A1 | 1/2009 |
| WO | WO2009009186 | 1/2009 |
| WO | WO2009039854 | 4/2009 |
| WO | WO2009044162 A1 | 4/2009 |
| WO | WO2009059972 | 5/2009 |
| WO | WO2009061681 A2 | 5/2009 |
| WO | WO2009069862 | 6/2009 |
| WO | WO2009077864 | 6/2009 |
| WO | WO2009111088 A2 | 9/2009 |
| WO | WO2009114942 | 9/2009 |
| WO | WO2009134370 A1 | 11/2009 |
| WO | WO2009144230 A1 | 12/2009 |
| WO | WO2010003127 A2 | 1/2010 |
| WO | WO2010014141 A1 | 2/2010 |
| WO | WO2010017479 A1 | 2/2010 |

| | | |
|---|---|---|
| WO | WO2010033207 | 3/2010 |
| WO | WO2010033220 | 3/2010 |
| WO | WO2010033240 | 3/2010 |
| WO | WO2010037408 A1 | 4/2010 |
| WO | WO2010037539 A1 | 4/2010 |
| WO | WO2010/060186 | 6/2010 |
| WO | WO2011/054112 | 5/2011 |

OTHER PUBLICATIONS

Agrawal et al., "RNA interference: biology, mechanism, and applications," *Microbiol Mol Biol Rev* 67(4):657-685 (2003).
Berek et al., "Neoplasms of the Female Reproductive Organs," *Cancer Medicine*, 5th Ed., London: B.C. Decker, Inc. (2000), pp. 1687-1720.
Bonome et al., "Expression Profiling of Serous Low Malignant Potential, Low-Grade, and High-Grade Tumors of the Ovary," *Cancer Res* 65(22):10602-10612 (2005).
Bristow, "Surgical standards in the management of ovarian cancer," *Curr Opin Oncol.* 12:474-480 (2000).
Brown et al., "Carcinosarcoma of the Ovary: 19 Years of Prospective Data from a Single Center," *Cancer* 100:2148-2153 (2004).
Brummelkamp et al., "A system for stable expression of short interfering RNAs in mammalian cells," *Science* 296(5567):550-553 (2002).
Chambers et al., "Ovarian Cancer Biomarkers in Urine," *Clin Cancer Res* 12(2):323-327 (2006).
Elbashir et al., "Duplexes of 21-nucleotide RNAs mediate RNA interference in cultured mammalian cells," *Nature* 411(6836):494-8 (2001).
Gorelik et al., "Multiplexed Immunobead-based Cytokine Profiling for Early Detection of Ovarian Cancer," *Cancer Epidemiol Biomarkers Prev* 14(4):981-987 (2005).
Hannon, "RNA interference," *Nature* 418(6894):244-251 (2002).
Jemal et al., "Cancer Statistics, 2005," *CA Cancer J Clin* 55:10-30 (2005).
Kozak et al., "Identification of biomarkers for ovarian cancer using strong anion-exchange ProteinChips: Potential use in diagnosis and prognosis," *PNAS* 100:12343-12348 (2003).
Leamon et al., "Folate-mediated targeting: from diagnostics to drug and gene delivery," *Drug Discov Today* 6:44-51 (2001).
McIntosh et al., "Combining CA125 and SMR serum markers for diagnosis and early detection of ovarian carcinoma," *Gynecol Oncol.* 95(1):9-15 (2004).
Menon et al., "Prospective Study Using the Risk of Ovarian Cancer Algorithm to Screen for Ovarian Cancer," *J Clin Oncol* 23(31):7919-7926 (2005).
Mor et al., "Serum protein markers for early detection of ovarian cancer," *PNAS* 102:7677-7682 (2005).
Mosmann, "Rapid Colorimetric Assay for Cellular Growth and Survival: Application to Proliferation and Cytotoxicity Assays," *J Immunol Methods* 65:55-63 (1983).
Provencher et al., "Characterization of Four Novel Epithelial Ovarian Cancer Cell Lines," *In Vitro Cell Dev Biol Anim* 36:357-361 (2000).
Samouelian et al., "Chemosensitivity and radiosensitivity profiles of four new human epithelial ovarian cancer cell lines exhibiting genetic alterations in BRCA2, TGFβ-RII, KRAS2, TP53 and/or CDNK2A," *Cancer Chemother Pharmacol* 54:497-504 (2004).
Schorge et al., "Osteopontin as an Adjunct to CA125 in Detecting Recurrent Ovarian Cancer," *Clin Cancer Res* 10:3474-3478 (2004).
Seidman et al., "Surface Epithelial Tumors of the Ovary," *Blaustein's Pathology of the Female Genital Tract*, Kurman, R.J. (Ed.), 5th Ed., New York: Springer-Verlag (2002), pp. 791-904.
Shin et al., "Molecular Pathogenesis of Ovarian Borderline Tumors: New Insights and Old Challenges," *Clin Cancer Res* 11(20):7273-7279 (2005).
Woolas et al., "Elevation of Multiple Serum Markers in Patients with Stage I Ovarian Cancer," *J Natl Cancer Inst* 85(21):1748-1751 (1993).
GenBank Acc. No. AA744939.1, GI: 2783703, 1998.
GenBank Acc. No. AC002060.4, GI:22507090, first referenced 1997, updated 2002.
GenBank Acc. No. AC068288.6, GI:16418276, first referenced 2001, updated 2005.
GenBank Acc. No. AC104837.2, GI:18249998, first referenced 2001, updated 2002.
GenBank Acc. No. AC109350.5, GI:19526559, first referenced 1998, updated 2002.
GenBank Acc. No. AC117457.11, GI:28557825, first referenced 2002, updated 2003.
GenBank Acc. No. AI922121.1, GI:5658085, first referenced 1999, updated 2000.
GenBank Acc. No. AK092857.1, GI:21751554, first referenced 2002, updated 2004.
GenBank Acc. No. AK092936.1, GI:21751648, first referenced 2002, updated 2004.
GenBank Acc. No. AL157931.17, GI:11493240, first referenced 2000, updated 2009.
GenBank Acc. No. AL583809.3, GI:14250883, 2001.
GenBank Acc. No. AY683003.1, GI:56384942, 2004.
GenBank Acc. No. BC009078.1, GI:14290598, first referenced 2001, updated 2008.
GenBank Acc. No. BC073793.1, Gi:49258111, first referenced 2002, updated 2006.
GenBank Acc. No. BC092518.1, GI:62201665, first referenced 2002, updated 2005.
GenBank Acc. No. BG213598.1, GI:13735285, 2001.
GenBank Acc. No. BU595315.1, GI:23247074, 2002.
GenBank Acc. No. NM_022357.3, GI:193211607, first referenced 2003, updated 2008.
GenBank Acc. No. BC037243.1, GI:23337025, first referenced 2002, updated 2008.
GenBank Acc. No. NM_000077.3, GI:47132606, first referenced 1994, updated 2004.
GenBank Acc. No. NM_000096.3, GI:189458860, first referenced 1977, updated 2008.
GenBank Acc. No. NM_000170.2, GI:108773800, first referenced 1989, updated 2006.
GenBank Acc. No. NM_000802.2, GI:12056965, first referenced 1990, updated 2001.
GenBank Acc. No., NM_001001887.1, GI:49574525, first referenced 1983, updated 2006.
GenBank Acc. No. NM_001007027.2, GI:91984777, first referenced 1995, updated 2006.
GenBank Acc. No. NM_001017920.2, GI:217272871, first referenced 2002, updated 2008.
GenBank Acc. No. NM_001039548.1, GI:88196793, 2004.
GenBank Acc. No. NM_001463.2, GI:38455387, first referenced 1996, updated 2003.
GenBank Acc. No. NM_001565.2, GI:149999381, first referenced 1985, updated 2007.
GenBank Acc. No. NM_001719.2, GI:187608319, first referenced 1990, updated 2008.
GenBank Acc. No. NM_001826.2, GI:206725531, first referenced 1990, updated 2008.
GenBank Acc. No. NM_001878.2, GI:6382069, first referenced 1991, updated 1999.
GenBank Acc. No. NM_003543.3, GI:21264599, first referenced 1997, updated 2002.
GenBank Acc. No. NM_005101.3, GI:193083170, first referenced 1987, updated 2008.
GenBank Acc. No. NM_005192.3, GI:195927023, first referenced 1993, updated 2008.
GenBank Acc. No. NM_005698.2, GI:16445418, first referenced 1997, updated 2001.
GenBank Acc. No. NM_005733.2, GI:195539383, first referenced 1998, updated 2008.
GenBank Acc. No. NM_005832.3, GI:31317293, first referenced 1999, updated 2003.
GenBank Acc. No. NM_006115.3, GI:46249365, first referenced 1997, updated 2004.
GenBank Acc. No. NM_006681.2, GI:195539393, first referenced 1995, updated 2008.
GenBank Acc. No. NM_006820.2, GI:166706908, first referenced 1997, updated 2008.
GenBank Acc. No. NM_006898.4, GI:23510372, first referenced 1989, updated 2002.

GenBank Acc. No. NM_007019.2, GI:32967292, first referenced 1997, updated 2003.
GenBank Acc. No. NM_012112.4, GI:40354199, first referenced 1997, updated 2003.
GenBank Acc. No. NM_013277.3, GI:186910298, first referenced 1997, updated 2008.
GenBank Acc. No. NM_018279.3, GI:89145418, first referenced 1997, updated 2006.
GenBank Acc. No. NM_021955.3, GI:74316012, first referenced 1984, updated 2005.
GenBank Acc. No. NM_024501.1, Gl:13375631, 1989.
GenBank Acc. No. NM_024626.2, Gl:99028880, first referenced 2003, updated 2006.
GenBank Acc. No. NM_033445.2, Gl:28872747, first referenced 1998, updated 2003.
GenBank Acc. No. NM_152864.2, Gl:42476063, first referenced 2001, updated 2004.
GenBank Acc. No. NM_178580.1, Gl:30581108, 2001.
GenBank Acc. No. NM_181337.3, Gl:198278499, first referenced 1999, updated 2008.
GenBank Acc. No. NM_202003.1, Gl:42544160, 1994.
Gene Bank Accession No. BC037243, Strausberg et al., Sep. 27, 2002.

* cited by examiner

FIG. 3

| | M | 1 | 2 | 3 | 4 | 5 | 6 | 7 | 8 | 9 | 10 |
|---|---|---|---|---|---|---|---|---|---|---|---|
| | | LMPs | Malignants | Breast cancer | | Prostate cancer | | Normal tissues | | | |
| A | ● | | | | | | | | ● | | |
| B | | | | | | | | | | | |
| C | | | | | | | | | | | |
| D | | | | | | | | | | | |
| E | | | | | | | | | | | |
| F | | | | | | | | | | | |
| G | | | | | | | | | | | |
| H | | | | | | | | | | | |

0671-SL126
(HOXD1)
(SEQ ID NO.:3)

FIG-5

0713-SL126
(IFIT1)
(SEQ ID NO.:5)

FIG. 7

|   | M | 1 | 2 | 3 | 4 | 5 | 6 | 7 | 8 | 9 | 10 |
|---|---|---|---|---|---|---|---|---|---|---|----|
| A |   |   |   |   |   |   |   |   |   |   |    |
| B |   |   |   |   |   |   |   |   |   |   |    |
| C |   |   |   |   | ● |   |   |   |   |   |    |
| D |   |   |   |   | · |   |   |   |   |   |    |
| E |   |   | ● |   |   |   |   |   |   |   |    |
| F |   |   |   | · |   |   |   |   |   |   |    |
| G |   |   |   |   |   |   |   |   |   |   |    |
| H |   |   |   | ● |   |   |   |   |   |   |    |

LMPs | Malignants | Breast cancer | Prostate cancer | Normal tissues

1096-SL126
(DPEP3)
(SEQ ID NO.:7)

FIG. 11

0239-SL127
(CKS1B)
(SEQ ID NO.:11)

FIG-17

0291-SL126
(PRAME)
(SEQ ID NO.:12)

FIG. 13

0972-SL123
(ISG15)
(SEQ ID NO.:13)

FIG-15

0420-SL123
(FLJ33790)
(SEQ ID NO.:15)

FIG. 17

|   | LMPs | Malignants | Breast cancer | Prostate cancer | Normal tissues |   |   |   |   |   |
|---|---|---|---|---|---|---|---|---|---|---|
| M | 1 | 2 | 3 | 4 | 5 | 6 | 7 | 8 | 9 | 10 |

A
B
C
D
E
F
G
H

0531-SL124
(VTCN1)
(SEQ ID NO.:17)

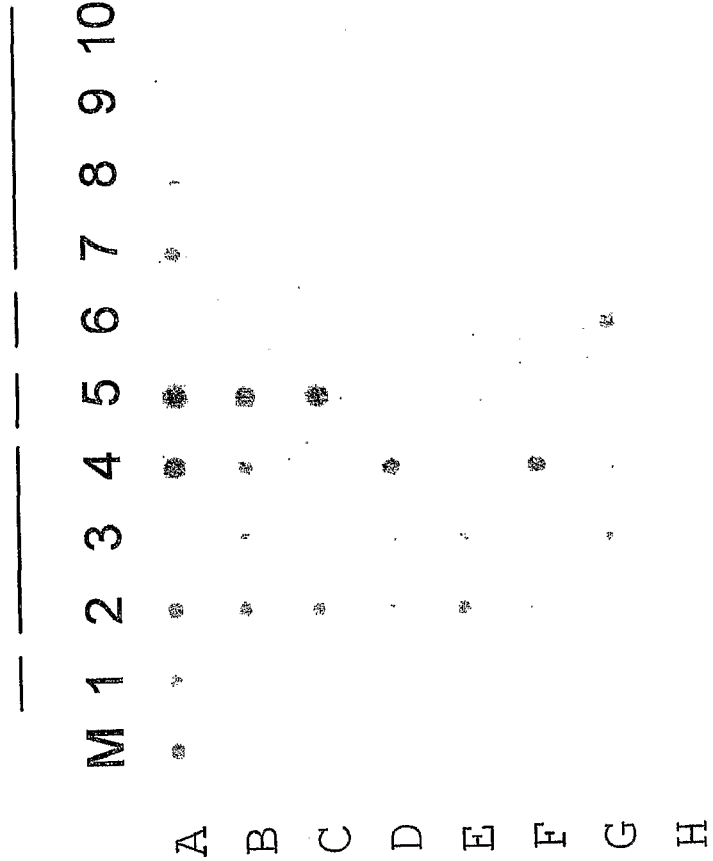

0889-SL124
(genomic hit)
(SEQ ID NO.:19)

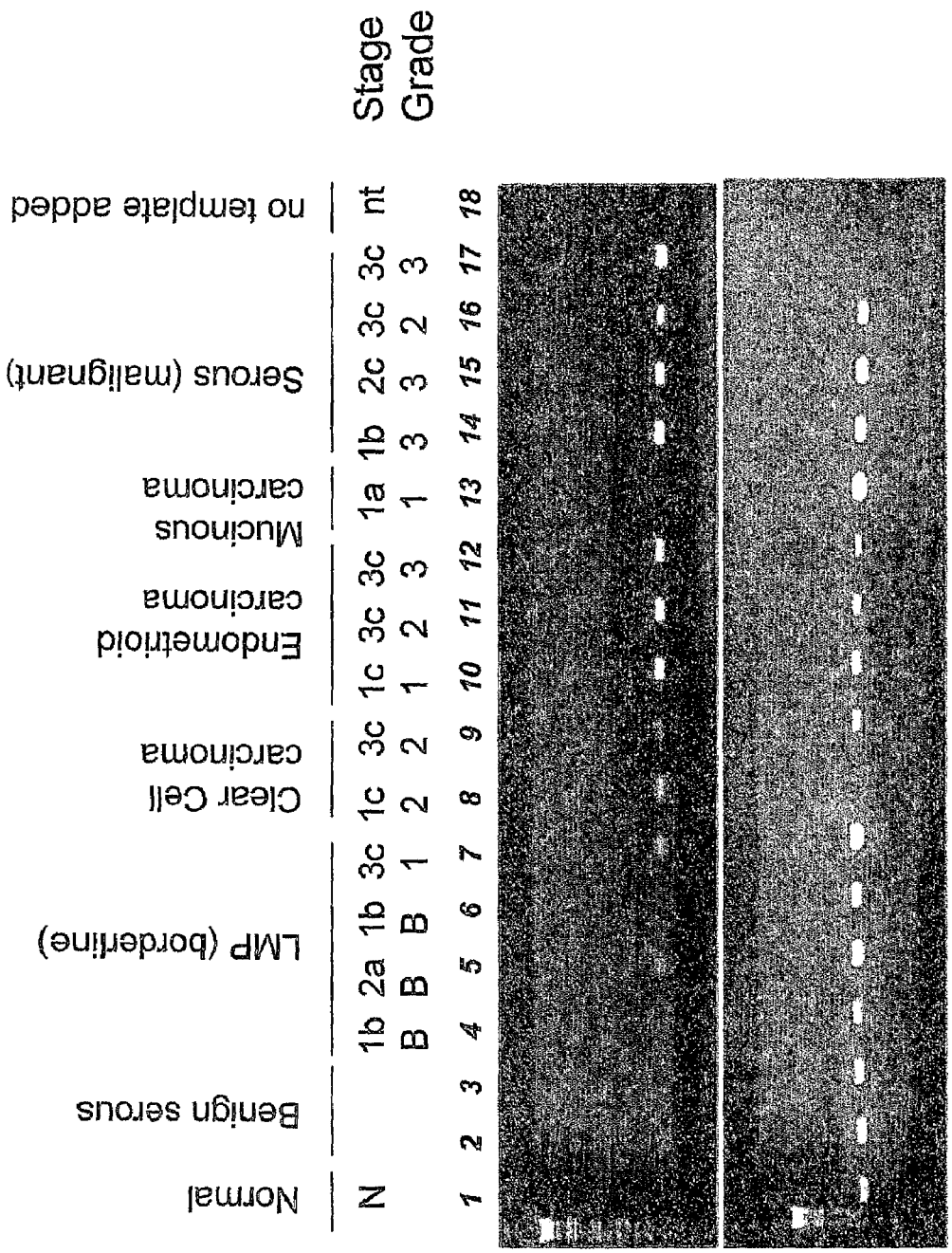

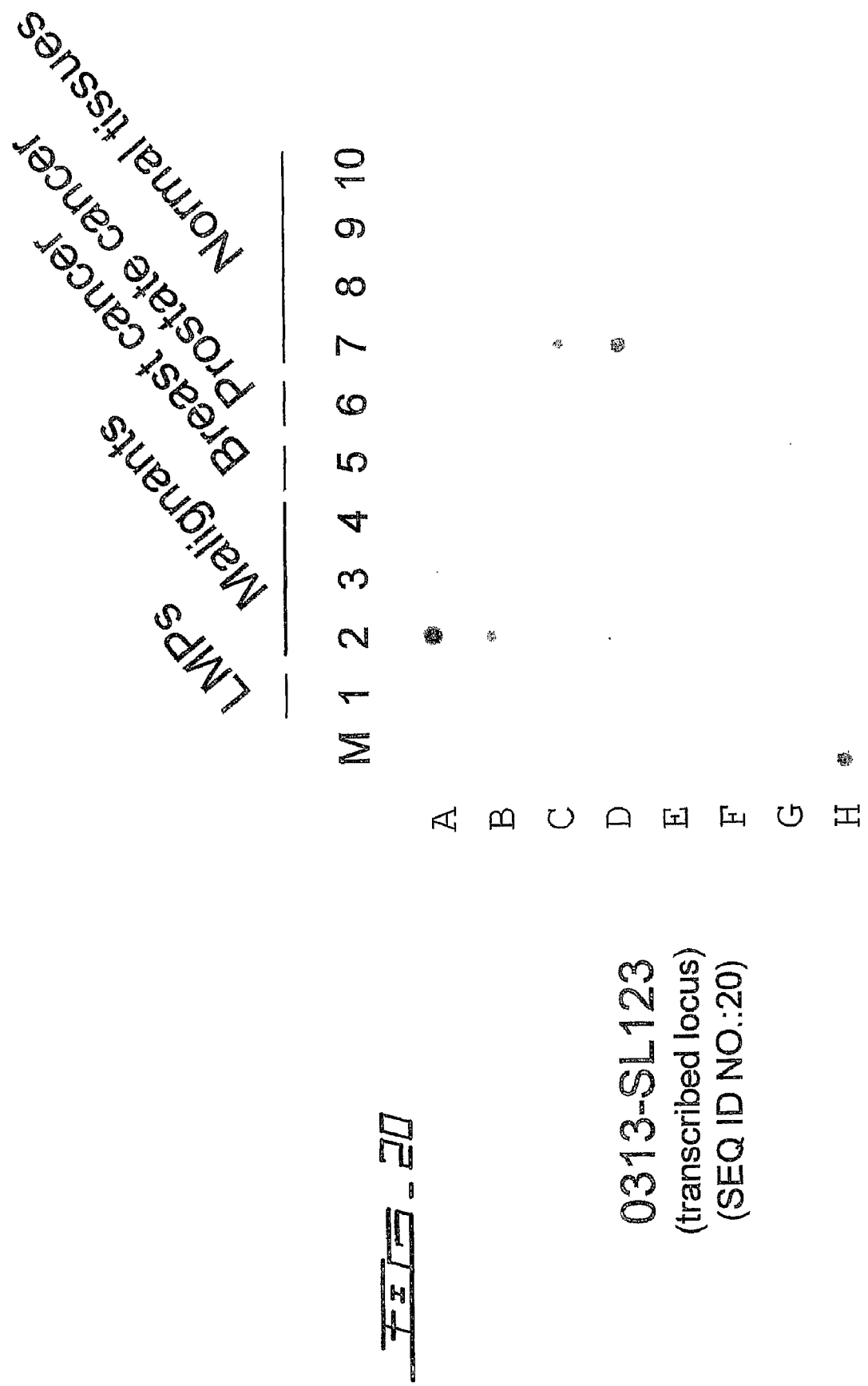

1134-SL126
(CXCL11)
(SEQ ID NO.:21)

FIG. 22

0488-SL123
(genomic hit)
(SEQ ID NO:22)

0447-SL124
(KAAG1)
(SEQ ID NO:24)

FIG. 25

1066-SL126
(CDKN2A)
(SEQ ID NO.:25)

FIG. 26

0698-SL127
(TPX2)
(SEQ ID NO.:26)

FIG. 27

1223-SL123
(UBE2C)
(SEQ ID NO.:27)

FIG. 28

1448-SL123
(FLJ35538)
(SEQ ID NO:28)

0635-SL126
(CRABP2)
(SEQ ID NO:29)

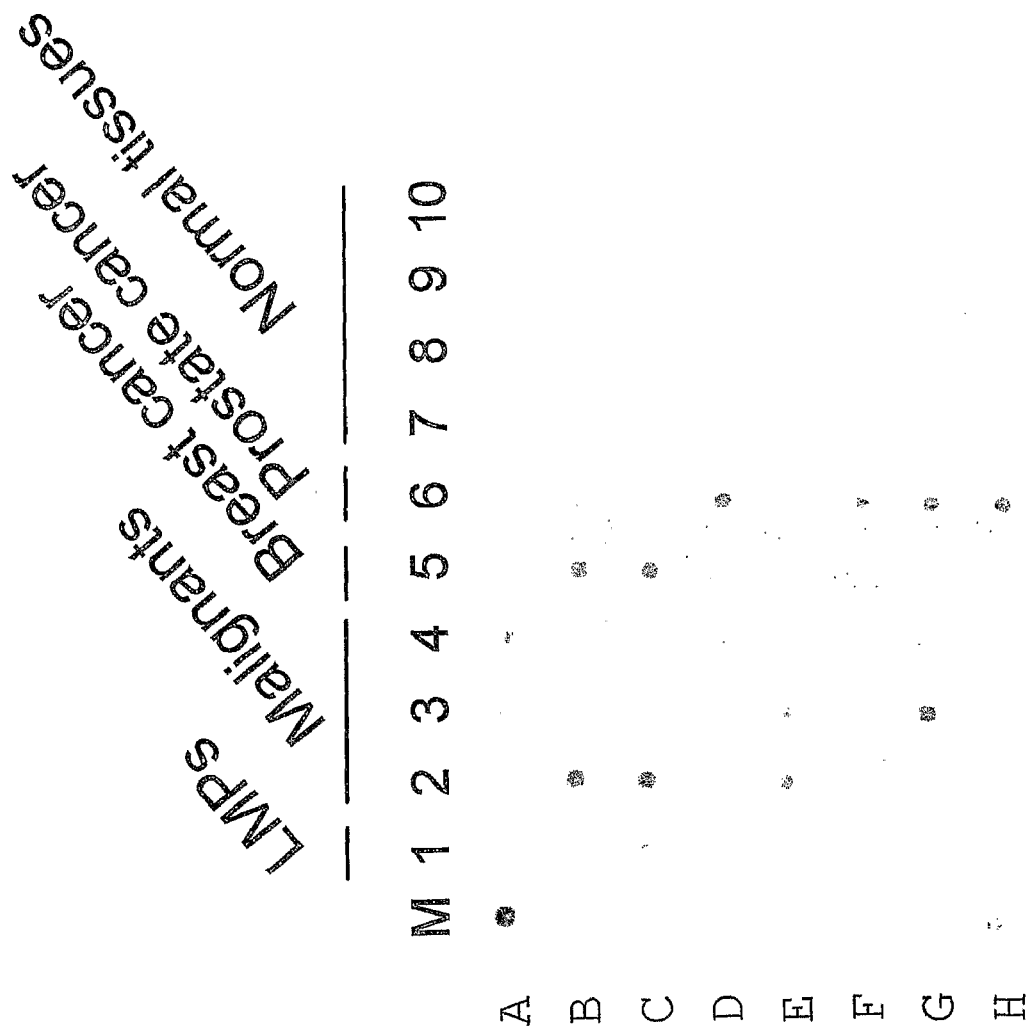

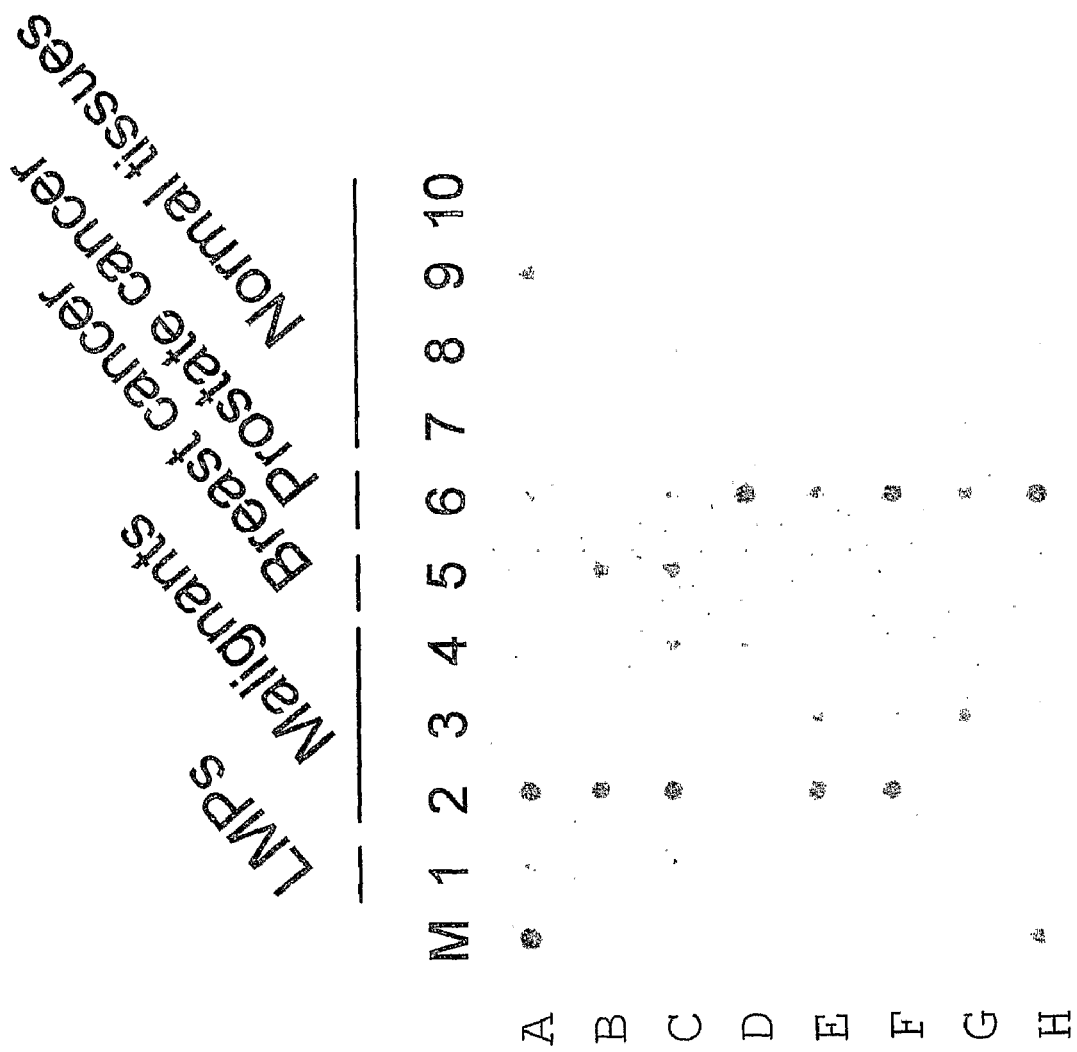

FIG. 37

1133-SL127
(HOX D3)

RT-PCR: 25 cycles

FIG. 33

|   | LMPs | Malignants | Breast cancer | Prostate cancer | Normal tissues |
|---|---|---|---|---|---|

0120-SL126
(IGHG1)
(SEQ ID NO.:33)

FIG-34

| | LMPs | Malignants | Breast cancer | Prostate cancer | Normal tissues |

0192-SL126
(IGKC)
(SEQ ID NO.:34)

FIG. 36

0205-SL127
(HM13)
(SEQ ID NO.:36)

LMPs | Malignants | Breast cancer | Prostate cancer | Normal tissues

LMPs | Malignants | Breast cancer | Prostate cancer | Normal tissues

M 1 2 3 4 5 6 7 8 9 10

0319-SL124
(Novel genomic hit)
(SEQ ID NO.:37)

FIG. 39

0344-SL127
(FOXM1)
(SEQ ID NO.:39)

FIG. 40

LMPs | Malignants Breast cancer Prostate cancer | Normal tissues
M 1 2 3 4 5 6 7 8 9 10

0405-SL123
(Chr. 20 ORF58)
(SEQ ID NO.:40)

FIG. 42

0567-SL123
(Chr. 16 ORF74)
(SEQ ID NO.:42)

FIG. 43

0721-SL124
(RACGAP1)
(SEQ ID NO.:43)

Ovarian cancer expression analysis using PCR
0795-SL125 (RACGAP1)
(SEQ ID NO:44)

1, adrenal; 2, breast; 3, jejunum; 4, trachea; 5, liver; 6, placenta; 7, aorta; 8, brain; 9, lung; 10, adrenal cortex; 11, esophagus; 12, colon; 13, ovary; 14, kidney; 15, prostate; 16, thymus; 17, skeletal muscle; 18, vena cava; 19, stomach; 20, small intestine; 21, heart; 22, fallopian tube; 23, spleen; 24, bladder; 25, cervix; 26, pancreas; 27, ileum; 28, duodenum; 29, thyroid; 30, testicle.

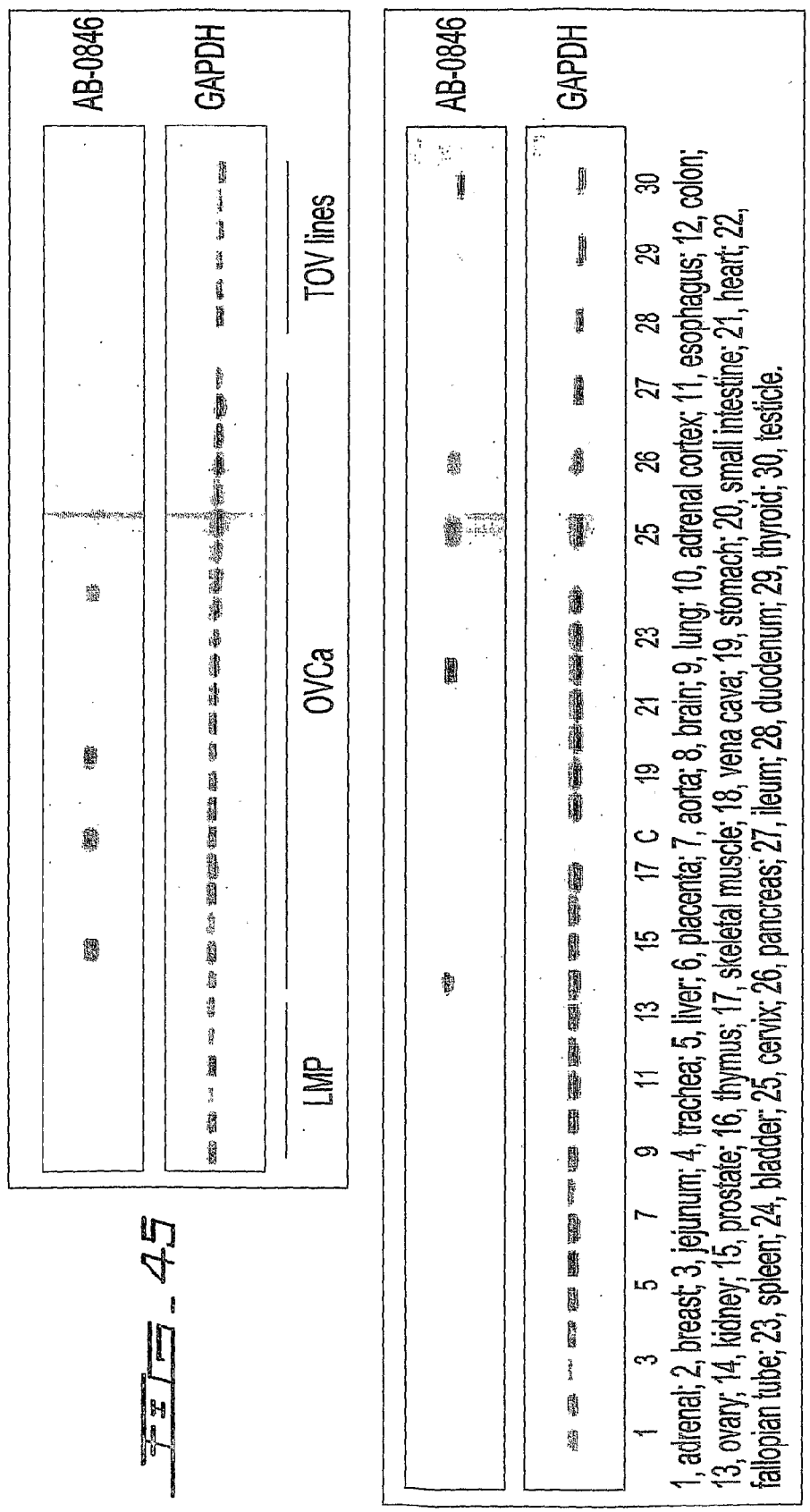

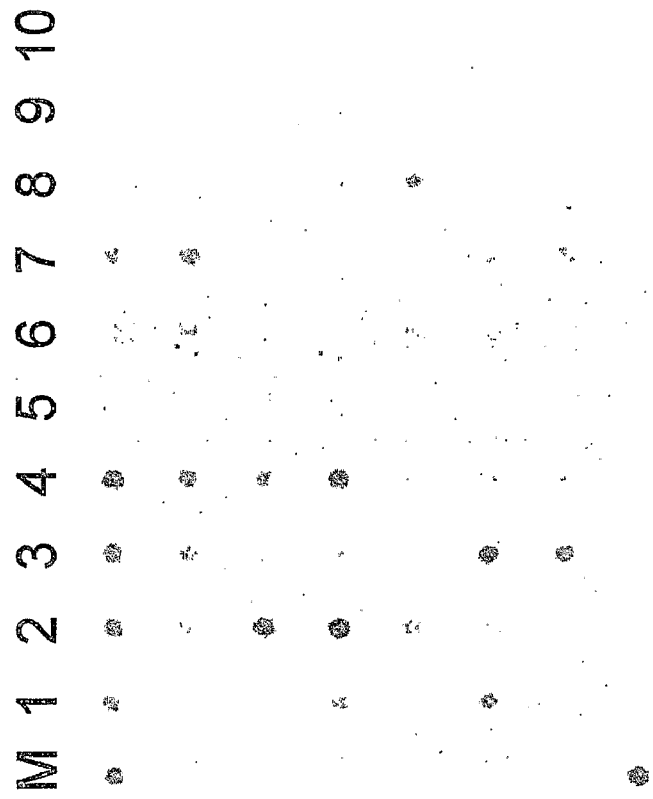

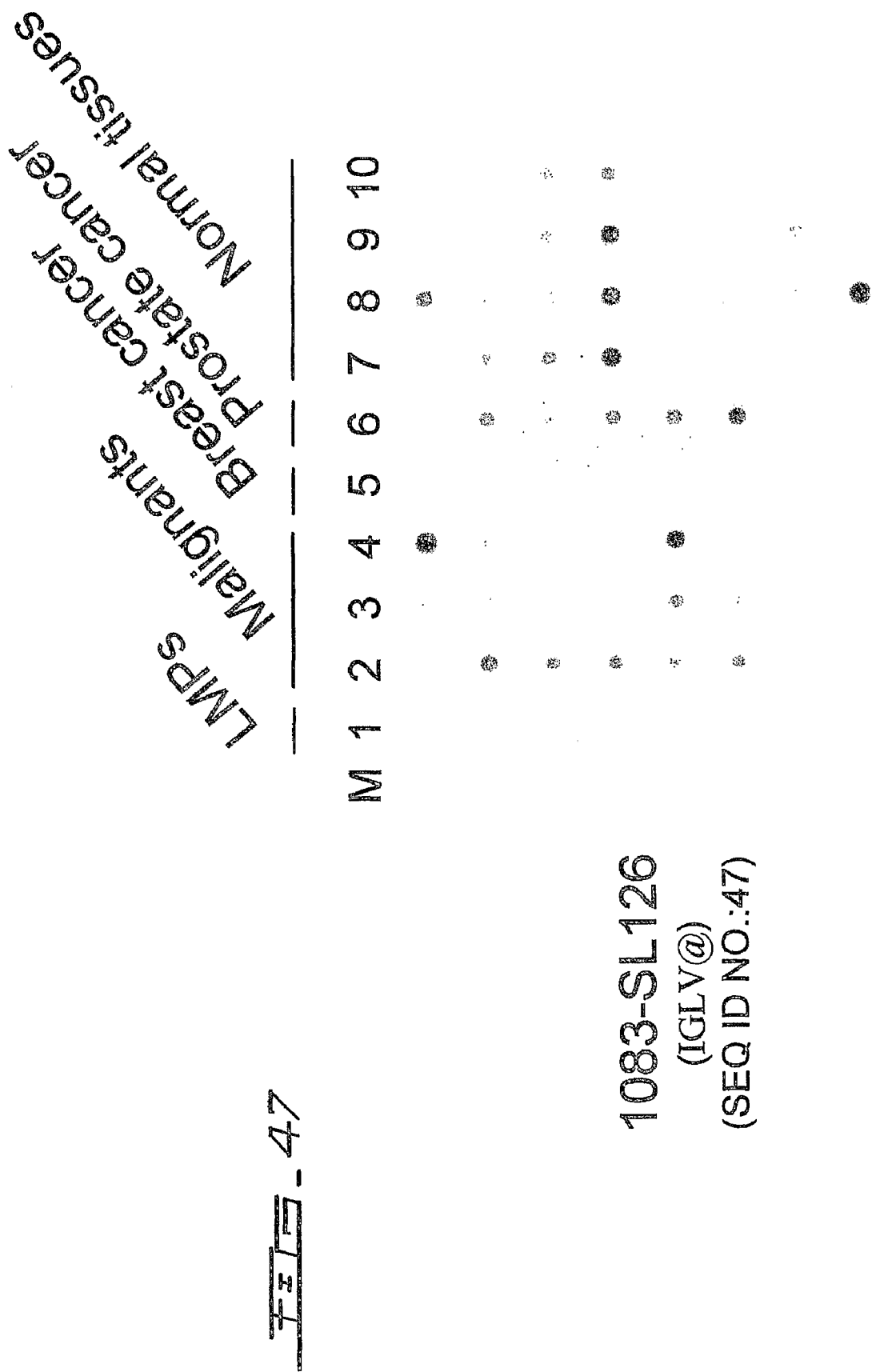

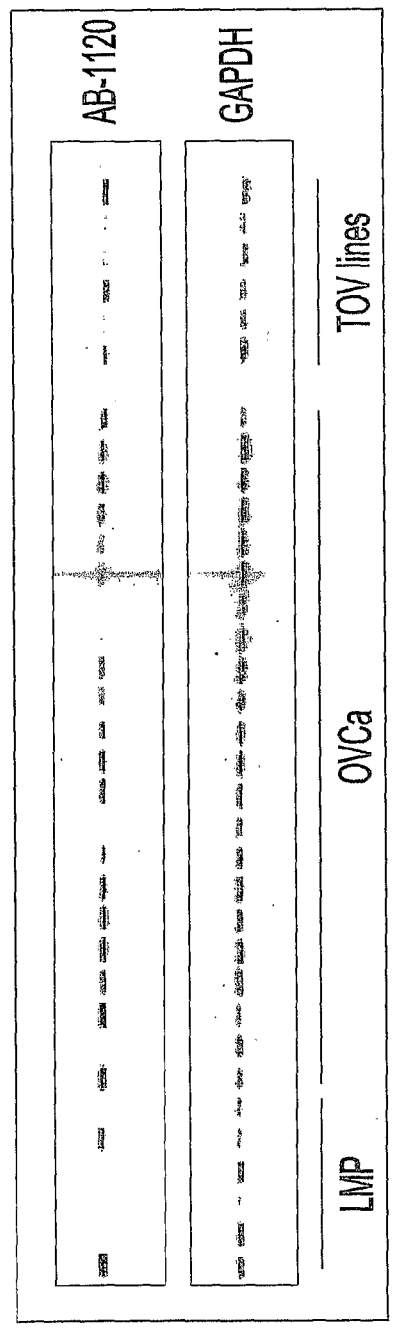
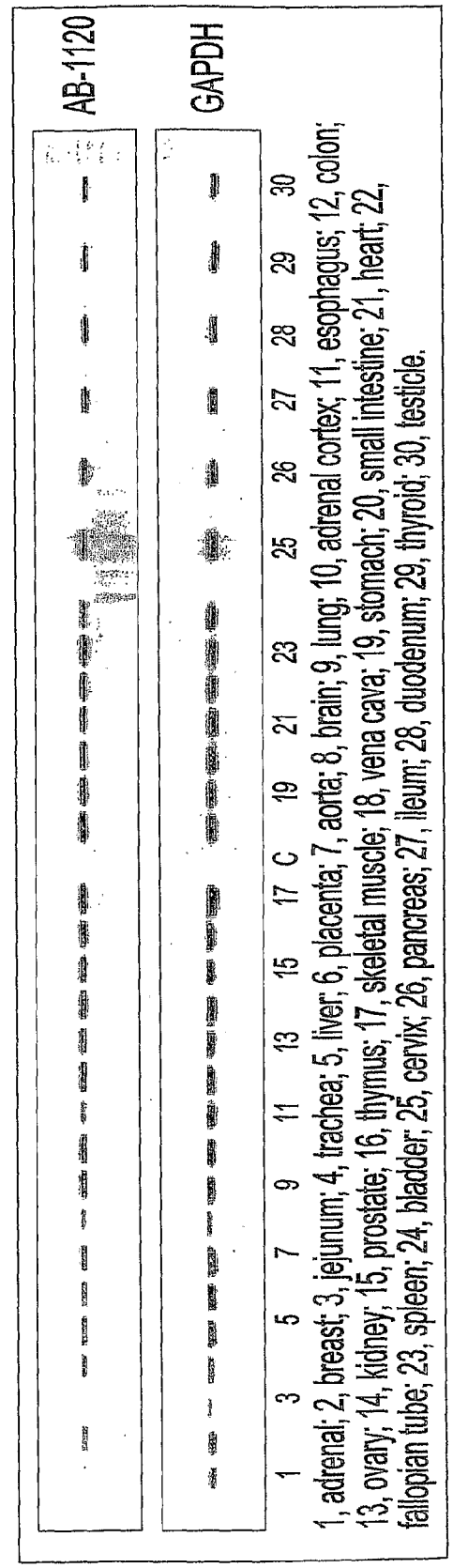
FIG. 49
Ovarian cancer expression analysis using PCR
1120-SL123 (SCAMP3)
(SEQ ID NO.:48)
1, adrenal; 2, breast; 3, jejunum; 4, trachea; 5, liver; 6, placenta; 7, aorta; 8, brain; 9, lung; 10, adrenal cortex; 11, esophagus; 12, colon; 13, ovary; 14, kidney; 15, prostate; 16, thymus; 17, skeletal muscle; 18, vena cava; 19, stomach; 20, small intestine; 21, heart; 22, fallopian tube; 23, spleen; 24, bladder; 25, cervix; 26, pancreas; 27, ileum; 28, duodenum; 29, thyroid; 30, testicle.

FIG. 49

1448-SL123
(genomic hit)
(SEQ ID NO.:49)

Effect of shRNAs on Expression of SEQ.ID. Nos. 1 and 3
RT-PCRs from transfected TOV-21G cells
|  | neg. | pSil-scr | pSil-0094-sh1 | pSil-0094-sh2 |
|---|---|---|---|---|
 0094
|  | neg. | pSil-scr | pSil-0671-sh1 | pSil-0671-sh2 |
|---|---|---|---|---|
 0671
|  | neg. | pSil-scr | pSil-0094-sh1 | pSil-0094-sh2 | pSil-scr | pSil-0671-sh1 | pSil-0671-sh2 |
|---|---|---|---|---|---|---|---|
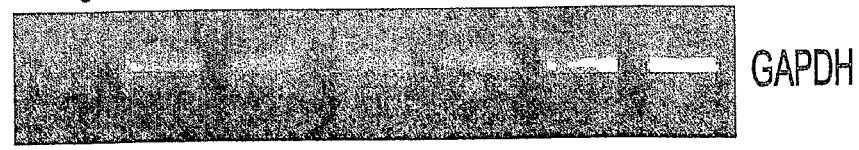 GAPDH
FIG. 52

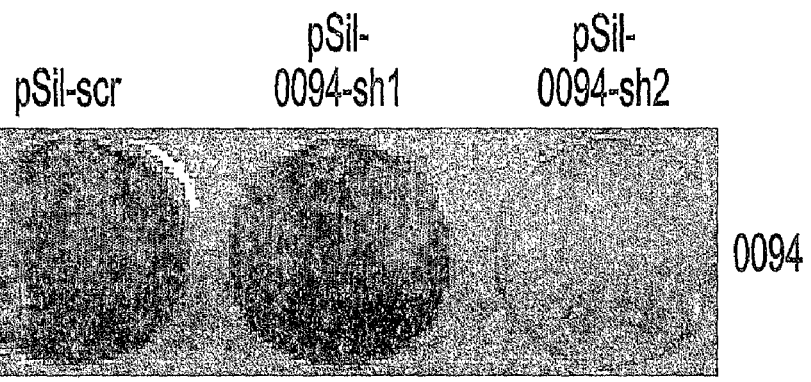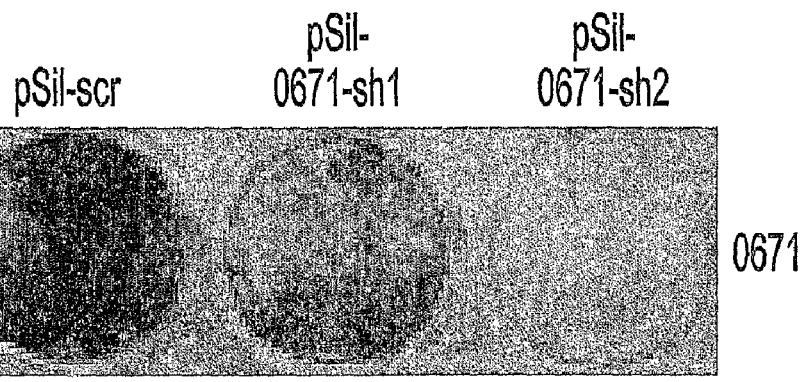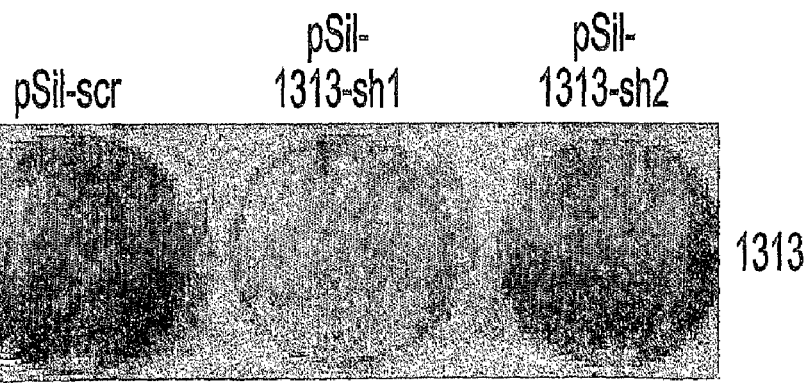
FIG. 54

0064-SL126
(Ceruloplasmin)
(SEQ ID NO.:169)

FIG. 57

SEQ ID NO 1/0094-SL123

SEQ ID NO. 1

Leukemia | CNS | Breast | Colon | Lung

Melanoma | Ovarian | Prostate | Renal

SEQ ID NO 5/0713-SL126

Leukemia | CNS | Breast | Colon | Lung

Melanoma | Ovarian | Prostate | Renal

SEQ ID NO. 5

SEQ ID NO 9/1313-SL123

SEQ ID NO. 9

Leukemia  CNS  Breast  Colon  Lung

Melanoma  Ovarian  Prostate  Renal

SEQ ID NO 10/0059-SL125

SEQ ID NO. 10

Leukemia | CNS | Breast | Colon | Lung

Melanoma | Ovarian | Prostate | Renal

SEQ ID NO 11/0239-SL127

Leukemia | CNS | Breast | Colon | Lung

Melanoma | Ovarian | Prostate | Renal

SEQ ID NO. 11

SEQ ID NO 18/0967-SL123

Leukemia | CNS | Breast | Ovarian | Prostate | Colon | Lung
Melanoma | | | | Renal | |

SEQ ID NO. 18

SEQ ID NO 24/0447-SL124

SEQ ID NO. 24

Leukemia | CNS | Breast | Colon | Lung
Melanoma | Ovarian | Prostate | Renal

SEQ ID NO 26/0698-SL127

Leukemia | CNS | Breast | Colon | Lung

Melanoma | Ovarian | Prostate | Renal

SEQ ID NO. 26

FIG. 82

SEQ ID NO 28/1448-SL123

Leukemia | CNS | Breast | Colon | Lung
Melanoma | Ovarian | Prostate | Renal

SEQ ID NO. 28

SEQ ID NO 33/0120-SL126
SEQ ID NO. 33

Leukemia | CNS | Lung | Colon | Breast | Ovarian | Prostate | Renal | Melanoma

SEQ ID NO 35/0201-SL125 — Leukemia, CNS, Breast, Colon, Lung, Ovarian, Prostate, Renal, Melanoma — SEQ ID NO. 35

SEQ ID NO 50/0967-SL126

SEQ ID NO. 50

Leukemia | CNS | Breast | Colon | Lung

Melanoma | Ovarian | Prostate | Renal

POLYNUCLEOTIDES AND POLYPEPTIDE SEQUENCES INVOLVED IN CANCER

This patent application is a national stage filing under 35 U.S.C. §371 of international application No. PCT/CA2007/001134 filed on Jun. 22, 2007 which claimed priority to U.S. provisional application No. 60/815,829 filed on Jun. 23, 2006 and U.S. provisional application No. 60/874,471 filed Dec. 13, 2006. The entire contents of each of these priority applications are incorporated herein by reference.

FIELD OF THE INVENTION

The present invention relates to polynucleotide and polypeptide sequences which are differentially expressed in cancer compared to normal cells. The present invention more particularly relates to the use of these sequences in the diagnosis, prognosis or treatment of cancer and in the detection of cancer cells.

BACKGROUND OF THE INVENTION

Among gynecologic malignancies, ovarian cancer accounts for the highest tumor-related mortality in women in the United States (Jemal et al., 2005). It is the fourth leading cause of cancer-related death in women in the U.S (Menon et al., 2005). The American Cancer Society estimated a total of 22,220 new cases in 2005 and attributed 16,210 deaths to the disease (Bonome et al., 2005). For the past 30 years, the statistics have remained largely the same—the majority of women who develop ovarian cancer will die of this disease (Chambers and Vanderhyden, 2006). The disease carries a 1:70 lifetime risk and a mortality rate of >60% (Chambers and Vanderhyden, 2006). The high mortality rate is due to the difficulties with the early detection of ovarian cancer when the malignancy has already spread beyond the ovary. Indeed, >80% of patients are diagnosed with advanced staged disease (stage III or IV) (Bonome et al., 2005). These patients have a poor prognosis that is reflected in <45% 5-year survival rate, although 80% to 90% will initially respond to chemotherapy (Berek et al., 2000). This increased success compared to 20% 5-year survival rate years earlier is, at least in part, due to the ability to optimally debulk tumor tissue when it is confined to the ovaries, which is a significant prognostic factor for ovarian cancer (Bristow R. E., 2000 and Brown et al., 2004). In patients who are diagnosed with early disease (stage I), the 5-yr survival ranges from >90 (Chambers and Vanderhyden, 2006).

Ovarian cancer comprises a heterogeneous group of tumors that are derived from the surface epithelium of the ovary or from surface inclusions. They are classified into serous, mucinous, endometrioid, clear cell, and Brenner (transitional) types corresponding to the different types of epithelia in the organs of the female reproductive tract (Shih and Kurman, 2005). Of these, serous tumors account for ~60% of the ovarian cancer cases diagnosed. Each histologic subcategory is further divided into three groups: benign, intermediate (borderline tumor or low malignancy potential (LMP)), and malignant, reflecting their clinical behavior (Seidman et al., 2002). LMP represents 10% to 15% of tumors diagnosed as serous and is a conundrum as they display atypical nuclear structure and metastatic behavior, yet they are considerably less aggressive than high-grade serous tumors. The 5-year survival for patients with LMP tumors is 95% in contrast to a <45% survival for advanced high-grade disease over the same period (Berek et al., 2000).

Despite improved knowledge of the etiology of the disease, aggressive cytoreductive surgery, and modern combination chemotherapy, there has been only little change in mortality. Poor outcomes have been attributed to (1) lack of adequate screening tests for early disease detection, in combination with only subtle presentation of symptoms at this stage—diagnosis is frequently being made only after progression to later stages, at which point the peritoneal dissemination of the cancer limits effective treatment and (2) the frequent development of resistance to standard chemotherapeutic strategies limiting improvement in the 5-year survival rate of patients. The initial chemotherapy regimen for ovarian cancer includes the combination of carboplatin (PARAPLATIN) and paclitaxel (TAXOL). Years of clinical trials have proved this combination to be most effective after effective surgery reduces tumor volume in about 80% of the women with newly diagnosed ovarian cancer and 40% to 50% will have complete regression but studies continue to look for ways to improve it. Recent abdominal infusion of chemotherapeutics to target hard-to-reach cells in combination with intravenous delivery has increased the effectiveness. However, severe side effects often lead to an incomplete course of treatment. Some other chemotherapeutic agents include doxorubicin, cisplatin, cyclophosphamide, bleomycin, etoposide, vinblastine, topotecan hydrochloride, ifosfamide, 5-fluorouracil and melphalan. The excellent survival rates for women with early stage disease receiving chemotherapy provide a strong rationale for research efforts to develop strategies to improve the detection of ovarian cancer. Furthermore, the discovery of new ovarian cancer-related biomarkers will lead to the development of more effective therapeutic strategies with minimal side effects for the future treatment of ovarian cancer.

Presently, the diagnosis of ovarian cancer is accomplished, in part, through routine analysis of the medical history of patients and by performing physical, ultrasound and x-ray examinations, and hematological screening. Two alternative strategies have been reported for early hematological detection of serum biomarkers. One approach is the analysis of serum samples by mass spectrometry to find proteins or protein fragments of unknown identity that detect the presence or absence of cancer (Mor et al., 2005 and Kozak et al., 2003). However, this strategy is expensive and not broadly available. Alternatively, the presence or absence of known proteins/peptides in the serum is being detected using antibody microarrays, ELISA, or other similar approaches. Serum testing for a protein biomarker called CA-125 (cancer antigen-125) has long been widely performed as a marker for ovarian cancer. However, although ovarian cancer cells may produce an excess of these protein molecules, there are some other cancers, including cancer of the fallopian tube or endometrial cancer (cancer of the lining of the uterus), 60% of people with pancreatic cancer, and 20%-25% of people with other malignancies with elevated levels of CA-125. The CA-125 test only returns a true positive result for about 50% of Stage I ovarian cancer patients and has a 80% chance of returning true positive results from stage II, III, and IV ovarian cancer patients. The other 20% of ovarian cancer patients do not show any increase in CA-125 concentrations. In addition, an elevated CA-125 test may indicate other benign activity not associated with cancer, such as menstruation, pregnancy, or endometriosis. Consequently, this test has very limited clinical application for the detection of early stage disease when it is still treatable, exhibiting a positive predictive value (PPV) of <10%. And, even with the addition of ultrasound screening to CA-125, the PPV only improves to around 20% (Kozak et al., 2003). Thus, this test is not an effective screening test.

Other studies have yielded a number of biomarker combinations with increased specificity and sensitivity for ovarian cancer relative to CA-125 alone (McIntosh et al., 2004, Woolas et al., 1993, Schorge et., 2004). Serum biomarkers that are often elevated in women with epithelial ovarian cancer, but not exclusively, include carcinoembryonic antigen, ovarian cystadenocarcinoma antigen, lipidassociated sialic acid, NB/70, TAG72.3, CA-15.3, and CA-125. Unfortunately, although this approach has increased the sensitivity and specificity of early detection, published biomarker combinations still fail to detect a significant percentage of stage I/II epithelial ovarian cancer. Another study (Elieser et al., 2005) measured serum concentrations of 46 biomarkers including CA-125 and amongst these, 20 proteins in combination correctly recognized more than 98% of serum samples of women with ovarian cancer compared to other benign pelvic disease. Although other malignancies were not included in this study, this multimarker panel assay provided the highest diagnostic power for early detection of ovarian cancer thus far.

Additionally, with the advent of differential gene expression analysis technologies, for example DNA microarrays and subtraction methods, many groups have now reported large collections of genes that are upregulated in epithelial ovarian cancer (United States Patent Application published under numbers; 20030124579, 20030087250, 20060014686, 20060078941, 20050095592, 20050214831, 20030219760, 20060078941, 20050214826). However, the clinical utilities with respect to ovarian cancer of one or combinations of these genes are not as yet fully determined.

There is a need for new tumor biomarkers for improving diagnosis and/or prognosis of cancer. In addition, due to the genetic diversity of tumors, and the development of chemoresistance by many patients, there exists further need for better and more universal therapeutic approaches for the treatment of cancer. Molecular targets for the development of such therapeutics may preferably show a high degree of specificity for the tumor tissues compared to other somatic tissues, which will serve to minimize or eliminate undesired side effects, and increase the efficacy of the therapeutic candidates.

This present invention tries to address these needs and other needs.

SUMMARY OF THE INVENTION

In accordance with the present invention, there is provided new polynucleotide sequences and new polypeptide sequences as well as compositions, antibodies specific for these sequences, vectors and cells comprising a recombinant form of these new sequences.

The present invention also provides methods of detecting cancer cells using single or multiple polynucleotides and/or polypeptide sequences which are specific to these tumor cells. Some of the polynucleotides and/or polypeptides sequences provided herein are differentially expressed in ovarian cancer compared to normal cells and may also be used to distinguish between malignant ovarian cancer and an ovarian cancer of a low malignancy potential and/or a normal state (individual free of ovarian cancer).

Also encompassed by the present invention are diagnostic methods, prognostic methods, methods of detection, kits, arrays, libraries and assays which comprises one or more polypeptide and/or polynucleotide sequences or antibodies described herein as well as new therapeutic avenues for cancer treatment.

The Applicant has come to the surprising discovery that polynucleotide and/or polypeptide sequences described herein are preferentially upregulated in malignant ovarian cancer compared to low malignancy potential ovarian cancer and/or compared to normal cells. More interestingly, some of these sequences appear to be overexpressed in late stage ovarian cancer.

The Applicant has also come to the surprising discovery that some of the sequences described herein are not only expressed in ovarian cancer cells but in other cancer cells such as cells from breast cancer, prostate cancer, renal cancer, colon cancer, lung cancer, melanoma, leukemia and from cancer of the central nervous system. As such, several of these sequences, either alone or in combination may represent universal tumor markers. Therefore, some NSEQs and PSEQs described herein not only find utility in the field of ovarian cancer detection and treatment but also in the detection and treatment of other types of tumors Therefore, using NSEQs or PSEQs of the present invention, one may readily identify a cell as being cancerous. As such NSEQs or PSEQs may be used to identify a cell as being a ovarian cancer cell, a prostate cancer cell, a breast cancer cell, a lung cancer cell, a colon cancer cell, a renal cancer cell, a cell from a melanoma, a leukemia cell or a cell from a cancer of the central nervous system.

Even more particularly, NSEQs or PSEQs described herein may be used to identify a cell as being a malignant ovarian cancer or a low malignant potential ovarian cancer.

The presence of some NSEQs or PSEQs in ovarian cancer cell may preferentially be indicative that the ovarian cancer is of the malignant type. Some NSEQs or PSEQs of the present invention may also more particularly indicate that the cancer is a late-stage malignant ovarian cancer.

The NSEQs or PSEQs may further be used to treat cancer or to identify compounds useful in the treatment of cancer including, ovarian cancer (i.e, LMP and/or malignant ovarian cancer), prostate cancer, breast cancer, lung cancer, colon cancer, renal cancer, melanoma, leukemia or cancer of the central nervous system.

As used herein and in some embodiments of the invention, the term "NSEQ" refers generally to polynucleotides sequences comprising or consisting of any one of SEQ. ID. NOs:1 to 49, and 169 (e.g., an isolated form) or comprising or consisting of a fragment of any one of SEQ. ID. NOs: 1 to 49 and 169. The term "NSEQ" more particularly refers to a polynucleotide sequence comprising or consisting of a transcribed portion of any one of SEQ. ID. NOs:1 to 49 and 169, which may be, for example, free of untranslated or untranslatable portion(s) (i.e., a coding portion of any one of SEQ ID Nos.: 1-49 and 169). The term "NSEQ" additionally refers to a sequence substantially identical to any one of the above and more particularly substantially identical to polynucleotide sequence comprising or consisting of a transcribed portion of any one of SEQ. ID. NOs:1 to 49 and 169, which may be, for example, free of untranslated or untranslatable portion(s). The term "NSEQ" additionally refers to a nucleic acid sequence region of any one of SEQ. ID. NOs:1 to 49 and 169 which encodes or is able to encode a polypeptide. The term "NSEQ" also refers to a polynucleotide sequence able to encode any one of the polypeptides described herein or a polypeptide fragment of any one of the above. Finally, the term "NSEQ" refers to a sequence substantially complementary to any one of the above.

In other embodiments of the invention such as those which relate to detection and/or treatment of cancers other than ovarian cancer, NSEQ may also relates to SEQ ID NO.:50 including any polynucleotide comprising or consisting of SEQ. ID. NO:50 (e.g., an isolated form) or comprising or consisting of a fragment of any one of SEQ. ID. NO:50, such as a polynucleotide sequence comprising or consisting of a transcribed portion of any one of SEQ. ID. NO:50, which may be, for example, free of untranslated or untranslatable portion (s) (i.e., a coding portion of SEQ. ID. NO:50). The term "NSEQ" additionally refers to a sequence substantially identical to any one of the above and more particularly substantially identical to polynucleotide sequence comprising or consisting of a transcribed portion of SEQ. ID. NO:50, which may be, for example, free of untranslated or untranslatable portion(s). The term "NSEQ" additionally refers to a nucleic acid sequence region of SEQ. ID. NO:50 which encodes or is able to encode a polypeptide. Finally, the term "NSEQ" refers to a sequence substantially complementary to any one of the above.

As such, in embodiments of the invention NSEQ encompasses, for example, SEQ. ID. NOs:1 to 49, 50 and 169 and also encompasses polynucleotide sequences which comprises, are designed or derived from SEQ. ID. NOs:1 to 49, 50 or 169. Non-limiting examples of such sequences includes, for example, SEQ ID NOs.: 103-150 or 151-152.

The term "inhibitory NSEQ" generally refers to a sequence substantially complementary to any one of SEQ. ID. NOs:1 to 49, 50 or 169, substantially complementary to a fragment of any one of SEQ. ID. Nos: 1 to 49, 50 or 169, substantially complementary to a sequence substantially identical to SEQ. ID. NOs:1 to 49, 50 or 169 and more particularly, substantially complementary to a transcribed portion of any one of SEQ. ID. NOs:1 to 49, 50 or 169 (e.g., which may be free of unstranslated or untranslatable portion) and which may have attenuating or even inhibitory action against the transcription of a mRNA or against expression of a polypeptide encoded by a corresponding SEQ ID NOs.:1 to 49, 50 or 169. Suitable "inhibitory NSEQ" may have for example and without limitation from about 10 to about 30 nucleotides, from about 10 to about 25 nucleotides or from about 15 to about 20 nucleotides.

As used herein the term "PSEQ" refers generally to each and every polypeptide sequences mentioned herein such as, for example, any polypeptide sequences encoded (putatively encoded) by any one of NSEQ described herein (e.g., any one of SEQ. ID. NOs:1 to 49 or 169) including their isolated or substantially purified form. Therefore, in embodiments of the invention, a polypeptide comprising or consisting of any one of SEQ. ID. NOs:51 to 88 or 170 including variants (e.g., an isolated natural protein variant), analogs, derivatives and fragments thereof are collectively referred to herein as "PSEQ". In other embodiments of the invention, such as those related to detection and/or treatment of cancers other than ovarian cancer, PSEQ also refers to polypeptide comprising or consisting of SEQ ID NO.:89 including variants (e.g., an isolated natural protein variant), analogs, derivatives and fragments.

Some of the NSEQs or PSEQs described herein have been previously characterized for purposes other than those described herein. As such diagnostics and therapeutics which are known to target those NSEQs or PSEQs (e.g., antibodies and/or inhibitors) may thus now be applied for inhibition of these NSEQ or PSEQ in the context of treatment of ovarian cancer, prostate cancer, renal cancer, colon cancer, lung cancer, melanoma, leukemia or cancer of the central nervous system. The use of these known therapeutics and diagnostics for previously undisclosed utility such as those described herein is encompassed by the present invention.

For example, antibodies capable of binding to folate receptor-1 may thus be used for specific binding of tumor cells other than ovarian cancer cells, such as breast cancer, prostate cancer, renal cancer, colon cancer, lung cancer, melanoma, leukemia and from cancer of the central nervous system. As such the use of antibodies and/or inhibitors of folate receptor-1 (e.g., CB300638, CB300945 which are Cyclopenta[g] quinazoline-based Thymidylate Synthase Inhibitor, those described in US20040242606, US20050009851, etc.) in the use of treatment of prostate cancer, renal cancer, colon cancer, lung cancer, melanoma, leukemia and cancer of the central nervous system is encompassed by the present invention.

Non-Limitative Exemplary Embodiments of the Invention

Use of NSEQ as a Screening Tool

The NSEQ described herein may be used either directly or in the development of tools for the detection and isolation of expression products (mRNA, mRNA precursor, hnRNA, etc.), of genomic DNA or of synthetic products (cDNA, PCR fragments, vectors comprising NSEQ etc.). NSEQs may also be used to prepare suitable tools for detecting an encoded polypeptide or protein. NSEQ may thus be used to provide an encoded polypeptide and to generate an antibody specific for the polypeptide.

Those skilled in the art will also recognize that short oligonucleotides sequences may be prepared based on the polynucleotide sequences described herein. For example, oligonucleotides having 10 to 20 nucleotides or more may be prepared for specifically hybridizing to a NSEQ having a substantially complementary sequence and to allow detection, identification and isolation of nucleic sequences by hybridization. Probe sequences of for example, at least 10-20 nucleotides may be prepared based on a sequence found in any one of SEQ ID NO.:1 to 49, 50 or 169 and more particularly selected from regions that lack homology to undesirable sequences. Probe sequences of 20 or more nucleotides that lack such homology may show an increased specificity toward the target sequence. Useful hybridization conditions for probes and primers are readily determinable by those of skill in the art. Stringent hybridization conditions encompassed herewith are those that may allow hybridization of nucleic acids that are greater than 90% homologous but which may prevent hybridization of nucleic acids that are less than 70% homologous. The specificity of a probe may be determined by whether it is made from a unique region, a regulatory region, or from a conserved motif. Both probe specificity and the stringency of diagnostic hybridization or amplification (maximal, high, intermediate, or low) reactions depend on whether or not the probe identifies exactly complementary sequences, allelic variants, or related sequences. Probes designed to detect related sequences may have, for example, at least 50% sequence identity to any of the selected polynucleotides.

Furthermore, a probe may be labelled by any procedure known in the art, for example by incorporation of nucleotides linked to a "reporter molecule". A "reporter molecule", as used herein, may be a molecule that provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes may be conjugated to avidin or streptavidin for use with a biotinylated probe. Similarly, probes may be conjugated to avidin or streptavidin for use with a biotinylated enzyme. Incorporation of a reporter molecule into a DNA probe may be effected by any method known to the skilled artisan, for example by nick translation, primer extension, random oligo priming, by 3' or 5' end labeling or by other means. In addition, hybridization probes include the cloning of nucleic acid sequences into vectors for the production of mRNA probes. Such vectors are known in the art, are commercially available, and may be used to synthesize RNA probes in vitro. The labelled polynucleotide sequences may be used in Southern or northern analysis, dot blot, or other membrane-based technologies; in PCR technologies; and in micro arrays utilizing samples from subjects to detect altered expression. Oligonucleotides useful as probes for screening of samples by hybridization assays or as primers for amplification may be packaged into kits. Such kits may contain the probes or primers in a pre-measured or pre-determined amount, as well as other suitably packaged reagents and materials needed for the particular hybridization or amplification protocol.

The expression of mRNAs identical or substantially identical to the NSEQs of the present invention may thus be detected and/or isolated using methods which are known in the art. Exemplary embodiment of such methods includes, for example and without limitation, hybridization analysis using oligonucleotide probes, reverse transcription and in vitro nucleic acid amplification methods.

Such procedures may therefore, permit detection of mRNAs in ovarian cells (e.g., ovarian cancer cells) or in any other cells expressing such mRNAs. Expression of mRNA in a tissue-specific or a disease-specific manner may be useful for defining the tissues and/or particular disease state. One of skill in the art may readily adapt the NSEQs for these purposes.

It is to be understood herein that the NSEQs may hybridize to a substantially complementary sequence found in a test sample (e.g., cell, tissue, etc.). Additionally, a sequence substantially complementary to NSEQ (including fragments) may bind a NSEQ and substantially identical sequences found in a test sample (e.g., cell, tissue, etc.).

Polypeptide encoded by an isolated NSEQ, polypeptide variants, polypeptide analogs or polypeptide fragments thereof are also encompassed herewith. The polypeptides whether in a premature, mature or fused form, may be isolated from lysed cells, or from the culture medium, and purified to the extent needed for the intended use. One of skill in the art may readily purify these proteins, polypeptides and peptides by any available procedure. For example, purification may be accomplished by salt fractionation, size exclusion chromatography, ion exchange chromatography, reverse phase chromatography, affinity chromatography and the like. Alternatively, PSEQ may be made by chemical synthesis.

Natural variants may be identified through hybridization screening of a nucleic acid library or polypeptide library from different tissue, cell type, population, species, etc using the NSEQ and derived tools.

Use of NSEQ for Development of an Expression System

In order to express a polypeptide, a NSEQ able to encode any one of a PSEQ described herein may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA from NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, NSEQ may be transformed into cell lines using expression vectors that may contain viral origins of replication and/or endogenous expression elements and a selectable or visible marker gene on the same or on a separate vector. The invention is not to be limited by the vector or host cell employed.

Alternatively, RNA and/or polypeptide may be expressed from a vector comprising NSEQ using an in vitro transcription system or a coupled in vitro transcription/translation system respectively.

In general, host cells that contain NSEQ and/or that express a polypeptide encoded by the NSEQ, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising NSEQ may thus be cultured under conditions for the transcription of the corresponding RNA (mRNA, siRNA, shRNA etc.) and/or the expression of the polypeptide from cell culture. The polypeptide produced by a cell may be secreted or may be retained intracellularly depending on the sequence and/or the vector used. As will be understood by those of skill in the art, expression vectors containing NSEQ may be designed to contain signal sequences that direct secretion of the polypeptide through a prokaryotic or eukaryotic cell membrane. Due to the inherent degeneracy of the genetic code, other DNA sequences that encode the same, substantially the same or a functionally equivalent amino acid sequence may be produced and used, for example, to express a polypeptide encoded by NSEQ. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth. In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation.

Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein, the fusion protein may comprise a fusion partner fused to a peptide fragment of a protein encoded by, or a naturally occurring allelic variant polypeptide encoded by, the polynucleotide sequence described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

The present invention additionally relates to a bioassay for evaluating compounds as potential antagonists of the polypeptide described herein, the bioassay may comprise:
a) culturing test cells in culture medium containing increasing concentrations of at least one compound whose ability to inhibit the action of a polypeptide described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter
b) monitoring in the cells the level of expression of the product of the reporter gene (encoding a reporter molecule) as a function of the concentration of the potential antagonist compound in the culture medium, thereby indicating the ability of the potential antagonist compound to inhibit activation of the polypeptide encoded by, the polynucleotide sequence described herein.

The present invention further relates to a bioassay for evaluating compounds as potential agonists for a polypeptide encoded by the polynucleotide sequence described herein, the bioassay may comprise:
a) culturing test cells in culture medium containing increasing concentrations of at least one compound whose ability to promote the action of the polypeptide encoded by the polynucleotide sequence described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter
b) monitoring in the cells the level of expression of the product of the reporter gene as a function of the concentration of the potential agonist compound in the culture medium, thereby indicating the ability of the potential agonist compound to promote activation of a polypeptide encoded by the polynucleotide sequence described herein.

Use of NSEQ as a Identification Tool or as a Diagnostic Screening Tool

The skilled artisan will readily recognize that NSEQ may be used to identify a particular cell, cell type, tissue, disease and thus may be used for diagnostic purposes to determine the absence, presence, or altered expression (i.e. increased or decreased compared to normal) of the expression product of a gene. Suitable NSEQ may be for example, between 10 and 20 or longer, i.e., at least 10 nucleotides long or at least 12 nucleotides long, or at least 15 nucleotides long up to any desired length and may comprise, for example, RNA, DNA, branched nucleic acids, and/or peptide nucleic acids (PNAs). In one alternative, the polynucleotides may be used to detect and quantify gene expression in samples in which expression of NSEQ is correlated with disease. In another alternative, NSEQ may be used to detect genetic polymorphisms associated with a disease. These polymorphisms may be detected, for example, in the transcript, cDNA or genomic DNA.

The invention provides for the use of at least one of the NSEQ described herein on an array and for the use of that array in a method of detection of a particular cell, cell type, tissue, disease for the prognosis or diagnosis of cancer. The method may comprise hybridizing the array with a patient sample (putatively comprising or comprising a target polynucleotide sequence substantially complementary to a NSEQ) under conditions to allow complex formation (between NSEQ and target polynucleotide), detecting complex formation, wherein the complex formation is indicative of the presence of the polynucleotide and wherein the absence of complex formation is indicative of the absence of the polynucleotide in the patient sample. The presence or absence of the polynucleotide may be indicative of cancer such as, for example, ovarian cancer or other cancer as indicated herein.

The method may also comprise the step of quantitatively or qualitatively comparing (e.g., with a computer system, apparatus) the level of complex formation in the patient sample to that of standards for normal cells or individual or other type, origin or grade of cancer.

The present invention provides one or more compartmentalized kits for detection of a polynucleotide and/or polypeptide for the diagnosis or prognosis of ovarian cancer. A first kit may have a receptacle containing at least one isolated NSEQ or probe comprising NSEQ. Such a probe may bind to a nucleic acid fragment which is present/absent in normal cells but which is absent/present in affected or diseased cells. Such a probe may be specific for a nucleic acid site that is normally active/inactive but which may be inactive/active in certain cell types. Similarly, such a probe may be specific for a nucleic acid site that may be abnormally expressed in certain cell types. Finally, such a probe may identify a specific mutation. The probe may be capable of hybridizing to the nucleic acid sequence which is mutated (not identical to the normal nucleic acid sequence), or may be capable of hybridizing to nucleic acid sequences adjacent to the mutated nucleic acid sequences. The probes provided in the present kits may have a covalently attached reporter molecule. Probes and reporter molecules may be readily prepared as described above by those of skill in the art.

Antibodies (e.g., isolated antibody) that may specifically bind to a protein or polypeptide described herein (a PSEQ) as well as nucleic acids encoding such antibodies are also encompassed by the present invention.

As used herein the term "antibody" means a monoclonal antibody, a polyclonal antibody, a single chain antibody, a chimeric antibody, a humanized antibody, a deimmunized antibody, an antigen-binding fragment, an Fab fragment; an $F(ab')_2$ fragment, and Fv fragment; CDRs, or a single-chain antibody comprising an antigen-binding fragment (e.g., a single chain Fv).

The antibody may originate for example, from a mouse, rat or any other mammal or from other sources such as through recombinant DNA technologies.

The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

The antibody of the present invention may be mutated and selected based on an increased affinity, solubility, stability, specificity and/or for one of a polypeptide described herein and/or based on a reduced immunogenicity in a desired host or for other desirable characteristics.

Suitable antibodies may bind to unique antigenic regions or epitopes in the polypeptides, or a portion thereof. Epitopes and antigenic regions useful for generating antibodies may be found within the proteins, polypeptides or peptides by procedures available to one of skill in the art. For example, short, unique peptide sequences may be identified in the proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the proteins and polypeptides. These surface epitopes are more readily detected in samples tested for the presence of the proteins and polypeptides. Such antibodies may include, but are not limited to, polyclonal, monoclonal, chimeric, and single chain antibodies, Fab fragments, and fragments produced by a Fab expression library. The production of antibodies is well known to one of skill in the art and is not intended to be limited herein.

Peptides may be made by any procedure known to one of skill in the art, for example, by using in vitro translation or chemical synthesis procedures or by introducing a suitable expression vector into cells. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary widely. The minimum size must be sufficient to provide an antigenic epitope that is specific to the protein or polypeptide. The maximum size is not critical unless it is desired to obtain antibodies to one particular epitope. For example, a large polypeptide may comprise multiple epitopes, one epitope being particularly useful and a second epitope being immunodominant, etc. Typically, antigenic peptides selected from the present proteins and polypeptides will range without limitation, from 5 to about 100 amino acids in length. More typically, however, such an antigenic peptide will be a maximum of about 50 amino acids in length, and preferably a maximum of about 30 amino acids. It is usually desirable to select a sequence of about 6, 8, 10, 12 or 15 amino acids, up to about 20 or 25 amino acids (and any number therebetween).

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

As mentioned herein, antigenic polypeptides and peptides are useful for the production of monoclonal and polyclonal antibodies. Antibodies to a polypeptide encoded by the polynucleotides of NSEQ, polypeptide analogs or portions thereof, may be generated using methods that are well known in the art. For example, monoclonal antibodies may be prepared using any technique that provides for the production of antibody molecules by continuous cell lines in culture. These include, but are not limited to, the hybridoma, the human B-cell hybridoma, and the EBV-hybridoma techniques. In addition, techniques developed for the production of chimeric antibodies may be used. Alternatively, techniques described for the production of single chain antibodies may be employed. Fabs that may contain specific binding sites for a polypeptide encoded by the polynucleotides of NSEQ, or a portion thereof, may also be generated. Various immunoassays may be used to identify antibodies having the desired specificity. Numerous protocols for competitive binding or immunoradiometric assays using either polyclonal or monoclonal antibodies with established specificities are well known in the art.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (MAbs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of MAbs from mRNA extracted from bone marrow and spleen cells of immunized animals using combinatorial antibody library technology.

One drawback of MAbs derived from animals or from derived cell lines is that although they may be administered to a patient for diagnostic or therapeutic purposes, to they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Chimeric antibodies may be constructed in which regions of a non-human MAb are replaced by their human counterparts. A preferred chimeric antibody is one that has amino acid sequences that comprise one or more complementarity determining regions (CDRs) of a non-human Mab that binds to a polypeptide encoded by the polynucleotides of NSEQ, or a portion thereof, grafted to human framework (FW) regions. Methods for producing such antibodies are well known in the art. Amino acid residues corresponding to CDRs and FWs are known to one of average skill in the art.

A variety of methods have been developed to preserve or to enhance affinity for antigen of antibodies comprising grafted CDRs. One way is to include in the chimeric antibody the foreign framework residues that influence the conformation of the CDR regions. A second way is to graft the foreign CDRs onto human variable domains with the closest homology to the foreign variable region. Thus, grafting of one or more non-human CDRs onto a human antibody may also involve the substitution of amino acid residues which are adjacent to a particular CDR sequence or which are not contiguous with the CDR sequence but which are packed against the CDR in the overall antibody variable domain structure and which affect the conformation of the CDR. Humanized antibodies of the invention therefore include human antibodies which comprise one or more non-human CDRs as well as such antibodies in which additional substitutions or replacements have been made to preserve or enhance binding characteristics.

Chimeric antibodies of the invention also include antibodies that have been humanized by replacing surface-exposed residues to make the MAb appear human. Because the internal packing of amino acid residues in the vicinity of the antigen-binding site remains unchanged, affinity is preserved. Substitution of surface-exposed residues of a polypeptide encoded by the polynucleotides of NSEQ (or a portion thereof)-antibody according to the invention for the purpose of humanization does not mean substitution of CDR residues or adjacent residues that influence affinity for a polypeptide encoded by the polynucleotides of NSEQ, or a portion thereof.

Chimeric antibodies may also include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Antibodies of the invention include human antibodies that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide encoded by the polynucleotides of NSEQ, or a portion thereof. Preferred variable domain combinations may also be characterized by high specificity for a polypeptide encoded by the polynucleotides of NSEQ, or a portion thereof, and little cross-reactivity to other related antigens. By screening from very large repertoires of antibody fragments, $(2\text{-}10 \times 10^{10})$ a good diversity of high affinity Mabs may be isolated, with many expected to have sub-nanomolar affinities for a polypeptide encoded by the polynucleotides of NSEQ, or a portion thereof.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific Mabs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of *E. coli*. These methods of mutagenesis are illustrative of the many methods known to one of skill in the art.

The antibody may further comprise a detectable label (reporter molecule) attached thereto.

There is provided also methods of producing antibodies able to specifically bind to one of a polypeptide, polypeptide fragments, or polypeptide analogs described herein, the method may comprise:
 a) immunizing a mammal (e.g., mouse, a transgenic mammal capable of producing human Ig, etc.) with a suitable amount of a PSEQ described herein including, for example, a polypeptide fragment comprising at least 6 (e.g., 8, 10, 12 etc.) consecutive amino acids of a PSEQ;
 b) collecting the serum from the mammal; and
 c) isolating the polypeptide-specific antibodies from the serum of the mammal.

The method may further comprise the step of administering a second dose to the mammal (e.g., animal).

Methods of producing a hybridoma which secretes an antibody that specifically binds to a polypeptide are also encompassed herewith and are known in the art.

The method may comprise:
 a) immunizing a mammal (e.g., mouse, a transgenic mammal capable of producing human Ig, etc.) with a suitable amount of a PSEQ thereof;
 b) obtaining lymphoid cells from the immunized animal obtained from (a);
 c) fusing the lymphoid cells with an immortalizing cell to produce hybrid cells; and
 d) selecting hybrid cells which produce antibody that specifically binds to a PSEQ thereof.

Also encompassed by the present invention is a method of producing an antibody that specifically binds to one of the polypeptide described herein, the method may comprise:
a) synthesizing a library of antibodies (e.g., antigen binding fragment) on phage or ribosomes;
b) panning the library against a sample by bringing the phage or ribosomes into contact with a composition comprising a polypeptide or polypeptide fragment described herein;
c) isolating phage which binds to the polypeptide or polypeptide fragment, and;
d) obtaining an antibody from the phage or ribosomes.

The antibody of the present invention may thus be obtained, for example, from a library (e.g., bacteriophage library) which may be prepared, for example, by
a) extracting cells which are responsible for production of antibodies from a host mammal;
b) isolating RNA from the cells of (a);
c) reverse transcribing mRNA to produce cDNA;
d) amplifying the cDNA using a (antibody-specific) primer; and
e) inserting the cDNA of (d) into a phage display vector or ribosome display cassette such that antibodies are expressed on the phage or ribosomes.

In order to generate antibodies, the host animal may be immunized with polypeptide and/or a polypeptide fragment and/or analog described herein to induce an immune response prior to extracting the cells which are responsible for production of antibodies.

The antibodies obtained by the means described herein may be useful for detecting proteins, variant and derivative polypeptides in specific tissues or in body fluids. Moreover, detection of aberrantly expressed proteins or protein fragments is probative of a disease state. For example, expression of the present polypeptides encoded by the polynucleotides of NSEQ, or a portion thereof, may indicate that the protein is being expressed at an inappropriate rate or at an inappropriate developmental stage. Hence, the present antibodies may be useful for detecting diseases associated with protein expression from NSEQs disclosed herein.

For in vivo detection purposes, antibodies may be those which preferably recognize an epitope present at the surface of a tumor cell.

A variety of protocols for measuring polypeptides, including ELISAs, RIAs, and FACS, are well known in the art and provide a basis for diagnosing altered or abnormal levels of expression. Standard values for polypeptide expression are established by combining samples taken from healthy subjects, preferably human, with antibody to the polypeptide under conditions for complex formation. The amount of complex formation may be quantified by various methods, such as photometric means. Quantities of polypeptide expressed in disease samples may be compared with standard values. Deviation between standard and subject values may establish the to parameters for diagnosing or monitoring disease.

Design of immunoassays is subject to a great deal of variation and a variety of these are known in the art. Immunoassays may use a monoclonal or polyclonal antibody reagent that is directed against one epitope of the antigen being assayed. Alternatively, a combination of monoclonal or polyclonal antibodies may be used which are directed against more than one epitope. Protocols may be based, for example, upon competition where one may use competitive drug screening assays in which neutralizing antibodies capable of binding a polypeptide encoded by the polynucleotides of NSEQ, or a portion thereof, specifically compete with a test compound for binding the polypeptide. Alternatively one may use, direct antigen-antibody reactions or sandwich type assays and protocols may, for example, make use of solid supports or immunoprecipitation. Furthermore, antibodies may be labelled with a reporter molecule for easy detection. Assays that amplify the signal from a bound reagent are also known. Examples include immunoassays that utilize avidin and biotin, or which utilize enzyme-labelled antibody or antigen conjugates, such as ELISA assays.

Kits suitable for immunodiagnosis and containing the appropriate labelled reagents include antibodies directed against the polypeptide protein epitopes or antigenic regions, packaged appropriately with the remaining reagents and materials required for the conduct of the assay, as well as a suitable set of assay instructions.

The present invention therefore provides a kit for specifically detecting a polypeptide described herein, the kit may comprise, for example, an antibody or antibody fragment capable of binding specifically to the polypeptide described herein.

In accordance with the present invention, the kit may be a diagnostic kit, which may comprise:
a) one or more antibodies described herein; and
b) a detection reagent which may comprise a reporter group.

In accordance with the present invention, the antibodies may be immobilized on a solid support. The detection reagent may comprise, for example, an anti-immunoglobulin, protein G, protein A or lectin etc. The reporter group may be selected, without limitation, from the group consisting of radioisotopes, fluorescent groups, luminescent groups, enzymes, biotin and dye particles Use of NSEQ, PSEQ as a Therapeutic or Therapeutic Targets One of skill in the art will readily appreciate that the NSEQ, PSEQ, expression systems, assays, kits and array discussed above may also be used to evaluate the efficacy of a particular therapeutic treatment regimen, in animal studies, in clinical trials, or to monitor the treatment of an individual subject. Once the presence of disease is established and a treatment protocol is initiated, hybridization or amplification assays may be repeated on a regular basis to determine if the level of mRNA or protein in the patient (patient's blood, tissue, cell etc.) begins to approximate the level observed in a healthy subject. The results obtained from successive assays may be used to show the efficacy of treatment over a period ranging from several days to many years.

In yet another aspect of the invention, NSEQ may be used therapeutically for the purpose of expressing mRNA and polypeptide, or conversely to block transcription and/or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art may be used to construct vectors to express nucleic acid sequences or their complements.

Alternatively, NSEQ may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods that are well known in the art. Additionally, endogenous NSEQ expression may be inactivated using homologous recombination methods that insert an inactive gene sequence into the coding region or other targeted region of NSEQ.

Depending on the specific goal to be achieved, vectors containing NSEQ may be introduced into a cell or tissue to express a missing polypeptide or to replace a non-functional polypeptide. Of course, when one wishes to express PSEQ in a cell or tissue, one may use a NSEQ able to encode such PSEQ for that purpose or may directly administer PSEQ to that cell or tissue.

On the other hand, when one wishes to attenuate or inhibit the expression of PSEQ, one may use a NSEQ (e.g., an inhibitory NSEQ) which is substantially complementary to at least a portion of a NSEQ able to encode such PSEQ.

The expression of an inhibitory NSEQ may be done by cloning the inhibitory NSEQ into a vector and introducing the vector into a cell to down-regulate the expression of a polypeptide encoded by the target NSEQ. Complementary or anti-sense sequences may also comprise an oligonucleotide derived from the transcription initiation site; nucleotides between about positions −10 and +10 from the ATG may be used. Therefore, inhibitory NSEQ may encompass a portion which is substantially complementary to a desired nucleic acid molecule to be inhibited and a portion (sequence) which binds to an untranslated portion of the nucleic acid.

Similarly, inhibition may be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. 1994)

Ribozymes, enzymatic RNA molecules, may also be used to catalyze the cleavage of mRNA and decrease the levels of particular mRNAs, such as those comprising the polynucleotide sequences of the invention. Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

Pharmaceutical compositions are also encompassed by the present invention. The pharmaceutical composition may comprise at least one NSEQ or PSEQ and a pharmaceutically acceptable carrier.

As it will be appreciated form those of skill in the art, the specificity of expression NSEQ and/or PSEQ in tumor cells may advantageously be used for inducing an immune response (through their administration) in an individual having, or suspected of having a tumor expressing such sequence. Administration of NSEQ and/or PSEQ in individuals at risk of developing a tumor expressing such sequence is also encompassed herewith.

In addition to the active ingredients, a pharmaceutical composition may contain pharmaceutically acceptable carriers comprising excipients and auxiliaries that facilitate processing of the active compounds into preparations that may be used pharmaceutically.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Use of NSEQ in General Research

The invention also provides products, compositions, processes and methods that utilize a NSEQ described herein, a polypeptide encoded by a NSEQ described herein, a PSEQ described herein for research, biological, clinical and therapeutic purposes. For example, to identify splice variants, mutations, and polymorphisms and to generate diagnostic and prognostic tools.

NSEQ may be extended utilizing a partial nucleotide sequence and employing various PCR-based methods known in the art to detect upstream sequences such as promoters and other regulatory elements. Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence.

The polynucleotides (NSEQ) may also be used as targets in a microarray. The microarray may be used to monitor the expression patterns of large numbers of genes simultaneously and to identify splice variants, mutations, and polymorphisms. Information derived from analyses of the expression patterns may be used to determine gene function, to identify a particular cell, cell type or tissue, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genomic level.

The polynucleotides (NSEQ) may also be used to generate hybridization probes useful in mapping the naturally occurring genomic sequence. Fluorescent in situ hybridization (FISH) may be correlated with other physical chromosome mapping techniques and genetic map data.

It is to be understood herein that a sequence which is upregulated in an ovarian cancer cell (e.g., malignant ovarian cancer cell) may represent a sequence which is involved in or responsible for the growth, development, maligancy and so on, of the cancer cell (referred herein as a positive regulator of ovarian cancer). It is also to be understood that a sequence which is downregulated (unexpressed or expressed at low levels) in a malignant ovarian cancer cell may represent a sequence which is responsible for the maintenance of the normal status (untransformed) of an ovarian cell (referred herein as a negative regulator of ovarian cancer). Therefore, both the presence or absence of some sequences may be indicative of the disease or may be indicative of the disease, probability of having a disease, degree of severity of the disease (staging).

Therefore, the present invention relates in an aspect thereof to an isolated polynucleotide (e.g., exogenous form of) which may comprise a member selected from the group consisting of;
a) a polynucleotide which may comprise or consist of any one of SEQ ID NO.:1 to SEQ ID NO.49 and SEQ ID NO.169,
b) a polynucleotide which may comprise the open reading frame of any one of SEQ ID NO.:1 to SEQ ID NO.49 and SEQ ID NO.169,
c) a polynucleotide which may comprise a transcribed or transcribable portion of any one of SEQ. ID. NOs:1 to 49 and 169, which may be, for example, free of untranslated or untranslatable portion(s),
d) a polynucleotide which may comprise a translated or translatable portion of any one of SEQ. ID. NOs:1 to 49 and 169 (e.g., coding portion),
e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b), c), or d);
f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c), or d) and;
g) a fragment of any one of a) to f)
including polynucleotides which consist in the above.

More specifically, the present invention relates to expressed polynucleotides which are selected from the group consisting of;
a) a polynucleotide which may comprise or consist of any one of SEQ ID NO.: 1, SEQ ID NO.:14, SEQ ID NO.:16, SEQ ID NO.:19, SEQ ID NO.:20, SEQ ID NO.:22, SEQ ID NO.:28, SEQ ID NO.:37, SEQ ID NO.:41, SEQ ID NO.:45, SEQ ID NO.:46, SEQ ID NO.:47 and SEQ ID NO.:49 and even more specifically those which are selected from the group consisting of SEQ ID NO.: 14, SEQ ID NO.:19, SEQ ID NO.: 22, SEQ ID NO.:37, SEQ ID NO.:41, SEQ ID NO.:45, SEQ ID NO.:46 and SEQ ID NO.:49,
b) a polynucleotide which may comprise the open reading frame of any one of SEQ ID NO.: 1, SEQ ID NO.:14, SEQ ID NO.:16, SEQ ID NO.:19, SEQ ID NO.:20, SEQ ID NO.:22, SEQ ID NO.:28, SEQ ID NO.:37, SEQ ID NO.:41, SEQ ID NO.:45, SEQ ID NO.:46, SEQ ID NO.:47 and SEQ ID NO.:49 and even more specifically those which are selected from the group consisting of SEQ ID NO.: 14, SEQ ID NO.:19, SEQ ID NO.: 22, SEQ ID NO.:37, SEQ ID NO.:41, SEQ ID NO.:45, SEQ ID NO.:46 and SEQ ID NO.:49,
c) a polynucleotide which may comprise a transcribed or transcribable portion of any one of SEQ ID NO.: 1, SEQ ID NO.:14, SEQ ID NO.:16, SEQ ID NO.:19, SEQ ID NO.:20, SEQ ID NO.:22, SEQ ID NO.:28, SEQ ID NO.:37, SEQ ID NO.:41, SEQ ID NO.:45, SEQ ID NO.:46, SEQ ID NO.:47 and SEQ ID NO.:49 and even more specifically those which are selected from the group consisting of SEQ ID NO.: 14, SEQ ID NO.:19, SEQ ID NO.: 22, SEQ ID NO.:37, SEQ ID NO.:41, SEQ ID NO.:45, SEQ ID NO.:46 and SEQ ID NO.:49, which may be, for example, free of untranslated or untranslatable portion(s),
d) a polynucleotide which may comprise a translated or translatable portion of any one of SEQ ID NO.: 1, SEQ ID NO.:14, SEQ ID NO.:16, SEQ ID NO.:19, SEQ ID NO.:20, SEQ ID NO.:22, SEQ ID NO.:28, SEQ ID NO.:37, SEQ ID NO.:41, SEQ ID NO.:45, SEQ ID NO:46, SEQ ID NO.:47 and SEQ ID NO.:49 and even more specifically those which are selected from the group consisting of SEQ ID NO.: 14, SEQ ID NO.:19, SEQ ID NO.: 22, SEQ ID NO.:37, SEQ ID NO.:41, SEQ ID NO.:45, SEQ ID NO.:46 and SEQ ID NO.:49, (e.g., coding portion),
e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b), c), or d);
f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c), or d) and;
g) a fragment of any one of a) to f)
including polynucleotides which consist in the above.

Vectors (e.g., a viral vector, a mammalian vector, a plasmid, a cosmid, etc.) which may comprise the polynucleotides described herein are also encompassed by the present invention. The vector may be, for example, an expression vector.

The present invention also provides a library of polynucleotide comprising at least one polynucleotide (e.g., at least two, etc.) described herein (may include SEQ ID NO.:50). The library may be, for example, an expression library. Some or all of the polynucleotides described herein may be contained within an expression vector. The present invention also relates to a polypeptide library which may comprise at least one (e.g., at least two, etc.) polypeptide as described herein.

In another aspect, the present invention provides arrays which may comprise at least one polynucleotide (e.g., at least two, etc.) described herein.

The present invention also provides an isolated cell (e.g., an isolated live cell such as an isolated mammalian cell, a bacterial cell, a yeast cell, an insect cell, etc.) which may comprise the polynucleotide, the vector or the polypeptide described herein.

In yet a further aspect the present invention relates to a composition comprising the polynucleotide and/or polypeptide described herein.

In accordance with the present invention, the composition may be, for example, a pharmaceutical composition which may comprise a polynucleotide and/or a polypeptide described herein and a pharmaceutically acceptable carrier. More specifically, the pharmaceutical composition may be used for the treatment of ovarian cancer and/or for inhibiting the growth of an ovarian cancer cell.

Polynucleotides fragments of those listed above includes polynucleotides comprising at least 10 nucleic acids which may be identical to a corresponding portion of any one of a) to e) and more particularly a coding portion of any one of SEQ ID NO.:1 to 49, 50 or 169.

Another examplary embodiment of polynucleotide fragments encompassed by the present invention includes polynucleotides comprising at least 10 nucleic acids which may be substantially complementary to a corresponding portion of a coding portion of any one of SEQ ID NO.:1 to 49, 50 or 169 and encompasses, for example, fragments selected from the group consisting of any one of SEQ ID NO.: 103 to 150.

These above sequences may represent powerful markers of cancer and more particularly of, ovarian cancer, breast cancer, prostate cancer, leukemia, melanoma, renal cancer, colon cancer, lung cancer, cancer of the central nervous system and any combination thereof.

Based on the results presented herein and upon reading the present description, a person skilled in the art will understand that the appearance of a positive signal upon testing (hybridization, PCR amplification etc.) for the presence of a given sequence amongst those expressed in a cancer cell, indicates that such sequence is specifically expressed in that type of cancer cell. A person skilled in the art will also understand that, sequences which are specifically expressed in a certain types of cancer cell may be used for developing tools for the detection of this specific type of cancer cell and may also be used as targets in the development of anticancer drugs.

A positive signal may be in the form of a band in a gel following electrophoresis, Northern blot or Western blot, a PCR fragment detected by emission of fluorescence, etc.

As it will be understood, sequences which are particularly useful for the development of tools for the detection of cancer cell may preferably be expressed at lower levels in at least some normal cells (non-cancerous cells). For example, in FIG. 57 and related description, the appearance of a band upon RT-PCR amplification of mRNAs obtained from ovarian cancer cells, renal cancer cells, lung cancer cells, breast cancer cells and melanoma cells indicates that SEQ ID NO.:1 is expressed in such cancer cells and that SEQ ID NO.:1 may therefore represent a valid marker and target for these types of cancer cells. Similar conclusions may be derived from the results obtained from other Figures and related description.

NSEQs chosen among those which are substantially complementary to those listed in Table 2, or to fragments of those of Table 2, may be used for the treatment of cancer.

The present invention therefore relates to a method for identifying a cancer cell. The method may comprise contacting a cell, a cell sample (cell lysate), a body fluid (blood, urine, plasma, saliva etc.) or a tissue with a reagent which may be, for example, capable of specifically binding at least one NSEQ or PSEQ described herein. The method may more particularly comprise contacting a sequence isolated or derived such cell, sample, fluid or tissue. The complex formed may be detected using methods known in the art.

In accordance with the present invention, the presence of the above mentioned complex may be indicative (a positive indication of the presence) of the presence of a cancer cell.

The present invention also relates in an additional aspect thereof to a method for the diagnosis or prognosis of cancer. The method may comprise, for example, detecting, in a cell, tissue, sample, body fluid, etc., at least one NSEQ or PSEQ described herein.

The cell, cell sample, body fluid or tissue may originate, for example, from an individual which has or is suspected of having a cancer and more particularly ovarian cancer, breast cancer, prostate cancer, leukemia, melanoma, renal cancer, colon cancer, lung cancer and/or cancer of the central nervous system Any of the above mentioned methods may further comprise comparing the level obtained with at least one reference level or value.

Detection of NSEQ may require an amplification (e.g., PCR) step in order to have sufficient material for detection purposes.

In accordance with the present invention, the polynucleotide described herein may comprise, for example, a RNA molecule, a DNA molecule, including those which are partial or complete, single-stranded or double-stranded, hybrids, modified by a group etc.

Other aspects of the present invention which are encompassed herewith comprises the use of at least one NSEQ or PSEQ described herein and derived antibodies in the manufacture of a composition for identification or detection of a cancer cell (e.g., a tumor cell) or for inhibiting or lowering the growth of cancer cell (e.g., for treatment of ovarian cancer or other cancer).

As some NSEQ and PSEQ are expressed at higher levels in malignant ovarian cancer than in LMP detection of such NSEQ or PSEQ in a sample from an individual (or in vivo) one may rule-out a low malignant potential ovarian cancer and may therefore conclude in a diagnostic of a malignant ovarian cancer. Furthermore, detection of the NSEQ or PSEQ in a cell, tissue, sample or body fluid from an individual may also be indicative of a late-stage malignant ovarian cancer. As such, therapies adapted for the treatment of a malignant ovarian cancer or a late-stage malignant ovarian cancer may be commenced.

In accordance with an embodiment of the present invention, the method may also comprise a step of qualitatively or quantitatively comparing the level (amount, presence) of at least one complex present in the test cell, test sample, test fluid or test tissue with the level of complex in a normal cell, a normal cell sample, a normal body fluid, a normal tissue or a reference value (e.g., for a non-cancerous condition).

The normal cell may be any cell which does not substantially express the desired sequence to be detected. Examples of such normal cells are included for example, in the description of the drawings section. A normal cell sample or tissue thus include, for example, a normal (non-cancerous) ovarian cell, a normal breast cell, a normal prostate cell, a normal lymphocyte, a normal skin cell, a normal renal cell, a normal colon cell, a normal lung cell and/or a normal cell of the central nervous system. For comparison purposes, a normal cell may be chosen from those of identical or similar cell type.

Of course, the presence of more than one complex may be performed in order to increase the precision of the diagnostic method. As such, at least two complexes (e.g., formed by a first reagent and a first polynucleotide and a second reagent or a second polynucleotide) or multiple complexes may be detected.

An exemplary embodiment of a reagent which may be used for detecting a NSEQ described herein is a polynucleotide which may comprise a sequence substantially complementary to the NSEQ.

A suitable reference level or value may be, for example, derived from the level of expression of a specified sequence in a low malignant potential ovarian cancer and/or from a normal cell.

It will be understood herein that a higher level of expression measured in a cancer cell, tissue or sample in comparison with a reference value or sample is a indicative of the presence of cancer in the tested individual.

For example, the higher level measured in an ovarian cell, ovarian tissue or a sample of ovarian origin compared to a reference level or value for a normal cell (normal ovarian cell or normal non-ovarian cell) may be indicative of an ovarian cancer. For comparison purpose, the presence or level of expression of a desired NSEQ or PSEQ to be detected or identified may be compared with the presence, level of expression, found in a normal cell which has been shown herein not to express the desired sequence.

Therapeutic uses and methods are also encompassed herewith.

The invention therefore provides polynucleotides which may be able to lower or inhibit the growth of an ovarian cancer cell (e.g., in a mammal or mammalian cell thereof).

The present invention therefore relates in a further aspect to the use of a polynucleotide sequence which may be selected from the group consisting of
- a) a polynucleotide which may comprise a sequence substantially complementary to any of SEQ ID NO.:1 to SEQ ID NO.49, 50 or 169
- b) a polynucleotide which may comprise a sequence substantially complementary to a transcribed or transcribable portion of any one of SEQ. ID. NOs:1 to 49, 50 or 169,
- c) a polynucleotide which may comprise a sequence substantially complementary to a translated or translatable portion of any one of SEQ. ID. NOs:1 to 49, 50 or 169, and;
- d) a fragment of any one of a) to c)

for reducing, lowering or inhibiting the growth of a cancer cell.

The polynucleotide may be selected, for example, from the group consisting of polynucleotides which may comprise a sequence of at least 10 nucleotides which is complementary to the nucleic acid sequence of any one of SEQ ID NO.: 1 to 49, 50 and 169 (to a translated portion which may be free, for example, of untranslated portions).

Of course, the present invention encompasses immunizing an individual by administering a NSEQ (e.g., in an expression vector) or a PSEQ.

The present invention also relates to a method of reducing or slowing the growth of an ovarian cancer cell in an individual in need thereof. The method may comprise administering to the individual a polynucleotide sequence which may be selected from the group consisting of
- a) a polynucleotide which may comprise a sequence substantially complementary (also including 100% complementary over a portion, e.g., a perfect match) to any of SEQ ID NO.:1 to SEQ ID NO.49 and 169 or 50,
- b) a polynucleotide which may comprise a sequence substantially complementary (also including 100% complementary over a portion, e.g., a perfect match) to a transcribed or transcribable portion of any one of SEQ. ID. NOs:1 to 49 and 169 or 50,
- c) a polynucleotide which may comprise a sequence substantially complementary (also including 100% complementary over a portion, e.g., a perfect match) to a translated or translatable portion of any one of SEQ. ID. NOs:1 to 49 and 169 or 50, and;
- d) a fragment of any one of a) to c).

The present invention therefore provides in yet another aspect thereof, a siRNA or shRNA molecule that is able to lower the expression of a nucleic acid selected from the group consisting of
- a) a polynucleotide which may comprise any one of SEQ ID NO.:1 to SEQ ID NO.:49 and SEQ ID NO.:169, or SEQ ID NO.:50,
- b) a polynucleotide which may comprise a transcribed or transcribable portion of any one of SEQ. ID. NOs:1 to 49 and 169, or SEQ ID NO.:50,
- c) a polynucleotide which may comprise a translated or translatable portion of any one of SEQ. ID. NOs:1 to 49 and 169 or SEQ ID NO.:50, and;
- d) a polynucleotide which may comprise a sequence substantially identical to a), b), or c).

Exemplary embodiment of polynucleotides are those which, for example, may be able to inhibit the growth of an ovarian cancer cell, such as, for example, a polynucleotide having or comprising a sequence selected from the group consisting of any one of SEQ ID NO. 103 to 150. These specific sequences are provided as guidance only and are not intended to limit the scope of the invention.

The present invention also provides a kit for the diagnosis of cancer. The kit may comprise at least one polynucleotide as described herein and/or a reagent capable of specifically binding at least one polynucleotide described herein.

In a further aspect, the present invention relates to an isolated polypeptide encoded by the polynucleotide described herein.

The present invention more particularly provides an isolated polypeptide which may be selected from the group consisting of
- a) a polypeptide which may comprise any one of SEQ ID NO.:51 to 88 and 170
- b) a polypeptide which may be encoded by any one of the polynucleotide described herein,
- c) a fragment of any one of a) or b),
- d) a derivative of any one of a) or b) and;
- e) an analog of any one of a) or b).

In accordance with the present invention, the analog may comprise, for example, at least one amino acid substitution, deletion or insertion in its amino acid sequence.

The substitution may be conservative or non-conservative. The polypeptide analog may be a biologically active analog or an immunogenic analog which may comprise, for example, at least one amino acid substitution (conservative or non conservative), for example, 1 to 5, 1 to 10, 1 to 15, 1 to 20, 1 to 50 etc. (including any number there between) compared to the original sequence. An immunogenic analog may comprise, for example, at least one amino acid substitution compared to the original sequence and may still be bound by an antibody specific for the original sequence.

In accordance with the present invention, a polypeptide fragment may comprise, for example, at least 6 consecutive amino acids, at least 8 consecutive amino acids or more of an amino acid sequence selected from the group consisting of polypeptides encoded by a polynucleotide selected from the group consisting of SEQ ID NO.: 1 to 49 and 169 or any one of SEQ. ID. NOs:51 to 88 and 170, including variants and analogs thereof. The fragment may be immunogenic and may be used for the purpose, for example, of generating antibodies.

Exemplary embodiments of polypeptide encompassed by the present invention are those which may be encoded by any one of SEQ ID NO.:1-49 and 169, more particularly those encoded by any one of SEQ ID NO.:1, 14, 16, 19, 20, 22, 28, 37, 41, 45, 46, 47 or 49 and even more particularly those encoded by any one of SEQ ID NO.: 14, 19, 22, 37, 41, 45, 46 or 49.

In a further aspect the present invention relates to a polypeptide which may be encoded by the isolated differentially expressed sequence of the present invention. The present invention as well relates to the polypeptide encoded by the non-human ortholog polynucleotide, analogs, derivatives and fragments thereof.

A person skilled in the art may easily determine the possible peptide sequence encoded by a particular nucleic acid sequence as generally, a maximum of 6 possible open-reading frames exist in a particular coding sequence. The first possible open-reading frame may start at the first nucleotide (5'-3') of the sequence, therefore using in a 5' to 3' direction nucleotides No. 1 to 3 as the first codon, using nucleotides 4 to 6 as the second codon, etc. The second possible open-reading frame may start at the second nucleotide (5'-3') of the sequence, therefore using in a 5' to 3' direction nucleotides No. 2 to 4 as the first codon, using nucleotides 5 to 7 as the second codon, etc. Finally, the third possible open-reading frame may start at the third nucleotide (5'-3') of the sequence, therefore using in a 5' to 3' direction nucleotides No. 3 to 5 as the first codon, using nucleotides 6 to 8 as the second codon, etc. The fourth possible open-reading frame may start at the first nucleotide of the sequence in a 3' to 5' direction, therefore using in 3' to 5' direction, nucleotides No. 1 to 3 as the first codon, using nucleotides 4 to 6 as the second codon, etc. The fifth possible open-reading frame may start at the second nucleotide of the sequence in a 3' to 5' direction, therefore using in a 3' to 5' direction, nucleotides No. 2 to 4 as the first codon, using nucleotides 5 to 7 as the second codon, etc. Finally, the sixth possible open-reading frame may start at the third nucleotide of the sequence in a 3' to 5' direction, therefore using in a 3' to 5' direction nucleotides No. 3 to 5 as the first codon, using nucleotides 6 to 8 as the second codon, etc.

In an additional aspect, the present invention relates to the use of at least one polypeptide in the manufacture of a composition for the identification or detection of a cancer cell (tumor cell). The polypeptide may be used, for example, as a standard in an assay and/or for detecting antibodies specific for the particular polypeptide, etc. In yet an additional aspect, the present invention relates to the use of at least one polypeptide described herein in the identification or detection of a cancer cell, such as for example, an ovarian cancer cell or any other cancer cell as described herein.

The present invention therefore relates in a further aspect, to the use of at least one polypeptide described herein in the prognosis or diagnosis of cancer, such as, for example, a malignant ovarian cancer or a low malignant potential ovarian cancer.

As such and in accordance with the present invention, detection of the polypeptide in a cell (e.g., ovarian cell), tissue (e.g., ovarian tissue), sample or body fluid from an individual may preferentially be indicative of a malignant ovarian cancer diagnosis over a low malignant potential ovarian cancer diagnosis and therefore may preferentially be indicative of a malignant ovarian cancer rather than a low malignant potential ovarian cancer.

Further in accordance with the present invention, the presence of the polypeptide in a cell, tissue, sample or body fluid from an individual may preferentially be indicative of a late-stage malignant ovarian cancer.

There is also provided by the present invention, methods for identifying a is cancer cell, which may comprise, for example, contacting a test cell, a test cell sample (cell lysate), a test body fluid (blood, urine, plasma, saliva etc.) or a test tissue with a reagent which may be capable of specifically binding the polypeptide described herein, and detecting the complex formed by the polypeptide and reagent. The presence of a complex may be indicative (a positive indication of the presence) of a cancer cell such as for example, an ovarian cancer cell, a breast cancer cell, a prostate cancer cell, leukemia, melanoma, a renal cancer cell, a colon cancer cell, a lung cancer cell, a cancer cell of the central nervous system and any combination thereof.

The presence of a complex formed by the polypeptide and the specific reagent may be indicative, for example, of ovarian cancer including, for example, a low malignant potential ovarian cancer or a malignant ovarian cancer.

However, the method is more particularly powerful for the detection of ovarian cancer of the malignant type. Therefore, the presence of a complex may preferentially be indicative of a malignant ovarian cancer relative (rather than) to a low malignant potential ovarian cancer.

Detection of the complex may also be indicative of a late stage malignant ovarian cancer.

In accordance with the present invention, the method may also comprise a step of qualitatively or quantitatively comparing the level (amount, presence) of at least one complex present in a test cell, a test sample, a test fluid or a test tissue with the level of complex in a normal cell, a normal cell sample, a normal body fluid, a normal tissue or a reference value (e.g., for a non-cancerous condition).

Of course, the presence of more than one polypeptide or complex (two complexes or more (multiple complexes)) may be determined, e.g., one formed by a first specific reagent and a first polypeptide and another formed by a second specific reagent and a second polypeptide may be detected. Detection of more than one polypeptide or complex may help in the determination of the tumorigenicity of the cell.

An exemplary embodiment of a reagent, which may be used for the detection of the polypeptide described herein, is an antibody and antibody fragment thereof.

The present invention also relates to a kit which may comprise at least one of the polypeptide described herein and/or a reagent capable of specifically binding to at least one of the polypeptide described herein.

As one skill in the art will understand, compositions which comprises a polypeptide may be used, for example, for generating antibodies against the particular polypeptide, may be used as a reference for assays and kits, etc.

Additional aspects of the invention relates to isolated or purified antibodies (including an antigen-binding fragment thereof) which may be capable of specifically binding to a polypeptide selected from the group consisting of;
a) a polypeptide comprising or consisting of any one of SEQ ID NO.:51 to 89 or 170, and;
b) a polypeptide comprising a polypeptide sequence encoded by any one of the polynucleotide sequence described herein (e.g., a fragment of at least 6 amino acids of the polypeptide).

More particularly, exemplary embodiments of the present invention relates to antibodies which may be capable of specifically binding a polypeptide comprising a polypeptide sequence encoded by any one of SEQ ID NO.: 1, 14, 16, 19, 20, 22, 28, 37, 41, 45, 46, 47 or 49, or a fragment of at least 6 amino acids of the polypeptide.

Even more particular exemplary embodiments of the present invention relates to antibodies which may be capable of specifically binding a polypeptide comprising a polypeptide sequence encoded by any one of SEQ ID NO.: 14, 19, 22, 37, 41, 45, 46 or 49, or a fragment of at least 6 amino acids of the polypeptide.

In yet an additional aspect, the present invention relates to a hybridoma cell which is capable of producing an antibody which may specifically bind to a polypeptide selected from the group consisting of;

a) a polypeptide which may comprise any one of SEQ ID NO.:51 to 88, 89 and 170, and;
b) a polypeptide which may comprise a polypeptide sequence encoded by any one of the polynucleotide sequence described herein or a fragment of at least 6 amino acids of the polypeptide.

Exemplary hybridoma which are more particularly encompassed by the present invention are those which may produce an antibody which may be capable of specifically binding a polypeptide comprising a polypeptide sequence encoded by any one of SEQ ID NO.: 1, 14, 16, 19, 20, 22, 28, 37, 41, 45, 46, 47 or 49 or a fragment of at least 6 amino acids of the polypeptide.

Exemplary embodiments of hybridoma which are even more particularly encompassed by the present invention are those which may produce an antibody which is capable of specifically binding a polypeptide comprising a polypeptide sequence encoded by any one of SEQ ID NO.: 14, 19, 22, 37, 41, 45, 46 or 49 or a fragment of at least 6 amino acids of the polypeptide.

The present invention also relates to a composition which may comprise an antibody described herein.

In a further aspect the present invention provides a method of making an antibody which may comprise immunizing a non-human animal with an immunogenic fragment (at least 6 amino acids, at least 8 amino acids, etc.) of a polypeptide which may be selected, for example, from the group consisting of;
a) a polypeptide which may comprise or consist in any one of SEQ ID NO.:51 to 88, 89 and 170 or a fragment thereof, and;
b) a polypeptide which may comprise a polypeptide sequence encoded by any one of the polynucleotide sequence described herein or a portion thereof.

Exemplary polypeptides which may, more particularly, be used for generating antibodies are those which are encoded by any one of SEQ ID NO.: 1, 14, 16, 19, 20, 22, 28, 37, 41, 45, 46, 47 or 49 (and polypeptide comprising a polypeptide fragment of these particular PSEQ). Even more particular polypeptides encompassed by the present invention are those which are encoded by any one of SEQ ID NO.: 14, 19, 22, 37, 41, 45, 46 or 49.

In a further aspect, the present invention relates to a method of identifying a compound which is capable of inhibiting the activity or function of a polypeptide which may be selected, for example from the group consisting of any one of SEQ ID NO.:51 to 88 and 170 or a polypeptide comprising a polypeptide sequence encoded by any one of SEQ ID NO.:1 to 49 and 169 (e.g., a transcribed portion, a translated portion, a fragment, substantially identical and even substantially complementary sequences). The method may comprise contacting the polypeptide with a putative compound an isolating or identifying a compound which is capable of specifically binding any one of the above mentioned polypeptide. The compound may originate from a combinatorial library.

The method may also further comprise determining whether the activity or function of the polypeptide (e.g., such as a function indicated at Table 2) is affected by the binding of the compound. Those compounds which capable of binding to the polypeptide and which and/or which are capable of altering the function or activity of the polypeptide represents a desirable compound to be used in cancer therapy.

The method may also further comprise a step of determining the effect of the putative compound on the growth of a cancer cell such as an ovarian cancer cell.

The present invention also relates to an assay and method for identifying a nucleic acid sequence and/or protein involved in the growth or development of ovarian cancer. The assay and method may comprise silencing an endogenous gene of a cancer cell such as an ovarian cancer cell and providing the cell with a candidate nucleic acid (or protein). A candidate gene (or protein) positively involved in inducing cancer cell death (e.g., apoptosis) (e.g., ovarian cancer cell) may be identified by its ability to complement the silenced endogenous gene. For example, a candidate nucleic acid involved in ovarian cancer provided to a cell for which an endogenous gene has been silenced, may enable the cell to undergo apoptosis more so in the presence of an inducer of apoptosis.

Alternatively, an assay or method may comprise silencing an endogenous gene (gene expression) corresponding to the candidate nucleic acid or protein sequence to be evaluated and determining the effect of the candidate nucleic acid or protein on cancer growth (e.g., ovarian cancer cell growth). A sequence involved in the promotion or inhibition of cancer growth, development or malignancy may change the viability of the cell, may change the ability of the cell to grow or to form colonies, etc. The activity of a polypeptide may be impaired by targeting such polypeptide with an antibody molecule or any other type of compound. Again, such compound may be identified by screening combinatorial libraries, phage libraries, etc.

The present invention also provides a method for identifying an inhibitory compound (inhibitor, antagonist) able to impair the function (activity) or expression of a polypeptide described herein. The method may comprise, for example, contacting the (substantially purified or isolated) polypeptide or a cell expressing the polypeptide with a candidate compound and measuring the function (activity) or expression of the polypeptide. A reduction in the function or activity of the polypeptide (compared to the absence of the candidate compound) may thus positively identify a suitable inhibitory compound.

In accordance with the present invention, the impaired function or activity may be associated, for example, with a reduced ability of the polypeptide to reduce growth of an ovarian cancer cell or a reduced enzymatic activity or function identified for example in Table 2.

The cell used to carry the screening test may not naturally (endogenously) express the polypeptide or analogs, or alternatively the expression of a naturally expressed polypeptide analog may be repressed.

As used herein the term "sequence identity" relates to (consecutive) nucleotides of a nucleotide sequence with reference to an original nucleotide sequence which when compared are the same or have a specified percentage of nucleotides which are the same.

The identity may be compared over a region or over the total sequence of a nucleic acid sequence. Thus, "identity" may be compared, for example, over a region of 10, 19, 20 nucleotides or more (and any number therebetween) and more preferably over a longer region or over the entire region of a polynucleotide sequence described at Table 4 (e.g., any one of SEQ ID NO.:1 to 49 and 169). It is to be understood herein that gaps of non-identical nucleotides may be found between identical nucleic acids regions (identical nucleotides). For example, a polynucleotide may have 100% identity with another polynucleotide over a portion thereof. However, when the entire sequence of both polynucleotides is compared, the two polynucleotides may have 50% of their overall (total) sequence identity to one another.

Percent identity may be determined, for example, with n algorithm GAP, BESTFIT, or FASTA in the Wisconsin Genetics Software Package Release 7.0, using default gap weights.

Polynucleotides of the present invention or portion thereof having from about 50 to about 100% and any range therebetween, or about 60 to about 100% or about 70 to about 100% or about 80 to about 100% or about 85% to about 100%, about 90% to about 100%, about 95% to about 100% sequence identity with an original polynucleotide are encompassed herewith. It is known by those of skill in the art, that a polynucleotide having from about 50% to 100% identity may function (e.g., anneal to a substantially complementary sequence) in a manner similar to an original polynucleotide and therefore may be used in replacement of an original polynucleotide. For example a polynucleotide (a nucleic acid sequence) may comprise or have from about 50% to about 100% identity with an original polynucleotide over a defined region and may still work as efficiently or sufficiently to achieve the present invention. The term "substantially identical" used to define the polynucleotides of the present invention refers to polynucleotides which have, for example, from 50% to 100% sequence identity and any range therebetween but preferably at least 80%, at least 85%, at least 90%, at least 95% sequence identity and also include 100% identity with that of an original sequence (including sequences 100% identical over the entire length of the polynucleotide sequence).

"Substantially identical" polynucleotide sequences may be identified by providing a probe of about 10 to about 25, or more or about 10 to about 20 nucleotides long (or longer) based on the sequence of any one of SEQ ID NOs.:1 to 49 and 169 (more particularly, a transcribed and/or translated portion of any one of SEQ ID NOs.: 1 to 49 and 169) and complementary sequence thereof and hybridizing a library of polynucleotide (e.g., cDNA or else) originating from another species, tissue, cell, individual etc. A polynucleotide which hybridizes under highly stringent conditions (e.g., 6×SCC, 65° C.) to the probe may be isolated and identified using methods known in the art. A sequence "substantially identical" includes for example, an isolated allelic variant, an isolated splice variant, an isolated non-human ortholog, a modified NSEQ etc.

As used herein the terms "sequence complementarity" refers to (consecutive) nucleotides of a nucleotide sequence which are complementary to a reference (original) nucleotide sequence. The complementarity may be compared over a region or over the total sequence of a nucleic acid sequence.

Polynucleotides of the present invention or portion thereof having from about 50 to about 100%, or about 60 to about 100% or about 70 to about 100% or about 80 to about 100% or about 85%, about 90%, about 95% to about 100% sequence complementarity with an original polynucleotide are thus encompassed herewith. It is known by those of skill in the art, that a polynucleotide having from about 50% to 100% complementarity with an original sequence may anneal to that sequence in a manner sufficient to carry out the present invention (e.g., inhibit expression of the original polynucleotide).

The term "substantially complementary" used to define the polynucleotides of the present invention refers to polynucleotides which have, for example, from 50% to 100% sequence complementarity and any range therebetween but preferably at least 80%, at least 85%, at least 90%, at least 95% sequence complementarity and also include 100% complementarity with that of an original sequence (including sequences 100% complementarity over the entire length of the polynucleotide sequence).

As used herein the term "polynucleotide" generally refers to any polyribonucleotide or polydeoxyribo-nucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "polynucleotide" embraces chemically, enzymatically or metabolically modified forms of polynucleotides as typically found or not in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred to as peptides, oligopeptides or oligomers, and to longer chains generally referred to as proteins. As described above, polypeptides may contain amino acids other than the 20 gene-encoded amino acids.

As used herein the term "polypeptide analog" or "analog" relates to mutants, chimeras, fusions, a polypeptide comprising at least one amino acid deletion, a polypeptide comprising at least one amino acid insertion or addition, a polypeptide comprising at least one amino acid substitutions, and any other type of modifications made relative to a given polypeptide.

An "analog" is thus to be understood herein as a molecule having a biological activity and/or chemical structure similar to that of a polypeptide described herein. An "analog" may have sequence similarity with that of an original sequence or a portion of an original sequence and may also have a modification of its structure as discussed herein. For example, an "analog" may have at least 80% or 85% or 90° A) sequence similarity with an original sequence or a portion of an original sequence. An "analog" may also have, for example; at least 70% or even 50% sequence similarity with an original sequence or a portion of an original sequence and may function in a suitable manner.

A "derivative" is to be understood herein as a polypeptide originating from an original sequence or from a portion of an original sequence and which may comprise one or more modification; for example, one or more modification in the amino acid sequence (e.g., an amino acid addition, deletion, insertion, substitution etc.), one or more modification in the backbone or side-chain of one or more amino acid, or an addition of a group or another molecule to one or more amino acids (side-chains or backbone). Biologically active derivatives of the carrier described herein are encompassed by the present invention. Also, an "derivative" may have, for example, at least 50%, 70%, 80%, 90% sequence similarity to an original sequence with a combination of one or more modification in a backbone or side-chain of an amino acid, or an addition of a group or another molecule, etc.

As used herein the term "biologically active" refers to an analog which retains some or all of the biological activity of the original polypeptide, i.e., to have some of the activity or function associated with the polypeptide described at Table 2, or to be able to promote or inhibit the growth ovarian cancer.

Therefore, any polypeptide having a modification compared to an original polypeptide which does not destroy significantly a desired activity, function or immunogenicity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be desirable. Polypeptides of the present invention may comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion, deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogs may be generated by substitutional mutagenesis and retain the biological activity of the polypeptides of the present invention. These analogs have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table A. If such substitutions result in a change not desired, then other type of substitutions, denominated "exemplary substitutions" in Table A, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE A

Examplary amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc. with respect to a length of "about 10 to about 25" it is to be understood as specifically incorporating each and every individual number such as for example 10, 11, 12, 13, 14, 15 up to and including 25; and similarly with respect to other parameters such as, concentrations, elements, etc. . . . .

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

In the appended drawings:

FIG. 1 to FIG. 31, FIG. 33, FIG. 34, FIG. 36, FIG. 37, FIG. 39, FIG. 40, FIG. 42, FIG. 43, FIG. 46, FIG. 47, FIG. 49, FIG. 50 and FIG. 56 are pictures of macroarray hybridization results showing the differential expression data for STAR selected ovarian cancer-related human sequences. Macroarrays were prepared using RAMP amplified RNA from six human LMP samples (A-F 1) and twenty malignant ovarian tumor samples (Table B) (A-F 2 and A-G 3-4), and 30 different normal human tissues (adrenal (A7), breast (B7), jejunum (C7), trachea (D7), liver (E7), placenta (F7), aorta (G7), brain (H7), lung (A8), adrenal cortex (B8), esophagus (C8), colon (D8), ovary (E8), kidney (F8), prostate (G8), thymus (H8), skeletal muscle (A9), vena cava (B9), stomach (C9), small intestine (D9), heart (E9), fallopian tube (F9), spleen (G9), bladder (H9), cervix (A10), pancreas (B10), ileum (C10), duodenum (D10), thyroid (E10) and testicle (F10)). Also included on the RNA macroarray were breast cancer cell lines (MDA (A5), MCF7 (B5) and MCF7+estradiol (C5)) and LCM microdissected prostate normal epithelium (A-C 6) and prostate cancer (D-F 6), prostate cancer cell line, LNCap (G6) and LNCap+androgen (H6). In these figures, the probe labeling reaction was also spiked with a dsDNA sequence for *Arabidopsis*, which hybridizes to the same sequence spotted on the macroarray (M) in order to serve as a control for the labeling reaction.

FIG. 32, FIG. 35, FIG. 38, FIG. 41, FIG. 44, FIG. 45 and FIG. 48 are pictures of RT-PCR results showing the differential expression data for STAR selected ovarian cancer-related human sequences. Complimentary DNAs were prepared using random hexamers from RAMP amplified RNA from six human LMP samples and at least twenty malignant ovarian tumor samples (Table B) as indicated in the figures. The cDNAs were quantified and used as templates for PCR with gene-specific primers using standard methods known to those skilled in the art.

FIG. 57 to FIG. 105 are pictures of RT-PCR results showing the differential expression data for STAR selected cancer-related human sequences in RNA samples derived from the NCI-60 panel of cancer cell lines. These 59 cell lines are derived from tumors that encompass 9 human cancer types that include leukemia, the central nervous system, breast, colon, lung, melanoma, ovarian, prostate, and renal. Complimentary DNAs were prepared using random hexamers from RAMP amplified RNA from 59 human cancer cell lines (Table C). The cDNAs were quantified and used as templates for PCR with gene-specific primers using standard methods known to those skilled in the art. For each PCR result depicted in FIG. 57 to FIG. 105, equal amounts of template cDNA used in each PCR reaction was confirmed by reamplifying GAPDH with a specific primer pair, OGS 315 (TGAAG-GTCGGAGTCAACGGATTTGGT; SEQ. ID. NO. 167) and OGS 316 (CATGTGGGCCATGAGGTCCACCAC; SEQ. ID. NO. 168) for this housekeeping gene.

Figure 1:
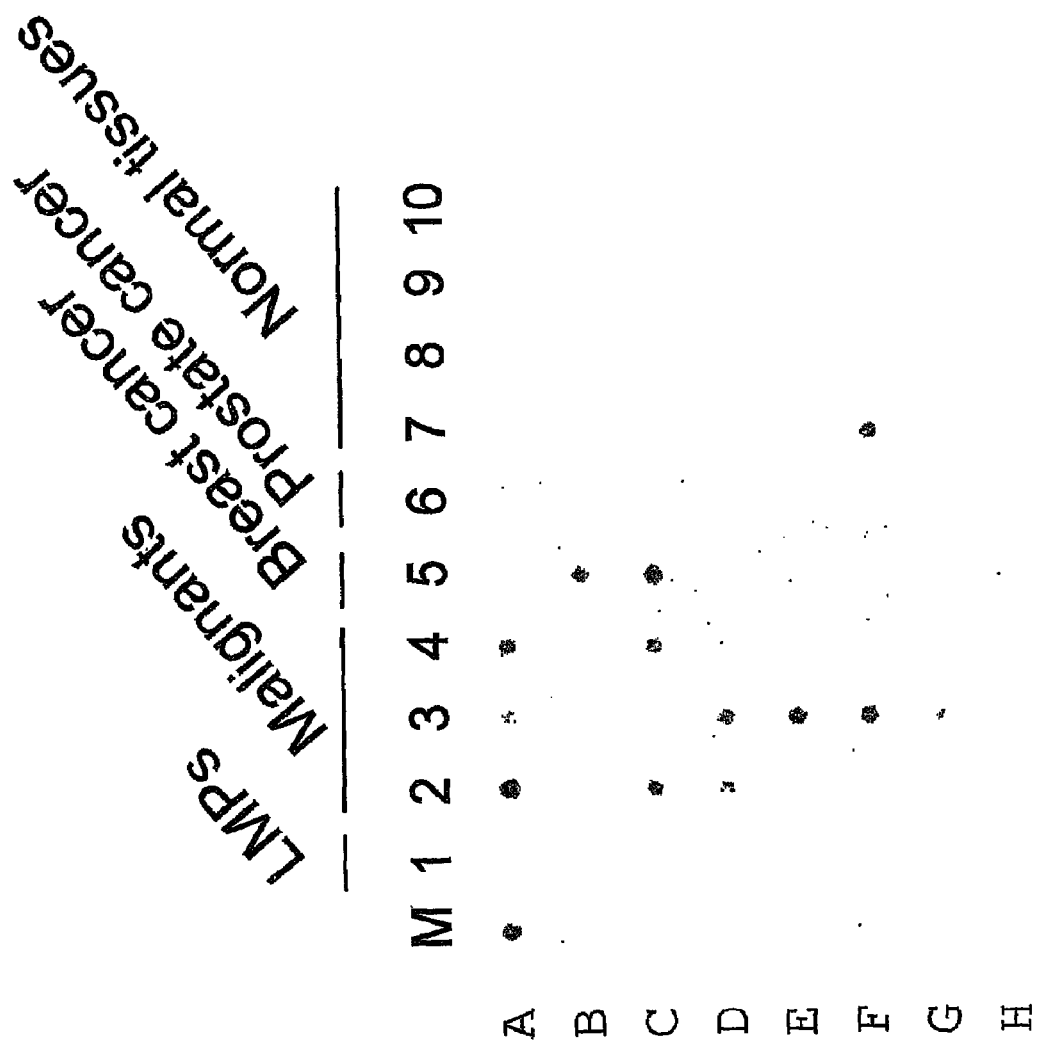
Figure 2:
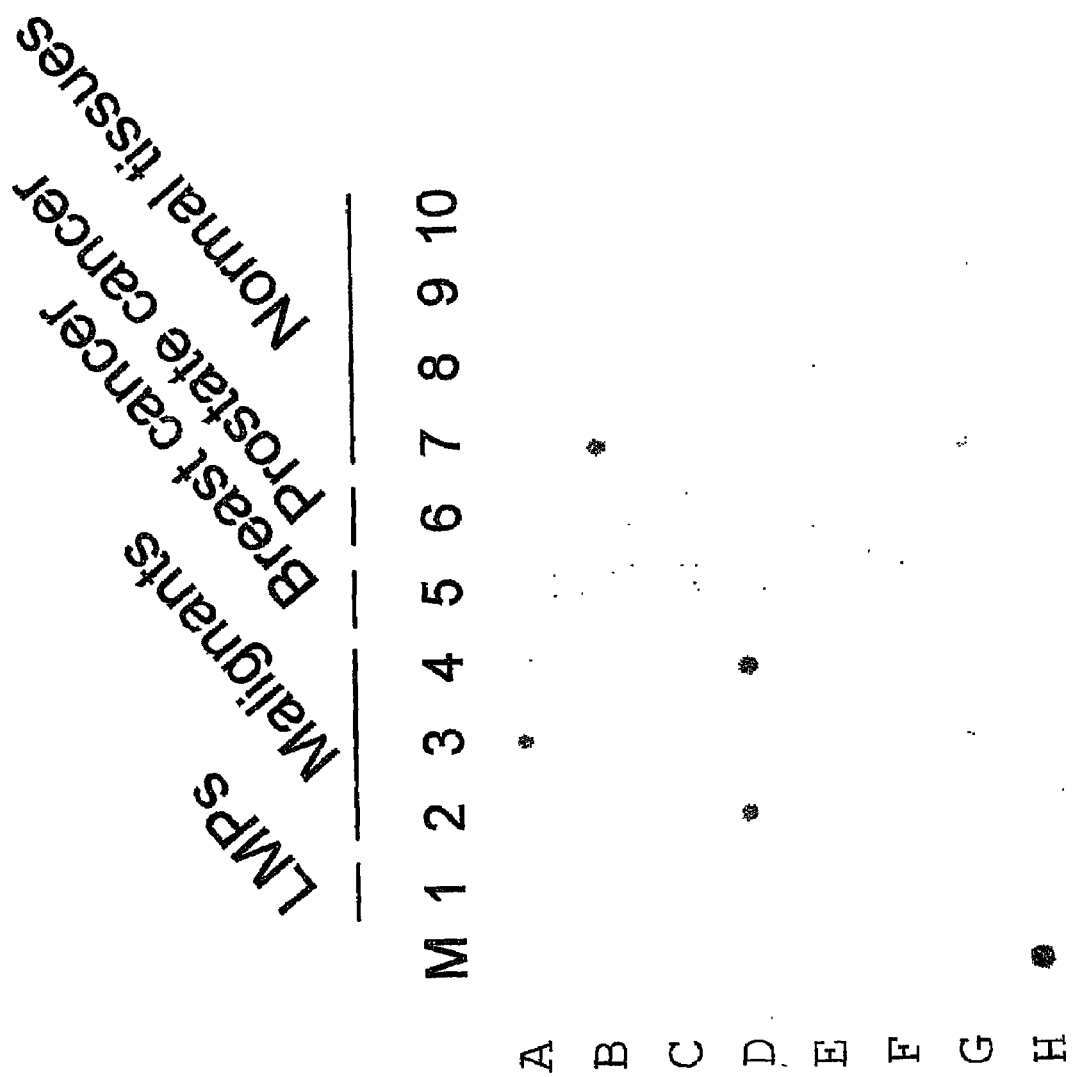
Figure 4:
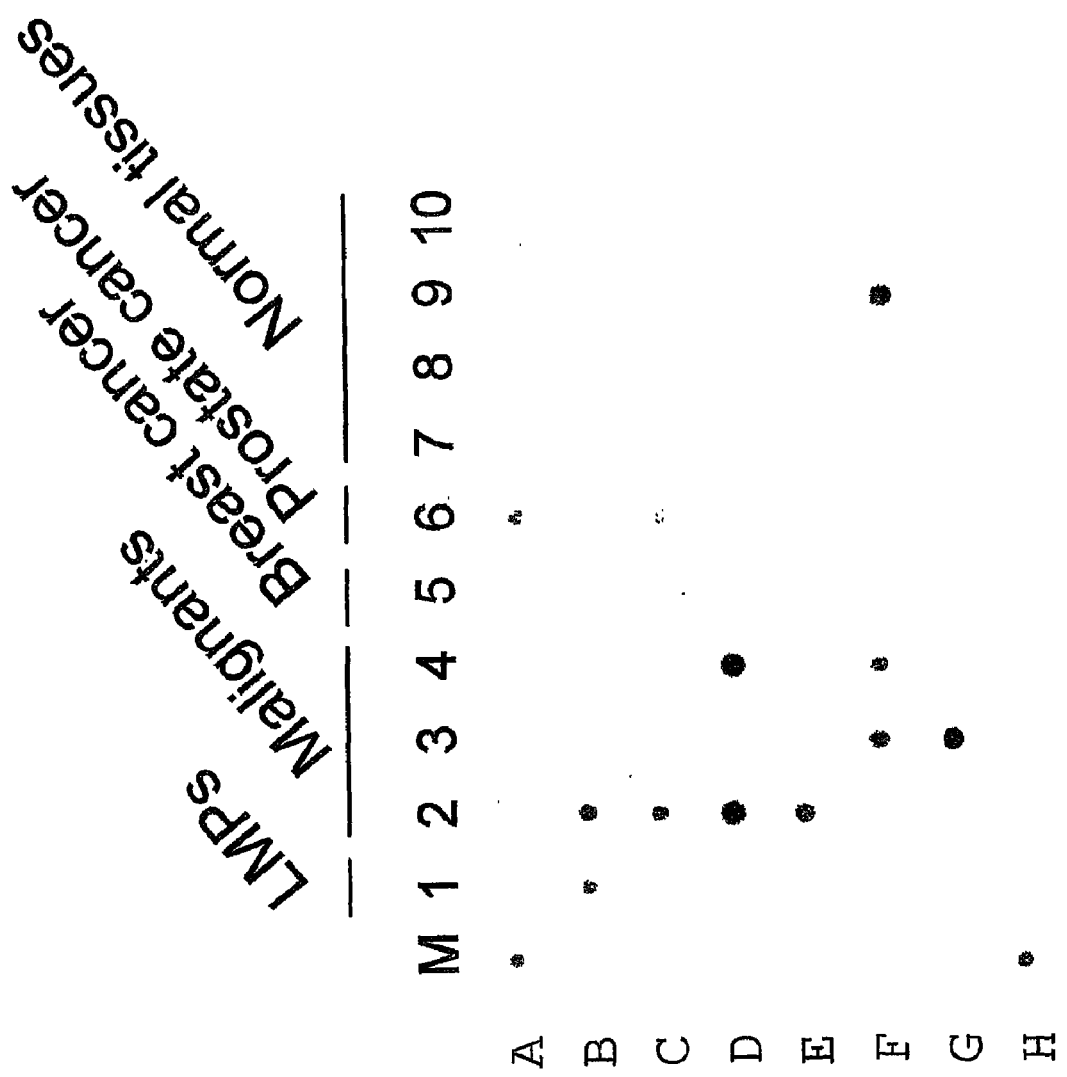
Figure 6:
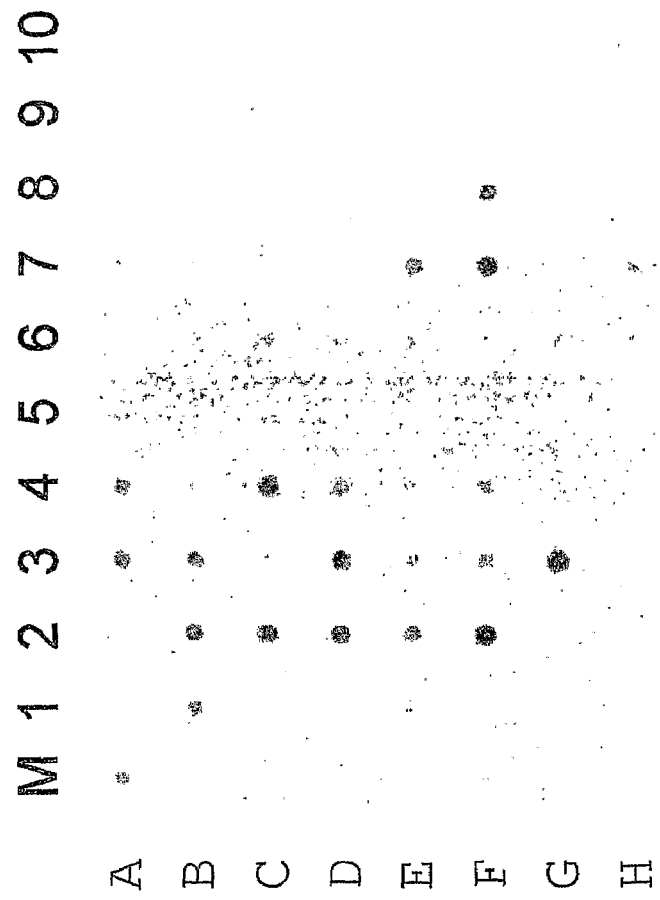
Figure 8:
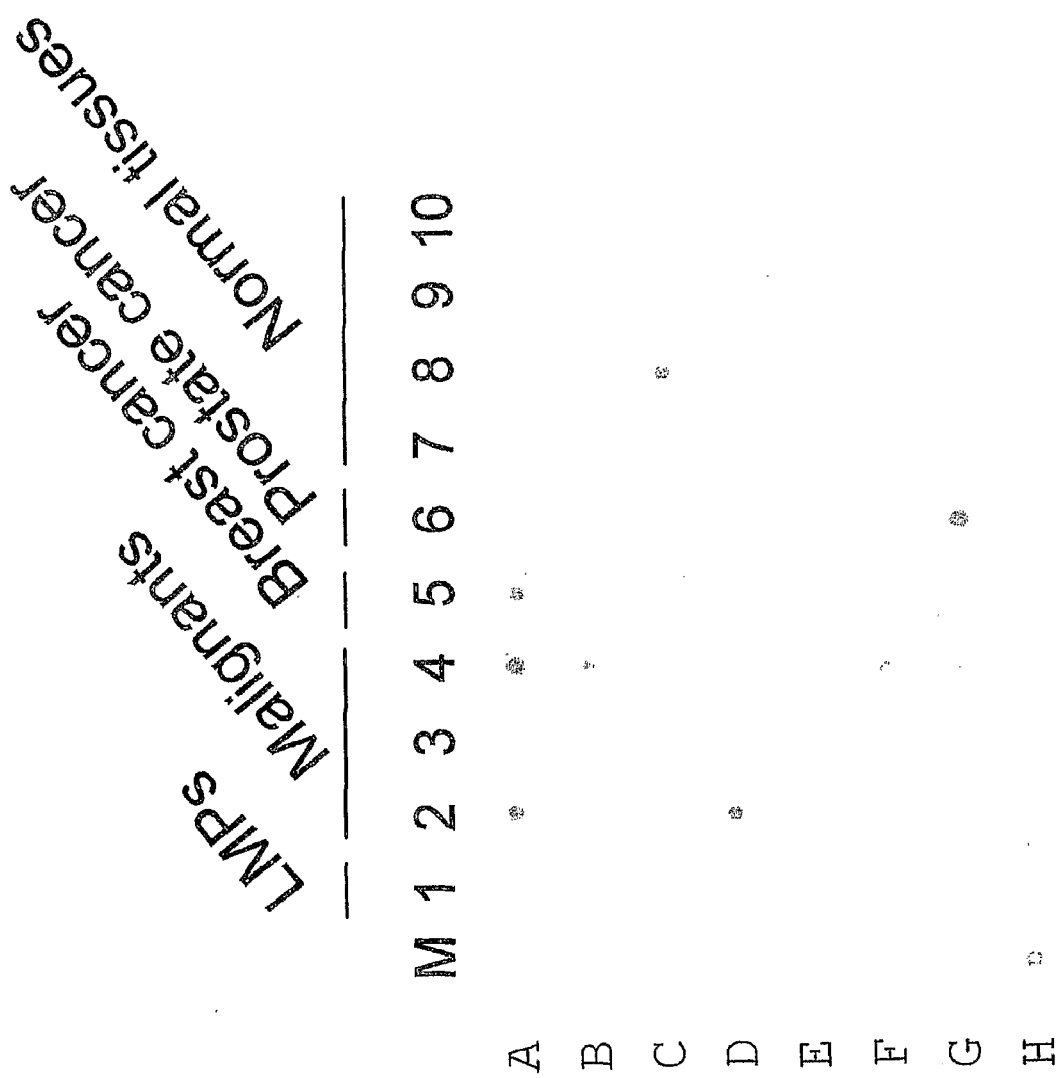
Figure 9:
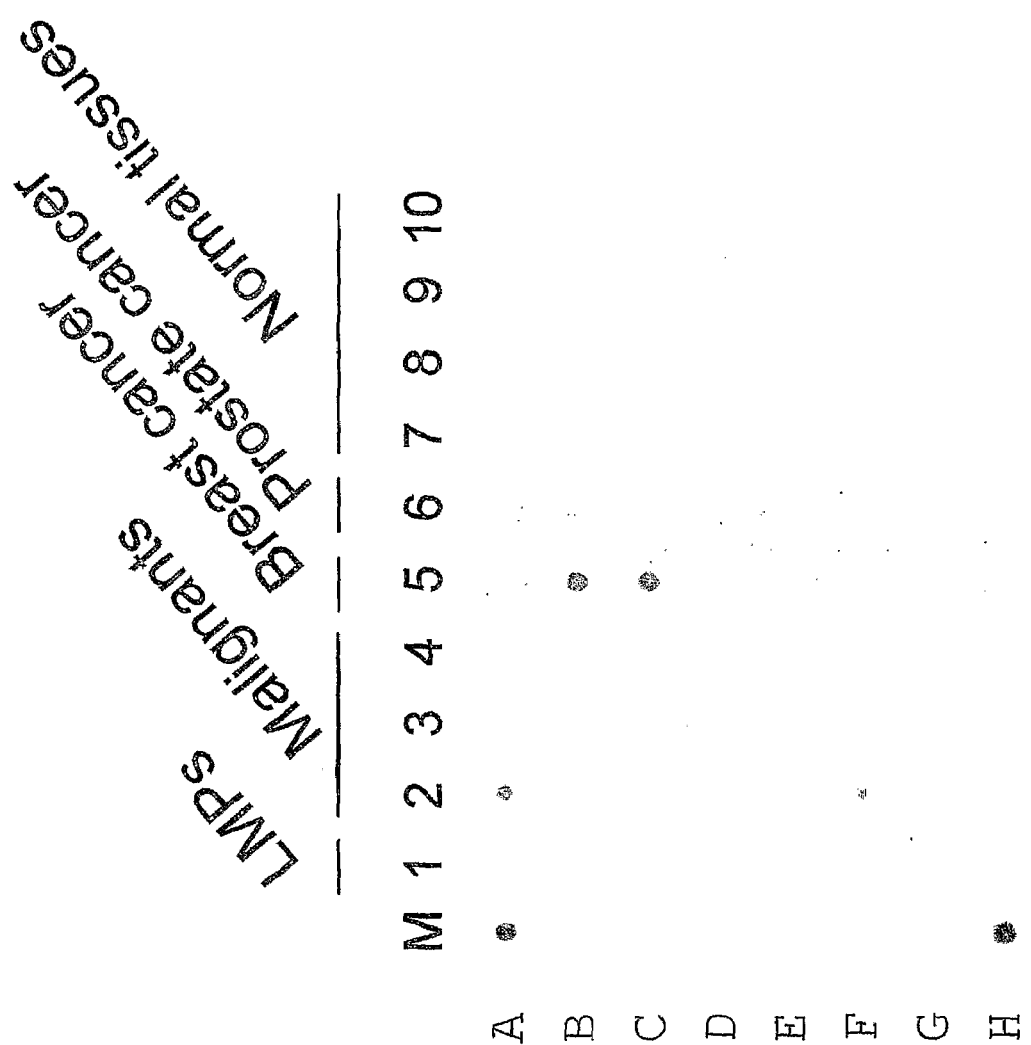
Figure 10:
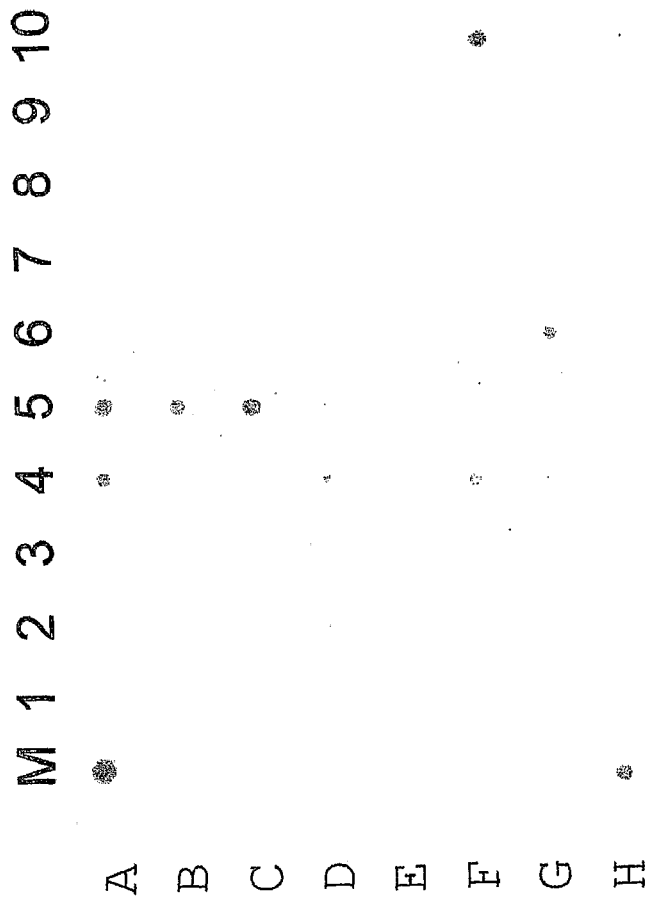
Figure 14:
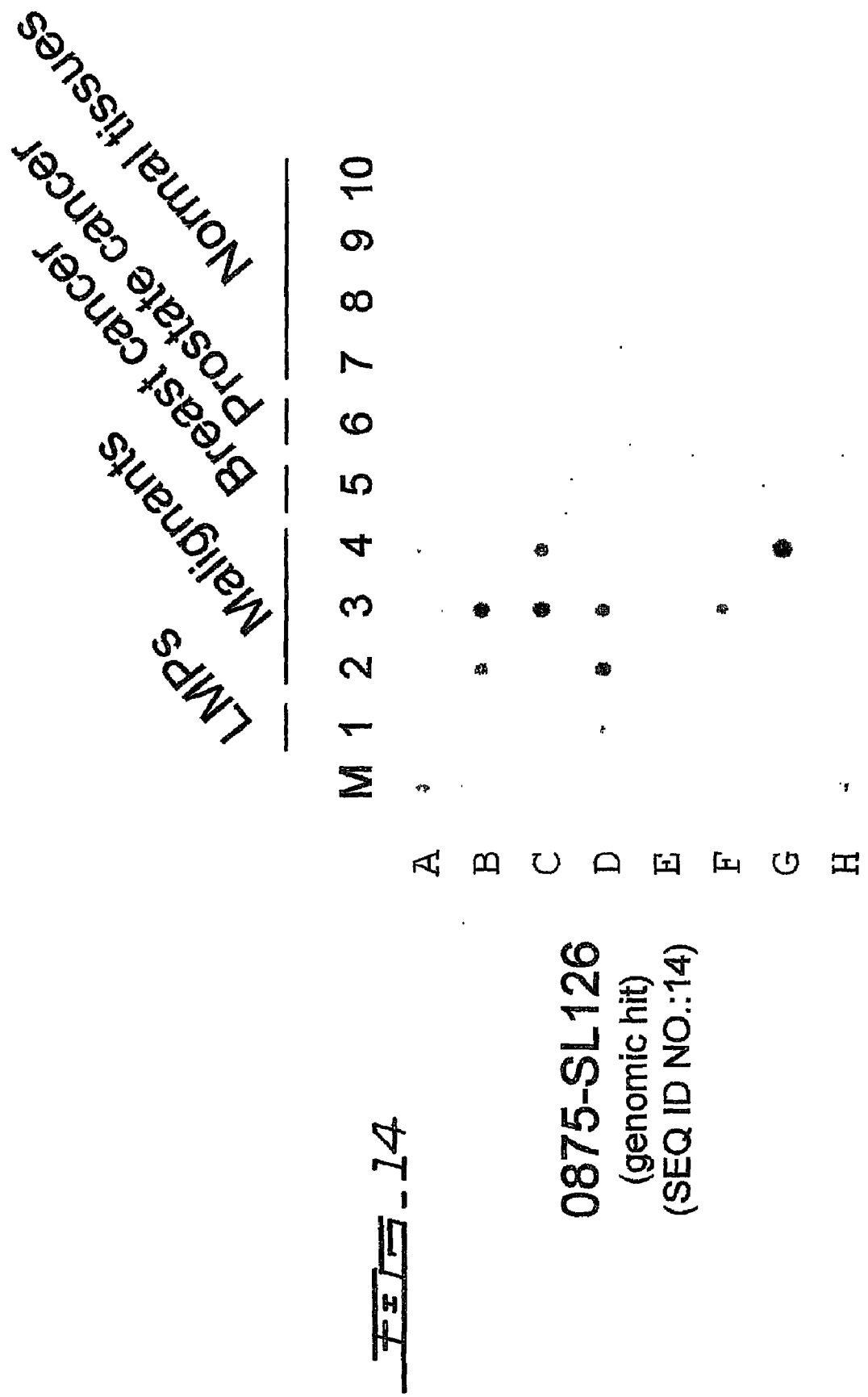
Figure 16:
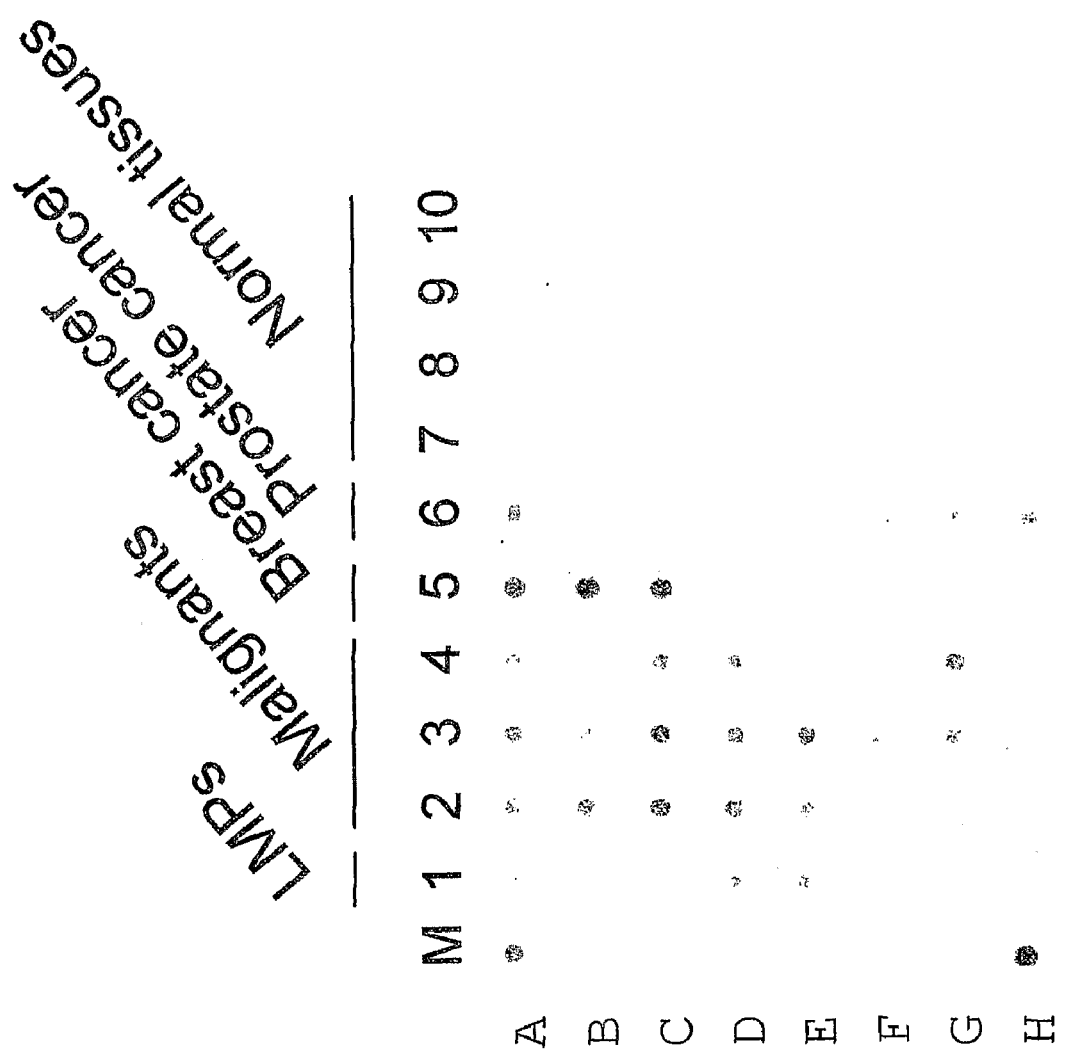
Figure 19A:
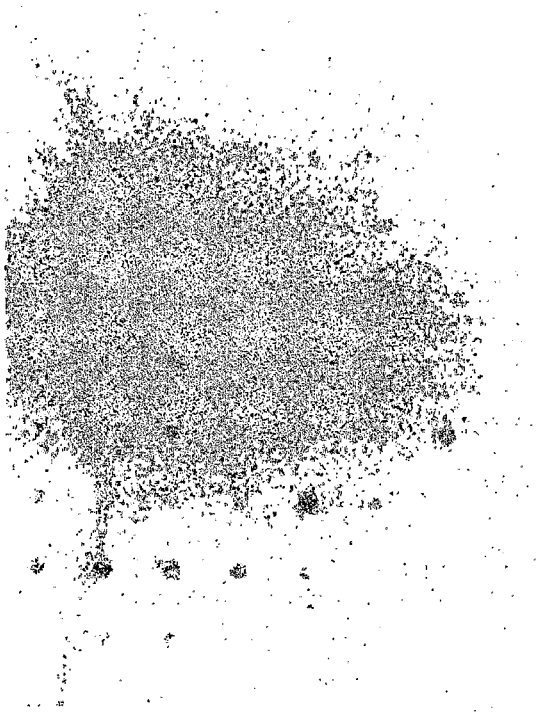
Figure 21:
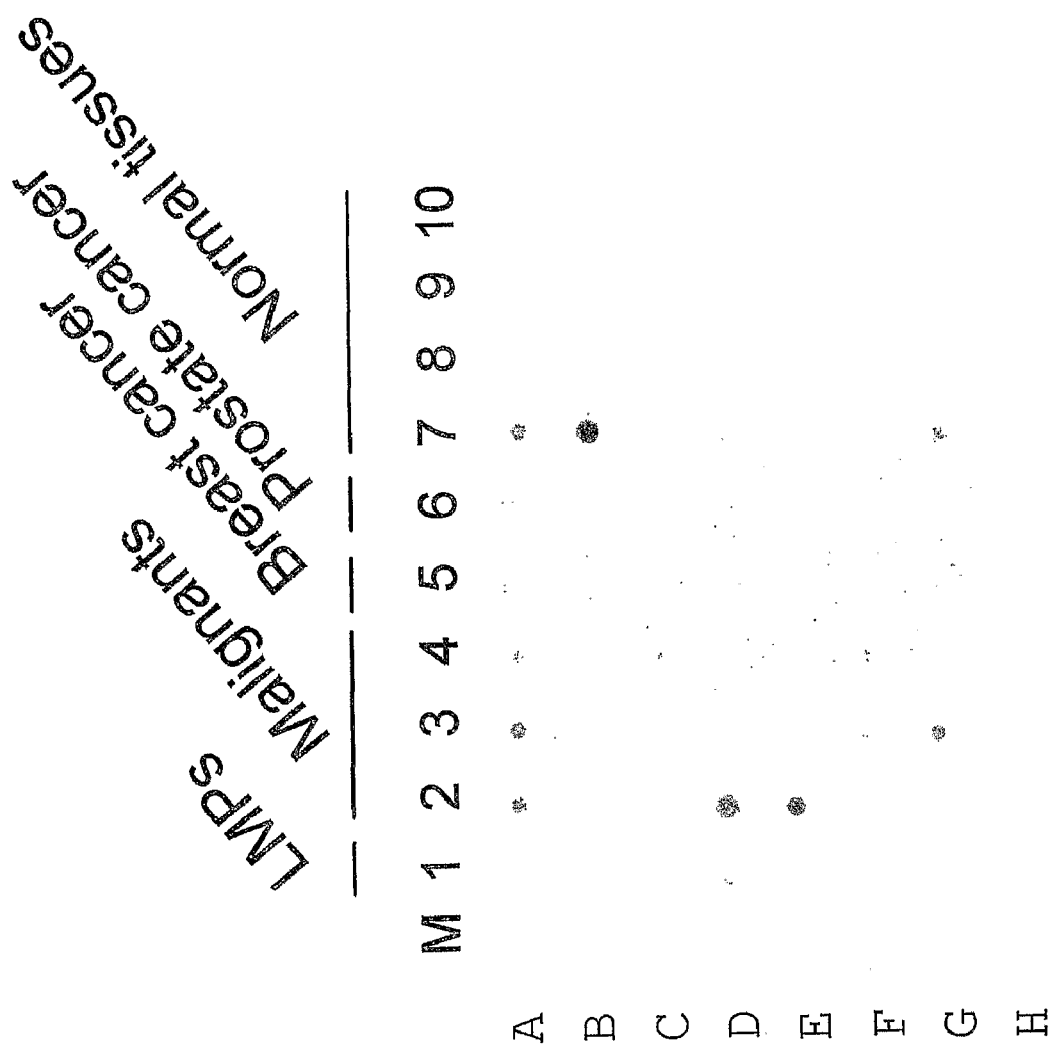
Figure 23:
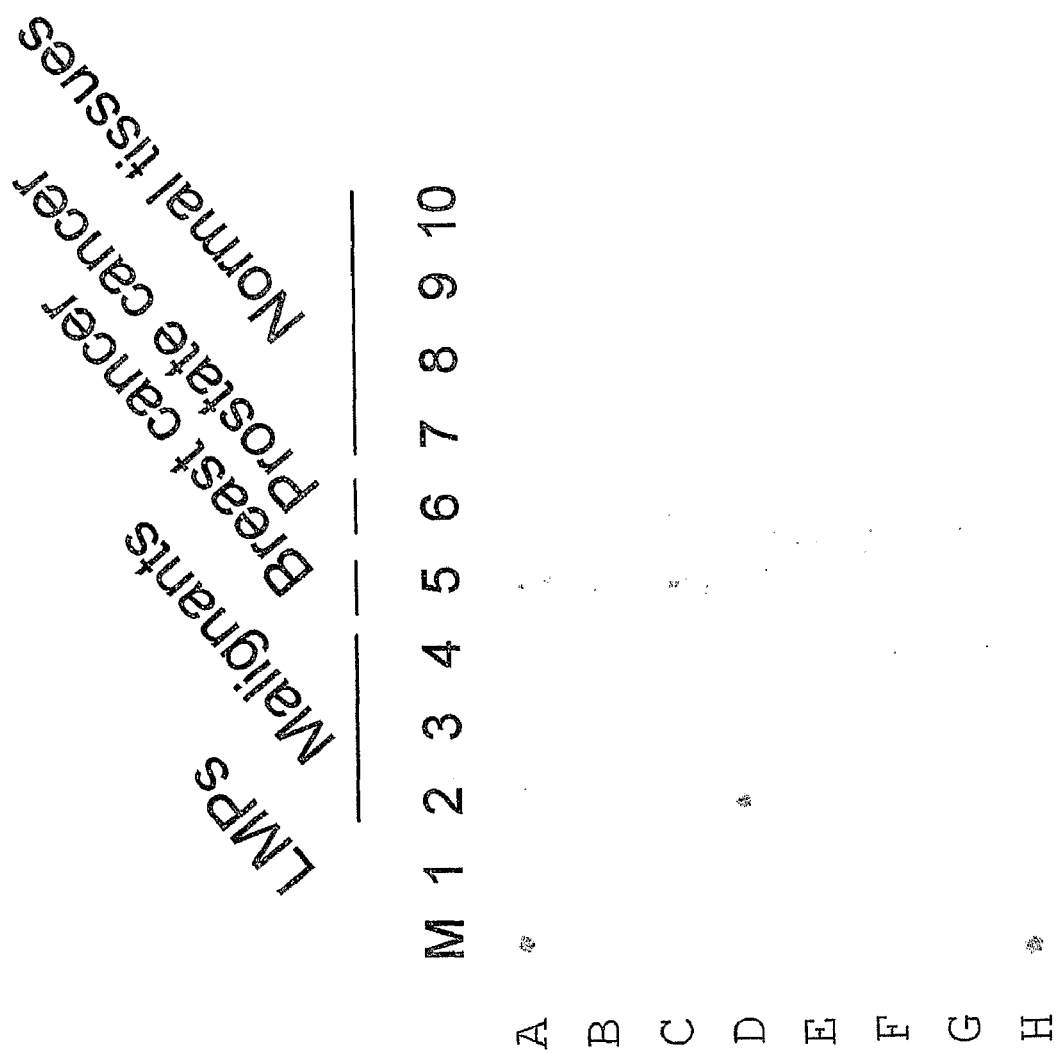
Figure 24:
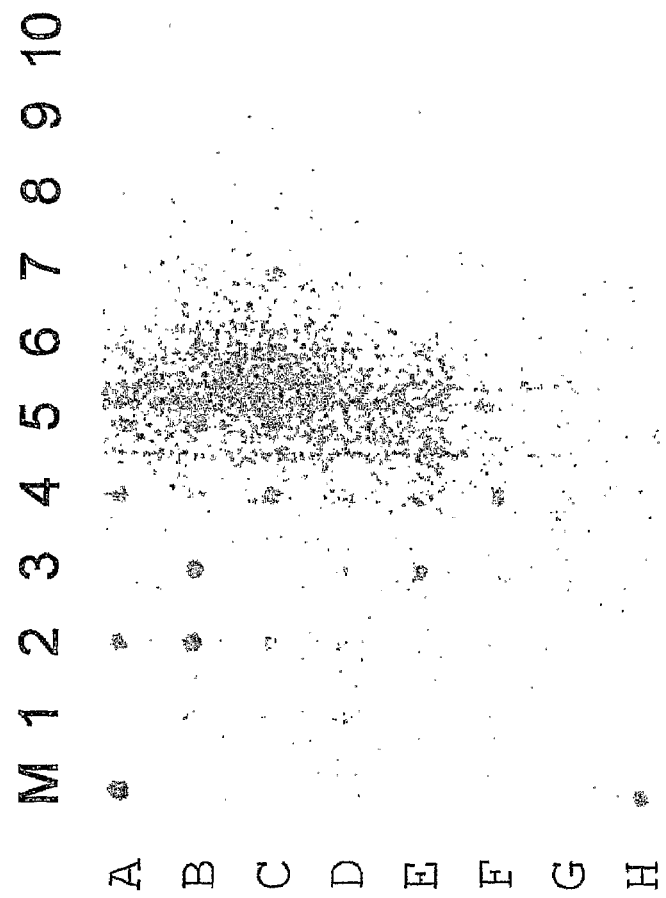
Figure 29:
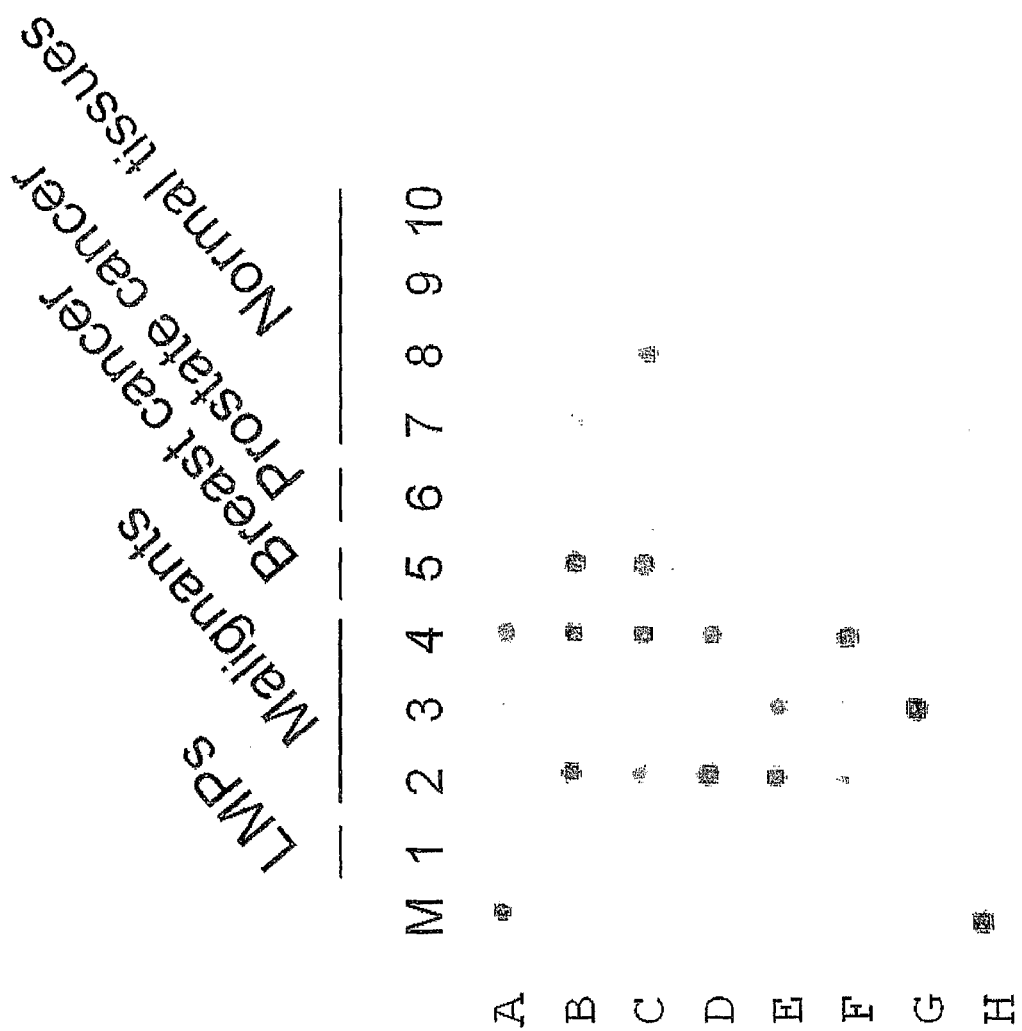
Figure 35:
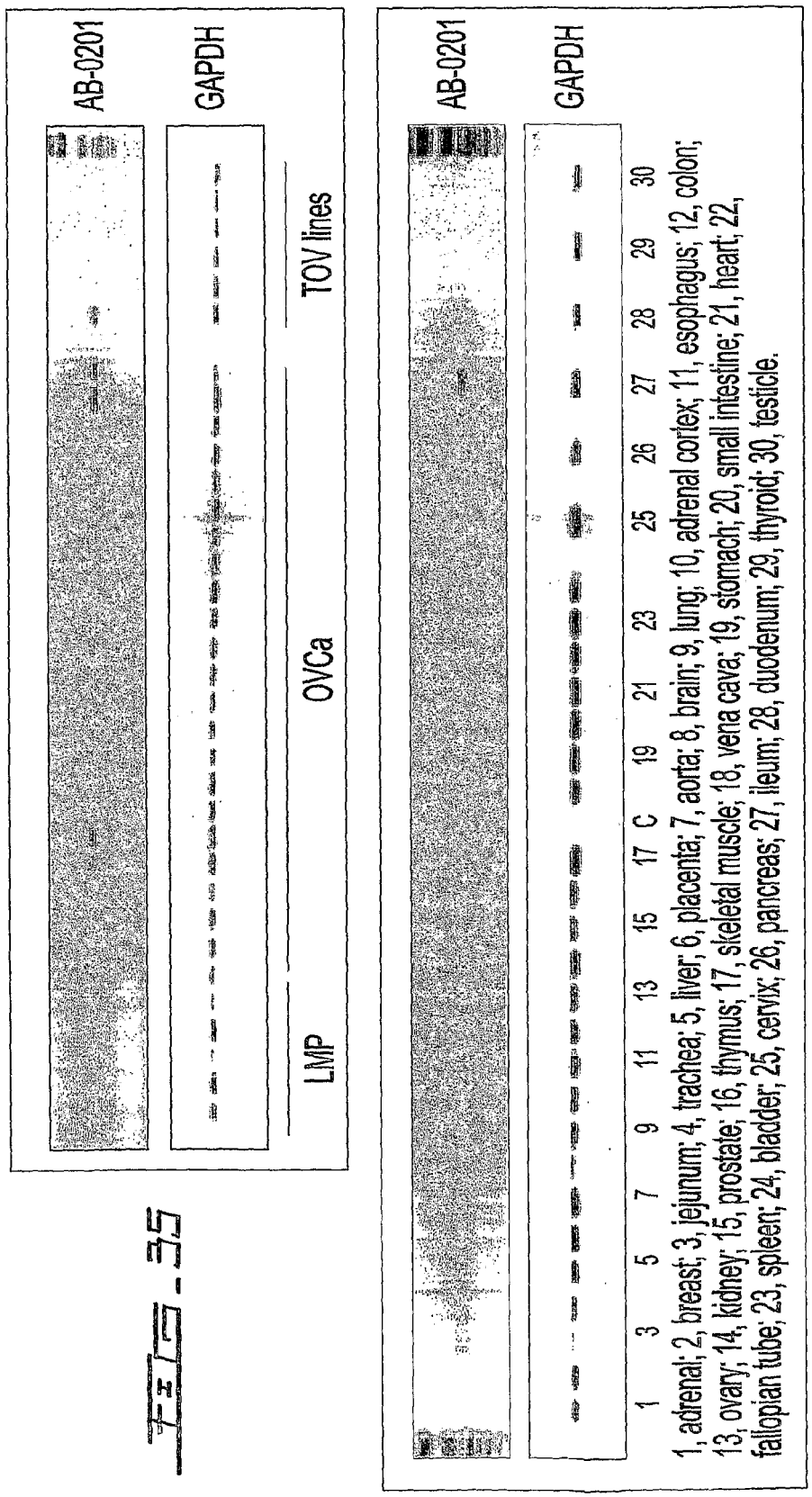
Figure 38:
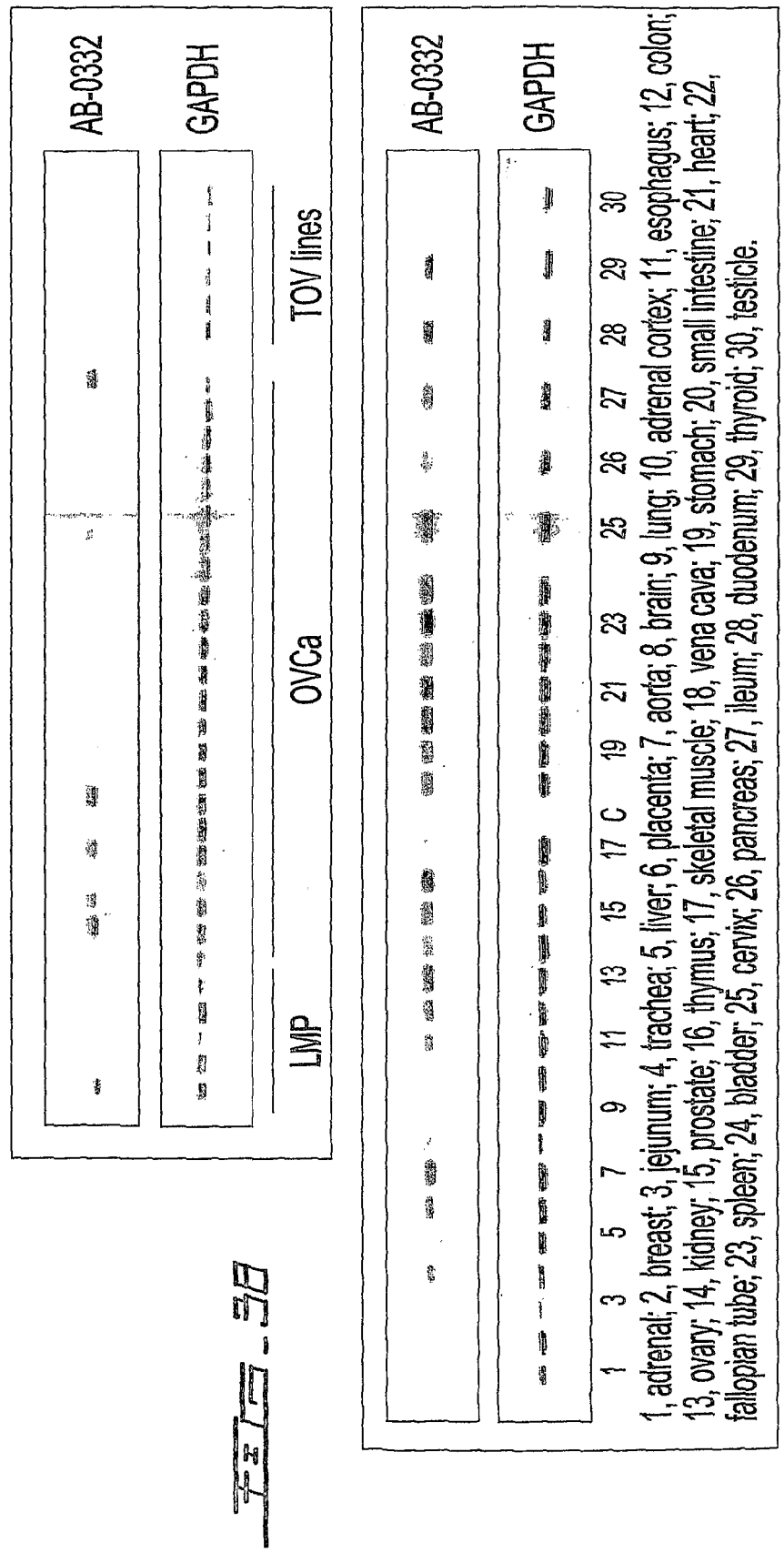
Figure 41:
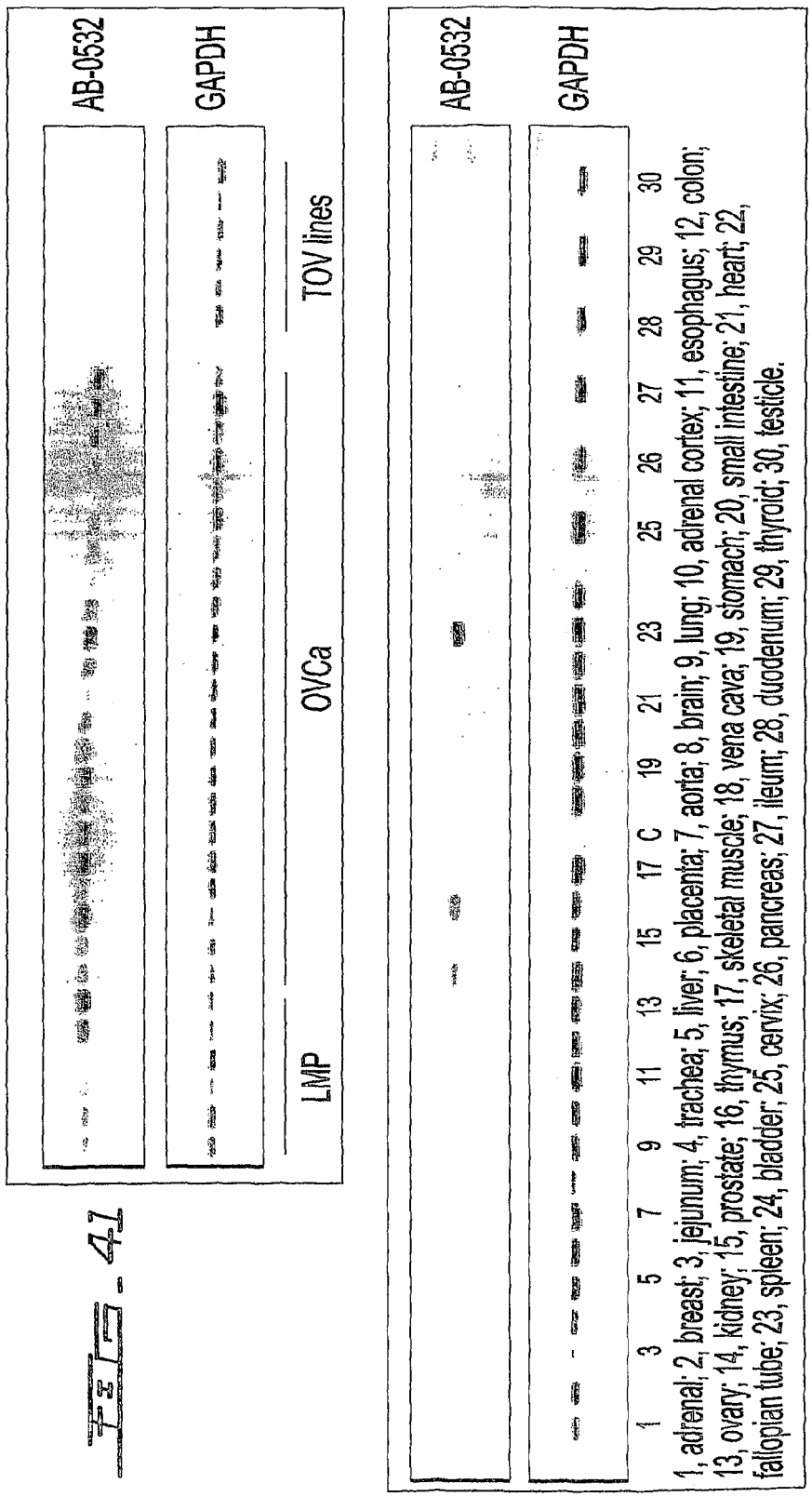
Figure 44:
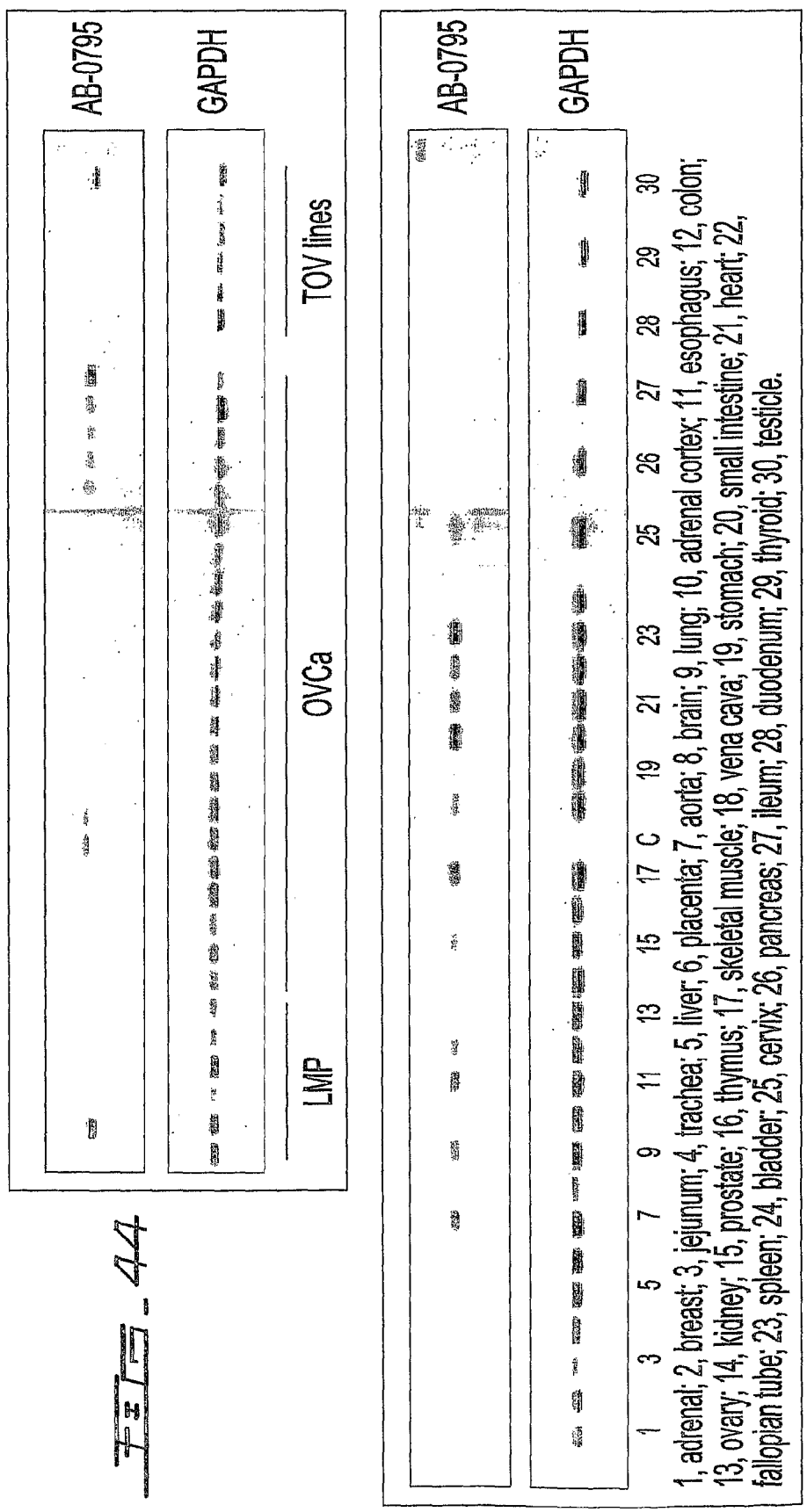
Figure 50:
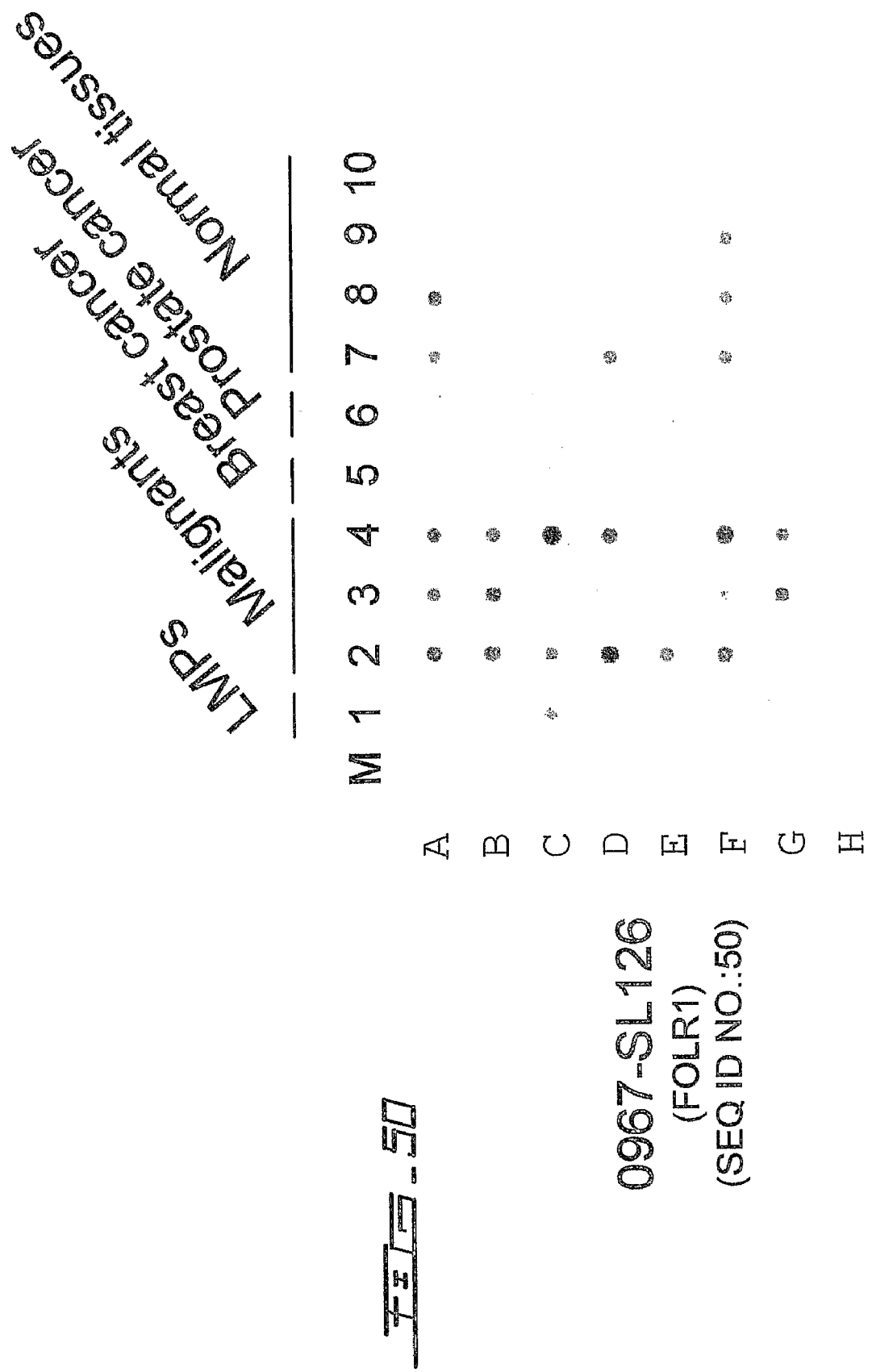
Figure 51:
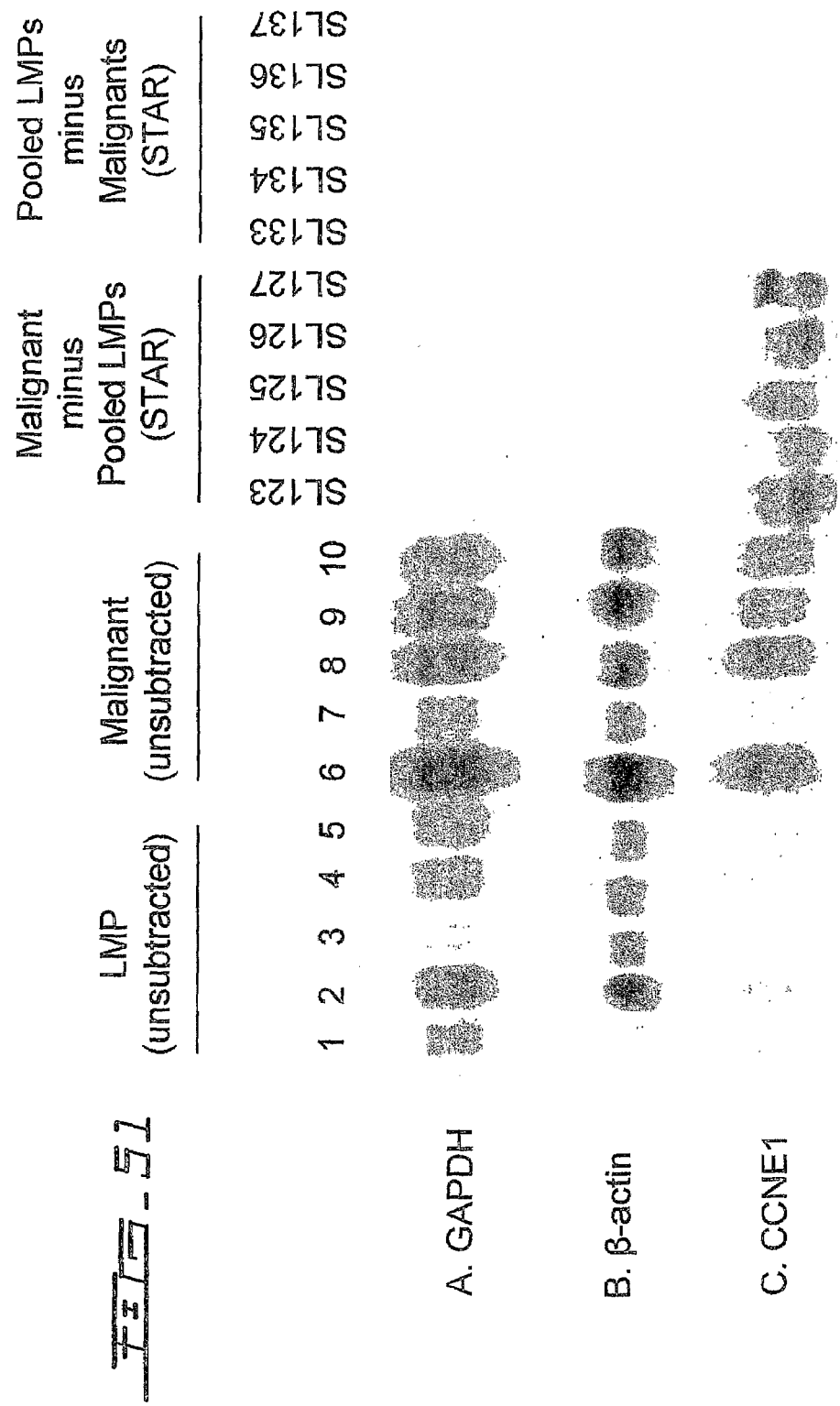
Figure 53:
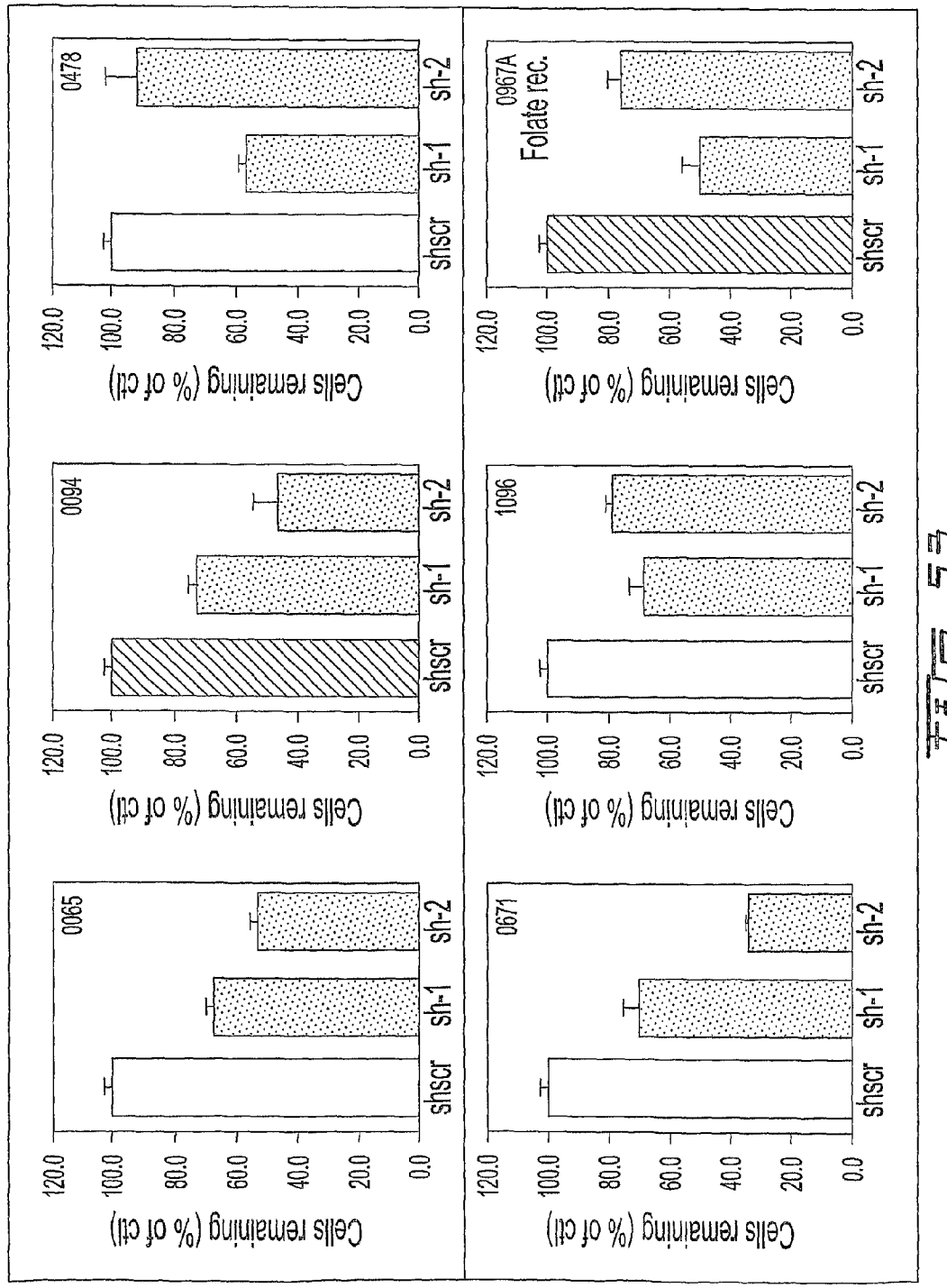
Figure 55A:
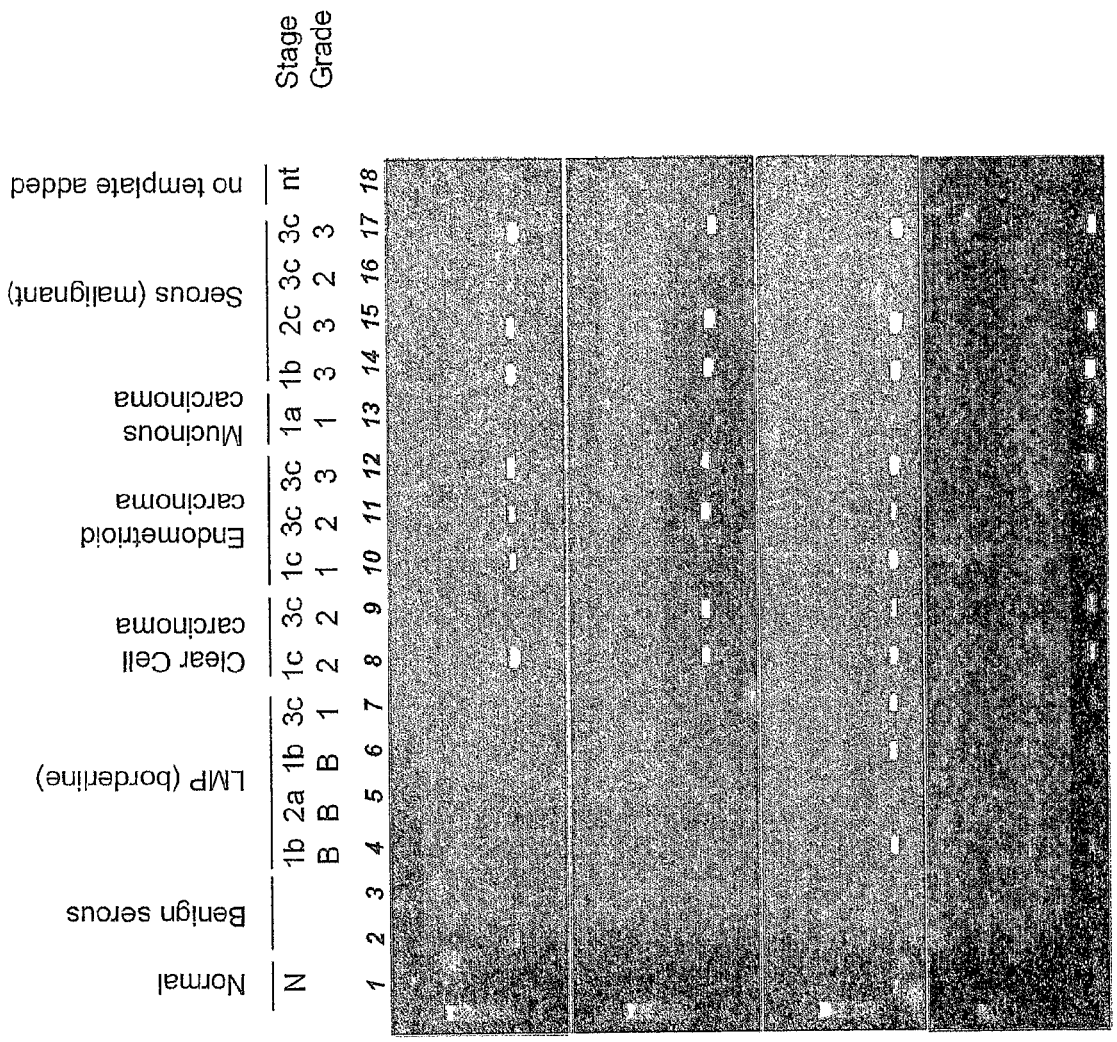
Figure 60:
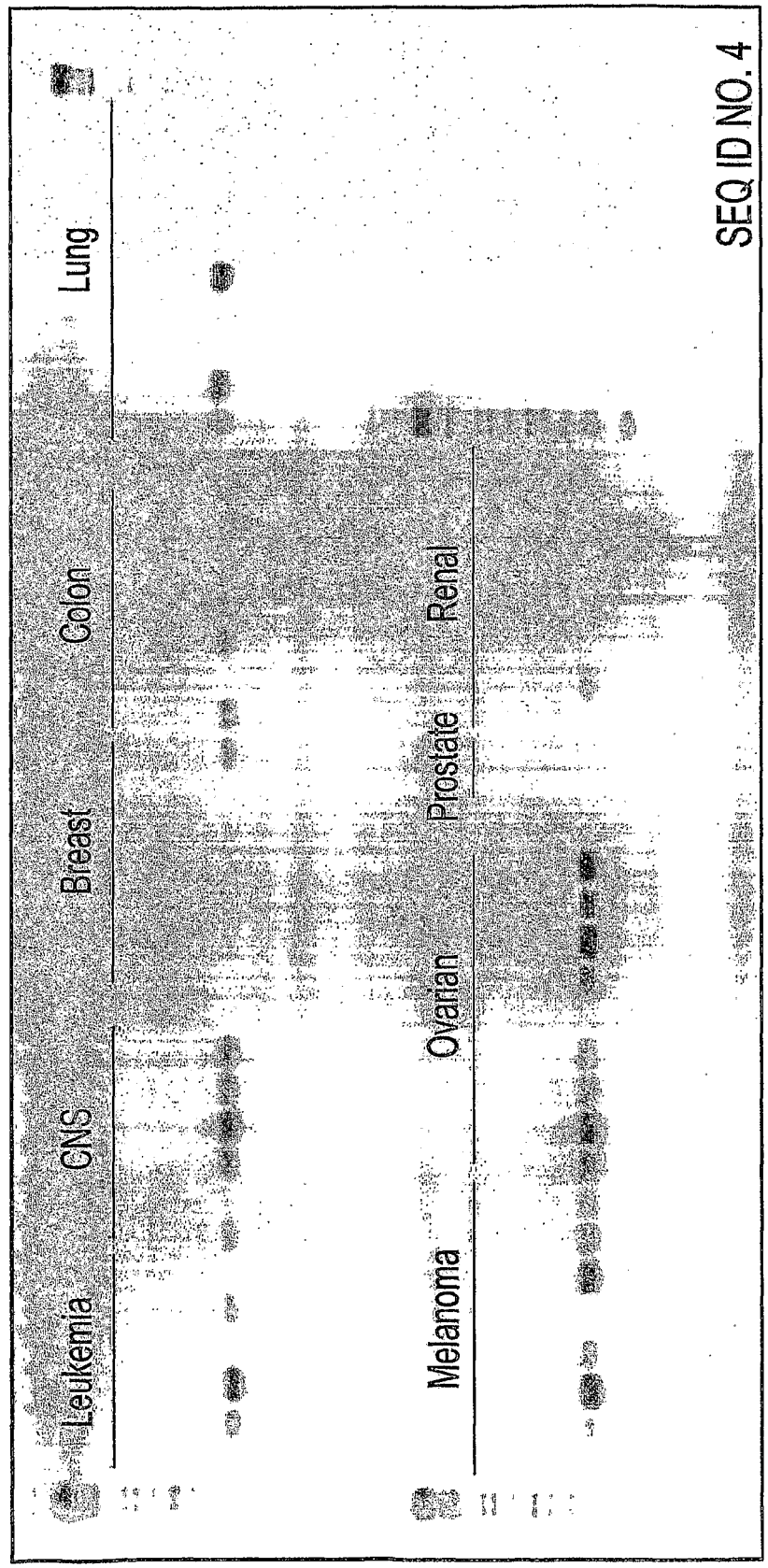
Figure 62:
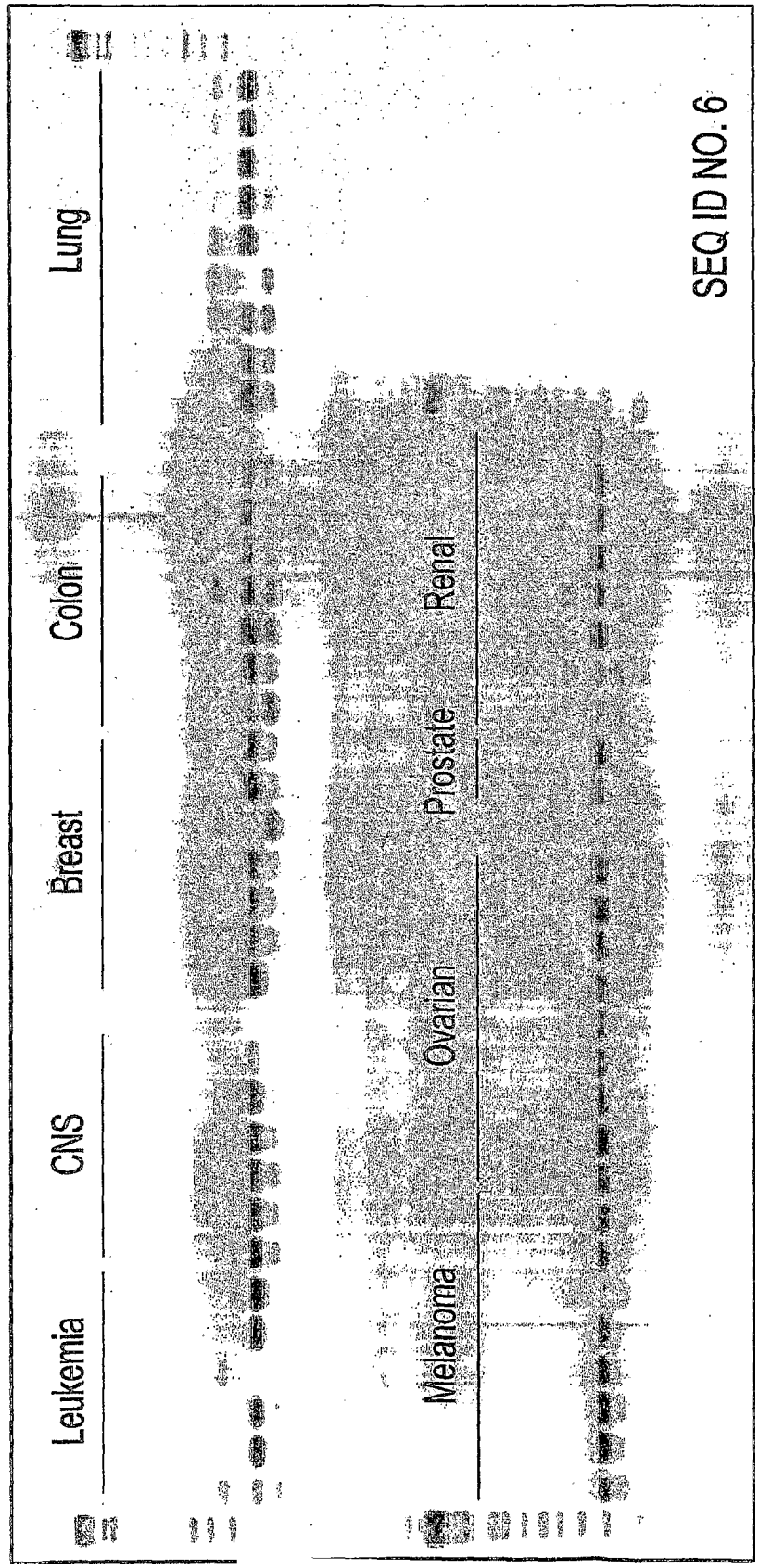
Figure 105:
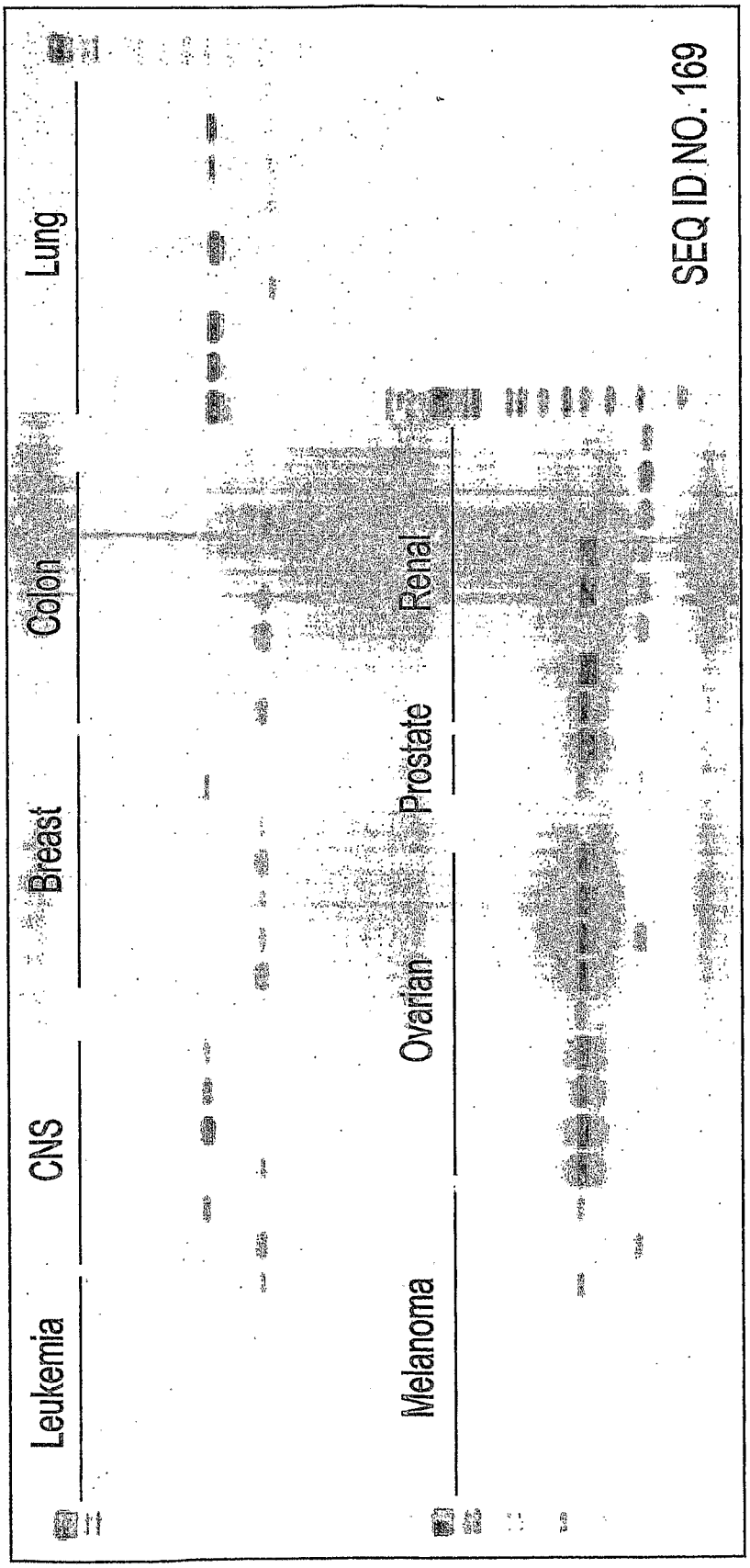

More particularly,

FIG. 1 is a picture of the macroarray hybridization results showing the differential expression data for STAR selected ovarian cancer-related human SEQ. ID. NO. 1. The STAR dsDNA clone representing SEQ. ID. NO. 1 was labeled with $^{32}P$ and hybridized to the macroarray. The hybridization results obtained confirm its upregulation in a majority of malignant ovarian cancer samples (A-F 2 and A-G 3-4) compared to LMP samples (A-F 1). Expression of this sequence was only observed in one (placenta (F7)) of the 30 normal tissues and the breast cancer cell line, MCF7 (B-C 5);

FIG. 2 is a picture of the macroarray hybridization results showing the differential expression data for STAR selected ovarian cancer-related human SEQ. ID. NO. 2. The STAR dsDNA clone representing SEQ. ID. NO. 2 was labeled with $^{32}P$ and hybridized to the macroarray. The hybridization results obtained confirm its upregulation in a majority of malignant ovarian cancer samples (A-F 2 and A-G 3-4) compared to LMP samples (A-F 1). Expression of this sequence was also evident in six (breast (B7), placenta (F7), aorta (G7), colon (D8), ovary (E8) and thymus (H8)) of the 30 normal tissues;

FIG. 3 is a picture of the macroarray hybridization results showing the differential expression data for STAR selected ovarian cancer-related human SEQ. ID. NO. 3. The STAR dsDNA clone representing SEQ. ID. NO. 3 was labeled with $^{32}$P and hybridized to the macroarray. The hybridization results obtained confirm its upregulation in a majority of malignant ovarian cancer samples (A-F 2 and A-G 3-4) compared to LMP samples (A-F 1) but overall, only low levels of expression. No significant expression was seen in any of the normal tissues;

FIG. 4 is a picture of the macroarray hybridization results showing the differential expression data for STAR selected ovarian cancer-related human SEQ. ID. NO. 4. The STAR dsDNA clone representing SEQ. ID. NO. 4 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Expression of this sequence was also evident in two (esophagus (C8) and fallopian tube (F9)) of the 30 normal tissues;

FIG. 5 is a picture of the macroarray hybridization results showing the differential expression data for STAR selected ovarian cancer-related human SEQ. ID. NO. 5. The STAR dsDNA clone representing SEQ. ID. NO. 5 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Weak expression of this sequence similar to that of LMPs was also observed in many of the normal tissues;

FIG. 6 is a picture of the macroarray hybridization results showing the differential expression data for STAR selected ovarian cancer-related human SEQ. ID. NO. 6. The STAR dsDNA clone representing SEQ. ID. NO. 6 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Expression of this sequence was also evident in three (liver (E7), placenta (F7) and kidney (F8)) of the 30 normal tissues;

FIG. 7 is a picture of the macroarray hybridization results showing the differential expression data for STAR selected ovarian cancer-related human SEQ. ID. NO. 7. The STAR dsDNA clone representing SEQ. ID. NO. 7 was labeled with $^{32}$P and hybridized to the macroarray. The hybridization results obtained confirm its upregulation in several malignant ovarian cancer samples (A-F 2 and A-G 3-4) compared to LMP samples (A-F 1). Expression of this sequence was only evident in one (testicle (F10)) of the 30 normal tissues;

FIG. 8 is a picture of the macroarray hybridization results showing the differential expression data for STAR selected ovarian cancer-related human SEQ. ID. NO. 8. The STAR dsDNA clone representing SEQ. ID. NO. 8 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Expression of this sequence was only evident in two (esophagus (C8) and stomach (C9)) of the 30 normal tissues and the breast and prostate cancer cell lines, MDA (A5) and LNCap (G6 and H6), respectively;

FIG. 9 is a picture of the macroarray hybridization results showing the differential expression data for STAR selected ovarian cancer-related human SEQ. ID. NO. 9. The STAR dsDNA clone representing SEQ. ID. NO. 9 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Expression of this sequence was only evident in one (placenta (F7)) of the 30 normal tissues, the breast cancer cell line, MCF7 (B-C 5) and LCM microdissected prostate cancer samples (D6 and F6);

FIG. 10 is a picture of the macroarray hybridization results showing the differential expression data for STAR selected ovarian cancer-related human SEQ. ID. NO. 10. The STAR dsDNA clone representing SEQ. ID. NO. 10 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Expression of this sequence was only evident in one (testicle (F10)) of the 30 normal tissues, the breast cancer cell lines, MDA (A5) and MCF7 (B-C 5) and prostate cancer cell line, LNCap (G-H 6);

FIG. 11 is a picture of the macroarray hybridization results showing the differential expression data for STAR selected ovarian cancer-related human SEQ. ID. NO. 11. The STAR dsDNA clone representing SEQ. ID. NO. 11 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was only evident in the breast cancer cell lines, MDA (A5) and MCF7 (B-C 5);

FIG. 12 is a picture of the macroarray hybridization results showing the differential expression data for STAR selected ovarian cancer-related human SEQ. ID. NO. 12. The STAR dsDNA clone representing SEQ. ID. NO. 12 was labeled with $^{32}$P and hybridized to the macroarray. The hybridization results obtained confirm its upregulation in the majority of malignant ovarian cancer samples (A-F 2 and A-G 3-4) compared to LMP samples (A-F 1). Significant expression of this sequence was only evident in one (testicle (F10)) of the 30 normal tissues and the prostate cancer cell line, LNCap (G-H 6). Weaker expression was also observed in normal ovary (E8);

FIG. 13 is a picture of the macroarray hybridization results showing the differential expression data for STAR selected ovarian cancer-related human SEQ. ID. NO. 13. The STAR dsDNA clone representing SEQ. ID. NO. 13 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was only evident in the breast cancer cell lines, MDA (A5) and MCF7 (B-C 5). Weaker expression was also observed in some normal tissues and the prostate cancer cell line, LNCap (G-H 6);

FIG. 14 is a picture of the macroarray hybridization results showing the differential expression data for STAR selected ovarian cancer-related human SEQ. ID. NO. 14. The STAR dsDNA clone representing SEQ. ID. NO. 14 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Weaker expression of this sequence was only observed in the normal kidney (F8) tissue;

FIG. 15 is a picture of the macroarray hybridization results showing the differential expression data for STAR selected ovarian cancer-related human SEQ. ID. NO. 15. The STAR dsDNA clone representing SEQ. ID. NO. 15 was labeled with $^{32}$P and hybridized to the macroarray. The hybridization results obtained confirm its upregulation in the majority of malignant ovarian cancer samples (A-F 2 and A-G 3-4) compared to LMP samples (A-F 1). Weaker expression of this sequence similar to that of the LMPs was noted in many of the normal tissues as well;

FIG. 16 is a picture of the macroarray hybridization results showing the differential expression data for STAR selected ovarian cancer-related human SEQ. ID. NO. 16. The STAR dsDNA clone representing SEQ. ID. NO. 16 was labeled with $^{32}$P and hybridized to the macroarray. The hybridization results obtained confirm its upregulation in the majority of malignant ovarian cancer samples (A-F 2 and A-G 3-4) compared to LMP samples (A-F 1). Significant expression of this sequence was also evident in the breast cancer cell lines, MDA (A5) and MCF7 (B-C 5). Weaker expression similar to that of the LMPs was seen in prostate and some normal tissue samples;

FIG. 17 is a picture of the macroarray hybridization results showing the differential expression data for STAR selected ovarian cancer-related human SEQ. ID. NO. 17. The STAR dsDNA clone representing SEQ. ID. NO. 17 was labeled with $^{32}$P and hybridized to the macroarray. The hybridization results obtained confirm its upregulation in the majority of malignant ovarian cancer samples (A-F 2 and A-G 3-4) compared to LMP samples (A-F 1). Significant expression of this sequence was only evident in two (breast (B7) and bladder (H9)) of the 30 normal tissues;

FIG. 18 is a picture of the macroarray hybridization results showing the differential expression data for STAR selected ovarian cancer-related human SEQ. ID. NO. 18. The STAR dsDNA clone representing SEQ. ID. NO. 18 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell lines, MDA (A5) and MCF7 (B-C 5), and somewhat lower expression in prostate cancer cell line, LNCap (G-H 6) and eight normal tissues (adrenal (A7), placenta (F7), lung (A8), adrenal cortex (B8), esophagus (C8), colon (D8), ovary (E8) and testicle (F10));

FIG. 19A is a picture of the macroarray hybridization results showing the differential expression data for STAR selected ovarian cancer-related human SEQ. ID. NO. 19. The STAR dsDNA clone representing SEQ. ID. NO. 19 was labeled with $^{32}$P and hybridized to the macroarray. The hybridization results obtained confirm its upregulation in several malignant ovarian cancer samples (A-F 2 and A-G 3-4) compared to LMP samples (A-F 1). Significant expression of this sequence was also only evident in the breast cancer cell line, MCF7 (B-C 5);

FIG. 19B (panels A and B) is a picture of RT-PCR data showing the differential expression data for STAR selected ovarian cancer-related human SEQ. ID. NO. 19 and KCNMB2 gene belonging to Unigene cluster, Hs.478368. Primer pairs specific to either the STAR clone sequence for SEQ. ID. NO. 19 or the KCNMB2 gene were used to perform RT-PCR on normal ovarian tissue, and benign and different stages/grades of ovarian cancer. As indicated by the expected PCR amplicon product (FIG. 19B, panel A), compared to normal (Lane 1), benign (Lanes 2-3) and LMPs (Lanes 4-7) samples, increased expression of SEQ. ID. NO. 19 mRNA was evident in clear cell carcinoma (Lanes 8-9), late stage endometrioid (Lane 12) and malignant serous (Lanes 15-17). These results confirm the upregulation of the gene expression for SEQ. ID. NO. 19 in malignant ovarian cancer. However, the expression of KCNMB2 was markedly different from that of SEQ. ID. NO. 19 showing essentially no difference in its expression amongst the different ovarian samples (FIG. 19B, panel B);

FIG. 20 is a picture of the macroarray hybridization results showing the differential expression data for STAR selected ovarian cancer-related human SEQ. ID. NO. 20. The STAR dsDNA clone representing SEQ. ID. NO. 20 was labeled with $^{32}$P and hybridized to the macroarray. The hybridization results obtained confirm its upregulation in several malignant ovarian cancer samples (A-F 2 and A-G 3-4) compared to LMP samples (A-F 1). Significant expression of this sequence was also evident in the four (jejunum (C7), trachea (D7), colon (D8) and thymus (H8)) of the 30 normal tissues;

FIG. 21 is a picture of the macroarray hybridization results showing the differential expression data for STAR selected ovarian cancer-related human SEQ. ID. NO. 21. The STAR dsDNA clone representing SEQ. ID. NO. 21 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the three (adrenal (A7), breast (B7) and aorta (G7)) of the 30 normal tissues;

FIG. 22 is a picture of the macroarray hybridization results showing the differential expression data for STAR selected ovarian cancer-related human SEQ. ID. NO. 22. The STAR dsDNA clone representing SEQ. ID. NO. 22 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell line, MCF7 (B-C 5). Weaker expression similar to that of the LMPs was seen in a majority of the normal tissues;

FIG. 23 is a picture of the macroarray hybridization results showing the differential expression data for STAR selected ovarian cancer-related human SEQ. ID. NO. 23. The STAR dsDNA clone representing SEQ. ID. NO. 23 was labeled with $^{32}$P and hybridized to the macroarray. The hybridization results obtained confirm its upregulation in several malignant ovarian cancer samples (A-F 2 and A-G 3-4) compared to LMP samples (A-F 1). Significant expression of this sequence was also evident in the breast cancer cell lines, MDA (A5) and MCF7 (B-C 5) and prostate cancer cell line, LNCap (G-H 6);

FIG. 24 is a picture of the macroarray hybridization results showing the differential expression data for STAR selected ovarian cancer-related human SEQ. ID. NO. 24. The STAR dsDNA clone representing SEQ. ID. NO. 24 was labeled with $^{32}$P and hybridized to the macroarray. The hybridization results obtained confirm its upregulation in several of the malignant ovarian cancer samples (A-F 2 and A-G 3-4) compared to LMP samples (A-F 1). Significant expression of this sequence was also evident in the breast cancer cell line, MCF7 (B-C 5);

FIG. 25 is a picture of the macroarray hybridization results showing the differential expression data for STAR selected ovarian cancer-related human SEQ. ID. NO. 25. The STAR dsDNA clone representing SEQ. ID. NO. 25 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the prostate cancer cell line, LNCap (G-H 6);

FIG. 26 is a picture of the macroarray hybridization results showing the differential expression data for STAR selected ovarian cancer-related human SEQ. ID. NO. 26. The STAR dsDNA clone representing SEQ. ID. NO. 26 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell lines, MDA (A5) and MCF7 (B-C 5), prostate cancer cell line, LNCap (G-H 6) and one normal tissue, testicle (F10). Weaker expression similar to that of the LMPs was seen in some normal tissues as well;

FIG. 27 is a picture of the macroarray hybridization results showing the differential expression data for STAR selected ovarian cancer-related human SEQ. ID. NO. 27. The STAR dsDNA clone representing SEQ. ID. NO. 27 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell lines, MDA (A5) and MCF7 (B-C 5), prostate cancer cell line, LNCap (G-H 6). Weaker expression similar to that of the LMPs was seen in seven (adrenal (A7), placenta (F7), lung (A8), esophagus (C8), colon (D8), ovary (E8) and testicle (F10)) of the 30 normal tissues as well;

FIG. 28 is a picture of the macroarray hybridization results showing the differential expression data for STAR selected ovarian cancer-related human SEQ. ID. NO. 28. The STAR dsDNA clone representing SEQ. ID. NO. 28 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell lines, MDA (A5) and MCF7 (B-C 5). Weaker expression similar to that of LMPs was seen for all other tissues;

FIG. 29 is a picture of the macroarray hybridization results showing the differential expression data for STAR selected ovarian cancer-related human SEQ. ID. NO. 29. The STAR dsDNA clone representing SEQ. ID. NO. 29 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell line, MCF7 (B-C 5) and three (breast (B7), esophagus (C8) and fallopian tube (F9)) of the 30 normal tissues;

FIG. 30 is a picture of the macroarray hybridization results showing the differential expression data for STAR selected ovarian cancer-related human SEQ. ID. NO. 30. The STAR dsDNA clone representing SEQ. ID. NO. 30 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell line, MCF7 (B-C 5), prostate cancer samples (D-H 6). Weaker expression similar to that of LMPs was seen in only very few normal tissues;

FIG. 31 is a picture of the macroarray hybridization results showing the differential expression data for STAR selected ovarian cancer-related human SEQ. ID. NO. 31. The STAR dsDNA clone representing SEQ. ID. NO. 31 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the breast cancer cell line, MCF7 (B-C 5), prostate cancer samples (D-H 6). Weaker expression similar to that of LMPs was seen in only very few normal tissues;

FIG. 32 is a picture of RT-PCR data showing the differential expression data for STAR selected ovarian cancer-related human SEQ. ID. NO. 32. For this gene, the macroarray data was not available. A primer pair, OGS 1077 (GCGTC-CGGGCCTGTCTTCAACCT; SEQ. ID. NO. 153) and OGS 1078 (GCCCCACCCTCTACCCCACCACTA; SEQ. ID. NO. 154) for SEQ. ID. NO. 32 was used to perform RT-PCR on normal ovarian tissue, and benign and different stages/grades of ovarian cancer. As indicated by the expected PCR amplicon product, compared to normal (Lane 1) and benign (Lanes 2-3), increased expression of SEQ. ID. NO. 32 mRNA was evident in LMPs (Lanes 4-7), clear cell carcinoma (Lanes 8-9), late stage endometrioid (Lane 12) and malignant serous (Lanes 15-17). These results confirm the upregulation of the gene expression for SEQ. ID. NO. 32 in malignant ovarian cancer;

FIG. 33 is a picture of the macroarray hybridization results showing the differential expression data for STAR selected ovarian cancer-related human SEQ. ID. NO. 33. The STAR dsDNA clone representing SEQ. ID. NO. 33 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the prostate cancer samples (B-F 6). Weaker expression was seen in many normal tissues and strong expression was seen trachea (D7), colon (D8), small intestine (D9), thymus (H8) and spleen (G9). These results confirm the upregulation of the gene expression for SEQ. ID. NO. 33 in malignant ovarian cancer;

FIG. 34 is a picture of the macroarray hybridization results showing the differential expression data for STAR selected ovarian cancer-related human SEQ. ID. NO. 34. The STAR dsDNA clone representing SEQ. ID. NO. 34 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the prostate cancer samples (B-F 6). Weaker expression was seen in many normal tissues and strong expression was seen trachea (D7), colon (D8), small intestine (D9), thymus (H8) and spleen (G9). These results confirm the upregulation of the gene expression for SEQ. ID. NO. 34 in malignant ovarian cancer;

FIG. 35 is a picture of RT-PCR data showing the differential expression data for STAR selected ovarian cancer-related human SEQ. ID. NO. 35. For this gene, the macroarray data was not available. A primer pair, OGS 1141 (GAGATCCT-GATCAAGGTGCAGG; SEQ. ID. NO. 155) and OGS 1142 (TGCACGCTCACAGCAGTCAGG; SEQ. ID. NO. 156) for SEQ. ID. NO. 35 was used to perform RT-PCR on LMP samples, different stages/grades of ovarian cancer and normal human tissue samples. As indicated by the expected PCR amplicon product (indicated as AB-0201), increased expression of SEQ. ID. NO. 35 mRNA was evident in some ovarian cancer lanes (lanes 10, 11, 14, 18, 28 and 29) and the mRNA was not expressed in LMP samples. Expression was observed in only one normal tissue sample, ileum (lane 27). Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAG-GTCCACCAC; SEQ. ID. NO. 168) for this housekeeping gene. These results confirm the upregulation of the gene expression for SEQ. ID. NO. 35 in malignant ovarian cancer;

FIG. 36 is a picture of the macroarray hybridization results showing the differential expression data for STAR selected ovarian cancer-related human SEQ. ID. NO. 36. The STAR dsDNA clone representing SEQ. ID. NO. 36 was labeled with $^{32}$P and hybridized to the macroarray. The hybridization results obtained confirm its upregulation in a few of the malignant ovarian cancer samples (A-F 2 and A-G 3-4) compared to LMP samples (A-F 1). No expression was seen in other cancer types nor in normal human tissues. These results confirm the upregulation of the gene expression for SEQ. ID. NO. 36 in malignant ovarian cancer;

Figure 37:
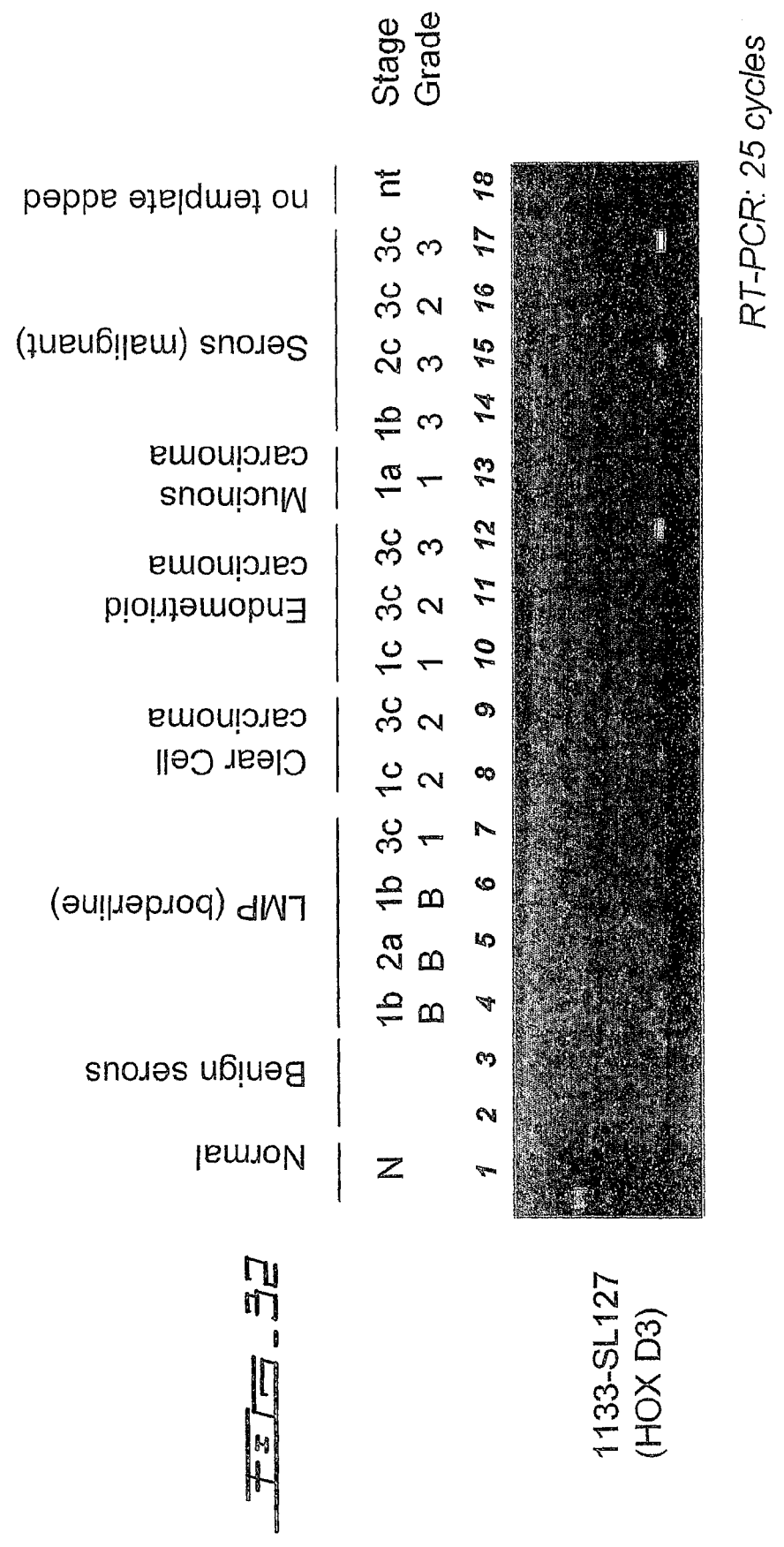

FIG. 37 is a picture of the macroarray hybridization results showing the differential expression data for STAR selected ovarian cancer-related human SEQ. ID. NO. 37. The STAR dsDNA clone representing SEQ. ID. NO. 37 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Weak expression of this sequence was also evident in the prostate cancer samples (B-F 6). Weaker expression was seen in some normal tissues. These results confirm the upregulation of the gene expression for SEQ. ID. NO. 37 in malignant ovarian cancer;

FIG. 38 is a picture of RT-PCR data showing the differential expression data for STAR selected ovarian cancer-related human SEQ. ID. NO. 38. For this gene, the macroarray data was not available. A primer pair, OGS 1202 (AACATGACTAAGATGCCCAACC; SEQ. ID. NO. 157) and OGS 1203 (AATCTCCTTCACCTCCACTACTG; SEQ. ID. NO. 158) for SEQ. ID. NO. 38 was used to perform RT-PCR on LMP samples, different stages/grades of ovarian cancer and normal human tissue samples. As indicated by the expected PCR amplicon product (indicated as AB-0332), increased expression of SEQ. ID. NO. 38 mRNA was evident in approximately half of the ovarian cancer lanes and weaker expression was seen in LMP samples. Expression was observed in many normal tissue samples. Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAGGTCCACCAC; SEQ. ID. NO. 168) for this housekeeping gene. These results confirm the upregulation of the gene expression for SEQ. ID. NO. 38 in malignant ovarian cancer;

Figure 39:
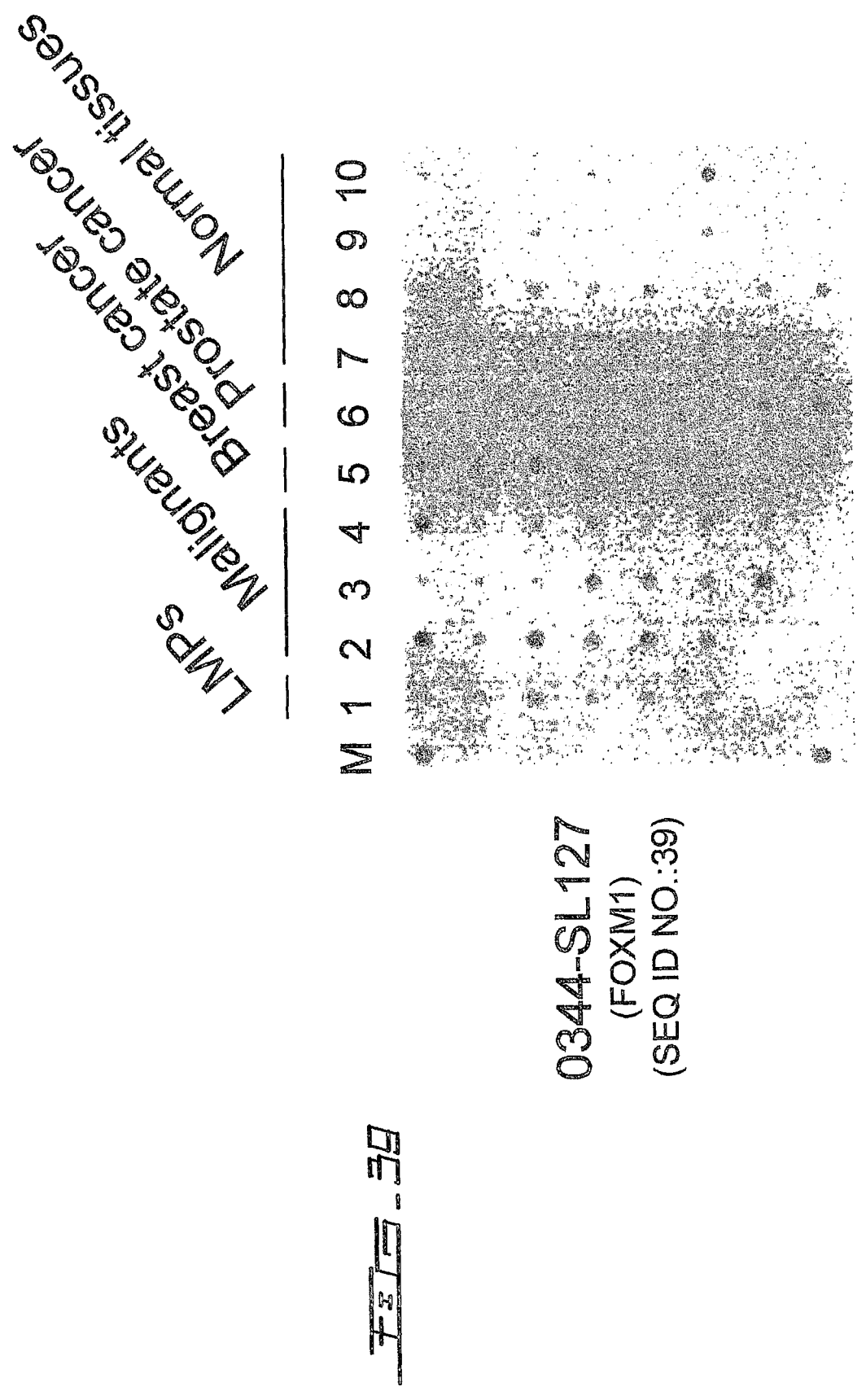

FIG. 39 is a picture of the macroarray hybridization results showing the differential expression data for STAR selected ovarian cancer-related human SEQ. ID. NO. 39. The STAR dsDNA clone representing SEQ. ID. NO. 39 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Strong expression was also observed in breast cancer samples (A-C 5) and weak expression in prostate cancer samples (A-H 6). Weaker expression was seen in a few normal tissues with strong expression in testes (F 10). These results confirm the upregulation of the gene expression for SEQ. ID. NO. 39 in malignant ovarian cancer;

FIG. 40 is a picture of the macroarray hybridization results showing the differential expression data for STAR selected ovarian cancer-related human SEQ. ID. NO. 40. The STAR dsDNA clone representing SEQ. ID. NO. 40 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Weak expression was seen in a few normal tissues with strong expression in kidney (F 8). These results confirm the upregulation of the gene expression for SEQ. ID. NO. 40 in malignant ovarian cancer;

FIG. 41 is a picture of RT-PCR data showing the differential expression data for STAR selected ovarian cancer-related human SEQ. ID. NO. 41. For this gene, the macroarray data was not available. A primer pair, OGS 1212 (AAGCATAGCCATAGGTGATTGG; SEQ. ID. NO. 159) and OGS 1213 (ACAGGTATCAGACAAGGGAGCAG; SEQ. ID. NO. 160) for SEQ. ID. NO. 41 was used to perform RT-PCR on LMP samples, different stages/grades of ovarian cancer and normal human tissue samples. As indicated by the expected PCR amplicon product (indicated as AB-0532), increased expression of SEQ. ID. NO. 41 mRNA was evident in a large majority of the ovarian cancer lanes and weaker expression was seen in LMP samples. Expression was observed in a few normal tissue samples such as kidney, thymus and spleen (lanes 14, 16 and 23, respectively). Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAGGTCCACCAC; SEQ. ID. NO. 168) for this housekeeping gene. These results confirm the upregulation of the gene expression for SEQ. ID. NO. 41 in malignant ovarian cancer;

Figure 42:
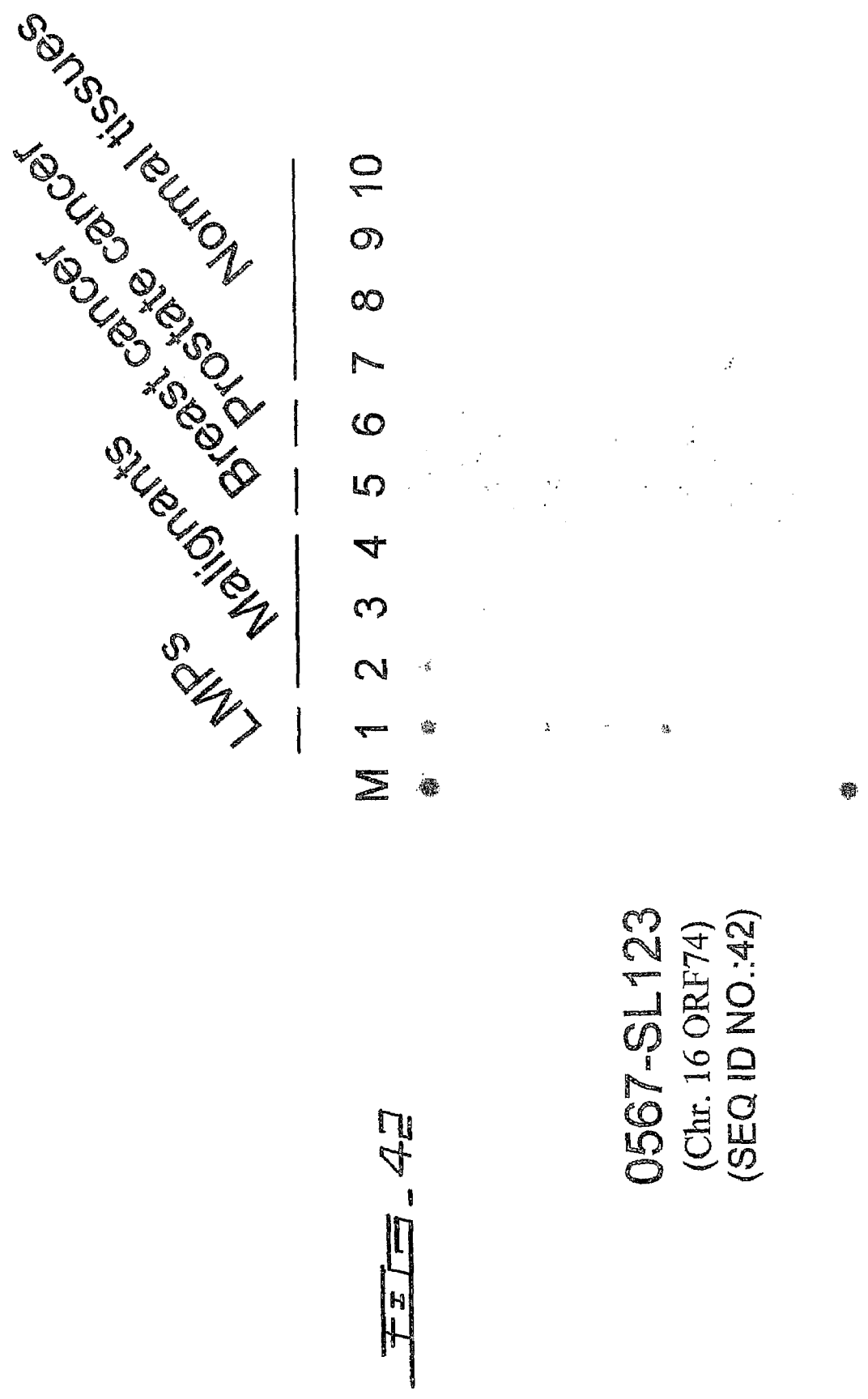

FIG. 42 is a picture of the macroarray hybridization results showing the differential expression data for STAR selected ovarian cancer-related human SEQ. ID. NO. 42. The STAR dsDNA clone representing SEQ. ID. NO. 42 was labeled with $^{32}$P and hybridized to the macroarray. The hybridization results obtained showed its expression in both malignant ovarian cancer samples (A-F 2 and A-G 3-4) and LMP samples (A-F 1). Weak expression was also observed in breast cancer samples (A-C 5). Weak expression was seen in a few normal tissues with moderate expression in placenta (F 7). These results confirm the expression for SEQ. ID. NO. 42 in malignant ovarian cancer;

Figure 43:
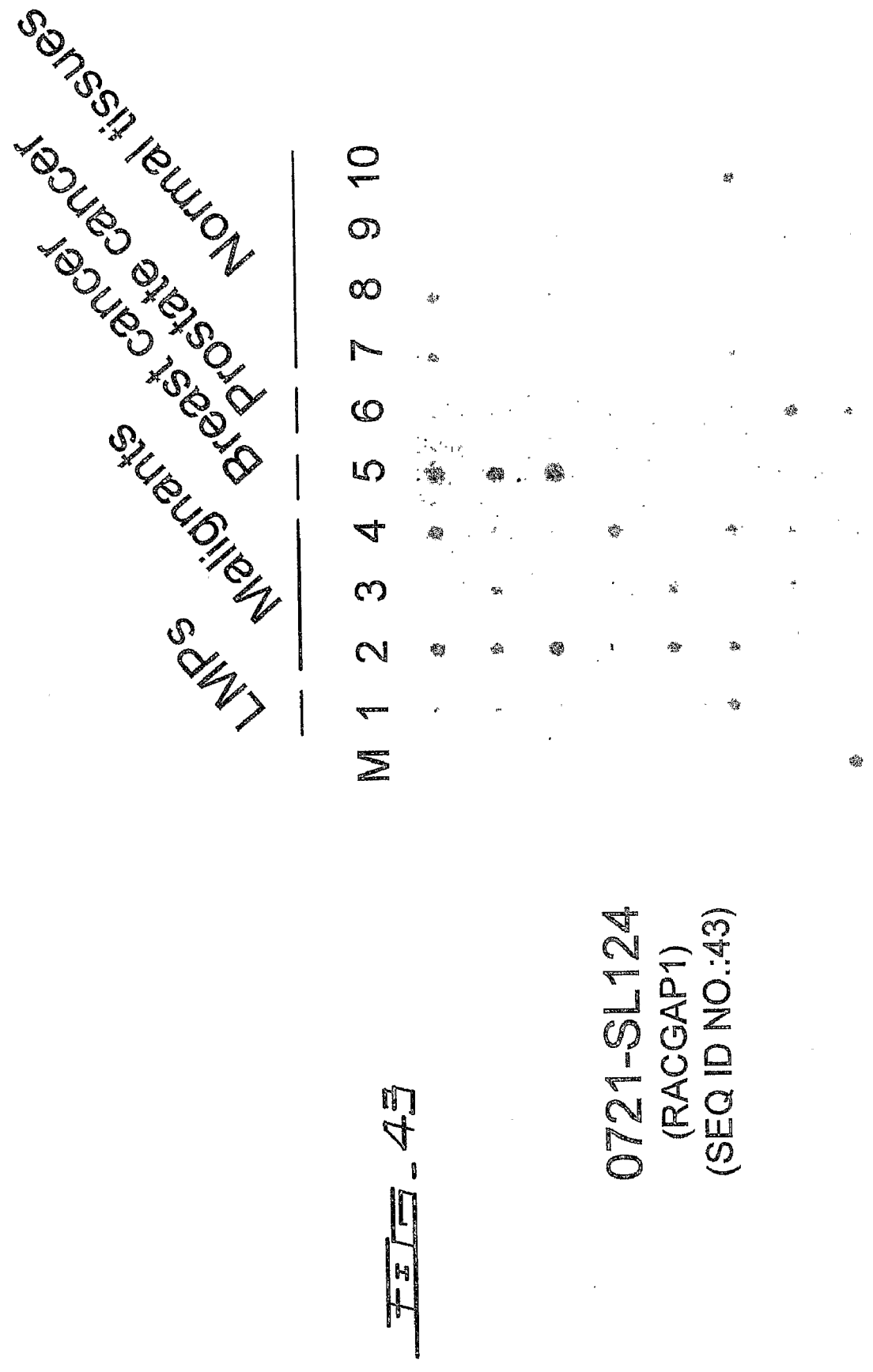

FIG. 43 is a picture of the macroarray hybridization results showing the differential expression data for STAR selected ovarian cancer-related human SEQ. ID. NO. 43. The STAR dsDNA clone representing SEQ. ID. NO. 43 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Strong expression was also observed in breast cancer samples (A-C 5) and weak expression in prostate cancer samples (A-H 6). Weaker expression was seen in normal tissues with strong expression in testes (F 10). These results confirm the upregulation of the gene expression for SEQ. ID. NO. 43 in malignant ovarian cancer;

FIG. 44 is a picture of RT-PCR data showing the differential expression data for STAR selected ovarian cancer-related human SEQ. ID. NO. 44. For this gene, the macroarray data was not available. A primer pair, OGS 1171 (TTACGACCTATTTCTCCGTGG; SEQ. ID. NO. 161) and OGS 1172 (AATGCAATAATTGGCCACTGC; SEQ. ID. NO. 162) for SEQ. ID. NO. 44 was used to perform RT-PCR on LMP samples, different stages/grades of ovarian cancer and normal human tissue samples. As indicated by the expected PCR amplicon product (indicated as AB-0795), increased expression of SEQ. ID. NO. 44 mRNA was evident in a large majority of the ovarian cancer lanes and weaker expression was seen in LMP samples. Expression was observed in several normal tissue samples such as aorta, skeletal muscle, small intestine and spleen (lanes 7, 17, 20 and 23, respectively). Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAGGTCCACCAC; SEQ. ID. NO. 168) for this housekeeping gene. These results confirm the upregulation of the gene expression for SEQ. ID. NO. 44 in malignant ovarian cancer;

FIG. 45 is a picture of RT-PCR data showing the differential expression data for STAR selected ovarian cancer-related human SEQ. ID. NO. 45. For this gene, the macroarray data was not available. A primer pair, OGS 1175 (ACACATCAAACTGCTTATCCAGG; SEQ. ID. NO. 163) and OGS 1176 (ACTGATGTGAAAATGCACATCC; SEQ. ID. NO. 164) for SEQ. ID. NO. 45 was used to perform RT-PCR on LMP samples, different stages/grades of ovarian cancer and normal human tissue samples. As indicated by the expected PCR amplicon product (indicated as AB-0846), increased expression of SEQ. ID. NO. 45 mRNA was evident in half of the ovarian cancer lanes and weaker expression was seen in LMP samples. Expression was observed in only a few normal tissue samples such as kidney, fallopian tube and testes (lanes 14, 22 and 30, respectively). Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAGGTCCACCAC; SEQ. ID. NO. 168) for this housekeeping gene. These results confirm the upregulation of the gene expression for SEQ. ID. NO. 45 in malignant ovarian cancer;

FIG. 46 is a picture of the macroarray hybridization results showing the differential expression data for STAR selected ovarian cancer-related human SEQ. ID. NO. 46. The STAR dsDNA clone representing SEQ. ID. NO. 46 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Weak expression was also observed in prostate cancer samples (A-H 6). Weaker expression was seen in a few normal tissues with moderate expression in breast (B 7) and ovary (E 8). These results confirm the upregulation of the gene expression for SEQ. ID. NO. 46 in malignant ovarian cancer;

FIG. 47 is a picture of the macroarray hybridization results showing the differential expression data for STAR selected ovarian cancer-related human SEQ. ID. NO. 47. The STAR dsDNA clone representing SEQ. ID. NO. 47 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the prostate cancer samples (B-F 6). Weaker expression was seen in many normal tissues and strong expression was seen trachea (D7), colon (D8), small intestine (D9), thymus (H8) and spleen (G9). These results confirm the upregulation of the gene expression for SEQ. ID. NO. 47 in malignant ovarian cancer;

FIG. 48 is a picture of RT-PCR data showing the differential expression data for STAR selected ovarian cancer-related human SEQ. ID. NO. 48. For this gene, the macroarray data was not available. A primer pair, OGS 1282 (ATGGCTCATACAGCACTCAGG; SEQ. ID. NO. 165) and OGS 1283 (GAACTGTCACTCCGGAAAGCCT; SEQ. ID. NO. 166) for SEQ. ID. NO. 48 was used to perform RT-PCR on LMP samples, different stages/grades of ovarian cancer and normal human tissue samples. As indicated by the expected PCR amplicon product (indicated as AB-1120), increased expression of SEQ. ID. NO. 48 mRNA was evident in a majority of the ovarian cancer lanes and weaker expression was seen in LMP samples. Expression was evident in virtually all normal tissues. Equal amounts of template cDNA used in each PCR reaction was confirmed by reamplifying GAPDH with a specific primer pair, OGS 315 (TGAAGGTCGGAGTCAACGGATTTGGT; SEQ. ID. NO. 167) and OGS 316 (CATGTGGGCCATGAGGTCCACCAC; SEQ. ID. NO. 168) for this housekeeping gene. These results confirm the upregulation of the gene expression for SEQ. ID. NO. 48 in malignant ovarian cancer;

Figure 49:
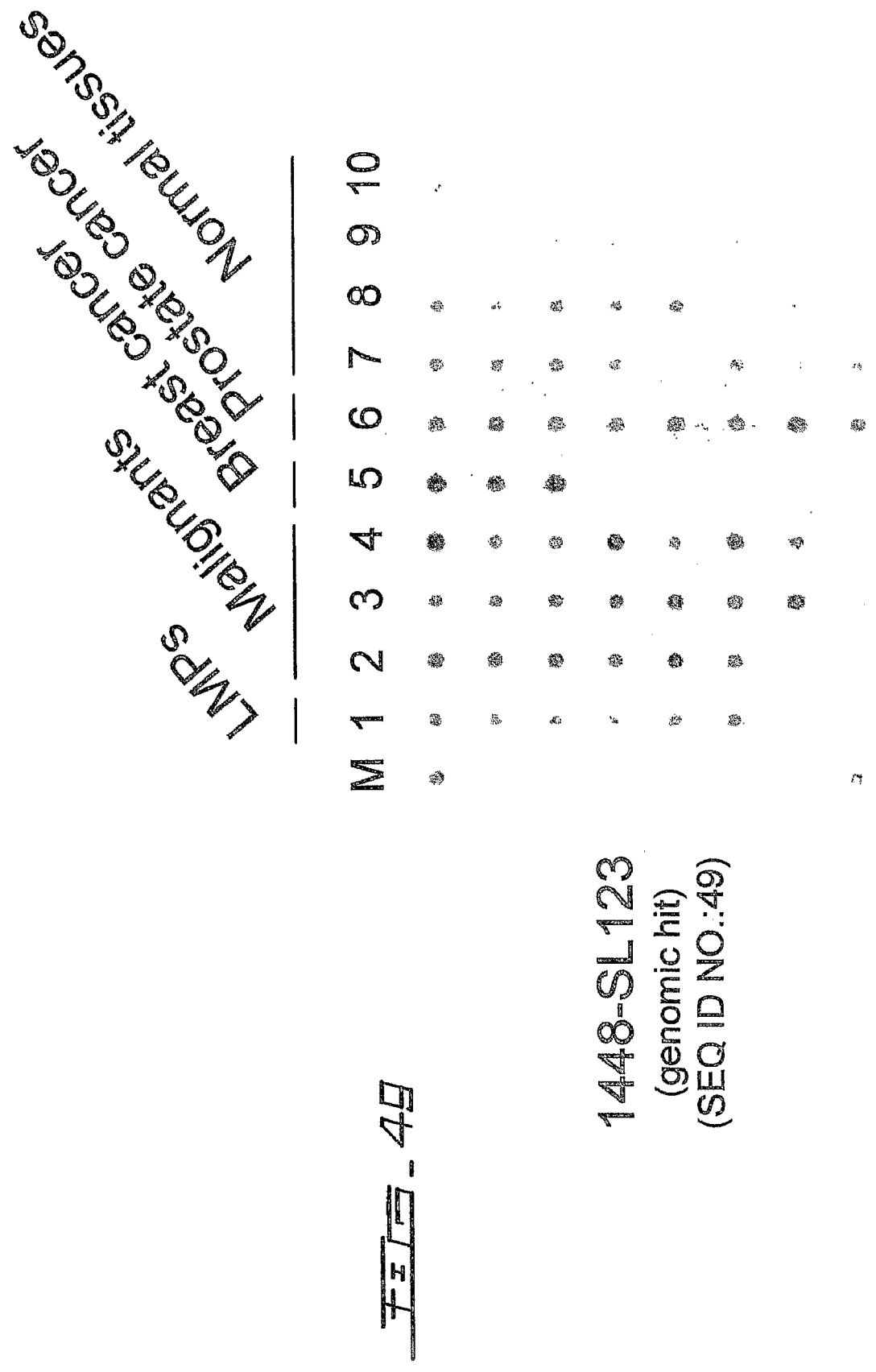

FIG. 49 is a picture of the macroarray hybridization results showing the differential expression data for STAR selected ovarian cancer-related human SEQ. ID. NO. 49. The STAR dsDNA clone representing SEQ. ID. NO. 49 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Strong expression was also observed in breast cancer samples (A-C 5) and weak expression in prostate cancer samples (A-H 6). Weaker expression was seen in normal tissues. These results confirm the upregulation of the gene expression for SEQ. ID. NO. 49 in malignant ovarian cancer;

FIG. 50 is a picture of the macroarray hybridization results showing the differential expression data for STAR selected ovarian cancer-related human SEQ. ID. NO. 50. The STAR dsDNA clone representing SEQ. ID. NO. 50 was labeled with $^{32}$P and hybridized to the macroarray. The hybridization results obtained confirm its upregulation in a majority of malignant ovarian cancer samples (A-F 2 and A-G 3-4) compared to LMP samples (A-F 1). Significant expression of this sequence was also evident in the seven (adrenal (A7), breast (B7), trachea (D7), placenta (F7), lung (A8), kidney (F8) and fallopian tube (F9)) of the 30 normal tissues;

FIG. 51 is a picture showing an example of STAR subtraction for the ovarian cancer samples. The housekeeping genes, GAPDH (Panel A) and 1'-actin (Panel B) were nicely subtracted for both LMP minus Malignant (SL133 to SL137) and Malignant minus LMP (SL123 to SL127) whereas, a known differentially expressed upregulated gene, CCNE1 (Panel C) in malignant ovarian tumors was not subtracted in Malignant minus LMP STAR libraries but instead, enriched (Lanes SL123 to SL127 compared to Lanes 6 to 10);

FIG. 52 is a picture showing the effect of shRNAs on the expression of endogenous genes encoded by SEQ. ID Nos. 1 and 3 in transfected TOV-21G cells. Two shRNAs per SEQ. ID. were transfected in TOV-21G ovarian cancer cell lines and monitored by RT-PCR using gene-specific primers. In each case, both shRNAs attenuated the expression of the genes;

FIG. 53 is a picture showing the effect of SEQ. ID.-specific shRNAs on the proliferation of TOV-21G cells. Decreased proliferation is indicative of a gene that, when attenuated, is required for normal growth of the cancer cells. The cells were stably transfected with two separate shRNA expression vectors and the proliferation of the cells was measured in an MTT assay. The positive control plasmid expresses a shRNA that has homology to no known gene in humans;

FIG. 54 is a picture showing SEQ. ID.-specific shRNAs on the survival of TOV-21G cells. Less staining is indicative of a gene that, when attenuated, is required for survival of the cancer cells in this assay. The cells were transiently transfected with two separate shRNA expression vectors and the remaining colonies were stained with crystal violet and photographed. The positive control plasmid expresses a shRNA that has homology to no known gene in humans;

Figure 55B:
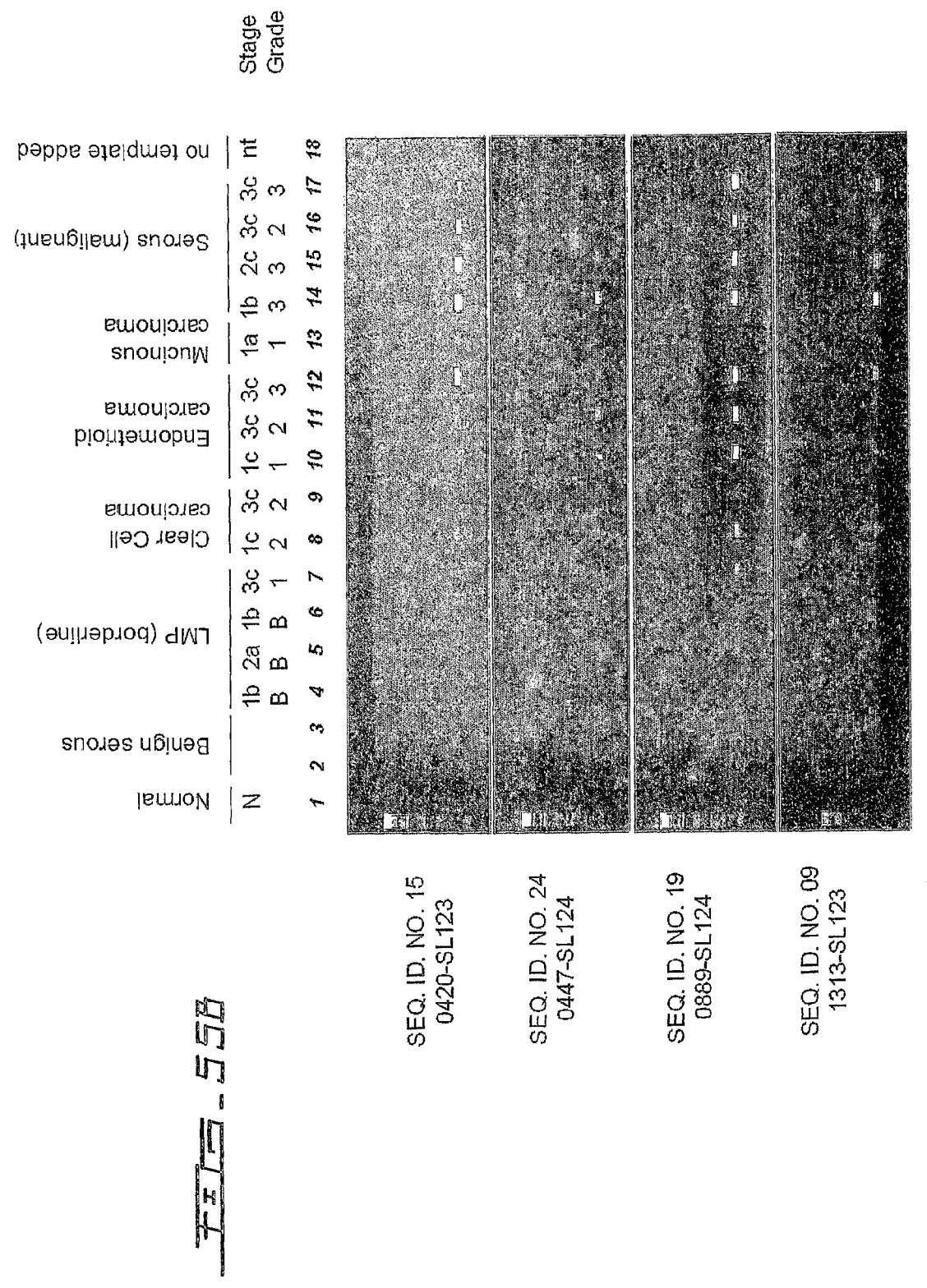

FIGS. 55A and 55B are pictures of RT-PCR data showing the differential expression data for STAR selected ovarian cancer-related human SEQ. ID. NO. 01, 09, 12, 15, 17, 19, 20 and 24. To further demonstrate that the STAR SEQ. ID. NOs, selected after macroarray analysis were upregulated in malignant ovarian cancer samples compared to LMPs and normal ovarian samples, semi-quantitative RT-PCR was performed for 25 cycles using HOTSTARTAQ polymerase according to the supplier instructions (Qiagen). Furthermore, these results serve to demonstrate the utility of these sequences as potential diagnostic, prognostic or theranostic markers for ovarian cancer. For SEQ. ID. NOs. 01, 09, 12, 15, 17, 19, 20 and 24, a specific primer pair for each was used. The differential expression results obtained for each SEQ. ID. NO. tested are shown in FIGS. 55A and 55B. As indicated by the expected PCR amplicon product for each SEQ. ID. NO., there is a clear tendency towards increased expression of the mRNAs corresponding to SEQ. ID. NOs. 01, 09, 12, 15, 17, 19, 20 and 24 in clear cell carcinoma (Lanes 8-9), late stage endometrioid (Lane 12) and different stages of malignant serous (Lanes 15-17) compared to normal (Lane 1), benign (Lanes 2-3) and LMPs (Lanes 4-7) ovarian samples. These results confirm the upregulation of the gene expression for SEQ. ID. NOs. 01, 09, 12, 15, 17, 19, 20 and 24 in the different stages of malignant ovarian cancer as was observed using the macroarrays;

Figure 56:
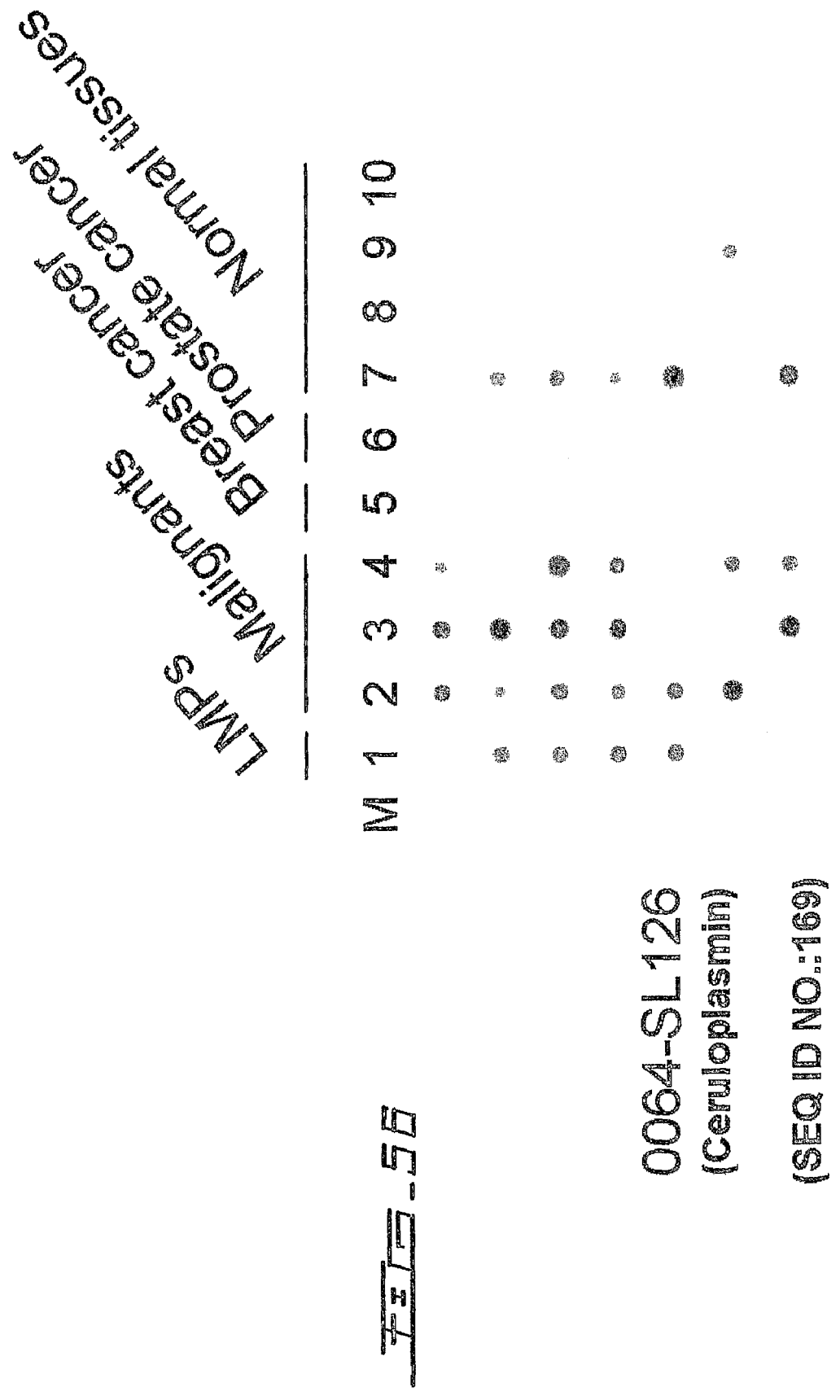

FIG. 56 is a picture of the macroarray hybridization results showing the differential expression data for STAR selected ovarian cancer-related human SEQ. ID. NO. 169. The STAR dsDNA clone representing SEQ. ID. NO. 169 was labeled with $^{32}$P and hybridized to the macroarray. The hybridization results obtained confirm its upregulation in malignant ovarian cancer samples (A-F 2 and A-G 3-4) compared to LMP samples (A-F 1). Weaker expression was seen in some normal tissues and strong expression was seen liver (E7) and aorta (G7). These results confirm the upregulation of the gene expression for SEQ. ID. NO. 169 in malignant ovarian cancer;

FIG. 57 is a picture of RT-PCR data showing the differential expression data for the STAR selected ovarian cancer-related human SEQ. ID. NO. 1 in RNA samples derived from the NCI-60 panel of cancer cell lines. A primer pair, OGS 1136 (GCTTAAAAGAGTCCTCCTGTGGC; SEQ. ID. NO. 171) and OGS 1044 (TGGACATTGTTCTTAAAGTGTGG; SEQ. ID. NO. 172) for SEQ. ID. NO. 1 was used to perform RT-PCR. As indicated by the expected PCR amplicon, increased expression of SEQ. ID. NO. 1 mRNA was evident in ovarian, renal, lung, colon, breast cancers and weaker expression was seen in melanoma samples;

FIG. 58 is a picture of RT-PCR data showing the differential expression data for the STAR selected ovarian cancer-related human SEQ. ID. NO. 2 in RNA samples derived from the NCI-60 panel of cancer cell lines. A primer pair, OGS 1250 (AGGTTTTATGGCCACCGTCAG; SEQ. ID. NO. 173) and OGS 1251 (ATCCTATACCGCTCGGTTATGC; SEQ. ID. NO. 174) for SEQ. ID. NO. 2 was used to perform RT-PCR. As indicated by the expected PCR amplicon, increased expression of SEQ. ID. NO. 2 mRNA was evident in all nine cancer types but weaker expression was seen in melanoma and leukemia samples;

FIG. 59 is a picture of RT-PCR data showing the differential expression data for the STAR selected ovarian cancer-related human SEQ. ID. NO. 3 in RNA samples derived from the NCI-60 panel of cancer cell lines. A primer pair, OGS 1049 (GGGCGGCGGCTCTTTCCTCCTC; SEQ. ID. NO. 175) and OGS 1050 (GCTAGCGGCCCCATACTCG; SEQ. ID. NO. 176) for SEQ. ID. NO. 3 was used to perform RT-PCR. As indicated by the expected PCR amplicon, increased expression of SEQ. ID. NO. 3 mRNA was evident in eight cancer types and absent in the leukemia samples;

FIG. 60 is a picture of RT-PCR data showing the differential expression data for the STAR selected ovarian cancer-related human SEQ. ID. NO. 4 in RNA samples derived from the NCI-60 panel of cancer cell lines. A primer pair, OGS 1051 (ACACTGGATGCCCTGAATGACACA; SEQ. ID. NO. 177) and OGS 1052 (GCTTTGGCCCTTTTTGCTAA; SEQ. ID. NO. 178) for SEQ. ID. NO. 4 was used to perform RT-PCR. As indicated by the expected PCR amplicon, increased expression of SEQ. ID. NO. 4 mRNA was evident in melanoma, ovarian, CNS, and lung cancers and weakly expressed in the leukemia samples;

FIG. 61 is a picture of RT-PCR data showing the differential expression data for the STAR selected ovarian cancer-related human SEQ. ID. NO. 5 in RNA samples derived from the NCI-60 panel of cancer cell lines. A primer pair, OGS 1252 (CCCACTTCTGTCTTACTGCATC; SEQ. ID. NO. 179) and OGS 1253 (CATAGTACTCCAGGGCTTATTC; SEQ. ID. NO. 180) for SEQ. ID. NO. 4 was used to to perform RT-PCR. As indicated by the expected PCR amplicon, increased expression of SEQ. ID. NO. 5 mRNA was evident all cancer types;

FIG. 62 is a picture of RT-PCR data showing the differential expression data for the STAR selected ovarian cancer-related human SEQ. ID. NO. 6 in RNA samples derived from the NCI-60 panel of cancer cell lines. A primer pair, OGS 1083 (AACGATTGCCCGGATTGATGACA; SEQ. ID. NO. 181) and OGS 1084 (TACTTGAGGCTGGGGTGG-GAGATG; SEQ. ID. NO. 182) for SEQ. ID. NO. 6 was used to perform RT-PCR. As indicated by the expected PCR amplicon, increased expression of SEQ. ID. NO. 6 mRNA was evident all cancer types;

FIG. 63 is a picture of RT-PCR data showing the differential expression data for the STAR selected ovarian cancer-related human SEQ. ID. NO. 7 in RNA samples derived from the NCI-60 panel of cancer cell lines. A primer pair, OGS 1053 (CACTACGCCAGGCACCCCCAAAAC; SEQ. ID. NO. 183) and OGS 1054 (CGAGGCGCACGGCAGTCT; SEQ. ID. NO. 184) for SEQ. ID. NO. 7 was used to perform RT-PCR. As indicated by the expected PCR amplicon, increased expression of SEQ. ID. NO. 7 mRNA was evident only in ovarian cancer samples;

FIG. 64 is a picture of RT-PCR data showing the differential expression data for the STAR selected ovarian cancer-related human SEQ. ID. NO. 8 in RNA samples derived from the NCI-60 panel of cancer cell lines. A primer pair, OGS 1037 (ATCCGTTGCTGCAGCTCGTTCCTC; SEQ. ID. NO. 185) and OGS 1038 (ACCCTGCTGACCTTCTTCCAT-TCC; SEQ. ID. NO. 186) for SEQ. ID. NO. 8 was used to perform RT-PCR. As indicated by the expected PCR amplicon, increased expression of SEQ. ID. NO. 8 mRNA was evident in all cancer types;

FIG. 65 is a picture of RT-PCR data showing the differential expression data for the STAR selected ovarian cancer-related human SEQ. ID. NO. 9 in RNA samples derived from the NCI-60 panel of cancer cell lines. A primer pair, OGS 1045 (TCGGAGGAGGGCTGGCTGGTGTTT; SEQ. ID. NO. 187) and OGS 1046 (CTTGGGCGTCTTGGAGCGGT-TCTG; SEQ. ID. NO. 188) for SEQ. ID. NO. 9 was used to perform RT-PCR. As indicated by the expected PCR amplicon, (lower band on the gel; the top band is an artifact of the PCR reaction) increased expression of SEQ. ID. NO. 9 mRNA was evident in ovarian, lung, colon, breast cancer, and melanoma and weakly expressed in leukemia and CNS cancer;

FIG. 66 is a picture of RT-PCR data showing the differential expression data for the STAR selected ovarian cancer-related human SEQ. ID. NO. 10 in RNA samples derived from the NCI-60 panel of cancer cell lines. A primer pair, OGS 1240 (AGAGCCTATTGAAGATGAACAG; SEQ. ID. NO. 189) and OGS 1241 (TGATTGCCCCGGATCCTCTTAGG; SEQ. ID. NO. 190) for SEQ. ID. NO. 10 was used to perform RT-PCR. As indicated by the expected PCR amplicon, increased expression of SEQ. ID. NO. 10 mRNA was evident in all cancer types;

FIG. 67 is a picture of RT-PCR data showing the differential expression data for the STAR selected ovarian cancer-related human SEQ. ID. NO. 11 in RNA samples derived from the NCI-60 panel of cancer cell lines. A primer pair, OGS 1304 (GGACAAATACGACGACGAGG; SEQ. ID. NO. 191) and OGS 1305 (GGTTTCTTGGGTAGTGGGC; SEQ. ID. NO. 192) for SEQ. ID. NO. 11 was used to perform RT-PCR. As indicated by the expected PCR amplicon, increased expression of SEQ. ID. NO. 11 mRNA was evident in all cancer types;

FIG. 68 is a picture of RT-PCR data showing the differential expression data for the STAR selected ovarian cancer-related human SEQ. ID. NO. 12 in RNA samples derived from the NCI-60 panel of cancer cell lines. A primer pair, OGS 1039 (CCCCGGAGAAGGAAGAGCAGTA; SEQ. ID. NO. 193) and OGS 1040 (CGAAAGCCGGCAGTTAGTTATTGA; SEQ. ID. NO. 194) for SEQ. ID. NO. 12 was used to perform RT-PCR. As indicated by the expected PCR amplicon, increased expression of SEQ. ID. NO. 12 mRNA was evident in all cancer types but weakly in CNS cancer and leukemia;

FIG. 69 is a picture of RT-PCR data showing the differential expression data for the STAR selected ovarian cancer-related human SEQ. ID. NO. 13 in RNA samples derived from the NCI-60 panel of cancer cell lines. A primer pair, OGS 1095 (GGCGGGCAACGAATTCCAGGTGTC; SEQ. ID. NO. 195) and OGS 1096 (TCAGAGGTTCGTCGCATTTGTCCA; SEQ. ID. NO. 196) for SEQ. ID. NO. 13 was used to perform RT-PCR. As indicated by the expected PCR amplicon, increased expression of SEQ. ID. NO. 13 mRNA was evident in all cancer types;

FIG. 70 is a picture of RT-PCR data showing the differential expression data for the STAR selected ovarian cancer-related human SEQ. ID. NO. 15 in RNA samples derived from the NCI-60 panel of cancer cell lines. A primer pair, OGS 1284 (CAACAGTCATGATGTGTGGATG; SEQ. ID. NO. 197) and OGS 1285 (ACTGCACCTTGTCCGTGTTGAC; SEQ. ID. NO. 198) for SEQ. ID. NO. 15 was used to perform RT-PCR. As indicated by the expected PCR amplicon, increased expression of SEQ. ID. NO. 15 mRNA was evident in ovarian, prostate, lung, colon, and breast cancer;

FIG. 71 is a picture of RT-PCR data showing the differential expression data for the STAR selected ovarian cancer-related human SEQ. ID. NO. 16 in RNA samples derived from the NCI-60 panel of cancer cell lines. A primer pair, OGS 1063 (CCGGCTGGCTGCTTTGTTTA; SEQ. ID. NO. 199) and OGS 1064 (ATGATCAGCAGGTTCGTTGGTAGG; SEQ. ID. NO. 200) for SEQ. ID. NO. 16 was used to perform RT-PCR. As indicated by the expected PCR amplicon, increased expression of SEQ. ID. NO. 16 mRNA was evident in ovarian, lung, colon, and breast cancer;

FIG. 72 is a picture of RT-PCR data showing the differential expression data for the STAR selected ovarian cancer-related human SEQ. ID. NO. 17 in RNA samples derived from the NCI-60 panel of cancer cell lines. A primer pair, OGS 1031 (ATGCCGGAAGTGAATGTGG; SEQ. ID. NO. 201) and OGS 1032 (GGTGACTCCGCCTTTTGAT; SEQ. ID. NO. 202) for SEQ. ID. NO. 17 was used to perform RT-PCR. As indicated by the expected PCR amplicon, increased expression of SEQ. ID. NO. 17 mRNA was evident in ovarian, renal, lung, colon, and breast cancer but weakly in CNS cancer;

FIG. 73 is a picture of RT-PCR data showing the differential expression data for the STAR selected ovarian cancer-related human SEQ. ID. NO. 18 in RNA samples derived from the NCI-60 panel of cancer cell lines. A primer pair, OGS 1308 (ACATTCGCTTCTCCATCTGG; SEQ. ID. NO. 203) and OGS 1309 (TGTCACGGAAGGGAACCAGG; SEQ. ID. NO. 204) for SEQ. ID. NO. 18 was used to perform RT-PCR. As indicated by the expected PCR amplicon, increased expression of SEQ. ID. NO. 18 mRNA was evident in all cancer types;

FIG. 74 is a picture of RT-PCR data showing the differential expression data for the STAR selected ovarian cancer-related human SEQ. ID. NO. 19 in RNA samples derived from the NCI-60 panel of cancer cell lines. A primer pair, OGS 1069 (ACGCTGCCTCTGGGTCACTT; SEQ. ID. NO. 205) and OGS 1070 (TTGGCAAATCAATGGCTTGTAAT; SEQ. ID. NO. 206) for SEQ. ID. NO. 19 was used to perform RT-PCR. As indicated by the expected PCR amplicon, increased expression of SEQ. ID. NO. 19 mRNA was evident in all cancer types;

FIG. 75 is a picture of RT-PCR data showing the differential expression data for the STAR selected ovarian cancer-related human SEQ. ID. NO. 20 in RNA samples derived from the NCI-60 panel of cancer cell lines. A primer pair, OGS 1061 (ATGGCTTGGGTCATCAGGAC; SEQ. ID. NO. 207) and OGS 1062 (GTGTCACTGGGCGTAAGATACTG; SEQ. ID. NO. 208) for SEQ. ID. NO. 20 was used to perform RT-PCR. As indicated by the expected PCR amplicon, increased expression of SEQ. ID. NO. 20 mRNA was evident in all cancer types but weakly in breast and colon cancer;

FIG. 76 is a picture of RT-PCR data showing the differential expression data to for the STAR selected ovarian cancer-related human SEQ. ID. NO. 21 in RNA samples derived from the NCI-60 panel of cancer cell lines. A primer pair, OGS 1097 (CACCAAATCAGCTGCTACTACTCC; SEQ. ID. NO. 209) and OGS 1098 (GATAAACCCCAAAGCAGAAAGATT; SEQ. ID. NO. 210) for SEQ. ID. NO. 21 was used to perform RT-PCR. As indicated by the expected PCR amplicon, increased expression of SEQ. ID. NO. 21 mRNA was evident in all cancer types but weakly in leukemia;

FIG. 77 is a picture of RT-PCR data showing the differential expression data for the STAR selected ovarian cancer-related human SEQ. ID. NO. 22 in RNA samples derived from the NCI-60 panel of cancer cell lines. A primer pair, OGS 1075 (CGAGATTCCGTGGGCGTAGG; SEQ. ID. NO. 211) and OGS 1076 (TGAGTGGGAGCTTCGTAGG; SEQ. ID. NO. 212) for SEQ. ID. NO. 22 was used to perform RT-PCR. As indicated by the expected PCR amplicon, increased expression of SEQ. ID. NO. 22 mRNA was evident in ovarian, lung, breast, and CNS cancer. Another larger transcript was weakly expressed in colon and renal cancer ion addition to melanoma;

FIG. 78 is a picture of RT-PCR data showing the differential expression data for the STAR selected ovarian cancer-related human SEQ. ID. NO. 23 in RNA samples derived from the NCI-60 panel of cancer cell lines. A primer pair, OGS 1232 (TCAGAGTGGACGTTGGATTAC; SEQ. ID. NO. 213) and OGS 1233 (TGCTTGAAATGTAGGAGAACA; SEQ. ID. NO. 214) for SEQ. ID. NO. 23 was used to perform RT-PCR. As indicated by the expected PCR amplicon, increased expression of SEQ. ID. NO. 23 mRNA was evident in all cancer types;

FIG. 79 is a picture of RT-PCR data showing the differential expression data for the STAR selected ovarian cancer-related human SEQ. ID. NO. 24 in RNA samples derived from the NCI-60 panel of cancer cell lines. A primer pair, OGS 1067 (GAGGGGCATCAATCACACCGAGAA; SEQ. ID. NO. 215) and OGS 1068 (CCCCACCGCCCACCCATT-TAGG; SEQ. ID. NO. 216) for SEQ. ID. NO. 24 was used to perform RT-PCR. As indicated by the expected PCR amplicon, increased expression of SEQ. ID. NO. 24 mRNA was evident in ovarian, renal, lung, colon, breast cancer, and melanoma but weakly in CNS cancer and leukemia;

FIG. 80 is a picture of RT-PCR data showing the differential expression data for the STAR selected ovarian cancer-related human SEQ. ID. NO. 25 in RNA samples derived from the NCI-60 panel of cancer cell lines. A primer pair, OGS 1099 (GGGGGCACCAGAGGCAGTAA; SEQ. ID. NO. 217) and OGS 1100 (GGTTGTGGCGGGGGCAGT-TGTG; SEQ. ID. NO. 218) for SEQ. ID. NO. 25 was used to perform RT-PCR. As indicated by the expected PCR amplicon, increased expression of SEQ. ID. NO. 25 mRNA was evident in all cancer types but weakly in leukemia;

FIG. 81 is a picture of RT-PCR data showing the differential expression data for the STAR selected ovarian cancer-related human SEQ. ID. NO. 26 in RNA samples derived from the NCI-60 panel of cancer cell lines. A primer pair, OGS 1246 (ACAGACTCCTGTACTGCAAACC; SEQ. ID. NO. 219) and OGS 1247 (TACCGGTTCGTCCTCTTCCTC; SEQ. ID. NO. 220) for SEQ. ID. NO. 26 was used to perform RT-PCR. As indicated by the expected PCR amplicon, increased expression of SEQ. ID. NO. 26 mRNA was evident in all cancer types;

FIG. 82 is a picture of RT-PCR data showing the differential expression data for the STAR selected ovarian cancer-related human SEQ. ID. NO. 27 in RNA samples derived from the NCI-60 panel of cancer cell lines. A primer pair, OGS 1093 (GAAGTTCCTCACGCCCTGCTATC; SEQ. ID. NO. 221) and OGS 1094 (CTGGCTGGTGACCT-GCTTTGAGTA; SEQ. ID. NO. 222) for SEQ. ID. NO. 27 was used to perform RT-PCR. As indicated by the expected PCR amplicon, increased expression of SEQ. ID. NO. 27 mRNA was evident in all cancer types;

FIG. 83 is a picture of RT-PCR data showing the differential expression data for the STAR selected ovarian cancer-related human SEQ. ID. NO. 28 in RNA samples derived from the NCI-60 panel of cancer cell lines. A primer pair, OGS 1332 (TAGGCGCGCCTGACATACAGCAATGC-CAGTT; SEQ. ID. NO. 223) and OGS 1333 (TAAGAAT-GCGGCCGCGCCACATCTTGAACACTTTGC; SEQ. ID. NO. 224) for SEQ. ID. NO. 28 was used to perform RT-PCR. As indicated by the expected PCR amplicon, increased expression of SEQ. ID. NO. 28 mRNA was evident in ovarian, prostate, and renal cancer but weakly in all other types;

FIG. 84 is a picture of RT-PCR data showing the differential expression data for the STAR selected ovarian cancer-related human SEQ. ID. NO. 29 in RNA samples derived from the NCI-60 panel of cancer cell lines. A primer pair, OGS 1101 (TGGGGAGGAGTTTGAGGAGCAGAC; SEQ. ID. NO. 225) and OGS 1102 (GTGGGACG-GAGGGGGCAGTGAAG; SEQ. ID. NO. 226) for SEQ. ID. NO. 29 was used to perform RT-PCR. As indicated by the expected PCR amplicon, increased expression of SEQ. ID. NO. 29 mRNA was evident in ovarian, renal, lung, colon, and breast cancer but weakly in CNS cancer and melanoma;

FIG. 85 is a picture of RT-PCR data showing the differential expression data for the STAR selected ovarian cancer-related human SEQ. ID. NO. 30 in RNA samples derived from the NCI-60 panel of cancer cell lines. A primer pair, OGS 1300 (GCAACTATTCGGAGCGCGTG; SEQ. ID. NO. 227) and OGS 1301 (CCAGCAGCTTGTTGAGCTCC; SEQ. ID. NO. 228) for SEQ. ID. NO. 30 was used to perform RT-PCR. As indicated by the expected PCR amplicon, increased expression of SEQ. ID. NO. 30 mRNA was evident in all cancer types;

FIG. 86 is a picture of RT-PCR data showing the differential expression data for the STAR selected ovarian cancer-related human SEQ. ID. NO. 31 in RNA samples derived from the NCI-60 panel of cancer cell lines. A primer pair, OGS 1302 (GGAGGAGCTAAGCGTCATCGC; SEQ. ID. NO. 229) and OGS 1303 (TCGCTTCAGCGCGTAGACC; SEQ. ID. NO. 230) for SEQ. ID. NO. 31 was used to perform RT-PCR. As indicated by the expected PCR amplicon, increased expression of SEQ. ID. NO. 31 mRNA was evident in all cancer types;

FIG. 87 is a picture of RT-PCR data showing the differential expression data for the STAR selected ovarian cancer-related human SEQ. ID. NO. 32 in RNA samples derived from the NCI-60 panel of cancer cell lines. A primer pair, OGS 1077 (GCGTCCGGGCCTGTCTTCAACCT; SEQ. ID. NO. 153) and OGS 1078 (GCCCCACCCTCTAC-CCCACCACTA; SEQ. ID. NO. 154) for SEQ. ID. NO. 32 was used to perform RT-PCR. As indicated by the expected PCR amplicon, increased expression of SEQ. ID. NO. 32 mRNA was evident in ovarian cancer and melanoma but weaker expression was detectable in CNS, breast, colon, lung, and renal cancer;

FIG. 88 is a picture of RT-PCR data showing the differential expression data for the STAR selected ovarian cancer-related human SEQ. ID. NO. 33 in RNA samples derived from the NCI-60 panel of cancer cell lines. A primer pair, OGS 1292 (TATTAGTTGGGATGGTGGTAGCAC; SEQ. ID. NO. 231) and OGS 1294 (GAGAATTCGAGTCGAC-GATGAC; SEQ. ID. NO. 232) for SEQ. ID. NO. 33 was used to perform RT-PCR. As indicated by the expected PCR amplicon, increased expression of SEQ. ID. NO. 33 mRNA was evident only in ovarian cancer samples;

FIG. 89 is a picture of RT-PCR data showing the differential expression data for the STAR selected ovarian cancer-related human SEQ. ID. NO. 34 in RNA samples derived from the NCI-60 panel of cancer cell lines. A primer pair, OGS 1242 (GAAATTGTGTTGACGCAGTCTCC; SEQ. ID. NO. 233) and OGS 1243 (AGGCACACAACAGAG-GCAGTTC; SEQ. ID. NO. 234) for SEQ. ID. NO. 34 was used to perform RT-PCR. As indicated by the expected PCR amplicon, increased expression of SEQ. ID. NO. 34 mRNA was evident only in ovarian cancer samples;

FIG. 90 is a picture of RT-PCR data showing the differential expression data for the STAR selected ovarian cancer-related human SEQ. ID. NO. 35 in RNA samples derived from the NCI-60 panel of cancer cell lines. A primer pair, OGS 1141 (GAGATCCTGATCAAGGTGCAGG; SEQ. ID. NO. 155) and OGS 1142 (TGCACGCTCACAGCAGT-CAGG; SEQ. ID. NO. 156) for SEQ. ID. NO. 35 was used to perform RT-PCR. As indicated by the expected PCR amplicon, increased expression of SEQ. ID. NO. 35 mRNA was evident in ovarian, lung and breast cancer, but weakly in colon and CNS cancer;

FIG. 91 is a picture of RT-PCR data showing the differential expression data for the STAR selected ovarian cancer-related human SEQ. ID. NO. 36 in RNA samples derived from the NCI-60 panel of cancer cell lines. A primer pair, OGS 1280 (GTACATCAACCTCCTGCTGTCC; SEQ. ID. NO. 235) and OGS 1281 (GACATCTCCAAGTCCCAG-CATG; SEQ. ID. NO. 236) for SEQ. ID. NO. 36 was used to perform RT-PCR. As indicated by the expected PCR amplicon, increased expression of SEQ. ID. NO. 36 mRNA was evident in all cancer types;

FIG. 92 is a picture of RT-PCR data showing the differential expression data for the STAR selected ovarian cancer-related human SEQ. ID. NO. 37 in RNA samples derived from the NCI-60 panel of cancer cell lines. A primer pair, OGS 1159 (AGTCTCTCACTGTGCCTTATGCC; SEQ. ID. NO. 237) and OGS 1160 (AGTCCTAAGAACTGTAAACG; SEQ. ID. NO. 238) for SEQ. ID. NO. 37 was used to perform RT-PCR. As indicated by the expected PCR amplicon, increased expression of SEQ. ID. NO. 37 mRNA was evident only in ovarian and renal cancer;

FIG. 93 is a picture of RT-PCR data showing the differential expression data for the STAR selected ovarian cancer-related human SEQ. ID. NO. 38 in RNA samples derived from the NCI-60 panel of cancer cell lines. A primer pair, OGS 1202 (AACATGACTAAGATGCCCAACC; SEQ. ID. NO. 157) and OGS 1203 (AATCTCCTTCACCTCCAC-TACTG; SEQ. ID. NO. 158) for SEQ. ID. NO. 38 was used to perform RT-PCR. As indicated by the expected PCR amplicon, increased expression of SEQ. ID. NO. 38 mRNA was evident in all cancer types;

FIG. 94 is a picture of RT-PCR data showing the differential expression data for the STAR selected ovarian cancer-related human SEQ. ID. NO. 39 in RNA samples derived from the NCI-60 panel of cancer cell lines. A primer pair, OGS 1310 (CATCTATACGTGGATTGAGGA; SEQ. ID. NO. 239) and OGS 1311 (ATAGGTACCAGGTAT-GAGCTG; SEQ. ID. NO. 240) for SEQ. ID. NO. 39 was used to perform RT-PCR. As indicated by the expected PCR amplicon, increased expression of SEQ. ID. NO. 39 mRNA was evident in all cancer types;

FIG. 95 is a picture of RT-PCR data showing the differential expression data for the STAR selected ovarian cancer-related human SEQ. ID. NO. 40 in RNA samples derived from the NCI-60 panel of cancer cell lines. A primer pair, OGS 1155 (TGTCCACATCATCATCGTCATCC; SEQ. ID. NO. 241) and OGS 1156 (TGTCACTGGTCGGTCGCT-GAGG; SEQ. ID. NO. 242) for SEQ. ID. NO. 39 was used to perform RT-PCR. As indicated by the expected PCR amplicon, increased expression of SEQ. ID. NO. 39 mRNA was evident in all cancer types;

FIG. 96 is a picture of RT-PCR data showing the differential expression data for the STAR selected ovarian cancer-related human SEQ. ID. NO. 41 in RNA samples derived from the NCI-60 panel of cancer cell lines. A primer pair, OGS 1212 (AAGCATAGCCATAGGTGATTGG; SEQ. ID. NO. 159) and OGS 1213 (ACAGGTATCAGACAAGGGAG-CAG; SEQ. ID. NO. 160) for SEQ. ID. NO. 41 was used to perform RT-PCR. As indicated by the expected PCR amplicon, increased expression of SEQ. ID. NO. 41 mRNA was evident only in ovarian and renal cancer and leukemia;

FIG. 97 is a picture of RT-PCR data showing the differential expression data for the STAR selected ovarian cancer-related human SEQ. ID. NO. 42 in RNA samples derived from the NCI-60 panel of cancer cell lines. A primer pair, OGS 1316 (CATGGGGCTTAAGATGTC; SEQ. ID. NO. 243) and OGS 1317 (GTCGATTTCTCCATCATCTG; SEQ. ID. NO. 244) for SEQ. ID. NO. 42 was used to perform RT-PCR. As indicated by the expected PCR amplicon, increased expression of SEQ. ID. NO. 42 mRNA was evident in all cancer types;

FIG. 98 is a picture of RT-PCR data showing the differential expression data for the STAR selected ovarian cancer-related human SEQ. ID. NO. 43 in RNA samples derived from the NCI-60 panel of cancer cell lines. A primer pair, OGS 1306 (AAGAGGCGCTCTACTAGCCG; SEQ. ID. NO. 245) and OGS 1307 (CTTTCCACATGGAACACAGG; SEQ. ID. NO. 246) for SEQ. ID. NO. 43 was used to perform RT-PCR. As indicated by the expected PCR amplicon, increased expression of SEQ. ID. NO. 43 mRNA was evident in all cancer types;

FIG. 99 is a picture of RT-PCR data showing the differential expression data for the STAR selected ovarian cancer-related human SEQ. ID. NO. 44 in RNA samples derived from the NCI-60 panel of cancer cell lines. A primer pair, OGS 1171 (TTACGACCTATTTCTCCGTGG; SEQ. ID. NO. 161) and OGS 1172 (AATGCAATAATTGGC-CACTGC; SEQ. ID. NO. 162) for SEQ. ID. NO. 44 was used to perform RT-PCR. As indicated by the expected PCR amplicon, increased expression of SEQ. ID. NO. 44 mRNA was evident in all cancer types;

FIG. 100 is a picture of RT-PCR data showing the differential expression data for the STAR selected ovarian cancer-related human SEQ. ID. NO. 45 in RNA samples derived from the NCI-60 panel of cancer cell lines. A primer pair, OGS 1175 (ACACATCAAACTGCTTATCCAGG; SEQ. ID. NO. 163) and OGS 1176 (ACTGATGTGAAAATGCA-CATCC; SEQ. ID. NO. 164) for SEQ. ID. NO. 45 was used to perform RT-PCR. As indicated by the expected PCR amplicon, increased expression of SEQ. ID. NO. 45 mRNA was evident only in ovarian cancer samples;

FIG. 101 is a picture of RT-PCR data showing the differential expression data for the STAR selected ovarian cancer-related human SEQ. ID. NO. 46 in RNA samples derived from the NCI-60 panel of cancer cell lines. A primer pair, OGS 1286 (CATTTTCCTGGAATTTGATACAG; SEQ. ID. NO. 247) and OGS 1287 (GTAGAGAGTTTATTTGGGC-CAAG; SEQ. ID. NO. 248) for SEQ. ID. NO. 46 was used to perform RT-PCR. As indicated by the expected PCR amplicon, increased expression of SEQ. ID. NO. 46 mRNA was evident in all cancer types;

FIG. 102 is a picture of RT-PCR data showing the differential expression data for the STAR selected ovarian cancer-related human SEQ. ID. NO. 47 in RNA samples derived from the NCI-60 panel of cancer cell lines. A primer pair, OGS 1244 (CATCTATGGTAACTACAATCG; SEQ. ID. NO. 249) and OGS 1245 (GTAGAAGTCACTGATCAGA-CAC; SEQ. ID. NO. 250) for SEQ. ID. NO. 47 was used to perform RT-PCR. As indicated by the expected PCR amplicon, increased expression of SEQ. ID. NO. 47 mRNA was evident only in ovarian cancer;

FIG. 103 is a picture of RT-PCR data showing the differential expression data for the STAR selected ovarian cancer-related human SEQ. ID. NO. 48 in RNA samples derived from the NCI-60 panel of cancer cell lines. A primer pair, OGS 1282 (ATGGCTCATACAGCACTCAGG; SEQ. ID. NO. 165) and OGS 1283 (GAACTGTCACTCCG-GAAAGCCT; SEQ. ID. NO. 166) for SEQ. ID. NO. 48 was used to perform RT-PCR. As indicated by the expected PCR amplicon, increased expression of SEQ. ID. NO. 48 mRNA was evident in all cancer types;

FIG. 104 is a picture of RT-PCR data showing the differential expression data for the STAR selected ovarian cancer-related human SEQ. ID. NO. 50 in RNA samples derived from the NCI-60 panel of cancer cell lines. A primer pair, OGS 1035 (CTGCCTGCCAACCTTTCCATTTCT; SEQ. ID. NO. 251) and OGS 1036 (TGAGCAGCCACAGCAG-CATTAGG; SEQ. ID. NO. 252) for SEQ. ID. NO. 50 was used to perform RT-PCR. As indicated by the expected PCR amplicon, increased expression of SEQ. ID. NO. 50 mRNA was evident in all cancer types but weak in CNS cancer and leukemia, and;

FIG. 105 is a picture of RT-PCR data showing the differential expression data for the STAR selected ovarian cancer-related human SEQ. ID. NO. 169 in RNA samples derived from the NCI-60 panel of cancer cell lines. A primer pair, OGS 1248 (CACCTGATCAGGTGGATAAGG; SEQ. ID. NO. 253) and OGS 1249 (TCCCAGGTAGAAGGTG-GAATCC; SEQ. ID. NO. 254) for SEQ. ID. NO. 169 was used to perform RT-PCR. As indicated by the expected PCR amplicon, increased expression of SEQ. ID. NO. 169 mRNA was evident in ovarian, renal, and lung cancer but weak in CNS cancer.

DESCRIPTION OF ILLUSTRATIVE EMBODIMENTS

The applicant employed a carefully planned strategy to identify and isolate genetic sequences involved in ovarian cancer. The process involved the following steps: 1) preparation of highly representative cDNA libraries using mRNA isolated from LMPs and malignant ovarian cancer samples of human origin; 2) isolation of sequences upregulated in the malignant ovarian cancer samples; 3) identification and characterization of upregulated sequences; 4) selection of upregulated sequences for tissue specificity; 5) determination of knock-down effects on ovarian cancer cell line proliferation and migration; and 6) determination of the expression pattern of each upregulated sequence in samples derived from nine different cancer types. The results discussed in this disclosure demonstrate the advantage of targeting ovarian cancer-related genes that are highly specific to this differentiated cell type compared to normal tissues and provide a more efficient screening method when studying the genetic basis of diseases and disorders. Polynucleotide and/or polypeptide sequences that are known but have not had a role assigned to them until the present disclosure have also been isolated and shown to have a critical role in ovarian cancer cell line proliferation and migration. Finally, novel polynucleotide and/or polypeptide sequences have been identified that play a role as well.

The present invention is illustrated in further details below in a non-limiting fashion.

A—Material and Methods

Commercially available reagents referred to in the present disclosure were used according to supplier's instructions unless otherwise indicated. Throughout the present disclosure certain starting materials were prepared as follows:

B—Preparation of LMP and Malignant Ovarian Cancer Cells

LMP and malignant ovarian tumor samples were selected based on histopathology to identify the respective stage and grade (Table B). LMP was chosen instead of normal ovarian tissue to avoid genes that associated with proliferation due to ovulation. Also very few cells would have been recovered and stromal cells would have been a major contaminant. LMP and serous (most common) ovarian tumors represent the extremes of tumorigenicity, differentiation and invasion. Once the sample were selected, total RNA was extracted with TRIZOL (InVitrogen, Grand Island, N.Y.) after the tissues were homogenized. The quality of the RNA was assessed using a 2100 Bioanalyzer (Agilent Technologies, Palo Alto, Calif.)

TABLE B shows the pathologies including grade and stage of the different ovarian cancer samples used on the macroarrays.

| MF Code No. | Pathologies | Symbol | Stage | Grade | Position on Macroarray |
|---|---|---|---|---|---|
| 15 | Borderline serous | B | 1b | B | A1 |
| 16 | Borderline serous | B | 2a | B | B1 |
| 17 | Borderline/carcinoma serous | B/CS | 3c | 1 | F1 |
| 18 | Borderline serous | B | 3c | B | C1 |
| 19 | Borderline serous | B | 1b | B | D1 |
| 20 | Borderline serous | B | 1a | B | E1 |
| 42 | Carcinoma serous of the surface | CSS | 3a | 3 | A4 |
| 22 | Carcinoma serous | CS | 1b | 3 | A2 |
| 30 | Carcinoma serous | CS | 2c | 3 | E2 |
| 23 | Carcinoma serous | CS | 3c | 3 | F2 |
| 25 | Carcinoma serous | CS | 3c | 3 | B2 |
| 26 | Carcinoma serous | CS | 3c | 3 | A3 |
| 27 | Carcinoma serous | CS | 3c | 3 | C2 |
| 28 | Carcinoma serous | CS | 3c | 3 | D2 |
| 43 | Carcinoma serous | CS | 3c | 3 | B4 |
| 45 | Carcinoma serous | CS | 3c | 3 | D4 |
| 49 | Carcinoma serous | CS | 3c | 2 | F4 |
| 41 | Carcinoma endometrioide | CE | 3b | 3 | G3 |
| 40 | Carcinoma endometrioide | CE | 3c | 3 | F3 |
| 44 | Carcinoma endometrioide | CE | 3c | 3 | C4 |
| 39 | Carcinoma endometrioide | CE | 3c | 2 | E3 |
| 50 | Carcinoma endometrioide | CE | 1c | 1 | G4 |
| 46 | Carcinoma endometrioide | CE | 1a | 2 | E4 |
| 34 | Clear cell carcinoma | CCC | 3c | 2 | B3 |
| 38 | Clear cell carcinoma | CCC | 3c | 3 | D3 |
| 37 | Clear cell carcinoma | CCC | 1c | 2 | C3 |

C—Method of Isolating Differentially Expressed mRNA

Key to the discovery of differentially expressed sequences unique to malignant ovarian cancer is the use of the applicant's patented STAR technology (Subtractive Transcription-based Amplification of mRNA; U.S. Pat. No. 5,712,127 Malek et al., 1998). Based on this procedure, mRNA isolated from malignant ovarian tumor sample is used to prepare "tester RNA", which is hybridized to complementary single-stranded "driver DNA" prepared from mRNA from LMP sample and only the un-hybridized "tester RNA" is recovered, and used to create cloned cDNA libraries, termed "subtracted libraries". Thus, the "subtracted libraries" are enriched for differentially expressed sequences inclusive of rare and novel mRNAs often missed by micro-array hybridization analysis. These rare and novel mRNA are thought to be representative of important gene targets for the development of better diagnostic and therapeutic strategies.

The clones contained in the enriched "subtracted libraries" are identified by DNA sequence analysis and their potential function assessed by acquiring information available in public databases (NCBI and GeneCard). The non-redundant clones are then used to prepare DNA micro-arrays, which are used to quantify their relative differential expression patterns by hybridization to fluorescent cDNA probes. Two classes of cDNA probes may be used, those which are generated from either RNA transcripts prepared from the same subtracted libraries (subtracted probes) or from mRNA isolated from different ovarian LMP and malignant samples (standard probes). The use of subtracted probes provides increased sensitivity for detecting the low abundance mRNA sequences that are preserved and enriched by STAR. Furthermore, the specificity of the differentially expressed sequences to malignant ovarian cancer is measured by hybridizing radio-labeled probes prepared from each selected sequence to macroarrays containing RNA from different LMP and malignant ovarian cancer samples and different normal human tissues.

A major challenge in gene expression profiling is the limited quantities of RNA available for molecular analysis. The amount of RNA isolated from many human specimens (needle aspiration, laser capture micro-dissection (LCM) samples and transfected cultured cells) is often insufficient for preparing: 1) conventional tester and driver materials for STAR; 2) standard cDNA probes for DNA micro-array analysis; 3) RNA macroarrays for testing the specificity of expression; 4) Northern blots and; 5) full-length cDNA clones for further biological validation and characterization etc. Thus, the applicant has developed a proprietary technology called RAMP (RNA Amplification Procedure) (U.S. patent application Ser. No. 11/000,958 published under No. US 200510153333A1 on Jul. 14, 2005 and entitled "Selective Terminal Tagging of Nucleic Acids"), which linearly amplifies the mRNA contained in total RNA samples yielding microgram quantities of amplified RNA sufficient for the various analytical applications. The RAMP RNA produced is largely full-length mRNA-like sequences as a result of the proprietary method for adding a terminal sequence tag to the 3'-ends of single-stranded cDNA molecules, for use in linear transcription amplification. Greater than 99.5% of the sequences amplified in RAMP reactions show <2-fold variability and thus, RAMP provides unbiased RNA samples in quantities sufficient to enable the discovery of the unique mRNA sequences involved in ovarian cancer.

D—Preparation of Human Malignant Ovarian Cancer Subtracted Library

Total RNA from five human ovarian LMP samples (MF-15, -16, -18, -19 and 20) (Table B) and five malignant ovarian cancer samples (MF-22, -25, -27, -28 and 30) (Table B) (CHUM, Montreal, QC) were prepared as described above. Following a slight modification of the teachings of Malek et al., 1998 (U.S. Pat. No. 5,712,127) i.e., preparation of the cDNA libraries on the paramagnetic beads as described below), 1 µg of total RNA from each sample were used to prepare highly representative cDNA libraries on streptavidin-coated paramagnetic beads (InVitrogen, Grand Island, N.Y.) for preparing tester and driver materials. In each case, first-strand cDNA was synthesized using an oligo $dT_{11}$ primer with 3' locking nucleotides (e.g., A, G or C), a 5'-biotin moiety and containing a Not I recognition site (OGS 364: SEQ. ID. NO. 90) Next, second-strand cDNA synthesis was performed according to the manufacturer's procedure for double-stranded cDNA synthesis (Invitrogen, Burlington, ON) and the resulting double-stranded cDNA ligated to linkers containing an Asc I recognition site (New England Biolabs, Pickering, ON). The double-stranded cDNAs were then digested with Asc I and Not I restriction enzymes (New England Biolabs, Pickering, ON), purified from the excess linkers using the cDNA fractionation column from Invitrogen (Burlington, ON) as specified by the manufacturer. Each sample was equally divided and ligated separately to specialized oligonucleotide promoter tags, TAG1 (OGS 594 and 595: SEQ. ID. NO: 91 and SEQ. ID. NO:92) and TAG2 (OGS458 and 459: SEQ. ID. NO:93 and SEQ. ID. NO:94) used for preparing tester and driver materials, respectively. Thereafter, each ligated cDNA was purified by capturing on the streptavidin beads as described by the supplier (InVitrogen, Grand Island, N.Y.), and transcribed in vitro with T7 RNA polymerase (Ambion, Austin, Tex.).

Next, in order to prepare 3'-represented tester and driver libraries, a 10-µg aliquot of each of the in vitro synthesized RNA was converted to double-stranded cDNA by performing first-strand cDNA synthesis as described above followed by primer-directed (primer OGS 494 (SEQ. ID. NO:95) for TAG1 and primer OGS 302 (SEQ. ID. NO:96) for TAG2) second-strand DNA synthesis using ADVANTAGE 2 Taq polymerase (BD Biosciences Clontech, Mississauga, ON). The double-stranded cDNA was purified using QIAQUICK columns and quantified at $A_{260nm}$. Thereafter, 6×1-µg aliquots of each double-stranded cDNA was digested individually with one of the following 4-base recognition restriction enzymes Rsa I, Sau3AI, Mse I, Msp I, HinPI I and Bsh 12361 (MBI Fermentas, Burlington, ON), yielding up to six possible 3'-fragments for each RNA species contained in the cDNA library. Following digestion, the restriction enzymes were inactivated with phenol and the set of six reactions pooled. The restriction enzymes sites were then blunted with T4 DNA polymerase and ligated to linkers containing an Asc I recognition site. Each linker-adapted pooled DNA sample was digested with Asc I and Not I restriction enzymes, desalted and ligated to specialized oligonucleotide promoter tags, TAG1 (OGS 594 and 595) for the original TAG1-derived materials to generate tester RNA and TAG2-related OGS 621 and 622 (SEQ. ID. NO:97 and SEQ. ID. NO:98) with only the promoter sequence for the original TAG2-derived materials for generating driver DNA. The promoter-ligated materials were purified using the streptavidin beads, which were then transcribed in vitro with either T7 RNA polymerase (Ambion, Austin, Tex.), purified and quantified at $A_{260nm}$. The resulting TAG1 3'-represented RNA was used directly as "tester RNA" whereas, the TAG2 3'-represented RNA was used to synthesize first-strand cDNA, which then served as single-stranded "driver DNA". Each "driver DNA" reaction was treated with RNase A and RNase H to remove the RNA, phenol extracted and purified before use. An equivalent amount of each driver RNA for the five LMP samples were pooled before synthesis of the single-stranded driver DNA.

The following 3'-represented libraries were prepared:

Tester 1 (MF-22)—human malignant ovarian cancer donor 1

Tester 2 (MF-25)—human malignant ovarian cancer donor 2

Tester 3 (MF-27)—human malignant ovarian cancer donor 3

Tester 4 (MF-28)—human malignant ovarian cancer donor 4

Tester 5 (MF-30)—human malignant ovarian cancer donor 5

Driver 1 (MF-15)—human ovarian LMP donor 1
Driver 2 (MF-16)—human ovarian LMP donor 2
Driver 3 (MF-18)—human ovarian LMP donor 3
Driver 4 (MF-19)—human ovarian LMP donor 4
Driver 5 (MF-20)—human ovarian LMP donor 5

Each tester RNA sample was subtracted following the teachings of U.S. Pat. No. 5,712,127 with the pooled driver DNA (MF-15, -16, -18, -19 and -20) in a ratio of 1:100 for 2-rounds following the teachings of Malek et al., 1998 (U.S. Pat. No. 5,712,127). Additionally, control reactions containing tester RNA and no driver DNA, and tester RNA plus driver DNA but no RNase H were prepared. The tester RNA remaining in each reaction after subtraction was converted to double-stranded DNA, and a volume of 5% removed and amplified in a standard PCR reaction for 30-cycles for analytical purposes. The remaining 95% of only the tester-driver plus RNase H subtracted samples after 2-rounds were amplified for 4-cycles in PCR, digested with Asc I and Not I restriction enzymes, and one half ligated into the pCATR-MAN (SEQ. ID. NO:99) plasmid vector and the other half, into the p20 (SEQ. ID. NO:100) plasmid vector. The ligated materials were transformed into *E. coli* DH10B and individual clones contained in the pCATRMAN libraries were picked for further analysis (DNA sequencing and hybridization) whereas, clones contained in each p20 library were pooled for use as subtracted probes. Each 4-cycles amplified cloned subtracted library contained between 15,000 and 25,000 colonies. Additionally, in order to prepare subtracted cDNA probes, reciprocal subtraction for 2-rounds was performed using instead, the pooled driver RNA as "tester" and each of the malignant tester RNA as "driver". The materials remaining after subtraction for each were similarly amplified for 4-cycles in PCR, digested with Asc I and Not I restriction enzymes, and one half ligated into the p20 plasmid vector.

The following cloned subtracted libraries were prepared:
SL123—Tester 1 (MF-22) minus Pooled Driver (MF-15, -16, -18, -19 and -20)
SL124—Tester 2 (MF-25) minus Pooled Driver (MF-15, -16, -18, -19 and -20)
SL125—Tester 3 (MF-27) minus Pooled Driver (MF-15, -16, -18, -19 and -20)
SL126—Tester 4 (MF-28) minus Pooled Driver (MF-15, -16, -18, -19 and -20)
SL127—Tester 5 (MF-30) minus Pooled Driver (MF-15, -16, -18, -19 and -20)
SL133—Pooled Driver (MF-15, -16, -18, -19 and -20) minus Tester 1 (MF-22)
SL134—Pooled Driver (MF-15, -16, -18, -19 and -20) minus Tester 2 (MF-25)
SL135—Pooled Driver (MF-15, -16, -18, -19 and -20) minus Tester 3 (MF-27)
SL136—Pooled Driver (MF-15, -16, -18, -19 and -20) minus Tester 4 (MF-28)
SL137—Pooled Driver (MF-15, -16, -18, -19 and -20) minus Tester 5 (MF-30)

A 5-µL aliquot of the 30-cycles PCR amplified subtracted and non-subtracted materials were visualized on a 1.5% agarose gel containing ethidium bromide and then transferred to HYBOND N+ (Amersham Biosciences, Piscataway, N.J.) nylon membrane for Southern blot analysis. Using radiolabeled probes specific for GAPDH (glyceraldehyde-3-phosphate dehydrogenase; Accession #M32599.1) and β-actin (Accession #X00351), which are typically nondifferentially expressed house-keeping genes, it was evident that there was subtraction of both GAPDH and β-actin (FIG. 51, Panels A and B). Yet, at the same time, a probe specific for CCNE1 (Accession #NM_$001238$, a gene known to be upregulated in malignant ovarian cancer, indicated that it was not subtracted (FIG. 51, Panel C). Based on these results, it was anticipated that the subtracted libraries would be enriched for differentially expressed upregulated sequences.

E—Sequence Identification and Annotation of Clones Contained in the Subtracted Libraries:

Approximately ~5300 individual colonies contained in the pCATRMAN subtracted libraries (SL123 to SL127) described above were randomly picked using a Qbot (Genetix Inc., Boston, Mass.) into 60 µL of autoclaved water. Then, 42 µL of each was used in a 100-µL standard PCR reaction containing oligonucleotide primers, OGS 1 and OGS 142 and amplified for 40-cycles (94° C. for 10 minutes, 40×(94° C. for 40 seconds, 55° C. for 30 seconds and 72° C. for 2 minutes) followed by 72° C. for 7 minutes) in 96-wells microtitre plates using HOTSTARTAQ polymerase (Qiagen, Mississauga, ON). The completed PCR reactions were desalted using the 96-well filter plates (Corning) and the amplicons recovered in 100 µL 10 mM Tris (pH 8.0). A 5-1 µL aliquot of each PCR reaction was visualized on a 1.5% agarose gel containing ethidium bromide and only those reactions containing a single amplified product were selected for DNA sequence analysis using standard DNA sequencing performed on an ABI 3100 instrument (Applied Biosystems, Foster City, Calif.). Each DNA sequence obtained was given a Sequence Identification Number and entered into a database for subsequent tracking and annotation.

Each sequence was selected for BLAST analysis of public databases (e.g. NCBI). Absent from these sequences were the standard housekeeping genes (GAPDH, actin, most ribosomal proteins etc.), which was a good indication that the subtracted library was depleted of at least the relatively abundant non-differentially expressed sequences.

Once sequencing and annotation of the selected clones were completed, the next step involved identifying those sequences that were actually upregulated in the malignant ovarian cancer samples compared to the LMP samples.

F—Hybridization Analysis for Identifying Upregulated Sequences

The PCR amplicons representing the annotated sequences from the pCATRMAN libraries described above were used to prepare DNA microarrays. The purified PCR amplicons contained in 70 µL of the PCR reactions prepared in the previous section was lyophilized and each reconstituted in 20 µL of spotting solution comprising 3×SSC and 0.1% sarkosyl. DNA micro-arrays of each amplicon in triplicate were then prepared using CMT-GAP2 slides (Corning, Corning, N.Y.) and the GMS 417 spotter (Affymetrix, Santa Clara, Calif.).

The DNA micro-arrays were then hybridized with either standard or subtracted cy3 and cy5 labelled cDNA probes as recommended by the supplier (Amersham Biosciences, Piscataway, N.J.). The standard cDNA probes were synthesized using RAMP amplified RNA prepared from the different human ovarian LMP and malignant samples. It is well known to the skilled artisan that standard cDNA probes only provide limited sensitivity of detection and consequently, low abundance sequences contained in the cDNA probes are usually missed. Thus, the hybridization analysis was also performed using cy3 and cy5 labelled subtracted cDNA probes prepared from in vitro transcribed RNA generated from subtracted libraries (SLP123 to SLP127 and SLP133 to SLP137) cloned into the p20 plasmid vector and represent the different tester and driver materials. These subtracted libraries may be enriched for low abundance sequences as a result of following the teachings of Malek et al., 1998 (U.S. Pat. No. 5,712,127), and therefore, may provide increased detection sensitivity.

All hybridization reactions were performed using the dye-swap procedure as recommended by the supplier (Amersham Biosciences, Piscataway, N.J.) and approximately 750 putatively differentially expressed upregulated (>2-fold) sequences were selected for further analysis.

G—Determining Malignant Ovarian Cancer Specificity of the Differentially Expressed Sequences Identified:

The differentially expressed sequences identified in Section F for the different human malignant ovarian cancer subtracted libraries (SL123 to SL127) were tested for specificity by hybridization to nylon membrane-based macroarrays. The macroarrays were prepared using RAMP amplified RNA from 6 LMP and 20 malignant human ovarian samples, and 30 normal human tissues (adrenal, liver, lung, ovary, skeletal muscle, heart, cervix, thyroid, breast, placenta, adrenal cortex, kidney, vena cava, fallopian tube, pancreas, testicle, jejunum, aorta, esophagus, prostate, stomach, spleen, ileum, trachea, brain, colon, thymus, small intestine, bladder and duodenum) purchased commercially (Ambion, Austin, Tex.).

In addition, RAMP RNA prepared from breast cancer cell lines, MDA and MCF7, prostate cancer cell line, LNCap, and a normal and prostate cancer LCM microdissected sample. Because of the limited quantities of mRNA available for many of these samples, it was necessary to first amplify the mRNA using the RAMP methodology. Each amplified RNA sample was reconstituted to a final concentration of 250 ng/µL in 3×SSC and 0.1% sarkosyl in a 96-well microtitre plate and 1 µL spotted onto HYBOND N+ nylon membranes using the specialized MULTI-PRINT apparatus (VP Scientific, San Diego, Calif.), air dried and UV-cross linked. Of the ~750 different sequences selected from SL123 to SL127 for macroarray analysis, only 250 sequences were individually radiolabeled with $\alpha$-$^{32}$P-dCTP using the random priming procedure recommended by the supplier (Amersham, Piscataway, N.J.) and used as probes on the macroarrays thus far. Hybridization and washing steps were performed following standard procedures well known to those skilled in the art.

Occasionally, the results obtained from the macroarray methodology were inconclusive. For example, probing the membranes with certain STAR clones resulted in patterns where all the RNA samples appeared to express equal levels of the message or in patterns where there was no signal. This suggested that not all STAR clones were useful tools to verify the expression of their respective genes. To circumvent this problem, RT-PCR was used to determine the specificity of expression. Using the same RAMP RNA samples that were spotted on the macroarrays, 500 µg of RNA was converted to single-stranded cDNA with THERMOSCRIPT RT (Invitrogen, Burlington, ON) as described by the manufacturer. The cDNA reaction was diluted so that 1/200 of the reaction was used for each PCR experiment. After trial PCR reactions with gene-specific primers designed against each SEQ. ID NOs. to be tested, the linear range of the reaction was determined and applied to all samples, PCR was conducted in 96-well plates using HOTSTARTAQ Polymerase from Qiagen (Mississauga, ON) in a DNA ENGINE TETRAD from MJ Research. Half of the reaction mixture was loaded on a 1.2% agarose/ethidium bromide gel and the amplicons visualized with UV light.

Of the 250 sequences tested, approximately 55% were found to be upregulated in many of the malignant samples compared to the LMPs. However, many of these sequences were also readily detected in a majority of the different normal human tissues. Based on these results, those sequences that were detected in many of the other human tissues at significantly elevated levels were eliminated. Consequently, only 49 sequences, which appeared to be upregulated and highly malignant ovarian cancer-specific, were selected for biological validation studies. This subset of 49 sequences include some genes previously reported in the literature to be upregulated in ovarian cancer but without demonstration of their relative expression in normal tissues. The macroarray data for FOLR1 (SEQ. ID. NO.50) is included to exemplify the hybridization pattern and specificity of a gene that is already known to be involved in the development of ovarian cancer.

FIGS. 1-49 and 51 show the macroarray hybridization signal patterns and RT-PCR amplification data for the malignant ovarian cancer and normal human tissues relative to LMPs for the 50 sequences isolated and selected for biological validation. Amongst the 50 selected sequences, 27 were associated with genes having functional annotation 15 were associated with genes with no functional annotation and 8 were novel sequences (genomic hits). The identification of gene products involved in regulating the development of ovarian cancer has thus led to the discovery of highly specific, including novel targets, for the development of new therapeutic strategies for ovarian cancer management. Representative sequences summarized in Table 2 are presented below and corresponding sequences are illustrated in Table 4.

The present invention thus relates in one aspect thereof to a method of representatively identifying a differentially expressed sequence involved in ovarian cancer. The sequence may be, for example, differentially expressed in a malignant ovarian cancer cell compared to a LMP ovarian cancer cell or normal ovarian cells. The sequence may be, for example, differentially expressed in a malignant ovarian cancer cell and a LMP ovarian cancer cell compared to a normal ovarian cell.

The method of the present invention may comprise the following steps or some of the following steps;

a) separately providing total messenger RNA from malignant and LMP ovarian cancer cells, and normal ovarian cells, the total messenger RNA may comprise, for example, at least one endogenously differentially expressed sequence, b) generating (e.g., single copy) of a) single-stranded cDNA from each messenger RNA of malignant ovarian cancer cell and (e.g., randomly) tagging the 3'-end of the single-stranded cDNA with a RNA polymerase promoter sequence and a first sequence tag;

c) generating (e.g., single copy) of a) single-stranded cDNA from each messenger RNA of LMP ovarian cancer cells or normal ovarian cell and (e.g., randomly) tagging the 3'-end of the single-stranded cDNA with a RNA polymerase promoter sequence and a second sequence tag;

d) separately generating partially or completely double-stranded 5'-tagged-DNA from each of b) and c), the double-stranded 5'-tagged-DNA may thus comprise in a 5' to 3' direction, a double-stranded RNA polymerase promoter, a first or second sequence tag and an expressed nucleic acid sequence, e) separately linearly amplifying a first and second tagged sense RNA from each of d) with a RNA polymerase enzyme (which may be selected based on the promoter used for tagging), f) generating single-stranded complementary first or second tagged DNA from one of e), g) hybridizing the single-stranded complementary first or second tagged DNA of f) with the other linearly amplified sense RNA of e), h) recovering unhybridized RNA with the help of the first or second sequence tag (for example by PCR or hybridization), and;

i) identifying (determining) the nucleotide sequence of unhybridized RNA.

The method may further comprise the step of comparatively determining the presence of the identified differentially expressed sequence in a cancer cell relative to a normal cell (e.g., a normal ovarian cell, a normal prostate cell, a normal breast cell etc.) or relative to a standard value.

The method may be used to preferentially identify a sequence which is upregulated in malignant ovarian cancer cell compared to a cell from a low malignancy potential ovarian cancer and/or compared to a normal cell.

In accordance with the present invention, a sequence may be further selected based on a reduced, lowered or substantially absent expression in a subset of other normal cell (e.g., a normal ovarian cell) or tissue, therefore representing a candidate sequence specifically involved in ovarian cancer.

The method may also further comprise a step of determining the complete sequence of the nucleotide sequence and may also comprise determining the coding sequence of the nucleotide sequence.

A sequence may also be selected for its specificity to other types of tumor cells, thus identifying a sequence having a more generalized involvement in the development of cancer. These types of sequence may therefore represent desirable candidates having a more universal utility in the treatment and/or detection of cancer.

The present invention also relates in a further aspect, to the isolated differentially expressed sequence (polynucleotide and polypeptide) identified by the method of the present invention.

SEQ. ID. NO:1:

The candidate STAR sequence for SEQ. ID. NO:1 maps to a genomic hit and est hits according to NCBI's nr and est databases (see Table 2). Although, the matching ests are clustered into a new Unigene identifier number, Hs.555871, the STAR sequence does not map to any of the known mRNA sequences listed in this cluster, which codes for guanine nucleotide binding protein (G protein), gamma transducing activity polypeptide 1 (GNGT1). We have demonstrated that this STAR clone sequence is markedly upregulated in malignant ovarian cancer samples compared to ovarian LMP samples and a majority of normal human tissues (FIG. 1), which have not been previously reported. Thus, it is believed that the gene comprising this STAR sequence or a related gene member as is outlined in the Unigene cluster may be required for ovarian cancer tumorigenesis.

SEQ. ID. NO:2:

The candidate protein encoded by the isolated SEQ. ID. NO:2 is associated with a previously identified gene that encodes a predicted polypeptide, interferon-induced protein 44-like (IFI44L) with an unknown function (see Table 2). We have demonstrated that expression of this gene is markedly upregulated in malignant ovarian cancer samples compared to ovarian LMP samples and a majority of normal human tissues (FIG. 2), which have not been previously reported. Thus, it is believed that expression of this gene may be required for or involved for ovarian cancer tumorigenesis.

SEQ. ID. NO:3:

The candidate protein encoded by the isolated SEQ. ID. NO:3 is associated with a previously identified gene that encodes a known polypeptide, HOX D1, which contains a homeobox DNA-binding domain. This gene is a member of the Antp homeobox family and is nuclear sequence-specific transcription factor that is previously known to be involved in differentiation and limb development (see Table 2). We have demonstrated that expression of this gene is markedly upregulated in malignant ovarian cancer samples compared to ovarian LMP samples and the normal human tissues (FIG. 3), which have not been previously reported. Thus, it is believed that the gene may be required for, or involved in ovarian cancer tumorigenesis as well.

SEQ. ID. NO:4:

The candidate protein encoded by the isolated SEQ. ID. NO:4 is associated with a previously identified gene that encodes a hypothetical polypeptide, LOC92196, similar to death-associated protein with an unknown function (see Table 2). We have demonstrated that expression of this gene is markedly upregulated in malignant ovarian cancer samples compared to ovarian LMP samples and a majority of normal human tissues (FIG. 4), which have not been previously reported. Thus, it is believed that expression of this gene may be required for, or involved in ovarian cancer tumorigenesis.

SEQ. ID. NO:5

The candidate protein encoded by the isolated SEQ. ID. NO:5 is associated with a previously identified gene that encodes a predicted polypeptide, interferon-induced protein with tetratricopeptide repeats 1 (IFIT1), with unknown function (see Table 2). We have demonstrated that expression of this gene is markedly upregulated in malignant ovarian cancer samples compared to ovarian LMP samples and a majority of normal human tissues (FIG. 5), which have not been previously reported. Thus, it is believed that expression of this gene may be required for, or involved in ovarian cancer tumorigenesis.

SEQ. ID. NO:6:

The candidate protein encoded by the isolated SEQ. ID. NO:6 is associated with a previously identified gene that encodes a known protein, glycine dehydrogenase (GLDC) (decarboxylating; glycine decarboxylase, glycine cleavage system protein P), which is a mitochondrial enzyme that catalyzes the degradation of glycine (see Table 2). We have demonstrated that expression of this gene is markedly upregulated in malignant ovarian cancer samples compared to ovarian LMP samples and a majority of normal human tissues (FIG. 6), which have not been previously reported. Thus, it is believed that expression of this gene may be required for, or involved in ovarian cancer tumorigenesis. The GLDC activity may be detected, for example, by measuring the degradation of glycine into urea.

SEQ. ID. NO:7:

The candidate protein encoded by the isolated SEQ. ID. NO:7 is associated with a previously identified gene that encodes a protein, dipeptidase 3 (DPEP3), which has membrane dipeptidase (proteolysis and peptidolysis) activity (see Table 2). We have demonstrated that expression of this gene is markedly upregulated in malignant ovarian cancer samples compared to ovarian LMP samples and a majority of normal human tissues (FIG. 7), which have not been previously reported. Thus, it is believed that expression of this gene may be required for, or involved in ovarian cancer tumorigenesis.

SEQ. ID. NO:8

The candidate protein encoded by the isolated SEQ. ID. NO:8 is associated with a previously identified gene that encodes a protein, neuromedin U (NMU), which is a neuropeptide with potent activity on smooth muscle (see Table 2). We have demonstrated that expression of this gene is markedly upregulated in malignant ovarian cancer samples compared to ovarian LMP samples and a majority of normal human tissues (FIG. 8), which have not been previously reported. Thus, it is believed that expression of the gene may be required for, or involved in ovarian cancer tumorigenesis.

SEQ. ID. NO:9

The candidate protein encoded by the isolated SEQ. ID. NO:9 is associated with a previously identified gene that encodes a protein, bone morphogenetic protein 7 (BMP7), which plays a role in calcium regulation and bone homeostasis (see Table 2). We have demonstrated that expression of this gene is markedly upregulated in malignant ovarian cancer samples compared to ovarian LMP samples and a majority of normal human tissues (FIG. 9), which have not been previously reported. Thus, it is believed that expression of the gene may be required for, or involved in ovarian cancer tumorigenesis.

SEQ. ID. NO:10

The candidate protein encoded by the isolated SEQ. ID. NO:10 is associated with a previously identified gene that encodes a protein, cyclin-dependent kinase inhibitor 3 (CDKN3) (CDK2-associated dual specificity phosphatase), which is expressed at the G1 to S transition of the cell cycle (see Table 2). We have demonstrated that expression of this gene is markedly upregulated in malignant ovarian cancer samples compared to ovarian LMP samples and a majority of normal human tissues (FIG. 10), which have not been previously reported. Thus, it is believed that expression of the gene may be required for, or involved in ovarian cancer tumorigenesis.

SEQ. ID. NO:11

The candidate protein encoded by the isolated SEQ. ID. NO:11 is associated with a previously identified gene that encodes a protein, CDC28 protein kinase regulatory subunit 1B (CKS1B), which has cyclin-dependent protein kinase activity in cell cycle regulation (see Table 2). We have demonstrated that expression of this gene is markedly upregulated in malignant ovarian cancer samples compared to ovarian LMP samples and a majority of normal human tissues (FIG. 11), which have not been previously reported. Thus, it is believed that expression of the gene may be required for, or involved in ovarian cancer tumorigenesis.

SEQ. ID. NO:12

The candidate protein encoded by the isolated SEQ. ID. NO:12 is associated with a previously identified gene that encodes a protein, preferentially expressed antigen in melanoma (PRAME), which has no known function (see Table 2). We have demonstrated that expression of this gene is markedly upregulated in malignant ovarian cancer samples compared to ovarian LMP samples and a majority of normal human tissues (FIG. 12), which have not been previously reported. Thus, it is believed that expression of the gene may be required for, or involved in ovarian cancer tumorigenesis.

SEQ. ID. NO:13

The candidate protein encoded by the isolated SEQ. ID. NO:13 is associated with a previously identified gene that encodes a protein, ISG15 ubiquitin-like modifier (ISG15), which is associated with ubiquitin-dependent protein catabolism (see Table 2). We have demonstrated that expression of this gene is markedly upregulated in malignant ovarian cancer samples compared to ovarian LMP samples and a majority of normal human tissues (FIG. 13), which have not been previously reported. Thus, it is believed that expression of the gene may be required for, or involved in ovarian cancer tumorigenesis.

SEQ. ID. NO:14

The candidate STAR sequence represented by the isolated SEQ. ID. NO:14 is associated with a previously identified partial gene sequence related to Accession #A1922121.1 (see Table 2), which codes for a yet unknown protein. We have demonstrated that this STAR clone sequence is markedly upregulated in malignant ovarian cancer samples compared to ovarian LMP samples and a majority of normal human tissues (FIG. 14), which have not been previously reported. Thus, it is believed that expression of the gene corresponding to this STAR sequence (and polynucleotide sequences comprising the STAR sequence) may be required for, or involved in ovarian cancer tumorigenesis.

SEQ. ID. NO:15

The candidate protein encoded by the isolated SEQ. ID. NO:15 is associated with a previously identified gene that encodes a hypothetical protein, FLJ33790, which has no known function (see Table 2). We have demonstrated that expression of this gene is markedly upregulated in malignant ovarian cancer samples compared to ovarian LMP samples and a majority of normal human tissues (FIG. 15), which have not been previously reported. Thus, it is believed that expression of the gene may be required for, or involved in ovarian cancer tumorigenesis.

SEQ. ID. NO:16

The STAR sequence represented by the isolated SEQ. ID. NO:16 maps to a previously identified est, BG213598 that is from a transcribed genomic locus contained in the Unigene cluster, Hs.334302, which encodes a yet unknown protein (see Table 2). We have demonstrated that this STAR clone sequence is markedly upregulated in malignant ovarian cancer samples compared to ovarian LMP samples and a majority of normal human tissues (FIG. 16), which have not been previously reported. Thus, it is believed that expression of the gene corresponding to this STAR sequence (and polynucleotides comprising this STAR sequence) or a related gene member as is outlined in the Unigene cluster may be required for, or involved in ovarian cancer tumorigenesis.

SEQ. ID. NO:17

The candidate protein encoded by the isolated SEQ. ID. NO:17 is associated with a previously identified gene that encodes a protein, V-set domain containing T cell activation inhibitor 1 (VTCN1), which has no known function (see Table 2). We have demonstrated that expression of this gene is markedly upregulated in malignant ovarian cancer samples compared to ovarian LMP samples and a majority of normal human tissues (FIG. 17), which have not been previously reported. Thus, it is believed that expression of the gene may be required for, or involved in ovarian cancer tumorigenesis.

SEQ. ID. NO:18

The candidate protein encoded by the isolated SEQ. ID. NO:18 is associated with a previously identified gene that encodes a protein, kinesin family member 20A (KIF20A), which is involved in cell division in and membrane traffic within the Golgi apparatus (see Table 2). We have demonstrated that expression of this gene is markedly upregulated in malignant ovarian cancer samples compared to ovarian LMP samples and a majority of normal human tissues (FIG. 18), which have not been previously reported. Thus, it is believed that expression of the gene may be required for, or involved in ovarian cancer tumorigenesis.

SEQ. ID. NO:19

The STAR sequence represented by the isolated SEQ. ID. NO:19 maps to a genomic hit, Accession #AY769439 and to a group of ests represented by Accession #AA744939. The ests are clustered into Unigene identifier, Hs.478368 representing the protein, potassium large conductance calcium-activated channel, subfamily M, beta member 2 (KCNMB2). However, the STAR sequence does not overlap with any of the mRNA sequences listed thus far in the Hs.478368 Unigene cluster (see Table 2). We have demonstrated that this STAR clone sequence is markedly upregulated in malignant ovarian cancer samples compared to ovarian LMP samples and a majority of normal human tissues (FIG. 19A), which have not been previously reported. In addition, performing RT-PCR using primers specific to either the STAR clone sequence for SEQ. ID. NO. 19 or the KCNMB2 sequence represented by Accession No. NM_005832, the amplification profiles were not the same across a number of ovarian samples tested (FIG. 19B). It was obvious that KCNMB2 was expressed in essentially all ovarian samples including the normal at similar levels whereas, PCR amplicons for SEQ. ID. NO. 19 was observed at higher levels in the malignant ovarian tumor samples compared to the LMPs and normal ovarian samples (FIG. 19B). Thus, it is believed that the expression of the gene corresponding to this STAR sequence (and polynucleotide sequences comprising the STAR sequence) or a related gene member may be required for, or involved in ovarian cancer tumorigenesis.

SEQ. ID. NO:20

The STAR sequence represented by the isolated SEQ. ID. NO:20 maps to a previously identified est, BU595315 belonging to a group of ests that is from a transcribed genomic locus contained in the Unigene cluster, Hs.603908, which encodes a yet unknown protein (see Table 2). We have demonstrated that this STAR clone sequence is markedly upregulated in malignant ovarian cancer samples compared to ovarian LMP samples and a majority of normal human tissues (FIG. 20), which have not been previously reported. Thus, it is believed that expression of the gene corresponding to this STAR sequence (and polynucleotide sequences comprising this STAR sequence) or a related gene member as is outlined in the Unigene cluster may be required for, or involved in ovarian cancer tumorigenesis.

SEQ. ID. NO:21

The candidate protein encoded by the isolated SEQ. ID. NO:21 is a previously identified gene that encodes a protein, chemokine (C-X-C motif) ligand 10 (CXCL10), which has chemokine activity (see Table 2). We have demonstrated that expression of this gene is markedly upregulated in malignant ovarian cancer samples compared to ovarian LMP samples and a majority of normal human tissues (FIG. 21), which have not been previously reported. Thus, it is believed that expression of the gene may be required for, or involved in ovarian cancer tumorigenesis.

SEQ. ID. NO:22

The STAR sequence represented by the isolated SEQ. ID. NO:22 maps to chromosome 14, and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 22), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:23

The candidate protein encoded by the isolated SEQ. ID. NO:23 is a previously identified gene that encodes a protein, asparagine-linked glycosylation 8 homolog (yeast, alpha-1,3-glucosyltransferase) (ALG8), which catalyzes the addition of the second glucose residue to the lipid-linked oligosaccharide precursor for N-linked glycosylation of proteins (see Table 2). We have demonstrated that expression of this gene is markedly upregulated in malignant ovarian cancer samples compared to ovarian LMP samples and a majority of normal human tissues (FIG. 23), which have not been previously reported. Thus, it is believed that expression of the gene may be required for, or involved in ovarian cancer tumorigenesis.

SEQ. ID. NO:24

The candidate protein encoded by the isolated SEQ. ID. NO:24 is a previously identified gene that encodes a protein, kidney associated antigen 1 (KAAG1), which has no known function (see Table 2). We have demonstrated that expression of this gene is markedly upregulated in malignant ovarian cancer samples compared to ovarian LMP samples and a majority of normal human tissues (FIG. 24), which have not been previously reported. Thus, it is believed that expression of the gene may be required for, or involved in ovarian cancer tumorigenesis.

SEQ. ID. NO:25

The candidate protein encoded by the isolated SEQ. ID. NO:25 is a previously identified gene that encodes a protein, cyclin-dependent kinase inhibitor 2A (CDKN2A), which is involved in cell cycle control, G1/S Checkpoint (see Table 2). We have demonstrated that expression of this gene is markedly upregulated in malignant ovarian cancer samples compared to ovarian LMP samples and a majority of normal human tissues (FIG. 25), which have not been previously reported. Thus, it is believed that expression of the gene may be required for, or involved in ovarian cancer tumorigenesis.

SEQ. ID. NO:26

The candidate protein encoded by the isolated SEQ. ID. NO:26 is a previously identified gene that encodes a protein, microtubule-associated protein homolog (*Xenopus laevis*) (TPX2), which is involved in cell proliferation from the transition G1/S until the end of cytokinesis (see Table 2). We have demonstrated that expression of this gene is markedly upregulated in malignant ovarian cancer samples compared to ovarian LMP samples and a majority of normal human tissues (FIG. 26), which have not been previously reported. Thus, it is believed that expression of the gene may be required for, or involved in ovarian cancer tumorigenesis.

SEQ. ID. NO:27

The candidate protein encoded by the isolated SEQ. ID. NO:27 is a previously identified gene that encodes a protein, ubiquitin-conjugating enzyme E2C (UBE2C), which is required for the destruction of mitotic cyclins and for cell cycle progression (see Table 2). We have demonstrated that expression of this gene is markedly upregulated in malignant ovarian cancer samples compared to ovarian LMP samples and a majority of normal human tissues (FIG. 27), which have not been previously reported. Thus, it is believed that expression of the gene may be required for, or involved in ovarian cancer tumorigenesis.

SEQ. ID. NO:28

The STAR sequence represented by the isolated SEQ. ID. NO:28 maps to cDNA FLJ35538 fis, clone SPLEN2002463 of Unigene cluster, Hs.590469 and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 28), which have not been previously reported. Thus, it is believed that expression of the gene corresponding to this STAR sequence (and polynucleotides comprising this STAR sequence) or a related gene member as is outlined in the Unigene cluster may be required for, or involved in ovarian cancer tumorigenesis.

SEQ. ID. NO:29

The candidate protein encoded by the isolated SEQ. ID. NO:29 is a previously identified gene that encodes a protein, cellular retinoic acid binding protein 2 (CRABP2), whose function has not been precisely determined but this isoform is important in retinoic acid-mediated regulation of human skin growth and differentiation (see Table 2). We have demonstrated that expression of this gene is markedly upregulated in malignant ovarian cancer samples compared to ovarian LMP samples and a majority of normal human tissues (FIG. 29), which have not been previously reported. Thus, it is believed that expression of the gene may be required for, or involved in ovarian cancer tumorigenesis.

SEQ. ID. NO:30

The candidate protein encoded by the isolated SEQ. ID. NO:30 is a previously identified gene that encodes a protein, H1stone 3, H2a (H1ST3H2A), which is involved in nucleosome formation (see Table 2). We have demonstrated that expression of this gene is markedly upregulated in malignant ovarian cancer samples compared to ovarian LMP samples and a majority of normal human tissues (FIG. 30), which have not been previously reported. Thus, it is believed that expression of the gene may be required for, or involved in ovarian cancer tumorigenesis.

SEQ. ID. NO:31

The candidate protein encoded by the isolated SEQ. ID. NO:31 is a previously identified gene that encodes a protein, Histone 1, H4h (HIST1H4H), which is involved in nucleosome formation (see Table 2). We have demonstrated that expression of this gene is markedly upregulated in malignant ovarian cancer samples compared to ovarian LMP samples and a majority of normal human tissues (FIG. 30), which have not been previously reported. Thus, it is believed that expression of the gene may be required for, or involved in ovarian cancer tumorigenesis.

SEQ. ID. NO:32

The candidate protein encoded by the isolated SEQ. ID. NO:32 is a previously identified gene that encodes a hypothetical protein, Homeo box D3 (HOXD3), which is a nuclear transcription factor involved in development and differentiation (see Table 2). We have demonstrated that expression of this gene is markedly upregulated in malignant ovarian cancer samples compared to ovarian LMP samples and a majority of normal human tissues (FIG. 32), which have not been previously reported. Thus, it is believed that expression of the gene may be required for ovarian cancer tumorigenesis.

SEQ. ID. NO:33

The candidate protein encoded by the isolated SEQ. ID. NO:33 is a previously identified gene that encodes a member of the immunoglobulin gene family, immunoglobulin constant gamma 1 (IGHG1), which probably plays a role in immune response and antigen binding (see Table 2). We have demonstrated that expression of this gene is markedly upregulated in malignant ovarian cancer samples compared to ovarian LMP samples and a majority of normal human tissues (FIG. 33), which have not been previously reported. The expression pattern of this gene is similar to two other genes disclosed here, SEQ. ID. NO. 34 and SEQ. ID. NO. 47, which also encode immunoglobulins. This type of clustered immunoglobulin expression in ovarian cancer has not been previously described. Thus, it is believed that expression of the gene may be required for ovarian cancer tumorigenesis.

SEQ. ID. NO:34

The candidate protein encoded by the isolated SEQ. ID. NO:34 is a previously identified gene that encodes a member of the immunoglobulin gene family, immunoglobulin kappa constant (IGKC), which probably plays a role in immune response and antigen binding (see Table 2). We have demonstrated that expression of this gene is markedly upregulated in malignant ovarian cancer samples compared to ovarian LMP samples and a majority of normal human tissues (FIG. 34), which have not been previously reported. The expression pattern of this gene is similar to two other genes disclosed here, SEQ. ID. NO. 33 and SEQ. ID. NO. 47, which also encode immunoglobulins. This type of clustered immunoglobulin expression in ovarian cancer has not been previously described. Thus, it is believed that expression of the gene may be required for ovarian cancer tumorigenesis.

SEQ. ID. NO:35

The candidate protein encoded by the isolated SEQ. ID. NO:35 is a gene located on chromosome 10 that encodes an open reading frame of unknown function. (see Table 2). The gene may encode a protein termed astroprincin that was found to be expressed in a critical region in DiGeorge syndrome. We have demonstrated that expression of this gene is markedly upregulated in malignant ovarian cancer samples compared to ovarian LMP samples and a majority of normal human tissues (FIG. 35), which have not been previously reported. Thus, it is believed that expression of the gene may be required for, or involved in ovarian cancer tumorigenesis.

SEQ. ID. NO:36

The candidate protein encoded by the isolated SEQ. ID. NO:36 is a previously identified gene that encodes a protein, histocompatibility (minor) 13 (HM13), which has no known function (see Table 2). We have demonstrated that expression of this gene is markedly upregulated in malignant ovarian cancer samples compared to ovarian LMP samples and a majority of normal human tissues (FIG. 36), which have not been previously reported. Thus, it is believed that expression of the gene may be required for, or involved in ovarian cancer tumorigenesis.

SEQ. ID. NO:37

The STAR sequence represented by the isolated SEQ. ID. NO:37 maps to chromosome 13, and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 37), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:38

The candidate protein encoded by the isolated SEQ. ID. NO:38 is a previously identified gene that encodes a protein, frizzled-related protein (FRZB), which is associated with symptomatic osteoarthritis and may play a role in skeletal morphogenesis (see Table 2). We have demonstrated that expression of this gene is markedly upregulated in malignant ovarian cancer samples compared to ovarian LMP samples and a majority of normal human tissues (FIG. 38), which have not been is previously reported. Thus, it is believed that expression of the gene may be required for, or involved in ovarian cancer tumorigenesis.

SEQ. ID. NO:39

The candidate protein encoded by the isolated SEQ. ID. NO:39 is a previously identified gene that encodes a protein, forkhead box M1 (FOXM1), which is a transcription factor that regulates genes involved in cell proliferation (see Table 2). We have demonstrated that expression of this gene is markedly upregulated in malignant ovarian cancer samples compared to ovarian LMP samples and a majority of normal human tissues (FIG. 39), which have not been previously reported. Thus, it is believed that expression of the gene may be required for, or involved in ovarian cancer tumorigenesis.

SEQ. ID. NO:40

The candidate protein encoded by the isolated SEQ. ID. NO:40 is a gene located on chromosome 20 that encodes an open reading frame of unknown function. (see Table 2). The gene is predicted to encode a membrane protein. We have demonstrated that expression of this gene is markedly upregulated in malignant ovarian cancer samples compared to ovarian LMP samples and a majority of normal human tissues (FIG. 40), which have not been previously reported. Thus, it is believed that expression of the gene may be required for, or involved in ovarian cancer tumorigenesis.

SEQ. ID. NO:41

The STAR sequence represented by the isolated SEQ. ID. NO:41 maps to chromosome 1, and may represent a portion of an unknown gene sequence (see Table 2). Weak homology has been found between SEQ. ID. NO. 41 and the envelop proteins present at the surface of human endogenous retroviruses. We have demonstrated that this STAR clone sequence is markedly upregulated in malignant ovarian cancer samples compared to ovarian LMP samples and a majority of normal human tissues (FIG. 41), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:42

The candidate protein encoded by the isolated SEQ. ID. NO:42 is a gene located on chromosome 16 that encodes an open reading frame of unknown function. (see Table 2). The gene is predicted to encode a membrane protein. We have demonstrated that expression of this gene is markedly upregulated in malignant ovarian cancer samples compared to ovarian LMP samples and a majority of normal human tissues (FIG. 42), which have not been previously reported. Thus, it is believed that expression of the gene may be required for, or involved in ovarian cancer tumorigenesis.

SEQ. ID. NO:43

The candidate protein encoded by the isolated SEQ. ID. NO:43 is a previously identified gene that encodes a protein, Rac GTPase activating protein 1 (RACGAP1), which is a GTPase that interacts with Rho GTPases to control many cellular processes (see Table 2). These types of proteins are important effector molecules for the downstream signaling of Rho GTPases. We have demonstrated that expression of this gene is markedly upregulated in malignant ovarian cancer samples compared to ovarian LMP samples and a majority of normal human tissues (FIG. 43), which have not been previously reported. Thus, it is believed that expression of the gene may be required for, or involved in ovarian cancer tumorigenesis.

SEQ. ID. NO:44

The candidate protein encoded by the isolated SEQ. ID. NO:44 is a gene that encodes transmembrane protein 19 (TMEM19) that has no known function. (see Table 2). The gene is predicted to encode a membrane protein. We have demonstrated that expression of this gene is markedly upregulated in malignant ovarian cancer samples compared to ovarian LMP samples and a majority of normal human tissues (FIG. 44), which have not been previously reported. Thus, it is believed that expression of the gene may be required for, or involved in ovarian cancer tumorigenesis.

SEQ. ID. NO:45

The STAR sequence represented by the isolated SEQ. ID. NO:45 maps to chromosome 4, and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 45), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:46

The STAR sequence represented by the isolated SEQ. ID. NO:46 maps to chromosome 1, and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 46), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:47

The candidate protein encoded by the isolated SEQ. ID. NO:47 is a previously identified gene with the Unigene cluster, Hs.449585, and may represent a portion immunoglobulin lambda locus (IGLV@), which probably plays a role in immune response and antigen binding (see Table 2). We have demonstrated that expression of this gene is markedly upregulated in malignant ovarian cancer samples compared to ovarian LMP samples and a majority of normal human tissues (FIG. 47), which have not been previously reported. The expression pattern of this gene is similar to two other genes disclosed here, SEQ. ID. NO. 33 and SEQ. ID. NO. 34, which also encode immunoglobulins. This type of clustered immunoglobulin expression in ovarian cancer has not been previously described. Thus, it is believed that expression of the gene may be required for ovarian cancer tumorigenesis.

SEQ. ID. NO:48

The candidate protein encoded by the isolated SEQ. ID. NO:48 is a previously identified gene that encodes a protein, secretory carrier membrane protein 3 (SCAMP3), which functions as a cell surface carrier protein during vesicular transport (see Table 2). We have demonstrated that expression of this gene is markedly upregulated in malignant ovarian cancer samples compared to ovarian LMP samples but it is also expressed in a majority of normal human tissues (FIG. 48), which have not been previously reported. Thus, it is believed that expression of the gene may be required for, or involved in ovarian cancer tumorigenesis.

SEQ. ID. NO:49

The STAR sequence represented by the isolated SEQ. ID. NO:49 maps to chromosome 2, and may represent a portion of an unknown gene sequence (see Table 2). We have demonstrated that this STAR clone sequence is markedly upregulated in malignant ovarian cancer samples compared to ovarian LMP samples and a majority of normal human tissues (FIG. 49), which have not been previously reported. Thus, it is believed that expression of the gene corresponding to this STAR sequence (and polynucleotides comprising this STAR sequence) may be required for, or involved in ovarian cancer tumorigenesis.

SEQ. ID. NO:50

The candidate protein encoded by the isolated SEQ. ID. NO:50 is a previously identified gene that encodes a protein, Folate receptor 1 (adult) (FOLR1), with members of this gene family having a high affinity for folic acid and for several reduced folic acid derivatives, and mediate delivery of 5-methyltetrahydrofolate to the interior of cells (see Table 2). We have demonstrated that this gene is markedly upregulated in malignant ovarian cancer samples compared to ovarian LMP samples and a majority of normal human tissues (FIG. 50). The potential role of FOLR1 in ovarian cancer therapeutics has been previously documented (Leamon and Low, 2001 and Jhaveri et al., 2006, U.S. Pat. No. 7,030,236). By way of example of the FOLR1 gene target, similar genes described herein with upregulation in malignant ovarian tumors and limited or no expression in a majority of normal tissues may also serve as potential therapeutic targets for ovarian cancer.

SEQ. ID. NO:169

The candidate protein encoded by the isolated SEQ. ID. NO:169 is a previously identified gene that encodes a protein, ceruloplasmin (CP), that binds most of the copper in plasma and is involved in the peroxidation of Fe(II)transferrin. The deficiency of this metalloprotein, termed aceruloplasminemia, leads to iron accumulation and tissue damage, and is associated diabetes and neurologic diseases (see Table 2). We have demonstrated that this gene is markedly upregulated in malignant ovarian cancer samples compared to ovarian LMP samples and a majority of normal human tissues (FIG. 56) which have not been previously reported. Thus, it is believed that expression of the gene corresponding to this STAR sequence (and polynucleotides comprising this STAR sequence) may be required for, or involved in ovarian cancer tumorigenesis.

H—RNA Interference Studies

RNA interference is a recently discovered gene regulation mechanism that involves the sequence-specific decrease in a gene's expression by targeting the mRNA for degradation and although originally described in plants, it has been discovered across many animal kingdoms from protozoans and invertebrates to higher eukaryotes (reviewed in Agrawal et al., 2003). In physiological settings, the mechanism of RNA interference is triggered by the presence of double-stranded RNA molecules that are cleaved by an RNAse III-like protein active in cells, called Dicer, which releases the 21-23 by siRNAs. The siRNA, in a homology-driven manner, complexes into a RNA-protein amalgamation termed RISC (RNA-induced silencing complex) in the presence of mRNA to cause degradation resulting in attenuation of that mRNA's expression (Agrawal et al., 2003).

Current approaches to studying the function of genes, such as gene knockout mice and dominant negatives, are often inefficient, and generally expensive, and time-consuming. RNA interference is proving to be a method of choice for the analysis of a large number of genes in a quick and relatively inexpensive manner. Although transfection of synthetic siRNAs is an efficient method, the effects are often transient at best (Hannon G. J., 2002). Delivery of plasmids expressing short hairpin RNAs by stable transfection has been successful in allowing for the analysis of RNA interference in longer-term studies (Brummelkamp et al., 2002; Elbashir et al., 2001).

I—Determination of Knockdown Effects on the Proliferation of Ovarian Cancer Cell Lines In order to determine which ovarian cancer-specific genes participate in the proliferation of ovarian cancer cells, an assay was developed using stably transfected cell lines that contain attenuated (i.e., knocked down) levels of the specific gene being investigated. Two human ovarian cancer cell lines derived from chemotherapy-naïve patients were utilized that have been previously characterized in terms of their morphology, tumorigenicity, and global expression profiles. In addition, these analyses revealed that these cell lines were excellent models for in vivo behavior of ovarian to tumors in humans (Provencher et al., 2000 and Samouelian et al., 2004). These cell lines are designated TOV-21G and TOV-112D.

The design and subcloning of individual shRNA expression cassettes and the procedure utilized for the characterisation of each nucleotide sequence is described below. Selection of polynucleotides were chosen based on their upregulation in ovarian tumors and the selective nature of their expression in these tumors compared to other tissues as described above. The design of shRNA sequences was performed using web-based software that is freely available to those skilled in the art (Qiagen for example). These chosen sequences, usually 19-mers, were included in two complementary oligonucleotides that form the template for the shRNAs, i.e. the 19-nt sense sequence, a 9-nt linker region (loop), the 19-nt antisense sequence followed by a 5-6 poly-T tract for termination of the RNA polymerase III. Appropriate restriction sites were inserted at the ends of these oligonucleotides to facilitate proper positioning of the inserts so that the transcriptional start point is at a precise location downstream of the hU6 promoter. The plasmid utilized in all RNA interference studies, pSilencer 2.0 (SEQ. ID. NO. 101), was purchase from a commercial supplier (Ambion, Austin, Tex.). For each sequence selected, at least two different shRNA expression vectors were constructed to increase the chance of observing RNA interference.

TOV-21G or TOV-112D cells were seeded in 6-well plates in OSE (Samouelian et al., 2004) containing 10% fetal bovine serum at a density of 600 000 cells/well, allowed to plate overnight and transfected with 1 μg of pSil-shRNA plasmid (FIG. 53, sh-1 and sh-2) using the FUGENE 6 reagent (Roche, Laval, QC). After 16 h of incubation, fresh medium was added containing 2 μg/ml puromycin (Sigma, St. Louis, Mo.) to select for stable transfectants. Control cells were transfected with a control pSil (sh-scr (SEQ. ID. NO. 102) that contains a scrambled shRNA sequence that displays homology to no known human gene. After approximately 4-5 days, pools and/or individual clones of cells were isolated and expanded for further analyses. The effectiveness of attenuation was verified in all shRNA cells lines. Total RNA was prepared by standard methods using TRIZOL reagent from cells grown in 6-well plates and expression of the target gene was determined by RT-PCR using gene-specific primers. First strand cDNA was generated using THERMOSCRIPT (Invitrogen, Burlington, ON) and semi-quantitative PCR was performed by standard methods (Qiagen, Mississauga, ON). 100% expression levels for a given gene was assigned to those found in the cell lines transfected with the control pSil plasmid (sh-scr). FIG. 52 shows representative results from the attenuation of two candidate genes, SEQ. ID. NO. 1 and SEQ. ID. NO. 3. When RT-PCR was performed using total RNA from the control cell lines (FIG. 52, pSil-scr), a single band of expected size was observed. When the total RNA from the cell line containing shRNAs to SEQ. ID. NO. 1(0094) (sh-1: SEQ. ID. NO. 103 and sh-2: SEQ. ID. NO. 104) or SEQ. ID. NO. 3 (0671) (sh-1: SEQ. ID. NO. 107 and sh-2: SEQ. ID. NO. 108) was amplified under identical conditions, significant reduction in the levels of expression of these genes were observed. These results indicate that the shRNAs that were expressed in the TOV-21G stable transfectants were successful in attenuating the expression of their target genes. As a control for equal quantities of RNA in all reactions, the expression of glyceraldehyde-3-phosphate dehydrogenase (FIG. 52, GAPDH) was monitored and found to be expressed at equal levels in all samples used.

The proliferative ability of each shRNA-expressing cell line was determined and compared to cells expressing the scrambled shRNA (control). Cell number was determined spectrophotometrically by MTT assay at 570 nm (Mosmann, 1983). After selection of stably shRNA expressing pools and expansion of the lines, 5 000 cells/well of each cell lines was plated in 48-well plates in triplicate and incubated for 4 days under standard growth conditions. Representative data from 2 experiments ±SEM is displayed and experiments were typically repeated at least three times to confirm the results observed. FIG. 53 shows representative results that were obtained when the proliferation assay was applied to stable TOV-21G cells lines. The cell number after 4 days in the control cell line expressing the scrambled shRNA (FIG. 53, sh scr) was arbitrarily set to 100%. TOV-21G cell lines containing shRNA against SEQ. ID. NO. 1 (sh-1: SEQ. ID. NO. 103 and sh-2: SEQ. ID. NO. 104), SEQ. ID. NO. 3 (sh-1: SEQ. ID. NO. 107 and sh-2: SEQ. ID. NO. 108) and SEQ. ID. NO. 8 (0065) (sh-1: SEQ. ID. NO. 117 and sh-2: SEQ. ID. NO. 118) exhibited less than 50% proliferation for at least one shRNA compared to the control cell line (FIG. 53, sh-1 and sh-2 for each). The proliferation of TOV-21G cell lines containing shRNA against SEQ. ID. NO. 2 (0478) (sh-1: SEQ. ID. NO. 105 and sh-2: SEQ. ID. NO. 106) and SEQ. ID. NO.

7 (1096) (sh-1: SEQ. ID. NO. 115 and sh-2: SEQ. ID. NO. 116) was not affected to the same extent but significant inhibition of growth was still observed nevertheless. These results indicate that attenuation of these genes causes retardation in the growth of this ovarian cancer cell line. Several of these shRNA expression vectors were also transfected into the TOV-112D cell line and similar results were obtained (data not shown). This suggested that these genes are important for proliferation of ovarian cancer cells.

The gene encoding the folate receptor 1, SEQ. ID. NO. 50 (0967A) (FIG. 53, 0967A), which has been documented as being an important marker for ovarian cancer (Leamon and Low, 2001), was also attenuated in TOV-21G cells, and marked growth inhibition was observed in the presence of the shRNAs (sh-1: SEQ. ID. NO. 151 and sh-2: SEQ. ID. NO. 152). This gives credibility to the approach used to validate the genes presented in this patent and substantiated their functional importance in the proliferation of ovarian cancer cells.

Table 1 below lists all of the genes tested and the average growth inhibition (n=3-4) that was observed in TOV-21G cells. Differences of less than 20% (see Table 1, <20) compared to the control cell lines represent cells where statistically significant reduction in proliferation was measured within a range of 5-20%.

TABLE 1

List of genes tested in cell proliferation assay and results

| Gene SEQ. ID. NO. | Alethia's Gene Code | shRNA SEQ. ID. NO. | Average Growth inhibition in TOV-21G cells (%) (n = 3-4) |
|---|---|---|---|
| Control | | SEQ. ID. NO. 102 | 0 |
| SEQ. ID. NO. 1 | 0094 | SEQ. ID. NOs. 103 and 104 | 47.9 |
| SEQ. ID. NO. 2 | 0478 | SEQ. ID. NOs. 105 and 106 | 41.7 |
| SEQ. ID. NO. 3 | 0671 | SEQ. ID. NOs. 107 and 108 | 65.7 |
| SEQ. ID. NO. 4 | 0851 | SEQ. ID. NOs. 109 and 110 | 21.5 |
| SEQ. ID. NO. 5 | 0713 | SEQ. ID. NOs. 111 and 112 | 42.3 |
| SEQ. ID. NO. 6 | 1064 | SEQ. ID. NOs. 113 and 114 | 28.9 |
| SEQ. ID. NO. 7 | 1096 | SEQ. ID. NOs. 115 and 116 | 25.8 |
| SEQ. ID. NO. 8 | 0065 | SEQ. ID. NOs. 117 and 118 | 32.5 |
| SEQ. ID. NO. 9 | 1313 | SEQ. ID. NOs. 119 and 120 | 50.5 |
| SEQ. ID. NO. 10 | 0059 | SEQ. ID. NOs. 121 and 122 | 52.4 |
| SEQ. ID. NO. 11 | 0239 | SEQ. ID. NOs. 123 and 124 | 22.8 |
| SEQ. ID. NO. 12 | 0291 | SEQ. ID. NOs. 125 and 126 | <20 |
| SEQ. ID. NO. 13 | 0972 | SEQ. ID. NOs. 127 and 128 | <20 |
| SEQ. ID. NO. 14 | 0875 | SEQ. ID. NOs. 129 and 130 | <20 |
| SEQ. ID. NO. 15 | 0420 | SEQ. ID. NOs. 131 and 132 | <20 |
| SEQ. ID. NO. 16 | 0125 | SEQ. ID. NOs. 133 and 134 | <20 |
| SEQ. ID. NO. 17 | 0531 | SEQ. ID. NOs. 135 and 136 | 0 |
| SEQ. ID. NO. 18 | 0967B | SEQ. ID. NOs. 137 and 138 | 0 |
| SEQ. ID. NO. 19 | 0889 | SEQ. ID. NOs. 139 and 140 | <20 |
| SEQ. ID. NO. 20 | 0313 | SEQ. ID. NOs. 141 and 142 | <20 |
| SEQ. ID. NO. 21 | 1134 | SEQ. ID. NOs. 143 and 144 | <20 |
| SEQ. ID. NO. 22 | 0488 | SEQ. ID. NOs. 145 and 146 | 0 |
| SEQ. ID. NO. 23 | 0216 | SEQ. ID. NOs. 147 and 148 | <20 |
| SEQ. ID. NO. 24 | 0447 | SEQ. ID. NOs. 149 and 150 | 0 |
| SEQ. ID. NO. 50 | 0967A | SEQ. ID. NOs. 151 and 152 | 47.4 |

J—A Method for Determining the Requirement for Specific Genes in the Survival of Ovarian Cancer Cells As a means of complementing the growth inhibition data that was generated with the stable TOV-21G cell lines, a colony survival assay was used to determine the requirement of the selected genes in the survival of the cancer cells. The 'colony formation assay' or 'clonogenic assay' is a classical test to evaluate cell growth after treatment. The assay is widespread in oncological research areas where it is used to test the proliferating power of cancer cell lines after radiation and/or treatment with anticancer agents. It was expected that the results obtained when analyzing the genes that were functionally important in ovarian cancer would correlate between the growth inhibition study and the colony survival assay.

TOV-21G cells were seeded in 12-well plates at a density of 50 000 cells/well and transfected 24 h later with 1 μg of pSil-shRNA vector, the same plasmids used in the previous assay. The next day, fresh medium was applied containing 2 μg/ml puromycin and the selection of the cells was carried out for 3 days. The cells were washed and fresh medium without puromycin was added and growth continued for another 5 days. To visualize the remaining colonies, the cells were washed in PBS and fixed and stained simultaneously in 1% crystal violet/10% ethanol in PBS for 15 minutes at room temperature. Following extensive washing in PBS, the dried plates were scanned for photographic analysis.

As shown in FIG. 37 and as exemplified by SEQ. ID. NO. 1 (0094), SEQ. ID. NO. 3 (0671), and SEQ. ID. NO. 9 (1313), the amount of TOV-21G-derived colonies that survived correlated with the growth inhibition data. For example, the growth inhibition in the proliferation assay (FIG. 53) and cell death in the colony assay (FIG. 54) was greater in TOV-21G cells containing shRNA-2 compared to shRNA-1 for SEQ. ID. NO. 1 (0094) (0094-sh2 stronger than 0094-sh1) and SEQ. ID. NO. 3 (0671) (0671-sh2 stronger than 0671-sh1) whereas, for SEQ. ID. NO. 9 (1313), the 1313-sh1 was stronger than 1313-sh2. Similar convergence was observed with several other genes that were analyzed using these two assays (data not shown). Therefore, these results implied that a phenotypic manifestation in both assays was indicative of important genes that are functionally required in ovarian cancer cells and suggest that inhibition of the proteins they encode could be serve as important targets to develop new anticancer drugs.

K—A Method for Broadening the Scope of Intervention to Other Oncology Indications One skilled in the art will recognize that the sequences described in this invention have utilities in not only ovarian cancer, but these applications can also be expanded to other oncology indications where the genes are expressed. To address this, a PCR-based method was adapted to determine the expression pattern of all sequences described above in cancer cell lines isolated from nine types of cancer. The cancer types represented by the cell lines are leukemia, central nervous system, breast, colon, lung, melanoma, ovarian, prostate, and renal cancer (see Table C). These RNA samples were obtained from the Developmental Therapeutics Program at the NCI/NIH. Using the same RAMP RNA samples that amplified from the total RNA samples obtained from the NCI, 500 μg of RNA was converted to single-stranded cDNA with THERMOSCRIPT RT (Invitrogen, Burlington, ON) as described by the manufacturer. The cDNA reaction was diluted so that 1/200 of the reaction was used for each PCR experiment. After trial PCR reactions with gene-specific primers designed against each SEQ. ID NOs, to be tested, the linear range of the reaction was determined and applied to all samples. PCR was conducted in 96-well plates using HOT-STARTAQ Polymerase from Qiagen (Mississauga, ON) in a DNA ENGINE TETRAD from MJ Research. Half of the reaction mixture was loaded on a 1.2% agarose/ethidium bromide gel and the amplicons visualized with UV light. To verify that equal quantities of RNA was used in each reaction, the level of RNA was monitored with GAPDH expression.

TABLE C

List of cancer cell lines from the NCI-60 panel

| Cell line | Cancer type |
|---|---|
| K-562 | leukemia |
| MOLT-4 | leukemia |
| CCRF-CEM | leukemia |
| RPMI-8226 | leukemia |
| HL-60(TB) | leukemia |
| SR | leukemia |
| SF-268 | CNS |
| SF-295 | CNS |
| SF-539 | CNS |
| SNB-19 | CNS |
| SNB-75 | CNS |
| U251 | CNS |
| BT-549 | breast |
| HS 578T | breast |
| MCF7 | breast |
| NCI/ADR-RES | breast |
| MDA-MB-231 | breast |
| MDA-MB-435 | breast |
| T-47D | breast |
| COLO 205 | colon |
| HCC-2998 | colon |
| HCT-116 | colon |
| HCT-15 | colon |
| HT29 | colon |
| KM12 | colon |
| SW-620 | colon |
| A549/ATCC | non-small cell lung |
| EKVX | non-small cell lung |
| HOP-62 | non-small cell lung |
| HOP-92 | non-small cell lung |
| NCI-H322M | non-small cell lung |
| NCI-H226 | non-small cell lung |
| NCI-H23 | non-small cell lung |
| NCI-H460 | non-small cell lung |
| NCI-H522 | non-small cell lung |
| LOX IMVI | melanoma |
| M14 | melanoma |
| MALME-3M | melanoma |
| SK-MEL-2 | melanoma |
| SK-MEL-28 | melanoma |
| SK-MEL-5 | melanoma |
| UACC-257 | melanoma |
| UACC-62 | melanoma |
| IGROV-1 | ovarian |
| OVCAR-3 | ovarian |
| OVCAR-4 | ovarian |
| OVCAR-5 | ovarian |
| OVCAR-8 | ovarian |
| SK-OV-3 | ovarian |

TABLE C-continued

List of cancer cell lines from the NCI-60 panel

| Cell line | Cancer type |
|---|---|
| DU-145 | prostate |
| PC-3 | prostate |
| 786-O | renal |
| A498 | renal |
| ACHN | renal |
| CAKI-1 | renal |
| RXF-393 | renal |
| SN-12C | renal |
| TK-10 | renal |
| UO-31 | renal |

One of skill in the art will readily recognize that orthologues for all mammals maybe identified and verified using well-established techniques in the art, and that this disclosure is in no way limited to one mammal. The term "mammal(s)" for purposes of this disclosure refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The sequences in the experiments discussed above are representative of the NSEQ being claimed and in no way limit the scope of the invention. The disclosure of the roles of the NSEQs in proliferation of ovarian cancer cells satisfies a need in the art to better understand ovarian cancer disease, providing new compositions that are useful for the diagnosis, prognosis, treatment, prevention and evaluation of therapies for ovarian cancer and other cancers where said genes are expressed as well.

The art of genetic manipulation, molecular biology and pharmaceutical target development have advanced considerably in the last two decades. It will be readily apparent to those skilled in the art that newly identified functions for genetic sequences and corresponding protein sequences allows those sequences, variants and derivatives to be used directly or indirectly in real world applications for the development of research tools, diagnostic tools, therapies and treatments for disorders or disease states in which the genetic sequences have been implicated.

Although the present invention has been described herein above by way of preferred embodiments thereof, it maybe modified, without departing from the spirit and nature of the subject invention as defined in the appended claims.

TABLE 2

Differentially expressed sequences found in malignant ovarian cancer.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 1 | STAR clone but possibly belonging to cluster Hs.555871 | BX094904 NM_021955 for Hs.555871 | Unknown 149-373 for Hs.555871 encoding SEQ ID NO.: 51 | Transcribed locus guanine nucleotide binding protein (G protein), gamma transducing activity polypeptide 1 |
| SEQ ID NO. 2 | Hs.389724/ IFI44L/ 10964 | NM_006820 | 242-1483 encoding SEQ ID NO.: 52 | interferon-induced protein 44-like; function unknown |
| SEQ ID NO. 3 | Hs.83465/ HOXD1/ 3231 | NM_024501 | 224-1210 encoding SEQ ID NO.: 53 | homeobox D1; sequence-specific transcription factor that is involved in differentiation and limb development |

TABLE 2-continued

Differentially expressed sequences found in malignant ovarian cancer.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 4 | Hs.59761/ LOC92196/ 92196 | NM_001017920 | 45-368 encoding SEQ ID NO.: 54 | hypothetical protein LOC92196; function unknown |
| SEQ ID NO. 5 | Hs.20315/ IFIT1/ 3434 | NM_001001887 | 93-1529 encoding SEQ ID NO.: 55 | interferon-induced protein with tetratricopeptide repeats 1; function unknown |
| SEQ ID NO. 6 | Hs.584238/ GLDC/ 2731 | NM_000170 | 151-3213 encoding SEQ ID NO.: 56 | glycine dehydrogenase (decarboxylating; glycine decarboxylase, glycine cleavage system protein P); mitochondrial glycine cleavage system catalyzes the degradation of glycine |
| SEQ ID NO. 7 | Hs.302028/ DPEP3/ 64180 | NM_022357 | 9-1550 encoding SEQ ID NO.: 57 | dipeptidase 3; proteolysis and peptidolysis |
| SEQ ID NO. 8 | Hs.418367/ NMU/ 10874 | NM_006681 | 106..630 encoding SEQ ID NO.: 58 | neuromedin U (NMU); neuropeptide signaling pathway, regulation of smooth muscle contraction |
| SEQ ID NO. 9 | Hs.473163/ BMP7/ 655 | NM_001719 | 123-1418 encoding SEQ ID NO.: 59 | bone morphogenetic protein 7; cell growth and/or maintenance, growth, skeletal development, cytokine activity, growth factor activity |
| SEQ ID NO. 10 | Hs.84113/ CDKN3/ 1033 | NM_005192 | 62-700 encoding SEQ ID NO.: 60 | cyclin-dependent kinase inhibitor 3; a cyclin-dependent kinase inhibitor, as well as, dephosphorylate CDK2 kinase which prevent the activation of CDK2 kinase |
| SEQ ID NO. 11 | Hs.374378/ CKS1B/ 1163 | NM_001826 | 10-249 encoding SEQ ID NO.: 61 | CDC28 protein kinase regulatory subunit 1B; cell cycle, cytokinesis, cyclin-dependent protein kinase activity |
| SEQ ID NO. 12 | Hs.30743/ PRAME/ 23532 | NM_006115 | 250-1779 encoding SEQ ID NO.: 62 | preferentially expressed antigen in melanoma; function unknown |
| SEQ ID NO. 13 | Hs.458485/ ISG15/ 9636 | NM_005101 | 76-573 encoding SEQ ID NO.: 63 | ISG15 ubiquitin-like modifier; protein binding |
| SEQ ID NO. 14 | STAR clone | AI922121.1 | | Novel genomic hit |
| SEQ ID NO. 15 | Hs.292451/ FLJ33790/ 283212 | NM_001039548 | 220-1311 encoding SEQ ID NO.: 64 | hypothetical protein LOC283212; function unknown |
| SEQ ID NO. 16 | Hs.334302 | BG213598 | | Transcribed locus; function unknown |
| SEQ ID NO. 17 | Hs.546434/ VTCN1/ 79679 | NM_024626 | 71-919 encoding SEQ ID NO.: 65 | V-set domain containing T cell activation inhibitor 1; function unknown |
| SEQ ID NO. 18 | Hs.73625/ KIF20A/ 10112 | NM_005733 | 28..2700 encoding SEQ ID NO.: 66 | kinesin family member 20A; kinesin family, interacts with guanosine triphosphate (GTP)-bound forms of RAB6A and RAB6B |
| SEQ ID NO. 19 | STAR clone but a possibly of it belonging to cluster Hs.478368 according to NCBI | AC117457 NM_005832 for Hs.478368 | 300-1007 encoding SEQ ID NO.: 67 | novel genomic hit potassium large conductance calcium-activated channel, subfamily M, beta member 2 for Hs.478368 |
| SEQ ID NO. 20 | Hs.603908 | BU595315 | | Transcribed locus; function unknown |

TABLE 2-continued

Differentially expressed sequences found in malignant ovarian cancer.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 21 | Hs.632586/ CXCL10/ 3627 | NM_001565 | 67-363 encoding SEQ ID NO.: 68 | chemokine (C—X—C motif) ligand 10; chemokine |
| SEQ ID NO. 22 | STAR clone | AL583809 | | Novel genomic hit |
| SEQ ID NO. 23 | Hs.503368/ ALG8/ 79053 | NM_001007027 | 66-1469 encoding SEQ ID NO.: 69 | asparagine-linked glycosylation 8 homolog (S. cerevisiae, alpha-1,3-glucosyltransferase); catalyzes the addition of the second glucose residue to the lipid-linked oligosaccharide precursor for N-linked glycosylation of proteins |
| SEQ ID NO. 24 | Hs.591801/ KAAG1 | NM_181337 | 738-992 encoding SEQ ID NO.: 70 | kidney associated antigen 1; function unknown |
| SEQ ID NO. 25 | Hs.512599/ CDKN2A/ 1029 | NM_000077 | 213-683 encoding SEQ ID NO.: 71 | cyclin-dependent kinase inhibitor 2A; cell cycle G1 control |
| SEQ ID NO. 26 | Hs.244580/ TPX2/ 22974 | NM_012112 | 699-2942 encoding SEQ ID NO.: 72 | TPX2, microtubule-associated, homolog (Xenopus laevis); involve in cell proliferation |
| SEQ ID NO. 27 | Hs.93002/ UBE2C/ 11065 | NM_007019 | 81-620 encoding SEQ ID NO.: 73 | ubiquitin-conjugating enzyme E2C; required for the destruction of mitotic cyclins and for cell cycle progression |
| SEQ ID NO. 28 | Hs.590469 | AK092857 | | cDNA FLJ35538 fis, clone SPLEN2002463; function unknown |
| SEQ ID NO. 29 | Hs.405662/ CRABP2/ 1382 | NM_001878 | 138-554 encoding SEQ ID NO.: 74 | cellular retinoic acid binding protein 2; function unknown but may be involved in human skin growth and differentiation |
| SEQ ID NO. 30 | Hs.26331/ HIST3H2A/ 92815 | NM_033445 | 43-435 encoding SEQ ID NO.: 75 | histone 3, H2a; nucleosome formation |
| SEQ ID NO. 31 | Hs.591790/ HIST1H4H/ 8365 | NM_003543 | 1-312 encoding SEQ ID NO.: 76 | histone 1, H4h; nucleosome formation |
| SEQ ID NO. 32 | Hs.93574/ HOXD3/ 3232 | NM_006898 | 177-1475 encoding SEQ ID NO.: 77 | homeobox D3; may play a role in the regulation of cell adhesion processes |
| SEQ ID NO. 33 | Hs.525641/ IGHG1/ 3500 | BC092518 | 61-1470 encoding SEQ ID NO.: 78 | Immunoglobulin heavy constant gamma 1; may play a role in immune response and antigen binding |
| SEQ ID NO. 34 | Hs.592988/ IGKC/ 3514 | BC073793 | 10-717 encoding SEQ ID NO.: 79 | Immunoglobulin kappa constant; may play a role in immune response and antigen binding |
| SEQ ID NO. 35 | Hs.66762 | AY683003 | 55-2727 encoding SEQ ID NO.: 80 | Chromosome 10 ORF 38; unknown function |
| SEQ ID NO. 36 | Hs.373741/ SPP/ 81502 | NM_178580 | 115-1299 encoding SEQ ID NO.: 81 | Histocompatibility (minor) 13; unknown function |
| SEQ ID NO. 37 | STAR clone | AL157931 | | Novel genomic hit |
| SEQ ID NO. 38 | Hs.128453/ FRZB/ 2487 | NM_001463 | 219-1196 encoding SEQ ID NO.: 82 | Frizzled-related protein; Wnt receptor signaling pathway, development. skeletal, transmembrane receptor activity |
| SEQ ID NO. 39 | Hs.239/ FOXM1/ 2305 | NM_202003 | 266-2512 encoding SEQ ID NO.: 83 | Forkhead box M1; transcriptional regulation |

TABLE 2-continued

Differentially expressed sequences found in malignant ovarian cancer.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 40 | Hs.46627 | NM_152864 | 89-715 encoding SEQ ID NO.: 84 | Chromosome 20 ORF 58; unknown function |
| SEQ ID NO. 41 | STAR clone | AK092936 | | Novel genomic hit |
| SEQ ID NO. 42 | Gene ID 404550 | BC009078 | 552-746 encoding SEQ ID NO.: 85 | Chromosome 16 ORF 74; unknown function |
| SEQ ID NO. 43 | Hs.645513/ RACGAP1/ 29127 | NM_013277 | 225-2123 encoding SEQ ID NO.: 86 | Rac GTPase activating protein 1; electron transport, intracellular signaling cascade; iron ion binding |
| SEQ ID NO. 44 | Hs.645522/ TMEM19/ 55266 | NM_018279 | 584-1594 encoding SEQ ID NO.: 87 | Transmembrane protein 19; unknown function |
| SEQ ID NO. 45 | STAR clone | AC109350 | | Novel genomic hit |
| SEQ ID NO. 46 | STAR clone | AC104837 | | Novel genomic hit |
| SEQ ID NO. 47 | STAR clone | AC002060 | | Immunoglobulin lambda variable group @; may play a role in antigen binding |
| SEQ ID NO. 48 | Hs.200600/ SCAMP3/ 10067 | NM_005698 | 254-1297 encoding SEQ ID NO.: 88 | Secretory carrier membrane protein 3; post-Golgi transport, protein transport |
| SEQ ID NO. 49 | STAR clone | AC068288 | | |
| SEQ ID NO. 50 | Hs.73769/ FOLR1/ 2348 | NM_000802 | 26-799 encoding SEQ ID NO.: 89 | folate receptor 1 (adult); mediate delivery of 5-methyltetrahydrofolate to the interior of cells |
| SEQ ID NO. 169 | Hs.558314/ CP/ 1356 | NM_000096 | 251-3448 encoding SEQ ID NO.: 170 | Ceruloplasmin; secreted protein; copper ion binding or transport |

TABLE 3

List of additional sequences identification of plasmids, oligonucleotides and shRNA oligonucleotides

| Sequence Identification | name | Description |
|---|---|---|
| SEQ. ID. NO. 90 | OGS 364 | Oligo dT$_{11}$ + Not 1 + biotin |
| SEQ. ID. NO. 91 | OGS 594 | Oligonucleotide promoter tag 1 |
| SEQ. ID. NO. 92 | OGS 595 | Oligonucleotide promoter tag 1 |
| SEQ. ID. NO. 93 | OGS 458 | Oligonucleotide promoter tag 2 |
| SEQ. ID. NO. 94 | OGS 459 | Oligonucleotide promoter tag 2 |
| SEQ. ID. NO. 95 | OGS 494 | Primer for second-strand synthesis from tag 1 |
| SEQ. ID. NO. 96 | OGS 302 | Primer for second-strand synthesis from tag 2 |
| SEQ. ID. NO. 97 | OGS 621 | Oligonucleotide promoter |
| SEQ. ID. NO. 98 | OGS 622 | Oligonucleotide promoter |
| SEQ. ID. NO. 99 | pCATRMAN | Vector for STAR |
| SEQ. ID. NO. 100 | p20 | Vector for STAR |
| SEQ. ID. NO: 101 | pSilencer2.0 vector | Vector for shRNA |
| SEQ. ID. NO: 102 | sh-scr | Control shRNA (Ambion) |
| SEQ. ID. NO: 103 | sh-1 0094 | shRNA sequence for SEQ. ID. NO. 1 |
| SEQ. ID. NO: 104 | sh-2 0094 | shRNA sequence for SEQ. ID. NO. 1 |
| SEQ. ID. NO: 105 | sh-1 0478 | shRNA sequence for SEQ. ID. NO. 2 |
| SEQ. ID. NO: 106 | sh-2 0478 | shRNA sequence for SEQ ID NO. 2 |
| SEQ. ID. NO: 107 | sh-1 0671 | shRNA sequence for SEQ. ID. NO. 3 |
| SEQ. ID. NO: 108 | sh-2 0671 | shRNA sequence for SEQ. ID. NO. 3 |
| SEQ. ID. NO: 109 | sh-1 0851 | shRNA sequence for SEQ. ID. NO. 4 |
| SEQ. ID. NO: 110 | sh-2 0851 | shRNA sequence for SEQ ID NO. 4 |
| SEQ. ID. NO: 111 | sh-1 0713 | shRNA sequence for SEQ. ID. NO. 5 |
| SEQ. ID. NO: 112 | sh-2 0713 | shRNA sequence for SEQ. ID. NO. 5 |
| SEQ. ID. NO: 113 | sh-1 1064 | shRNA sequence for SEQ. ID. NO. 5 |
| SEQ. ID. NO: 114 | sh-2 1064 | shRNA sequence for SEQ ID NO. 6 |
| SEQ. ID. NO: 115 | sh-1 1096 | shRNA sequence for SEQ. ID. NO. 7 |
| SEQ. ID. NO: 116 | sh-2 1096 | shRNA sequence for SEQ. ID. NO. 7 |

TABLE 3-continued

List of additional sequences identification of plasmids, oligonucleotides and shRNA oligonucleotides

| Sequence Identification | name | Description |
|---|---|---|
| SEQ. ID. NO: 117 | sh-1 0065 | shRNA sequence for SEQ. ID. NO. 8 |
| SEQ. ID. NO: 118 | sh-2 0065 | shRNA sequence for SEQ ID NO. 8 |
| SEQ. ID. NO: 119 | sh-1 1313 | shRNA sequence for SEQ. ID. NO. 9 |
| SEQ. ID. NO: 120 | sh-2 1313 | shRNA sequence for SEQ ID NO. 9 |
| SEQ. ID. NO: 121 | sh-1 0059 | shRNA sequence for SEQ. ID. NO. 10 |
| SEQ. ID. NO: 122 | sh-2 0059 | shRNA sequence for SEQ ID NO. 10 |
| SEQ. ID. NO: 123 | sh-1 0239 | shRNA sequence for SEQ. ID. NO. 11 |
| SEQ. ID. NO: 124 | sh-2 0239 | shRNA sequence for SEQ ID NO. 11 |
| SEQ. ID. NO: 125 | sh-1 0291 | shRNA sequence for SEQ. ID. NO. 12 |
| SEQ. ID. NO: 126 | sh-2 0291 | shRNA sequence for SEQ ID NO. 12 |
| SEQ. ID. NO: 127 | sh-1 0972 | shRNA sequence for SEQ. ID. NO. 13 |
| SEQ. ID. NO: 128 | sh-2 0972 | shRNA sequence for SEQ ID NO. 13 |
| SEQ. ID. NO: 129 | sh-1 0875 | shRNA sequence for SEQ. ID. NO. 14 |
| SEQ. ID. NO: 130 | sh-2 0875 | shRNA sequence for SEQ ID NO. 14 |
| SEQ. ID. NO: 131 | sh-1 0420 | shRNA sequence for SEQ. ID. NO. 15 |
| SEQ. ID. NO: 132 | sh-2 0420 | shRNA sequence for SEQ ID NO. 15 |
| SEQ. ID. NO: 133 | sh-1 0125 | shRNA sequence for SEQ. ID. NO. 16 |
| SEQ. ID. NO: 134 | sh-2 0125 | shRNA sequence for SEQ ID NO. 16 |
| SEQ. ID. NO: 135 | sh-1 0531 | shRNA sequence for SEQ. ID. NO. 17 |
| SEQ. ID. NO: 136 | sh-2 0531 | shRNA sequence for SEQ ID NO. 17 |
| SEQ. ID. NO: 137 | sh-1 0967B | shRNA sequence for SEQ. ID. NO. 18 |
| SEQ. ID. NO: 138 | sh-2 0967B | shRNA sequence for SEQ ID NO. 18 |
| SEQ. ID. NO: 139 | sh-1 0889 | shRNA sequence for SEQ. ID. NO. 19 |
| SEQ. ID. NO: 140 | sh-2 0889 | shRNA sequence for SEQ ID NO. 19 |
| SEQ. ID. NO: 141 | sh-1 0313 | shRNA sequence for SEQ. ID. NO. 20 |
| SEQ. ID. NO: 142 | sh-2 0313 | shRNA sequence for SEQ ID NO. 20 |
| SEQ. ID. NO: 143 | sh-1 1134 | shRNA sequence for SEQ. ID. NO. 21 |
| SEQ. ID. NO: 144 | sh-2 1134 | shRNA sequence for SEQ ID NO. 21 |
| SEQ. ID. NO: 145 | sh-1 0488 | shRNA sequence for SEQ. ID. NO. 22 |
| SEQ. ID. NO: 146 | sh-2 0488 | shRNA sequence for SEQ ID NO. 22 |
| SEQ. ID. NO: 147 | sh-1 0216 | shRNA sequence for SEQ. ID. NO. 23 |
| SEQ. ID. NO: 148 | sh-2 0216 | shRNA sequence for SEQ ID NO. 23 |
| SEQ. ID. NO: 149 | sh-1 0447 | shRNA sequence for SEQ. ID. NO. 24 |
| SEQ. ID. NO: 150 | sh-2 0447 | shRNA sequence for SEQ ID NO. 24 |
| SEQ. ID. NO: 151 | sh-1 0967 | shRNA sequence for SEQ. ID. NO. 50 |
| SEQ. ID. NO: 152 | sh-2 0967 | shRNA sequence for SEQ ID NO. 50 |
| SEQ. ID. NO: 153 | OGS 1077 | Forward primer for SEQ ID NO. 32 |
| SEQ. ID. NO: 154 | OGS 1078 | Reverse primer for SEQ ID NO. 32 |
| SEQ. ID. NO: 155 | OGS 1141 | Forward primer for SEQ ID NO. 35 |
| SEQ. ID. NO: 156 | OGS 1142 | Reverse primer for SEQ ID NO. 35 |
| SEQ. ID. NO: 157 | OGS 1202 | Forward primer for SEQ ID NO. 38 |
| SEQ. ID. NO: 158 | OGS 1203 | Reverse primer for SEQ ID NO. 38 |
| SEQ. ID. NO: 159 | OGS 1212 | Forward primer for SEQ ID NO. 41 |
| SEQ. ID. NO: 160 | OGS 1213 | Reverse primer for SEQ ID NO. 41 |
| SEQ. ID. NO: 161 | OGS 1171 | Forward primer for SEQ ID NO. 44 |
| SEQ. ID. NO: 162 | OGS 1172 | Reverse primer for SEQ ID NO. 44 |
| SEQ. ID. NO: 163 | OGS 1175 | Forward primer for SEQ ID NO. 45 |
| SEQ. ID. NO: 164 | OGS 1176 | Reverse primer for SEQ ID NO. 45 |
| SEQ. ID. NO: 165 | OGS 1282 | Forward primer for SEQ ID NO. 48 |
| SEQ. ID. NO: 166 | OGS 1283 | Reverse primer for SEQ ID NO. 48 |
| SEQ. ID. NO: 167 | OGS 315 | Forward primer for human GAPDH |
| SEQ. ID. NO: 168 | OGS 316 | Reverse primer for human GAPDH |
| SEQ. ID NO. 171 | OGS 1136 | Forward primer for SEQ ID NO. 1 |
| SEQ. ID NO. 172 | OGS 1044 | Reverse primer for SEQ ID NO. 1 |
| SEQ. ID NO. 173 | OGS 1250 | Forward primer for SEQ ID NO. 2 |
| SEQ. ID NO. 174 | OGS 1251 | Reverse primer for SEQ ID NO. 2 |
| SEQ. ID NO. 175 | OGS 1049 | Forward primer for SEQ ID NO. 3 |
| SEQ. ID NO. 176 | OGS 1050 | Reverse primer for SEQ ID NO. 3 |
| SEQ. ID NO. 177 | OGS 1051 | Forward primer for SEQ ID NO. 4 |
| SEQ. ID NO. 178 | OGS 1052 | Reverse primer for SEQ ID NO. 4 |
| SEQ. ID NO. 179 | OGS 1252 | Forward primer for SEQ ID NO. 5 |
| SEQ. ID NO. 180 | OGS 1253 | Reverse primer for SEQ ID NO. 5 |
| SEQ. ID NO. 181 | OGS 1083 | Forward primer for SEQ ID NO. 6 |
| SEQ. ID NO. 182 | OGS 1084 | Reverse primer for SEQ ID NO. 6 |
| SEQ. ID NO. 183 | OGS 1053 | Forward primer for SEQ ID NO. 7 |
| SEQ. ID NO. 184 | OGS 1054 | Reverse primer for SEQ ID NO. 7 |
| SEQ. ID NO. 185 | OGS 1037 | Forward primer for SEQ ID NO. 8 |
| SEQ. ID NO. 186 | OGS 1038 | Reverse primer for SEQ ID NO. 8 |
| SEQ. ID NO. 187 | OGS 1045 | Forward primer for SEQ ID NO. 9 |
| SEQ. ID NO. 188 | OGS 1046 | Reverse primer for SEQ ID NO. 9 |
| SEQ. ID NO. 189 | OGS 1240 | Forward primer for SEQ ID NO. 10 |
| SEQ. ID NO. 190 | OGS 1241 | Reverse primer for SEQ ID NO. 10 |
| SEQ. ID NO. 191 | OGS 1304 | Forward primer for SEQ ID NO. 11 |
| SEQ. ID NO. 192 | OGS 1305 | Reverse primer for SEQ ID NO. 11 |

TABLE 3-continued

List of additional sequences identification of plasmids, oligonucleotides and shRNA oligonucleotides

| Sequence Identification | name | Description |
|---|---|---|
| SEQ. ID NO. 193 | OGS 1039 | Forward primer for SEQ ID NO. 12 |
| SEQ. ID NO. 194 | OGS 1040 | Reverse primer for SEQ ID NO. 12 |
| SEQ. ID NO. 195 | OGS 1095 | Forward primer for SEQ ID NO. 13 |
| SEQ. ID NO. 196 | OGS 1096 | Reverse primer for SEQ ID NO. 13 |
| SEQ. ID NO. 197 | OGS 1284 | Forward primer for SEQ ID NO. 15 |
| SEQ. ID NO. 198 | OGS 1285 | Reverse primer for SEQ ID NO. 15 |
| SEQ. ID NO. 199 | OGS 1063 | Forward primer for SEQ ID NO. 16 |
| SEQ. ID NO. 200 | OGS 1064 | Reverse primer for SEQ ID NO. 16 |
| SEQ. ID NO. 201 | OGS 1031 | Forward primer for SEQ ID NO. 17 |
| SEQ. ID NO. 202 | OGS 1032 | Reverse primer for SEQ ID NO. 17 |
| SEQ. ID NO. 203 | OGS 1308 | Forward primer for SEQ ID NO. 18 |
| SEQ. ID NO. 204 | OGS 1309 | Reverse primer for SEQ ID NO. 18 |
| SEQ. ID NO. 205 | OGS 1069 | Forward primer for SEQ ID NO. 19 |
| SEQ. ID NO. 206 | OGS 1070 | Reverse primer for SEQ ID NO. 19 |
| SEQ. ID NO. 207 | OGS 1061 | Forward primer for SEQ ID NO. 20 |
| SEQ. ID NO. 208 | OGS 1062 | Reverse primer for SEQ ID NO. 20 |
| SEQ. ID NO. 209 | OGS 1097 | Forward primer for SEQ ID NO. 21 |
| SEQ. ID NO. 210 | OGS 1098 | Reverse primer for SEQ ID NO. 21 |
| SEQ. ID NO. 211 | OGS 1075 | Forward primer for SEQ ID NO. 22 |
| SEQ. ID NO. 212 | OGS 1076 | Reverse primer for SEQ ID NO. 22 |
| SEQ. ID NO. 213 | OGS 1232 | Forward primer for SEQ ID NO. 23 |
| SEQ. ID NO. 214 | OGS 1233 | Reverse primer for SEQ ID NO. 23 |
| SEQ. ID NO. 215 | OGS 1067 | Forward primer for SEQ ID NO. 24 |
| SEQ. ID NO. 216 | OGS 1068 | Reverse primer for SEQ ID NO. 24 |
| SEQ. ID NO. 217 | OGS 1099 | Forward primer for SEQ ID NO. 25 |
| SEQ. ID NO. 218 | OGS 1100 | Reverse primer for SEQ ID NO. 25 |
| SEQ. ID NO. 219 | OGS 1246 | Forward primer for SEQ ID NO. 26 |
| SEQ. ID NO. 220 | OGS 1247 | Reverse primer for SEQ ID NO. 26 |
| SEQ. ID NO. 221 | OGS 1093 | Forward primer for SEQ ID NO. 27 |
| SEQ. ID NO. 222 | OGS 1094 | Reverse primer for SEQ ID NO. 27 |
| SEQ. ID NO. 223 | OGS 1332 | Forward primer for SEQ ID NO. 28 |
| SEQ. ID NO. 224 | OGS 1333 | Reverse primer for SEQ ID NO. 28 |
| SEQ. ID NO. 225 | OGS 1101 | Forward primer for SEQ ID NO. 29 |
| SEQ. ID NO. 226 | OGS 1102 | Reverse primer for SEQ ID NO. 29 |
| SEQ. ID NO. 227 | OGS 1300 | Forward primer for SEQ ID NO. 30 |
| SEQ. ID NO. 228 | OGS 1301 | Reverse primer for SEQ ID NO. 30 |
| SEQ. ID NO. 229 | OGS 1300 | Forward primer for SEQ ID NO. 31 |
| SEQ. ID NO. 230 | OGS 1303 | Reverse primer for SEQ ID NO. 31 |
| SEQ. ID NO. 231 | OGS 1292 | Forward primer for SEQ ID NO. 33 |
| SEQ. ID NO. 232 | OGS 1294 | Reverse primer for SEQ ID NO. 33 |
| SEQ. ID NO. 233 | OGS 1242 | Forward primer for SEQ ID NO. 34 |
| SEQ. ID NO. 234 | OGS 1243 | Reverse primer for SEQ ID NO. 34 |
| SEQ. ID NO. 235 | OGS 1280 | Forward primer for SEQ ID NO. 36 |
| SEQ. ID NO. 236 | OGS 1281 | Reverse primer for SEQ ID NO. 36 |
| SEQ. ID NO. 237 | OGS 1159 | Forward primer for SEQ ID NO. 37 |
| SEQ. ID NO. 238 | OGS 1160 | Reverse primer for SEQ ID NO. 37 |
| SEQ. ID NO. 239 | OGS 1310 | Forward primer for SEQ ID NO. 39 |
| SEQ. ID NO. 240 | OGS 1311 | Reverse primer for SEQ ID NO. 39 |
| SEQ. ID NO. 241 | OGS 1155 | Forward primer for SEQ ID NO. 40 |
| SEQ. ID NO. 242 | OGS 1156 | Reverse primer for SEQ ID NO. 40 |
| SEQ. ID NO. 243 | OGS 1316 | Forward primer for SEQ ID NO. 42 |
| SEQ. ID NO. 244 | OGS 1317 | Reverse primer for SEQ ID NO. 42 |
| SEQ. ID NO. 245 | OGS 1306 | Forward primer for SEQ ID NO. 43 |
| SEQ. ID NO. 246 | OGS 1307 | Reverse primer for SEQ ID NO. 43 |
| SEQ. ID NO. 247 | OGS 1286 | Forward primer for SEQ ID NO. 46 |
| SEQ. ID NO. 248 | OGS 1287 | Reverse primer for SEQ ID NO. 46 |
| SEQ. ID NO. 249 | OGS 1244 | Forward primer for SEQ ID NO. 47 |
| SEQ. ID NO. 250 | OGS 1245 | Reverse primer for SEQ ID NO. 47 |
| SEQ. ID NO. 251 | OGS 1035 | Forward primer for SEQ ID NO. 50 |
| SEQ. ID NO. 252 | OGS 1036 | Reverse primer for SEQ ID NO. 50 |
| SEQ. ID NO. 253 | OGS 1248 | Forward primer for SEQ ID NO. 51 |
| SEQ. ID NO. 254 | OGS 1249 | Reverse primer for SEQ ID NO. 51 |

TABLE 4

Nucleotide and amino acid sequences of the SEQ. ID NOs.

Nucleotide Sequence
(5'-3')                                                                                           ORFs SEQ.ID NO. 1                                                                                      SEQ.ID NO. 51
STAR clone:                                                                                       MPVINIEDLTEKDKLKMEVDQL
CTGGAAGCTGAAGAATCACCGGCTTCAGTGACATGGAACCCAGCGATTTGATTTTTGACGAGTATCGGGTGACTTTGAGG                  KKEVTLERMLVSKCCEEVRDYV
TGGTCAAGAAACCACACTTTAAGAACAATGTCCA                                                                EERSGEDPLVKGIPEDKNPFKE
NM_021955:                                                                                        LKGGCVIS
AATCATATTAGTGAAGATTAGGAAGAAGCTTTAAAATCCCAAGGCTAGTGTGCATTGCTAGAATTGTTAAGAGAGAGC
TCATATGAAATTGGTTATCGTGGGATATTTAAAATAAAACAAAGAACAGTTTACTTTCAGGCAAAAAGATGCCAGTAATC
AATATTGAGGACCTGACAGAAAAAGACAAATTGAAGATGGAAGTTGACCAGCTCAAGAAAGAAGTGACACTGGAAAGAAT
GCTAGTTTCCAAATGTTGTGAAGAAGTAAGAGATTACGTTGAAGAACGATCTGGCGAGGATCCACTGGTAAAGGGCATCC
CAGAGGACAAAAATCCCTTCAAGGAGCTCAAAGGAGGCTGTGTGATTTCATAATACAAACAAAAAGAAAAAAATTAAAC
AAATTCTTGGAAATATCTCAAATGTTAATAACAATATGAATTTTTCTCATGCACTATTACTACTAAGCATGTACGTGA
ATTTTTAAATTTATAGATGTAAACTTTTAATAAAAATTGGGGTGTGGTAACCCATCATTCTATGTTTTTCTTAACATAGC
TGGCACAGGGTTTAACACATAATTGCCAATAAATATTGCTTAAAGTTCTTTAAAAAGAACTATGTTTT SEQ.ID NO. 2                                                                                      SEQ.ID NO. 52
GCACGAGGAAGCCACAGATCTCTTAAGAACTTTCTGTCTCCAAACCGTGGCTGCTCGATAAATCAGACAGAACAGTTAAT                  MVERCSRQGCTITMAYIDYNMI
CCTCAATTTAAGCCTGATCTAACCCCTAGAAACAGATATAGAACAATGGAAGTGACAACAAGATTGACATGGAATGATGA                  VAFMLGNYINLRESSTEPNDSL
AAATCATCTGCGCAACTGCTTGGAAATGTTTCTTTGAGTCTTCTCTATAAGTCTAGTGTTCATGGAGGTAGCATTGAAGA                  WFSLQKKNDTTEIETLLLNTAP
TATGGTTGAAAGATGCAGCCGTCAGGGATGTACTATAACAATGGCTTACATTGATTACAATATGATTGTAGCCTTTATGC                  KIIDEQLVCRLSKTDIFIICRG
TTGGAAATTATATTAATTTACGTGAAAGTTCTACAGAGCCAAATGATTCCCTATGGTTTCACTTCAAAAGAAAAATGAC                   KIIDEQLVCRLSKTDIFIICRG
ACCACTGAAATAGAAACTTTACTCTTAAATACAGCACCAAAAATTATTGATGAGCAACTGGTCGTGCGTTTATCGAAAC                   NKIYLNLDDIKRIIKAREHRNR
GGATATTTCATTATATGTCGAGATAATAAAATTTATCTAGATAAAATGATAACAAGAAACTTGAAACGTAAGGTTTTATG                  LLADIRDYRPYADLVSEIRILL
GCCACCGTCAGTATTTGGAATGTGAAGTTTTTCGAGTTGAAGGAATTAAGGATAACCTAGACGACATAAAGAGGATAATT                  VGPVGSGKSSFFNSVKSIFHGH
AAAGCCAGAGAGCACAGAAATAGGCTTCTAGCAGACATCAGAGACTATAGGCCCTATGCAGACTTGGTTTCAGAAATTCG                  VTGQAVVGSDTTSITERYRIYS
TATTCTTTTGGTGGGTCCAGTTGGGTCTGGAAAGTCCAGTTTTTTCAATTCAGTCAAGTCTATTTTTCATGGCCATGTGA                  VKDGKNGKSLPFMLCDTMGLDG
CTGCCAAGCGTAGTGGGGTCTGATACCACCAGCATAACCGAGCGGTATAGGATATATTCTGTTAAAGATGGAAAAAAT                    AEGAGLCMDDIPHILKGCMPDR
GGAAAATCTCTGCCATTTATGTTGTGTGACACTATGGGGCTAGATGGGGCAGAAGGAGCAGGACTGTGCATGGATGACAT                  YQFNSRKPITPEHSTFITSPSL
TCCCCACATCTTAAAAGGTTGCATGCCAGACAGATATCAGTTTAATTCCCGTAAACCAATTACACCTGAGCATTCTACTT                  KDRIHCVAYVLDINSIDNLYSK
TTATCACCTCTCCATCTCTGAAGGACAGGATTCACTGTGTGGCTTATGTCTTAGACATCAACTCTATTGACAATCTCTAC                  MLAKVKQVHKEVLNCGIAYVAL
TCTAAAATGTTGGCAAAAGTGAAGCAAGTTCACAAAGAAGTATTAAACTGTGGTATAGCATATGTGGCCTTGCTTACTAA                  LTKVDDCSEVLQDNFLNMSRSM
AGTGGATGATTGCAGTGAGGTTCTTCAAGACAACTTTTTAAACATGAGTAGATCTATGACTTCTCAAAGCCGGGTCATGA                  TSQSRVMNVHKMLGIPISNILM
ATGTCCATAAAATGCTAGGCATTCCTATTTCCAATATTTTGATGGTTGGAAATTATGCTTCAGATTTGGAACTGGACCCC                  VGNYASDLELDPMKDILILSAL
ATGAAGGATATTCTCATCCTCTCTGCACTGAGGCAGATGCTGCGGGCTGCAGATGATTTTTTAGAAGATTTGCCTCTTGA                  RQMLRAADDFLEDLPLEETGAI
GGAAACTGGTGCAATTGAGAGAGCGTTACAGCCCTGCATTTGAGATAAGTTGCCTTGATTCTGACATTTGGCCCAGCCTG                  ERALQPCI
TACTGGTGTGCCGCAATGAGAGTCAATCTCTATTGACAGCCTGCTTCAGATTTTGCTTTTGTTCGTTTTGCCTTCTGTCC
TTGGAACAGTCATATCTCAAGTTCAAAGGCCAAAACCTGAGAAGCGGTGGGCTAAGATAGGTCCTACTGCAAACCACCCC
TCCATATTTCCGTACCATTTACAATTCAGTTTCTGTGACATCTTTTTAAACCACTGGAGGAAAAATGAGATATTCTCTAA
TTTATTCTTCCTATAACACTCTATATAGAGCTATGTGAGTACTAATCACATTGAATAATAGTTATAAAATTATTGTATAGA
CATCTGCTTCTTAAACAGATTGTGAGTTCTTTGAGAAACAGCGTGGATTTTACTTATCTGTGTATTCACAGAGCTTAGCA
CAGTCCCTGGTAATGAGCAAGCATACTTGCCATTACTTTTCCTTCCCACTCTCTCCAACATCACATTCACTTTAAATTTT
TCTGTATATAGATAGGAAAACTAGCCTGGGCAACATGATGAAACCCCATCTCCACTGC SEQ.ID NO. 3                                                                                      SEQ.ID NO. 53
GCCGAGCGGAGAGGCCGCCCATTGGCCGGCCAGCGCCACGTGGCCGCCCCCGCCGGTATATTAGGCCACTATTTACCTCC                  MSSYLEYVSCSSSGGVGGDVLS
GGCTCACTCGCCATGGGTTGGAGAGGGCAGCTCGGGTAGAGAGGGCTGGCGGAGCGGCGCAGACGGCGGCAGTCCTGCTC                  LAPKFCRSDARPVALQPAFPLG
AGCCTCTGCCCGGCTCCGTACTCCGGCCCCGGCCTGCGCCCTCAGAAAGGTGGGGCCCGAACCATGAGCTCCTACCTGGA                  NGDGAFVSCLPLAAARPSPSPP
GTACGTGTCATGCAGCAGCAGCGGCGGGGTCGGCGGCGACGTGCTCAGCTTGGCACCCAAGTTCTGCCGCTCCGACGCCC                  AAPARPSVPPPAAPQYAQCTLE
GGCCCGTGGCTCTGCAGCCCGCCTTCCCTCTGGGCAACGGCGACGGCGCCTTCGTCAGCTGTCTGCCCCTGGCCGCCGCC                  GAYEPGAAPAAAAGGADYGFLG
CGACCCTCGCCTTCGCCCCCGGCCGCCCCCGCGGCGTGCTACCGCCTCCGGCCGCGCCCCAGTACGGCGCAGTGCAG                     SGPAYDFPGVLGRAADDGGSHV
CCTGGAGGGGGCCTACGAACCTGGTGCGCCACCTGCCGCGGCAGCTGGGGGCGGACTACGACTTCCTGGGGTCCGGGC                     HYATSAVFSGGGSFLLSGQVDY
CGGCGTACGACTTCCCGGGCGTGCTGGGGCGGGCGGCCGACGACGGCGGGTCTCACGTCCACTACGCCACCTCGGCCGTC                  AAEGEPGPFPACLKASADGHPG
TTCTCGGGCGGCGGCTCTTTCCTCCTCAGCGGCCAGGTGGATTACGCGGCCTTCGGCGAACCCGGCCCTTTTCCGGCTTG                  AFQTASPAPGTYPKSVSPASGL
TCTCAAAGCGTCAGCCGACGGCCACCCTGGTGCTTTCCAGACCGCATCCCCGGCCCCAGGCACCTACCCCAAGTCCGTCT                  PAAFSTFEWMKVKRNASKKGKL
CTCCGGCCTCCGGCCTCCCTGCCGCCTTCAGCACGTTCGAGTGGATGAAAGTGAAGAGGAATGCCTCTAAGAAAGGTAAA                  AEYGAASPSSAIRTNFSTKQLT
CTCGCCGAGTATGGGGCCGCTAGCCCCTCCAGCGCGATCCGCACGAATTTCAGCACCAAGCAACTGACAGAACTGGAAAA                  ELEKEFHFNKYLTRARRIEIAN
AGAGTTTCATTTCAATAAGTACTTAACTCGAGCCCGGCGCATCGAGATAGCCAACTGCTTGCACCTGAATGACACGCAAG                  CLHLNDTQVKIWFQNRRMKQKK
TCAAAATCTGGTTCCAGAACCGCAGGATGAAACAGAAGAAAAGGGAACGAGAAGGGCTTCTGGCCACGGCCATTCCTGTG                  REREGLLATAIPVAPLQLPLSG
GCTCCCCTCCAACTTCCCCTCTCTGGAACAACCCCCACTAAGTTTATCAAGAACCCCGGCAGCCCTTCTCAGTCCCAAGA                  TTPTKFTKNPGSPSQSQEPS
GCCTTCGTGAGGCCGGTACTTGGGGCCGAAAAACTGTGGCCTGCAGAAGTCCCAGGCGACCCCCATCCCATCTAGACTT
AGGAGCTCAGTTTGGGATGAGGTGGGAGAACAAAAATGAATAGGGATTTCACTTGGGAAATGAAGTACTTTAGTTGGCT
TCCGAGTTCCAGACTATATGTCCAGATATTAATTGACTGTCTTGTAAGCCACTTGTTTGGTTATGATTTGTGTCTTATCA
GGGAAAAGGTGCCAGCTGCCAGCCCAGCTCCGCTGCTATCTTTGCCTCACTTAGTCATGTGCAATTCGCGTTGCAGAGT
GGCAGACCATTAGTTGCTGAGTTCTGTCAGCACTCTGATGTGCTCAGAAGACACCTGCCCAAAGTTTTTCTGGTTTTAA
TTTAAAGGACAAGGCTACATATATTCAGCTTTTTGAGATGACCAAAGTCAGTTAGGGTCTCCTTGATGTAGCTAAGCTGC
TTCAGTGATCTTCACATTTGCACTCCAGTTTTTTTTCTTTAAAAAAGCGGTTTCTACCTCTCTATGTGCCTGAGTGATG
ATACAATCGCTGTTTAGTTACTAGATGAACAAATCCACAGATGGGTAAAGATGGTAGAATCTGAACTATATCTTGACAAAT
ATTATTCAAACTTGAATGTAAATATATACAGTATGTATATTTTTAAAAAGATTTGCTTGCAATGACCTTATAAGTGACA
TTTAATGTCATAGCATGTAAAGGGTTTTTTTGTAATAAAAATTATAGAATCTGCAAAAAAAAAAAAAAA SEQ.ID NO. 4                                                                                      SEQ.ID NO. 54
CAGCCTCCAGAGCACCAGCACTGGCACTGGCACTGGCACACGCTATGGCAAATGAAGTGCAAGACCTGCTCTCCCCTCGG                  MANEVQDLLSPRKGGHPPAVKA
AAAGGGGGACATCCTCCTGCAGTAAAAGCTGGAGGAATGAGAATTTCCAAAAACAAGAAATTGGCACCTTGGAAAGACA                   GGMRISKKQEIGTLERHTKKTG
TACCAAAAAAACAGGATTCGAGAAAACAAGTGCCATTGCAAATGTTGCCAAAATACAGACACTGGATGCCCTGAATGACA                  FEKTSATANVAKIQTLDALNDT
CACTGGAGAAGCTCAACTATAAATTTCCAGCAACAGTGCACATGGCACATCAAAAACCCACACCTGCTCTGGAAAAGGTT                  LEKLNYKFPATVHMAHQKPTPA
GTTCCACTGAAAAGGATCTACATTATTCAGCAGCCTCGAAAATGTTAAGCCTGGATTTAAAACACAGCCGTCGGCCAGC                   LEKVVPLKRIYIIQQPRKC TABLE 4-continued Nucleotide and amino acid sequences of the SEQ. ID NOs.

Nucleotide Sequence
(5'-3')                                                                                                    ORFs TGCCTCGAATATCTGACAGCTTAGCAAAAAGGGCCAAAGCTTTTCCATAGGCGTGCTGCACTTGCTTGGTAAATTAAACAG
CTTTTGTATCTTCCCCTTTGACTTTAGGTAATAAAGCATCCAAACTTGTAAAAAAAAA SEQ.ID NO. 5                                                                                               SEQ.ID NO. 55
GTAACTGAAAATCCACAAGACAGAATAGCCAGATCTCAGAGGAGCCTGGCTAAGCAAAACCCTGCAGAACGGCTGCCTAA    MSTNGDDHQVKDSLEQLRCHFT
TTTACAGCAACCATGAGTACAAATGGTGATGATCATCAGGTCAAGGATAGTCTGGAGCAATTGAGATGTCACTTTACATG    WELSIDDDEMPDLENRVLDQIE
GGAGTTATCCATTGATGACGATGAAATGCCTGATTTAGAAAACAGAGTCTTGGATCAGATTGAATTCCTAGACACCAAAT    FLDTKYSVGIHNLLAYVKHLKG
ACAGTGTGGGAATACACAACCTACTAGCCTATGTGAAACACCTGAAAGGCCAGAATGAGGAAGCCCTGAAGACTTAAAA    QNEEALKSLKEAENLMQEEHDN
GAAGCTGAAAACTTAATGCAGGAAGAACATGACAACCAAGCAAATGTGAGGAGTCTGGTGACCTGGGGCAACTTTGCTG    QANVRSLVTWGNFAWMYYHMGR
GATGTATTACCACATGGGCAGACTGGCAGAAGCCCAGACTTACCTGGACAAGGTGGAGAACATTTGCAAGAAGCTTTCAA    LAEAQTYLDKVENICKKLSNPF
ATCCCTTCCGCTATAGAATGGAGTGTCCAGAAATAGACTGTGAGGAAGGATGGGCCTTGCTGAAGTGTGGAGGAAAGAAT    RYRMECPEIDCEEGWALLKCGG
TATGAACGGGCCAAGGCCTGCTTTGAAAAGGTGCTTGAAGTGGACCCTGAAAACCCTGAATCCAGCGCTGGGTATGCGAT    KNYERAKACFEKVLEVDPENPE
CTCTGCCTATCGCCTGGATGGCTTTAAATTAGCCACAAAAAATCACAAGCCATTTTCTTTGCTTCCCCTAAGGCAQGCTG    SSAGYAISAYRLDGFKLATKNH
TCCGCTTAAATCCAGACAATGGATATATTAAGGTTCTCCTTGCCCTCAAGCTTCAGGATGAAGGACAGGAAACTGAAGGA    KPFSLLPLRQAVRLNPDNGYIK
GAAAAGTACATTGAAGAAGCTCTAGCCAACATGTCCTCACAGACCTATGTCTTTCGATATGCAGCCAAGTTTTACCGAAG    VLLALKLQDEGQEAEGEKYIEE
AAAAGGCTCTGTGGATAAAGCTCTTGAGTTATTAAAAAAGGCCTTGCAGGAAACACCCACTTCTGTCTTACTGCATCACC    ALANMSSQTYVFRYAAKFYRRK
AGATAGGGCTTTGCTACAAGGCACAAATGATCCAAATCAAGGAGGCTACAAAAAGGGCAGCCTAGAGGGCAGAACAAGAA    GSVDKALELLKKALQETPTSVL
AAGCTAGACAAAATGATAAGATCAGCCATATTTCATTTTGAATCTGCAGTGGAAAAAAAGCCCACATTTGAGGTGGCTCA    LHHQIGLCYKAQMIQIKEATKG
TCTAGACCTGGCAAGAATGTATATAGAAGCAGGCAATCACAGAAAAGCTGAAGAGAATTTTCAAAAATTGTTATGCATGA    QPRGQNREKLDKMIRSAIFHFE
AACCAGTGGTAGAAGAAACAATGCAAGACATACATTTCCACTATGGTCGGTTTCAGGAATTTCAAAAGAAATCTGACGTC    SAVEKKPTFEVAHLDLARMYIE
AATGCAATTATCCATTATTTAAAAGCTATAAAAATAGAACAGGCATCATTAACAAGGGATAAAAGTATCAATTCTTTGAA    AGNHRKAEENFQKLLCMKPVVE
GAAATTGTTTTAAGGAAACTTCGGAGAAAGGCATTAGATCTGGAAAGCTTGAGCCTCCTTGGGTTCGTCTACAAATTGG    ETMQDIHPHYGRFQEFQKKSDV
AAGGAAATATGAATGAAGCCCTGGAGTACTATGAGCGGGCCCTGAGACTGGCTGCTGACTTTGAGAACTCTGTGAGACAA    NAIIHYLKAIKIEQASLTRDKS
GGTCTTAGGCACCCAGATATCAGCCACTTTCACATTTCATTTCATTTTATGCTAACATTTACTAATCATCTTTTCTGCT    INSLKKLVLRKLRRKALDLESL
TACTGTTTTCAGAAACATTATAATTCACTGTAATGATGTAATTCTTGAATAATAAATCTGACAAAAAAAAAAAAAAAAA    SLLGFVYKLEGNMNEALEYYER
AAAAAAAAAA                                                                                                 ALRLAADFENSVRQGP SEQ.ID NO. 6                                                                                               SEQ.ID NO. 56
CCCGCGAGCGTCCATCCATCTGTCCGGCCGACTGTCCAGCGAAAGGGGCTCCAGGCCGGGCGCACGTCGACCCGGGGGAC    MQSCARAWGLRLRGRGVGGGRRL
CGAGGCCAGGAGAGGGGCCAAGAGCGCGGCTGACCCTTGCGGGCCGGGCAGGGACGGTGGCCGCGGCCATGCAGTCCT    AGGSGPCWAPRSDSSSGGGDS
GTGCCAGGGCGTGGGGCTGCGCCTGGGCCGCGGGGTCGGGGGCGGCCGCCGCCTGGCTGGGGGATCGGGGCCGTGCTGG    AAAGASRLLERLLPRHDDFARR
GCGCCGCGGAGCCGGGACAGCAGTGGCGGGGGACAGCGCCGCGGCCTCGGGGCCTCGCGCCTCCTGGAGCGCCTTCT    HIGPGDKDQREMLQTLGLASID
GCCCAGACACGACGACTTCGCTCGGAGGCACATCGGCCCTGGGGACAAAGACCAGAGAGAGATGCTGCAGACCTTGGGC    ELIEKTVPANIRLKRPLKMEDP
TGGCGAGCATTGATGAATTGATCGAGAAGACGGTCCCTGCCAACATCCGTTTGAAAAGACCCTTGAAATGGAAGACCCT    VCENEILATLHAISSKNQIWRS
GTTTGTGAAAATGAATCCTTGCAACTCTGCATGCCATTTCAAGCAAAAACCAGATCTGGAGATCGTATATTGGCATGGG    YIGMGYYNCSVPQTILRNLLEN
CTATTATAACTGCTCAGTGCCACAGACGATTTTGCGGAACTTACTGGAGAACTCAGGATGGATCACCCAGTATACTCAT    SGWITQYTPYQPEVSQGRLESL
ACCAGCTGAGGTGTCTCAGGGGAGGCTGGAGAGTTTACTCAACTACCAGACCATGTGTGTGACATACAGGCCTGGAC    LNYQTMVCDITGLDMANASLLD
ATGGCCAATGCATCCCTGCTGGATGAGGGACTGCAGCCGCAGAGGCACTGCAGCTGTGCTACAGACACAAGAGGA    EGTAAAEALQLCYRHNKRRKFL
GAAATTTCTCGTTGATCCCGTTGCCACCCACAGACAATAGCTGTTGTCCAGACTCGAGCCAAATATACTGGAGTCCTCA    VDPRCHPQTIAVVQTRAKYTGV
CTGAGCTGAAGTTACCCTGTGAAATGGACTTCAGTGGAAAAGATGTCAGTGGAGTGTTGTTCCAGTACCCAGACACGGAG    LTELKLPCEMDFSGKDVSGVLF
GGGAAGGTGGAAGACTTTACGGAACTCGTGGAGAGAGCTCATCAGAGTGGGAGCCTGGCCTGCTGCTACTGACCTTT    QYPDTEGKVEDFTELVERAHQS
AGCTTTGTGCATCTTGAGGCCACCTGGAGAATTTGGGGTAGACATCGCCCTGGGCAGCTCCCAGAGATTTGGAGTGCCAC    GSLACCATDLLALCILRPPGEF
TGGGCTATGGGGGACCCATGCAGCATTTTTTGCTGTCCGAGAAAGCTTGGTGAGAATGATGCCTGGAAGAATGGTGGG    GVDIALGSSQRFGVPLGYGGPH
GTAACAAGAGATGCCACTGGGAAGAAGTGTATCGTCTTGCTCTTCAAACCAGGGAGCAACACATTCGGAGAGACAAGGC    AAFFAVRESLVRMMPGRMVGVT
TACCAGCAACATCTGTACAGCTCAGGCCCTCTTGGCGAATATGGCTGCCATGTTTCGAATCTACCATGGTTCCCATGGGC    RDATGKEVYRLALQTREQHIRR
TGGAGCATATTGCTAGGAGGGTACATAATGCCACTTTGATTTTGTCAGAAGGTCTCAAGCGAGCAGGGCATCAACTCCAG    DKATSNICTAQALLANMAAMFR
CATGACCTGTTCTTTGATACCTTGAAGATTCATTGTGGCTGCTCAGTGAAGGAGGTCTTGGGCAGGCGGCTCAGCGGCA    IYHGSHGLEHIARRVHNATLIL
GATCAATTTTCGGCTTTTTGAGGATGGCACACTTGGTATTTCTCTTGATGAAACAGTCAATGAAAAGATCTGGACGATT    SEGLKRAGHQLQHDLFFDTLKI
TGTTGTGGATCTTTGGTTGTGAGTCATCTGCAGAACTGGTTGCTGAAAGCATGGGAGAGGAGTGCAGAGGTATTCCAGGG    HCGCSVKEVLGRAAQRQINFRL
TCTGTGTTCAAGAGGACCAGCCCGTTCCTCACCCATCAAGTGTTCAACAGCTACCACTCTGAAACAACATTGTCCGGTA    FEDGTLGISLDETVNEKDLDDL
CATGAAGAAACTGGAAAATAAAGACATTTCCCTTGTTCACAGCATGATTCCACTGGGATCCTGCACCATGAAACTGAACA    LWIFGCESSAELVAESMGEECR
GTTCGTCTGAACTCGCACCTATCACATGGAAAGAATTTGCAAACATCCACCCCTTTGTGCCTCTGGATCAAGCTCAGG    GIPGSVFKRTSPFLTHQVFNSY
TATCAGCAGCTTTTCCGAGAGCTTGAGAAGGATTTGTGAACTCACAGGTTATGACCAGGTCTGTTTCCAGCCAAACAG    HSETNIVRYMKKLENKDISLVH
CGGAGCCCAGGGAGAATATGCTGGACTGGCCACTATCCGAGCCTACTTAACCAGAAAGGAGAGGGGCACAGAACGGTTT    SMIPLGSCTMKLNSSSELAPIT
GCCTCATTCCGAAATCAGCACATGGGACCAACCCAGCAAGTGCCCACATGGCAGGCATGAAGATTCAGCCTGTGAGGTG    WKEFANIHPFVPLDQAQGYQQL
GATAAATATGGGAATATCGATGCAGTTCACCTCAAGGCCATGGTGGATAAGCACAAGGAGAACCTAGCAGCTATCATGAT    FRELEKDLCELTGYDQVCFQPN
TACATACCCATCCACCAATGGGTGTTTGAAGAGAACATCAGTGACGTCATGGACCTCATCCATCAACATGGAGGACAGG    SGAQGEYAGLATIRAYLNQKGE
TCTACCTAGACGGGGCAAATATGAATGCTCAGGTGGGAATCTGTCGCCCTGGAGACTTCGGGTCTGATGTCTCGACCTA    GHRTVCLIPKSAHGTNPASAHM
AATCTTCACAAGACCTTCTGCATTCCCACGGAGGAGGTGGTCCTGGCATGGGCCATCGGAGTGAAGAAACATCTCGC    AGMKIQPVEVDKYGNIDAVHLK
CCCGTTTTGCCCAATCATCCCGTCATTTCACTAAAGCGGAATGAGGATGCCTGTCCTGTGGGAACCGTCAGTCGGCCC    ANVDKHKENLAAIMITYPSTNG
CATGGGGCTCCAGTTCCATCTTGCCCATTTCCTGGGCTTATATCAAGATGATGGGAGGCAAGGGTCTTAAACAAGCCACG    VFEENISDVCDLIHQHGGQVYL
GAAACTGCGATATTAAATGCCAACTACATGGCCAAGCGATTAGAAACACACTACAGATTCTTTTCAGGGGTGCAAGAGG    DGANMNAQVGICRPGDFGSDVS
TTATGTGGGTCATGAATTTATTTTGGACACGAGACCCTTCAAAAGTCTGCAAATATTGAGGCTGTGGATGGCCAAGA    HLNLHKTFCIPHGGGGPGMGPI
GACTCCAGGATTATGGATTTCACGCCCCTACCATGTCCTGGCCTGTGGCAGGGACCCTCATGGTGGAGCCCACTGAGTCG    GVKKHLAPFLPNHPVISLKRNE
GAGGACAAGGCAGAGCTGGACAGATTCTGTGATGCCATGATCAGCATTCGGCAGGAATTGCTGACATTGAGGAGGCCG    DACPVGTVSAAPWGSSSILPIS
CATCGACCCCAGGGTCAATCCGCTGAAGATGTCTCCACACTCCCTGACCTGCGTTACATCTTCCCACTGGGACCGGCTTT    WAYIKMMGGKGLKQATETAILN
ATTCCAGAGAGGTGGCAGTTCCCACTCCCCTTCAGTGAAACCAGAAACAAATTCTGGCCAACGATTGCCGGATTTGA    ANYMAKRLETHYRILFRGARGY
GACATATATGGAGATCAGCACCTGGTTTGTACCTGCCCACCCATGAAGTTTATGAGTCTCATTTTCTGACAAAAAGAG    VGHEFILDTRPFKKSANIEAVD
GGCGTCTTCTTAGTCCTCTCTCCCTAAGTTTAAAGGACTGATTTGATGCCTCTCCCCAGACATTTGATAAGCAAGAAG    VAKRLQDYGFHAPTMSWPVAGT
ATTTCATCTCCCACCCCAGCCTCAAGTAGGAGTTTTATATACTGTGTATATCTCTGTAATCTCTGTCAAGGTAAATGAA    LMVEPTESEDKAELDRFCDANE
ATACAGTAGCTGGAGGGAGTCGAAGCTGATGGTTGGAAGACGGATTTGCTTTGGTATTCTGCTTCCACATGTGCCAGTTG    SIRQETADTEEGRIDPRVNPLK
CCTGGATTGGGAGCCATTTTGTGTTTTGCGTAGAAAGTTTTAGGAACTTTAACTTTTAATGTGGCAAGTTTGCAGATGTC    MSPHSLTCVTSSHWDRPYSREV
ATAGAGGCTATCCTGGAGACTTAATAGACATTTTTTTGTTCCAAAAGAGTCCATGTGGACTGTGCCATCTGTGGGAAATC    AAFPLPFMKPENKFWPTIARID TABLE 4-continued Nucleotide and amino acid sequences of the SEQ. ID NOs.

| Nucleotide Sequence (5'-3') | ORFs |
|---|---|
| CCAGGGCAAATGTTTACATTTTGTATACCCTGAAGAACTCTTTTTCCTCTAATATGCCTAATCTGTAATCACATTTCTGA<br>GTGTTTTCCTCTTTTTCTGTGTGAGGTTTTTTTTTTTTTTAATCTGCATTTATTAGTATTCTAATAAAAGCATTTTGATC<br>GGAAAAAAAAAAAAAAAAAAAA | DIYGDQHLVCTCPPMEVYESPF<br>SEQKRASS |
| SEQ.ID NO. 7<br>GGGTCGTCATGATCCGGACCCCATTGTCGGCCTCTGCCCATCGCCTGCTCCTCCCAGGCTCCCGCGGCCGACCCCCGCGC<br>AACATGCAGCCCACGGGCCGCGAGGGTTCCCGCGCGCTCAGCCGGCGGTATCTGCGCGTCTGCTGCTCCTGCTACTGCT<br>GCTGCTGCTGCGGCAGCCCGTAACCCGCGCGGAGACCACGCCGGGCGCCCCCAGAGCCCTCTCCACGCTGGGCTCCCCCA<br>GCCTCTTCACCACGCCGGGTGTCCCCAGCGCCCTCACTACCCCAGGCCTCACTACGCCAGGCACCCCCAAAACCCTGGAC<br>CTTCGGGGTCGCGCGCAGGCCCTGATGCGGAGTTTCCCCACTCGTGGACGGCCACAATGACCTGCCCCAGGTCCTGAGACA<br>GCGTTACAAGAATGTGCTTCAGGATGTTAACCTGCGAAATTTCAGCCATGGTCAGACCAGCCTGGACAGGCTTAGAGACG<br>GCCTCGTGGGTGCCCAGTTCTGGTCAGCCTCCGTCTCATGCCAGTCCCAGGACCAGACTGCCGTGCGCCTCGCCCTGGAA<br>CAGATTGACCTCATTCACCGCATGTGTGCCTCCTACTCTGAACTCGAGCTTGTGACCTCAGCTGAAGGTCTGAACAGCTC<br>TCAAAAGCTGGCCTGCCTCATTGGCGTGGAGGGTGGTCACTCACTGGACAGCAGCCTCTCTGTGCTGCGCAGTTTCTATG<br>TGCTGGGGGTGCGCTACCTGACACTTACCTTCACCTGCAGTACACCATGGGCAGAGAGTTCCACCAAGTTCAGACACCAC<br>ATGTACACCAACGTCAGCGGATTGACAAGCTTTGGTGAGAAAGTAGTAGAGGAGTTGAACCGCCTGGGCATGATGATAGA<br>TTTGTCCTATGCATCGGACACCTTGATAAGAAGGGTCCTGGAAGTGTCTCAGGCTCCTGTGATCTTCTCCCACTCAGCTG<br>CCAGAGCTGTGTGTGACAATTTGTTGAATGTTCCCGATGATATCCTGCAGCTTCTGAAGAAGAACGGTGGCATCGTGATG<br>GTGACACTGTCCATGGGGGTGCTGCAGTGCAACCTGCTTGCTAACGTGTCCACTGTGGCAGATCACTTTGACCACATCAG<br>GGCAGTCATTGGATCTGAGTTCATCGGGATTGGTGAAATTATGACGGGACTGGCCGGTTCCTCAGGGGCTGGAGGATG<br>TGTCCAACATACCCAGTCCTGATAGAGGAGTTGCTGAGTCGTAGCTGGAGCGGAGGAAGAGCTTCAAGGTGTCCTTCGTGGA<br>AACCTGCTGCGGGTCTTCAGACAAGTGGAAAAGGTGAGAGAGGAGAGCAGGGCGCAGAGCCCCGTGGAGGCTGAGTTTCC<br>ATATGGGCAACTGAGCACATCCTGCCACTCCCACCTCGTGCCTCAGAATGGACACCAGGCTACTCATCTGGAGGTGACCA<br>AGCAGCCAACCAATCGGGTCCCCTGGAGGTCCTCAAATGCCTCCCCATACCTTGTTCCAGGCCTTGTGGCTGCTGCCACC<br>ATCCCAACCTTCACCCAGTGGCTCTGCTGACACAGTCGGTCCCCGCAGAGGTCACTGTGGCAAAGCCTCACAAAGCCCCC<br>TCTCCTAGTTCATTCACAAGCATATGCTGAGATAACATGTTACACATGGAAAAAAAAAAAAAAAAAAAAA | SEQ.ID NO. 57<br>MIRTPLSASAHRLLLPGSRGRP<br>PRNMQPTGREGSRALSRRYLRR<br>LLLLLLLLLLRQPVTRAETTPG<br>APRALSTLGSPSLFTTPGVPSA<br>LTTPGLTTPGTPKTLDLRGRAQ<br>ALMRSFPLVDGHNDLPQVLRQR<br>YKNVLQDVNLRNFSHGQTSLDR<br>LRDGLVGAQFWSASVSCQSQDQ<br>TAVRLALEQIDLIHRMCASYSE<br>LELVTSAEGLNSSQKLACLIGV<br>EGGHSLDSSLSVLRSFYVLGVR<br>YLTLTFTCSTPWAESSTKFRHH<br>MYTNVSGLTSFGEKVVEELNRL<br>GMMIDLSYASDTLIRRVLEVSQ<br>APVIFSHSAARAVCDNLLNVPD<br>DILQLLKKNGGIVMVTLSMGVL<br>QCNLLANVSTVADHFDHIRAVI<br>GSEFIGIGGNYDGTGRFPQGLE<br>DVSTYPVLIEEELLSRSWSEEEL<br>QGVLRGNLLRVFRQVEKVREES<br>RAQSPVEAEFPYGQLSTSCHSH<br>LVPQNGHQATHLEVTKQPTNRV<br>PWRSSNASPYLVPGLVAAATIP<br>TFTQWLC |
| SEQ.ID NO. 8<br>AGTCCTGCGTCCGGGCCCCGAGGCGCAGCAGGGCACCAGGTGGAGCACCAGCTACGCGTGGCGCAGCGCAGCGTCCCTAG<br>CACCGAGCCTCCCGCAGCCGCCGAGATGCTGCGAACAGAGAGCTGCCGCCCCAGGTCGCCCGCCGGACAGGTGGCCGCGG<br>CGTCCCCGCTCCTGCTGCTGCTGCTGCTGCTCGCCTGGTGCGCGGGCGCCTGCCGAGGTGCTCCAATATTACCTCAAGGA<br>TTACAGCCTGAACAACAGCTACAGTTGTGGAATGAGATAGATGATACTTGTTCGTCTTTTCTGTCCATTGATTCTGCAGCC<br>TCAGGCATCCAACGCACTGGAGGAGCTTTGCTTTATGATTATGGGAATGCTACCAAAGCCTCAGGAACAAGATGAAAAAG<br>ATAATACTAAAAGGTTCTTATTTCATTATTCGAAGACACAGAAGTTGGGCAAGTCAAATGTTTGTCGTCAGTTGTGCAT<br>CCGTTGCTGCAGCTCGTTCCTCACCTGCATGAGAGAAGAATGAAGAGATTCAGAGTGGACGAAGAATTCAAAGTCCCTT<br>TGCAAGTCAAAGTCGAGGATATTTTTATTCAGGCCACGGAATGAAGAAGGTCAGCAGGGTTCATTTAAAATGGATGCC<br>AGCTAATTTTCCACAGAGCAATGCTATGGAATACAAAATGTACTGACATTTTGTTTTCTTCTGAAAAAAATCCTTGCTAA<br>ATGTACTCTGTTGAAAATCCCTGTGTTGTCAATGTTCTCAGTTGTAACATGTTGTAAATGTTCAATTTGTTGAAAATTA<br>AAAAATCTAAAAATAAA | SEQ.ID NO. 58<br>MLRTESCRPRSPAGQVAAASPL<br>LLLLLLLAWCAGACRGAPILPQ<br>GLQPEQQLQLWNEIDDTCSSFL<br>SIDSQPQASNALEELCFMIMQM<br>LPKPQEQDEKDNTKRFLFHYSK<br>TQKLGKSNVVSSVVHPLLQLVP<br>HLHERRMKRFRVDEEFQSPFAS<br>QSRGYFLFRPRNGRRSAGFI |
| SEQ.ID NO. 9<br>GGGCAGCGGGGCCCGTCTGCAGCAAGTGACCGACGGCCGGGACGGCCGCCTGCCCCCTCTGCCACCTGGGGCGGTGCG<br>GGCCCGGAGCCCGGAGCCCGGGTAGCGCGTAGAGCCGGCGCGATGCACGTGCGCTCACTGCGAGCTGCGGCGCCGCACAG<br>CTTCGTGGCGCTCTGGGCACCCCTGTTCCTGCTGCGCTCCGCCCTGGCCGACTTCAGCCTGGACAACGAGGTGCACTGA<br>GCTTCATCCACCGGCGCCTCCGCAGCCAGGAGCGGCGGGAGATGCAGCGCGAGATCCTCTCCATTTTGGGCTTGCCCCAC<br>CGCCCGCCCGCCACCTCCAGGGCAAGCACAATTCGGCACCCATGTTCATGCTGGACTACAACGCCATGGCGGTGGA<br>GGAGGGCGGCGGGCCCGGCGGCCAGGGCTTCTCTACCCCTACAAGGCCGTCTTCAGTACCCAGGGCCCCCTCTGGCCA<br>GCCTGCAAGATAGCCATTTCCTCACCGACGCCGACATGGTCATGAGCTTCGTCAACCTCGTGGAACATGACAAGGAATTC<br>TTCCACCCACGCTACCACCATCGAGAGTTCCGGTTTGATCTTTCCAAGATCCCAGAAGGGGAAGCTGTCACGGCAGCCGA<br>ATTCCGGATCTACAAGGACTACATCTCGGAACGATTCGACAATGACGTTGCAGATCAGCGTTTATCAGGTGCTCCAGG<br>AGCACTTGGGCAGGGAATCGGATCTCTTCCTGCTCGACAGCCGTACCCTCTGGGCCTCCGAGGAGGGCTGGCTGGTGTTT<br>GACATCACAGCCACCAGCAACCACTGGGTGGTCAATCCGCGGCACAACCTGGGCCTGCAGCTCTCGGTGGAGACGCTGGA<br>TGGGCAGAGCATCAACCCCAAGTTGGCGGGCCTGATTGGCGGCACGGGCCCAGAACAAGCAGCCCTTCATGGTGGCTT<br>TCTTCAAGGCCACGGAGGTCCACTTCCGCAGCATCCGGTCCAGGGGAGCAAACAGCGCAGCCAGAACCGCTCCAAGACG<br>CCCGAAGGACCAGGAAGCCTGCGGATGGCCAACGTGGCAGAGAACAGCAGCGACCAGAGGCAGGCCTGTAAGAAGCA<br>CGAGCTGTATGTCAGCTTCCGAGACTTGGGCTGGCAGGACTGGATCATCGCGCCTGAAGGCTACGCCGCCTACTACTGTG<br>AGGGGGAGTGTGCCTTCCCTCTGAACTCCTACATGAACGCCACCAACCACGCCATCGTCAGACGCTGGTCCACTTCATC<br>AACCCGGAAACGGTGCCCAAGCCCTGCTGTGCGCCCACGCAGCTCAATGCCATCTCCGTCCTCTACTTCGATGACAGCTC<br>CAACGTCATCCTGAAGAAATACAGAAACATGGTGGTCCGGGCCTGTGGCTGCCACTAGCTCCTCCAGAATTCAGACCGT<br>TGGGGGCCAAGTTTTTCTGGATCCTCCATTGCTCGCCTTGGCCAGGAACCACAGACCAACTGCCTTTTGTGAGACCTTC<br>CCCTCCCTATCCCCAACTTTAAGGTGTGAGAGTATTAGGAAACATGAGCAGCATATGGCTTTTGATCAGTTTTTCAGTG<br>GCAGCATCCAATGAACAAGATCCTACAAGCTGTGCAGGCAAAACCTAGCAGGAAAAAAAACAACGCATAAAGAAAATG<br>GCCGGGCCAGGTCATTGGCTGGGAAGTCTCAGCCATGCACGGACTCGTTTCCAGAGGTAATTATGAGCGCCTACCAGCCA<br>GGCCACCCAGCCGTGGGAGGAAGGGGGCGTGGCCAAGGGGTGGGCACATTGGTGTCTGTGCGAAAGGAAATTGACCCGGA<br>AGTTCCTGTAATAAATGTCACAATAAAACGAATGAATG | SEQ.ID NO. 59<br>MHVRSLRAAAPHSFVALWAPLF<br>LLRSALADFSLDNEVHSSFIHR<br>RLRSQERREMQREILSILGLPH<br>RPRPHLQGKHNSAPMFMLDYN<br>AMAVEEGGPGGQGFSYPYKAV<br>FSTQGPPLASLQDSHFLTDADM<br>VMSFVNLVEHDKEFFHPRYHHR<br>EFRFDLSKIPEGEAVTAAEFRI<br>YKDYIRERFDNETFRISVYQVL<br>QEHLGRESDLFLLDSRTLWASE<br>EGWLVFDITATSNHWVVNPRHN<br>LGLQLSVETLDGQSINPKLAGL<br>IGRHGPQNKQPFMVAFFKATEV<br>HFRSIRSTGSKQRSQNRSKTPK<br>NQEALRMANVAENSSSDQRQAC<br>KKHELYVSFRDLGWQDWIIAPE<br>GYAAYYCEGECAFPLNSYMNAT<br>NHAIVQTLVHFINPETVPKPCC<br>APTQLNAISVLYFDDSSNVTLK<br>KYRNMVVPACGCH |
| SEQ.ID NO. 10<br>CCGGTGAGTCGCCGGCGCTGCAGAGGGAGGCGGCACTGGTCTCGACGTGGGCGGCCAGCGATGAAGCCGCCCAGTTCAA<br>TACAAACAAGTGAGTTTGACTCATCAGATGAAGAGCCTATTGAAGATGAACAGACTCCAATTCATATATCATGGCTATCT<br>TTGTCACGAGTGAATTGTTCTCAGTTTCTCGGTTTATGTGCTCTTCCAGGTTGTAAATTTAAAGATGTTAGAAGAAATGT<br>CCAAAAAGATACAGAAGAACTAAAGAGCTGTGGTATACAAGACATATTTGTTTTCTGCACCAGAGGGGAACTGTCAAAAT<br>ATAGAGTCCCAAACCTTCTGGATCTCTACCAGCAATGTGGAATTATCACCCATCATCATCCAATCGCAGATGGAGGGACT | SEQ.ID NO. 60<br>MKPPSSIQTSEFDSSDEEPIED<br>EQTPIHISWLSLSRVNCSQFLG<br>LCALPGCKFKDVRRNVQKDTEE<br>LKSCGIQDIFVFCTRGELSKYR<br>VPNLLDLYQQCGIITHHHPIAD |

TABLE 4-continued

Nucleotide and amino acid sequences of the SEQ. ID NOs.

| Nucleotide Sequence (5'-3') | ORFs |
|---|---|
| CCTGACATAGCCAGCTGCTGTGAAATAATGGAAGAGCTTACAACCTGCCTTAAAAATTACCGAAAAACCTTAATACACTG<br>CTATGGAGGACTTGGGAGATCTTGTCTTGTAGCTGCTTGTCTCCTACTATACCTGTCTGACACAATATCACCAGAGCAAG<br>CCATAGACAGCCTGCGAGACCTAAGAGGATCCGGGGCAATACAGACCATCAAGCAATACAATTATCTTCATGAGTTTCGG<br>GACAAATTAGCTGCACATCTATCATCAAGAGATTCACAATCAAGATCTGTATCAAGATAAAGGAATTCAAATAGCATATA<br>TATGACCATGTCTGAAATGTCAGTTCTCTAGCATAATTTGTATTGAAATGAAACCACCAGTGTTATCAACTTGAATGTAA<br>ATGTACATGTGCAGATATTCCTAAAGTTTTATTGAC | GGTPDIASCCEIMEELTTCLKN<br>YRKTLIHCYGGLGRSCLVAACL<br>LLYLSDTISPEQAIDSLRDLRG<br>SGAIQTIKQYNYLHEFRDKLAA<br>HLSSRDSQSRSVSR |

SEQ.ID NO. 11

| | |
|---|---|
| AGAGCGATCATGTCGCACAAACAAATTTACTATTCGGACAAATACGACGACGAGGAGTTTGAGTATCGACATGTCATGCT<br>GCCCAAGGACATAGCCAAGCTGGTCCCTAAAACCCATCTGATGTCTGAATCTGAATGGAGGAATCTTGGCGTTCAGCAGA<br>GTCAGGGATGGGTCCATTATATGATCCATGAACCAGAACCTCACATCTTGCTGTTCCGGCGCCCACTACCCAAGAAACCA<br>AAGAAATGAAGCTGGCAAGCTACTTTTCAGCCTCAAGCTTTACACAGCTGTCCTTACTTCCTAACATCTTTCTGATAACA<br>TTATTATGTTGCCTTCTTGTTTCTCACTTTTGATATTTAAAAGATGTTCAATACACTGTTTGAATGTGCTGGTAACTGTT<br>TGCTTCTTGAGTAGAGCCACCACCACCATAGCCCAGCCAGATGAGTGCTCTGTGGACCCACAGCCTAAGCTGAGTGTGAC<br>CCCAGAAGCCACGATGTGCTCTGTATCCAGAACACACTTGGCAGATGGAGGAAGCATCTGAGTTTGAGACCATGGCTGTT<br>ACAGGGATCATGTAAACTTGCTGTTTTTGTTTTTCTGCCGGGTGTTGTATGTGTGGTGACTTGCGGATTTATGTTTCAG<br>TGTACTGGAAACTTTCCATTTTATTCAAAGAAATCTGTTCATGTTAAAAGCCTTGATTAAAGAGGAAGTTTTTATAAT | MSHKQIYYSDKYDDEEFEYRHV<br>MLPKDIAKLVPKTHLMSESEWR<br>NLGVQQSQGWVHYMIHEPEPHI<br>LLFRRPLPKKPKK |

SEQ.ID NO. 12

| | |
|---|---|
| CGAGTTCCGGCGAGGCTTCAGGGTACAGCTCCCCCGCAGCCAGAAGCCGGGCCTGCAGCGCCTCAGCACCGCTCCGGGAC<br>ACCCCACCCGCTTCCCAGGCGTGACCTGTCAACAGCAACTTCGCGGTGTGGTGAACTCTCTGAGGAAAAACCATTTTGAT<br>TATTACTCTCAGACGTGCGTGGCAACAAGTGACTGAGACCTAGAAATCCAAGCGTTGGAGGTCCTGAGGCCAGCCTAAGT<br>CGCTTCAAAATGGAACGAAGGCGTTTGTGGGGTTCCATTCAGAGCCGATACATCAGCATGAGTGTGTGGACAAGCCCACG<br>GAGACTTGTGGAGCTGGCAGGGCAGAGCCTGCTGAAGGATGAGGCCCTGGCCATTGCCGCCCTGGAGTTGCTGCCCAGGG<br>AGCTCTTCCCGCCACTCTTCATGGCAGCCTTTGACGGGAGACACAGCCAGACCCTGAAGGCAATGGTGCAGGCCTGGCC<br>TTCACCTGCCTCCCTCTGGGAGTGCTGATGAAGGGACAACATCTTCACCTGGAGACCTTCAAAGCTGTGCTTGATGGACT<br>TGATGTGCTCCTTGCCCAGGAGGTTCGCCCCAGGAGGTGGAAACTTCAAGTGCTGGATTTACGGAAGAACTCTCATCAGG<br>ACTTCTGGACTGTATGGTCTGGAAACAGGGCCAGTCTGTACTCATTTCCAGAGCCAGAAGCAGCTCAGCCCATGACAAAG<br>AAGCGAAAAGTAGATGGTTTGAGCACAGAGGCAGAGCAGCCCTTCATTCAGTAGAGGTGCTCGTAGACCTGTTCCTCAA<br>GGAAGGTGCCTGTGATGAATTGTTCTCCTACCTCATTGAGAAGTGAAGCGAAAGAAAAATGTACTACGCCTGTGCTGTA<br>AGAAGCTGAAGATTTTTGCAATGCCCATGCAGGATATCAAGATGATCCTGAAAATGGTGCAGCTGGACTCTATTGAAGAT<br>TTGGAAGTGACTTGTACCTGGAAGCTACCCACCTTGGCGAAATTTTCTCCTTACCTGGGCCAGATGATTAATCTGCGTAG<br>ACTCCTCCTCTCCCACATCCATGCATCTTCCTACATTTCCCCGOAGAAGGAAGAGCAGTAATAGCCCAGTTCACCTCTC<br>AGTTCCTCCAGTCTGCAGTGCCTGCAGGCCTCTCTATGTGGACTCTTTATTTTTCCTTAGAGGCCGCCTGGATCAGTTGCTC<br>AGGCACOTGATGAACCCCTTGGAAACCCTCTCAATAACTAACTGCCGGCTTTCGGAAGGGGATGTGATGCATCTGTCCCA<br>GAGTCCCAGCGTCAGTCAGCTAAGTGTCCTGAGTCTAAGTGGGGTCATGCTGACCGATGTAAGTCCCGAGCCCCTCCAAG<br>CTCTGCTGGAGAGAGCCTCTGCCACCCTCCAGGACCTGGTCTTTGATGAGTGTGGGATCACGGATGATCAGCTCCTTGCC<br>CTCCTGCCTTCCTGAGCCACTGCTCCCAGCTTACAACCTTAAGCTTCTACGGGAATTCCATCTCCATATCTGCCTTGCA<br>GAGTCTCCTGCAGCACCTCATCGGGCTGAGCAATCTGACCCACGTGCTGTATCCTGTCCCCTGGAGAGTTATGAGGACA<br>TCCATGGTACCCTCCACCTGGAGAGGCTTGCCTATCTGCATGCCAGGCTCAGGGAGTTGCTGTGTGAGTTGGGGCGGCCC<br>AGCATGGTCTGGCTTAGTGCCAACCCCTGTCCTCACTGTGGOGACAGAACCTTCTATGACCCGGAGCCCATCCTGTGCCC<br>CTGTTTCATGCCTAACTAGCTGGGTGCACATATCAAATGCTTCATTCTGCATACTTGGACACTAAAGCCAGGATGTGCAT<br>GCATCTTGAAGCAACAAAGCAGCCACAGTTTCAGACAAATGTTCAGTGTGAGTGAGGAAAACATGTTCAGTGAGGAAAA<br>ACATTCAGACAAATGTTCAGTGAGGAAAAAAAGGGGAAGTTGGGGATAGGACAGATGTTGACTTGAGGAGTTAATGTGATC<br>TTTGGGGAGATACATCTTATAGAGTTAGAAATAGAATCTGAATTTCTAAAGGGAGATTCTGGCTTGGGAAGTACATGTAG<br>GAGTTAATCCCTGTGTAGACTGTTGTAAAGAAACTGTTGAAAATAAAGAGAAGCAATGTGAAGCAAAAAAAAAAAAAAAAA<br>AA | MERRRLWGSIQSRYISMSVWTS<br>PRRLVELAGQSLLKDEALAIAA<br>LELLPRELFPPLFMAAFDGRHS<br>QTLKANVQAWPFTCLPLGVLMK<br>GQHLHLETFKAVLDGLDVLLAQ<br>EVRPRRWKLQVLDLRKNSHQDF<br>WTVWSGNRASLYSFPEPEAAQP<br>MTKKRKVDGLSTEAEQPFIPVE<br>VLVDLFLKEGACDELFSYLIEK<br>VKRKKNVLRLCCKKLKIFAMPM<br>QDIKMILKMVQLDSIEDLEVTC<br>TWKLPTLAKESPYLGQMINLRR<br>LLLSHIHASSYISPEKEEQYIA<br>QFTSQFLSLQCLQALYVDSLFF<br>LRGRLDQLLRHVMNPLETLSIT<br>NCRLSEGDVNHLSQSPSVSQLS<br>VLSLSGVMLTDVSPEPLQALLE<br>RASATLQDLVFDECGITDDQLL<br>ALLPSLSHCSQLTTLSFYGNSI<br>SISALQSLLQHLIGLSNLTHVL<br>YPVPLESYEDIHGTLHLERLAY<br>LHARLRELLCELGRPSMVWLSA<br>NPCPHCGDRTFYDPEPILCPCF<br>MPN |

SEQ.ID NO. 13

| | |
|---|---|
| CGGCTGAGAGGCAGCGAACTCATCTTTGCCAGTACAGGAGCTTGTGCCGTGGCCCACAGCCCACAGCCCACAGCCATGGG<br>CTGGGACCTGACGGTGAAGATGCTGGCGGGCAACGAATTCCAGGTGTCCCTGAGCAGCTCCATGTCGGTGTCAGAGCTGA<br>AGGCGCAGATCACCCAGAAGATTGGCGTGCACGCCTTCCAGCAGCGTCTGGCTGTCCACCCGAGCGGTGTGGCGCTGCAG<br>GACAGGGTCCCCCTTGCCAGCCAGGGCCTGGGCCCTGGCAGCACGGTCCTGCTGGTGGTGGACAAATGCGACGAACCTCT<br>GAGCATCCTGGTGAGGAATAACAAGGGCCGCAGCAGCACCTACGAGGTCCGGCTGACGCAGACCGTGGCCCACCTGAAGC<br>AGCAAGTGAGCGGGCTGGAGGGTGTGCAGGACGACCTGTTCTGGCTGACCTTCGAGGGGAAGCCCCTGGAGGACCAGCTC<br>CCGCTGGGGGAGTACGGCCTCAAGCCCCTGAGCACCGTGTTCATGAATCTGCGCCTGCGGGGAGGCGGCACAGAGCCTGG<br>CGGGCGGAGCTAAGGGCCTCCACCAGCATCCGAGCAGGATCAAGGGCCGGAAATAAAGGCTGTTGTAAGAGAAT | MGWDLTVKMLAGNEFQVSLSSS<br>MSVSELKAQITQKIGVHAFQQR<br>LAVHPSGVALQDRVPLASQGLG<br>PGSTVLLVVDKCDEPLSILVRN<br>NKGRSSTYEVRLTQTVAHLKQQ<br>VSGLEGVQDDLFWLTFEGKPLE<br>DQLPLGEYGLKPLSTVFMNLRL<br>RGGGTEPGGRS |

SEQ.ID NO. 14
STAR clone:

| | |
|---|---|
| TGCCCACTTGGCCCCTCCTTCCAAGGTGTACTTTACTTCCTTTCATTCCTGCTCTAATACTGTTAGTACATTTTCACTC<br>CTGCTCTAAAACTTGCCTCAGTCTCTCACTGTGCCTTATGCCCCTCAGCTGAATTCTTTCTTCTGAGCAGGCAGGAATTG<br>AGGTTGCTGCAGACGTGTATGCATTTGCCACCAGTAACACATACTTTGGTGCCACATGACTAGGATATGTTCTCTAGTGCTA<br>ACATGTTCGTTTACAGTTCTTAGGACTCCCTGATA | |

SEQ.ID NO. 15

| | |
|---|---|
| GGCCGCCTGCGCGCCGCCAACAGCCTAGCGCTGCGCCGCGTGGCCGCCGCCTTCTCGCTGGCCCCGCTGGCCGAGCTG<br>CGGCCGCGTCCTGCGTCAGGCCTTCGCCOAGGTGGCGCGCCACGCCGACTTCCTGGAGCTGGCGCCTGACGAGGTGGTGG<br>CGCTGCTGGCGGACCCCGCGCTGGGCGTGGCGCGCGAGGAGGCCGTGTTTGAAGCGGCCATGCGCTGGGTGCGCCACGAC<br>GCGCCGGCCCCGCCGGCCAGCTGCGACGCCTGCTGGAGCACGTGCCGCTGCCGCTACTAGCGCCCGCTTACTTCCTGGA<br>GAAGGTGGAGGCGGACGAGCTGCTGCAGGCCTGCGGCGAGTGCCGCCCGCTGCTGCTGGAGGCTCGCGCCTGCTTCATCC<br>TGGGCCGCGAGGCCGGTGCGCTGCGGACCCGGCCGCGGAGATTCATGGACCTAGCTGAAGTGATCGTGGTCATCGGCGGT<br>TGCGACCGCAAAGGTCTCCTGAAGCTGCCCTTCGCCGATGCCTACCATCCAGAGAGCCAGCGGTGGACCCCACTGCCCAG<br>CCTGCCCGGCTACACTCGCTCAGAATTCGCCGCCTGTGCTCTCCGCAATGACGTTCTACGTCTCCGGAGGCCACATCAACA<br>GTCATGATGTGTGGATGTTTAGCTCCCATCTGCACACCTGGATCAAGGTAGCCTCTCTGCACAAGGGCAGGTGGAGGCAC | MRWVRHDAPARRGQLRRLLEHV<br>RLPLLAPAYFLEKVEADELLQA<br>CGECRPLLLEARACFILGREAG<br>ALRTRPRRFMDLAEVIVVIGGC<br>DRKGLLKLPFADAYHPESQRWT<br>PLPSLPGYTRSEFAACALRNDV<br>YVSGGHINSHDVWMFSSHLHTW<br>IKVASLHKGRWRHKMAVVQGQL<br>FAVGGFDGLRRLHSVERYDPFS |

TABLE 4-continued

Nucleotide and amino acid sequences of the SEQ. ID NOs.

| Nucleotide Sequence (5'-3') | ORFs |
|---|---|
| AAGATGGCAGTTGTGCAGGGGCAGCTGTTCGCGGTGGGTGGCTTCGACGGCCTGAGGCGCCTGCACAGCGTGGAGCGCTA<br>CGACCCCTTCTCCAACACCTGGGCGGCCGCCGCGCCCCTCCCGGAGGCCGTGAGCTCGGCGGCGGTGGCGTCCTGCGCGG<br>GCAAGCTCTTCGTGATTGGGGGCGCCAGGCAGGGCGGCGTCAACACGGACAAGGTGCAGTGCTTTGACCCCAAGGAGGAC<br>CGGTGGAGCCTGCGGTCACCAGCACCCTTCTCACAGCGGTGTCTCGAGGCTGTCTCCCTTGAGGACACCATCTATGTCAT<br>GGGGGGTCTCATGAGCAAAATCTTCACCTATGATCCAGGCACAGATGTGTGGGGGAGGCAGCTGTCCTCCCCAGCCCTG<br>TGGAAAGCTGTGGAGTCACTGTGTGTGACGGGAAGGTCCACATCCTTGGCGGGCGGGATGATCGCGGAGAAAGCACCGAT<br>AAGGTCTTCACCTTTGACCCCAGCAGTGGGCAGGTGGAGGTCCAGCCATCCCTGCAGCGCTGCACCAGCTCCCACGGCTG<br>TGTCACCATCATCCAGAGCTTGGGCAGGTGATTCAGATTTGGACAGCCTGAGCCAGGAGGCGGAGAGGCAGGCGGAGCTC<br>AGATGCACACTCTGCTCCCTCATGGCACCTCCACGCAAACAGCCCTTAACTTAATGGTCCCTTTTCTTGTATAAATAAAA<br>TCTTGTTGGGTCTGTGTTCCAGCTGCAGTC<br>TGCCCTGCCTGGAGATGGAATGTCTAAAAAAAAAAAAAAAA | NTWAAAAPLPEAVSSAAVASCA<br>GKLFVIGGARQGGVNTDKVQCF<br>DPKEDRWSLRSPAPFSQRCLEA<br>VSLEDTIYVMGGLMSKIFTYDP<br>GTDVWGEAAVLPSPVESCGVTV<br>CDGKVHILGGRDDRGESTDKVF<br>TFDPSSGQVEVQPSLQRCTSSH<br>GCVTIIQSLGR |
| SEQ.ID NO. 16<br>STAR clone:<br>TTTCTAGCAGCCTGGGCAATGGCGGGCGCCCCTCCCCCAGCCTCGCTGCTGCCTTGCAGTTTGATCTCAGACTGCTGTGC<br>TAGCAATCAGCAAGACTCCGTGGGCGTAGGACCCTCCAGGCCAGGTTGCAAGAAAGCTCAAGTAGCCTATGGAGAGGATG<br>CAAGGCTTCCAGCTGATGCCCTCAGCCAGGCTCAGTAGCAGCCAGAACTAGCCTACCAACGAACCTGCTGATCATGTGCA<br>TAAGCCACCTTGAACGTCGATCCTCCTGCCTGGTGGAGCCATCCCAGCTGATGCCACATGAAGCAGACACAAGCTGTCCC<br>TACTAAGCTCTGCTCAAGTTGGATATTCATGAGTGAAATAAATGACTGTTACTAA | |
| SEQ.ID NO. 17<br>GAGTCACCAAGGAAGGCAGCGGCAGCTCCACTCAGCCAGTACCCAGATACGCTGGGAACCTTCCCCAGCCATGGCTTCCC<br>TGGGGCAGATCCTCTTCTGGAGCATAATTAGCATCATCATTATTCTGGCTGGAGCAATTGCACTCATCATTGGCTTTGGT<br>ATTTCAGGGAGACACTCCATCACAGTCACTACTGTGCGCCTCAGCTGGGAACATTGGGGAGGATGGAATCCAGAGCTGCAC<br>TTTTGAACCTGACATCAAACTTTCTGATATCGTGATACAATGGCTGAAGGAAGGTGTTTAGGCTTGGTCCATGAGTTCA<br>AAGAAGGCAAAGATGAGCTGTCGGAGCAGGATGAAATGTTCAGAGGCCGGACAGCAGTGTTTGCTGATCAAGTGATAGTT<br>GGCAATGCCTCTTTGCGGCTGAAAAACGTGCAACTCACAGATGCTGGCACCTACAAATGTTATATCATCACTTCTAAAGG<br>CAAGGGGAATGCTAACCTTGAGTATAAAACTGGAGCCTTCAGCATGCCGGAAGTGAATGTGGACTATAATGCCAGCTCAG<br>AGACCTTGCGGTGTGAGGCTCCCCGATGGTTCCCCCAGCCCACAGTGGTCTGGGCATCCCAAGTTGACCAGGGAGCCAAC<br>TTCTCGGAAGTCTCCAATACCAGCTTTGAGCTGAACTCTGAGAATGTGACCATGAAGGTTGTGTCTGTGCTCTACAATGT<br>TACGATCAACAACACATACTCCTGTATGATTGAAAATGACATTGCCAAAGCAACAGGGGATATCAAAGTGACAGAATCGG<br>AGATCAAAAGGCGGAGTCACCTACAGCTGCTAAACTCPAAGGCTTCTCTGTGTGTCTCTTCTTTCTTTGCCATCAGCTGG<br>GCACTTCTGCCTCTCAGCCCTTACCTGATGCTAAAATAATGTGCCTCGGCCACAAAAAAGCATGCAAAGTCATTGTTACA<br>ACAGGGATCTACAGAACTATTTCACCACCAGATATGACCTAGTTTTATATTTCTGGGAGGAAATGAATTCATATCTAGAA<br>GTCTGGAGTGAGCAAACAAGAGCAAGAAACAAAAGAAGCCATAAGCAGAAGGCTCCAATATGAACAAGATAAATCTATC<br>TTCAAAGACATATTAGAAGTTGGGAAAATAATTCATGTGAACTAGAGTCAACTGTGTCAGGGCTAAGAAACCCTGGTTTT<br>GAGTAGAAAAGGGCCTGGAAAGGGGGCCAACAAATCTGTCTGCTTCCTCACATTAGTCATTGGCAAATAAGCATTCT<br>GTCTCTTTGGCTGCTGCCTCAGCACAGAGAGCCAGAACTCTATCGGGCACCAGGATAACATCTCTCAGTGAACAGAGTTG<br>ACAAGGCCTATGGGAAATGCCTGATGGGATTATCTTCAGCTTGTTGAGCTTCTAAGTTTCTTTCCCTTCATTCTACCCTG<br>CAAGCCAAGTTCTGTAAGAGAAATGCCTGAGTTCTAGCTCAGGTTTTCTTACTCTGAATTTAGATCTCCAGACCCTGCCT<br>GGCCACAATTCAAATTAAGGCAACAAACATATACCTTCCATGAAGCACACAAAACATACCATCAAGGATGGAGG<br>CTTGAATTGAGGCCTTGAGGAATGAAGCTTTGAAGGAAAAGAATACTTTGTTTCCAGCCCCCTTCCCACACTCTTCATGT<br>GTTAACCACTGCCTTCCTGGACCTTGGAGCCACGGTGACTGTATTACATGTTGTTATAGAAAACTGATTTTAGAGTTCTG<br>ATCGTTCAAGAGAATGATTAATATACATTTCCTAAAAAAAAAAAAAAAAAAA | SEQ.ID NO. 65<br>MASLGQILFWSIISIIIILAGA<br>IALIIGFGISGRHSITVTTVAS<br>AGNIGEDGIQSCTFEPDIKLSD<br>IVIQWLKEGVLGLVHEFKEGKD<br>ELSEQDEMFRGRTAVFADQVIV<br>GNASLRLKNVQLTDAGTYKCYI<br>ITSKGKGNANLEYKTGAFSMPE<br>VNVDYNASSETLRCEAPRWFPQ<br>PTVVWASQVDQGANFSEVSNTS<br>FELNSENVTMKVVSVLYNVTIN<br>NTYSCMIENDIAKATGDIKVTE<br>SEIKRRSHLQLLNSKASLCVSS<br>FFAISWALLPLSFYLMLK |
| SEQ.ID NO. 18<br>TCTTCGGACCTAGGCTGCCCTGCCGTCATGTCGCAAGGGATCCTTTCTCCGCCAGCGGGCTTGCTGTCCGATGACGATGT<br>CGTAGTTTCTCCCATGTTTGAGTCCACAGCTGCAGATTTGGGGTCTGTGGTACGCAAGAACCTGCTATCAGACTGCTCTG<br>TCGTCTCTACCTCCCTAGAGGACAAGCAGCAGGTTCCATCTGAGGACAGTATTGGAGGAAGGTGAAAGTATACTTGAGGGTT<br>AGGCCCTTGTTACCTTCAGAGTTGGAACGACAGGAAGATCAGGGTTGTGTCCGTATTGAGAATGTGGAGACCCTTGTTCT<br>ACAAGCACCCAAGGACTCGTTTGCCCTGAAGAGCAATGAACGGGGAATTGGCCAAGCCACACACAGGTTCACCTTTTCCC<br>AGATCTTTGGGCCAGAAGTGGGACAGGCATCCTTCTTCAACCTAACTGTGAAGGAGATGGTAAAGGATGTACTCAAAGGG<br>CAGAACTGGCTCATCTATACATATGGAGTCACTAACTCAGGGAAAACCCACACAGTTCAAGGTACCATCAAGGATGGAGG<br>GATTCTCCCCCGGTCCCTGGCGCTGCATCTTCAATAGCCTCCAAGGCCAACTTCATCCAACACCTCATCTGAAGCCCTTGC<br>TCTCCAATGAGGTAATCTGGCTAGACAGCAAGCAGATCCGACAGGAGGAAATGAAGAAGCTGTCCCTGCTAAATGGAGGC<br>CTCCAAGAGGAGGAGCTGTCCACTTCCTTGAAGAGGAGTGTCTACATCGAAAGTCGGATAGGTACCAGCACCAGCTTCGA<br>CAGTGGCATTGCTGGGCTCTCTTCTATCAGTCAGTGTACCAGCAGTAGCCAGCTGGATGAAACAAGTCATCGATGGGCAC<br>AGCCAGACACTGCCCCACTCACCTGTCCCGGCAAACATTCGCTTCTCCATCTGGACTTCATTCTTTGAGATCTACAACGAA<br>CTGCTTTATGCTACTATTGAAGACCGCCTAGCCAACAGCGCAAGAGGCAGACTTTGCGGCTATGCGAGGATCAAAATGGAA<br>TCCCTATGTGAAAGATCTCAACTGGATTCATGTGCAAGATGCTGAGGAGGCCTGGAAGCTCCTAAAAGTGGGTCGTAAGA<br>ACCAGAGCTTTGCCAGCACCCACCTCAACCAGAACTCCAGCCGCAGTCACAGCATCTTCTCAATCAGGATCCTACACCTT<br>CAGGGGGAAGGAGATAGTCCCAAGATCAGCGAGCTGTCACTCTGTGATCTGGCTGGCTCAGAGCGCTGCAAAGATCA<br>GAAGAGTGGTGAACGGTTGAAGGAAGCAGGAAACATTAACCTCTCTACACACCCTGGGCCGCTGTATTGCTGCCCTTC<br>GTCAAAACCAGCAGAACCGGTCAAAGCAGAACCTGGTTCCCTTCCGTGACAGCAAGTTGACTCGAGTGTTCCAAGGTTTC<br>TTCACAGGCCGAGGCCGTTCCTGCATGATTGTCAATGTGAATCCCTGTGCATCTACCTATGATGAAACTCTTCATGTGGC<br>CAAGTTCTCAGCCATTGCTCAGCCAGCTTGTGCATGCCCCACCTATGCAACTGGGATTCCCATCCCTGCACTCGTTCATCA<br>AGGAACATAGTCTTCAGGTATCCCCAGCTTGAGAAAGGGGCTAAGGCAGACAGGCCTTGATGATGATATTGAAAAT<br>GAAGCTGACATCTCCATGTATGGCAAAGAGGAGCTCCTACAAGTTGTGGAAGCCATGAAGACACTGCTTTTGAAGGAACG<br>ACAGGAAAAGCTACAGCTGGAGATGCATCTCCGAGATGAAATTTGCAATGAGATGGTAGAACAGATGCAACAGCGGGAAC<br>AGTGGTGCAGTGAACATTTGGACACCAAAGGAACTATTGAGGAAATGTATGAAGAAAAACTAAATATCCTCAAGGAATCG<br>TCACTGACAAGTTTTTACCAAGAAGAATCAGGAGCCGGGATGAAAAGATTGAAGACTAGAAGCTCTCTTCAGGAAGC<br>CAGACAACAGTCAGTGGCCATCAGCAATCAGGGTCTGAATTGGCCCTACGCGGTCACAAAGGTTGCAGCTTCTGCCT<br>CCACCCAGCAGCTTCAGGAGGTTAAAGCTAAATTACAGCAGTGCAAAGCAGAGCTAAACTCTACCACTGAAGAGTTGCAT<br>AAGTATCAGAAAATGTTAGAACCACCACCCTCAGCCAAGCCCTTCACCATTGATGTGGACAAGAAGTTAGAAGAGGGCCA<br>GAAGAATATAAGGCTGTTCGGACAGAGCTTCAGAAACTTGGTGAGTCTCTCCAATCAGCAGAGAGAGCTTGTTGCCACA | SEQ.ID NO. 66<br>MSQGILSPPAGLLSDDDVVVSP<br>MFESTAADLGSVVRKNLLSDCS<br>VVSTSLEDKQQVPSEDSMEKVK<br>VYLRVRPLLPSELERQEDQGCV<br>RIENVETLVLQAPKDSFALKSN<br>ERGIGQATHRFTFSQIFGPEVG<br>QASFFNLTVKEMVKDVLKGQNW<br>LIYTYGVTNSGKTHTIQGTIKD<br>GGILPRSLALIFNSLQGQLHPT<br>PDLKPLLSNEVIWLDSKQIRQE<br>EMKKLSLLNGGLQEEELSTSLK<br>RSVYIESRIGTSTSFDSGIAGL<br>SSISQCTSSSQLDETSHRWAQP<br>DTAPLPVPANIRFSIWISFFET<br>YNELLYDLLEPPSQQRKRQTLR<br>LCEDQNGNPYVKDLNWIHVQDA<br>EEAWKLLKVGRKNQSFASTHLN<br>QNSSRSHSIFSIRILHLQGEGD<br>IVPKISELSLCDLAGSERCKDQ<br>KSGERLKEAGNINTSLHTLGRC<br>IAALRQNQQNRSKQNLVPFRDS<br>KLTRVFQGFFTGRGRSCMIVNV<br>NPCASTYDETLHVAKFSAIASQ<br>LVHAPPMQLGFPLSLHSFIKEHS<br>LQVSPSLEKGAKADTGLDDDIE<br>NEADISMYGKEELLQVVEAMKT<br>LLLKERQEKLQLEMHLRDEICN<br>EMVEQMQQREQWCSEHLDTQKE<br>LLEEMYEEKLNILKESLTSFYQ |

TABLE 4-continued

Nucleotide and amino acid sequences of the SEQ. ID NOs.

| Nucleotide Sequence (5'-3') | ORFs |
|---|---|
| GCACTGGGGCAGGAAAACTTCGTCAAGCCTTGACCACTTGTGATGACATCTTAATCAAACAGGACCAGACTCTGGCTGAA<br>CTGCAGAACAACATGGTGCTAGTGAAACTGGACCTTCGGAAGAAGGCAGCATGTATTGCTGAGCAGTATCATACTGTGTT<br>GAAACTCCAAGGCCAGGTTTCTGCCAAAAAGCGCCTTGGTACCACCAGGAAATCAAGCAAACCAACCAACAACCACCAG<br>GGAAGAAACCATTCCTTCGAAATTTACTTCCCCGAACACCAACCTGCCAAAGCTCAACAGACTGCAGCCCTTATGCCCGG<br>ATCCTACGCTCACGGCGTTCCCCTTTACTCAATCTGGGCCTTTTGGCAAGTACTAAGGCTGTGGGGAAAGAAGAGAAGA<br>GCAGTCATGGCCCTGAGGTGGGTCAGCTACTCTCCTGAAGAAATAGGTCTCTTTTATGCTTTACCATATATCAGGAATTA<br>TATCCAGGATGCAATACTCAGACACTAGCTTTTTTCTCACTTTTGTATTATAACCACCTATGTAATCTCATGTTGTTGTT<br>TTTTTTTATTTACTTATATGATTTCTATGCACACAAAAACAGTTATATTAAAGATATTAT<br>TGTTCACATTTTTTATTGAAAAAAAAAAAA | EEIQERDEKIEELEALLQEARQ<br>QSVAHQQSGSELALRRSQRLAA<br>SASTQQLQEVKAKLQQCKAELN<br>STTEELHKYQKMLEPPPSAKPF<br>TIDVDKKLEEGQKNIRLLRTEL<br>QKLGESLQSAERACCHSTGAGK<br>LRQALTTCDDILIKQDQTLAEL<br>QNNMVLVKLDLRKKAACIAEQY<br>HTVLKLQGQVSAKKRLGTNQEN<br>QQPNQQPPGKKPFLRNLLPRTP<br>TCQSSTDCSPYARILRSRRSPL<br>LKSGPFGKKY |
| STAR clone (SEQ.ID NO. 19):<br>TCCTTGTTACGATGAAGAAACTAAATCTCAGGAAGAAAAAACTAAGTGAAGACNAAAGAAGGATTTGAACTGAGGTTTGT<br>CAGACTCTCGGGACCATGCTGTTGAAACCACTAAACCACGCTGCCTCTGGGTCATTGGTAAACAGCATTTAACCATTAA<br>GAAAGTCATTAATAAAATTCCTTGTGCTCTCCTTGAGATTACAAGCCATTGATTTGCCAA<br>NM_005832:<br>GCTGGGCACCGTTCTGTTTTCTTTCTTTTCTTAATCCTATCCAAGTATGCAGTACGCTCTTGGGTCGTCTCATGAGACCC<br>AGGOGCATGTTGGAAAGAACTGAGAGAAGAGCAACAAAGCGGCGAGTGGTGTGAGAGGGCAGCACGCGCTGTGGGGCCC<br>TTCCAGAGAAATGTACTGAAAAAGTCTACGCAATGTCTGGGATTTGCTAAACAATACCTGGAAAGCAGACAGGTCTTTTT<br>GCCATTCCTCCAGGACATCCACCATAAGGAAAGGAGACCCTGGACCAACATTCTCTAAGATGTTTATATGGACCAGTGGC<br>CGGACCTCTTCATCTTATAGACATGATGAAAAAGAAATATTTACCAGAAAATCAGGGACCATGACCTCCTGGACAAAAG<br>GAAAACAGTCACAGCACTGAAGGCAGGAGAGGACCGAGCTATTCCTGGGACTGGCTATGATGGTGTGCTCCATCATGA<br>TGTATTTTCTGCTGGGAATCACACTCCTGCGCTCATACATGCAGAGCGTGTGGACCGAAGAGTCTCAATGCACCTTGCTG<br>AATGCGTCCATCACGGAAACATTTAATTGCTCCTTCAGCTGTGGTCCAGACTGCTGGAAACTTTCTCAGTACCCCTGCCT<br>CCAGGTGTACGTTAACCTGACTTCTTCCGGGGAAAAGCTCCTCCTCTACCACACAGAAGAGACAATAAAAATCAATCAGA<br>AGTGCTCCTATATACCTAAATGTGGAAAAAATTTTGAAGAATCCATGTCCCTGGTGAATGTTGTCATGGAAAACTTCAGG<br>AAGTATCAACACTTCTCCTGCTATTCTGACCCAGAAGGAAACCAGAAGAGTGTTATCCTAACAAAACTCTACAGTTCCAA<br>CGTGCTGTTCCATTCACTCTTCTGGCCAACCTGTATGATGGCTGGGGGTGTGGCAATTGTTGCCATGGTGAAACTTACAC<br>AGTACCTCTCCCTACTATGTGAGAGGATCCAACGGATCAATAGATAAATGCAAAATGGATAAAATAATTTTTGTTAAAG<br>CTCAAATACTGTTTTCTTTCATTCTTCACCAAAGAACCTTAAGTTTGTAACGTGCAGTCTGTTATGAGTTCCCTAATATA<br>TTCTTATATGTAOAGCAATAATGCAAAAGCTGTTCTATATGCAAACATGATGTCTTTATTATTCAGGAGAATAAATAACT<br>GTTTTGTGTTGGTTGGTGGTTTTCATAATCTTATTTCTGTACTGGAACTAGTACTTTCTTCTCATTCCGCCAAAACAG<br>GGCTCAGTTATTCATTTGCCAAGCTTCGTGGAGGAAGTGTAGGTGACATCAATGTGATAAAGTCTGTGTTCTGAGTTGTCA<br>GATCTCTTGAAGACAATATTTTCATCACTTATTGTTTACTAAAGCTACAGCCAAAAATATTTTTTTTTCTTATTCTAAA<br>CTGAGCCCTATAGCAAGTGAAGGGACCAGATTTCCTAATTAAAGGAAGTTAOGTACTTTTCTTGTATTTTTTACCATATC<br>ACTGTAAAGAAGAGGGGAAACCCAGCCAGCTACTTTTTTTCATCACTTTTTATTCATAACTTCAGATTTGTAAAACTAAT<br>TTCCAAAATATAAGCTGTTTTCATTAGCCAGTTCTATAATATCTTCCTGTGATTTATGTAGAAAATGAACACACCCCTTT<br>TCCATTTAAGACCCTGCTACTGTGTGAAGAGATGATACTTACAAGGAGTGTCATTACCTGTGAGCTGACTGAATGTTGGT<br>AGGTGCTCCATTACAATCCAGGAAAGTCTGTGTTACTGATATTTGTGTGGAAATCTTTATTTCACTTCAATTTAACCATT<br>AGATGGTAAAATTAAGATGCTACTTGTTGGTAAAAATTGGTGGACTGGTTTCAATGGGTAAATGTTGTGGCAAATTAA<br>TGTGTTGGAATATTGCTCTTTGTGAATTTGTGCTTAAGTCAATGAATGTGTAGTATCTCCTTCTGACAAGCATTCCCTAT<br>TGGGATTTTAAAGCTATGTGCACAGAATATTAGTCTCTTCTACATGTTTTATTTTTCTATTTATAATTCCCTTTTTGTT<br>GTTATATTTTATACACAGAATAGATCTTTTTTCTAACACATATTTGAACTGAATAACGACTTAAAGAAAGCCTTTGTTC<br>ACATTGCTATTTACTTTTGTGTTTGGGGGAAAATACAGAGGGATTGATTTTAAATAAAAAACATTCCATCTTTCATTTAAT<br>ATCAATATCAAAAGAAGAAGACAAACATCTATCTTTCTCATCTATATTTAAGTACCTTTTTGTAATGTAGTATCAAAGTT<br>TTTTAGGTAATGCAAAATTTTACAAATCATTTGTGGAATGAATGGTAAAACTAATCTGATGAAATGGAAAATTATTCTGC<br>AATATTGTAATTCATAGTTTGACTTTTCATAAGCAAATAAATCCCTAGGA<br>TGTAATCAGGACTTCAAATGTGTAATTAAATTTTTTTAAAAAAAATCTA | SEQ. ID NO.67<br>MFIWTSGRTSSSYRHDEKRNIY<br>QKIRDHDLLDKRKTVTALKAGE<br>DRAILLGLAMMVCSIMMYFLLG<br>ITLLRSYMQSVWTEESQCTLLN<br>ASITETFNCSFSCGPDCWKLSQ<br>YPCLQVYVNLTSSGEKLLLYHT<br>EETIKINQKCSYIPKCGKNFEE<br>SMSLVNVVMENFRKYQHFSCYS<br>DPEGNQKSVILTKLYSSNVLFH<br>SLFWPTCMMAGGVAIVAMVKLT<br>QYLSLLCERIQRINR |
| SEQ.ID NO. 20<br>STAR clone:<br>GAACACAGCTAAGCAGATGGCTTGGGTCATCAGGACGTCCATTACATCCAAAGGAAGACAGCCTGTGACGTTTCAAAAGC<br>AAAAGTCCCCTACCAGCCAGTGAAGCTACCTGATTTCTCAGTATCTTACGCCCAGTGACACGATCTACCCTCAAAACTTA | |
| SEQ.ID NO. 21<br>GAGACATTCCTCAATTGCTTAGACATATTCTGAGCCTACAGCAGAGGAACCTCCAGTCTCAGCACCATGAATCAAACTGC<br>GATTCTGATTTGCTGCCTTATCTTTCTGACTCTAAGTGGCATTCAAGGAGTACCTCTCTAGAACCGTACGCTGTACCT<br>GCATCAGCATTAGTAATCAACCTGTTAATCCAAGGTCTTTAGAAAAACTTGAAATTATTCCTGCAAGCCAATTTTGTCCA<br>CGTGTTGAGATCATTGCTACAATGAAAAAGAAGGGTGAGAAGAGATGTCTGAATCCAGAATCGAAGGCCATCAAGAATTT<br>ACTGAAAGCAGTTAGCAAGGAAATGTCTAAAAGATCTCCTTAAAACCAGAGGGGAGCAAAATCGATGCAGTGCTTCCAAG<br>OATGGACCACACAGAGGCTGCCTCTCCCATCACTTCCCTACATGGAGTATATGTCAAGCCATAATTGTTCTTAGTTTGCA<br>GTTACACTAAAGGTGACCAATGATGGTCACCAAATCAGCTGCTACTACTCCTGTAGGAAGGTTAATGTTCATCATCCTA<br>AGCTATTCAGTAATAACTCTACCCTGGCACTATAATGTAAGCTCTACTGAGGTGCTATGTTCTTAGTGGATGTTCTGACC<br>CTGCTTCAAATATTTCCCTCACTTTCCCATCTTCCAAGGGTACTAAGATTTCCTTGCTTTGGGGTTTATCAGAATTC<br>TCAGAATCTCAAATAACTAAAAGGTATGCAATCAAATCTGCTTTTTAAAGAATGCTCTTTACTTCATGGACTTCCACTGC<br>CATCCTCCCAAGGGGCCCAAATTCTTTCAGTGGCTACCTACATACAATTCCAAACACATACAGGAAGGTAGAAATATCTG<br>AAAATGTATGTGTAAGTATTCTTATTTAATGAAAGACTGTACAAAGTATAAGTCTTAGATGTATATATTTCCTATATTGT<br>TTTCAGTCTACATGGAATAACATGTAATTAAGTACTATGTATCAATGAGTAACAOGAAAATTTTAAAAATACAGATAGAT<br>ATATGCTCTGCATGTTACATAAGATAAATGTGCTGAATGGTTTTCAAATAAAATGAGGTACTCTCCTGGAAATATTAAG<br>AAAGACTATCTPAATGTTGAAAGATCAAAAGGTTAATAAAGTAATTATAACT | SEQ.ID NO. 68<br>MNQTAILICCLIFLTLSGIQGV<br>PLSRTVRCTCISISNQPVNPRS<br>LEKLEIIPASQFCPRVEIIATM<br>KKKGEKRCLNPESKAIKNLLKA<br>VSKEMSKRSP |

TABLE 4-continued

Nucleotide and amino acid sequences of the SEQ. ID NOs.

| Nucleotide Sequence (5'-3') | ORFs |
|---|---|
| SEQ.ID NO. 22<br>STAR clone:<br>TTTGCAGGTTTGATCTCAGACTGCTGTGCTAGTAATCAGCGAGATTCCGTGGGCGTAGGAGCCTCCAAGCCAGGTCCTGA<br>AGAAAATGAAGTTGATGTTTCAGTGAGACACCTGTATGCCAGAGAGTAAAAGGGATTATTGTGGATTCCTGAGAATTTTC<br>TACATATGAAATCATGTCATCTATGAACAGAGATGGGACTGTCTCGTTGGAGGAAAACAAGCTCAGGGCTCCCACTGATT<br>CCACATTATGTTGCAAGCTCCTACGAAGCTCCCACTCA | |
| SEQ.ID NO. 23<br>TTTCTCCGCATGCGCGGGATCCCGGATGTGGATCAAGTTGGTGGGAAGCGTGCGGTGCCGCAGCAATGGCGGCGCTCACA<br>ATTGCCACGGGTACTGGCAATTGGTTTTCGGCTTTGGCGCTCGGGGTGACTCTTCTCAAATGCCTTCTCATCCCCACATA<br>CCATTCCACAGATTTTGAAGTACACCGAAACTGGCTTGCTACTCACAGTTGCCAATATCACAGTGGTATTATGAGG<br>CAACTTCAGAGTGGACGTTGGATTACCCCCCTTTCTTTGCATGGTTTGAGTATATCCTGTCACATGTTGCCAAATATTTT<br>GATCAAGAAATGCTGAATGTCCATAATTTGAATTACTCCAGCTCAAGGACCTTACTTTTCCAGAGATTTTCCGTCATCTT<br>TATGGATGTACTCTTTGTGTATGCTGTCCGTGAGTGCTGTAAATGCATTGATGGAAAAAAGTGGGTAAAGAACTTACAG<br>AAAAGCCAAPATTATTCTGTCGGTATTACTTCTGTGGAACTTCGGGTTATTAATTGTGGACCATATTCATTTTCAGTAC<br>AATGGCTTTTTATTTGGATTAATGCTACTCTCCATTGCACGATTATTCAGAAAAGGCATATGGAAGGAGCATTTCTCTT<br>TGCTGTTCTCCTACATTTCAAGCATATCTACCTCCTATGTAGCACCAGCTATGGTGTATATCTGCTGCGATCCTACTGTT<br>TCACTGCAAATAAACCAGATGGGTCTATTCGATGAAGAGTTTCAGCTTTGTTCGTGTTATTTCCCTGGGACTGGTTGTT<br>TTCTTAGTTTCTGCTCTTTCATTGGGTCCTTTCCTGGCCTTGAATCAGCTGCCTCAAGTCTTTTCCCGACTCTTTCCTTT<br>CAAGAGGGGCCTCTGTCATGCATATTGGGCTCCAAACTTCTGGGCTTTGTACAATGCTTTGGACAAAGTGCTGTCTGTCA<br>TCGGTTTGAAATTGAAATTTCTTGATCCCAACAATATTCCCAAGGCCTCAATGACAAGTGGTTTGGTTCAGCAGTTCAA<br>CACACAGTCCTTCCCTCAGTGACTCCCTTGGCAACCCTCATCTGCACACTGATTGCCATATTGCCCTCTATTTTCTGTCT<br>TTGGTTTAAACCCCAAGGGCCCAGAGGCTTTCTCCGATGTCTAACTCTTTGTGCCTTGAGCTCCTTTATGTTTGGGTGGC<br>ATGTTCATGAAAAAGCCATACTTCTAGCAATTCTCCCAATGAGCCTTTTGTCTGTGGGAAAAGCAGGAGACGCTTCGATT<br>TTTCTGATTCTGACCACAACAGGACATTATTCCCTCTTTCCTCTGCTCTTCACTGCACCAGAACTTCCCATTAAAATCTT<br>ACTCATGTTACTATTCACCATATATAGTATTTCGTCACTGAAGACTTTATTCAGACGGAGTTTCACCCTTGTTGCCCAGG<br>CTGGAGTGCAATGGCAGATCTCAGCTAACTGAAACCTCCGCCTCCCAGAAAAGAAAAACCTCTTTTTAATTGGATGGAA<br>ACTTTCTACCTGCTTGGCCTGGGGCCTCTGGAAGTCTGCTGTGAATTTGTATTCCCTTTCACCTCCTGGAAGGTGAAGTA<br>CCCCTTCATCCCTTTGTTACTAACCTCAGTGTATTGTGCAGTAGGCATCACATATGCTTGGTTCAAACTGTATGTTTCAG<br>TATTGATTGACTCTGCTATTGGCAAGACAAAGAAACAATGAATAAAGGAACTGCTTAGATATG | SEQ.ID NO. 69<br>MAALTIATGTGNWFSALALGVT<br>LLKCLLIPTYHSTDFEVHRNWL<br>AITHSLPISQWYYEATSEWTLD<br>YPPFFAWFEYILSHVAKYFDQE<br>MLNVHNLNYSSSRTLLFQRFSV<br>IFMDVLFVYAVRECCKCIDGKK<br>VGKELTEKPKFILSVLLLWNFG<br>LLIVDHIHFQYNGFLFGLMLLS<br>IARLFQKRHMEGAFLFAVLLHF<br>KHIYLYVAPAYGVYLLRSYCFT<br>ANKPDGSIRWKSFSFVRVISLG<br>LVVFLVSALSLGPFLALNQLPQ<br>VFSRLFPPKRGLCHAYWAPNFW<br>ALYNALDKVLSVIGLKLKFLDP<br>NNLPKASMTSGLVQQFQHTVLP<br>SVTPLATLICTLIAILPSIFCL<br>WFKPQGPRGFLRCLTLCALSSF<br>MFGWHVHEKAILLAILPMSLLS<br>VGKAGDASIFLILTTTGHYSLF<br>PLLFTAPELPIKILLMLLFTIY<br>SISSLKTLFRRSFTLVAQAGVQ<br>WHDLS |
| SEQ.ID NO. 24<br>CATTATGCTAACAGCATAAACATGCAGGGGGTGGGAGCAGGGTCACAAAAGTGAGTGTTGTCAATTCTACTTGGAATGAA<br>AGGTTGAAATAATTTAAACAGTACGGGAAATGCAGAGCAATTTTCTCCTCTGGTGACAATATAGTGTCCAACACTTGGAA<br>GTGATTTTTAAGAATGTTTATTTAAATTAAAAGGATGGATTTCCAAGGAAAAAAATAAGGAAAAGGAAAGAAAAAACTG<br>AACAGAAAACGCAAAAGTATCAGTTTGGTCACTAACCTTTGCAAGGATACCTTTTTATTTTCTTTAAGATTCCTGTTGTT<br>TATACACAGATTTTAAGTTTACTCCTACTGCTGACCCAAGTGAAATTCCTTCTCCAGTCACAGTGTCAACCTCTACCCC<br>CAACTGCAACGAGAGTTTTGAGGGCATCAATCACACCGAGAAGTCACAGCCCCTCAACCACTGAGGTGTGGGGGGTAG<br>GGATCTGCATTTCTTCATATCAACCCCACACTATAGGGCACCTAAATGGGTGGCGGTGGGGGAGACCGACTCACTTGAG<br>TTTCTTGAAGGCTTCCTGGCCTCCAGCCACGTAATTGCCCCGCTCTGGATCTGGTCTAGCTTCCGGATTCGGTGGCCAG<br>TCCGCGGGGTGTAGATGTTCCTGACGGCCCCAAAGGGTGCCTGAACGCCGCCGGTCACCTCCTTCAGGAAGACTTCGAAG<br>CTGGACACCTTCTTCTCATGGATGACGACGCGGCGCCCCGCGTAGAAGGGGTCCCCGTTGCGGTACACAAGCACGCTCTT<br>CACGACGGGCTGAGACAGGTGGCTGGACCTGGCGCTGCTGCCGCTCATCTTCCCCGCTGGCCGCCGCCTCAGCTCGCTGC<br>TTCGCGTCGGGAGGCACCTCCGCTGTCCCAGCGGCCTCACCGCACCCAGGGCGCGGATCCTCCTGAAACGAACGAGA<br>AACTGACGAATCCACAGGTGAAAGAGAAGTAACGGCCGTGCGCCTAGGCGTCACCCAGAGGAGACATAGGAGCTTGCA<br>GGACTCGGAGTAGACGCTCAAGTTTTTCACCGTGGCGTGCACAGCCAATCAGGACCCGCAGTGCGCGCACCACACCAGGT<br>TCACCTGCTACGGGCAGAATCAAGGTGGACAGCTTCTGAGCAGGAGCCGGAAACGCGCGGGCCTTCAAACAGGCACGCC<br>TAGTGAGGGCAGGAGGAGGAGGACGCACACACACACACACACAAATATGGTGAAACCCAATTTCTTACATCATATCT<br>GTGCTACCCTTTCCAAACAGCCTAATTTTTCTTTTCTCTCTTCTTGCACCTTTACCCCTCAATCTCCTGCTTCCTCCCAA<br>ATTAAAGCAATTAAGTTCCTGG | SEQ.ID NO. 70<br>MDDDAAPRVEGVPVAVHKHALH<br>DGLRQVAGPGAAAAHLPRWPPP<br>QLAASRREAPPLSQRPHRTQGA<br>GSPPETNEKLTNPQVKEK |
| SEQ.ID NO. 25<br>CTCCTCCGAGCACTCGCTCACGGCGTCCCCTTGCCTGGAAAGATACCGCGGTCCCTCCAGAGGATTTGAGGGACAGGGTC<br>GGAGGGGGCTCTTCCGCCAGCACCGGAGGAAGAAAGAGGAGGGGCTGGCTGGTCACCAGAGGGTGGGGCGGACCGCGTGC<br>GCTCGGCGGCTGCGGAGAGGGGAGAGCAGGCAGCGGGCGGCGGGGAGCAGCATGGAGCCGGCGGCGGGGAGCAGCATGG<br>AGCCTTCGGCTGACTGGCTGGCCACGGCCGCGGCCCGGGGTCGGGTAGAGGAGGTGCGGGCGCTGCTGGAGGCGGGGGCG<br>CTGCCCAACGCACCGAATAGTTACGGTCGGAGGCCGATCCAGGTCATGATGATGGGCAGCGCCCGAGTGGCCGGACCTGT<br>GCTGCTCCACGGCGCGAGCCCAACTGCGCGACCCCGCCACTCTCACCCGACCCGTGCACGACGCTGCCCGGGAGGGCT<br>TCCTGGACACGCTGGTGGTGCTGCACCGGGCCGGGGCGCGGCTGGACGTGCGCGATGCCTGGGGCCGTCTGCCCGTGGAC<br>CTGGCTGAGGAGCTGGGCCATCGCGATGTCGCACGGTACCTGCGCGCGGCTGCGGGGGGCACCAGAGGCAGTAACCATGC<br>CCGCATAGATGCGCGGAAGGTCCCTCAGACATCCCCGATTGAAAGACAACCAGAGAGCTCTGAGGAACCTCGGGAAACTT<br>AGATCATCAGTCACCGAAGGTCCTACAGGGCCACAACTGCCCCGCCACAACCCACCCCGCTTTCGTAGTTTTCATTTAG<br>AAAATAGAGCTTTTAAAAATGTCCTGCCTTTTAACGTAGATATATGCTTCCCCACTACCGTAAATGTCCATTTATATC<br>ATTTTTTATATATTCTTATAAAAATGTAAAAAGAAAAACACCGCTTCTGCCTTTTCACTGTGTTGGAGTTTTCTGGAGT<br>GAGCACTCACGCCTAAGCGCACATTCATGTGGGCATTTCTTGCGAGCCTCGCAGCCTCCGGAAGCTGTCGACTTCATGA<br>CAAGCATTTTGTGAACTAGGGAAGCTCAGGGGGGTTACTGGCTTCTTGAGTCACACTGCTAGCAAATGGCAGAACCAA<br>AGCTCAAATAAAAATAAAATAATTTTCATTCATTCACTCAAAA | SEQ.ID NO. 71<br>MEPAAGSSMEPSADWLATAAAR<br>GRVEEVRALLEAGALPNAPNSY<br>GRRPIQVMMMGSARVAELLLLH<br>GAEPNCADPATLTRPVHDAARE<br>GFLDTLVVLHRAGARLDVRDAW<br>GRLPVDLAEEELGHRDVARYLRA<br>AAGGTRGSNHARIDAAEGPSDI<br>PD |
| SEQ.ID NO. 26<br>AGTGGACTCACGCAGGCGCAGGAGACTACACTTCCCAGGAACTCCGGGCGCGTTGTTCGCTGGTACCTCCTTCTGACTT<br>CCGGTATTGCTGCGGTCTGTAGGGCCAATCGGGAGCTGGAATTGCTTTCCGGCGCTCTGATTGGTGCATTCGACTAGG<br>CTGCCTGGGTTCAAAATTTCAACGATACTGAATGAGTCCCGCGGCGGGTTGGCTCGCGCTTCGTTGTCAGATCTGAGGCG<br>AGGCTAGGTGAGCCGTGGGAAGAAAGAGGGAGCAGCTAGGGCGCGGGTCTCCCTCCTCCCGGAGTTTGGAACGGCTGAA<br>GTTCACCTTCCAGCCCCTAGCGCCGTTCGCGCCGCTAGGCCTGGCTTCTGAGGCGGTTGCGGTGCTCGGTCGCCGCCTAG | SEQ.ID NO. 72<br>MSQVKSSYSYDAPSDFINFSSL<br>DDEGDTQNIDSWFEEKANLENK<br>LLGKNGTGGLFQGKTPLRKANL<br>QQAIVTPLKPVDNTYYKEAEKE<br>NLVEQSIPSNACSSLEVEAAIS |

TABLE 4-continued

Nucleotide and amino acid sequences of the SEQ. ID NOs.

| Nucleotide Sequence (5'-3') | ORFs |
|---|---|
| GCGGGGCAGGGTGCGAGCAGGGGCTTCGGGCCACGCTTCTCTTGGCGACAGGATTTTGCTGTGAAGTCCGTCCGGGAAAC<br>GGAGGAAAAAAAGAGTTGCGGGAGGCTGTCGGCTAATAACGGTTCTTGATACATATTTGCCAGACTTCAAGATTTCAGAA<br>AAGGGGTGAAAGAGAAGATTGCAACTTTGAGTCAGACCTGTAGGCCTGATAGACTGATTAAACCACAGAAGGTGACCTGC<br>TGAGAAAAGTGGTACAAATACTGGGAAAAACCTGCTCTTCTGCGTTAAGTGGGAGACAATGCTCACAAGTTAAAAGCTCTT<br>ATTCCTATGATGCCCCCTCGGATTTCATCAATTTTTCATCCTTGGATGATGAAGGAGATACTCAAACATAGATTCATGG<br>TTTGAGGAGAAGGCCAATTTGGAGAATAAGTTACTGGGGAAGAATGGAACTGGAGGGCTTTTTCAGGGCAAAACTCCTTT<br>GAGAAAGGCTAATCTTCAGCAAGCTATTGTCACACCTTTGAAACCAGTTGACAACACTTACTACAAAGAGGCAGAAAAAG<br>AAAATCTTGTGGAACAATCCATTCCGTCAAATGCTTGTTCTTCCCTGGAAGTTGAGGCAGCCATATCAAGAAAAACTCCA<br>GCCCAGCCTCAGAGAAGATCTCTTAGGCTTTCTGCTCAGAAGGATTTGGAACAGAAAGAAAAGCATCATGTAAAAATGAA<br>AGCCAAGAGATGTGCCACTCCTGTAATCATCGATGAAATTCTACCCTCTAAGAAAATGAAAGTTTCTAACAACAAAAGA<br>AGCCAGAGGAAGAAGGCAGTGCTCATCAAGATACTGCTGAAAAGAATGCATCTTCCCCAGAGAAAGCCAAGGGTAGACAT<br>ACTGTGCCTTGTATGCCACCTGCAAAGCAGAAGTTTCTAAAAAGTACTGAGGAGCAAGAGCTGGAGAAGAGTATGAAAAT<br>GCAGCAAGAGGTGGTGGAGATGCGAAAAAGAATGAAGAATTCAAGAAACTTGCTCTGGCTGGAATAGGGCAACCTGTGA<br>AGAAATCAGTGAGCCAGGTCACCAAATCAGTTGACTTCCACTTCCGCACAGATGAGCGAATCAAACAACATCCTAAGAAC<br>CAGGAGGAATATAAGGAAGTGAACTTTACATCTGAACTACGAAAGCATCCTTCATCTCCTGCCCGAGTGACTAAGGGATG<br>TACCATTGTTAAGCCTTTCAACCTGTCCCAAGGAAGAAAGAAAACATTTGATGAAACAGTTTTCTACATATGTCGCCCTTG<br>CACAGCAAGTTGAAGACTTCCATAAACGAACCCCTAACAGATATCATTTGAGGAGCAAGAAGGATGATATTAACCTGTTA<br>CCCTCCAAATCTTCTGTGACCAAGATTTGCAGAGACCCACAGACTCCTGTACTGCAAACCAAACACCGTGCACGGGCGT<br>GACCTGCAAAAGTACAGCAGAGCTGGAGGCTGAGGAGCTCGAGAAATTGCAACAATACAAATTCAAAGCACGTGAACTTG<br>ATCCCAGAATACTTGAAGGTGGGCCCATCTTGCCCAAGAAACCACCTGTGAACACCCACCGAGCCTATTGGCTTTGAT<br>TGGAAATTGAGAAAAGAATCCAGGAGCGAGAATCAAAGAAGAAACAAGAGGATGACACTTTGAATTTCATTCCAGACC<br>TTGCCCTACTAAGATTTTGGAAGATGTTGTGGGTGTTCCTGAAAAGAAGGTACTTCCAATCACCGTCCCCAAGTCACCAG<br>CCTTTGCATTGAAGAACAGAATTCGAATGCCCACCAAAGAAGATGAGGAAGAGGACGAACCGGTAGTGATAAAAGCTCAA<br>CCTGTGCCACATTATGGGGTGCCTTTTAAGCCCCAAATCCCAGAGGCAAGAACTGTGGAAAATATGCCCTTTCTCGTTTGA<br>TTCTCGAGACAAAGAACGTCAGTTACAGAAGGAGAAGAAAATAAAAGAACTGCAGAAAGGGGAGGTGCCCAAGTTCAAGG<br>CACTTCCCTTGCCTCATTTTGACACCATTAACCTGCCAGAGAAGAAGGTAAAGAATGTGACCCAGATTGAACCTTTCTGC<br>TTGGAGACTGACAGAAGAGGTGCTCTGAAGGCACAGACTTGGAAGCACCAGCTGGAAGAAGAACTGAGACAGCAGAAAGA<br>AGCAGCTTGTTTCAAGGCTCGTCCAAACACCGTCATCTCTCAGGAGCCCTTTGTTCCCAAGAAAGAAGAAGAAGAATCAGTTG<br>CTGAGGGCCTTTCTGGTTCTCTAGTTCAGGAAGCCTTTTCAGCTGGCTACTGAGAAGAGAGCCAAAGAGCGGCAGGAGCTG<br>GAGAAGAGAATGGCTGAGGTAGAAGCCCAGAAAGCCCAGCAGTTGGAGGAGGCCAGACTACAGGAGGAAGAGCAGAAAGA<br>AGAGGAGCTGGCCAGGCTACGAGAGAACTGGTCATAAGGCAAATCCAATACGCAAGTACCAGGGTCTGGAGATAAAGT<br>CAAGTGACCAGCCTCTGACTGTGCCTGTATCTCCCAAATTCTCCACTCGATTCCACTGCTAAACTCAGCTGTGAGCTGCG<br>GATACCGCCCGCAATGGGACCTGCTCTTAACCTCAAACCTAGGACCGTCTTGTCATTGGGCATGGAGAGGAACCC<br>ATTTCTCCAGACTTTTACCTACCCGTGCCTGAGAAAGCATACTTGACAACTGTGGACTCCAGTTTTGTTGAGAATTGTTT<br>TCTTACATTACTAAGGCTAATAATGAGATGTAACTCATGAATGTCTCGATTAGACTCCATGTAGTTACTTCCTTTAAACC<br>ATCAGCCGGCCTTTTATATGGGTCTTCACTCTGACTAGAATTTAGTCTCTGTGTCAGCACAGTGTAATCTCTATTGCTAT<br>GAGATTAAGTCATGGTTTAAATGAGGAACAATCAGTAAATCAGATTCTGTCCTCTTCTCGATACCGTGAATTTATAGT<br>TAAGGATCCCTTTGCTGTGAGGGTAGAAAACCTCACCAACTGCACCAGTGAGGAAGAAGACTGCGTGGATTCATGGGAG<br>CCTCACAGCAGCCACGCAGCAGGCTCTGGGTGGGGCTGCCGTTAAGGCACGTTCTTTCCTTACTGGTGCTGATAACAACA<br>GGGAACCGTGCAGTGTGCATTTTAAGACCTGGCCTGGAATATACGTTTTGTCTTTCCCTCAAAAAAAAAAAAAAAAAAAAAA<br>AAAAA | RKTPAQPQRRSLRLSAQKDLEQ<br>KEKHHVKMKAKRCATPVIIDEI<br>LPSKKMKVSNNKKKPEEEGSAH<br>QDTAEKNASSPEKAGRHTVPC<br>MPPAKQKFLKSTEEQELEKSMK<br>MQQEVVEMRKKNEEFKKLALAG<br>IGQPVKKSVSQVTKSVDFHFRT<br>DERIKQHPKNQEEYKEVNFTSE<br>LRKHPPSPARVTKGCTIVKPFN<br>LSQGKKRTFDETVSTYVPLAQQ<br>VEDFHKRTPNRYHLRSKKDDIN<br>LLPSKSSVTKICRDPQTPVLQT<br>KHRARAVTCKSTAELEAEELEK<br>LQQYKFKARELDPRILEGGPIL<br>PKKPPVKPPTEPIGFDLETEKR<br>IQERESKKKTEDEHFEFHSRPC<br>PTKILEDVVGVPEKKVLPITVP<br>KSPAFALKNRIRMPTKEDEEED<br>EPVVIKAQPVPHYGVPFKPQIP<br>EARTVEICPFSFDSRDKERQLQ<br>KEKKIKELQKGEVPKFKALPLP<br>HFDTINLPEKKVKNVTQIEPFC<br>LETDRRGALKAQTWKHQLEEEL<br>RQQKEAACFKARPNTVISQEPF<br>VPKKEKKSVAEGLSGSLVQEPF<br>QLATEKRAKERQELEKRMAEVE<br>AQKAQQLEEARLQEEEQKKEEL<br>ARLRRELVHKANPIRKYQGLEI<br>KSSDQPLTVPVSPKFSTRFHC |
| SEQ.ID NO. 27<br>AAACGCGGGCGGGCGGGCCCGCAGTCCTGCAGTTGCAGTCGTGTTCTCCGAGTTCCTGTCTCTCTGCCAACGCCGCCGG<br>ATGGCTTCCCAAAACGCGACCCAGCCGCCACTAGCGTCGCCGCCGCCGTAAAGGAGCTGACGCTGATGATGCGCGC<br>CCGGGGTCCGGTGGGCAAAAGGCTACAGCAGGAGCTGATGACCCTCATGATGTCTGGCGATAAAGGGATTTCTGCCTTCC<br>CTGAATCAGACAACCTTTTCAAATGGGTAGGGACCATCCATGGAGCAGCTGGAACAGTATATGAAGACCTGAGGTATAAG<br>CTCTCGCTAGAGTTCCCCAGTGGCTACCCTTACAATGCGCCCACAGTGAAGTTCCTCACGCCCTGCTATCACCCCAACGT<br>GGACACCCAGGGTAACATATGCCTGGACATCCTCAAGGAAAAGTGGTCTGCCCTGTATGATGTCAGGACCATTCTGTCT<br>CCATCCAGAGCCTTCTAGGAGAACCCAACATTGATAGTCCCTTGAACACACATGCTGCCGAGCTCTGGAAAAACCCCACA<br>GCTTTTAAGAAGTACCTGCAAGAAACCTACTCAAAGCAGGTCACCAGCCAGGAGCCTGACCCAGGCTGCCCAGCCTGTC<br>CTTGTGTCGTCTTTTTAATTTTTCCTTAGATGGTCTGTCCTTTTTGTGATTTCTGTATAGGACTCTTTATCTTGAGCTGT<br>GGTATTTTGTTTGTTTTTGTCTTTTAAATTAAGCCTCGGTTGAGCCCTTGTATATTAAATAAATGCATTTTTGTCCTT<br>TTTTAGACAAAAAAAAAAAAAAAA | SEQ.ID NO. 73<br>MASQNRDPAATSVAAARKGAEP<br>SGGAARGPVGKRLQQELMTLMM<br>SGDKGISAFPESDNLFKWVGTI<br>HGAAGTVYEDLRYKLSLEFPSG<br>YPYNAPTVKFLTPCYHPNVDTQ<br>GNICLDILKEKWSALYDVRTIL<br>LSIQSLLGEPNIDSPLNTHAAE<br>LWKNPTAFKKYLQETYSKQVTS<br>QEP |
| SEQ.ID NO. 28<br>CAGCTAAATTTTAAAGGTGTTTTGTAGAGATGAGGTTTCACTATATTGCCCAGGCTGGTCTCGAACTCCTGGACTTAAG<br>TGATCCTTCCTCTTTGGCCTCCCAAAGTGCTGGGATTACAGGCATGAGCCACTGCCCCAGCCAAGACTGTCTTTTCTCCA<br>TTGTATTGCGTTTGCTTCCTTGTCAAAGATCAGTTGACTATATTTGTGTGGGGCTATTTCTGGGCTCCCTATTTGTTTCC<br>AGTGATTATGTCTATTTTTCACCATTACCACCCTATCTTAATTACTGTAGCTTTATAGTGAGTCTTAAAGTTGGGTAAT<br>ATCAGTCTTCTGACCTTTTTCTCTTTCAATATTGTGCCAGCTATTCTGGGTCTTTTGCCTTTCCATGTAAACTTTAGAAC<br>CAGTTTGTCAGGATCCACAAAATACTTTGCTGGGTTTTGATTGGGATTGCATTGAATCTCAAGTCAGTTGGCAAAAGAT<br>TGACATACAGCAATGCCAGTTTATTGTTTTGTGATAGCCTTAATCCAGCTAGTTTCTTCACAGGATGATGTTGAAAATAT<br>GGGATGCTCATAATCCCTGAATATTTTTATGTGGATAATTAAACTTGTTCTGGGTGGATGGTTGGATAGCCAGAATAGT<br>AATAACCTCTCTTCCAGCCACTCAAAGAAAATGATATAAACGTAGGGTTGGTTTAATTGTTGAGAGGTCACGTTTTTTCC<br>ATTCTTGCTCTCAGGTAAGGAAAGCACTGTTGGTTCACGCATTCCTCTTTTCCCTCATACACTTTGTTGGCACTGATA<br>TGGTTTGGCTCTGTGTTCCCACCCAAATCTCATGTTGAATTGTGATCCTGAGTGTTGAGGTGGGGCCTCGCGGGAGACG<br>ACTGGATCATGGGGCGGATTTTCCCCTTGCTGTTCTCATGATAGTGAGTTCTCATGAGATCTGGTTGTTAAAAGTGTA<br>TAGCACTTCCTGCTTCACTCTCTCCCACTCCACCATGTGAAGAAGGTGCCTTTGCCCTTCCGCCACGACTGTGTTTCCTG<br>AGGCCTCCAGCCATGCCTCCTGTACAGCCTGCGGAACTGTCAGTTAAACCTCTTTCTCATTAATTACCCACTCTCA<br>GGTGGTTTTTTATGGCAGTGTGAGAACGGACTAATACAGAAATTGGTACCAGAAGTGGGATATTGCTATAAAATACC<br>TGAAAATGTGGAAGTGACTTTGGAACTGGTAATGGGCAGAGGTTGGAACAGTTTGGAGGGCTCAGAAGAAGACAGGAAG<br>ATGAGGGAAAGTTTGCAGCTTCCTAGAGACTTGTTGAATGGTTGTGACCAAAGTGCTGATAGTGATATGGACAGTGAAGT<br>CCAGGCTGAGTTGGTCTCAGATGGGAGATGAGAATCTTATTCCGAACTGGAGTGAAGGTCACTCTTGGCTGTGCTTTAGC<br>AAAGAGAGTGGTGGCATTGTGCCCCTGCTCTAGAGATCTGTGAACTCTGAACTCGAGAGGGTATCTGGCAGAAAAAATT |  |

TABLE 4-continued

Nucleotide and amino acid sequences of the SEQ. ID NOs.

| Nucleotide Sequence (5'-3') | ORFs |
|---|---|
| TCTAAGCAGCAAAGTGTTCAAGATGTGGCCTGATTGCTTCTAAAAGCCTATGCTCATTTGCATGAACAAAGTGGAACTTA<br>TATTTAAAACAGAAGCTGAGCTTTTATAAAAGTTTGGAGAATTTGCAGCCCAACCATGTGGTGAAAAAGAAAAATCCATT<br>TTCTGGGGAGGTATTCAAGGCTGCAGAAATTTGCATAAGAAGAGCCTCATGTTAACAGCCAAGAGAGTGAGGAAAATGCC<br>TCTAGAGCATTTCAGAGACCTTCACAGCAGCTCCTCCCATCACAGGCATGGAAGCCCAGGAGGAAGAAATGCTTTTGTGG<br>GCCAGCCCAGGGCCCCACTGTTCTGTGCAGCCTTGGGACATGGTGCCCTGCATCCCAGCCACTCCAGCTCCAGCTGTGAC<br>TAAAAGGGGCCAAGGTACAGCTTGGGCTGCTGCTTCAGAGGGTGCAAGCCCCAAGCCTTGGTGGCTTCCATGTGGTGTTA<br>GGCAGGTGTGCAGAAGAGTTGAGGTTTAGGAACCTCTACCTAGATTTCAGAGGATGTATGGAAATGCCCGGATGTCCAGG<br>CAGAAGTTTGCTGCAGAGGCAGGAGCCCTCATAGATAACCTCTGCGAGGGCAGTGTGGAGGGGAAATGTGGGGTTGGAGCT<br>ATGAGAAGAGGGCCACCATCCACCAGACCCCAGAATTGTAGATCCACTGACAGCTTGCACTATGCACCTGTAAAAGTTGC<br>AGGCAGTTAATGCTAGCCTGTGAAAGCAGCTGTGGGGACTATATGCAGAGCCACAGAGGCAGAGCTGCCCAGAGCCTTGG<br>GAGCCCACTCCTTGTGTCAGTGTGGCCTGGATGTGAGACGTGGAGTCAAAGATCATTTTGGAGGTTTGAGATTTAATGAC<br>TGCCCTCCTGGATTTTGGACTTGCATGGGGCCCATAGCCCCTTTGTTTTGGCTGATTTCTCCTATTTGGAATGGAGCAT<br>TTACCCAATGCCTGTATCCCCATTGTATCTTGGAGATAACTGACTTGTTTTTGATTTTACAGGCTCACAGGAGGAAGGGA<br>CTTGGCTGGTCTCAGATGAGACTTGACTTGGACATTTGAGTTAATGCTGGAATGAGTTAAGACTTTAGGGGGCTATTGGG<br>AAGGCATGATTGTGTTTTGAAATGTGAGGACATGAGATTTGGGAGGGGCCAGGGTGGAATGATATGGTTTGGCTGTGTCC<br>CCCCACCCAAATCTCATGTTGAATTGTGATCCTGAGTCTTGGAGGTAGAGCCTGGTGGGAGGTGATTGGATCTGGAGCTG<br>AGATTTCCCCCTTGCTGTTCTCATGACAGTGAGTTCTCATGAGATCTGGTTAAGTGTGTAGCACTTCCCCCTTTGCTTGC<br>TCTCTCCCTCTGCCATGTGAAGAAGGTGCTTGCTTTCCCTTCGCCCTTCTGCCATGACTGTAAGTTTCTTGAGGCCTCGC<br>AGCCATGCTTCCTGTACAGCCTGCAGAACTGTGAGTTAATTAAACCTCTTTTCTTCAT | |
| SEQ.ID NO. 29<br>AGCTTTGGGGTTGTCCCTGGACTTGTCTTGGTTCCAGAACCTGACGACCCGGCGACGGCGACGTCTCTTTTGACTAAAAG<br>ACAGTGTCCAGTGCTCCAGCCTAGGAGTCTACGGGGACCGCCTCCCGCGCCGCCACCATGCCCAACTTCTCTGGCAACTG<br>GAAAATCATCCGATCGGAAAACTTCGAGGAATTGCTCAAAGTGCTGGGGGTGAATGTGATGCTGAGGAAGATTGCTGTGG<br>CTGCAGCGTCCAAGCCAGCAGTGGAGATCAAACAGGAGGGAGACACTTTCTACATCAAAACCTCCACCACCGTGCGCACC<br>ACAGAGATTAACTTCAAGGTTGGGGAGGAGTTTGAGGAGCAGACTGTGGATGGGAGGCCCTGTAAGAGCCTGGTGAAATG<br>GGAGAGTGAGAATAAAATGGTCTGTGAGCAGAAGCTCCTGAAGGGAGAGGGCCCCAAGACCTCGTGGACCAGAGAACTGA<br>CCAACGATGGGGAACTGATCCTGACCATGACGGCGGATGACGTTGTGTGCACCAGGGTCTACGTCCGAGAGTGAGTGGCC<br>ACAGGTAGAACCGCGGCCGAAGCCCACCACTGGCCATGCTCACCGCCCTGCTTCACTGCCCCTCCGTCCCCACCCCCTCC<br>TTCTAGGATAGCGCTCCCCTTACCCCAGTCACTTCTGGGGGTCACTGGGATGCCTCTTGCAGGGTCTTGCTTTCTTTGAC<br>CTCTTCTCTCCTCCCCTACACCAACAAAGAGGAATGGCTGCAAGAGCCCAGATCACCCATTCCGGGTTCACTCCCCGCCT<br>CCCCAAGTCAGCAGTCCTAGCCCCAAACCAGCCCAGAGCAGGGTCTCTCTAAAGGGGACTTGAGGGCCTGAGCAGGAAAG<br>ACTGGCCCTCTAGCTTCTACCCTTTGTCCCTGTAGCCTATACAGTTTAGAATATTTATTTGTTAATTTTATTAAAATGCT<br>TTAAAAAAA | SEQ.ID NO. 74<br>MPNFSGNWKIIRSENFEELLKV<br>LGVNVMLRKIAVAAASKPAVEI<br>KQEGDTFYIKTSTTVRTTEINF<br>KVGEEFEEQTVDGRPCKSLVKW<br>ESENKMVCEQKLLKGEGPKTSW<br>TRELTNDGELILTMTADDVVCT<br>RVYVRE |
| SEQ.ID NO. 30<br>CTCGCTTTTCGGTTGCCGTTGTCTTTTTTCCTTGACTCGGAAATGTCCGGTCGTGGTAAGCAGGGTGGCAAGGCGCGCGC<br>CAAGGCTAAGTCGCGCTCGTCGCGCGCGGGCTGCAGTTCCCCGTGGGCGCGTGCACCGGTTGCTCCGCAAGGGCAACT<br>ATTCGGAGCGCGTGGGCGCCGGCGCCCCGGTCTATCTGGCCGCGGTGCTCGAGTACTTGACTGCCGAGATCCTGGAGCTT<br>GCCGGCAACGCGGGCGCGACAACAAGAAGACGCGCATCATCCCGCGCCACCTGCAGCTGGCCATCCGCAACGACGAGGA<br>GCTCAACAAGCTGCTGGGCCGCGTGACCATCGCGCAGGGTGGCGTCCTGCCCAACATCCAGGCCGTACTGCTGCCCAAGA<br>AGACGGAGAGCCACCACAAGGCCAAGGGCAAGTGAGGCCGCCCGCCGCCCCCGGGGCCCCTTTGATGGACATAAAGGCTC<br>TTTTCAGAGC<br>CACCTA | SEQ.ID NO. 75<br>MSGRGKQGGKARAKAKSRSSRA<br>GLQFPVGRVHRLLRKGNYSERV<br>GAGAPVYLAAVLEYLTAEILEL<br>AGNAARDNKKTRIIPRHLQLAI<br>RNDEELNKLLGRVTIAQGGVLP<br>NIQAVLLPKKTESHHKAKGK |
| SEQ.ID NO. 31<br>ATGTCTGGCCGTGGTAAAGGTGGAAAAGGTTTGGGTAAGGGAGGAGCTAAGCGTCATCGCAAGGTTTTGCGCGATAACAT<br>CCAGGGCATCACTAAGCCAGCTATCCGGCGCCTTGCTCGTCGCGGCGGTGTCAAGCGAATTTCTGGCCTTATCTATGAGG<br>AGACTCGTGGTGTTCTGAAGGTGTTCCTGGAGAACGTGATTCGTGACGCTGTCACTTACACAGAGCACGCCAAACGCAAG<br>ACCGTGACAGCAATGGATGTGGTCTACGCGCTGAAGCGACAGGGACGGCACTCTTTACGGCTTCGGTGGCTAAGGCTCCTG<br>CTTGCTGCACTCTTATTTTCATTTTCAACCAAAGGCCCTTTTCAGGGCCGCCCA | SEQ.ID NO. 76<br>MSGRGKGGKGLGKGGAKRHRKV<br>LRDNIQGITKPAIRRLARRGGV<br>KRISGLIYEETRGVLKVFLENV<br>IRDAVTYTEHAKRKTVTANDVV<br>YALKRQGRTLYGFGG |
| SEQ.ID NO. 32<br>GCCTCCACAGATATCAAAAGAAACCTGAAGAGCCTACAAAAAAAAAGAGATAAAGACAAAATTCAAGAAAACACACACA<br>TACATAATTGTGGTCACCTGGAGCCTGGGGCCGGCCCAGCTCTCTCAGGATTCAGCAGACATTGGAGGTGGCAGTGAAG<br>GATACAGTGGTAGTCAATGTTATTTGAGCAGGGTCAGCAGGCCCTGGAGCTTCCTGAGTGCACAATGCAGAAGGCTGCTT<br>ACTATGAAAACCCAGGACTGTTTGGAGGCTATGGCTACAGCAAAACTACGGACACTTACGGCTACAGCACCCCCCACCAG<br>CCCTACCCACCCCCTGCTGCTGCCAGCTCCCTGGACACTGACTATCCAGGTTCTGCCTGCTCCATCCAGAGCTCTGCCC<br>TCTGAGAGCCCCAGCCCACAAAGGAGCTGAACTCAATGGCAGCTGCATGCGGCCGGGCACTGGGAACAGCCAGGGTGGGG<br>GTGGTGGCAGCCAGCCTCCTGGTCTGAACTCAGAGCAGCAGCCACCACAACCCCTCCTCCACCACCGACCCTGCCCCCA<br>TCTTCACCCACCAATCCTGGAGGTGGAGTGCCTGCCAAGAAGCCCAAAGGTGGGCCCAATGCTTCTAGCTCCTCAGCCAC<br>CATCAGCAAGCAGATCTTCCCCTGGATGAAAGAGTCTCGACAGAACTCCAAGCAGAAGAACAGCTGTGCCACTGCAGGAG<br>AGAGCTGCGAGGACAAGAGCCCGCCAGGCCCAGCATCCAAGCGGGTACGACCGGCATACACGAGCGCGCAGCTGGTGGAA<br>TTGGAAAAGGAATTCCACTTCAACCGCTACTTGTGCCGGCCGCGCCGCGTGGAGATGGCCAACCTGCTGAATCTCACGGA<br>ACGCCAGATCAAGATCTGGTTCCAGAACCGGCGCATGAAGTACAAGAAGGACCAGAAGGCCAAGGGCATCCTGCACTCGC<br>CGGCTAGCCAGTCCCCTGAGCCAGCCCACCGCTCGGCGGCCGCGTGGCTGCCACTGCTACTCCGGCAGCTGCCCGA<br>GTGCCCGGCCTGGCCTACGACGCGCCCTCGCCGCCTGCTTTCGCCAAATCACAGCCCAATATGTACGGCTGGCCGCCTA<br>CACGGCGCCACTCAGCAGCTGCCTGCCACAACAGAAGCGCTACGCAGCGCCGGAGTTCGAGCCCATCCCATGGCAGCA<br>ACGGCGGCGGCTTCGCCAGCGCCAACTTGCAGGGCAGCCCGGTGTACGTGGGCGGCAACTTCGTCGAGTCCATGGCGCCC<br>GCGTCCGGCCTGTCTTCAACCTGGGCCACCTCTCGCACCCGTCGTCGGCCAGCGTGGACTACAGTTGCGCCGCGCAGAT<br>TCCAGGCAACCACCACCATGGCCCTTGCGACCCTCATCCCACCTACACAGATCTCTCGGCCACCACTCGTCGTCAGGGAC<br>GACTGCCGGAGGCTCCCAAACTGACGCATCTGTAGCGGCCGCCGCCAGCCCGAACTCGCGGCAAAATTACCTCTCTTGCT<br>GTAGTGGTGGGGTAGAGGGTGGGGCCCGCGGGGCAGTTCGGGAACCCCCTTCCCCGCTCTTGCCCTGCCGCCGCCTCCCG<br>GGTCTCAGGCCTCCAGCGGCGGAGGCGCAGGCGACCGGGCCTCCCCTCCATGGGCGTCCTTTGGGTGACTCGCCATAAAT<br>CAGCCGCAAGGATCCTTCCCTGTAAATTTGACAGTGCCACATACTGCGGACCAAGGGACTCCAATCTGGTAATGGTGTCC | SEQ.ID NO. 77<br>MLFEGQQALELPECTMQKAAY<br>YENPGLFGGYGYSKTTDTYGYS<br>TPHQPYPFPAAASSLDTYPGS<br>ACSIQSSAPLRAPAHKGAELNG<br>SCMRPGTGNSQGGGGGSQPPGL<br>NSEQQPPQPPPPPPTLPPSSPT<br>NPGGGVPAKKPKGGPNASSSSA<br>TISKQIFPWMKESRQNSKQKNS<br>CATAGESCEDKSPPGPASKRVR<br>TAYTSAQLVELEKEFHFNRYLC<br>RPRRVEMANLLNLTERQIKIWF<br>QNRRMKYKKDQKAKGILHSPAS<br>QSPERSPPLGGAAGHVAYSGQL<br>PPVPGLAYDAPSPPAFAKSQPN<br>MYGLAAYTAPLSSCLPQQKRYA<br>APEFEPHPMASNGGGFASANLQ<br>GSPVYVGGNFVESMAPASGPVF<br>NLGHLSHPSSASVDYSCAAQIP<br>GNHHHGPCDPHPTYTDLSAHHS<br>SQGRLPEAPKLTHL |

TABLE 4-continued

Nucleotide and amino acid sequences of the SEQ. ID NOs.

| Nucleotide Sequence (5'-3') | ORFs |
|---|---|
| CAAAGGTAAGTCTGAGACCCATCAGCGGCGCGCCCTGCAGAGGGACCAGAGCTTGGAGAGTCTTGGGCCTGGCCCGCGTC<br>TAGCTTAGTTTCAGAGACCTTAATTTATATTCTCCTTCCTGTGCCGTAAGGATTGCATCGGACTAAACTATCTGTATTTA<br>TTATTTGAAGCGAGTCATTTCGTTCCCTGATTATTTATCCTTGTCTGAATGTATTTATGTGTATATTTGTAGATTTATCC<br>AGCCGAGCTTAGGAATTCGCTTCCAGGCCGTGGGGGCCACATTTCACCTCCTTAGTCCCCCTGGTCTGAACTAGTTGAGA<br>GAGTAGTTTTGAACAGTCGTAACCGTGGCTGGTGTTTGTAGTTGACATAAAGGATTAAGACCGCAAATTGTCCTTCATGG<br>GTAGAGTCAGGAAGCCCGGTGGCGTGGCACAACACACTTTGGTCATTTCTCAAAAACCACAGTCCTCACCACAGTTTATT<br>GATTTCAAATTGTCTGGTACTATTGGAACAATATTTAGAATAAAAAAATTTCCCAGTCAAAAAAAAAAAAAAAAAAAAAA | |
| SEQ.ID NO. 33<br>CCAGCCCTGAGATTCCCAGGTGTTTCCATTCGGTGATCAGCACTGAACACAGAACTCACCATGGAGTTTGGACTGAGCTG<br>GGTTTTCCTTGTTGCTATTTTAAAAGGTGTCCAGTGTGAAGTGCAGCTGGTGGAGTCTGGGGGAGTCGTGGTACAGCCTG<br>GGGGGTCCCTGAGACTCTCCTGTGCAGCCTCTGGATTCACCTTTGATGACTATGCCATGCACTGGGTCCGTCAAGCTCCG<br>GGGAAGGGTCTGGAGTGGGTCTCCCTTATTAGTTGGGATGGTGGTAGCACCTACTACGCAGATCTGTGAAGGGTCGATT<br>CACCATCTCCAGAGACAATAGTAAAAATTCCTTGTATCTGCAAATGAACAGTCTGAGAGCTGAGGACACCGCCTTGTATT<br>ACTGTGCAACCCGGGGGGTTATTCCACCGCCGGCTTTGACTACTGGGGCCAGGGAACCCTGGTCACCGTCTCCTCAGCC<br>TCCACCAAGGGCCCATCGGTCTTCCCCCTGGCACCCTCCTCCAAGAGCACCTCTGGGGGCACAGCGGCCCTGGGCTGCTT<br>GGTCAAGGACTACTTCCCCGAACCGGTGACGGTGTCGTGGAACTCAGGCGCCCTGACCAGCGGCGTGCACACCTTCCCGG<br>CTGTCCTACAGTCCTCAGGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATCTTGTGACAAAACTCACAC<br>ATGCCCACCGTGCCCAGCACCTGAACTCCTGGGGGGACCGTCAGTCTTCCTCTTCCCCCCAAAACCCAAGGACACCCTCA<br>TGATCTCCCGGACCCCTGAGGTCACATGCGTGGTGGTGGACGTGAGCCACGAAGACCCTGAGGTCAAGTTCAACTGGTAC<br>GTGGACGGCGTGGAGGTGCATAATGCCAAGACAAAGCCGCGGGAGGAGCAGTACAACAGCACGTACCGTGTGGTCAGCGT<br>CCTCACCGTCCTGCACCAGGACTGGCTGAATGGCAAGGAGTACAAGTGCAAGGTCTCCAACAAAGCCCTCCCAGCCCCCA<br>TCGAGAAAACCATCTCCAAAGCCAAAGGGCAGCCCCGAGAACCACAGGTGTACACCCTGCCCCCATCCCGGGATGAGCTG<br>ACCAAGAACCAGGTCAGCCTGACCTGCCTGGTCAAAGGCTTCTATCCCAGCGACATCGCCGTGGAGTGGGAGAGCAATGG<br>GCAGCCGGAGAACAACTACAAGACCACGCCTCCCGTGCTGGACTCCGACGGCTCCTTCTTCCTCTACAGCAAGCTCACCG<br>TGGACAAGAGCAGGTGGCAGCAGGGGAACGTCTTCTCATGCTCCGTGATGCATGAGGCTCTGCACAACCACTACACGCAG<br>AAGAGCCTCTCCCTGTCTCCGGGTAAATGAGTGCGACGGCCGGCAAGCCCCCGCTCCCCGGGCTCTCGCGGTCGCACGAG<br>GATGCTTGGCACGTACCCCGTGTACATACTTCCCGGGCGCCCAGCATGGAAATAAAGCACCCAGCGCTGCCCTGGGCCCC<br>TGCGAAAAAAAAAAAAAAAAAAAAAAAAAAAAAAAAAAAAAAAAAAAAAAAAAAAAAAAAAAAAAAAAAAAAAAAAAAAA<br>AAAAAAAAAAAAAAAAAAAAA | SEQ.ID NO. 78<br>MEFGLSWVFLVAILKGVQCEVQ<br>LVESGGVVQPGGSLRLSCAAS<br>GFTFDDYAMHWVRQAPGKGLEW<br>VSLISWDGGSTYYADSVKGRFT<br>ISRDNSKNSLYLQMNSLRAEDT<br>ALYYCATRGGYSTAGFDYWGQG<br>TLVTVSSASTKGPSVFPLAPSS<br>KSTSGGTAALGCLVKDYFPEPV<br>TVSWNSGALTSGVHTFPAVLQS<br>SGLYSLSSVVTVPSSSLGTQTY<br>ICNVNHKPSNTKVDKKVEPKSC<br>DKTHTCPPCPAPELLGGPSVFL<br>FPPKPKDTLMISRTPEVTCVVV<br>DVSHEDPEVKFNWYVDGVEVHN<br>AKTKPREEQYNSTYRVVSVLTV<br>LHQDWLNGKEYKCKVSNKALPA<br>PIEKTISKAKGQPREPQVYTLP<br>PSRDELTKNQVSLTCLVKGFYP<br>SDIAVEWESNGQPENNYKTTPP<br>VLDSDGSFFLYSKLTVDKSRWQ<br>QGNVFSCSVMHEALHNHYTQKS<br>LSLSPGK |
| SEQ.ID NO. 34<br>GAGGGAACCATGGAAACCCCAGCGCAGCTTCTCTTCCTCCTGCTACTCTGGCTCCCAGATATCACCGGAGAAATTGTGTT<br>GACGCAGTCTCCAGGCACCCTGTCTTTGTCTCCAGGAGAAAGAGCCGCCCTCTCATGCAGGGCCAGTCAGAGTGTTAACA<br>GCAAGTACTTAGCCTGGTACCAGCAGAAGCCTGGCCAGGCTCCCAGGCTCCTCATGTATGCTGCATCCATCAGGGCCACT<br>GGCATCCCAGACAGGTTCAGTGGCAGTGGGTCTGGGACAGACTTCACTCTCACCATCAGCAGACTGGAGTCTGAGGACTT<br>TGCACTGTATTTCTGTCAGCAATATGGTACTTCACCTCTCACTTTCGGCGGAGGGACCAAGGTGGAGATCAAACGAACTG<br>TGGCTGCACCATCTGTCTTCATCTTCCCGCCATCTGATGAGCAGTTGAAATCTGGAACTGCCTCTGTTGTGTGCCTGCTG<br>AATAACTTCTATCCCAGAGAGGCCAAAGTACAGTGGAAGGTGGATAACGCCCTCCAATCGGGTAACTCCCAGGAGAGTGT<br>CACAGAGCAGGACAGCAAGGACAGCACCTACAGCCTCAGCAGCACCCTGACGCTGAGCAAAGCAGACTACGAGAAACACA<br>AAGTCTACGCCTGCGAAGTCACCCATCAGGGCCTGAGCTCGCCCGTCACAAAGAGCTTCAACAGGGGAGAGTGTTAGAGG<br>GAGAAGTGCCCCCACCTGCTCCTCAGTTCCAGCCTGACCCCTCCCATCCTTTGGCCTCTGACCCTTTTTCCACAGGGGA<br>CCTACCCCTATTGCGGTCCTCCAGCTCATCTTTCACCTCACCCCCTCCTCCTCCTTGGCTTTAATTATGCTAATGTTGG<br>AGGAGAATGAATAAATAAGTGAATCTTTGCACCTAAAAAAAAAAAAAAAAAAAAAAAAAAAAAAAAAAAAAAAAAAAAAA<br>AAAAAAAAAAAAAAA | SEQ.ID NO. 79<br>METPAQLLFLLLLWLPDITGEI<br>VLTQSPGTLSLSPGERAALSCR<br>ASQSVNSKYLAWYQQKPGQAPR<br>LLMYAASIRATGIPDRFSGSGS<br>GTDFTLTISRLESEDFALYFCQ<br>QYGTSPLTFGGGTKVEIKRTVA<br>APSVFIFPPSDEQLKSGTASVV<br>CLLNNFYPREAKVQWKVDNALQ<br>SGNSQESVTEQDSKDSTYSLSS<br>TLTLSKADYEKHKVYACEVTHQ<br>GLSSPVTKSFNRGEC |
| SEQ.ID NO. 35<br>ACGCGGGGGGCCCGCTCTCGGCGAGCCCGACCCGCCGCCGGCCCCGCGGCGGAGATGAGCAGGTCCGCGACGCTGCTGCT<br>GTGCCTGCTGGGCTGCCACGTCTGGAAGGCGGTGACCAAGACGCTGCGGGAGCCCGGCGCCGGAGCCCAAGAGGTGACGT<br>TAAAGGTGCACATCAGCGACGCCAGCACCCACCAGCCCGTAGCAGATGCGCTCATCGAGATCTTCACCAACCAGGCCTCC<br>ATAGCCTCTGGCACCTCGGGGACTGATGGCGTCGCCTTTATCAAGTTCCAGTATAAGCTGGGCAGTCAGTTGATTGTCAC<br>CGCCTCGAAGCATGCCTACGTGCCAAACTCTGCCCCATGGAAGCCAATCCGGTTACCTGTATTTTCCTCTCTGAGCCTTG<br>GCCTGCTTCCAGAACGCTCTGCCACTCTAATGGTATATGAAGATGTCGTCCAAATAGTATCAGGATTCCAAGGTGCCCGG<br>CCACAGCCTCGCGTTCATTTCCAGAGAAGGGCTCTGAGGTTGCCTGAGAACACCAGCTACAGTGACCTGACCGCGTTTCT<br>CACGGCCGCCAGCTCCCCTTCGGAGGTGGACAGTTTTCCTTATTTGCGAGGATTAGACGGAAATGGAACAGGAAACAGCA<br>CCAGGCATGACCTGACCCCAGTCACAGCCGTCAGCGTCCACTTGCTGAGCAGTAATGGAACGCCGGTGCTGGTGGATGGT<br>CCCATCTATGTCACTGTCCCCTGGCCACGCAGAGCAGCTCGAGGCACAATGCCTATGTCGCGGCGTGGCGGTTTGACCA<br>GAAGCTGGGAACGTGGCTGAAGAGCGGTCTGGGTCTTGTGCACCAGGAAGGCAGCCAGCTGACGTGGACATACATTGCCC<br>CCCAGTTGGGGTACTGGGTGGCCGCCATGTCCCCTCCCATCCCAGGTCCCGTTGTAACACAGGACATTACCACGTATCAC<br>ACGGTGTTTCTTTTGGCCATTTTAGGAGGAATGGCTTTCATACTTTTGGTTTTGCTGTGTCTCCTTTTATATTATTGCAG<br>GAGGAAGTGCTTGAAACCTTCGTCAGCACCACAGAAAACTGCAGCTCCCTGCAGACGTGGGGAAGACTACCAAAGAGACCAGT<br>CCACGTCCATGTCACACATTAACTTGCTGTTTTCACGCCGAGCGTCAGAATTCCCTGGCCGCTGTCCGTCACCAGCCAGC<br>GGCCGCCCCGAGGCCCCGGCACGAAGGAACTGATGAGTGGAGTCCATTGGAAATGATGTCTCCGGCGGCGAAGGGGA<br>CCTGCACACCCCCATGCTCAAGCTCCTACAGCACCTCCCAGGAATTTAGCTCCCGGGAGGAGCTCCTCTCTTGCAAGG<br>AAGAGGATAAAAGCCAGATCTCCTTTGATAACCTCACTCCAAGTGGGACGCTGGGGAAAGACTACCATAAGTCAGTGGAGT<br>GTTTTTCCCTTAAAGGCAAGAAAATCTATGGAAAGAAAGGCTACAGTGTCCTGGGCAATGATGACTACAGGGGTAGTTA<br>CAACACCGTGCTCTCACAGCCTTTATTTGAAAAGCAGGACAGAGAAGGTCCAGCCTCCACGGGAAGCAAACTCACCATTC<br>AGGAACATCTGTACCCCGCGCCTTCATCACCTGAGAAAGAACAGCTGCTGGACCGCAGACCCACTGAATGTATGATGTCG<br>CGATCAGTAGATCACCTCGAGAGACCTACGTCCTTCCCACGGCCCGGCCAGTTAATCTGCTGCAGTTCTGTCGACCAGGT<br>CAATGACAGCGTTTACGAAAGTACTACCTCCTTGGTCATCCCGGCTCATTATATGAAACTCCCGGGACCACTCCT<br>ATGTCAGCCAGCCCCTCGTCGTCCCGGCTGATCAGCAGCTTGAGATAGAAAGACTACAGGCTGAGCTGTCCAATCCCAT<br>GCCGGGATCTTCCCACACCCGTCCTCACAGATCCAGCCCCAGCCCCTGTCTTCCCAGGCCATCTCTCAGCAGCACCTGCA<br>GGATGCGGGCACCCGGGAGTGGAGCCCTCAGAACGCATCCATGTCGGAGTCTCTCTCCATCCCAGCTTCCCTGAACACG<br>CGGCTTTGGCTCAGATGAACAGTGAGGTGCAGCTCCTGACTGAAAAGGCCCTGATGGAGCTTGGGGGTGGGAAGCCGCTT | SEQ.ID NO. 80<br>MSRSATLLLCLLGCHVWKAVTK<br>TLREPGAGAQEVTLKVHISDAS<br>THQPVADALIEIFTNQASIASG<br>TSGTDGVAFIKFQYKLGSQLIV<br>TASKHAYVPNSAPWKPIRLPVF<br>SSLSLGLLPERSATLMVYEDVV<br>QIVSGFQGARPQPRVHFQRRAL<br>RLPENTSYSDLTAFLTAASSPS<br>EVDSFPYLRGLDGNGTGNSTRH<br>DLTPVTAVSVHLLSSNGTPVLV<br>DGPIYVTVPLATQSSLRHNAYV<br>AAWRFDQKLGTWLKSGLGLVHQ<br>EGSQLTWTYIAPQLGYWVAAMS<br>PPIPGPVVTQDITTYHTVFLLA<br>ILGGMAFILLVLLCLLLYYCRR<br>KCLKPRQHHRKLQLPAGLESSK<br>RDQSTSMSHINLLFSRRASEFP<br>GPLSVTSHGRPEAPGTKELMSG<br>VHLEMMSPGGEGDLHTPMLKLS<br>YSTSQEFSSREELLSCKEEDKS<br>QISFDNLTPSGTLGKDYHKSVE<br>VFPLKARKSMEREGYESSGNDD<br>YRGSYNTVLSQPLFEKQDREGP<br>ASTGSKLTIQEHLYPAPSSPEK<br>EQLLDRRPTECMMSRSVDNLER<br>PTSFPRPGQLICCSSVDQVNDS<br>VYRKVLPALVIPAHYMKLPGDH |

TABLE 4-continued

Nucleotide and amino acid sequences of the SEQ. ID NOs.

| Nucleotide Sequence (5'-3') | ORFs |
|---|---|
| CCGCACCCCCGGGCGTGGTTCGTCTCCTTGGATGGCAGGTCCAACGCTCACGTTAGACATTCATACATTGATCTCCAAAG<br>AGCTGGAAGGAACGGAAGTAATGATGCCAGTTTGGACTCTGGCGTAGATATGAATGAACCAAAATCAGCCCGGAAGGGAA<br>GGGGAGATGCTTTGTCTGCAGCAGAACTACCCGCCCGTCCAAGAGCACCAGCAGAAGAGCCTCGAGCCCCAGACAGC<br>ACGGCCTACACGCAGCTCGTGTACCTGGATGACGTGGAACAGAGTGGTAGCGAATGTGGGACCACGGTCTGTACCCCGA<br>GGACAGTGCCCTGCGATGCTTGTTGGAGGGGTCGAGTCGGAGAAGTGGTGGCCAGCTGCCCAGCCTGCAGGAGGAGACGA<br>CCAGACGGACTGCGGATGCCCCCTCGGAGCCAGCAGCCAGCCCCACCAGAGAAGATCTGCCCACGAGGAAGAGGAAGAC<br>GATGATGATGATGACCAAGGAGAAGACAAGAAAAGCCCCTGGCAGAAACGGGAGGAGGAGGCCCCTGATGGCGTTTAACAT<br>TAAATGAGCTATCGCAGACCCACCTGACTGTGGAATATATAATTGCCAAATATCCTTTCTCATGGAAGCGCGTACCCGTT<br>CGTGGAGGAAACGGAACGGCAGCCCAGCCGTGGGACGGACGTGGACGTTTACTGCATTCCTGTTTGCCGTGTAAATGTTA<br>GAAAGGAATTAAAGTTATTACTCGGAATAAAGGATGACTTTGGCGGATGTCGCCCCTGCAAGGAGGTGGCTGAAAGTGGT<br>GTCCAGATGTCCTTCCGAGGACTCGGCGTATCCGCCACCAGGGACATTAAGAAACCGCACGTGATGTCGCTATGCTCAA<br>CGATCACCTCAGTTCTCCCTCGGATTCTGGGAACAGATGAAACTTTTTGCACTGCTTGAGTCATTTTTATCACAATAATC<br>CTACTGTGAAGCTGTCGTTGAGAACTTAGGTTGGCACGTAGCGTCTCAAGGTATGCGTTTCTCTCAAAGGAAAGCTATGCA<br>TCGCTGCTTCTTTGTCTGATTTTGCTTAGATTTTGCTTTGGTTAGGTTGCGTTTTGGGGTTTGCCTTTTTTTGTTGCGC<br>TTAAATGCAATTTGGTTGTAAAGATTTGATTCCTTTGTGTTCATCTGTTCCGCTTCTCAGCGGTCCATCTCAGCGTCTCC<br>CTTCAGGAACCGCTGAGTGTCCTCTCTTAACATCCAAGCCTTTTATGAAATCGTACTGAAATCTGTATCAGCTAAGAGT<br>CCTCCAATCCTGGTCCCATTAACTCCAAGTGCCTTTTTGTCAGTGACAACAGACAGTCCCTCGCTTTTTGTTGTTGTTGG<br>TTTTCTTAACCCCTTTAATGGAACTGCCTGGATTTTATACAGTTATTAAAGGATGTCTCTTTTGCTTTAAACTGCATGCT<br>GCCAAGTGCCATTTGGGGTCAGCATCCTCGTTTCAACACAGTGTGCTCTCTAGTTATCATGTGTAACGTGGGTTCTGTTT<br>AGCGAAGATAGACTAGAGGACACGTTAGAGATGCCCTTCCCTGCTCCATCCCTGTGGCACCATTATGTTTTTTGGCTGT<br>TTGTATATACGGTTACGTATTAACTCTGGAATCCTATGGGCTCATCTTGCTCACCCAATGTGGGAGTCTGGTTTGGAGCAA<br>GCGAGCTGAATGTGACTATTAAAAAAAATTTAAAAAAAAAAAGAAAATCTTATGTACTATCCAAAGTGCCAGAATGAC<br>TCTTCTGTGCATTCTTCTTAAAGAGCTGCTTGGTTATCCAAAAATGAAAATTCAAAATAAACTCTGAAAAAAAAAAAAA<br>AAAAAA | SYVSQPLVVPADQQLEIERLQA<br>ELSNPHAGIFPHPSSQIQPQPL<br>SSQAISQQHLQDAGTREWSPQN<br>ASMSESLSIPASLNDAALAQMN<br>SEVQLLTEKALMELGGGKPLPH<br>PRAWFVSLDGRSNAHVRHSYID<br>LQRAGRNGSNDASLDSGVDMNE<br>PKSARKGRGDALSLQQNYPPVQ<br>EHQQKEPRAPDSTAYTQLVYLD<br>DVEQSGSECGTTVCTPEDSALR<br>CLLEGSSRRSGGQLPSLQEETT<br>RRTADAPSEPAASPHQRRSAHE<br>EEEDDDDDQGEDKKSPWQKRE<br>ERPLMAFNIK |
| SEQ.ID NO. 36<br>CGTCACTTCCTGTTGCCTTAGGGGAACGTGGCTTTCCCTGCAGAGCCGGTGTCTCCGCCTGCGTCCCTGCTGCAGCAACC<br>GGAGCTGGAGTCGGATCCCGAACGCACCCTCGCCATGGACTCGGCCCTCAGCGATCCAGCATCAACGGCAGTGCCAGGCAG<br>GCGGCCCCACCAACAGCACTACGCGGCCGCCTTCCACGCCCGAGGGCATCGCGCTGGCCTACGGCAGCCTCCTGCTCATG<br>GCGCTGCTGCCCATCTTCTTCGGCGCCCTGCGCTCCGTACGCTGCGCCCGCGGCAAGAATGCTTCAGACATGCCTGAAAC<br>AATCACCAGCCGGGATGCCGCCCGCTTCCCCATCATCGCCAGCTGCACACTCTTGGGGCTCTACCTCTTTTTCAAAATAT<br>TCTCCCAGGAGTACATCAACCTCCTGCTGTCCATGTATTTCTTCGTGCTGGGAATCTGGCCTGTCCCACACCATCAGC<br>CCCTTCATGAATAAGTTTTTTCCAGCCAGCTTTCCAAATCGACAGTACCAGCTGCTCTTCACACAGGGTTCTGGGGAAA<br>CAAGGAAGAGATCATCAATTATGAATTTGACACCAAGGACCTGGTGTGCCTGGGCCTGAGCAGCATCGTTGGCGTCGGT<br>ACCTGCTGAGGAAGCACTGGATTGCCAACAACCTTTTTGGCCTGGCCTTCTCCCTTAATGGAGTAGAGCTCCTGCACCTC<br>AACAATGTCAGCACTGGCTGCATCCTGCTGGGCGGACTCTTCATCTACGATGTCTTCTGGGTATTTGGCACCAATGTGAT<br>GGTGACAGTGGCCAAGTCCTTCGAGGCACCAATAAAATTGGTGTTTCCCAGGATCTGCTGGAGAAAGGCCTCGAAGCAA<br>ACAACTTTGCCATGCTGGGACTTGGAGATGTCGTCATTCCAGGGATCTTCATTGCCTGCTGCTGCGCTTTGACATCAGC<br>TTGAAGAAGAATACCCACACCTACTTCTACACCAGCTTTGCAGCCTACATCTTCGGCTGGGCCTTACCATCTTCATCAT<br>GCACATCTTCAAGCATGCTCAGCCTGCCCTCCTATACCTGGTCCCCGCCTGCATCGGTTTTCCTGTCCTGGTGGCGCTGG<br>CCAAGGGAGAAGTGACAGAGTTCAGCTACGAGTCCTCGGCGGAAATCCTTGCCTCATACCCCGAGGCTCACCCACTTC<br>CCCACAGTCTCGGGCTCCCAGCCAGCCTGGCCGACTCCATGCAGCAGAAGCTAGCTGGCCCTCGCCGCCGGCCGCCCGCA<br>GAATCCCAGCGCCATGTAATGCCCAGCGGGTGCCCACCTGCCCGCTTCCCCCTACTGCCCGGGGCCCAAGTTATGAGGA<br>GTCAAATCCTAAGGATCCAGCGGCAGTGACAGAATCCAAAGAGGGAACAGAGGCATCAGCATCGAAGGGGCTGGAGAAGA<br>AAGAGAAATGATGCAGCTGGTGCCCGAGCCTCTCAGGGCCAGACCAGACAGATGGGGCTGGGCCCACACAGGCGTGCAC<br>CGGTAGAGGGCACAGGAGGCCAAGGGCAGCTCCAGGACAGGGCAGGGGGCAGCAGGATACCTCCAGCCAGGCCTCTGTGG<br>CCTCTGTTTCCTTCTCCCTTTCTTGGCCCTCCTCTGCTCCTCCCCACACCCTGCAGGCAAAAGAAACCCCCAGCTTCCCC<br>CCTCCCCGGGAGCCAGGTGGGAAAAGTGGGTGTGATTTTTAGATTTTGTATTGTGGACTGATTTTGCCTCACATTAAAAA<br>CTCATCCCATGGCCAGGGCGGGCCACTGTGCTCCTGGAAAAAAAAAA | SEQ.ID NO. 81<br>MDSALSDPHNGSAEAGGPTNST<br>TRPPSTPEGIALAYGSLLLMAL<br>LPIFFGALRSVRCARGKNASDM<br>PETITSRDAARFPIIASCTLLG<br>LYLFFKIFSQEYINLLLSMYFF<br>VLGILALSHTISPFMNKFFPAS<br>FPNRQYQLLFTQGSGENKEEII<br>NYEFDTKDLVCLGLSSIVGVWY<br>LLRKHWIANNLFGLAFSLNGVE<br>LLHLNNVSTGCILLGGLFIYDV<br>FWVFGTNVMVTVAKSFEAPIKL<br>VFPQDLLEKGLEANNFAMLGLG<br>DVVIPGIFIALLLRFDISLKKN<br>THTYFYTSFAAYIFGLGLTIFI<br>MHIFKHAQPALLYLVPACIGFP<br>VLVALAKGEVTEMFSYESSAEI<br>LPHTPRLTHFPTVSGSPASLAD<br>SMQQKLAGPRRRRPQNPSAM |
| SEQ.ID NO. 37<br>STAR Clone:<br>TGCCTCAGTCTCTCACTGTGCCTTATGCCCCTCAGCTGAATTCTTTCTTCTGAGCAGGCAGGAATTGAGGTTGCTGCAGA<br>CGTGTATGCATTTGCCACCAGTAACATACTTTGGTGCCACATGACTAGGATATGTTCTCTAGTGCTAACATGTTCGTTTA<br>CAGTTCTTAGGACTCCCTGATAGAAAAAAACAAAAAAAAACACAAAAAAACCCAACCA | |
| SEQ.ID NO. 38<br>GTTGGGAAAGAGCAGCCTGGGCGGCAGGGGCGGTGGCTGGAGCTCGGTAAAGCTCGTGGGACCCCATTGGGGGAATTGA<br>TCCAAGGAAGCGGTGATTGCCGGGGAGGAGAAGCTCCAGATCCTTGTGTCCACTTGCAGCGGGGGAGGCGGAGACGGC<br>GGAGCGGGCCTTTTGGCGTCCACTGCGCGGCTGCACCCTGCCCATCCTGCCGGGATCATGGTCTGCGGCAGCCCGGGAG<br>GGATGCTGCTGCTGCGGGCCGGGCTGCTTGCCCTGGCTGCTCTCTGCCTGCTCCGGGTGCCCGGGGCTCGGGCTGCAGCC<br>TGTGAGCCCGTCCGCATCCCCCTGTGCAAGTCCCTGCCCTGGAACATGACTAAGATGCCCAACCACCTGCACCACAGCAC<br>TCAGGCCAACGCCATCCTGGCCATCGAGCAGTTCGAAGGTCTGCTGGGCACCCACTGCAGCCCCGATCTGCTCTTCTTCC<br>TCTGTGCCATGTACGCGCCCATCTGCACCATTGACTTCCAGCACGAGCCCATCAAGCCCTGTAAGTCTGTGTGCGAGCGG<br>GCCCGGCAGGGCTGTGAGCCCATACTCATCAAGTACCGCCACTCGTGGCCGGAGAACCTGGCCTGCGAGGAGCTGCCAGT<br>GTACGACAGGGGCGTGTGCATCTCTCCCGAGGCCATCGTTACTGCGGACGGAGCTGATTTTCCTATGGATTCTAGTAACG<br>GAAACTGTAGAGGGCAAGCAGTGACAGTGAACGCTGTAAATGTAAGCCTATTAGAGCTACACAGAAGACCTATTTCCGGAACAAT<br>TACAACTATGTCATTCGGGCTAAAGTTAAAGAGATAAAGACTAAGTGCCATGATGTGACTGCAGTAGTGGAGGTGAAGGA<br>GATTCTAAAGTCCTCTCTGGTAAACATTCCACGGGACACTGTCAACCTCTATACCAGCTCTGGCTGCCTCTGCCCTCAC<br>TTAATGTTAATGAGGAATATATCATCATGGGCTATGAAGATGAGGAACGTTCAAGATTACTTTGGTGGAAGGCTCTATA<br>GCTGAGAAGTGGAAGGATCGACTCGGTAAAAAGTTAAGCGCTGGGATATGAAGCTTCGTCATCTGGACTCAGTAAAG<br>TGATTCTAGCAATAGTGATTCCACTCAGAGTCAGAAGTCTGCAGGAACTCGAACCCCCGGCAAGCACGCAACTAAATCC<br>CGAAATACAAAAGTAACACAGTGGACTTCCTATTAAGACTTACTTGCATTGCTGGACTAGCAAAGGAAAATTGCACTAT<br>TGCACATCATATTCTATTGTTTACTATAAAAATCATGTGATAACTGATTATTACTTCGTTTCTCTTTTGGTTTCTGCTT<br>CTCTCTTCTCTCAACCCCTTTGTAATGGTTTGGGGGCAGACTCTTAAGTATATTGTGAGTTTTCTATTTCACTAATCATG | SEQ.ID NO. 82<br>MVCGSPGGMLLLRAGLLALAAL<br>CLLRVPGARAAACEPVRIPLCK<br>SLPWNMTKMPNHLHHSTQANAI<br>LAIEQFEGLLGTHCSPDLLFFL<br>CAMYAPICTIDFQHEPIKPCKS<br>VCERARQGCEPILIKYRHSWPE<br>NLACEELPVYDRGVCISPEAIV<br>TADGADFPMDSSNONCRGASSE<br>RCKCKPTRATQKTYFRNNYNYV<br>IRAKVKEIKTKCHDVTAVVEVK<br>EILKSSLVNIPRDTVNLYTSSG<br>CLCPPLNVNEEYIIMGYEDEER<br>SRLLLVEGSILAEKWKDRLKKL<br>VKRWDMKLRHLGLSKSDSSNSD<br>STQSQKSGRNSNPRQARN |

TABLE 4-continued

Nucleotide and amino acid sequences of the SEQ. ID NOs.

| Nucleotide Sequence (5'-3') | ORFs |
|---|---|
| AGAAAAACTGTTCTTTTGCAATAATAATAAATTAAACATGCTGTTACCAGAGCCTCTTTGCTGGAGTCTCCAGATGTTAA<br>TTTACTTTCTGCACCCCAATTGGGAATGCAATATTGGATGAAAAGAGAGGTTTCTGGTATTCACAGAAAGCTAGATATGC<br>CTTAAAACATACTCTGCCGATCTAATTACAGCCTTATTTTTGTATGCCTTTTGGGCATTCTCCTCATGCTTAGAAAGTTC<br>CAAATGTTTATAAAGGTAAAATGGCAGTTTGAAGTCAAATGTCACATAGGCAAAGCAATCAAGCACCAGGAAGTGTTTAT<br>GAGGAAACAACACCCAAGATGAATTATTTTTGAGACTGTCAGGAAGTAAAATAAATAGGAGCTTAAGAAAGAACATTTTG<br>CCTGATTGAGAAGCACAACTGAAACCAGTAGCCGCTGGGGTGTTAATGGTAGCATTCTTCTTTTGGCAATACATTTGATT<br>TGTTCATGAATATATTAATCAGCATTAGAGAAATGAATTATAACTAGACATCTGCTGTTATCACCATAGTTTTGTTTAAT<br>TTGCTTCCTTTTAAATAAACCCATTGGTGAAGTCCCAAAAAAAAAAAAAAAAAAAA | |
| SEQ.ID NO. 39 | SEQ.ID NO. 83 |
| ACTGAAAGCTCCGGTGCCAGACCCCACCCCCGGCCCCGGCCCGGGACCCCTCCCCTCCCGGGATCCCCGGGGTTCCCA<br>CCCCGCCCGCACCGCCGGGGACCCGGCCGGTCCGGCGCGAGCCCCCGTCCGGGGCCCTGGCTCGGCCCCCAGGTTGGAGG<br>AGCCCGGAGCCCGCCTTCGGAGCTACGGCCTAACGGCGGCGGCGACTGCAGTCTGGAGGGTCCACACTTGTGATTCTCAA<br>TGGAGAGTGAAAACGCAGATTCATAATGAAAACTAGCCCCCGTCGGCCACTGATTCTCAAAAGACGGAGGCTGCCCCTTC<br>CTGTTCAAAATGCCCCAAGTGAAACATCAGAGGAGGAACCTAAGAGATCCCCTGCCCAACAGGAGTCTAATCAAGCAGAG<br>GCCTCCAAGGAAGTGGCAGAGTCCAACTCTTGCAAGTTTCCAGCTGGGATCAAGATTATTAACCACCCCACCATGCCACA<br>CACGCAAGTAGTGGCCATCCCCAACAATGCTAATATTCACAGCATCATCACAGCACTGACTGCCAAGGGAAAAGAGAGTG<br>GCAGTAGTGGGCCCAACAAATTCATCCTCATCAGCTGTGGGGGAGCCCCAACTCAGCCTCCAGGACTCCGGCCTCAAACC<br>CAAACCAGCTATGATGCCAAAAGGACAGAAGTGACCCTGGAGACCTTGGGACCAAAACCTGCAGCTAGGGATGTGAATCT<br>TCCTAGACCACGTGGAGCCCTTTGCGAGCAGAAACGGGAGACCTGTGCAGATGGTGAGGCAGCAGGCTGCACTATCAACA<br>ATAGCCTATCCAACATCCAGTGGCTTCGAAAGATGAGTTCTGATGGATCTGGCTCCCGCAGCATCAAGCAAGAGATGGAG<br>GAAAAGGAGAATTGTCACCTGGAGCAGCGACAGGTTAAGGTTGAGGAGCCTTCGAGACCATCAGCGTCCTGGCAGAACTC<br>TGTGTCTGAGCGGCCACCCTACTCTTACATGGCCATGATACAATTCGCCATCAACAGCACTGAGAGGAAGCGCATGCTT<br>TGAAAGACATCTATACGTGGATTGAGGACCACTTTCCCTACTTTAAGCACATTGCCAAGCCAGGCTGGAAGAACTCCATC<br>CGCCACAACCTTTCCCTGCACGACATGTTTGTCCGGGAGACGTCTGCCAATGGCAAGGTCTCCTTCTGGACCATTCACCC<br>CAGTGCCAACCGCTACTTGACATTGGACCAGGTGTTTAAGCAGCAGAAACGACCGAATCCAGAGCTCCGCCGGAACATGA<br>CCATCAAAACCGAACTCCCCCTGGGCGCACGGCGGAAGATGAAGCCACTGCTACCACGGGTCAGCTCATACCTGGTACCT<br>ATCCAGTTCCGGGTGAACCAGTCACTGGTGTTGCAGCCCTCGGTGAAGGTGCCATTGCCCCTGGCGGCTTCCCTCATGAG<br>CTCAGAGCTTGCCCGCCATAGCAAGCGAGTCCGCATTGCCCCCAAGGTGCTGCTAGCTGAGGAGGGGGATAGCTCCTCTTT<br>CTTCTGCAGGACAGGGAAAGAGGAGAAATCCTCTGTTTGGAGAAGGGTTTTCTCCTTTGCTTCCAGTTCAGACTATCAAG<br>GAGGAAGAAATCCAGCCTGGGGAGGAAATGCCACACTTAGCGAGACCCATCAAAGTGGAGAGCCCTCCCTTGGAAGAGTG<br>GCCCTCCCCGGCCCCATCTTTCAAAGAGGAATCATCTCACTCCTGGGAGGATTCGTCCAATCTCCCACCCCAAGACCCA<br>AGAAGTCCTACAGTGGGCTTAGGTCCCCAACCCGGTGTGTCTCGGAAATGCTTGTGATTCAACACAGGGAGAGGAGGGAG<br>AGGAGCCGGTCTCGGAGGAAACAGCATCTACTGCCTCCCTGTGTGGATGAGCCGGAGCTGCTCTTCTCAGAGGGGCCAG<br>TACTTCCCGCTGGGCCGCAGAGCTCCCGTTCCCAGCAGACTCCTCTGACCCTGCCTCCCAGCTCAGCTACTCCCAGGAAG<br>TGGGAGGACCTTTTAAGACACCCATTAAGGAAACGCTGCCCATCTCCTCCACCCCGAGCAAATCTGTCCTCCCCAGAACC<br>CCTGAATCCTGGAGGCTCACGCCCCCAGCCAAAGTAGGGGGACTGGATTTCAGCCCAGTACAAACCTCCCAGGGTGCCTC<br>TGACCCCTTGCCTGACCCCTCGGGGCTGATGGATCTCAGCACCACTCCCTTGCAAAGTGCTCCCCCCCTTGAATCACCGC<br>AAAGGCTCCTCAGTTCAGAACCCTTAGACCTCATCTCCGTCCCCTTTGGCAACTCTTCTCCCTCAGATATAGACGTCCCC<br>AAGCCAGGCTCCCCGGAGCCACAGGTTTCTGGCCTTGCAGCCAATCGTTCTCTGACAGAAGGCCTGGTCCTGGACACAAT<br>GAATGACAGCCTCAGCAAGATCCTGCTGGACATCAGCTTTCCTGGCCTGGACGAGGACCCACTGGGCCCTGACAACATCA<br>ACTGGTCCCAGTTTATTCCTGAGCTACAGTAGAGCCCTGCCCTTGCCCCTGCTGCCTCAAGCTGTCCACCATCCCGGGCACT<br>CCAAGGCTCAGTGCACCCCAAGCCTCTGAGTGAGGACAGCAGGCAGGGACTGTTCTGCTCCTCATAGCTCCCTGCTGCCT<br>GATTATGCAAAAGTAGCAGTCACACCCTAGCCACTGCTGGGACCTTGTGTTCCCCAAGAGTATCTGATTCCTCTGCTGTC<br>CCTGCCAGGAGCTGAAGGGTGGGAACAACAAAGGCAATGGTGAAAAGAGATTAGGAACCCCCCCAGCCTGTTTCCATTTG<br>TGCCCAGCAGTCTCTTACCTTCCCTGATCTTTGCAGGGTGGTCCGTGTAAATAGTATAAATTCTCCAAATTATCCTCTAA<br>TTATAAATGTAAGCTTATTTCCTTAGATCATTATCCAGAGACTGCCAGAAGGTGGGTAGGATGACCTGGGGTTTCAATTG<br>ACTTCTGTTCCTTGCTTTTAGTTTTGATAGAAGGGAAGACCTGCAGTGCACGGTTTCTTCCAGGCTGAGGTACCTGGATC<br>TTGGGTTCTTCACTGCAGGGACCCAGACAAGTGGATCTGCTTGCCAGAGTCCTTTTTGCCCCTCCCTGCCACCTCCCCGT<br>GTTTCCAAGTCAGCTTTCCTGCAAGAAGAAATCCTGGTTAAAAAAGTCTTTTGTATTGGGTCAGGAGTTTGAATTTGGGGT<br>GGGAGGATGGATGCAACTGAAGCAGAGTGTGGGTGCCCAGATGTGCGCTATTAGATGTTTCTCTGATAATGTCCCAATC<br>ATACCAGGGAGACTGGCATTGACGAGAACTCAGGTGGAGGCTTGAGAAGGCCGAAAGGGCCCTGACCTGCCTGGCTTCC<br>TTAGCTTGCCCCTCAGCTTTGCAAAGAGCCACCCTAGGCCCCAGCTGACCGCATGGGTGTGAGCCAGCTTGAGAACACTA<br>ACTACTCAATAAAAGCGAAGGTGGACAAAAAAAAAAAAAAAAAAAAAA | MKTSPRRPLILKRRRLPLPVQN<br>APSETSEEEPKRSPAQQESNQA<br>EASKEVAESNSCKFPAGIKIIN<br>HPTMPNTQVVAIPNNANIHSII<br>TALTAKGKESGSSGPNKFILIS<br>CGGAPTQPPGLRPQTQTSYDAK<br>RTEVTLETLGPKPAARDVNLPR<br>PPGALCEQKRETCADGEAAGCT<br>INNSLSNIQWLRKMSSDGLGSR<br>SIKQEMEEKENCHLEQRQVKVE<br>EPSRPSASWQNSVSERPPYSYM<br>AIVIIQFAINSTERKRMTLKDI<br>YTWIEDHFPYFKHIAKPGWKNS<br>IRHNLSLHDMFVRETSAIAGKV<br>SFWTIHPSANRYLTLDQVFKQQ<br>KRPNPELRRNMTIKTELPLGAR<br>RKMKPLLPRVSSYLVPIQFPVN<br>QSLVLQPSVKVPLPLAASLMSS<br>ELARHSKRVRIAPKVLLAEEGI<br>APLSSAGPGKEEKLLFGEGFSP<br>LLPVQTIKEEEIQPGEEMPHLA<br>RPIKVESPPLEEWPSPAPSFKE<br>ESSHSWEDSSQSPTPRPKKSYS<br>GLRSPTRCVSEMLVIQHRERRE<br>RSRSRRKQHLLPPCVDEPELLF<br>SEGPSTSRWAAELPFPADSSDP<br>ASQLSYSQEVGGPPFKTPIKETL<br>PISSTPSKSVLPRTPESWRLTP<br>PAKVGGLDFSPVQTSQGASDPL<br>PDPLGLMDLSTTPLQSAPPLES<br>PQRLLSSEPLDLISVPFGNSSP<br>SDIDVPKPGSPEPQVSGLAANR<br>SLTEGLVLDTMNDSLSKILLDI<br>SFPGLDEDPLGPDNINWSQFIP<br>ELQ |
| SEQ.ID NO. 40 | SEQ.ID NO. 84 |
| GTCGAGGCTGCGGCGCGTGGGGAGCGGGCGGAGCGGGGCGGGGGCCGAGCGCGGGGCACCCGGGGGCCTCCTGTATAGG<br>CGGGCACCATGGGCTCCTGCTCCGGCCGCTGCGCGCTCGTCGTCCTCTGCGCTTTTCAGCTGGTCGCCGCCCTGGAGAGG<br>CAGGTGTTTGACTTCCTGGGCTACCAGTGGGCGCCCATCCTGGCCAACTTTGTCCACATCATCATCGTCATCCTGGGACT<br>CTTCGGCACCATCCAGTACCGGCTGCGCTATGTCATGGTGTACACGCTGTGGGCAGCCGTCTGGGTCACCTGGAACGTCT<br>TCATCATCTGCTTCTACCTGGAAGTCGGTGGCCTCTTAAAGGACAGCGAGCTACTGACCTTCAGCCTCTCCCGGCATCGC<br>TCCTGGTGGCGTGAGCGCTGGCCAGGCGTCTGCATGAGGAGGTGCCAGCAGTGGGCTCGGGGCCCCCATGGCCAGGC<br>CCTGGTGTCAGGTGCTGGCTGTGCCCTGGAGCCCAGCTATGTGGAGGCCCTACACAGTTGCCTGCAGATCCTGATCGCGC<br>TTCTGGGCTTTGTCTGTGGCTGCCAGGTGGTCAGCGTGTTTACGGATGAAGAGGACAGCTTTGATTTCATTGGTGGATTT<br>GATCCATTTCCTCTCTACCATGTCAATGAAAAGCCATCCAGTCTCTTGTCCAAGCAGGTGTACTTGCCTGCGTAAGTGAG<br>GAAACAGCTGACCCTGCTCCTGTGCGCCTCCAGCCTCACCGACCGACCAGTGACAATGACAGGAGCTCCCAGGCCTTGGGA<br>CGCGCCCCCACCCAGCACCCCCAGGCGGCCGGCAGCACCTGCCCTGGGTTCTAAGTACTGGACACCAGCCAGGGCGGCA<br>GGGCAGTGCCACGGCTGCTGCAGCGTCAAGAGAGTTTGTAATTTCCTTTCTTAAAAAAAAAAAAAGAAAAGAAAACAT<br>ACAAAAGAAAAGGCAAAACCCCACATGCCCACCTCCTCTGGCAACATGGGGGTCACAGCTCTGCCCCCAGGCTGTCGTCT<br>CGTCGAGGAGCCCCTCCCTCAGGTGCCAACCTGGGGCTGCTGGACCCTCGGGCTGCAAGCACTGCTGCTGGGATGCAGCC<br>TCCCCAGGAAGTCAATGTGAGGCCCGAGACCCCTCAAGCGGTGAGGGCCCTGTTGAACATGGAGGGTTCCTAACCCCAA<br>ACTCGTGCCAGAAGAACCCCCACCCCACCCAGGAGCTGAGGCTGATGGAGCCCTAGGGTGGGGGCTGGGCTTGACCAGGA<br>ACAGCAGAGCCAGGCCCAAGGCATAGGGCAGGGCACATGGTGGTGACGAGCAGGCAGTACTCTTGTAAAGGGGCTCTT<br>GGGCAAACAGTCCCAAAGGCTCCCCCAGGTATCATCAAGTTGGTAAATAAACAGGAACATGGCCCAAAAAAAAAAAAAA<br>A | MGSCSGRCALVVLCAFQLVAAL<br>ERQVFDFLGYQWAPILANFVHI<br>IIVILGLFGTIQYRLRYVMVYT<br>LWAAVWVTWNVFIICFYLEVGG<br>LLKDSELLTFSLRHRSWWRER<br>WPGCLHEEVPAVGLGAPHGQAL<br>VSGAGCALEPSYVEALHSCLQI<br>LIALLGFVCGCQVVSVFTDEED<br>SFDFIGGFDPFPLYHVNEKPSS<br>LLSKQVYLPA |

TABLE 4-continued

Nucleotide and amino acid sequences of the SEQ. ID NOs.

| Nucleotide Sequence (5'-3') | ORFs |
|---|---|
| SEQ.ID NO. 41<br>STAR Clone:<br>AAAAAATAAGTATATCTGTCNAGAATCNTATTTATGTGAGATGTGTCAATACTGGTCTTGCGTTATTTCGGCTACTTGAA<br>AATAAGTTAAAAAAGATAGTGTTTGGTTCCAAAAAGGAAAAGTCAGCCTCTCCTGCNTGAGTGGGAGCTGCAACCTTTTA<br>GAATTGATAATCACAAACCCCTCAGACCCAAAGTGGAATAAAGAAAAATATGTAACATTAGGCATTGATGGAAAAGGACT<br>AGATCCTAGTGTAAGCATCCTAATAAAAGGAGAGGTTCACAA | |
| SEQ.ID NO. 42<br>GCAGCCAGATCTGCTGGGACACCTTTCCCAAGGAAGAGCCCGTTGCACTGGGCTTTGAAGGATAAGCAGGAGCTTGTTAC<br>TCAGGCAGAGGAAGAAAGAGCATCCCAGGCGGGGGGAGCAGCATATGCAAAGGCACGAAGGGGCCCCAGGAGCCTAGGGA<br>GTCTGGGGAAGTGTGAGCACTTTGGAGAGTGGAGGCTGGAGCGCTGTGGAGAGTGGGGGCTGGTGGCCGGGAATGAAGCT<br>GCAGCTGGCTGGGCCACATGGTAAAGGCTGACAACTGGACCCAGAGGCCAACTAGCCTATGATCAGCATTTCCCAAAATC<br>TGTTTCCCGACTCATGGTTCTGTGAGATGTGACAAGGGCTCCTTTTTCATTCCTGAGACGCCGGTTTTCATCTGTGATGC<br>GGGGACAGCTGCGCTCCTTGCTGCGAGGCGTCAGGACCCAGGTGATAGTGAAGGGAGGGTGGCGCCCGCGGTTCCCGGCG<br>GCCACTGATGCCTGTCTCTTCTGCTGCTGTGTACGTGCGTGTGCTCCACGCCTGGCTTCTCAGGCTTTCAAATGTGTGCT<br>AGCAGCAGCAGCAGCAGCCACGACGAGGCCCCCGTCCTGAACGACAAGCACCTGGACGTGCCCGACATCATCATCACGCC<br>CCCCACCCCCACGGGCATGATGCTGCCGAGGGACTTGGGGAGCACAGTCTGGCTGGATGAGACAGGGTCGTGCCCAGATG<br>ATGGAGAAATCGACCCAGAAGCCTGAGGAGGTGTCCTGGGTTTGGCTGGCTGGCTCCTGCTCCAGCGGCCCGGCTTCAGG<br>TGTCCGGGGCGTGGCTGCCTGGGACAGGTGTGCTGAATACCCTGGATGGGAACTGAGCGAACCCGGGCCTCCGCTCAGA<br>GAGACGTGGCAGGACCAGCGAGGAATCCAGCCTGTCCACTTCCAGAACAGTGTTTCCCAGGCCCGCTGAGTGGACCGGA<br>CCTCTGACACCTCCAGGTTCTTGCTGACTCCGGCCTGGTGAAAGGGAGCGCCATGGTCCTGGCTGTTGGGGTCCCAGGGA<br>GAGGCTCTCTTCTGGACAAACACACCCTCCCAGCCCCCAGGGCTGTGCAAACACATGCCCCTCCCATAAGCACCAACAAG<br>AACTTCTTGCAGGTGGAGTGGCTGTTTTTTATAAGTTGTTTTACAGATACGGAAACAGTCCAAAATGGGATTTATAATTT<br>CTTTTTTGCATTATAATAAGATCCTCTGTAACAAAAAAAAAAAAAAAAAAAAAAAAAAAA | SEQ.ID NO. 85<br>MCVSSSSSSHDEAPVLNDKHLD<br>VPDIIITPPTPTGMMLPRDLGS<br>TVWLDETGSCPDDGEIDPEA |
| SEQ.ID NO. 43<br>GCGAAGTGAAGGGTGGCCCAGGTGGGGCCAGGCTGACTGAATGTATCTCCTAGCTATGGACTAAATAATACATGGGGGA<br>AATAAACAAGTATTCATGAGGGTGAAAATGTGACCCAGCAGGAAAATTACAACTATTTTCAATTGACGTTGAATAGGATG<br>AGTCATGGAATTTAAGTGATTTACTGAAGATTATACTACTGGTAGATAGAAGAGCTAAAGAAAGATGGATACATGATGC<br>TGAATGTGCGGAATCTGTTTGAGCAGCTTGTGCGCCGGGTGGAGATTCTCAGTGAAGGAAATGAAGTCCAATTTATCCAG<br>TTGGCGAAGGACTTTGAGGATTTCCGTAAAAAGTGGCAGAGGACTGACCATGAGCTGGGGAAATACAAGGATCTTTTGAT<br>GAAAGCAGAGACTGAGCGAAGTGCTCTGGATGTTAAGCTGAAGCATGCACGTAATCAGGTGGATGTAGAGATCAAACGGA<br>GACAGAGAGCTGAGGCTGACTGCGAAAAGCTGGAACGACAGATTCAGCTGATTGAGAGATGCTCATGTGTGACACATCT<br>GGCAGCATTCAACTAAGCGAGGAGCAAAAATCAGCTCTGGCTTTTCTCAACAGAGGCCAACCATCCAGCAGCAATGCTGG<br>GAACAAAAGACTATCAACCATTGATGAATCTGGTTCCATTTTATCAGATATCAGCTTTGACAAGACTGATGAATCACTGG<br>ATTGGGACTCTTCTTTGGTGAAGACTTTCAAACTGAAGAAGAGAGAAAGAGGCGCTCTACTAGCCGACAGTTTGTTGAT<br>GGTCCCCCTGGACCTGTAAAGAAAACTCGTTCCATTGGCTCTGCAGTAGACCAGGGGAATGAATCCATAGTTGCAAAAAC<br>TACAGTGACTGTTCCCAATGATGGCGGGCCATCGAAGCTGTGTCCACTATTGAGACTGTGCCATATTGGACCAGGAGCC<br>GAAGGAAAACAGGTACTTTACAACCTTGGAACAGTGACTCCACCCTGAACAGCAGGCAGCTGGAGCCAAGAACTGAGACA<br>GACAGTGTGGGCACGCCACAGAGTAATGGAGGGATGCGCCTGCATGAGTTTGTTTCTAAGACGGTTATTAAACCTGAATC<br>CTGTGTTCCATGTGGAAAGCGGATAAAATTTGGCAAATTATCTCTGAAGTGTCGAGACTGTCGTGTGGTCTCTCATCCAG<br>AATGTCGGGACCGCTGTCCCCTTCCCTGCATTCCTACCCTGATAGGAACACCTGTCAAGATTGGAGAGGGAATGCTGGCA<br>GACTTTGTGTCCCAGACTTCTCCAATGATCCCCTCCATTGTTGTGCATTGTAAATGAGATTGAGCAAAGAGGTCTGAC<br>TGAGACAGGCCTGTATAGGATCTCTGGCTGTGACCGCACAGTAAAAGAGCTGAAAGAGAAATTCCTCAGAGTGAAAACTG<br>TACCCCTCCTCAGCAAAGTGGATGATATCCATGCTATCTGTAGCCTTCTAAAAGACTTTCTTCGAAACCTCAAAGAACCT<br>CTTCTGACCTTTCGCCTTAACAGAGCCTTTATGGAAGCAGCAGAAATCACAGATGAAGACAACAGCATAGCTGCCATGTA<br>CCAAGCTGTTGGTGAACTGCCCCAGGCCAACAGGGACACATTAGCTTTCCTCATGATTCACTTGCAGAGAGTGGCTCAGA<br>GTCCACATACTAAAATGGATGTTGCCAATCTGGCTAAAGTCTTTGGCCCTACAATAGTGGCCCATGCTGTGCCCAATCCA<br>GACCCAGTGACAATGTTACAGGACATCAAGCGCTCAACCCAAGGTGGTTGAGCGCCTGCTTTCCTTGCCTCTGGAGTATTG<br>GAGTCAGTTCATGATGGTGGAGCAAGAGAACATTGACCCCCTACATGTCATTGAAAACTCAAATGCCTTTTCAACACCAC<br>AGACACCAGATATTAAAGTGAGTTTACTGGGACCTGTGACCACTCCTGAACATCAGCTTCTCAAGACTCCTTCATCAGT<br>TCCCTGTCACAGAGAGTCCGTTCCACCCTCACCAAGAACATCTCCTAGATTTGGGAGCAAAAGCAAGTCTGCCACTAACCT<br>AGGACGACAAGGCAACTTTTTTGCTTCTCCAATGCTCAAGTGAAGTCACATCTGCCTGTTACTTCCCAGCATTGACTGAC<br>TATAAGAAAGGACACATCTGTACTCTGCTCTGCAGCCTCCTGTACTCATTACTACTTTTAGCATTCTCCAGGCTTTTACT<br>CAAGTTTAATTGTGCATGAGGGTTTTATTAAAACTATATATATCTCCCCTTCCTTCTCCTCAAGTCACATAATATCAGCA<br>CTTTGTGCTGGTCATTGTTGGGAGCTTTTAGATGAGACATCTTTCCAGGGGTAGAAGGGTTAGTATGGAATTGGTTGTGA<br>TTCTTTTTGGGGAAGGGGGTTATTGTTCCTTTGGCTTAAAGCCAAATGCTGCTCATAGAATGATCTTTCTCTAGTTTCAT<br>TTAGAACTGATTTCCGTGAGACAATGACAGAAACCTACCTATCTGATAAGATTAGCTTGTCTCAGGGTGGGAAGTGGGA<br>GGGCAGGGCAAAGAAAGGATTAGACCAGAGGATTAGGATGCCTCCTTCAAGAACCAGAAGTTCTCATTCCCCATTATG<br>AACTGAGCTATAATATGGAGCTTTCATAAAAATGGGATGCATTGAGGACAGAACTAGTGATGGGAGTATGCGTAGCTTTG<br>ATTTGGATGATTAGGTCTTTAATAGTGTTGGATGGACCAACCTTGTAATGTGAAGTACAACTCGTATTTATCTCTGAT<br>GTGCCGCTGGCTGAACTTTGGGTTCATTTGGGGTCAAAGCCAGTTTTTCTTTTAAAATTGAATTCATTCTGATGCTTGGC<br>CCCCATACCCCCAACCTTGTCCAGTGGAGCCCAACTTCTAAAGGTCAATATATCATCCTTTGGCATCCCAACTAACAATA<br>AAGAGTAGGCTATAAGGGAAGATTGTCAATATTTTGTGGTAAGAAAAGCTACAGTCATTTTTTCTTTGCACTTTGGATGC<br>TGAAATTTTCCCATGGAACATGACCACATCTAGATAGATGTGAGCTTTTCTTCTGTTAAAATTATTCTTAATGTCTGT<br>AAAAACGATTTTCTTCTGTAGAATGTTTGACTTCGTATTGACCCTTATCTGTAAAACACCTATTTGGGATAATATTTGGA<br>AAAAAAGTAATAGCTTTTTCAAAATGAAAAAAAAAAA | SEQ.ID NO. 86<br>MDTMMLNVRNLFEQLVRRVEIL<br>SEGNEVQFIQLAKDFEDFRKKW<br>QRTDHELGKYKDLLMKAETERS<br>ALDVKLKHARNQVDVEIKRRQR<br>AEADCEKLERQIQLIREMLCD<br>TSGSIQLSEEQKSALAFLNRGQ<br>PSSSNAGNKRLSTIDESGSILS<br>DISFDKTDESLDWDSSLVKTFK<br>LKKREKRRSTSRQFVDGPPGPV<br>KKTRSIGSAVDQGNESIVAKTT<br>VTVPNDGGPIEAVSTIETVPYW<br>TRSRRKTGTLQPWNSDSTLNSR<br>QLEPRTETDSVGTPQSNOGMRL<br>HDFVSKTVIKPESCVPCGKRIK<br>FGKLSLKCRDCRVVSHPECRDR<br>CPLPCIPTLIGTPVKIGEGMLA<br>DFVSQTSPMIPSIVVHCVNEIE<br>QRGLTETGLYRISGCDRTVKEL<br>KEKFLRVKTVPLLSKVDDIHAI<br>CSLLKDFLRNLKEPLLTFRLNR<br>AFMEAAEITDEDNSIAAMYQAV<br>GELPQANRDTLAFLMIHLQRVA<br>QSPHTKMDVANLAKVFGPTIVA<br>HAVNPNPDDVTMLQDIKRQPKVV<br>ERLLSLPLEYWSQFMMVEQENI<br>DPLHVIENSNAFSTPQTPDIKV<br>SLLGPVTTPEHQLLKTPSSSSL<br>SQRVRSTLTKNTPRFGSKSKSA<br>TNLGRQGNFFASPMLK |
| SEQ.ID NO. 44<br>AGGCGCTAGAGGCGGGGCGCCGGGAGGCGCGGGCTTTGCTCCTGGGGTCTCGGCCTTGGCCGGCTGGACCTGACCCTAG<br>GGCGGCTTGCGCAGCTGTCGGGACGTGACTGCGTTCAGCCGCGTCGGGCGTGCTTCCCAGACTTGCCCAAGTTCGGGTGC<br>CCTAGCTGCCCCTTTGCAGCCGCTGGCCTACCGGCCCCGGGTGAGAAGGTTGCGACGGGAGGTGGGTGGAACTCGCCA<br>GCGCCGGGGACCGCGGATTGGCTGCCTCGGCTTTCTCTTTTCCCCGTGGGCTCCGGCGTGAGGCGCTGAAGCGGCCGGCAG<br>CCGGCGACCGGCCCTCACCGTCCGCCGGGTTGCGCTCTGCTTTTGCGGTGAGGCGTTGACCACGCCCATATGAATTGGAG | SEQ.ID NO. 87<br>MTDLNDNICKRYIKMITNIVIL<br>SLIICISLAFWIISMTASTYYG<br>NLRPISPWRWLFSVVVPVLIVS<br>NGLKKKSLDHSGALGGLVVGFI<br>LTIANPSFFTSLLMFFLSSSKL |

TABLE 4-continued

Nucleotide and amino acid sequences of the SEQ. ID NOs.

| Nucleotide Sequence (5'-3') | ORFs |
|---|---|
| CTCTCCGCCAGTAGGAGTTTCCGGAAGGAGTTTGAATTTTTGTGATTTTTATGCTTGTTTGGTCGGTGGAATATGTTGGG<br>ATTTATGTTTGCCTCTGAACAAGTGTCTTGCTCACATCGTAAATGACTTTCTCTCCGAAACGCTAAATATTCTTTCCCGC<br>AGGAGCTCTATATCCTTATTTTCCATGACAGATCTTAACGACAATATATGCAAAAGATATATAAAGATGATAACTAATATA<br>GTTATACTGAGCCTGATCATTTGCATTTCGTTAGCTTTCTGGATTATATCAATGACTGCAAGCACCTATTATGCGTAACTT<br>ACGACCTATTTCTCCGTGGCGTTGGCTGTTTTCTGTTGTTGTTCCTGTTCTGATCGTCTCTAATGGCCTTAAAAAGAAAA<br>GTCTAGATCACAGTGGGGCTCTAGGAGGGCTAGTCGTTGGATTTATCCTAACCATTGCAAATTTCAGCTTTTTTACCTCT<br>TTGCTGATGTTTTTCTTGTCTTCTTCGAAACTCACTAAATGGAAGGGAGAAGTGAAGAAGCGTCTAGATTCAGAATATAA<br>GGAAGGTGGGCAAAGGAATTGGGTTCAGGTGTTCTGTAATGGAGCTGTACCCACAGAACTGGCCCTGCTGTACATGATAG<br>AAAATGGCCCCGGGGAAATCCCAGTCGATTTTTCCAAGCAGTACTCCGCTTCCTGGATGTGTTTGTCTCTCTTGGCTGCA<br>CTGGCCTGCTCTGCTGGAGACACATGGGCTTCAGAAGTTGGCCCAGTTCTGAGTAAAAGTTCTCCAAGACTGATAACAAC<br>CTGGGAGAAAGTTCCAGTTGGTACCAATGGAGGAGTTACAGTGGTGGCCTTGTCTCCAGTCTCCTTGGTGGTACCTTTG<br>TGGGCATTGCATACTTCCTCACACAGCTGATTTTTGTGAATGATTTAGACATTTCTGCCCCGCAGTGGCCAATTATTGCA<br>TTTGGTGGTTTAGCTGGATTACTAGGATCAATTGTGGACTCATACTTAGGGGCTACAATGCAGTATACTGGGTTGGATGA<br>AAGCACTGGCATGGTGGTCAACAGCCCAACAAATAAGGCAAGGCACATAGCAGGGAAACCCATTCTTGATAACAACGCAG<br>TGAATCTGTTTTCTTCGTTCTTATTGCCCTCTTGCTCCCAACTGCTGCTTGGGGTTTTTGGCCCAGGGGGTGAACTTTA<br>TTTCATTTCCACAGGTTGAAACTGGTGAGTCCAGCTAAATTTGCAATTCCAACTTTCATCCTAAGAATAATAACTGTAAT<br>GGCAAAGCGGAAATGCCAGTTCCTCCTGTATTCCATTGAGATGGGATTTCACATTTTCCTCTCATCAACTCCCCTGTAAT<br>AGCTAGCGTCTTTCTAGTGAAAGAGAAGAATTCCTAGAACTTATGCATTTTTTTCCTGCTGAATGGAAGTCTTGAGCAAT<br>GAAGCTATATTGTCCCTACATATTACTATATATTGAACTGAAAGTTCTTACATAATCAATGTCAAGTTTTGTCTTATTTT<br>GTTTTGTTTGTTTAAACCAGTGTAGGAAATAAAAGTGATGATATTTAAAATAGTTCTCAGTTGAAGCAGAGAAATGCCAC<br>TGTGCTAGTTGCCCAAATGTTGTATCTATTTTAAATAGTTTAAGCTGATGTGTATGGGAGCCTAAACAAGTGTAGTATCC<br>TGAACTTCTCCCATTAATTGCTATTCACAATTGGGAAAGTGTGGAGATTGGTTCCTAGTGAGTTTTGTGGCCTACTCCA<br>CATTTGTTCTTCCTTCCTCAGGGTTAGTGATGAAAAATAGTAATATCTTTTTCATATGTCCATTAGAATGTATGAAAAA<br>AATCATTTTAACTAAAGCAAAAGAATTTTATCTTATATCTAAAAAATATTACTATATGTTTCAGTTGCTCTCT<br>GAACAAAAATTATCTTCAATTTAATATGTGGAATGTGTTTTCTAGCTTTCTTTGAATTATGTATGGCAACCTGGTTTAGC<br>ACTGGCATCCTGAACAGTTAAGAGTCACTGGGAAATTATTGTATTCTTTATAAATTTACTGTCATATGAATTGCTGGAA<br>AATGCTATGATTTTCTATTATTACCTTCTAAGTTGTATTCTCTCTTACACTGTAGCCTCAACTAAGGCAATTCTGCTAT<br>GTTTGTTCTTCACTATGATTTACTGTGTGCCAAAGGAGTTTTGACAGGGTACAGAGTATTTTACTAAAAGTATTTTTAAA<br>TGTTTCTCATGTGATTTCTGTACCTTCTTCCTCCTGCCCCTTTTGCTTTTTTAAAGAAACTGGGGAAGGATTTATGAATA<br>CACCACCACCAGAGTGGATAATGCTTAGAATTCTTTATTGGTGGCCCTACTATGGTGATGATCTAGAACTGACTTACTTC<br>AGGACAGAAGAAAAAACAATCACACCCTTAACCTTTAAGCCAGTTAGATCAGGGGGTTGCAACAATTGGGTTAAACTTTG<br>GGTATACATTGGAAGCACCAGGGCATGTTTGCTTTTTTTGTTTATGTGTTTGTTTTTTGAGACAGAGTCTCACACTGTGG<br>CCCAGGCTGGACTCCACGCACAGTGGCATGATCTCAGCTCCCGACTCCTGGGTTCACGTGATTCTCATGCCTCAGCCTCCCA<br>AGTAGCTGGGATCACAGGCGTGCACCATCACGCCCGGCTAATTTTTGTATTTTCAGTAGAGACAGGGTTTCGCCACGTTG<br>GCTAGGCTGGTCTGAACTCCTGACCTCAAGTGATCTGCCCATCTCAGCCTCCCAAAGATCTATTACAAGATGTGAGCCA<br>CTGTGCCCAGCCACCAGGGCATGTTTTTAAAAAAGTACTGATGTCTGGGTTTCACACTGCAAAATTCTGATTTATCTGAT<br>CTAAGGTACAGCCTGGATATTGAGACTTTTTAAAGCTCTGACTGTCATCATGTAGGGAGTTTTTAAAACAT<br>TGTTGCCAGGGCCCCTTTCTAGACCAAGTTAGTCAGAATGTTGGACAATGAGGCCCATGCATGGGTATTTTTACAAAGCT<br>CTCTGGGAGATTCTAATGCTTAACCAAATTGAGAAGCACTGAATAAGAATATCCTGGGCCGGGCGCACTGGCTCATGCCT<br>GTAATCCCAGCATTTTGGAAGGCCGAGGCGGGTGGATCACTTGAGGTCAGGAGTTCGAGACCAGCCTGGCCAACATGGTG<br>AAACACCGTCTCTACTAAAAATACAAAAAATTAGGTGGTGGTGCGTGCCTGTATTCCCAGCTACTCAGGAGGCTGAGG<br>CAGGAGAATCGCTGGAACCTGGGATGTGGAGGTTGCAGTGAGCCAAGATTGCACCACTGTACTCCAGCCTGGGCAACAGA<br>GGGAGACTCCATCTAGACTCCATCTCAAAAGGTTAAAAAAAAAAAAAAAAAAAAAAAAAGAATATTCTAAGCAC<br>TAGAACTACATAAGAATGTCCTAAAGCACTGTATCTAAGCACTTGAAAAGAATGGGACTTTTCGGTTTTAGGGAGATAAC<br>TATTAGCAACCACACAATATGTTATCTTTATGGATGAATAACTTCTGGTAATGACACAGTGTCTTACAGCTACATCATTT<br>ATAAAATCATGTGTCAGTTTTCACACAGCCTGCACATCGTTCTGACATGCCCTTTTTTTCCCTGGAGATTTATCCTCATG<br>ACATACAAGGGGACAAAATATTTATTGGGACTGTCTTTGAATTTAGTAGAATCACTGTATCATTAACAGTTTGGGGAAG<br>TACTGCTTTGCAGTCCTTTATTTGAAAACTTAGGTCTAGCTGTGTTTTGCATCAAAATTTTTGAGCTATTCAAAAACTAA<br>TAGGATCTGTGTAAAATATTTCACTCAAAACTACTAAAAAAAAGTCTAGCAGTGCTCATTATCAAATATACTCCTAT<br>TTTTGTGGTGATTTATGAACATCCCCACTAAGTATAACTAAAGATCATAAAGAGCCTCAGATCAAGTTTGGTCAGGTTTT<br>GTCACCAAGCTTTGTAAATAAACTGGTTTTCATAGCTTTTTGGAGATGAGAATTGAGGATAAGAAATTGTGTCTCTGTCC<br>TTTTTTTTTTTTTTGTTAAGTCTTACATGTATTTTACTGTAACATCTTTTGAATTGGATATTTAACTAATTCAACATAT<br>TTTTCCTCTTTGCAGAATGGGCAGTTCATGTTAAAATCACTTTTCATGGAAAGAGCTCTATGTAACAGCATAATAAAACT<br>GCCTACCTAGCAGCATAAA | TKWKGEVKKRLDSEYKEGGQRN<br>WVQVFCNGAVPTELALLYMIEN<br>GPGEIPVDFSKQYSASWMCLSL<br>LAALACSAGDTWASEVGPVLSK<br>SSPRLITTWEKVPVGTNGGVTV<br>VGLVSSLLGGTFVGIAYFLTQL<br>IFVNDLDISAPQWPIIAFGGLA<br>GLLGSIVDSYLGATMQYTGLDE<br>STGMVVNSPTNKARHIAGKPIL<br>DNNAVNLFSSVLIALLLPTAAW<br>GFWPRG |

SEQ.ID NO. 45
STAR Clone:
CNOGACACATCAAACTGCTTATCCAGGNACCACTAGAAGTGAATCTCTTCTTGAGTATTCCATACTGCTGCCCCTGCTAT
TCACTTGGGGTCCCAGTCAGTTGTTACTATATATTTGTCATCTATTGTGAGAGTCGTGATATCACCTTCCACATCAGTGA
TACTGAGAAGGAACAAATCTGCCAAAGATGCTTCACAGTTAGTTGTTACCTTTTTAAGAAGACTGTGCTTGAAAATTATG
GTAAAACACATTTAGAAGAAGGATGTGCATTTTCACATCAGTCTATGAAGTATAACTTGACATTTAAATTAAAATGCTGT
TCTTCAAAATCGA SEQ.ID NO. 46
STAR Clone:
GTTCCCGACTAGCTGCCCNTGCACATTATCTTCATTTTCCTGGAATTTGATACAGAGAGCAATTTATAGCCNATTGATAG
CTTATGCTGTTTCAATGTAAATTCGTGGTAAATAACTTAGGAACTGCCTCTTCTTTTTCTTTGAAAACCTACTTATAACT
GTTGCTAATAAGAATGTGTATTGTTCAGGACAACTTGTCTCCATACAGTTGGGTTGTAACCCTCATGCTTGGCCCAAATA
AACTCTCTACTTATATCAGTA SEQ.ID NO. 47
STAR Clone:
CTAGGGGTCCTGACGGTTCTCTGGCTCCAAGTCTGGCCCCTCAACCTCCCTGGTCATCAGTGGGCTCCAGGCTGAGGATG
AGGCTGATTACTACTGTGCAGCATGGGATGACAGCCTGAAAGGTCCTGCGTTCGGAGGAGGCACCCACCTGACCGTCCTC
GGTCAGCCCAAGGCTGCCCCCTCGGTCACTCTGTTCCCACCCTCCTCTGAGGAGCTTCAAGCCAACAAGGCCACACTGGT

TABLE 4-continued

Nucleotide and amino acid sequences of the SEQ. ID NOs.

| Nucleotide Sequence (5'-3') | ORFs |
|---|---|
| GTGTCTCGTAAGTGACTTCTACCCGGGAGCCGTGACAGTGGCCTGGAAGGCAGATGGCAGCCCCGTCAAGGTGGGAGTGG<br>AGACCACCAAACCCTCCAPACAAAGCAACAACAAGTATGCGGCCAGCAGCTACCTGAGCCTGACGCCCGAGCAGTGGAAG<br>TCCCACAGAAGCTACAGCTGCCGGGTCACGCATGAAGGGAGCACCGTGGAGAAGACAGTGGCCCCTGCAGAATGCTCTTA<br>GGCCCCCGACCCTCACCCCACCCACAGGGGCCTGGAGCTGCAGGTTCCCAGGGGAGGGGTCTCTGCCCCCATCCCAAGTC<br>ATCCAGCCCTTCTCAATAAATATCCTCATCGTCAACGA | |

SEQ.ID NO. 48
GGTAGTTGGTTGTGGGCACTGGGTTAGAGGTATCACGTGGGGGCACTTTCGTCTTAGCTTTTGGACAAGACGCAGGCGCA
ACCCACGGCTGCTGCGGGGATCCTTGTGGCCCTTCCGGTCGGTGGAACCAATCCGTGCACAGAGAAGCGGGGCGAACTGA
GGCGAGTGAAGTGGACTCTGAGGGCTACCGCTACCGCCACTGCTGCGGCAGGGGCGTGGAGGGCAGAGGGCCGCGGAGGC
CGCAGTTGCAAACATGGCTCAGAGCAGAGACGGCGGAAACCCGTTCGCCGAGCCCAGCGAGCTTGACAACCCCTTTCAGG
ACCCAGCTGTGATCCAGCACCGACCCAGCCGCAGTATGCCACGCTTGACGTCTACAACCCTTTTGAGACCCGGGAGCCA
CCACCAGCCTATGAGCCTCCAGCCCCTGCCCCATTGCCTCCACCCTCAGCTCCCTCCTTGCAGCCCTCGAGAAAGCTCAG
CCCCACAGAACCTAAGAACTATGGCTCATACAGCACTCAGGCCTCAGCTGCAGCAGCCACAGCTGAGCTGCTGAAGAAAC
AGGAGGAGCTCAACCGGAAGGCAGAGGAGTTGGACCGAAGGGAGCGAGAGCTGCAGCATGCTGCCCTGGGGGGCACAGCT
ACTCGACAGAACAATTGGCCCCCTCTACCTTCTTTTTGTCCAGTTCAGCCCTGCTTTTTCCAGGACATCTCCATGGAGAT
CCCCAAGAATTTCAGAAGACTGTATCCACCATGTACTACCTCTGGATGTGCAGCACGCTGGCTCTTCTCCTGAACTTCC
TCGCCTGCCTGGCCAGCTTCTGTGTGGAAACCAACAATGGCGCAGGCTTTGGGCTTTCTATCCTCTGGGTCCTCCTTTTC
ACTCCCTGCTCCTTTGTCTGCTGGTACCGCCCCATGTATAAGGCTTTCCGGAGTGACAGTTCATTCAATTTCTTCGTTTT
CTTCTTCATTTTCTTCGTCCAGGATGTGCTCTTTGTCCTCCAGGCCATTGGATCCCAGGTTGGGGATTCAGTGGCTGGA
TCTCTGCTCTGGTGGTGCCGAAGGGCAACACAGCAGTATCCGTGCTCATGCTGCTGGTCGCCCTGCTCTTCACTGGCATT
GCTGTGCTAGGAATTGTCATGCTGAAACGGATCCACTCCTTATACCGCCGCACAGGTGCCAGCTTTCAGAAGGCCCAGCA
AGAATTTGCTGCTGGTGTCTTCTCCAACCCTGCGGTGCGAACCGCAGCTGCCAATGCAGCCGCTGGGGCTGCTGAAAATG
CCTTCCGGGCCCGTGACCCCTGACTGGGATGCCCTGGCCCTGCTACTTGAGGGAGCTGACTTAGCTCCCGTCCCTAAGG
TCTCTGGGACTTGGAGAGACATCACTAACTGATGGCTCCTCCGTAGTGCTCCCAATCCTATGGCCATGACTGCTGAACCT
GACAGGCGTGTGGGGAGTTCACTGTGACCTAGTCCCCCCATCAGGCCACACTGCTGCCACCTCTCACACGCCCCAACCCA
GCTTCCCTCTGCTGTGCCACGGCTGTTGCTTCGGTTATTTAAATAAAAGAAGTGGAACTGGAACTGACAAAAAAAAAAAA
AAAAAAAAAAAAA

SEQ.ID NO. 88
MAQSRDGGNPFAEPSELDNPFQ
DPAVIQHRPSRQYATLDVYNPF
ETREPPPAYEPPAPAPLPPPSA
PSLQPSRKLSPTEPKNYGSYST
QASAAAATAELLKKQEELNRKA
EELDRRERELQHAALGGTATRQ
NNWPPLPSFCPVQPCFFQDISM
EIPQEFQKTVSTMYYLWMCSTL
ALLLNFLACLASFCVETNNGAG
FGLSILWVLLFTPCSFVCWYRP
MYKAFRSDSSFNFFVFFFIFFV
QDVLFVLQAIGIPGWGFSGWIS
ALVVPKGNTAVSVLMLLVALLF
TGIAVLGIVMLKRIHSLYRRTG
ASFQKAQQEFAAGVFSNPAVRT
AAANAAAGAAENAFRAP

SEQ.ID NO. 49
STAR Clone:
CTGCAAGAACTANTCATTCNAGGTCACCAGANAGGAGCCCTGACCCNTCGCTGCCCAGCCTGTCCTTGTGTCGTCTTTTT
ACGGGAGACGACTGGATCATGGGGGCGGATTTTCCCTTGCTGTTCTCATGATAGTGAGTTCTCATGAGATCTGGTTGTT
TAAAAGTGTATAGCACTTCCTGCTTCACTCTCTCCCACTCCACCATGTGAAGAAGGTGCCTTTGCCCTTCCGCCACGACT
GTGTTTCCTGAGGCCTCCCCAGCCATGCTTCCTGTACAGCCTGCAGAACTGTGAGTTAATTAAACCTCTTTTCTTCATAA
AGAACA SEQ.ID NO. 50
TCAAGATTAAACGACAAGGACAGACATGGCTCAGCGGATGACAACACAGCTGCTGCTCCTTCTAGTGTGGGTGGCTGTAG
TAGGGGAGGCTCAGACAAGGATTGCATGGGCCAGGACTGAGCTTCTCAATGTCTGCATGAACGCCAAGCACCACAAGGAA
AAGCCAGGCCCCGAGGACAAGTTGCATGAGCAGTGTCGACCCTGGAGGAAGAATGCCTGCTGTTCTACCAACACCAGCCA
GGAAGCCCATAAGGATGTTTCCTACCTATATAGATTCAACTGGAACCACTGTGGAGAGATGGCACCTGCCTGCAAACGGC
ATTTCATCCAGGACACCTGCCTCTACGAGTGCTCCCCCAACTTGGGGCCCTGGATCCAGCAGGTGGATCAGAGCTGGCGC
AAAGAGCGGGTACTGAACGTGCCCCTGTGCAAAGAGGACTGTGAGCAATGGTGGGAAGATTGTCGCACCTCCTACACCTG
CAAGAGCAACTGGCACAAGGGCTGGAACTGGACTCAGGGTTTAACAAGTGCGCAGTGGGAGCTGCCTGCCAACCTTTCC
ATTTCTACTTCCCCACACCCACTGTTCTGTGCAATGAAATCTGGACTCACTCCTACAAGGTCAGCAACTACAGCCGAGGG
AGTGGCCGCTGCATCCAGATGTGGTTCGACCCAGCCAGGGCAACCCCAATGAGGAGGTGGCGAGGTTCTATGCTGCAGC
CATGAGTGGGCTGGGCCCTGGGCAGCCTGGCCTTTCCTGCTTAGCCTGGCCCTAATGCTGCTGTGGCTGCTCAGCTGAC
CTCCTTTTACCTTCTGATACCTGGAAATCCCTGCCCTGTTCAGCCCCACAGCTCCCAACTATTTGGTTCCTGCTCCATGG
TCGGGCCTCTGACAGCCACTTTGAATAAACCAGACACCGCACATGTGTCTTGAGAATTATTTGG SEQ.ID NO. 89
MAQRMTTQLLLLLVWVAVVGEA
QTRIAWARTELLNVCMNAKHHK
EKPGPEDKLHEQCRPWRKNACC
STNTSQEAHKDVSYLYRFNWNH
CGEMAPACKRHFIQDTCLYECS
PNLGPWIQQVDQSWRKERVLNV
PLCKEDCEQWWEDCRTSYTCKS
NWHKGWNWTSGFNKCAVGAACQ
PFHFYFPTPTVLCNEIWTHSYK
VSNYSRGSGRCIQMWFDPAQGN
PNEEVARFYAAANSGAGPWAAW
PFLLSLALMLLWLLS SEQ.ID NO. 90
biotin-actgtactAACCCTGCGGCCGCTTTTTTTTTTTTTTTTTTV

SEQ.ID NO. 91
GGAATTCTAATACGACTCACTATAGGGAGACGAAGACAGTAGACAGG

SEQ.ID NO. 92
CGCGCCTGTCTACTGTCTTCGTCTCCCTATAGTGAGTCGTATTAGAATTC

SEQ.ID NO. 93
GGAATTCTAATACGACTCACTATAGGGAGAGCCTGCACCAACAGTTAACAGG

SEQ.ID NO. 94
CGCGCCTGTTAACTGTTGGTGCAGGCTCTCCCTATAGTGAGTCGTATTAGAATTC

SEQ.ID NO. 95
GGGAGACGAAGACAGTAGA

SEQ.ID NO. 96
GCCTGCACCAACAGTTAACA

SEQ.ID NO. 97
GGAATTCTAATACGACTCACTATAGGGA

TABLE 4-continued

Nucleotide and amino acid sequences of the SEQ. ID NOs.

| Nucleotide Sequence (5'-3') | ORFs |
|---|---|

SEQ.ID NO. 98
CGCGTCCCTATAGTGAGTCGTATTAGAATTC

SEQ.ID NO. 99
TTTTCCCAGTCACGACGTTGTAAAACGACGGCCAGTGAATTCTAATACGACTCACTATAGGGAGATGGAGAAAAAAATCA
CTGGACGCGTGGCGCGCCATTAATTAATGCGGCCGCTAGCTCGAGTGATAATAAGCGGATGAATGGCTGCAGGCATGCAA
GCTTGGCGTAATCATGGTCATAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTTGCGCTCACTGCCCGCTTTCCA
GTCGGGAAACCTGTCGTGCCAGCTGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCTCAATGCTCACGCTGTAGGTATCTCAGTTC
GGTGTAGGTCGTTCGCTCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCGGCTCCAGATTTATCAGCAATAAACCA
GCCAGCCGGAAGGGCCGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAACCAAGTCATTCTGAGAATAGTGT
ATGCGGCGACCGAGTTGCTCTTGCCCGGCGTCAATACGGGATAATACCGCGCCACATAGCAGAACTTTAAAAGTGCTCAT
CATTGGAAAACGTTCTTCGGGGCGAAACTCTCAAGGATCTTACCGCTGTTGAGATCCAGTTCGATGTAACCCACTCGTG
CACCCAACTGATCTTCAGCATCTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTATTGAAGCATTTATCAGGGTTA
TTGTCTCATGAGCGGATACATATTTGAATGTATTTAGAAAAATAAACAAATAGGGGTTCCGCGCACATTTCCCCGAAAAGTG
CCACCTGACGTCTAAGAAACCATTATTATCATGACATTAACCTATAAAAATAGGCGTATCACGAGGCCCTTTCGTCTC
GCGCGTTTCGGTGATGACGGTGAAAACCTCTGACACATGCAGCTCCCGGAGACGGTCACAGCTTGTCTGTAAGCGGATGC
CGGGAGCAGACAAGCCCGTCAGGGCGCGTCAGCGGGTGTTGGCGGGTGTCGGGGCTGGCTTAACTATGCGGCATCAGAGC
AGATTGTACTGAGAGTGCACCATATGCGGTGTGAAATACCGCACAGATGCGTAAGGAGAAAATACCGCATCAGGCGCCAT
TCGCCATTCAGGCTGCGCAACTGTTGGGAAGGGCGATCGGTGCGGGCCTCTTCGCTATTACGCCAGCTGGCGAAAGGGGG
ATGTGCTGCAAGGCGATTAAGTTGGGTAACGCCAGGG

SEQ.ID NO. 100
TTTTCCCAGTCACGACGTTGTAAAACGACGGCCAGTGAATTCAATTAACCCTCACTAAAGGGAGACTTGTTCCAAATGTG
TTAGGcgCGCCGCATGCGTCGACGGATCCTGAGAACTTCAGGCTCCTGGGCAACGTGCTGGTTATTGTGCTGTCTCATCA
TTTTGGCAAAGAATTCACTCCTCAGGTGCAGGCTGCCTATCAGAAGGTGGTGGCTGGTGTGGCCAATGCCCTGGCTCACA
AATACCACTGAGATCTTTTTCCCTCTGCCAAAAATTATGGGGACATCATGAAGTCCCTTGAGCATCTGACTTCTGGCTAA
TAAAGGAAATTTATTTTCATTGCAAAAAAAAAAGCGGCCGCTCTTCTATAGTGTCACCTAAATGGCCCAGCGGCCGAGC
TTGGCGTAATCATGGTCATAGCTGTTTCCTGTGTGAAATTGTTATCCGCTCACAATTCCACACAACATACGAGCCGGAAG
CATAAAGTGTAAAGCCTGGGGTGCCTAATGAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCAAAGCTCACGCTGTAGGTATCTCAGTTCGG
TGTAGGTCGTTCGCTCCAAGCTGGGCTGTGTGCACCAACCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATCTGCGCTC
TGCTGAAGCCAGTTACCTTCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGGTTATGGCAGCACTGCATAAT
TCTCTTACTGTCATGCCATCCGTAAGATGCTTTTCTGTGACTGGTGAGTACTCAACCAAGTCATTCTGAGAATAGTGTAT
GCGGCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGCACATTTCCCCGAAAAGTG
CCACCTGACGTCTAAGAAACCATTATTATCATGACATTAACCTATAAAAATAGGCGTATCACGAGGCCCTTTCGTCTCGC
GCGTTTCGGTGATGACGGTGAAAACCTCTGACACATGCAGCTCCCGGAGACGGTCACAGCTTGTCTGTAAGCGGATGCCG

TABLE 4-continued

Nucleotide and amino acid sequences of the SEQ. ID NOs.

Nucleotide Sequence
(5'-3')                                                                                                                 ORFs GGAGCAGACAAGCCCGTCAGGGCGCGTCAGCGGGTGTTGGCGGGTGTCGGGGCTGGCTTAACTATGCGGCATCAGAGCAG
ATTGTACTGAGAGTGCACCATATGCGGTGTGAAATACCGCACAGATGCGTAAGGAGAAAATACCGCATCAGGCGCCATTC
GCCATTCAGGCTGCGCAACTGTTGGGAAGGGCGATCGGTGCGGGCCTCTTCGCTATTACGCCAGCTGGCGAAAGGGGGAT
GTGCTGCAAGGCGATTAAGTTGGGTAACGCCAGGG SEQ.ID NO. 101
TCGCGCGTTTCGGTGATGACGGTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGGCTGGCTTAACTATGCGGCATCAGA
GCAGATTGTACTGAGAGTGCACCATATGCGGTGTGAAATACCGCACAGATGCGTAAGGAGAAAATACCGCATCAGGCGCC
ATTCGCCATTCAGGCTGCGCAACTGTTGGGAAGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGTCACGACGTTGTAAAACGACGGCCAGTGCCAA
GCTTTTCCAAAAAACTACCGTTGTTATAGGTGTCTCTTGAACACCTATAACAACGGTAGTGGATCCCGCGTCCTTTCCAC
AAGATATATAAACCCAAGAAATCGAAATACTTTCAAGTTACGGTAAGCATATGATAGTCCATTTTAAAACATAATTTTAA
AACTGCAAACTACCCAAGAAATTATTACTTTCTACGTCACGTATTTTGTACTAATATCTTTGTGTTTACAGTCAAATTAA
TTCTAATTATCTCTCTAACAGCCTTGTATCGTATATGCAAATATGAAGGAATCATGGGAAATAGGCCCTCTTCCTGCCCG
ACCTTGGCGCGCGCTCGGCGCGCGGTCACGCTCCGTCACGTGGTGCGTTTTGCCTGCGCGTCTTTCCACTGGGGAATTCA
TGCTTCTCCTCCCTTTAGTGAGGGTAATTCTCTCTCTCCCTATAGTGAGTCGTATTAATTCCTTCTCTTCTATAGTGT
CACCTAAATCGTTGCAATTCGTAATCATGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCTGACGAGCATCACAAAAATCGACGCTCAA
GTCAGAGGTGGCGAAACCCGACAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTACACTAGAAGAACAGTATT
TGGTATCTGCGCTCTGCTGAAGCCAGTTACCTTCGGAAAAAGAGTTGGTAGCTCTTGATCCGGCAAAAAAACCACCGCTG
GTAGCGGTGGTTTTTTTGTTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATCAAAAAGGATCTTCACCTA
GATCCTTTTAAATTAAAAATGAAGTTTTAAATCAATCTAAAGTATATATGAGTAAACTTGGTCTGACAGTTACCAATGCT
TAATCAGTGAGGCACCTATCTCAGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCACGCTCACCGGCTCCAGATTTATC
AGCAATAAACCAGCCAGCCGGAAGGGCCGAGCGCAGAGTGGTCCTGCAACTTTATCCGCCTCCATCCAGTCTATTAATT
GTTGCCGGGAAGCTAGAGTAAGTAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAGTACTCAACCAAGTCATTC
TGAGAATAGTGTATGCGGCGACCGAGTTGCTCTTGCCCGGCGTCAATACGGGATAATACCGCGCCACATAGCAGAACTTT
AAAAGTGCTCATCATTGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAATAAACAAATAGGGGTTCCGCGCACAT
TTCCCCGAAAAGTGCCACCTATTGGTGTGGAAAGTCCCCAGGCTCCCCAGCAGGCAGAAGTATGCAAAGCATGCATCTCA
ATTAGTCAGCAACCAGGTGTGGAAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCTAACTCCGCCCAGTTCCGCCCATTCTCCGCCCCATGCTG
ACTAATTTTTTTTATTTATGCAGAGGCCGAGGCCGCCTCGGCCTCTGAGCTATTCCAGAAGTAGTGAGGAGGCTTTTTTG
GAGGCCTAGGCTTTTGCAAAAAGCTAGCTTGCATGCCTGCAGGTCGGCCGCCACGACCGGTGCCGCCACCATCCCCTGAC
CCACGCCCCTGACCCCTCACAAGGAGACGACCTTCCATGACCGAGTACAAGCCCACGGTGCGCCTCGCCACCCGCGACGA
CGTCCCCGGGCCGTACGCACCCTCGCCGCCGCGTTCGCCGACTACCCCGCCACGCGCCACACCGTCGACCCGGACCGCC
ACATCGAGCGGGTCACCGAGCTGCAAGAACTCTTCCTCACGCGCGTCGGGCTCGACATCGGCAAGGTGTGGGTCGCGGAC
GACGGCGCCGGCGGTGGCGGTCTGGACCACGCCGGAGAGCGTCGAAGCGGGGGCGGTGTTCGCCGAGATCGGCCCGCGCAT
GGCCGAGTTGAGCGGTTCCCGGCTGGCCGCGCAGCAACAGATGGAAGGCCTCCTGGCGCCGCACCGGCCCAAGGAGCCG
CGTGGTTCCTGGCCACCGTCGGCGTCTCGCCCGACCACCAGGGCAAGGGTCTGGGCAGCGCCGTCGTGCTCCCCGGAGTG
GAGGCGGCCGAGCGCGCCGGGGTGCCCGCCTTCCTGGAGACCTCCGCGCCCCGCAACCTCCCCTTCTACGAGCGGCTCGG
CTTCACCGTCACCGCCGACGTCGAGGTGCCCGAAGGACCGCGCACCTGGTGCATGACCCGCAAGCCCGGTGCCTGACGCC
CGCCCCACGACCCGCAGCGCCCGACCGAAAGGAGCGCACGACCCCATGGCTCCGAAGCCACCCGGGCCCCGGCCCGC
CGACCCCGCACCCGCCCCGAGGCCCACCGACTCTAGAGGATCATAATCAGCCATACCACATTTGTAGAGGTTTTACTTG
CTTTAAAAAACCTCCCACACCTCCCCCTGAACCTGAAACATAAAATGAATGCAATTGTTGTTGTTAACTTGTTTATTGCA
GCTTATAATGGTTACAAATAAAGCAATAGCATCACAAATTTCACAAATAAAGCATTTTTTCACTGCAATCTAAGAAACC
ATTATTATCATGACATTAACCTATAAAAATAGGCGTATCACGAGGCCCTTTCGTC SEQ.ID NO. 102
Sequence information not disclosed by Ambion

SEQ.ID NO. 103
GTCAAGAAACCACACTTTA

SEQ.ID NO. 104
GTGACATGGAACCCAGCGA

SEQ.ID NO. 105
ACCGTGGCTGCTCGATAAA

TABLE 4-continued

Nucleotide and amino acid sequences of the SEQ. ID NOs.

| Nucleotide Sequence (5'-3') | ORFs |
|---|---|

SEQ.ID NO. 106
GCCAGAGAGCACAGAAATA

SEQ.ID NO. 107
GAGGAATGCCTCTAAGAAA

SEQ.ID NO. 108
GGGAACGAGAAGGGCTTCT

SEQ.ID NO. 109
AGCTGGAGGAATGAGAATT

SEQ.ID NO. 110
AGGGCCAAAGCTTTCCATA

SEQ.ID NO. 111
GGCAGGCTGTCCGCTTAAA

SEQ.ID NO. 112
GGTCCTTAGGCACCCAGAT

SEQ.ID NO. 113
GCGGAGCCCAGGGAGAATA

SEQ.ID NO. 114
GCCCGGATTGATGACATAT

SEQ.ID NO. 115
GTGGAGGCTGAGTTTCCAT

SEQ.ID NO. 116
GGATGTTAACCTGCGAAAT

SEQ.ID NO. 117
GGTCAGCAGGGTTCATTTA

SEQ.ID NO. 118
GCCTCAGGAACAAGATGAA

SEQ.ID NO. 119
GCGCGAGATCCTCTCCATT

SEQ.ID NO. 120
GCGCCAGAGGAGCGGGAAG

SEQ.ID NO. 121
GCCGCCCAGTTCAATACAA

SEQ.ID NO. 122
GAGCTTACAACCTGCCTTA

SEQ.ID NO. 123
GGCGCCCACTACCCAAGAA

SEQ.ID NO. 124
GAGTCAGGGATGGGTCCAT

SEQ.ID NO. 125
GGGCCAGTCTGTACTCATT

SEQ.ID NO. 126
GGGAATTCCATCTCCATAT

SEQ.ID NO. 127
GGCGCAGATCACCCAGAAG

SEQ.ID NO. 128
GAGCATCCTGGTGAGGAAT

SEQ.ID NO. 129
GGTGCCACATGACTAGGAT

SEQ.ID NO. 130
GCTGCAGACGTGTATGCAT

123

TABLE 4-continued

Nucleotide and amino acid sequences of the SEQ. ID NOs.

| Nucleotide Sequence (5'-3') | ORFs |
|---|---|

SEQ.ID NO. 131
GCGGAGGCACTGGGCTTAT

SEQ.ID NO. 132
GCCCGCTTACTTCCTGGAG

SEQ.ID NO. 133
GCTCTGCTCAAGTTGGATA

SEQ.ID NO. 134
GCTGCTGCCTTGCAGTTTG

SEQ.ID NO. 135
GCCCTTACCTGATGCTAAA

SEQ.ID NO. 136
GGCACCTACAAATGTTATA

SEQ.ID NO. 137
GAGGCCTGGAAGCTCCTAA

SEQ.ID NO. 138
GCAGCTTCAGGAGGTTAAA

SEQ.ID NO. 139
GCCGGACCTCTTCATCTTA

SEQ.ID NO. 140
GCGTCCATCACGGAAACAT

SEQ.ID NO. 141
GTCATCAGGACGTCCATTA

SEQ.ID NO. 142
GACACGATCTACCCTCAAA

SEQ.ID NO. 143
GGGCCATAGGGAAGCTTGA

SEQ.ID NO. 144
GCCCACGTGTTGAGATCAA

SEQ.ID NO. 145
GCTCCCACTGATTCCACAT

SEQ.ID NO. 146
GCCAGAGAGTAAAAGGGAT

SEQ.ID NO. 147
GGCATATGGAAGGAGCATT

SEQ.ID NO. 148
GTGGTTTGGTTCAGCAGTT

SEQ.ID NO. 149
GGCCTCCAGCCACGTAATT

SEQ.ID NO. 150
GGCGCTGCTGCCGCTCATC

SEQ.ID NO. 151
GGGCTGGAACTGGACTTCA

SEQ.ID NO. 152
GCCCATAAGGATGTTTCCT

SEQ.ID NO. 153
GCGTCCGGGCCTGTCTTCAACCT

SEQ.ID NO. 154
GCCCCACCCTCTACCCCACCACTA

SEQ.ID NO. 155
GAGATCCTGATCAAGGTGCAGG

TABLE 4-continued

Nucleotide and amino acid sequences of the SEQ. ID NOs.

Nucleotide Sequence
(5'-3')                                                                                                      ORFs

SEQ.ID NO. 156
TGCACGCTCACAGCAGTCAGG

SEQ.ID NO. 157
AACATGACTAAGATGCCCAACC

SEQ.ID NO. 158
AATCTCCTTCACCTCCACTACTG

SEQ.ID NO. 159
AAGCATAGCCATAGGTGATTGG

SEQ.ID NO. 160
ACAGGTATCAGACAAGGGAGCAG

SEQ.ID NO. 161
TTACGACCTATTTCTCCGTGG

SEQ.ID NO. 162
AATGCAATAATTGGCCACTGC

SEQ.ID NO. 163
ACACATCAAACTGCTTATCCAGG

SEQ.ID NO. 164
ACTGATGTGAAAATGCACATCC

SEQ.ID NO. 165
ATGGCTCATACAGCACTCAGG

SEQ.ID NO. 166
GAACTGTCACTCCGGAAAGCCT

SEQ.ID NO. 167
TGAAGGTCGGAGTCAACGGATTTGGT

SEQ.ID NO. 168
CATGTGGGCCATGAGGTCCACCAC

SEQ.ID NO. 169                                                                                               SEQ.ID NO. 170
ccctaatgcctccaacaataactgttgacttttttattttcagtcagagaagcctggcaaccaagaactgttttttttggtg                           MKILILGIFLFLCSTPAWAKEK
gtttacgagaacttaactgaattggaaaatatttgctttaatgaaacaatttactcttgtgcaacactaaattgtgtcaa                           HYYIGIIETTWDYASDHGEKKL
tcaagcaaataaggaagaaagtcttatttataaaattgcctgctcctgattttacttcatttcttctcaggctccaagaa                           ISVDTEHSNIYLQNGPDRIGRL
ggggaaaaaaatgaagattttgatacttggtattttctgtttttatgtagtaccccagcctgggcgaaagaaaagcatt                            YKKALYLQYTDETFRTTIEKPV
cattacattggaattattaaacgacttgggattatgcctctgaccatggggaaaagaaacttattctgttgacacggaa                            WLGFLGPIIKAETGDKVYVHLK
cattccaatatctatcttcaaaatggcccagatagaattgggagactatataagaaggccctttatcttcagtacacaga                           NLASRPYTFHSHGITYYKEHEG
tgaaacctttaggacaactatagaaaaaccggtctggcttgggtttttaggccctattatcaaagctgaactggagata                             AIYPDNTTDFQRADDKVYPGEQ
aagtttatgtacacttaaaaaaccttgcctctaggccctacacctttcattcacatggaataacttactataaggaacat                            YTYMLLATEEQSPGEGDGNCVT
gaggggccatctaccctgataacaccacagattttcaaagagcagatgacaaagtatatccaggagagcagtatacata                             RIYHSNIDAFKDTASGLIGPLI
catgttgcttgccactgaagaacaaagtcctggggaaggagatggcaattgtgtgactaggatttaccattcccacattg                           ICKKDSLDKEKEKHIDREFVVM
atgctccaaaagatattgcctcaggactcatcggaccttaataatctgtaaaaaagattctctagataaagaaaaagaa                             FSVVDENFSWYLEDNIKTYCSE
aaacatattgaccgagaatttgtggtgatgtttctgtggtggatgaaaatttcagctggtacctagaagacaacattaa                             PEKVDKDNEDFQESNRMYSVNG
aacctactgctcagaaccagagaaagttgacaaagacaacgaagcttccaggagagtaacagaacgtattctgtgaatg                             YTFGSLPGLSMCAEDRVKWYLF
gatacacttttggaagtctcccaggactctccatgtgtgctgaagacagagtaaaatggtacctttttggtatgggtaat                            GMGNEVDVHAAFFHGQALTNKN
gaagttgatgtgcacgcagctttctttcacggggcaagcactgactaacaagaactaccgtattgacacaatcaacctctt                           YRIDTINLFPATLFDAYMVAQN
tcctgctaccctgtttgatgcttatatggtgggcccagaaccctggagaatggatgctcagctgtcagaatctaaaccatc                           PGEWMLSCQNLNHLKAGLQAFF
tgaaagccggtttgcaagccttttttccaggtccaggagtgtaacaagtcttcatcaaaggataatatccgtgggaagcat                           QVQECNKSSSKDNIRGKWVRHY
gttagacactactacattgccgctgaggaaatcatctggaactatgctccctctggtatagacatcttcactaaagaaaa                            YIAAEEIIWNYAPSGTDIFTKE
cttaacagcacctggaagtgactcagccggtgttttttgaacaaggtaccacaagaattggaggctcttataaaaagctgg                           NLTAPGSDSAVFFEQGTTRIGG
tttatcgtgagtacacagatgcctccttcacaaatcgaaaggagagaggccctgaagaagagcatcttggcatcctgggt                            SYKKLVREYTDASFTNRKERG
cctgtcatttgggcagaggtgggagacaccatcagagtaaccttccataacaaaggagcatatccctcagtattgagcc                             PEEEHLGILGPVIWAEVGDTIR
gattgggstgagattcaataagaacaacgagggcacatactattcccaaattacaacccccagagcagaagtgtgcctc                             VTFHNKGAYPLSIEPIGVRFNK
cttcagcctcccatgtggcacccacagaaacattcacctgtgaatggactgtccccaaagaagtaggacccactaatgca                            NNEGTYYSPNYNPQSRSVPPSA
gatcctgtgtgtcgagctaagatgtattattctgctgtggatcccactaaagatatattcactgggcttattgggccaat                            SWVAPTETFTYEWTVPKEVGPT
gaaaatatgcaagaaaggaagtttacatgcaaatgggagacagaaagatgtagacaaggaattctatttgttcctacag                             NADPVCLAKMYYSAVDPTKDIF
tatttgatgagaatgaggtttactcctggaagataatattagaatgtttacaactgcacctgatcaggtggataaggaa                             TGLIGPMKICKKGSLHANORQK
gatgaagactttcaggaatctaataaaatgcactccatgaatggattcatgtatgggaatcagccgggtctcactatgtg                            DVDKEFYLFPTVFDENESLLLE
caaaggagattcggtcgtgtggtacttattcagcgccggaaatgaggccgatgtacatgaatatacttttcaggaaaca                             DNIRMFTTAPDQVDKEDEDFQE
catatctgtggagaggagaacggagagacacagcaaacctcttccctcaaacaagtcttacgctccacatgtggcctgac                            SNKMHSMNGFMYGNQPGLTMCK
acagaggggacttttaatgttgaatgccttacaactgatcattacacaggcggcatgaagcaaaaaatatactgtgaacca                           GDSVVWYLFSAGNEADVHGIYF
atgcaggcggcagtctgaggattccaccttctacctgggagaggagacatactatatcgcagcagtggaggtggaatggg                            SGNTYLWRGERRDTANLFPQTS
attattcccacaaaggagtgggaaaaggagctgcatcatttacaagagcagaatgtttcaaatgcattttagataag                               LTLHMWPDTEGTFNVECLTTDH
ggagagttttacataggctcaaagtacaagaaagttgtgtatcggcagtatactgatagcacattccgtgttccagtgga                            YTGGMKQKYTVNQCRRQSEDST
gagaaaagctgaagaagaacatctgggaattctaggtccacaacttcatgcagatgttggagacaaagtcaaaattatct                            FYLGERTYYIAAVEVEWDYSPQ
ttaaaaaacatgccacaaggccctactcaatacatgcccatggggtacaaacagagagttctacagttactccaacatta                            REWEKELHHLQEQNVSNAFLDK

TABLE 4-continued

Nucleotide and amino acid sequences of the SEQ. ID NOs.

| Nucleotide Sequence (5'-3') | ORFs |
|---|---|
| ccaggtgaaactctcacttacgtatggaaaatcccagaaagatctggagctggaacagaggattctgcttgtattccatg<br>ggcttattattcaactgtggatcaagttaaggacctctacagtggattaattggccccccgattgtttgtcgaagacctt<br>acttgaaagtattcaatcccagaaggaaactggaatttgcccttctgtttctagttttttgatgagaatgaatcttggtac<br>ttagatgacaacatcaaaacatactctgatcaccccgagaaagtaaacaaagatgatgaggaattcatagaaagcaataa<br>aatgcatgctattaatggaagaatgtttggaaacctacaaggcctcacaatgcacgtgggagatgaagtcaactggtatc<br>tgatgggaatgggcaatgaaatagacttacacactgtacattttcacggccatagcttccaatacaagcacaggggagtt<br>tatagttctgatgtctttgacattttccctggaacataccaaaccctagaaatgtttccaagaacacctggaatttggtt<br>actccactgccatgtgaccgaccacattcatgctggaatggaaaccacttacaccgttctacaaaatgaagacaccaaat<br>ctggctgaatgaaataaattggtgataagtggaaaaaagagaaaaaccaatgattcataacaatgtatgtgaaagtgtaa<br>aatagaatgttactttggaatgactataaacattaaaagaagactggaagcatacaactttgtacatttgtgggggaaaa<br>ctattaattttttgcaaatggaaagatcaacagactatataatgatacatgactgacacttgtacactaggtaataaaac<br>tgattcatacagtctaatgatatcaccgctgttagggttttataaaactgcatttaaaaaaagatctatgaccagatatt<br>ctcctgggtgctcctcaaaggaacactattaaggttcattgaaatgttttcaatcattgccttcccattgatccttctaa<br>catgctgttgacatcacacctaatattcagagggaatgggcaaggtatgagggaaggaaataaaaaataaaatataaa<br>atagaatgacacaaatttgagttttgtgaaccccctgaacagatggtcttaaggacgttatctggaactggagaaaagcag<br>agttgagagacaattctatagattaaatcctggtaaggacaaacattgccattagaagaaaagcttcaaaatagacctgt<br>ggcagatgtcacatgagtagaatttctgcccagccttaactgcattcagaggataatatcaatgaactaaacttgaacta<br>aaaatttttttaaacaaaaagttataaatgaagacacatggttgtgaataacaatgatgtatttctttattttcacatacac<br>tctagctaaaagagcaagagtacacatcaacaaaaatggaaacaaggctttggctgaaaaaaacatgcatttgacaaatc<br>atgttaatagctagacaagaagaaagttagctttgtaaacttctacttcatttgattcagagaaacagagcatgagttttt<br>cttaaaagtaacaagaaaa | GEFYIGSKYKKVVYRQYTDSTF<br>RVPVERKAEEEHLGILGPQLHA<br>DVGDKVKIIFKNMATRPYSIHA<br>HGVQTESSTVTPTLPGETLTYV<br>WKLPERSGAGTEDSACIPWAYY<br>STVDQVKDLYSGLIGPLIVCRR<br>PYLKVFNPRRKLEFALLFLVFD<br>ENESWYLDDNIKTYSDHPEKVN<br>KDDEEFIESNKNWAINGRMFGN<br>LQGLTMHVGDEVNWYLNGMGNE<br>IDLHTVHFHGHSFQYKHRGVYS<br>SDVFDIFPGTYQTLEMFPRTPG<br>IWLLHCHVTDHIHAGMETTYTV<br>LQNEDTKSG |

SEQ.ID NO. 171
GCTTAAAAGAGTCCTCCTGTGGC

SEQ.ID NO. 172
TGGACATTGTTCTTAAAGTGTGG

SEQ.ID NO. 173
AGGTTTTATGGCCACCGTCAG

SEQ.ID NO. 174
ATCCTATACCGCTCGGTTATGC

SEQ.ID NO. 175
GGGCGGCGGCTCTTTCCTCCTC

SEQ.ID NO. 176
GCTAGCGGCCCCATACTCG

SEQ.ID NO. 177
ACACTGGATGCCCTGAATGACACA

SEQ.ID NO. 178
GCTTTGGCCCTTTTTGCTAA

SEQ.ID NO. 179
CCCACTTCTGTCTTACTGCATC

SEQ.ID NO. 180
CATAGTACTCCAGGGCTTATTC

SEQ.ID NO. 181
AACGATTGCCCGGATTGATGACA

SEQ ID NO. 182
TACTTGAGGCTGGGGTGGGAGATG

SEQ.ID NO. 183
CACTACGCCAGGCACCCCCAAA

SEQ.ID NO. 184
CGAGGCGCACGGCAGTCT

SEQ.ID NO. 185
ATCCGTTGCTGCAGCTCGTTCCTC

SEQ.ID NO. 186
ACCCTGCTGACCTTCTTCCATTCC

SEQ.ID NO. 187
TCGGAGGAGGGCTGGCTGGTGTTT

SEQ.ID NO. 188
CTTGGGCGTCTTGGAGCGGTTCTG

TABLE 4-continued

Nucleotide and amino acid sequences of the SEQ. ID NOs.

| Nucleotide Sequence (5'-3') | ORFs |
|---|---|

SEQ.ID NO. 189
AGAGCCTATTGAAGATGAACAG

SEQ.ID NO. 190
TGATTGCCCCGGATCCTCTTAGG

SEQ.ID NO. 191
GGACAAATACGACGACGAGG

SEQ.ID NO. 192
GGTTTCTTGGGTAGTGGGC

SEQ.ID NO. 193
CCCCGGAGAAGGAAGAGCAGTA

SEQ.ID NO. 194
CGAAAGCCGGCAGTTAGTTATTGA

SEQ.ID NO. 195
GGCGGGCAACGAATTCCAGGTGTC

SEQ.ID NO. 196
TCAGAGGTTCGTCGCATTTGTCCA

SEQ.ID NO. 197
CAACAGTCATGATGTGTGGATG

SEQ.ID NO. 198
ACTGCACCTTGTCCGTGTTGAC

SEQ.ID NO. 199
CCGGCTGGCTGCTTTGTTTA

SEQ.ID NO. 200
ATGATCAGCAGGTTCGTTGGTAGG

SEQ.ID NO. 201
ATGCCGGAAGTGAATGTGG

SEQ.ID NO. 202
GGTGACTCCGCCTTTTGAT

SEQ.ID NO. 203
ACATTCGCTTCTCCATCTGG

SEQ.ID NO. 204
TGTCACGGAAGGGAACCAGG

SEQ.ID NO. 205
ACGCTGCCTCTGGGTCACTT

SEQ.ID NO. 206
TTGGCAAATCAATGGCTTGTAAT

SEQ.ID NO. 207
ATGGCTTGGGTCATCAGGAC

SEQ.ID NO. 208
GTGTCACTGGGCGTAAGATACTG

SEQ.ID NO. 209
CACCAAATCAGCTGCTACTACTCC

SEQ.ID NO. 210
GATAAACCCCAAAGCAGAAAGATT

SEQ.ID NO. 211
CGAGATTCCGTGGGCGTAGG

SEQ.ID NO. 212
TGAGTGGGAGCTTCGTAGG

SEQ.ID NO. 213
TCAGAGTGGACGTTGGATTAC

TABLE 4-continued

Nucleotide and amino acid sequences of the SEQ. ID NOs.

Nucleotide Sequence
(5'-3')                                                                ORFs

SEQ.ID NO. 214
TGCTTGAAATGTAGGAGAACA

SEQ.ID NO. 215
GAGGGGCATCAATCACACCGAGAA

SEQ.ID NO. 216
CCCCACCGCCCACCCATTTAGG

SEQ.ID NO. 217
GGGGGCACCAGAGGCAGTAA

SEQ.ID NO. 218
GGTTGTGGCGGGGGCAGTTGTG

SEQ.ID NO. 219
ACAGACTCCTGTACTGCAAACC

SEQ.ID NO. 220
TACCGGTTCGTCCTCTTCCTC

SEQ.ID NO. 221
GAAGTTCCTCACGCCCTGCTATC

SEQ.ID NO. 222
CTGGCTGGTGACCTGCTTTGAGTA

SEQ.ID NO. 223
TAGGCGCGCCTGACATACAGCAATGCCAGTT

SEQ.ID NO. 224
TAAGAATGCGGCCGCGCCACATCTTGAACACTTTGC

SEQ.ID NO. 225
TGGGGAGGAGTTTGAGGAGCAGAC

SEQ.ID NO. 226
GTGGGACGGAGGGGGCAGTGAAG

SEQ.ID NO. 227
GCAACTATTCGGAGCGCGTG

SEQ.ID NO. 228
CCAGCAGCTTGTTGAGCTCC

SEQ.ID NO. 229
GGAGGAGCTAAGCGTCATCGC

SEQ.ID NO. 230
TCGCTTCAGCGCGTAGACC

SEQ.ID NO. 231
TATTAGTTGGGATGGTGGTAGCAC

SEQ.ID NO. 232
GAGAATTCGAGTCGACGATGAC

SEQ.ID NO. 233
GAAATTGTGTTGACGCAGTCTCC

SEQ.ID NO. 234
AGGCACACAACAGAGGCAGTTC

SEQ.ID NO. 235
GTACATCAACCTCCTGCTGTCC

SEQ.ID NO. 236
GACATCTCCAAGTCCCAGCATG

SEQ.ID NO. 237
AGTCTCTCACTGTGCCTTATGCC

SEQ.IG NO. 238
AGTCCTAAGAACTGTAAACG

TABLE 4-continued

Nucleotide and amino acid sequences of the SEQ. ID NOs.

Nucleotide Sequence
(5'-3')                                                                    ORFs

SEQ.ID NO. 239
CATCTATACGTGGATTGAGGA

SEQ.ID NO. 240
ATAGGTACCAGGTATGAGCTG

SEQ.ID NO. 241
TGTCCACATCATCATCGTCATCC

SEQ.ID NO. 242
TGTCACTGGTCGGTCGCTGAGG

SEQ.ID NO. 243
CATGGGCTTAAGATGTC

SEQ.ID NO. 244
GTCGATTTCTCCATCATCTG

SEQ.ID NO. 245
AAGAGGCGCTCTACTAGCCG

SEQ.ID NO. 246
CTTTCCACATGGAACACAGG

SEQ.ID NO. 247
CATTTTCCTGGAATTTGATACAG

SEQ.ID NO. 248
GTAGAGAGTTTATTTGGGCCAAG

SEQ.ID NO. 249
CATCTATGGTAACTACAATCG

SEQ.ID NO. 250
GTAGAAGTCACTGATCAGACAC

SEQ.ID NO. 251
CTGCCTGCCAACCTTTCCATTTCT

SEQ.ID NO. 252
TGAGCAGCCACAGCAGCATTAGG

SEQ.ID NO. 253
CACCTGATCAGGTGGATAAGG

SEQ.ID NO. 254
TCCCAGGTAGAAGGTGGAATCC

REFERENCES

Jemal A, Murray T, Ward E, Samuels A, Tiwari R C, Ghafoor A, Feuer E J and Thun M J. Cancer statistics, 2005. CA Cancer J Clin 2005; 55:10-30.

Menon U, Skates S J, Lewis S, Rosenthal A N, Rufford B, Sibley K, Macdonald N, Dawnay A, Jeyarajah A, Bast R C Jr, Oram D and Jacobs I J. Prospective study using the risk of ovarian cancer algorithm to screen for ovarian cancer. J Clin Oncol. 2005 Nov. 1; 23(31):7919-26.

Bonome T, Lee J Y, Park D C, Radonovich M, Pise-Masison C, Brady J, Gardner G J, Hao K, Wong W H, Barrett J C, Lu K H, Sood A K, Gershenson D M, Mok S C and Birrer M J. Expression profiling of serous low malignancy potential, low grade, and high grade tumors of the ovary. Cancer Res 2005; 65:10602-10612.

Chambers, A. and Vanderhyden, B. Ovarian Cancer Biomarkers in Urine. Clin Cancer Res 2006; 12(2):323-327.

Berek et al. Cancer Medicine. 5th ed. London: B.C. Decker, Inc.; 2000. p. 1687-1720.

Bristow R. E. Surgical standards in the management of ovarian cancer. Curr Opin Oncol 2000; 12:474-480.

Brown E, Stewart M, Rye T, Al-Nafussi A, Williams A R, Bradburn M, Smyth J and Gabra H. Carcinosarcoma of the ovary: 19 years of prospective data from a single center. Cancer 2004; 100:2148-2153.

Shih, L-M and Kurman, R J. Molecular Pathogenesis of Ovarian Borderline Tumors: New Insights and Old Challenges. Clin Cancer Res 2005; 11(20):7273-7279.

Seidman J D, Russell P, Kurman R J. Surface epithelial tumors of the ovary. In: Kurman R J, editor. Blaustein's pathology of the female genital tract. 5th ed. New York: Springer-Verlag; 2002. pp. 791-904.

Mor G, Visintin I, Lai Y, Zhao H, Schwartz P, Rutherford T, Yue L, Bray-Ward P and Ward D C Serum protein markers for early detection of ovarian cancer. PNAS 2005; 102: 7677-7682.

Kozak K R, Amneus M W, Pusey S M, Su F, Luong M N, Luong S A, Reddy S T and Farias-Eisner R. Identification of biomarkers for ovarian cancer using strong anion-exchange ProteinChips: potential use in diagnosis and prognosis. PNAS 2003; 100:12343-12348.

McIntosh M W, Drescher C, Karlan B, Scholler N, Urban N, Hellstrom K E and Hellstrom I. Gynecol Oncol. 2004 October; 95(1):9-15.

Woolas R P, Xu F J, Jacobs I J, Yu Y H, Daly L, Berchuck A, Soper J T, Clarke-Pearson D L, Oram DH and Bast R C Jr. Elevation of multiple serum markers in patients with stage I ovarian cancer. J Natl Cancer Inst. 1993 Nov. 3; 85(21): 1748-51.

Schorge J O, Drake R D, Lee H, Skates S J, Rajanbabu R, Miller D S, Kim J H, Cramer D W, Berkowitz R S and Mok S C. Osteopontin as an adjunct to CA125 in detecting recurrent ovarian cancer. Clin. Cancer Res. 10; 3474-3478.

Gorelik E, Landsittel D P, Marrangoni A M, Modugno F, Velikokhatnaya L, Winans M T, Bigbee W L, Herberman R B and Lokshin A E. Multiplexed Immunobead-Based Cytokine Profiling for Early Detection of Ovarian Cancer Cancer Epidemiol Biomarkers Prev. 2005 April; 14(4): 981-7. Mack et al., 2003. U.S. Patent Application 20030124579.

Monahan et al., 2003. U.S. Patent Application 20030087250.
Wonsey et al., 2006. U.S. Patent Application 20060014686.
Santin A. D., 2006. U.S. Patent Application 20060078941.
Santin A. D., 2006. U.S. Patent Application 20060084594.
Jazaeri et al., 2005. U.S. Patent Application 20050095592.
Monahan et al., 2005. U.S. Patent Application 20050214831.
Gordon et al., 2003. U.S. Patent Application 20030219760.
Mor et al., 2005. U.S. Patent Application 20050214826.
Jhaveri et al., 2006, Antisense oligonucleotides targeting folate receptor alpha, and use thereof. U.S. Pat. No. 7,030, 236.

Agrawal N, Dasaradhi P V, Mohmmed A, Malhotra P, Bhatnagar R K and Mukherjee S K. RNA interference: biology, mechanism, and applications. Microbiol Mol Biol Rev. 2003 December; 67(4):657-85.

Brummelkamp T R, Bernards R and Agami R. A system for stable expression of short interfering RNAs in mammalian cells. Science 2002. 296: 550-553.

Elbashir S M, Harborth J, Lendeckel W, Yalcin A, Weber K, and Tuschl T. Duplexes of 21-nucleotide RNAs mediate RNA interference in cultured mammalian cells. Nature 2001. 411: 494-498.

Hannon G J. RNA interference. Nature 2002. 418: 244-251.

Leamon C P and Low P S. Folate-mediated targeting: from diagnostics to drug and gene delivery. Drug Discov Today 2001. 6: 44-51.

Mosmann T. Rapid colorimetric assay for cellular growth and survival: application to proliferation and cytotoxicity assays. J Immunol Methods. 1983. 65: 55-63.

Provencher D M, Lounis H, Champoux L, Tetrault M, Manderson E N, Wang J C, Eydoux P, Savoie R, Tonin P N and Mes-Masson A M. Characterization of four novel epithelial ovarian cancer cell lines. In Vitro Cell Dev Biol Anim 2000. 36: 357-361.

Samouelian V, Maugard C M, Jolicoeur M, Bertrand R, Arcand S L Tonin P N, Provencher D M, and Mes-Masson A M. Chemosensitivity and radiosensitivity profiles of four new human epithelial ovarian cancer cell lines exhibiting genetic alterations in BRCA2, TGFbeta-RII, KRAS2, TP53 and/or CDNK2A. Cancer Chemother Pharmacol 2004. 54: 497-504.

What is claimed is:

1. A method for treating ovarian cancer, the method comprising administering to a subject having ovarian cancer an antibody, or an antigen binding fragment thereof, capable of specifically binding to a polypeptide having a sequence identical to SEQ ID NO.:70.

2. The method of claim 1, wherein the antibody, or antigen binding fragment thereof, is capable of impairing an activity of the polypeptide in ovarian cancer cells.

3. The method of claim 2, wherein the activity is ovarian cancer tumorigenesis.

4. The method of claim 1, wherein the ovarian cancer is of epithelial origin.

5. The method of claim 4, wherein the ovarian cancer is malignant.

6. The method of claim 4, wherein the ovarian cancer is classified as serous, clear cell or endometroid.

7. The method of claim 6, wherein the ovarian cancer is malignant.

8. The method of claim 1, wherein the ovarian cancer is characterized as a late-stage.

9. The method of claim 6, wherein the ovarian cancer is characterized as a late-stage.

10. The method of claim 1, wherein said antibody is a monoclonal antibody.

11. The method of claim 1, wherein the antibody is a chimeric antibody.

12. The method of claim 1, wherein the antibody is a humanized antibody.

13. The method of claim 1, wherein the antibody is a human antibody.

14. The method of claim 1, wherein the antigen binding fragment thereof is a FV, a Fab, a Fab' or a (Fab')$_2$.

15. A method for inhibiting ovarian tumorigenesis, the method comprising a step of contacting ovarian cancer cells with an antibody, or an antigen binding fragment thereof, capable of specifically binding to a polypeptide having a sequence identical to SEQ ID NO.:70.

* * * * *

SEQUENCE LISTING

```
<160> NUMBER OF SEQ ID NOS: 256

<210> SEQ ID NO 1
<211> LENGTH: 114
<212> TYPE: DNA
<213> ORGANISM: Homo sapiens

<400> SEQUENCE: 1
ctggaagctg aagaatcacc ggcttcagtg acatggaacc cagcgatttg attttttgacg      60 agtatcgggt gactttgagg tggtcaagaa accacacttt aagaacaatg tcca           114

<210> SEQ ID NO 2
<211> LENGTH: 2058
<212> TYPE: DNA
<213> ORGANISM: Homo sapiens

<400> SEQUENCE: 2
gcacgaggaa gccacagatc tcttaagaac tttctgtctc caaaccgtgg ctgctcgata      60
aatcagacag aacagttaat cctcaattta agcctgatct aacccctaga aacagatata     120
gaacaatgga agtgacaaca agattgacat ggaatgatga aaatcatctg cgcaactgct     180
tggaaatgtt tctttgagtc ttctctataa gtctagtgtt catggaggta gcattgaaga     240
tatggttgaa agatgcagcc gtcagggatg tactataaca atggcttaca ttgattacaa     300
tatgattgta gcctttatgc ttggaaatta tattaattta cgtgaaagtt ctacagagcc     360
aaatgattcc ctatggtttt cacttcaaaa gaaaaatgac accactgaaa tagaaacttt     420
actcttaaat acagcaccaa aaattattga tgagcaactg gtgtgtcgtt tatcgaaaac     480
```

```
ggatattttc attatatgtc gagataataa aatttatcta gataaaatga taacaagaaa      540
cttgaaacta aggttttatg gccaccgtca gtatttggaa tgtgaagttt ttcgagttga      600
aggaattaag gataacctag acgacataaa gaggataatt aaagccagag agcacagaaa      660
taggcttcta gcagacatca gagactatag gccctatgca gacttggttt cagaaattcg      720
tattcttttg gtgggtccag ttgggtctgg aaagtccagt tttttcaatt cagtcaagtc      780
tatttttcat ggccatgtga ctggccaagc cgtagtgggg tctgatacca ccagcataac      840
cgagcggtat aggatatatt ctgttaaaga tggaaaaaat ggaaaatctc tgccatttat      900
gttgtgtgac actatggggc tagatggggc agaaggagca ggactgtgca tggatgacat      960
tccccacatc ttaaaaggtt gtatgccaga cagatatcag tttaattccc gtaaaccaat     1020
tacacctgag cattctactt ttatcacctc tccatctctg aaggacagga ttcactgtgt     1080
ggcttatgtc ttagacatca actctattga caatctctac tctaaaatgt ggcaaaagt      1140 gaagcaagtt cacaaagaag tattaaactg tggtatagca tatgtggcct tgcttactaa     1200
agtggatgat tgcagtgagg ttcttcaaga caacttttta aacatgagta gatctatgac     1260
ttctcaaagc cgggtcatga atgtccataa aatgctaggc attcctatttt ccaatatttt     1320 gatggttgga aattatgctt cagatttgga actggacccc atgaaggata ttctcatcct     1380
ctctgcactg aggcagatgc tgcgggctgc agatgatttt ttagaagatt tgcctcttga     1440
ggaaactggt gcaattgaga gagcgttaca gccctgcatt tgagataagt tgccttgatt     1500
ctgacatttg gccagcctg tactggtgtg ccgcaatgag agtcaatctc tattgacagc      1560
ctgcttcaga ttttgctttt gttcgttttg ccttctgtcc ttggaacagt catatctcaa     1620
gttcaaaggc caaaacctga gaagcggtgg gctaagatag gtcctactgc aaaccacccc     1680
tccatatttc cgtaccattt acaattcagt ttctgtgaca tcttttttaaa ccactggagg    1740 aaaaatgaga tattctctaa tttattcttc tataacactc tatatagagc tatgtgagta     1800
ctaatcacat tgaataatag ttataaaatt attgtataga catctgcttc ttaaacagat     1860
tgtgagttct ttgagaaaca gcgtggattt tacttatctg tgtattcaca gagcttagca     1920
cagtgcctgg taatgagcaa gcatacttgc cattacttttt ccttcccact ctctccaaca    1980
tcacattcac tttaaatttt tctgtatata gaaaggaaaa ctagcctggg caacatgatg     2040 aaacccatc tccactgc                                                    2058

<210> SEQ ID NO 3
<211> LENGTH: 1991
<212> TYPE: DNA
<213> ORGANISM: Homo sapiens

<400> SEQUENCE: 3
gccgagcgga gaggccgccc attggccggc cagcgccacg tggccgcccc cgccggtata       60
ttaggccact atttacctcc ggctcactcg ccatgggttg gagagggcag ctcgggtaga      120
gagggctggc ggagcggcgc agacggcggc agtcctgctc agcctctgcc cggctccgta      180
ctccggcccc ggcctgcgcc ctcagaaagg tggggcccga accatgagct cctacctgga      240
gtacgtgtca tgcagcagca gcggcggggt cggcggcgac gtgctcagct ggcacccaa       300 gttctgccgc tccgacgccc ggccgtggc tctgcagccc gccttccctc tgggcaacgg      360
cgacggcgcc ttcgtcagct gtctgcccct ggccgccgcc cgaccctcgc cttcgccccc     420
ggccgccccc gcgcggccgt ccgtaccgcc tccggccgcg cccagtacg cgcagtgcac       480 cctggagggg gcctacgaac ctggtgccgc acctgccgcg gcagctgggg gcgcggacta      540
```

```
cggcttcctg gggtccgggc cggcgtacga cttcccgggc gtgctggggc gggcggccga    600
cgacggcggg tctcacgtcc actacgccac ctcggccgtc ttctcgggcg gcggctcttt    660
cctcctcagc ggccaggtgg attacgcggc cttcggcgaa cccggcccct tccggcttg     720
tctcaaagcg tcagccgacg gccaccctgg tgctttccag accgcatccc cggcccagg     780
cacctacccc aagtccgtct ctcccgcctc cggcctccct gccgccttca gcacgttcga    840
gtggatgaaa gtgaagagga atgcctctaa gaaaggtaaa ctcgccgagt atggggccgc    900
tagcccctcc agcgcgatcc gcacgaattt cagcaccaag caactgacag aactggaaaa    960
agagtttcat ttcaataagt acttaactcg agcccggcgc atcgagatag ccaactgctt   1020
gcacctgaat gacacgcaag tcaaaatctg gttccagaac cgcaggatga aacagaagaa   1080
aagggaacga gaagggcttc tggccacggc cattcctgtg ctcccctcc aacttcccct    1140
ctctggaaca accccacta agtttatcaa gaaccccggc agcccttctc agtcccaaga    1200
gccttcgtga ggccggtact tggggccgaa aaactgtggc ctgcagaagt cccaggcgac   1260
ccccatccct atctagactt aggagctcag tttgggatgg aggtgggaga acaaaaatga   1320
atagggatt cacttgggaa atgaagtact ttagttggct tccgagttcc agactatatg    1380
tccagatatt aattgactgt cttgtaagcc acttgtttgg ttatgatttg tgtcttatca   1440
gggaaaggt gcccagctgc cagcccagct ccgctgctat cttttgcctca cttagtcatg    1500
tgcaattcgc gttgcagagt ggcagaccat tagttgctga gttctgtcag cactctgatg   1560
tgctcagaag agcacctgcc caagttttt ctggttttaa tttaaaggac aaggctacat    1620
atattcagct ttttgagatg accaaagcta gttagggtct ccttgatgta gctaagctgc   1680
ttcagtgatc ttcacatttg cactccagtt ttttttcctt taaaaagcg gtttctacct   1740
ctctatgtgc ctgagtgatg atacaatcgc tgtttagtta ctagatgaac aaatccacag   1800
aatgggtaaa gagtagaatc tgaactatat cttgacaaat attattcaaa cttgaatgta   1860
aatatataca gtatgtatat ttttaaaaa gatttgcttg caatgacctt ataagtgaca    1920
tttaatgtca tagcatgtaa agggttttt ttgtaataaa aattatagaa tctgcaaaaa   1980
aaaaaaaaaa a                                                       1991

<210> SEQ ID NO 4
<211> LENGTH: 539
<212> TYPE: DNA
<213> ORGANISM: Homo sapiens

<400> SEQUENCE: 4
cagcctccag agcaccagca ctggcactgg cactggcaca cgctatggca aatgaagtgc     60
aagacctgct ctcccctcgg aaaggggac atcctcctgc agtaaaagct ggaggaatga    120
gaatttccaa aaaacaagaa attggcacct tggaaagaca taccaaaaaa acaggattcg    180
agaaaacaag tgccattgca aatgttgcca aaatacagac actggatgcc ctgaatgaca    240
cactggagaa gctcaactat aaatttccag caacagtgca catggcacat caaaaaccca    300
cacctgctct ggaaaaggtt gttccactga aaaggatcta cattattcag cagcctcgaa    360
aatgttaagc ctggatttaa aacacagccg tctggccagc tgcctcgaat atctgacagc    420
ttagcaaaaa gggccaaagc tttccatagg cgtgctgcac ttgcttggta aattaaacag    480
cttttgtatc ttcccctttg actttaggta ataaagcatc caaacttgta aaaaaaaa     539

<210> SEQ ID NO 5
<211> LENGTH: 1690
<212> TYPE: DNA
```

<213> ORGANISM: Homo sapiens

<400> SEQUENCE: 5

```
gtaactgaaa atccacaaga cagaatagcc agatctcaga ggagcctggc taagcaaaac    60
cctgcagaac ggctgcctaa tttacagcaa ccatgagtac aaatggtgat gatcatcagg   120
tcaaggatag tctggagcaa ttgagatgtc actttacatg ggagttatcc attgatgacg   180
atgaaatgcc tgatttagaa aacagagtct tggatcagat tgaattccta gacaccaaat   240
acagtgtggg aatacacaac ctactagcct atgtgaaaca cctgaaaggc cagaatgagg   300
aagccctgaa gagcttaaaa gaagctgaaa acttaatgca ggaagaacat gacaaccaag   360
caaatgtgag gagtctggtg acctggggca actttgcctg gatgtattac cacatgggca   420
gactggcaga agcccagact tacctggaca aggtggagaa catttgcaag aagctttcaa   480
atcccttccg ctatagaatg gagtgtccag aaatagactg tgaggaagga tgggccttgc   540
tgaagtgtgg aggaaagaat tatgaacggg ccaaggcctg cttttgaaaag gtgcttgaag   600
tggaccctga aaaccctgaa tccagcgctg ggtatgcgat ctctgcctat cgcctggatg   660
gctttaaatt agccacaaaa aatcacaagc catttttcttt gcttcccta aggcaggctg   720
tccgcttaaa tccagacaat ggatatatta aggttctcct tgccctgaag cttcaggatg   780
aaggacagga agctgaagga gaaaagtaca ttgaagaagc tctagccaac atgtcctcac   840
agacctatgt ctttcgatat gcagccaagt tttaccgaag aaaaggctct gtggataaag   900
ctcttgagtt attaaaaaag gccttgcagg aaacacccac ttctgtctta ctgcatcacc   960
agataggggct ttgctacaag gcacaaatga tccaaatcaa ggaggctaca aaagggcagc  1020
ctagagggca gaacagagaa aagctagaca aaatgataag atcagccata tttcattttg  1080
aatctgcagt ggaaaaaaag cccacatttg aggtggctca tctagacctg gcaagaatgt  1140
atatagaagc aggcaatcac agaaaagctg aagagaattt tcaaaaattg ttatgcatga  1200
aaccagtggt agaagaaaca atgcaagaca tacatttcca ctatggtcgg tttcaggaat  1260
ttcaaaagaa atctgacgtc aatgcaatta ccattatttt aaaagctata aaatagaaac  1320
aggcatcatt aacaagggat aaaagtatca attctttgaa gaaattggtt ttaaggaaac  1380
ttcggagaaa ggcattagat ctggaaagct tgagcctcct tgggttcgtc tacaaattgg  1440
aaggaaatat gaatgaagcc ctggagtact atgagcgggc cctgagactg ctgctgact   1500
ttgagaactc tgtgagacaa ggtccttagg cacccagata tcagccactt tcacatttca  1560
tttcatttta tgctaacatt tactaatcat cttttctgct tactgttttc agaaacatta  1620
taattcactg taatgatgta attcttgaat aataaatctg acaaaaaaaa aaaaaaaaa   1680
aaaaaaaaaa                                                         1690
```

<210> SEQ ID NO 6
<211> LENGTH: 3783
<212> TYPE: DNA
<213> ORGANISM: Homo sapiens

<400> SEQUENCE: 6

```
cccgcgagcg tccatccatc tgtccggccg actgtccagc gaaaggggct ccaggccggg    60
cgcacgtcga cccgggggac cgaggccagg agagggccca agagcgcggc tgacccttgc   120
gggccggggc aggggacggt ggccgcggcc atgcagtcct gtgccagggc gtgggggctg   180
cgcctgggcc gcggggtcgg gggcggccgc cgcctggctg ggggatcggg gccgtgctgg   240
gcgccgcgga gccgggacag cagcagtggc ggcggggaca gcgccgcggc tggggcctcg   300
```

```
cgcctcctgg agcgccttct gcccagacac gacgacttcg ctcggaggca catcggccct    360
ggggacaaag accagagaga gatgctgcag accttggggc tggcgagcat tgatgaattg    420
atcgagaaga cggtccctgc caacatccgt ttgaaaagac ccttgaaaat ggaagaccct    480
gtttgtgaaa atgaaatcct tgcaactctg catgccattt caagcaaaaa ccagatctgg    540
agatcgtata ttggcatggg ctattataac tgctcagtgc cacagacgat tttgcggaac    600
ttactggaga actcaggatg gatcacccag tatactccat accagcctga ggtgtctcag    660
gggaggctgg agagtttact caactaccag accatggtgt gtgacatcac aggcctggac    720
atggccaatg catccctgct ggatgagggg actgcagccg cagaggcact gcagctgtgc    780
tacagacaca acaagaggag gaaatttctc gttgatcccc gttgccaccc acagacaata    840
gctgttgtcc agactcgagc caaatatact ggagtcctca ctgagctgaa gttaccctgt    900
gaaatggact tcagtggaaa agatgtcagt ggagtgttgt tccagtaccc agacacggag    960
gggaaggtgg aagactttac ggaactcgtg gagagagctc atcagagtgg gagcctggcc   1020
tgctgtgcta ctgaccttt agctttgtgc atcttgaggc cacctggaga atttggggta   1080
gacatcgccc tgggcagctc ccagagattt ggagtgccac tgggctatgg ggaccccat   1140 gcagcatttt ttgctgtccg agaaagcttg gtgagaatga tgcctggaag aatggtgggg   1200
gtaacaagag atgccactgg gaaagaagtg tatcgtcttg ctcttcaaac cagggagcaa   1260
cacattcgga gagacaaggc taccagcaac atctgtacag ctcaggccct cttggcgaat   1320
atggctgcca tgtttcgaat ctaccatggt tcccatgggc tggagcatat tgctaggagg   1380
gtacataatg ccactttgat tttgtcagaa ggtctcaagc gagcagggca tcaactccag   1440
catgacctgt tctttgatac cttgaagatt cattgtggct gctcagtgaa ggaggtcttg   1500
ggcagggcgg ctcagcggca gatcaatttt cggcttttg aggatggcac acttggtatt   1560
tctcttgatg aaacagtcaa tgaaaaagat ctggacgatt tgttgtggat cttggttgt   1620 gagtcatctg cagaactggt tgctgaaagc atggagagg agtgcagagg tattccaggg   1680
tctgtgttca agaggaccag cccgttcctc acccatcaag tgttcaacag ctaccactct   1740
gaaacaaaca ttgtccggta catgaagaaa ctggaaaata agacatttc ccttgttcac   1800 agcatgattc cactgggatc ctgcaccatg aaactgaaca gttcgtctga actcgcacct   1860
atcacatgga aagaatttgc aaacatccac ccctttgtgc ctctggatca agctcaagga   1920
tatcagcagc ttttccgaga gcttgagaag gatttgtgtg aactcacagg ttatgaccag   1980 gtctgttcc agccaaacag cggagcccag ggagaatatg ctggactggc cactatccga   2040
gcctacttaa accagaaagg agaggggcac agaacggttt gcctcattcc gaaatcagca   2100
catgggacca acccagcaag tgcccacatg gcaggcatga agattcagcc tgtgaggtg   2160 gataaatatg ggaatatcga tgcagttcac ctcaaggcca tggtggataa gcacaaggag   2220
aacctagcag ctatcatgat tacatacccca tccaccaatg gggtgtttga agagaacatc   2280
agtgacgtgt gtgacctcat ccatcaacat ggaggacagg tctacctaga cggggcaaat   2340
atgaatgctc aggtgggaat ctgtcgccct ggagacttcg ggtctgatgt ctcgcaccta   2400
aatcttcaca agaccttctg cattccccac ggaggaggtg gtcctggcat ggggcccatc   2460
ggagtgaaga acatctcgc cccgtttttg cccaatcatc ccgtcatttc actaaagcgg   2520
aatgaggatg cctgtcctgt gggaaccgtc agtgcggccc catgggctc cagttccatc   2580 ttgcccattt cctgggctta tatcaagatg atggggaggca agggtcttaa acaagccacg   2640
gaaactgcga tattaaatgc caactacatg gccaagcgat tagaaacaca ctacagaatt   2700
```

-continued

| | |
|---|---|
| cttttcaggg gtgcaagagg ttatgtgggt catgaattta ttttggacac gagacccttc | 2760 |
| aaaaagtctg caaatattga ggctgtggat gtggccaaga gactccagga ttatggattt | 2820 |
| cacgccccta ccatgtcctg gcctgtggca gggaccctca tggtggagcc cactgagtcg | 2880 |
| gaggacaagg cagagctgga cagattctgt gatgccatga tcagcattcg gcaggaaatt | 2940 |
| gctgacattg aggagggccg catcgacccc agggtcaatc cgctgaagat gtctccacac | 3000 |
| tccctgacct gcgttacatc ttcccactgg gaccggcctt attccagaga ggtggcagca | 3060 |
| ttcccactcc ccttcatgaa accagagaac aaattctggc caacgattgc ccggattgat | 3120 |
| gacatatatg gagatcagca cctggtttgt acctgcccac ccatggaagt ttatgagtct | 3180 |
| ccattttctg aacaaaagag ggcgtcttct tagtcctctc tccctaagtt taaaggactg | 3240 |
| atttgatgcc tctccccaga gcatttgata agcaagaaag atttcatctc caccccagc | 3300 |
| ctcaagtagg agtttatat actgtgtata tctctgtaat ctctgtcaag gtaaatgtaa | 3360 |
| atacagtagc tggagggagt cgaagctgat ggttggaaga cggatttgct ttggtattct | 3420 |
| gcttccacat gtgccagttg cctggattgg gagccatttt gtgttttgcg tagaaagttt | 3480 |
| taggaacttt aactttaat gtggcaagtt tgcagatgtc atagaggcta tcctggagac | 3540 |
| ttaatagaca ttttttttgtt ccaaaagagt ccatgtggac tgtgccatct gtgggaaatc | 3600 |
| ccagggcaaa tgtttacatt ttgtataccc tgaagaactc ttttcctct aatatgccta | 3660 |
| atctgtaatc acattctga gtgttttcct ctttttctgt gtgaggtttt tttttttttt | 3720 |
| aatctgcatt tattagtatt ctaataaaag catttgatc ggaaaaaaaa aaaaaaaaa | 3780 |
| aaa | 3783 |

<210> SEQ ID NO 7
<211> LENGTH: 1670
<212> TYPE: DNA
<213> ORGANISM: Homo sapiens

<400> SEQUENCE: 7

| | |
|---|---|
| gggtcgtcat gatccggacc ccattgtcgg cctctgccca tcgcctgctc ctcccaggct | 60 |
| cccgcggccg accccgcgc aacatgcagc ccacgggccg cgagggttcc cgcgcgctca | 120 |
| gccggcggta tctgcggcgt ctgctgctcc tgctactgct gctgctgctg cggcagcccg | 180 |
| taacccgcgc ggagaccacg ccgggcgccc ccagagccct ctccacgctg gctcccccca | 240 |
| gcctcttcac cacgccgggt gtccccagcg ccctcactac cccaggcctc actacgccag | 300 |
| gcaccccaa aaccctggac cttcggggtc gcgcgcaggc cctgatgcgg agtttcccac | 360 |
| tcgtggacgg ccacaatgac ctgccccagg tcctgagaca gcgttacaag aatgtgcttc | 420 |
| aggatgttaa cctgcgaaat ttcagccatg gtcagaccag cctggacagg cttagagacg | 480 |
| gcctcgtggg tgcccagttc tggtcagcct ccgtctcatg ccagtcccag gaccagactg | 540 |
| ccgtgcgcct cgccctggag cagattgacc tcattcaccg catgtgtgcc tcctactctg | 600 |
| aactcgagct tgtgacctca gctgaaggtc tgaacagctc tcaaaagctg gcctgcctca | 660 |
| ttggcgtgga gggtggtcac tcactggaca gcagcctctc tgtgctgcgc agtttctatg | 720 |
| tgctggggt gcgctaccctg acacttacct tcacctgcag tacaccatgg gcagagagtt | 780 |
| ccaccaagtt cagacaccac atgtacacca acgtcagcgg attgacaagc tttggtgaga | 840 |
| aagtagtaga ggagttgaac cgcctgggca tgatgataga tttgtcctat gcatcggaca | 900 |
| ccttgataag aagggtcctg gaagtgtctc aggctcctgt gatcttctcc cactcagctg | 960 |
| ccagagctgt gtgtgacaat ttgttgaatg ttcccgatga tatcctgcag cttctgaaga | 1020 |

| | |
|---|---|
| agaacggtgg catcgtgatg gtgacactgt ccatgggggt gctgcagtgc aacctgcttg | 1080 |
| ctaacgtgtc cactgtggca gatcactttg accacatcag ggcagtcatt ggatctgagt | 1140 |
| tcatcgggat tggtggaaat tatgacggga ctggccggtt ccctcagggg ctggaggatg | 1200 |
| tgtccacata cccagtcctg atagaggagt tgctgagtcg tagctggagc gaggaagagc | 1260 |
| ttcaaggtgt ccttcgtgga aacctgctgc gggtcttcag acaagtggaa aaggtgagag | 1320 |
| aggagagcag ggcgcagagc ccgtggagg ctgagtttcc atatgggcaa ctgagcacat | 1380 |
| cctgccactc ccacctcgtg cctcagaatg acaccaggc tactcatctg gaggtgacca | 1440 |
| agcagccaac caatcgggtc ccctggaggt cctcaaatgc ctccccatac cttgttccag | 1500 |
| gccttgtggc tgctgccacc atcccaacct tcacccagtg gctctgctga cacagtcggt | 1560 |
| ccccgcagag gtcactgtgg caaagcctca caaagccccc tctcctagtt cattcacaag | 1620 |
| catatgctga gaataaacat gttacacatg gaaaaaaaaa aaaaaaaaaa | 1670 |

<210> SEQ ID NO 8
<211> LENGTH: 817
<212> TYPE: DNA
<213> ORGANISM: Homo sapiens

<400> SEQUENCE: 8

| | |
|---|---|
| agtcctgcgt ccgggcccccg aggcgcagca gggcaccagg tggagcacca gctacgcgtg | 60 |
| gcgcagcgca gcgtccctag caccgagcct cccgcagccg ccgagatgct gcgaacagag | 120 |
| agctgccgcc ccaggtcgcc cgccggacag gtggccgcgg cgtccccgct cctgctgctg | 180 |
| ctgctgctgc tcgcctggtg cgcggggcgcc tgccgaggtg ctccaatatt acctcaagga | 240 |
| ttacagcctg aacaacagct acagttgtgg aatgagatag atgatacttg ttcgtctttt | 300 |
| ctgtccattg attctcagcc tcaggcatcc aacgcactgg aggagctttg cttttatgatt | 360 |
| atgggaatgc taccaaagcc tcaggaacaa gatgaaaaag ataatactaa aaggttctta | 420 |
| tttcattatt cgaagacaca gaagttgggc aagtcaaatg ttgtgtcgtc agttgtgcat | 480 |
| ccgttgctgc agctcgttcc tcacctgcat gagagaagaa tgaagagatt cagagtggac | 540 |
| gaagaattcc aaagtccctt tgcaagtcaa agtcgaggat attttttatt caggccacgg | 600 |
| aatggaagaa ggtcagcagg gttcatttaa aatggatgcc agctaatttt ccacagagca | 660 |
| atgctatgga atacaaaatg tactgacatt ttgttttctt ctgaaaaaaa tccttgctaa | 720 |
| atgtactctg ttgaaaatcc ctgtgttgtc aatgttctca gttgtaacaa tgttgtaaat | 780 |
| gttcaatttg ttgaaaatta aaaaatctaa aaataaa | 817 |

<210> SEQ ID NO 9
<211> LENGTH: 1878
<212> TYPE: DNA
<213> ORGANISM: Homo sapiens

<400> SEQUENCE: 9

| | |
|---|---|
| gggcgcagcg gggcccgtct gcagcaagtg accgacggcc gggacggccg cctgcccccct | 60 |
| ctgccacctg ggcggtgcg ggcccggagc ccggagcccg ggtagcgcgt agagccggcg | 120 |
| cgatgcacgt gcgctcactg cgagctgcgg cgccgcacag cttcgtggcg ctctgggcac | 180 |
| ccctgttcct gctgcgctcc gccctggccg acttcagcct ggacaacgag gtgcactcga | 240 |
| gcttcatcca ccggcgcctc cgcagccagg agcggcggga gatgcagcgc gagatcctct | 300 |
| ccattttggg cttgccccac cgcccgcgcc cgcacctcca gggcaagcac aactcggcac | 360 |
| ccatgttcat gctggacctg tacaacgcca tggcggtgga ggagggcggc gggcccggcg | 420 |

```
gccagggctt ctcctacccc tacaaggccg tcttcagtac ccagggcccc cctctggcca    480
gcctgcaaga tagccatttc ctcaccgacg ccgacatggt catgagcttc gtcaacctcg    540
tggaacatga caaggaattc ttccacccac gctaccacca tcgagagttc cggtttgatc    600
tttccaagat cccagaaggg gaagctgtca cggcagccga attccggatc tacaaggact    660
acatccggga acgcttcgac aatgagacgt tccggatcag cgtttatcag gtgctccagg    720
agcacttggg cagggaatcg gatctcttcc tgctcgacag ccgtaccctc tgggcctcgg    780
aggagggctg gctggtgttt gacatcacag ccaccagcaa ccactgggtg gtcaatccgc    840
ggcacaacct gggcctgcag ctctcggtgg agacgctgga tgggcagagc atcaacccca    900
agttggcggg cctgattggg cggcacgggc ccagaacaa gcagcccttc atggtggctt     960
tcttcaaggc cacggaggtc cacttccgca gcatccggtc cacggggagc aaacagcgca    1020
gccagaaccg ctccaagacg cccaagaacc aggaagccct gcggatggcc aacgtggcag    1080
agaacagcag cagcgaccag aggcaggcct gtaagaagca cgagctgtat gtcagcttcc    1140
gagacctggg ctggcaggac tggatcatcg cgcctgaagg ctacgccgcc tactactgtg    1200 aggggagtg tgccttccct ctgaactcct acatgaacgc caccaaccac gccatcgtgc     1260
agacgctggt ccacttcatc aacccggaaa cggtgcccaa gccctgctgt gcgcccacgc    1320
agctcaatgc catctccgtc ctctacttcg atgacagctc caacgtcatc ctgaagaaat    1380
acagaaacat ggtggtccgg gcctgtggct gccactagct cctccgagaa ttcagaccct    1440 tggggccaa gttttctgg atcctccatt gctcgcttg gccaggaacc agcagaccaa       1500
ctgccttttg tgagaccttc ccctccctat ccccaacttt aaaggtgtga gagtattagg    1560
aaacatgagc agcatatggc ttttgatcag tttttcagtg gcagcatcca atgaacaaga    1620
tcctacaagc tgtgcaggca aaacctagca ggaaaaaaaa acaacgcata aagaaaaatg    1680
gccgggccag gtcattggct gggaagtctc agccatgcac ggactcgttt ccagaggtaa    1740
ttatgagcgc ctaccagcca ggccaccag ccgtgggagg aagggggcgt ggcaagggt      1800 gggcacattg tgtctgtgc gaaaggaaaa ttgacccgga agttcctgta ataaatgtca    1860
caataaaacg aatgaatg                                                  1878

<210> SEQ ID NO 10
<211> LENGTH: 836
<212> TYPE: DNA
<213> ORGANISM: Homo sapiens

<400> SEQUENCE: 10
ccggtgagtc gccggcgctg cagagggagg cggcactggt ctcgacgtgg ggcggccagc     60
gatgaagccg cccagttcaa tacaaacaag tgagtttgac tcatcagatg aagagcctat    120
tgaagatgaa cagactccaa ttcatatatc atggctatct ttgtcacgag tgaattgttc    180
tcagtttctc ggtttatgtg ctcttccagg ttgtaaattt aaagatgtta gaagaaatgt    240
ccaaaaagat acagaagaac taaagagctg tggtatacaa gacatatttg ttttctgcac    300
cagaggggaa ctgtcaaaat atagagtccc aaaccttctg gatctctacc agcaatgtgg    360
aattatcacc catcatcatc caatcgcaga tggagggact cctgacatag ccagctgctg    420
tgaaataatg gaagagctta caacctgcct taaaaattac cgaaaaacct taatacactg    480
ctatggagga cttgggagat cttgtcttgt agctgcttgt ctcctactat acctgtctga    540
cacaatatca ccagagcaag ccatagacag cctgcgagac ctaagaggat ccggggcaat    600
acagaccatc aagcaataca attatcttca tgagtttcgg gacaaattag ctgcacatct    660
```

| atcatcaaga gattcacaat caagatctgt atcaagataa aggaattcaa atagcatata | 720 |
| tatgaccatg tctgaaatgt cagttctcta gcataatttg tattgaaatg aaaccaccag | 780 |
| tgttatcaac ttgaatgtaa atgtacatgt gcagatattc ctaaagtttt attgac | 836 |

<210> SEQ ID NO 11
<211> LENGTH: 717
<212> TYPE: DNA
<213> ORGANISM: Homo sapiens

<400> SEQUENCE: 11

| agagcgatca tgtcgcacaa acaaatttac tattcggaca aatacgacga cgaggagttt | 60 |
| gagtatcgac atgtcatgct gcccaaggac atagccaagc tggtccctaa aacccatctg | 120 |
| atgtctgaat ctgaatggag gaatcttggc gttcagcaga gtcagggatg ggtccattat | 180 |
| atgatccatg aaccagaacc tcacatcttg ctgttccggc gcccactacc caagaaacca | 240 |
| aagaaatgaa gctggcaagc tactttcag cctcaagctt tacacagctg tccttacttc | 300 |
| ctaacatctt tctgataaca ttattatgtt gccttcttgt ttctcacttt gatatttaaa | 360 |
| agatgttcaa tacactgttt gaatgtgctg gtaactgctt tgcttcttga gtagagccac | 420 |
| caccaccata gcccagccag atgagtgctc tgtggaccca cagcctaagc tgagtgtgac | 480 |
| cccagaagcc acgatgtgct ctgtatccag aacacacttg gcagatggag gaagcatctg | 540 |
| agtttgagac catggctgtt acagggatca tgtaaacttg ctgtttttgt tttttctgcc | 600 |
| gggtgttgta tgtgtggtga cttgcggatt tatgtttcag tgtactggaa actttccatt | 660 |
| ttattcaaga aatctgttca tgttaaaagc cttgattaaa gaggaagttt ttataat | 717 |

<210> SEQ ID NO 12
<211> LENGTH: 2162
<212> TYPE: DNA
<213> ORGANISM: Homo sapiens

<400> SEQUENCE: 12

| cgagttccgg cgaggcttca gggtacagct ccccgcagc cagaagccgg gcctgcagcg | 60 |
| cctcagcacc gctccgggac accccacccg cttcccaggc gtgacctgtc aacagcaact | 120 |
| tcgcggtgtg gtgaactctc tgaggaaaaa ccattttgat tattactctc agacgtgcgt | 180 |
| ggcaacaagt gactgagacc tagaaaatcca agcgttggag gtcctgaggc cagcctaagt | 240 |
| cgcttcaaaa tggaacgaag gcgtttgtgg ggttccattc agagccgata catcagcatg | 300 |
| agtgtgtgga caagcccacg gagacttgtg gagctggcag ggcagagcct gctgaaggat | 360 |
| gaggccctgg ccattgccgc cctggagttg ctgcccaggg agctcttccc gccactcttc | 420 |
| atggcagcct tgacgggag acacagccag accctgaagg caatggtgca ggcctggccc | 480 |
| ttcacctgcc tccctctggg agtgctgatg aagggacaac atcttcacct ggagaccttc | 540 |
| aaagctgtgc ttgatggact tgatgtgctc cttgcccagg aggttcgccc caggaggtgg | 600 |
| aaacttcaag tgctggattt acggaagaac tctcatcagg acttctggac tgtatggtct | 660 |
| ggaaacaggg ccagtctgta ctcatttcca gagccagaag cagctcagcc catgacaaag | 720 |
| aagcgaaaag tagatggttt gagcacagag gcagagcagc ccttcattcc agtagaggtg | 780 |
| ctcgtagacc tgttcctcaa ggaaggtgcc tgtgatgaat tgttctccta cctcattgag | 840 |
| aaagtgaagc gaaagaaaaa tgtactacgc ctgtgctgta gaagctgaa gatttttgca | 900 |
| atgcccatgc aggatatcaa gatgatcctg aaaatggtgc agctggactc tattgaagat | 960 |
| ttggaagtga cttgtacctg gaagctaccc accttggcga aatttctcc ttacctgggc | 1020 |

| | | |
|---|---|---|
| cagatgatta atctgcgtag actcctcctc tcccacatcc atgcatcttc ctacatttcc | 1080 | |
| ccggagaagg aagagcagta tatcgcccag ttcacctctc agttcctcag tctgcagtgc | 1140 | |
| ctgcaggctc tctatgtgga ctctttattt ttccttagag gccgcctgga tcagttgctc | 1200 | |
| aggcacgtga tgaaccccct tggaaaccctc tcaataacta actgccggct ttcggaaggg | 1260 | |
| gatgtgatgc atctgtccca gagtcccagc gtcagtcagc taagtgtcct gagtctaagt | 1320 | |
| ggggtcatgc tgaccgatgt aagtcccgag cccctccaag ctctgctgga gagagcctct | 1380 | |
| gccacccctcc aggacctggt ctttgatgag tgtgggatca cggatgatca gctccttgcc | 1440 | |
| ctcctgcctt ccctgagcca ctgctcccag cttacaacct taagcttcta cgggaattcc | 1500 | |
| atctccatat ctgccttgca gagtctcctg cagcacctca tcgggctgag caatctgacc | 1560 | |
| cacgtgctgt atcctgtccc cctggagagt tatgaggaca tccatggtac cctccacctg | 1620 | |
| gagaggcttg cctatctgca tgccaggctc agggagttgc tgtgtgagtt ggggcggccc | 1680 | |
| agcatggtct ggcttagtgc caaccccctgt cctcactgtg gggacagaac cttctatgac | 1740 | |
| ccggagccca tcctgtgccc ctgtttcatg cctaactagc tgggtgcaca tatcaaatgc | 1800 | |
| ttcattctgc atacttggac actaaagcca ggatgtgcat gcatcttgaa gcaacaaagc | 1860 | |
| agccacagtt tcagacaaat gttcagtgtg agtgaggaaa acatgttcag tgaggaaaaa | 1920 | |
| acattcagac aaatgttcag tgaggaaaaa aaggggaagt tggggatagg cagatgttga | 1980 | |
| cttgaggagt taatgtgatc tttggggaga tacatcttat agagttagaa atagaatctg | 2040 | |
| aatttctaaa gggagattct ggcttgggaa gtacatgtag gagttaatcc ctgtgtagac | 2100 | |
| tgttgtaaag aaactgttga aaataaagag aagcaatgtg aagcaaaaaa aaaaaaaaaa | 2160 | |
| aa | 2162 | |

<210> SEQ ID NO 13
<211> LENGTH: 634
<212> TYPE: DNA
<213> ORGANISM: Homo sapiens

<400> SEQUENCE: 13

| | | |
|---|---|---|
| cggctgagag gcagcgaact catctttgcc agtacaggag cttgtgccgt ggcccacagc | 60 | |
| ccacagccca cagccatggg ctgggacctg acggtgaaga tgctggcggg caacgaattc | 120 | |
| caggtgtccc tgagcagctc catgtcggtg tcagagctga aggcgcagat cacccagaag | 180 | |
| attggcgtgc acgccttcca gcagcgtctg gctgtccacc cgagcggtgt ggcgctgcag | 240 | |
| gacagggtcc cccttgccag ccagggcctg ggccctggca gcacggtcct gctggtggtg | 300 | |
| gacaaatgcg acgaacctct gagcatcctg gtgaggaata caagggccg cagcagcacc | 360 | |
| tacgaggtcc ggctgacgca gaccgtgcc cacctgaagc agcaagtgag cgggctggag | 420 | |
| ggtgtgcagg acgacctgtt ctggctgacc ttcgagggga gcccctgga ggaccagctc | 480 | |
| ccgctggggg agtacggcct caagcccctg agcaccgtgt tcatgaatct gcgcctgcgg | 540 | |
| ggaggcggca cagagcctgg cgggcggagc taagggcctc caccagcatc cgagcaggat | 600 | |
| caagggccgg aaataaaggc tgttgtaaga gaat | 634 | |

<210> SEQ ID NO 14
<211> LENGTH: 275
<212> TYPE: DNA
<213> ORGANISM: Homo sapiens

<400> SEQUENCE: 14

| | | |
|---|---|---|
| tgcccacttg gcccctcctt ccaaggtgta ctttacttcc tttcattcct gctctaatac | 60 | |

```
tgtttagtac attttcactc ctgctctaaa acttgcctca gtctctcact gtgccttatg    120
cccctcagct gaattctttc ttctgagcag gcaggaattg aggttgctgc agacgtgtat    180
gcatttgcca ccagtaacat actttggtgc cacatgacta ggatatgttc tctagtgcta    240
acatgttcgt ttacagttct taggactccc tgata                                275

<210> SEQ ID NO 15
<211> LENGTH: 1511
<212> TYPE: DNA
<213> ORGANISM: Homo sapiens

<400> SEQUENCE: 15
ggccgcctgc gcgccgccaa cagcctagcg ctgcgccgcg tggccgccgc cttctcgctg     60
gccccgctgg ccgagcgctg cggccgcgtc ctgcgtcagg ccttcgccga ggtggcgcgc    120
cacgccgact tcctggagct ggcgcctgac gaggtggtgg cgctgctggc ggaccccgcg    180
ctgggcgtgg cgcgcgagga ggccgtgttt gaagcggcca tgcgctgggt gcgccacgac    240
gcgccggccc gccgcggcca gctgcgacgc ctgctggagc acgtgcgcct gccgctactg    300
gcgcccgctt acttcctgga gaaggtggag gcggacgagc tgctgcaggc ctgcggcgag    360
tgccgcccgc tgctgctcga ggctcgcgcc tgcttcatcc tgggccgcga ggccggtgcg    420
ctgcggaccc ggccgcggag attcatggac ctagctgaag tgatcgtggt catcggcggt    480
tgcgaccgca aggtctcct gaagctgccc ttcgccgatg cctaccatcc agagagccag    540
cggtggaccc cactgcccag cctgccggc tacactcgct cagaattcgc cgcctgtgct    600
ctccgcaatg acgtctacgt ctccggaggc cacatcaaca gtcatgatgt gtggatgttt    660
agctcccatc tgcacacctg gatcaaggta gcctctctgc acaagggcag gtggaggcac    720
aagatggcag ttgtgcaggg gcagctgttc gcggtgggtg gcttcgacgg cctgaggcgc    780
ctgcacagcg tggagcgcta cgacccttc tccaacacct gggcggccgc cgcgcccctc    840
ccggaggccg tgagctcggc ggcggtggcg tcctgcgcgg gcaagctctt cgtgattggg    900
ggcgccaggc agggcggcgt caacacggac aaggtgcagt gcttgacccc caaggaggac    960
cggtggagcc tgcggtcacc agcaccccttc tcacagcggt gtctcgaggc tgtctccctt   1020
gaggacacca tctatgtcat ggggggtctc atgagcaaaa tcttcaccta tgatccaggc   1080
acagatgtgt gggggaggc agctgtcctc cccagccctg tggaaagctg tggagtcact   1140
gtgtgtgacg ggaaggtcca tccttggc gggcgggatg atcgcggaga aagcaccgat   1200
aaggtcttca ccttttgaccc cagcagtggg caggtggagg tccagccatc cctgcagcgc   1260
tgcaccagct cccacggctg tgtcaccatc atccagagct gggcaggtg attcagattt   1320 ggacagcctg agccaggagg cggagaggca ggcggagctc agatgcacac tctgctccct   1380
catggcacct ccacgcaaac agcccttaac ttaatggtcc cttttcttgt ataaataaaa   1440
tcttgttggg tctgtgttcc agctgcagtc tgccctgcct ggagatggaa tgtctaaaaa   1500
aaaaaaaaaa a                                                         1511

<210> SEQ ID NO 16
<211> LENGTH: 375
<212> TYPE: DNA
<213> ORGANISM: Homo sapiens

<400> SEQUENCE: 16
tttctagcag cctgggcaat ggcgggcgcc cctcccccag cctcgctgct gccttgcagt     60
ttgatctcag actgctgtgc tagcaatcag caagactccg tgggcgtagg accctccgag    120
```

```
ccaggttgca agaaagctca agtagcctat ggagaggatg caaggcttcc agctgatgcc    180
ctcagccagg ctcagtagca gccagaacta gcctaccaac gaacctgctg atcatgtgca    240
taagccacct tgaacgtcga tcctcctgcc tggtggagcc atcccagctg atgccacatg    300
aagcagacac aagctgtccc tactaagctc tgctcaagtt ggatattcat gagtgaaata    360
aatgactgtt actaa                                                    375

<210> SEQ ID NO 17
<211> LENGTH: 1811
<212> TYPE: DNA
<213> ORGANISM: Homo sapiens

<400> SEQUENCE: 17
gagtcaccaa ggaaggcagc ggcagctcca ctcagccagt acccagatac gctgggaacc     60
ttccccagcc atggcttccc tggggcagat cctcttctgg agcataatta gcatcatcat    120
tattctggct ggagcaattg cactcatcat tggctttggt atttcaggga gacactccat    180
cacagtcact actgtcgcct cagctgggaa cattggggag gatggaatcc agagctgcac    240
ttttgaacct gacatcaaac tttctgatat cgtgatacaa tggctgaagg aaggtgtttt    300
aggcttggtc catgagttca agaaggcaaa agatgagctg tcggagcagg atgaaatgtt    360
cagaggccgg acagcagtgt ttgctgatca agtgatagtt ggcaatgcct ctttgcggct    420
gaaaaacgtg caactcacag atgctggcac ctacaaatgt tatatcatca cttctaaagg    480
caaggggaat gctaaccttg agtataaaac tggagccttc agcatgccgg aagtgaatgt    540
ggactataat gccagctcag agaccttgcg gtgtgaggct ccccgatggt tcccccagcc    600
cacagtggtc tgggcatccc aagttgacca gggagccaac ttctcggaag tctccaatac    660
cagctttgag ctgaactctg agaatgtgac catgaaggtt gtgtctgtgc tctacaatgt    720
tacgatcaac aacacatact cctgtatgat tgaaaatgac attgccaaag caacagggga    780
tatcaaagtg acagaatcgg agatcaaaag gcggagtcac ctacagctgc taaactcaaa    840
ggcttctctg tgtgtctctt cttcttttgc catcagctgg gcacttctgc ctctcagccc    900
ttacctgatg ctaaaataat gtgcctcggc cacaaaaaag catgcaaagt cattgttaca    960
acagggatct acagaactat ttcaccacca gatatgacct agttttatat ttctgggagg   1020
aaatgaattc atatctagaa gtctggagtg agcaaacaag agcaagaaac aaaaagaagc   1080
caaaagcaga aggctccaat atgaacaaga taaatctatc ttcaaagaca tattagaagt   1140
tgggaaaata attcatgtga actagagtca actgtgtcag ggctaagaaa ccctggtttt   1200
gagtagaaaa gggcctggaa agaggggagc caacaaatct gtctgcttcc tcacattagt   1260
cattggcaaa taagcattct gtctctttgg ctgctgcctc agcacagaga gccagaactc   1320
tatcgggcac caggataaca tctctcagtg aacagagttg acaaggccta tgggaaatgc   1380
ctgatgggat tatcttcagc ttgttgagct tctaagtttc tttcccttca ttctaccctg   1440
caagccaagt tctgtaagag aaatgcctga gttctagctc aggttttctt actctgaatt   1500
tagatctcca gaccctgcct ggccacaatt caaattaagg caacaaacat ataccttcca   1560
tgaagcacac acagactttt gaaagcaagg acaatgactg cttgaattga ggccttgagg   1620
aatgaagctt tgaaggaaaa gaatactttg tttccagccc ccttcccaca ctcttcatgt   1680
gttaaccact gccttcctgg accttggagc cacggtgact gtattacatg ttgttataga   1740
aaactgattt tagagttctg atcgttcaag agaatgatta aatatacatt tcctaaaaaa   1800
aaaaaaaaaa a                                                       1811
```

<210> SEQ ID NO 18
<211> LENGTH: 2972
<212> TYPE: DNA
<213> ORGANISM: Homo sapiens

<400> SEQUENCE: 18

| | | | | | |
|---|---|---|---|---|---|
| tcttcggacc | taggctgccc | tgccgtcatg | tcgcaaggga | tcctttctcc | gccagcgggc | 60 |
| ttgctgtccg | atgacgatgt | cgtagtttct | cccatgtttg | agtccacagc | tgcagatttg | 120 |
| gggtctgtgg | tacgcaagaa | cctgctatca | gactgctctg | tcgtctctac | ctccctagag | 180 |
| gacaagcagc | aggttccatc | tgaggacagt | atggagaagg | tgaaagtata | cttgagggtt | 240 |
| aggcccttgt | taccttcaga | gttggaacga | caggaagatc | agggttgtgt | ccgtattgag | 300 |
| aatgtggaga | cccttgttct | acaagcaccc | aaggactcgt | ttgccctgaa | gagcaatgaa | 360 |
| cggggaattg | gccaagccac | acacaggttc | accttttccc | agatctttgg | gccagaagtg | 420 |
| ggacaggcat | ccttcttcaa | cctaactgtg | aaggagatgg | taaaggatgt | actcaaaggg | 480 |
| cagaactggc | tcatctatac | atatggagtc | actaactcag | ggaaaaccca | cacgattcaa | 540 |
| ggtaccatca | aggatggagg | gattctcccc | cggtccctgg | cgctgatctt | caatagcctc | 600 |
| caaggccaac | ttcatccaac | acctgatctg | aagcccttgc | tctccaatga | ggtaatctgg | 660 |
| ctagacagca | agcagatccg | acaggaggaa | atgaagaagc | tgtccctgct | aaatggaggc | 720 |
| ctccaagagg | aggagctgtc | cacttccttg | aagaggagtg | tctacatcga | aagtcggata | 780 |
| ggtaccagca | ccagcttcga | cagtggcatt | gctgggctct | cttctatcag | tcagtgtacc | 840 |
| agcagtagcc | agctggatga | aacaagtcat | cgatgggcac | agccagacac | tgccccacta | 900 |
| cctgtcccgg | caaacattcg | cttctccatc | tggatctcat | tctttgagat | ctacaacgaa | 960 |
| ctgctttatg | acctattaga | accgcctagc | caacagcgca | agaggcagac | tttgcggcta | 1020 |
| tgcgaggatc | aaaatggcaa | tccctatgtg | aaagatctca | actggattca | tgtgcaagat | 1080 |
| gctgaggagg | cctggaagct | cctaaaagtg | ggtcgtaaga | accagagctt | tgccagcacc | 1140 |
| cacctcaacc | agaactccag | ccgcagtcac | agcatcttct | caatcaggat | cctacacctt | 1200 |
| caggggaag | gagatatagt | ccccaagatc | agcgagctgt | cactctgtga | tctggctggc | 1260 |
| tcagagcgct | gcaaagatca | gaagagtggt | gaacggttga | aggaagcagg | aaacattaac | 1320 |
| acctctctac | acaccctggg | ccgctgtatt | gctgcccttc | gtcaaaacca | gcagaaccgg | 1380 |
| tcaaagcaga | acctggttcc | cttccgtgac | agcaagttga | ctcgagtgtt | ccaaggtttc | 1440 |
| ttcacaggcc | gaggccgttc | ctgcatgatt | gtcaatgtga | atccctgtgc | atctacctat | 1500 |
| gatgaaactc | ttcatgtggc | caagttctca | gccattgcta | gccagcttgt | gcatgcccca | 1560 |
| cctatgcaac | tgggattccc | atccctgcac | tcgttcatca | aggaacatag | tcttcaggta | 1620 |
| tcccccagct | tagagaaagg | ggctaaggca | gacacaggcc | ttgatgatga | tattgaaaat | 1680 |
| gaagctgaca | tctccatgta | tggcaaagag | gagctcctac | aagttgtgga | agccatgaag | 1740 |
| acactgcttt | tgaaggaacg | acaggaaaag | ctacagctgg | agatgcatct | ccgagatgaa | 1800 |
| atttgcaatg | agatggtaga | acagatgcaa | cagcgggaac | agtggtgcag | tgaacatttg | 1860 |
| gacacccaaa | aggaactatt | ggaggaaatg | tatgaagaaa | aactaaatat | cctcaaggag | 1920 |
| tcactgacaa | gttttttacca | agaagagatt | caggagcggg | atgaaaagat | tgaagagcta | 1980 |
| gaagctctct | tgcaggaagc | cagacaacag | tcagtggccc | atcagcaatc | agggtctgaa | 2040 |
| ttggccctac | ggcggtcaca | aaggttggca | gcttctgcct | ccacccagca | gcttcaggag | 2100 |
| gttaaagcta | aattacagca | gtgcaaagca | gagctaaact | ctaccactga | agagttgcat | 2160 |

-continued

```
aagtatcaga aaatgttaga accaccaccc tcagccaagc ccttcaccat tgatgtggac    2220
aagaagttag aagagggcca gaagaatata aggctgttgc ggacagagct tcagaaactt    2280
ggtgagtctc tccaatcagc agagagagct tgttgccaca gcactggggc aggaaaactt    2340
cgtcaagcct tgaccacttg tgatgacatc ttaatcaaac aggaccagac tctggctgaa    2400
ctgcagaaca acatggtgct agtgaaactg gaccttcgga agaaggcagc atgtattgct    2460
gagcagtatc atactgtgtt gaaactccaa ggccaggttt ctgccaaaaa gcgccttggt    2520
accaaccagg aaaatcagca accaaaccaa caaccaccag ggaagaaacc attccttcga    2580
aatttacttc cccgaacacc aacctgccaa agctcaacag actgcagccc ttatgcccgg    2640
atcctacgct cacggcgttc ccctttactc aaatctgggc cttttggcaa aaagtactaa    2700
ggctgtgggg aaagaagaa gcagtcatgg ccctgaggtg ggtcagctac tctcctgaag    2760
aaataggtct cttttatgct ttaccatata tcaggaatta tatccaggat gcaatactca    2820
gacactagct tttttctcac ttttgtatta taaccaccta tgtaatctca tgttgttgtt    2880
tttttttatt tacttatatg atttctatgc acacaaaaac agttatatta aagatattat    2940
tgttcacatt ttttattgaa aaaaaaaaa aa                                    2972
```

<210> SEQ ID NO 19
<211> LENGTH: 220
<212> TYPE: DNA
<213> ORGANISM: Homo sapiens
<220> FEATURE:
<221> NAME/KEY: misc_feature
<222> LOCATION: (54)..(54)
<223> OTHER INFORMATION: n is a, c, g, or t

<400> SEQUENCE: 19

```
tccttgttac gatgaagaaa ctaaatctca ggaagaaaaa actaagtgaa gacnaaagaa     60
ggatttgaac tgaggtttgt cagactctcg ggaccatgct gttgaaacca ctaaccacg     120 ctgcctctgg gtcacttggt aaacagcatt taaccattaa gaaagtcatt aataaaattc    180
cttgtgctct ccttgagatt acaagccatt gatttgccaa                          220
```

<210> SEQ ID NO 20
<211> LENGTH: 160
<212> TYPE: DNA
<213> ORGANISM: Homo sapiens

<400> SEQUENCE: 20

```
gaacacagct aagcagatgg cttgggtcat caggacgtcc attacatcca aaggaagaca     60
gcctgtgacg tttcaaaagc aaaagtcccc taccagccag tgaagctacc tgatttctca    120
gtatcttacg cccagtgaca cgatctaccc tcaaaactta                          160
```

<210> SEQ ID NO 21
<211> LENGTH: 1172
<212> TYPE: DNA
<213> ORGANISM: Homo sapiens

<400> SEQUENCE: 21

```
gagacattcc tcaattgctt agacatattc tgagcctaca gcagaggaac ctccagtctc     60
agcaccatga atcaaactgc gattctgatt tgctgcctta tctttctgac tctaagtggc    120
attcaaggag tacctctctc tagaaccgta cgctgtacct gcatcagcat tagtaatcaa    180
cctgttaatc caaggtcttt agaaaaactt gaaattattc ctgcaagcca attttgtcca    240
cgtgttgaga tcattgctac aatgaaaaag aagggtgaga agagatgtct gaatccagaa    300
```

```
tcgaaggcca tcaagaattt actgaaagca gttagcaagg aaatgtctaa aagatctcct      360
taaaaccaga ggggagcaaa atcgatgcag tgcttccaag gatggaccac acagaggctg      420
cctctcccat cacttcccta catggagtat atgtcaagcc ataattgttc ttagtttgca      480
gttacactaa aaggtgacca atgatggtca ccaaatcagc tgctactact cctgtaggaa      540
ggttaatgtt catcatccta agctattcag taataactct accctggcac tataatgtaa      600
gctctactga ggtgctatgt tcttagtgga tgttctgacc ctgcttcaaa tatttccctc      660
acctttccca tcttccaagg gtactaagga atctttctgc tttggggttt atcagaattc      720
tcagaatctc aaataactaa aaggtatgca atcaaatctg ctttttaaag aatgctcttt      780
acttcatgga cttccactgc atcctccca aggggcccaa attctttcag tggctaccta       840
catacaattc caaacacata caggaaggta gaaatatctg aaaatgtatg tgtaagtatt      900
cttatttaat gaaagactgt acaaagtata agtcttagat gtatatattt cctatattgt      960
tttcagtgta catggaataa catgtaatta agtactatgt atcaatgagt aacaggaaaa     1020
ttttaaaaat acagatagat atatgctctg catgttacat aagataaatg tgctgaatgg     1080
ttttcaaata aaaatgaggt actctcctgg aaatattaag aaagactatc taaatgttga     1140
aagatcaaaa ggttaataaa gtaattataa ct                                    1172

<210> SEQ ID NO 22
<211> LENGTH: 278
<212> TYPE: DNA
<213> ORGANISM: Homo sapiens

<400> SEQUENCE: 22
tttgcaggtt tgatctcaga ctgctgtgct agtaatcagc gagattccgt gggcgtagga       60
gcctccaagc caggtcctga agaaaatgaa gttgatgttt cagtgagaca cctgtatgcc      120
agagagtaaa aaggattatt gtggattcct gagaattttc tacatatgaa atcatgtcat      180
ctatgaacag agatgggact gtctcgttgg aggaaaacaa gctcagggct cccactgatt      240
ccacattatg ttgcaagctc ctacgaagct cccactca                              278

<210> SEQ ID NO 23
<211> LENGTH: 1743
<212> TYPE: DNA
<213> ORGANISM: Homo sapiens

<400> SEQUENCE: 23
tttctccgca tgcgcgggat cccggatgtg gatcaagttg gtgggaagcg tgcggtgccg       60
cagcaatggc ggcgctcaca attgccacgg gtactggcaa ttggttttcg gctttggcgc      120
tcggggtgac tcttctcaaa tgccttctca tccccacata ccattccaca gattttgaag      180
tacaccgaaa ctggcttgct atcactcaca gtttgccaat atcacagtgg tattatgagg      240
caacttcaga gtgacgttg gattacccccc ctttctttgc atggtttgag tatatcctgt      300
cacatgttgc caaatatttt gatcaagaaa tgctgaatgt ccataatttg aattactcca      360
gctcaaggac cttactttc cagagatttt ccgtcatctt tatggatgta ctctttgtgt       420
atgctgtccg tgagtgctgt aaatgcattg atggaaaaaa agtgggtaaa gaacttacag      480
aaaagccaaa atttattctg tcggtattac ttctgtggaa cttcgggtta ttaattgtgg      540
accatattca ttttcagtac aatggctttt tatttggatt aatgctactc tccattgcac      600
gattatttca gaaaaggcat atggaaggag cattttctctt tgctgttctc ctacatttca      660
agcatatcta cctctatgta gcaccagctt atggtgtata tctgctgcga tcctactgtt      720
```

```
tcactgcaaa taaaccagat gggtctattc gatggaagag tttcagccttt gttcgtgtta    780 tttccctggg actggttgtt ttcttagttt ctgctctttc attgggtcct ttcctggcct    840
tgaatcagct gcctcaagtc ttttcccgac tctttccttt caagaggggc ctctgtcatg    900
catattgggc tccaaacttc tgggctttgt acaatgcttt ggacaaagtg ctgtctgtca    960
tcggtttgaa attgaaattt cttgatccca acaatattcc caaggcctca atgacaagtg   1020
gtttggttca gcagttccaa cacacagtcc ttccctcagt gactcccttg caaccctca    1080 tctgcacact gattgccata ttgccctcta ttttctgtct ttggtttaaa ccccaagggc   1140
ccagaggctt ctccgatgt ctaactcttt gtgccttgag ctcctttatg tttgggtggc    1200
atgttcatga aaaagccata cttctagcaa ttctcccaat gagccttttg tctgtgggaa   1260
aagcaggaga cgcttcgatt tttctgattc tgaccacaac aggacattat tccctctttc   1320
ctctgctctt cactgcacca gaacttccca ttaaaatctt actcatgtta ctattcacca   1380
tatatagtat ttcgtcactg aagactttat tcagacggag tttcacccctt gttgcccagg   1440 ctggagtgca atggcacgat ctcagctaac tgaaacctcc gcctcccaga aagaaaaac   1500 ctctttttaa ttggatggaa actttctacc tgcttggcct ggggcctctg gaagtctgct   1560
gtgaatttgt attcccttc acctcctgga aggtgaagta cccccttcatc cctttgttac   1620 taacctcagt gtattgtgca gtaggcatca catatgcttg gttcaaactg tatgtttcag   1680
tattgattga ctctgctatt ggcaagacaa agaaacaatg aataaaggaa ctgcttagat   1740
atg                                                                 1743

<210> SEQ ID NO 24
<211> LENGTH: 1382
<212> TYPE: DNA
<213> ORGANISM: Homo sapiens

<400> SEQUENCE: 24
cattatgcta acagcataaa catgcagggg gtgggagcag ggtcacaaaa gtgagtgttg     60
tcaattctac ttggaatgaa aggttgaaat aatttaaaca gtacgggaaa tgcagagcaa    120
ttttctcctc tggtgacaat atagtgtcca acacttggaa gtgattttta agaatgttta    180
tttaaattaa aaggatggat ttccaaggaa aaaaataag gaaaggaaa gaaaaaactg     240 aacagaaaac gcaaagtat cagtttggtc actaacctt gcaaggatac cttttattt     300 tcttttaagat tcctgttgtt tatacacaga ttttaagttt actcctactg ctgacccaag    360
tgaaattcct tctccagtca cagtgtcaac ctctaccccc caactgcaac gagagttttg    420 agggggcatca atcacaccga gaagtcacag ccctcaacc actgaggtgt ggggggggtag    480 ggatctgcat ttcttcatat caaccccaca ctataggggca cctaaatggg tgggcggtgg    540
gggagaccga ctcacttgag tttcttgaag gcttcctggc ctccagccac gtaattgccc    600
ccgctctgga tctggtctag cttccggatt cggtggccag tccgcggggt gtagatgttc    660
ctgacggccc caagggtgc ctgaacgccg ccggtcacct ccttcaggaa gacttcgaag    720
ctggacacct tcttctcatg gatgacgacg cggcgcccg cgtagaaggg gtccccgttg     780
cggtacacaa gcacgctctt cacgacgggc tgagacaggt ggctggacct ggcgctgctg    840
ccgctcatct tccccgctgg ccgccgcctc agctcgctgc ttcgcgtcgg gaggcacctc    900
cgctgtccca gcggcctcac cgcacccagg gcgcgggatc gcctcctgaa acgaacgaga    960
aactgacgaa tccacaggtg aaagagaagt aacggccgtg cgcctaggcg tccacccaga   1020
ggagacacta ggagcttgca ggactcggag tagacgctca agttttttcac cgtggcgtgc   1080
```

| | |
|---|---|
| acagccaatc aggacccgca gtgcgcgcac cacaccaggt tcacctgcta cgggcagaat | 1140 |
| caaggtggac agcttctgag caggagccgg aaacgcgcgg ggccttcaaa caggcacgcc | 1200 |
| tagtgagggc aggagagagg aggacgcaca cacacacaca cacacaaata tggtgaaacc | 1260 |
| caatttctta catcatatct gtgctaccct ttccaaacag cctaattttt cttttctctc | 1320 |
| ttcttgcacc tttacccctc aatctcctgc ttcctcccaa attaaagcaa ttaagttcct | 1380 |
| gg | 1382 |

<210> SEQ ID NO 25
<211> LENGTH: 1163
<212> TYPE: DNA
<213> ORGANISM: Homo sapiens

<400> SEQUENCE: 25

| | |
|---|---|
| ctcctccgag cactcgctca cggcgtcccc ttgcctggaa agataccgcg gtccctccag | 60 |
| aggatttgag ggacagggtc ggaggggggct cttccgccag caccggagga agaaagagga | 120 |
| ggggctggct ggtcaccaga gggtggggcg gaccgcgtgc gctcggcggc tgcggagagg | 180 |
| gggagagcag gcagcgggcg gcggggagca gcatggagcc ggcggcgggg agcagcatgg | 240 |
| agccttcggc tgactggctg ccacggccg cggcccgggg tcgggtagag gaggtgcggg | 300 |
| cgctgctgga ggcgggggcg ctgcccaacg caccgaatag ttacggtcgg aggccgatcc | 360 |
| aggtcatgat gatgggcagc gcccgagtgg cggagctgct gctgctccac ggcgcggagc | 420 |
| ccaactgcgc cgaccccgcc actctcaccc gacccgtgca cgacgctgcc cgggagggct | 480 |
| tcctggacac gctggtggtg ctgcaccggg ccggggcgcg gctggacgtg cgcgatgcct | 540 |
| ggggccgtct gcccgtggac ctggctgagg agctgggcca tcgcgatgtc gcacggtacc | 600 |
| tgcgcgcggc tgcgggggc accagaggca gtaaccatgc ccgcatagat gccgcggaag | 660 |
| gtccctcaga catccccgat tgaaagaacc agagaggctc tgagaaacct cgggaaactt | 720 |
| agatcatcag tcaccgaagg tcctacaggg ccacaactgc ccccgccaca acccaccccg | 780 |
| ctttcgtagt tttcatttag aaaatagagc ttttaaaaat gtcctgcctt ttaacgtaga | 840 |
| tatatgcctt cccccactac cgtaaatgtc catttatatc atttttttata tattcttata | 900 |
| aaaatgtaaa aagaaaaac accgcttctg ccttttcact gtgttggagt tttctggagt | 960 |
| gagcactcac gccctaagcg cacattcatg tgggcatttc ttgcgagcct cgcagcctcc | 1020 |
| ggaagctgtc gacttcatga caagcatttt gtgaactagg gaagctcagg ggggttactg | 1080 |
| gcttctcttg agtcacactg ctagcaaatg gcagaaccaa agctcaaata aaaataaaat | 1140 |
| aattttcatt cattcactca aaa | 1163 |

<210> SEQ ID NO 26
<211> LENGTH: 3685
<212> TYPE: DNA
<213> ORGANISM: Homo sapiens

<400> SEQUENCE: 26

| | |
|---|---|
| agtggactca cgcaggcgca ggagactaca cttcccagga actccgggcc gcgttgttcg | 60 |
| ctggtacctc cttctgactt ccggtattgc tgcggtctgt agggccaatc gggagcctgg | 120 |
| aattgctttc ccggcgctct gattggtgca ttcgactagg ctgcctgggt tcaaaatttc | 180 |
| aacgatactg aatgagtccc gcggcgggtt ggctcgcgct tcgttgtcag atctgaggcg | 240 |
| aggctaggtg agccgtggga agaaaagagg gagcagctag ggcgcgggtc tccctcctcc | 300 |
| cggagtttgg aacggctgaa gttcaccttc cagcccctag cgccgttcgc gccgctaggc | 360 |

```
ctggcttctg aggcggttgc ggtgctcggt cgccgcctag gcggggcagg gtgcgagcag      420
gggcttcggg ccacgcttct cttggcgaca ggattttgct gtgaagtccg tccgggaaac      480
ggaggaaaaa aagagttgcg ggaggctgtc ggctaataac ggttcttgat acatatttgc      540
cagacttcaa gatttcagaa aagggqtgaa agagaagatt gcaactttga gtcagacctg      600
taggcctgat agactgatta aaccacagaa ggtgacctgc tgagaaaagt ggtacaaata      660
ctgggaaaaa cctgctcttc tgcgttaagt gggagacaat gtcacaagtt aaaagctctt      720
attcctatga tgccccctcg gatttcatca attttttcatc cttggatgat gaaggagata      780
ctcaaaacat agattcatgg tttgaggaga aggccaattt ggagaataag ttactgggga      840
agaatggaac tggagggctt tttcagggca aaactccttt gagaaaggct aatcttcagc      900
aagctattgt cacacctttg aaaccagttg acaacactta ctacaaagag gcagaaaaag      960
aaaatcttgt ggaacaatcc attccgtcaa atgcttgttc ttccctggaa gttgaggcag     1020
ccatatcaag aaaaactcca gcccagcctc agagaagatc tcttaggctt tctgctcaga     1080
aggatttgga acagaaagaa aagcatcatg taaaaatgaa agccaagaga tgtgccactc     1140
ctgtaatcat cgatgaaatt ctaccctcta agaaaatgaa agtttctaac aacaaaaaga     1200
agccagagga agaaggcagt gctcatcaag atactgctga aaagaatgca tcttccccag     1260
agaaagccaa gggtagacat actgtgcctt gtatgccacc tgcaaagcag aagtttctaa     1320
aaagtactga ggagcaagag ctggagaaga gtatgaaaat gcagcaagag gtggtggaga     1380
tgcggaaaaa gaatgaagaa ttcaagaaac ttgctctggc tggaataggg caacctgtga     1440
agaaatcagt gagccaggtc accaaatcag ttgacttcca cttccgcaca gatgagcgaa     1500
tcaaacaaca tcctaagaac caggaggaat ataaggaagt gaactttaca tctgaactac     1560
gaaagcatcc ttcatctcct gcccgagtga ctaagggatg taccattgtt aagcctttca     1620
acctgtccca aggaaagaaa gaacattttg atgaaacagt ttctacatat gtgccccttg     1680
cacagcaagt tgaagacttc cataaacgaa cccctaacag atatcatttg aggagcaaga     1740
aggatgatat taacctgtta ccctccaaat cttctgtgac caagatttgc agagacccac     1800
agactcctgt actgcaaacc aaacaccgtg cacgggctgt gacctgcaaa agtacagcag     1860
agctggaggc tgaggagctc gagaaattgc aacaatacaa attcaaagca cgtgaacttg     1920
atcccagaat acttgaaggt gggcccatct tgcccaagaa accacctgtg aaaccaccca     1980
ccgagcctat tggctttgat ttggaaattg agaaagaat ccaggagcga gaatcaaaga     2040
agaaaacaga ggatgaacac tttgaatttc attccagacc ttgccctact aagattttgg     2100
aagatgttgt gggtgttcct gaaaagaagg tacttccaat caccgtcccc aagtcaccag     2160
cctttgcatt gaagaacaga attcgaatgc ccaccaaaga agatgaggaa gaggacgaac     2220
cggtagtgat aaaagctcaa cctgtgccac attatggggt gcctttaaa ccccaaatcc     2280 cagaggcaag aactgtggaa atatgccctt tctcgtttga ttctcgagac aaagaacgtc     2340
agttacagaa ggagaagaaa ataaaagaac tgcagaaagg ggaggtgccc aagttcaagg     2400 cacttcccctt gcctcatttt gacaccatta acctgccaga gaagaaggta aagaatgtga     2460
cccagattga accttttctgc ttggagactg acagaagagg tgctctgaag gcacagactt     2520
ggaagcacca gctggaagaa gaactgagac agcagaaaga agcagcttgt ttcaaggctc     2580
gtccaaacac cgtcatctct caggagccct tgttcccaa gaaagagaag aaatcagttg     2640
ctgagggcct ttctggttct ctagttcagg aaccttttca gctggctact gagaagagag     2700
ccaaagagcg gcaggagctg gagaagagaa tggctgaggt agaagcccag aaagcccagc     2760
```

| | |
|---|---|
| agttggagga ggccagacta caggaggaag agcagaaaaa agaggagctg ccaggctac | 2820 |
| ggagagaact ggtgcataag gcaaatccaa tacgcaagta ccagggtctg gagataaagt | 2880 |
| caagtgacca gcctctgact gtgcctgtat ctcccaaatt ctccactcga ttccactgct | 2940 |
| aaactcagct gtgagctgcg gataccgccc ggcaatggga cctgctctta acctcaaacc | 3000 |
| taggaccgtc ttgctttgtc attgggcatg gagagaaccc atttctccag acttttacct | 3060 |
| acccgtgcct gagaaagcat acttgacaac tgtggactcc agttttgttg agaattgttt | 3120 |
| tcttacatta ctaaggctaa taatgagatg taactcatga atgtctcgat tagactccat | 3180 |
| gtagttactt cctttaaacc atcagccggc ctttttatatg ggtcttcact ctgactagaa | 3240 |
| tttagtctct gtgtcagcac agtgtaatct ctattgctat tgccccttac gactctcacc | 3300 |
| ctctccccac tttttttaaa aatttttaacc agaaaataaa gatagttaaa tcctaagata | 3360 |
| gagattaagt catggtttaa atgaggaaca atcagtaaat cagattctgt cctcttctct | 3420 |
| gcataccgtg aatttatagt taaggatccc tttgctgtga gggtagaaaa cctcaccaac | 3480 |
| tgcaccagtg aggaagaaga ctgcgtggat tcatggggag cctcacagca gccacgcagc | 3540 |
| aggctctggg tggggctgcc gttaaggcac gttctttcct tactggtgct gataacaaca | 3600 |
| gggaaccgtg cagtgtgcat tttaagacct ggcctggaat aaatacgttt tgtctttccc | 3660 |
| tcaaaaaaaa aaaaaaaaaa aaaaa | 3685 |

<210> SEQ ID NO 27
<211> LENGTH: 823
<212> TYPE: DNA
<213> ORGANISM: Homo sapiens

<400> SEQUENCE: 27

| | |
|---|---|
| aaacgcgggc gggcgggccc gcagtcctgc agttgcagtc gtgttctccg agttcctgtc | 60 |
| tctctgccaa cgccgcccgg atggcttccc aaaaccgcga cccagccgcc actagcgtcg | 120 |
| ccgccgcccg taaggagct gagccgagcg ggggcgccgc ccggggtccg gtgggcaaaa | 180 |
| ggctacagca ggagctgatg accctcatga tgtctggcga taagggatt tctgccttcc | 240 |
| ctgaatcaga caacctttc aaatgggtag ggaccatcca tggagcagct ggaacagtat | 300 |
| atgaagacct gaggtataag ctctcgctag agttccccag tggctaccct tacaatgcgc | 360 |
| ccacagtgaa gttcctcacg ccctgctatc accccaacgt ggacacccag ggtaacatat | 420 |
| gcctggacat cctgaaggaa aagtggtctg ccctgtatga tgtcaggacc attctgctct | 480 |
| ccatccagag cctttctagga gaacccaaca ttgatagtcc cttgaacaca catgctgccg | 540 |
| agctctggaa aaaccccaca gcttttaaga agtacctgca agaaacctac tcaaagcagg | 600 |
| tcaccagcca ggagccctga cccaggctgc ccagcctgtc cttgtgtcgt cttttaatt | 660 |
| tttccttaga tggtctgtcc tttttgtgat ttctgtatag gactctttat cttgagctgt | 720 |
| ggtattttg ttttgttttt gtcttttaaa ttaagcctcg gttgagccct tgtatattaa | 780 |
| ataaatgcat ttttgtcctt ttttagacaa aaaaaaaaaa aaa | 823 |

<210> SEQ ID NO 28
<211> LENGTH: 3018
<212> TYPE: DNA
<213> ORGANISM: Homo sapiens

<400> SEQUENCE: 28

| | |
|---|---|
| cagctaaatt ttaaaggtgt ttttgtagag atgaggtttc actatattgc ccaggctggt | 60 |
| ctcgaactcc tggacttaag tgatccttcc tctttggcct cccaaagtgc tgggattaca | 120 |

```
ggcatgagcc actgccccag ccaagactgt cttttctcca ttgtattgcg tttgcttcct    180
tgtcaaagat cagttgacta tatttgtgtg gggctatttc tgggctccct atttgtttcc    240
agtgattatg tctattttt caccattacc accctatctt aattactgta gctttatagt     300
gagtcttaaa gttgggtaat atcagtcttc tgaccttttt ctctttcaat attgtgccag    360
ctattctggg tcttttgcct ttccatgtaa actttagaac cagtttgtca ggatccacaa    420
aatactttgc tgggttttga ttgggattgc attgaatcca caggtcaagt tggcaaaaac    480
tgacatacag caatgccagt ttattgtttt gtgatagcct taatccagct agtttcttca    540
caggatgatg ttgaaaatat gggatgctca taatccctga atattttta tgtggataat     600
taaacttgtt ctgggtggat ggttggatag ccagaatagt aataacctct cttccagcca    660
ctcaaagaaa atgatataaa cgtagggttg gtttaattgt tgagaggtca cgttttttcc    720
attcttgctc tcaggtaagg aaagagcact gttggttcac gcattccttt ttccctcata    780
cactttgttg ggcactgata tggtttggct ctgtgttccc acccaaatct catgttgaat    840
tgtgatcctg agtgttggag gtggggcctc gcgggagacg actggatcat ggggggcgat    900
tttccccttg ctgttctcat gatagtgagt tctcatgaga tctggttgtt taaaagtgta    960
tagcacttcc tgcttcactc tctcccactc caccatgtga agaaggtgcc tttgcccttc    1020
cgccacgact gtgtttcctg aggcctcccc agccatgcct cctgtacagc ctgcggaact    1080
gtcagttaaa cctctttttct tcattaatta cccactctca ggtggttttt tatggcagtg    1140
tgagaacgga ctaatacaga aaattggtac cagagaagtg ggatattgct ataaaatacc    1200
tgaaaatgtg gaagtgactt tggaactggg taatgggcag aggttggaac agtttggagg    1260
gctcagaaga agacaggaag atgagggaaa gtttgcagct tcctagagac ttgttgaatg    1320
gttgtgacca aagtgctgat agtgatatgg acagtgaagt ccaggctgag ttggtctcag    1380
atggagatg agaatcttat tccgaactgg agtgaaggtc actcttggct gtgctttagc     1440
aaagagagtg gtggcattgt gcccctgctc tagagatctg tgaactctga actcgagagg    1500
gtatctggca gaaaaaaatt tctaagcagc aaagtgttca agatgtggcc tgattgcttc    1560
taaaagccta tgctcatttg catgaacaaa gtggaactta tatttaaaac agaagctgag    1620
cttttataaa agtttggaga atttgcagcc caaccatgtg gtgaaaaaga aaaatccatt    1680
ttctggggag gtattcaagg ctgcagaaat ttgcataaga agagcctcat gttaacagcc    1740
aagagagtga ggaaaatgcc tctagagcat ttcagagacc ttcacagcag ctcctcccat    1800
cacaggcatg gaagcccagg aggaagaaat gcttttgtgg gccagcccag ggccccactg    1860
ttctgtgcag ccttgggaca tggtgccctg catcccagcc actccagctc cagctgtgac    1920
taaaaggggc caaggtacag cttgggctgc tgcttcagag ggtgcaagcc ccaagccttg    1980
gtggcttcca tgtggtgtta ggcaggtgtg cagaagagtt gaggtttagg aacctctacc    2040
tagatttcag aggatgtatg gaaatgcccg gatgtccagg cagaagtttg ctgcagaggc    2100
agagccctca tagataacct ctgcgagggc agtgtggagg ggaaatgtgg ggttggagct    2160
atgagaagag ggccaccatc caccagaccc cagaattgta gatccactga cagcttgcac    2220
tatgcacctg taaaagttgc aggcagttaa tgctagcctg tgaaagcagc tgtggggact    2280
atatgcagag ccacagaggc agagctgccc agagccttgg gagcccactc cttgtgtcag    2340
tgtggcctgg atgtgagacg tggagtcaaa gatcattttg gaggtttgag atttaatgac    2400
tgccctcctg gatttggac ttgcatgggg cccatagccc ctttgttttg gctgatttct     2460
cctatttgga atgggagcat ttacccaatg cctgtatccc cattgtatct tggagataac    2520
```

| | |
|---|---:|
| tgacttgttt ttgattttac aggctcacag gaggaaggga cttggctggt ctcagatgag | 2580 |
| acttgacttg gacatttgag ttaatgctgg aatgagttaa gactttaggg ggctattggg | 2640 |
| aaggcatgat tgtgttttga aatgtgagga catgagattt gggaggggcc agggtggaat | 2700 |
| gatatggttt ggctgtgtcc ccccacccaa atctcatgtt gaattgtgat cctgagtctt | 2760 |
| ggaggtagag cctggtggga ggtgattgga tcatggggc agatttcccc cttgctgttc | 2820 |
| tcatgacagt gagttctcat gagatctggt taagtgtgta gcacttcccc cttttgcttgc | 2880 |
| tctctccctc tgccatgtga agaaggtgct tgctttccct tcgcccttct gccatgactg | 2940 |
| taagtttctt gaggcctcgc agccatgctt cctgtacagc ctgcagaact gtgagttaat | 3000 |
| taaacctctt ttcttcat | 3018 |

<210> SEQ ID NO 29
<211> LENGTH: 969
<212> TYPE: DNA
<213> ORGANISM: Homo sapiens

<400> SEQUENCE: 29

| | |
|---|---:|
| agctttgggg ttgtccctgg acttgtcttg gttccagaac ctgacgaccc ggcgacggcg | 60 |
| acgtctcttt tgactaaaag acagtgtcca gtgctccagc ctaggagtct acggggaccg | 120 |
| cctcccgcgc cgccaccatg cccaacttct ctggcaactg gaaaatcatc cgatcggaaa | 180 |
| acttcgagga attgctcaaa gtgctggggg tgaatgtgat gctgaggaag attgctgtgg | 240 |
| ctgcagcgtc caagccagca gtggagatca acaggaggg agacactttc tacatcaaaa | 300 |
| cctccaccac cgtgcgcacc acagagatta acttcaaggt tggggaggag tttgaggagc | 360 |
| agactgtgga tgggaggccc tgtaagagcc tggtgaaatg ggagagtgag aataaaatgg | 420 |
| tctgtgagca gaagctcctg aagggagagg gccccaagac ctcgtggacc agagaactga | 480 |
| ccaacgatgg ggaactgatc ctgaccatga cggcggatga cgttgtgtgc accagggtct | 540 |
| acgtccgaga gtgagtggcc acaggtagaa ccgcggccga agcccaccac tggccatgct | 600 |
| caccgccctg cttcactgcc ccctccgtcc caccccctcc ttctaggata gcgctcccct | 660 |
| taccccagtc acttctgggg gtcactggga tgcctcttgc agggtcttgc tttctttgac | 720 |
| ctcttctctc ctccctaca ccaacaaaga ggaatggctg caagagccca gatcacccat | 780 |
| tccgggttca ctccccgcct ccccaagtca gcagtcctag ccccaaacca gcccagagca | 840 |
| gggtctctct aaaggggact tgagggcctg agcaggaaag actggccctc tagcttctac | 900 |
| cctttgtccc tgtagcctat acagtttaga atatttattt gttaatttta ttaaaatgct | 960 |
| ttaaaaaaa | 969 |

<210> SEQ ID NO 30
<211> LENGTH: 496
<212> TYPE: DNA
<213> ORGANISM: Homo sapiens

<400> SEQUENCE: 30

| | |
|---|---:|
| ctcgcttttc ggttgccgtt gtcttttttc cttgactcgg aaatgtccgg tcgtggtaag | 60 |
| cagggtggca aggcgcgcgc caaggctaag tcgcgctcgt cgcgcgcggg gctgcagttc | 120 |
| cccgtgggcc gcgtgcaccg gttgctccgc aagggcaact attcggagcg cgtgggcgcc | 180 |
| ggcgccccgg tctatctggc cgcggtgctc gagtacttga ctgccgagat cctggagctt | 240 |
| gccggcaacg cggcgcgcga caacaagaag acgcgcatca tcccgcgcca cctgcagctg | 300 |
| gccatccgca acgacgagga gctcaacaag ctgctgggcc gcgtgaccat cgcgcagggt | 360 |

| | |
|---|---|
| ggcgtcctgc ccaacatcca ggccgtactg ctgcccaaga agacggagag ccaccacaag | 420 |
| gccaagggca agtgaggccg cccgccgccc ccggggcccc tttgatggac ataaaggctc | 480 |
| ttttcagagc caccta | 496 |

<210> SEQ ID NO 31
<211> LENGTH: 374
<212> TYPE: DNA
<213> ORGANISM: Homo sapiens

<400> SEQUENCE: 31

| | |
|---|---|
| atgtctggcc gtggtaaagg tggaaaaggt ttgggtaagg gaggagctaa gcgtcatcgc | 60 |
| aaggttttgc gcgataacat ccagggcatc actaagccag ctatccggcg ccttgctcgt | 120 |
| cgcggcggtg tcaagcgaat ttctggcctt atctatgagg agactcgtgg tgttctgaag | 180 |
| gtgttcctgg agaacgtgat tcgtgacgct gtcacttaca cagagcacgc caaacgcaag | 240 |
| accgtgacag caatggatgt ggtctacgcg ctgaagcgac aggacgcac tctttacggc | 300 |
| ttcggtggct aaggctcctg cttgctgcac tcttattttc attttcaacc aaaggccctt | 360 |
| ttcagggccg ccca | 374 |

<210> SEQ ID NO 32
<211> LENGTH: 2319
<212> TYPE: DNA
<213> ORGANISM: Homo sapiens

<400> SEQUENCE: 32

| | |
|---|---|
| gcctccacag atatcaaaag aaacctgaag agcctacaaa aaaaaagag ataaagacaa | 60 |
| aattcaagaa aacacacaca tacataattg tggtcacctg gagcctgggg gccggcccag | 120 |
| ctctctcagg attcagcaga cattggaggt ggcagtgaag gatacagtgg tagtcaatgt | 180 |
| tatttgagca gggtcagcag gccctggagc ttcctgagtg cacaatgcag aaggctgctt | 240 |
| actatgaaaa cccaggactg tttggaggct atggctacag caaaactacg gacacttacg | 300 |
| gctacagcac cccccaccag ccctacccac cccctgctgc tgccagctcc ctggacactg | 360 |
| actatccagg ttctgcctgc tccatccaga gctctgcccc tctgagagcc ccagcccaca | 420 |
| aaggagctga actcaatggc agctgcatgc ggccgggcac tgggaacagc cagggtgggg | 480 |
| gtggtggcag ccagcctcct ggtctgaact cagagcagca gccaccacaa ccccctcctc | 540 |
| caccaccgac cctgccccca tcttcaccca ccaatcctgg aggtggagtg cctgccaaga | 600 |
| agcccaaagg tgggcccaat gcttctagct cctcagccac catcagcaag cagatcttcc | 660 |
| cctggatgaa agagtctcga cagaactcca gcagaagaa cagctgtgcc actgcaggag | 720 |
| agagctgcga ggacaagagc ccgccaggcc cagcatccaa gcgggtacgc acggcataca | 780 |
| cgagcgcgca gctggtggaa ttggaaaagg aattccactt caaccgctac ttgtgccggc | 840 |
| cgcgccgcgt ggagatggcc aacctgctga atctcacgga acgccagatc aagatctggt | 900 |
| tccagaaccg gcgcatgaag tacaagaagg accagaaggc caagggcatc ctgcactcgc | 960 |
| cggctagcca gtcccctgag cgcagcccac cgctcggcgg cgccgctggc cacgtggcct | 1020 |
| actccggcca gctgccgcca gtgcccggcc tggcctacga cgcgccctcg ccgcctgctt | 1080 |
| tcgccaaatc acagcccaat atgtacgcc tggccgccta cacggcgcca ctcagcagct | 1140 |
| gcctgccaca acagaagcgc tacgcagcgc cggagttcga gccccatccc atggcgagca | 1200 |
| acggcggcgg cttcgccagc gccaacttgc agggcagccc ggtgtacgtg ggcggcaact | 1260 |
| tcgtcgagtc catggcgccc gcgtccgggc ctgtcttcaa cctgggccac ctctcgcacc | 1320 |

```
cgtcgtcggc cagcgtggac tacagttgcg ccgcgcagat tccaggcaac caccaccatg   1380
gaccttgcga ccctcatccc acctacacga atctctcggc ccaccactcg tctcagggac   1440
gactgccgga ggctcccaaa ctgacgcatc tgtagcggcc gccgccagcc cgaactcgcg   1500
gcaaaattac ctctcttgct gtagtggtgg ggtagagggt ggggcccgcg gggcagttcg   1560
ggaaccccct tccccgctct tgccctgccg ccgcctcccg ggtctcaggc ctccagcggc   1620
ggaggcgcag gcgaccgggc ctcccctcca tgggcgtcct ttgggtgact cgccataaat   1680
cagccgcaag gatccttccc tgtaaatttg acagtgccac atactgcgga ccaagggact   1740
ccaatctggt aatggtgtcc caaaggtaag tctgagaccc atcagcggcg cgccctgcag   1800
agggaccaga gcttggagag tcttgggcct ggcccgcgtc tagcttagtt tcagagacct   1860
taatttatat tctccttcct gtgccgtaag gattgcatcg gactaaacta tctgtattta   1920
ttatttgaag cgagtcattt cgttccctga ttatttatcc ttgtctgaat gtatttatgt   1980
gtatatttgt agatttatcc agccgagctt aggaattcgc ttccaggccg tgggggccac   2040
atttcacctc cttagtcccc ctggtctgaa ctagttgaga gagtagtttt gaacagtcgt   2100
aaccgtggct ggtgtttgta gttgacataa aggattaaga ccgcaaattg tccttcatgg   2160
gtagagtcag gaagcccggt ggcgtggcac aacacacttt ggtcatttct caaaaaccac   2220
agtcctcacc acagtttatt gatttcaaat tgtctggtac tattggaaca aatatttaga   2280
ataaaaaaat ttcccagtca aaaaaaaaaa aaaaaaaa                           2319

<210> SEQ ID NO 33
<211> LENGTH: 1702
<212> TYPE: DNA
<213> ORGANISM: Homo sapiens

<400> SEQUENCE: 33
ccagccctga gattcccagg tgtttccatt cggtgatcag cactgaacac agaactcacc     60
atggagtttg gactgagctg ggttttcctt gttgctattt taaaaggtgt ccagtgtgaa    120
gtgcagctgg tggagtctgg gggagtcgtg gtacagcctg ggggtccct gagactctcc    180 tgtgcagcct ctggattcac cttttgatgac tatgccatgc actgggtccg tcaagctccg    240
gggaagggtc tggagtgggt ctcccttatt agttgggatg gtggtagcac ctactatgca    300
gactctgtga agggtcgatt caccatctcc agagacaata gtaaaaattc cttgtatctg    360
caaatgaaca gtctgagagc tgaggacacc gccttgtatt actgtgcaac ccggggggt    420 tattccaccg ccggctttga ctactggggc caggaacccc tggtcaccgt ctcctcagcc    480
tccaccaagg gcccatcggt cttccccctg gcaccctcct ccaagagcac ctctggggc    540 acagcggccc tgggctgcct ggtcaaggac tacttccccg aaccggtgac ggtgtcgtgg    600
aactcaggcg ccctgaccag cggcgtgcac accttcccgg ctgtcctaca gtcctcagga    660
ctctactccc tcagcagcgt ggtgaccgtg ccctccagca gcttgggcac ccagacctac    720
atctgcaacg tgaatcacaa gcccagcaac accaaggtgg acaagaaagt tgagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ccagccccca tcgagaaaac catctccaaa   1140
```

```
gccaaagggc agccccgaga accacaggtg tacaccctgc ccccatcccg ggatgagctg    1200
accaagaacc aggtcagcct gacctgcctg gtcaaaggct tctatcccag cgacatcgcc    1260
gtggagtggg agagcaatgg gcagccggag aacaactaca agaccacgcc tcccgtgctg    1320
gactccgacg gctccttctt cctctacagc aagctcaccg tggacaagag caggtggcag    1380
caggggaacg tcttctcatg ctccgtgatg catgaggctc tgcacaacca ctacacgcag    1440
aagagcctct ccctgtctcc gggtaaatga gtgcgacggc cggcaagccc ccgctccccg    1500
ggctctcgcg gtcgcacgag gatgcttggc acgtaccccg tgtacatact tcccgggcgc    1560
ccagcatgga aataaagcac ccagcgctgc cctgggcccc tgcgaaaaaa aaaaaaaaa     1620 aaaaaaaaaa aaaaaaaaaa aaaaaaaaaa aaaaaaaaaa aaaaaaaaaa aaaaaaaaaa    1680
aaaaaaaaaa aaaaaaaaaa aa                                             1702

<210> SEQ ID NO 34
<211> LENGTH: 975
<212> TYPE: DNA
<213> ORGANISM: Homo sapiens

<400> SEQUENCE: 34
gagggaacca tggaaacccc agcgcagctt ctcttcctcc tgctactctg gctcccagat      60
atcaccggag aaattgtgtt gacgcagtct ccaggcaccc tgtctttgtc tccaggagaa     120
agagccgccc tctcatgcag ggccagtcag agtgttaaca gcaagtactt agcctggtac     180
cagcagaagc ctggccaggc tcccaggctc ctcatgtatg ctgcatccat cagggccact     240
ggcatcccag acaggttcag tggcagtggg tctgggacag acttcactct caccatcagc     300
agactggaat ctgaggactt tgcactgtat ttctgtcagc aatatggtac ttcacctctc     360
actttcggcg gagggaccaa ggtggagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc gcccgtcaca aagagcttca caggggaga gtgttagagg      720 gagaagtgcc cccacctgct cctcagttcc agcctgaccc cctcccatcc tttggcctct     780
gacccttttt ccacagggga cctaccccta ttgcggtcct ccagctcatc tttcacctca     840 ccccctcct cctccttggc tttaattatg ctaatgttgg aggagaatga ataaataaag     900
tgaatctttg cacctaaaaa aaaaaaaaaa aaaaaaaaaa aaaaaaaaaa aaaaaaaaaa     960
aaaaaaaaaa aaaaa                                                     975

<210> SEQ ID NO 35
<211> LENGTH: 4006
<212> TYPE: DNA
<213> ORGANISM: Homo sapiens

<400> SEQUENCE: 35
acgcgggggg cccgctctcg gcgagcccga gccgccgccg gccccgcggc ggagatgagc      60
aggtccgcga cgctgctgct gtgcctgctg ggctgccacg tctggaaggc ggtgaccaag     120
acgctgcggg agcccggcgc cggagcccaa gaggtgacgt taaaggtgca catcagcgac     180
gccagcaccc accagcccgt agcagatgcg ctcatcgaga tcttcaccaa ccaggcctcc     240
atagcctctg gcacctcggg gactgatggc gtcgccttta tcaagttcca gtataagctg     300
```

```
ggcagtcagt tgattgtcac cgcctcgaag catgcctacg tgccaaactc tgccccatgg    360
aagccaatcc ggttacctgt attttcctct ctgagccttg gcctgcttcc agaacgctct    420
gccactctaa tggtatatga agatgtcgtc caaatagtat caggattcca aggtgcccgg    480
ccacagcctc gcgttcattt ccagagaagg gctctgaggt tgcctgagaa caccagctac    540
agtgacctga ccgcgtttct cacggccgcc agctccccCt cggaggtgga cagttttcct    600
tatttgcgag gattagacgg aaatggaaca ggaaacagca ccaggcatga cctgacccca    660
gtcacagccg tcagcgtcca cttgctgagc agtaatggaa cgccggtgct ggtggatggt    720
cccatctatg tcactgtgcc cctggccacg cagagcagcc tgaggcacaa tgcctatgtc    780
gcggcgtggc ggtttgacca aagctgggaa cgtggctga agagcggtct gggtcttgtg    840
caccaggaag gcagccagct gacgtggaca tacattgccc ccagttgggg gtactgggtg    900
gccgccatgt cccctcccat cccaggtccc gttgtaacac aggacattac cacgtatcac    960
acggtgtttc ttttggccat tttaggagga atggcttttca tactttttggt tttgctgtgt   1020 ctccttttat attattgcag gaggaagtgc ttgaaacctc gtcagcacca cagaaaactg   1080
cagctccctg caggactgga gagttccaaa agagaccagt ccacgtccat gtcacacatt   1140
aacttgctgt tttcacgccg agcgtcagaa ttccctggcc cgctgtccgt caccagccac   1200
ggccgcccCg aggccccCgg cacgaaggaa ctgatgagtg gagtccattt ggaaatgatg   1260
tctccgggcg gcgaagggga cctgcacacc cccatgctca agctctccta cagcacctcc   1320 caggaatttta gctcccggga ggagctcctc tcttgcaagg aagaggataa aagccagatc   1380
tcctttgata acctcactcc aagtgggacg ctggggaaag actaccataa gtcagtggag   1440 gttttttccct taaaggcaag aaaatctatg gaaagagaag gctacgagtc ctcgggcaat   1500
gatgactaca ggggtagtta caacaccgtg ctctcacagc ctttatttga aaagcaggac   1560
agagaaggtc cagcctccac gggaagcaaa ctcaccattc aggaacatct gtaccccgcg   1620
ccttcatcac ctgagaaaga acagctgctg gaccgcagac ccactgaatg tatgatgtcg   1680
cgatcagtag atcacctcga gagacctacg tccttcccac ggcccggcca gttaatctgc   1740
tgcagttctg tcgaccaggt caatgacagc gtttacagga aagtactgcc tgccttggtc   1800
atcccggctc attatatgaa actccccggg gaccactcct atgtcagcca gcccctcgtc   1860
gtcccggctg atcagcagct tgagatagaa agactacagg ctgagctgtc caatccccat   1920
gccgggatct tcccacaccc gtcctcacag atccagcccc agccctgtc ttcccaggcc   1980 atctctcagc agcacctgca ggatgcgggc acccggggagt ggagccctca gaacgcatcc   2040
atgtcggagt ctctctccat cccagcttcc ctgaacgacg cggctttggc tcagatgaac   2100
agtgaggtgc agctcctgac tgaaaaggcc ctgatggagc ttggggggtgg gaagccgctt   2160 ccgcaccccc gggcgtggtt cgtctccttg gatggcaggt ccaacgctca cgttagacat   2220
tcatacattg atctccaaag agctggaagg aacggaagta atgatgccag tttggactct   2280
ggcgtagata tgaatgaacc aaaatcagcc cggaagggaa ggggagatgc tttgtctctg   2340
cagcagaact acccgcccgt ccaagagcac cagcagaaag agcctcgagc cccagacagc   2400
acggcctaca cgcagctcgt gtacctggat gacgtggaac agagtggtag cgaatgtggg   2460
accacggtct gtaccccga ggacagtgcc ctgcgatgct tgttggaggg gtcgagtcgg   2520
agaagtggtg gccagctgcc cagcctgcag gaggagacga ccagacggac tgcggatgcc   2580
ccctcggagc cagcagccag cccccaccag agaagatctg cccacgagga gaggaagac   2640 gatgatgatg atgaccaagg agaagacaag aaaagcccct ggcagaaacg ggaggagagg   2700
```

-continued

| | |
|---|---|
| cccctgatgg cgtttaacat taaatgagct atcgcagacc cacctgactg tggaatataa | 2760 |
| aattgccaaa tatcctttct catgaagcg cgtacccgtt cgtggaggaa acggaacggc | 2820 |
| agcccagccg tgggacggac gtggacgttt actgcattcc tgtttgccgt gtaaatgtta | 2880 |
| gaaaggaatt aaagttatta ctcggaataa aggatgactt tggcggatgt cgcccctgca | 2940 |
| aggaggtggc tgaaagtggt gtccagatgt ccttccgagg actcggcgta ccgccacca | 3000 |
| gggacattaa gaaaccgcac gtgatgtcgc tatgctctaa cgatcacctc agttctccct | 3060 |
| cggattctgg gaacagatga aacttttgc atcgcttgag tcattttat cacaataatc | 3120 |
| ctactgtgaa gctgtcgttg agaacttagg ttggcacgta gcgtctcaag gtatgcgttc | 3180 |
| tctcaaagga aagctatgca tcgctgcttc tttgtctgat tttgcttaga ttttgctttg | 3240 |
| gttaggttgc gttttggggt ttgccttttt tgttgtcgc ttaaatgcaa tttggttgta | 3300 |
| aagatttgat tcctttgtgt tcatctgttc cgcttctcag cggtccatct cagcgtctcc | 3360 |
| cttcaggaac cgctgagtgt cctctcttaa catccaagcc ttttaatgaa atcgtactga | 3420 |
| aatctgtatc agctaagagt cctccaatcc tggtcccatt aactccaagt gccttttgt | 3480 |
| cagtgacaac agacagtccc tcgcttttg ttgttgttgg ttttcttaac ccctttaatg | 3540 |
| gaactgcctg gattttatac agttattaaa ggatgtctct tttgctttaa actgcatgct | 3600 |
| gccaagtgcc atttggggtc agcatcctcg tttcaacaca gtgtgctctc tagttatcat | 3660 |
| gtgtaacgtg ggttctgttt agcgaagata gactagagga cacgttagag atgcccttcc | 3720 |
| ctgctccatc cctgtggcac cattatggtt ttttggctgt tgtatatac ggttacgtat | 3780 |
| taactctgga atcctatggg ctcatcttgc tcacccaatg tgggagtctg gtttgagcaa | 3840 |
| gcgagctgaa tgtgactatt aaaaaaaatt taaaaaaaaa aagaaaaatc ttatgtacta | 3900 |
| tccaaaagtg ccagaatgac tcttctgtgc attcttctta aagagctgct tggttatcca | 3960 |
| aaaatgaaaa ttcaaaataa actctgaaaa aaaaaaaa aaaaaa | 4006 |

<210> SEQ ID NO 36
<211> LENGTH: 1807
<212> TYPE: DNA
<213> ORGANISM: Homo sapiens

<400> SEQUENCE: 36

| | |
|---|---|
| cgtcacttcc tgttgcctta ggggaacgtg gctttccctg cagagccggt gtctccgcct | 60 |
| gcgtccctgc tgcagcaacc ggagctggag tcggatcccg aacgcaccct cgccatggac | 120 |
| tcggccctca gcgatccgca taacggcagt gccgaggcag gcggcccac caacagcact | 180 |
| acgcggccgc cttccacgcc cgagggcatc gcgctggcct acggcagcct cctgctcatg | 240 |
| gcgctgctgc ccatcttctt cggcgccctg cgctccgtac gctgcgcccg cggcaagaat | 300 |
| gcttcagaca tgcctgaaac aatcaccagc cgggatgccg cccgcttccc catcatcgcc | 360 |
| agctgcacac tcttggggct ctacctcttt ttcaaaatat tctcccagga gtacatcaac | 420 |
| ctcctgctgt ccatgtattt cttcgtgctg ggaatcctgg ccctgtccca caccatcagc | 480 |
| cccttcatga ataagttttt tccagccagc ttttccaaatc gacagtacca gctgctcttc | 540 |
| acacagggtt ctggggaaaa caaggaagag atcatcaatt atgaatttga caccaaggac | 600 |
| ctggtgtgcc tgggcctgag cagcatcgtt ggcgtctggt acctgctgag gaagcactgg | 660 |
| attgccaaca accttttggg cctggccttc tcccttaatg gagtagagct cctgcacctc | 720 |
| aacaatgtca gcactggctg catcctgctg ggcggactct tcatctacga tgtcttctgg | 780 |
| gtatttggca ccaatgtgat ggtgacagtg gccaagtcct tcgaggcacc aataaaattg | 840 |

```
gtgtttcccc aggatctgct ggagaaaggc ctcgaagcaa acaactttgc catgctggga      900
cttggagatg tcgtcattcc agggatcttc attgccttgc tgctgcgctt tgacatcagc      960
ttgaagaaga atacccacac ctacttctac accagctttg cagcctacat cttcggcctg     1020
ggccttacca tcttcatcat gcacatcttc aagcatgctc agcctgccct cctatacctg     1080
gtccccgcct gcatcggttt tcctgtcctg gtggcgctgg ccaagggaga agtgacagag     1140
atgttcagct acgagtcctc ggcggaaatc ctgcctcata ccccgaggct cacccacttc     1200
cccacagtct cgggctcccc agccagcctg gccgactcca tgcagcagaa gctagctggc     1260
cctcgccgcc ggcgcccgca gaatcccagc gccatgtaat gcccagcggg tgcccacctg     1320
cccgcttccc cctactgccc cggggcccaa gttatgagga gtcaaatcct aaggatccag     1380
cggcagtgac agaatccaaa gagggaacag aggcatcagc atcgaagggg ctggagaaga     1440
aagagaaatg atgcagctgg tgcccgagcc tctcagggcc agaccagaca gatgggggct     1500
gggcccacac aggcgtgcac cggtagaggg cacaggaggc caagggcagc tccaggacag     1560
ggcagggggc agcaggatac ctccagccag gcctctgtgg cctctgtttc cttctcccctt    1620 tcttggccct cctctgctcc tccccacacc ctgcaggcaa agaaacccc cagcttcccc      1680 cctccccggg agccaggtgg gaaaagtggg tgtgattttt agattttgta ttgtggactg     1740
attttgcctc acattaaaaa ctcatcccat ggccagggcg ggccactgtg ctcctggaaa     1800
aaaaaaa                                                              1807

<210> SEQ ID NO 37
<211> LENGTH: 220
<212> TYPE: DNA
<213> ORGANISM: Homo sapiens

<400> SEQUENCE: 37
tgcctcagtc tctcactgtg ccttatgccc ctcagctgaa ttctttcttc tgagcaggca       60
ggaattgagg ttgctgcaga cgtgtatgca tttgccacca gtaacatact ttggtgccac      120
atgactagga tatgttctct agtgctaaca tgttcgttta cagttcttag gactccctga      180
tagaaaaaaa cacaaaaaaa aacacaaaaa aacccaacca                           220

<210> SEQ ID NO 38
<211> LENGTH: 2058
<212> TYPE: DNA
<213> ORGANISM: Homo sapiens

<400> SEQUENCE: 38
gttgggaaag agcagcctgg gcggcagggg cggtggctgg agctcggtaa agctcgtggg       60
accccattgg gggaatttga tccaaggaag cggtgattgc cggggagga gaagctccca      120 gatccttgtg tccacttgca gcggggagg cggagacggc ggagcgggcc ttttggcgtc       180
cactgcgcgc ctgcaccctg ccccatcctg ccggatcat ggtctgcggc agcccggag        240 ggatgctgct gctgcgggcc gggctgcttg ccctggctgc tctctgcctg ctccgggtgc      300
ccggggctcg ggctgcagcc tgtgagcccg tccgcatccc cctgtgcaag tccctgccct      360
ggaacatgac taagatgccc aaccacctgc accacagcac tcaggccaac gccatcctgg      420
ccatcgagca gttcgaaggt ctgctgggca cccactgcag cccgatctg ctcttcttcc       480 tctgtgccat gtacgcgccc atctgcacca ttgacttcca gcacgagccc atcaagccct      540
gtaagtctgt gtgcgagcgg gcccggcagg gctgtgagcc catactcatc aagtaccgcc      600
actcgtggcc ggagaacctg gcctgcgagg agctgccagt gtacgacagg ggcgtgtgca      660
```

```
tctctcccga ggccatcgtt actgcggacg gagctgattt tcctatggat tctagtaacg      720
gaaactgtag aggggcaagc agtgaacgct gtaaatgtaa gcctattaga gctacacaga      780
agacctattt ccggaacaat tacaactatg tcattcgggc taaagttaaa gagataaaga     840
ctaagtgcca tgatgtgact gcagtagtgg aggtgaagga gattctaaag tcctctctgg      900
taaacattcc acgggacact gtcaacctct ataccagctc tggctgcctc tgccctccac      960
ttaatgttaa tgaggaatat atcatcatgg gctatgaaga tgaggaacgt tccagattac     1020
tcttggtgga aggctctata gctgagaagt ggaaggatcg actcggtaaa aaagttaagc     1080
gctgggatat gaagcttcgt catcttggac tcagtaaaag tgattctagc aatagtgatt     1140
ccactcagag tcagaagtct ggcaggaact cgaaccccg gcaagcacgc aactaaatcc      1200
cgaaatacaa aaagtaacac agtggacttc ctattaagac ttacttgcat tgctggacta     1260
gcaaaggaaa attgcactat tgcacatcat attctattgt ttactataaa aatcatgtga     1320
taactgatta ttacttctgt ttctcttttg gtttctgctt ctctcttctc tcaaccccctt    1380 tgtaatggtt tgggggcaga ctcttaagta tattgtgagt tttctatttc actaatcatg     1440
agaaaaactg ttcttttgca ataataataa attaaacatg ctgttaccag agcctctttg     1500
ctggagtctc cagatgttaa tttacttttct gcaccccaat tgggaatgca atattggatg    1560
aaaagagagg tttctggtat tcacagaaag ctagatatgc cttaaaacat actctgccga     1620
tctaattaca gccttatttt tgtatgcctt ttgggcattc tcctcatgct tagaaagttc     1680
caaatgttta taaaggtaaa atggcagttt gaagtcaaat gtcacatagg caaagcaatc     1740
aagcaccagg aagtgtttat gaggaaacaa cacccaagat gaattatttt tgagactgtc    1800
aggaagtaaa ataaatagga gcttaagaaa gaacattttg cctgattgag aagcacaact     1860
gaaaccagta gccgctgggg tgttaatggt agcattcttc ttttggcaat acatttgatt     1920
tgttcatgaa tatattaatc agcattagag aaatgaatta taactagaca tctgctgtta     1980
tcaccatagt tttgtttaat ttgcttcctt ttaaataaac ccattggtga aagtcccaaa    2040
aaaaaaaaaa aaaaaaaa                                                   2058

<210> SEQ ID NO 39
<211> LENGTH: 3487
<212> TYPE: DNA
<213> ORGANISM: Homo sapiens

<400> SEQUENCE: 39
actgaaagct ccggtgccag accccacccc cggccccggc ccgggacccc ctcccctccc       60
gggatccccc ggggttccca ccccgcccgc accgccgggg accggccgg tccggcgcga       120 gccccgtcc ggggccctgg ctcggccccc aggttgagg agcccggagc ccgccttcgg        180
agctacggcc taacggcggc ggcgactgca gtctggaggg tccacacttg tgattctcaa      240
tggagagtga aaacgcagat tcataatgaa aactagcccc cgtcggccac tgattctcaa      300
aagacggagg ctgcccctc ctgttcaaaa tgccccaagt gaaacatcag aggaggaacc      360
taagagatcc cctgcccaac aggagtctaa tcaagcagag gcctccaagg aagtggcaga     420
gtccaactct tgcaagtttc cagctgggat caagattatt aaccacccca ccatgcccaa     480
cacgcaagta gtggccatcc ccaacaatgc taatattcac agcatcatca cagcactgac    540
tgccaaggga aaagagagtg gcagtagtgg gcccaacaaa ttcatcctca tcagctgtgg     600
gggagcccca actcagcctc caggactccg gcctcaaacc caaaccagct atgatgccaa     660
aaggacagaa gtgaccctgg agaccttggg accaaaacct gcagctaggg atgtgaatct     720
```

```
tcctagacca cctggagccc tttgcgagca gaaacgggag acctgtgcag atggtgaggc    780
agcaggctgc actatcaaca atagcctatc caacatccag tggcttcgaa agatgagttc    840
tgatggactg ggctcccgca gcatcaagca agagatggag gaaaaggaga attgtcacct    900
ggagcagcga caggttaagg ttgaggagcc ttcgagacca tcagcgtcct ggcagaactc    960
tgtgtctgag cggccaccct actcttacat ggccatgata caattcgcca tcaacagcac   1020
tgagaggaag cgcatgactt tgaaagacat ctatacgtgg attgaggacc actttcccta   1080
ctttaagcac attgccaagc caggctggaa gaactccatc cgccacaacc tttccctgca   1140
cgacatgttt gtccgggaga cgtctgccaa tggcaaggtc tccttctgga ccattcaccc   1200
cagtgccaac cgctacttga cattggacca ggtgtttaag cagcagaaac gaccgaatcc   1260
agagctccgc cggaacatga ccatcaaaac cgaactcccc ctgggcgcac ggcggaagat   1320
gaagccactg ctaccacggg tcagctcata cctggtacct atccagttcc cggtgaacca   1380
gtcactggtg ttgcagccct cggtgaaggt gccattgccc ctggcggctt ccctcatgag   1440
ctcagagctt gcccgccata gcaagcgagt ccgcattgcc cccaaggtgc tgctagctga   1500 ggagggggata gctcctcttt cttctgcagg accaggaaaa gaggagaaac tcctgtttgg   1560
agaagggttt tctcctttgc ttccagttca gactatcaag gaggaagaaa tccagcctgg   1620
ggaggaaatg ccacacttag cgagacccat caaagtggag agccctccct tggaagagtg   1680
gccctccccg gccccatctt tcaaagagga atcatctcac tcctgggagg attcgtccca   1740
atctcccacc ccaagaccca agaagtccta cagtgggctt aggtccccaa cccgtgtgt   1800 ctcggaaatg cttgtgattc aacacaggga gaggaggag aggagccggt ctcggaggaa   1860
acagcatcta ctgcctccct gtgtggatga gccggagctg ctcttctcag aggggcccag   1920
tacttcccgc tgggccgcag agctcccgtt cccagcagac tcctctgacc ctgcctccca   1980
gctcagctac tcccaggaag tgggaggacc ttttaagaca cccattaagg aaacgctgcc   2040
catctcctcc accccgagca aatctgtcct ccccagaacc cctgaatcct ggaggctcac   2100
gcccccagcc aaagtagggg gactggattt cagcccagta caaacctccc agggtgcctc   2160
tgaccccttg cctgacccc tgggctgat ggatctcagc accactccct tgcaaagtgc    2220
tccccccctt gaatcaccgc aaaggctcct cagttcagaa cccttagacc tcatctccgt   2280
cccctttggc aactcttctc cctcagatat agacgtcccc aagccaggct ccccggagcc   2340
acaggtttct ggccttgcag ccaatcgttc tctgacagaa ggcctggtcc tggacacaat   2400
gaatgacagc ctcagcaaga tcctgctgga catcagcttt cctggcctgg acgaggaccc   2460
actgggccct gacaacatca actggtccca gtttattcct gagctacagt agagccctgc   2520 ccttgccct gtgctcaagc tgtccaccat cccgggcact ccaaggctca gtgcacccca   2580
agcctctgag tgaggacagc aggcagggac tgttctgctc ctcatagctc cctgctgcct   2640
gattatgcaa aagtagcagt cacaccctag ccactgctgg gaccttgtgt tcccaagag   2700 tatctgattc ctctgctgtc cctgccagga gctgaagggt gggaacaaca aaggcaatgg   2760
tgaaaagaga ttaggaaccc cccagcctgt ttccattctc tgcccagcag tctcttacct   2820
tccctgatct ttgcagggtg gtccgtgtaa atagtataaa ttctccaaat tatcctctaa   2880
ttataaatgt aagcttattt ccttagatca ttatccagag actgccagaa ggtgggtagg   2940
atgacctggg gtttcaattg acttctgttc cttgctttta gttttgatag aagggaagac   3000
ctgcagtgca cggtttcttc caggctgagg tacctggatc ttgggttctt cactgcaggg   3060
acccagacaa gtggatctgc ttgccagagt ccttttttgcc cctccctgcc acctccccgt   3120
```

```
gtttccaagt cagctttcct gcaagaagaa atcctggtta aaaaagtctt ttgtattggg      3180
tcaggagttg aatttggggt gggaggatgg atgcaactga agcagagtgt gggtgcccag      3240
atgtgcgcta ttagatgttt ctctgataat gtccccaatc ataccaggga gactggcatt      3300
gacgagaact caggtggagg cttgagaagg ccgaaagggc ccctgacctg cctggcttcc      3360
ttagcttgcc cctcagcttt gcaaagagcc accctaggcc ccagctgacc gcatgggtgt      3420
gagccagctt gagaacacta actactcaat aaaagcgaag gtggacaaaa aaaaaaaaa      3480 aaaaaaa                                                                3487

<210> SEQ ID NO 40
<211> LENGTH: 1441
<212> TYPE: DNA
<213> ORGANISM: Homo sapiens

<400> SEQUENCE: 40
gtcgaggctg cggcgcgtgg ggagcgggcg gagcggggc ggggccgag cgcggggcac         60 ccgggggcct cctgtatagg cgggcaccat gggctcctgc tccggccgct gcgcgctcgt       120
cgtcctctgc gcttttcagc tggtcgccgc cctggagagg caggtgtttg acttcctggg      180
ctaccagtgg gcgcccatcc tggccaactt tgtccacatc atcatcgtca tcctgggact      240
cttcggcacc atccagtacc ggctgcgcta tgtcatggtg tacacgctgt gggcagccgt      300
ctgggtcacc tggaacgtct tcatcatctg cttctacctg gaagtcggtg gcctcttaaa      360
ggacagcgag ctactgacct tcagcctctc ccggcatcgc tcctggtggc gtgagcgctg      420
gccaggctgt ctgcatgagg aggtgccagc agtgggcctc ggggcccccc atggccaggc      480
cctggtgtca ggtgctggct gtgccctgga gcccagctat gtggaggccc tacacagttg      540
cctgcagatc ctgatcgcgc ttctgggctt tgtctgtggc tgccaggtgg tcagcgtgtt      600
tacggatgaa gaggacagct ttgatttcat tggtggattt gatccatttc ctctctacca      660
tgtcaatgaa aagccatcca gtctcttgtc caagcaggtg tacttgcctg cgtaagtgag      720
gaaacagctg accctgctcc tgtggcctcc agcctcagcg accgaccagt gacaatgaca      780
ggagctccca ggccttggga gcgcgccccca cccagcaccc cccaggcggc cggcagcacc       840
tgccctgggt tctaagtact ggacaccagc cagggcggca gggcagtgcc acggctggct      900
gcagcgtcaa gagagtttgt aatttccttt ctcttaaaaa aaaaaagaa aagaaaacat      960 acaaagaaa aggcaaaacc ccacatgccc acctcctctg gcaacatggg ggtcacagct      1020 ctgccccag gctgtcgtct cgtcgaggag cccctccctc aggtgccaac ctggggctgc      1080
tggaccctcg gctgcaagc actgctgctg ggatgcagcc tccccaggaa gtcaatgtga      1140
ggcccgagac ccctcaagcg gtgagggccc tgttgaaca tggagggttc ctaaccccaa      1200
actcgtgcca gaagaacccc acccccaccc aggagctgag gctgatggag ccctagggtg      1260
ggggctgggc ttgaccagga acagcagagc caggccccaa ggcatagggc agggcacatg      1320
gtggtgacga gcaggcagta ctcttgtaaa gggggctctt gggcaaacag tcccaaggc      1380 tcccccaggt atcatcaagt tggtaaataa acaggaacat ggcccaaaaa aaaaaaaaa      1440 a                                                                      1441

<210> SEQ ID NO 41
<211> LENGTH: 282
<212> TYPE: DNA
<213> ORGANISM: Homo sapiens
<220> FEATURE:
<221> NAME/KEY: misc_feature
<222> LOCATION: (21)..(21)
```

```
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 41
aaaaaataag tatatctgtc nagaatcnta tttatgtgag atgtgtcaat actggtcttg    60
cgttatttcg gctacttgaa aataagttaa aaaagatagt gtttggttcc aaaaaggaaa   120
agtcagcctc tcctgcntga gtgggagctg caacctttta gaattgataa tcacaaaccc   180
ctcagaccca aagtggaata aagaaaaata tgtaacatta ggcattgatg gaaaaggact   240
agatcctagt gtaagcatcc taataaaagg agaggttcac aa                      282

<210> SEQ ID NO 42
<211> LENGTH: 1261
<212> TYPE: DNA
<213> ORGANISM: Homo sapiens

<400> SEQUENCE: 42
gcagccagat ctgctgggac acctttccca aggaagagcc cgttgcactg ggctttgaag    60
gataagcagg agcttgttac tcaggcagag gaagaaagag catcccaggc gggggagca   120 gcatatgcaa aggcacgaag gggccccagg agcctaggga gtctggggaa gtgtgagcac   180
tttggagagt ggaggctgga gcgctgtgga gagtgggggc tggtggccgg gaatgaagct   240
gcagctggct gggccacatg gtaaaggctg acaactggac ccagaggcca actagcctat   300
gatcagcatt tcccaaaatc tgtttcccga ctcatggttc tgtgagatgt gacaagggct   360
cctttttcat tcctgagacg ccggtttttca tctgtgatgc ggggacagct gcgctccttg   420
ctgcgaggcg tcaggaccca ggtgatagtg aagggagggt ggcgcccgcg gttcccggcg   480
gccactgatg cctgtctctc tgtcgtgtgt acgtgcgtgt gtgctccacg cctggcttct   540
caggctttca aatgtgtgtc agcagcagca gcagcagcca cgacgaggcc cccgtcctga   600
acgacaagca cctggacgtg cccgacatca tcatcacgcc ccccaccccc acgggcatga   660
tgctgccgag ggacttgggg agcacagtct ggctggatga gacagggtcg tgcccagatg   720
atggagaaat cgacccagaa gcctgaggag gtgtcctggg tttggctggc tggctcctgc   780
tccagcggcc cggcttcagg tgtccggggg cgtggctgcc tggagcaggt gtgctgaata   840
ccctggatgg gaactgagcg aacccggcc tccgctcaga gagacgtggc aggaccagcg   900
aggaatccag cctgtccact tccagaacag tgtttcccag gccccgctga gtggaccgga   960
cctctgacac ctccaggttc ttgctgactc cggcctggtg aaagggagcg ccatggtcct  1020
ggctgttggg gtcccaggga gaggctctct tctggacaaa cacaccctcc cagccccag   1080 ggctgtgcaa acacatgccc ctcccataag caccaacaag aacttcttgc aggtggagtg  1140
gctgtttttt ataagttgtt ttacagatac ggaaacagtc caaatggga tttataattt   1200 cttttttgca ttataaataa agatcctctg taacaaaaaa aaaaaaaaaa aaaaaaaaa   1260 a                                                                 1261

<210> SEQ ID NO 43
<211> LENGTH: 3237
<212> TYPE: DNA
<213> ORGANISM: Homo sapiens
```

```
<400> SEQUENCE: 43
gcgaagtgaa gggtggccca ggtggggcca ggctgactga atgtatctcc tagctatgga      60
ctaaataata catgggggga aataaacaag tattcatgag ggtgaaaatg tgacccagca     120
ggaaaattac aactattttc aattgacgtt gaataggatg agtcatggaa tttaagtgat     180
ttactgaaga ttatactact ggtagataga agagctaaag aaagatggat actatgatgc     240
tgaatgtgcg gaatctgttt gagcagcttg tgcgccgggt ggagattctc agtgaaggaa     300
atgaagtcca atttatccag ttggcgaagg actttgagga tttccgtaaa aagtggcaga     360
ggactgacca tgagctgggg aaatacaagg atcttttgat gaaagcagag actgagcgaa     420
gtgctctgga tgttaagctg aagcatgcac gtaatcaggt ggatgtagag atcaaacgga     480
gacagagagc tgaggctgac tgcgaaaagc tggaacgaca gattcagctg attgagaga      540
tgctcatgtg tgacacatct ggcagcattc aactaagcga ggagcaaaaa tcagctctgg     600
cttttctcaa cagaggccaa ccatccagca gcaatgctgg gaacaaaaga ctatcaacca     660
ttgatgaatc tggttccatt ttatcagata tcagctttga caagactgat gaatcactgg     720
attgggactc ttcttttggtg aagactttca aactgaagaa gagagaaaag aggcgctcta     780
ctagccgaca gtttgttgat ggtcccctg gacctgtaaa gaaaactcgt tccattggct     840
ctgcagtaga ccaggggaat gaatccatag ttgcaaaaac tacagtgact gttcccaatg     900
atggcgggcc catcgaagct gtgtccacta ttgagactgt gccatattgg accaggagcc     960
gaaggaaaac aggtacttta caaccttgga acagtgactc cacctgaac agcaggcagc    1020
tggagccaag aactgagaca gacagtgtgg gcacgccaca gagtaatgga gggatgcgcc    1080
tgcatgactt tgtttctaag acggttatta aacctgaatc ctgtgttcca tgtggaaagc    1140
ggataaaatt tggcaaatta tctctgaagt gtcgagactg tcgtgtggtc tctcatccag    1200
aatgtcggga ccgctgtccc cttccctgca ttcctaccct gataggaaca cctgtcaaga    1260
ttggagaggg aatgctggca gactttgtgt cccagacttc tccaatgatc ccctccattg    1320
ttgtgcattg tgtaaatgag attgagcaaa gaggtctgac tgagacaggc ctgtatagga    1380
tctctggctg tgaccgcaca gtaaaagagc tgaaagagaa attcctcaga gtgaaaactg    1440
tacccctcct cagcaaagtg gatgatatcc atgctatctg tagccttcta aaagactttc    1500
ttcgaaacct caaagaacct cttctgacct ttcgccttaa cagagccttt atggaagcag    1560
cagaaatcac agatgaagac aacagcatag ctgccatgta ccaagctgtt ggtgaactgc    1620
cccaggccaa cagggacaca ttagctttcc tcatgattca cttgcagaga gtggctcaga    1680
gtccacatac taaaatggat gttgccaatc tggctaaagt cttttggccct acaatagtgg    1740
cccatgctgt gcccaatcca gacccagtga caatgttaca ggacatcaag cgtcaaccca    1800
aggtggttga gcgcctgctt tccttgcctc tggagtattg gagtcagttc atgatggtgg    1860
agcaagagaa cattgacccc ctacatgtca ttgaaaactc aaatgccttt tcaacaccac    1920
agacaccaga tattaaagtg agtttactgg gacctgtgac cactcctgaa catcagcttc    1980
tcaagactcc ttcatctagt tccctgtcac agagagtccg ttccaccctc accaagaaca    2040
ctcctagatt tgggagcaaa agcaagtctg ccactaacct aggacgacaa ggcaactttt    2100
ttgcttctcc aatgctcaag tgaagtcaca tctgcctgtt acttcccagc attgactgac    2160
tataagaaag gacacatctg tactctgctc tgcagcctcc tgtactcatt actactttta    2220
gcattctcca ggcttttact caagtttaat tgtgcatgag ggttttatta aaactatata    2280
tatctcccct tccttctcct caagtcacat aatatcagca ctttgtgctg gtcattgttg    2340
```

```
ggagctttta gatgagacat cttcccaggg gtagaagggt tagtatggaa ttggttgtga    2400 ttcttttgg ggaaggggt tattgttcct ttggcttaaa gccaaatgct gctcatagaa      2460
tgatctttct ctagtttcat ttagaactga tttccgtgag acaatgacag aaaccctacc    2520
tatctgataa gattagcttg tctcaggtg ggaagtggga gggcagggca agaaaggat      2580 tagaccagag gatttaggat gcctccttct aagaaccaga agttctcatt ccccattatg    2640
aactgagcta taatatggag ctttcataaa aatgggatgc attgaggaca gaactagtga    2700
tgggagtatg cgtagctttg atttggatga ttaggtcttt aatagtgttg agtggcacaa    2760
ccttgtaaat gtgaaagtac aactcgtatt tatctctgat gtgccgctgg ctgaactttg    2820
ggttcatttg gggtcaaagc cagttttct tttaaaattg aattcattct gatgcttggc     2880
ccccataccc ccaaccttgt ccagtggagc ccaacttcta aaggtcaata tatcatcctt    2940
tggcatccca actaacaata aagagtaggc tataagggaa gattgtcaat attttgtggt    3000
aagaaaagct acagtcattt tttctttgca ctttggatgc tgaaattttt cccatggaac    3060
atagccacat ctagatagat gtgagctttt tcttctgtta aaattattct taatgtctgt    3120
aaaaacgatt ttcttctgta gaatgtttga cttcgtattg acccttatct gtaaaacacc    3180
tatttgggat aatatttgga aaaaagtaa atagcttttt caaaatgaaa aaaaaaa       3237

<210> SEQ ID NO 44
<211> LENGTH: 4659
<212> TYPE: DNA
<213> ORGANISM: Homo sapiens

<400> SEQUENCE: 44
aggcgctaga ggcgggggcg ccgggaggcg cgggctttgc tcctgggtc tcggccttgg       60 ccggctggac ctgaccctag ggcggcttgc gcagctgtcg ggacgtgact gcgttcagcc     120
gcgtcgggcg tgcttcccag acttgcccaa gttcgggtgc cctagctgcc cctttgcagc     180
cgctggccta cccggcccgc gggtgagaag gttgcgacgg gaggtgggtg gaactcgcca     240
gcgccgggac cgcggattgg ctgcctcggc tttctctttt ccccgtgggc tccggcgtga     300
ggcgctgaag cggccggcag ccggcgaccg gccctcaccg tccgccgggt tgcgctctgc     360
ttttgcggtg aggcgttgac cacgcccata tgaattggag ctctccgcca gtaggagttt     420
ccggaaggag tttgaatttt tgtgattttt atgcttgttt ggtcggtgga atatgttggg     480
atttatgttt gcctctgaac aagtgtcttg ctcacatcgt aaatgacttt ctctccgaaa     540
cgctaaatat tctttcccgc aggagctcat atccttattt tccatgacag atcttaacga     600
caatatatgc aaaagatata taagatgat aactaatata gttatactga gcctgatcat      660
ttgcatttcg ttagctttct ggattatatc aatgactgca agcacctatt atggtaactt     720
acgacctatt tctccgtggc gttggctgtt ttctgttgtt gttcctgttc tgatcgtctc     780
taatggcctt aaaaagaaaa gtctagatca cagtggggct ctaggaggc tagtcgttgg      840 atttatccta accattgcaa atttcagctt tttttacctct ttgctgatgt ttttcttgtc     900
ttcttcgaaa ctcactaaat ggaagggaga agtgaagaag cgtctagatt cagaatataa     960
ggaaggtggg caaaggaatt gggttcaggt gttctgtaat ggagctgtac ccacagaact    1020
ggccctgctg tacatgatag aaaatggccc cgggaaatc ccagtcgatt tttccaagca     1080
gtactccgct tcctggatgt gtttgtctct cttggctgca ctggcctgct ctgctggaga    1140
cacatgggct tcagaagttg gcccagttct gagtaaaagt tctccaagac tgataacaac    1200
ctgggagaaa gttccagttg gtaccaatgg aggagttaca gtggtgggcc ttgtctccag    1260
```

-continued

```
tctccttggt ggtaccttg tgggcattgc atacttcctc acacagctga tttttgtgaa    1320
tgatttagac atttctgccc cgcagtggcc aattattgca tttggtggtt tagctggatt    1380
actaggatca attgtggact catacttagg ggctacaatg cagtatactg ggttggatga    1440
aagcactggc atggtggtca acagcccaac aaataaggca aggcacatag cagggaaacc    1500
cattcttgat aacaacgcag tgaatctgtt ttcttctgtt cttattgccc tcttgctccc    1560
aactgctgct gggggttttt ggcccagggg gtgaacttta tttcatttcc acaggttgaa    1620
actggtgagt ccagctaaat ttgcaattcc aactttcatc ctaagaataa taactgtaat    1680
ggcaaagcgg aaatgccagt tcctcctgta ttccattgag atgggatttc acattttcct    1740
ctcatcaact cccctgtaat agctagcgtc tttctagtga agagaagaa ttcctagaac    1800 ttatgcattt ttttcctgct gaatggaagt cttgagcaat gaagctatat tgtccctaca    1860
tattactata tattgaactg aaagttctta cataatcaat gtcaagtttt gtcttatttt    1920
gttttgtttg tttaaaccag tgtaggaaat aaaagtgatg atatttaaaa tagttctcag    1980
ttgaagcaga gaaatgccac tgtgctagtt gcccaaatgt tgtatctatt ttaaatagtt    2040
taagctgatg tgtatgggag cctaaacaag tgtagtatcc tgaacttctc ccattaattg    2100
ctattcacaa ttgggaaaag tgtggagatt ggttcctagt gagttttgtg gcctactcca    2160
catttgttct tccttcctca gggttagtga tgaaaaaaag taaatatctt tttcatatgt    2220
ccattagaat gtatgaaaaa aatcatttta actaaaagca aagaattttt atcttatatc    2280
taaaaaatat ataacttact atatgtttca gttgctctct gaacaaaaat tatcttcaat    2340
ttaatatgtg gaatgtgttt tctagctttc tttgaattat gtatggcaac ctggtttagc    2400
actggcatcc tgaacagtta agagtcactg ggaaattatt gtatttcttt ataaatttac    2460
tgtcatatca attgctggaa aatgctatga tttttctatt attaccttct aagttgtatt    2520
ctctcttaca ctgtagcctc aactaaggca attctgctat gtttgttctt cactatgatt    2580
tactgtgtgc caaggagtt ttgacagggt acagagtatt ttactaaaag tattttaaa    2640 tgtttctcat gtgatttctg taccttcttc ctcctgcccc ttttgctttt ttaaagaaac    2700
tggggaagga tttatgaata caccaccacc agagtggata atgcttagaa ttcttattg    2760 gtggccctac tatggtgatg atctagaact gacttacttc aggacagaag aaaaaacaat    2820
cacaccctta acctttaagc cagttagatc agggggttgc aacaattggg ttaaactttg    2880
ggtatacatt ggaagcacca gggcatgttt gctttttttg tttatgtgtt tgttttttga    2940
gacagagtct cacactgtgg cccaggctgg actccagcac agtggcatga tctcagctcc    3000
gcctcctggg ttcacgtgat tctcatgcct cagcctccca gtagctggg atcacaggcg    3060 tgcaccatca cgcccggcta atttttgtat tttcagtaga cagggtttt cgccacgttg    3120 gctaggctgg tctcgaactc ctgacctcaa gtgatctgcc catctcagcc tcccaaagat    3180
ctattacaag atgtgagcca ctgtgcccag ccaccagggc atgtttttaa aaaagtactg    3240
atgtctgggt ttcacactgc aaaattctga tttatctgat ctaaggtaca gcctggatat    3300
tgagactttt taaagctctg actgtacatt gaatcatcat gtaaggagtt tttaaaacat    3360
tgttgccagg gccccttct agaccaagtt agtcagaatg ttggacaatg aggcccatgc    3420
atgggtattt ttacaaagct ctctgggaga ttcaatgct taaccaaatt gagaagcact    3480
gaataagaat atcctgggcc gggcgcactg gctcatgcct gtaatcccag cattttggaa    3540
ggccgaggcg ggtggatcac ttgaggtcag gagttcgaga ccagcctggc caacatggtg    3600
aaacaccgtc tctactaaaa atacaaaaaa ttaggtgtgg tggtgcgtgc ctgtattccc    3660
```

-continued

```
agccactcag gaggctgagg caggagaatc gctggaacct gggatgtgga ggttgcagtg    3720
agccaagatt gcaccactgt actccagcct gggcaacaga gggagactcc atctagactc    3780
catctcaaaa aaaaaaaaaa aaaaaaaaaa aaaaaaaaaa aaaagaata ttctaagcac     3840 tagaactaca taagaatgtc ctaaagcact gtatctaagc acttgaaaag aatgggactt    3900
ttcggtttta gggagataac tattagcaac cacacaatat gttatcttta tggatgaata    3960
acttctggta atgacacagt gtcttacagc tacatcattt ataaaatcat gtgtcagttt    4020
tcacacagcc tgcacatcgt tctgacatgc ccttttttc cctggagatt tatcctcatg     4080
acatacaagg ggacaaaaat atttattggg actgtctttg aatttagtag aatcactgta    4140
tcattaacag tttggggaag tactgctttg cagtccttta tttgaaaact taggtctagc    4200
tgtgttttgc atcaaaattt ttgagctatt caaaaactaa taggatctgt gtaaaatatt    4260
tcactcaaaa ctactaaaaa aaagtctggg atggcagctc attatcaaat atactcctat    4320
ttttgtggtg atttatgaac atccccacta agtataacta aagatcataa agagcctcag    4380
atcaagtttg gtcaggtttt gtcaccaagc tttgtaaata aactggtttt catagctttt    4440
tggagatgag aattgaggat aagaaattgt gtctctgtcc tttttttttt tttttgttaa    4500
gtcttacatg tattttactg taacatcttt tgaattggat atttaactaa ttcaacatat    4560
ttttcctctt tgcagaatgg gcagttcatg ttaaaatcac ttttcatgga aagagctcta    4620
tgtaacagca taataaaact gcctacctag cagcataaa                            4659
```

```
<210> SEQ ID NO 45
<211> LENGTH: 333
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 45
```

```
cnggacacat caaactgctt atccaggnac cactagaagt gaatctcttc ttgagtattc     60
catactgctg cccctgctat tcacttgggg tcccagtcag ttgttactat atatttgtca    120
tctattgtga gagtcgtgat atcaccttcc acatcagtga tactgagaag gaacaaatct    180
gccaaagatt cttcacagtt agttgttacc ttttaagaa gactgtgctt gaaaattatg     240
gtaaaacaca tttagaagaa ggatgtgcat tttcacatca gtctatgaag tataacttga    300
catttaaatt aaaatgctgt tcttcaaaat cga                                  333
```

```
<210> SEQ ID NO 46
<211> LENGTH: 261
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 46
```

```
gttcccgact agctgcccnt gcacattatc ttcatttcc tggaatttga tacagagagc     60
```

```
aatttatagc cnattgatag cttatgctgt ttcaatgtaa attcgtggta aataacttag    120
gaactgcctc ttcttttttct ttgaaaacct acttataact gttgctaata agaatgtgta    180
ttgttcagga caacttgtct ccatacagtt gggttgtaac cctcatgctt ggcccaaata    240
aactctctac ttatatcagt a                                              261
```

<210> SEQ ID NO 47
<211> LENGTH: 598
<212> TYPE: DNA
<213> ORGANISM: Homo sapiens

<400> SEQUENCE: 47

```
ctagggtcc tgacggttct ctggctccaa gtctggcccc tcaacctccc tggtcatcag     60
tgggctccag gctgaggatg aggctgatta ctactgtgca gcatgggatg acagcctgaa    120
aggtcctgcg ttcggaggag gcacccacct gaccgtcctc ggtcagccca aggctgcccc    180
ctcggtcact ctgttcccac cctcctctga ggagcttcaa gccaacaagg ccacactggt    240
gtgtctcgta agtgacttct acccgggagc cgtgacagtg gcctggaagg cagatggcag    300
ccccgtcaag gtgggagtgg agaccaccaa accctccaaa caaagcaaca caagtatgc     360 ggccagcagc tacctgagcc tgacgcccga gcagtggaag tcccacagaa gctacagctg    420
ccgggtcacg catgaaggga gcaccgtgga aagacagtg gcccctgcag aatgctctta    480 ggccccgac cctcacccca cccacaggg cctggagctg caggttccca ggggaggggt    540
ctctgccccc atcccaagtc atccagccct tctcaataaa tatcctcatc gtcaacga     598
```

<210> SEQ ID NO 48
<211> LENGTH: 1614
<212> TYPE: DNA
<213> ORGANISM: Homo sapiens

<400> SEQUENCE: 48

```
ggtagttggt tgtgggcact gggttagagg tatcacgtgg gggcactttc gtcttagctt    60
ttggacaaga cgcaggcgca acccacggct gctgcgggga tccttgtggc ccttccggtc    120
ggtggaacca atccgtgcac agagaagcgg ggcgaactga ggcgagtgaa gtggactctg    180
agggctaccg ctaccgccac tgctgcggca ggggcgtgga gggcagaggg ccgcggaggc    240
cgcagttgca aacatggctc agagcagaga cggcggaaac ccgttcgccg agcccagcga    300
gcttgacaac cccttttcagg acccagctgt gatccagcac cgacccagcc ggcagtatgc    360
cacgcttgac gtctacaacc cttttgagac ccggggagcca ccaccagcct atgagcctcc    420 agccccctgcc ccattgcctc cacccctcagc tccctccttg cagccctcga aaagctcag    480 ccccacagaa cctaagaact atggctcata gcagcactcag gcctcagctg cagcagccac    540
agctgagctg ctgaagaaac aggaggagct caaccggaag gcagaggagt tggaccgaag    600
ggagcgagag ctgcagcatg ctgccctggg gggcacagct actcgacaga caattggcc    660 ccctctacct tctttttgtc cagttcagcc ctgcttttc caggacatct ccatggagat     720 ccccaagaa tttcagaaga ctgtatccac catgtactac ctctggatgt gcagcacgct    780
ggctcttctc ctgaacttcc tcgcctgcct ggccagcttc tgtgtggaaa ccaacaatgg    840
cgcaggcttt gggcttttcta tcctctgggt cctcctttc actccctgct cctttgtctg    900
ctggtaccgc cccatgtata aggctttccg gagtgacagt tcattcaatt tcttcgttt     960 cttcttcatt ttcttcgtcc aggatgtgct ctttgtcctc caggccattg gtatcccagg    1020
ttggggattc agtggctgga tctctgctct ggtggtgccg aagggcaaca cagcagtatc    1080
```

```
cgtgctcatg ctgctggtcg ccctgctctt cactggcatt gctgtgctag gaattgtcat    1140
gctgaaacgg atccactcct tataccgccg cacaggtgcc agctttcaga aggcccagca    1200
agaatttgct gctggtgtct tctccaaccc tgcggtgcga accgcagctg ccaatgcagc    1260
cgctggggct gctgaaaatg ccttccgggc cccgtgaccc ctgactggga tgccctggcc    1320
ctgctacttg agggagctga cttagctccc gtccctaagg tctctgggac ttggagagac    1380
atcactaact gatggctcct ccgtagtgct cccaatccta tggccatgac tgctgaacct    1440
gacaggcgtg tggggagttc actgtgacct agtcccccca tcaggccaca ctgctgccac    1500
ctctcacacg ccccaaccca gcttccctct gctgtgccac ggctgttgct tcggttattt    1560
aaataaaaag aaagtggaac tggaactgac aaaaaaaaaa aaaaaaaaa aaaa           1614
```

<210> SEQ ID NO 49
<211> LENGTH: 326
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t

<400> SEQUENCE: 49

```
ctgcaagaac tantcattcn aggtcaccag anaggagccc tgacccntcg ctgcccagcc     60
tgtccttgtg tcgtcttttt acgggagacg actggatcat gggggcggat tttcccttg    120 ctgttctcat gatagtgagt tctcatgaga tctggttgtt taaaagtgta tagcacttcc    180
tgcttcactc tctcccactc caccatgtga agaaggtgcc tttgcccttc cgccacgact    240
gtgtttcctg aggcctcccc agccatgctt cctgtacagc ctgcagaact gtgagttaat    300
taaacctctt ttcttcataa agaaca                                         326
```

<210> SEQ ID NO 50
<211> LENGTH: 944
<212> TYPE: DNA
<213> ORGANISM: Homo sapiens

<400> SEQUENCE: 50

```
tcaagattaa acgacaagga cagacatggc tcagcggatg acaacacagc tgctgctcct     60
tctagtgtgg gtggctgtag taggggaggc tcagacaagg attgcatggg ccaggactga    120
gcttctcaat gtctgcatga acgccaagca ccacaaggaa aagccaggcc ccgaggacaa    180
gttgcatgag cagtgtcgac cctggaggaa gaatgcctgc tgttctacca acaccagcca    240
ggaagcccat aaggatgttt cctacctata tagattcaac tggaaccact gtggagagat    300
ggcacctgcc tgcaaacggc atttcatcca ggacacctgc ctctacgagt gctcccccaa    360
cttggggccc tggatccagc aggtggatca gagctggcgc aaagagcggg tactgaacgt    420 gccccctgtgc aaagaggact gtgagcaatg tgggaagat tgtcgcacct cctacacctg    480
caagagcaac tggcacaagg gctggaactg gacttcaggg tttaacaagt gcgcagtggg    540
```

```
agctgcctgc caacctttcc atttctactt ccccacaccc actgttctgt gcaatgaaat      600
ctggactcac tcctacaagg tcagcaacta cagccgaggg agtggccgct gcatccagat      660
gtggttcgac ccagcccagg caaccccaa tgaggaggtg gcgaggttct atgctgcagc       720
catgagtggg gctgggccct gggcagcctg gcctttcctg cttagcctgg ccctaatgct      780
gctgtggctg ctcagctgac ctccttttac cttctgatac ctggaaatcc ctgccctgtt      840
cagccccaca gctcccaact atttggttcc tgctccatgg tcgggcctct gacagccact      900
ttgaataaac cagacaccgc acatgtgtct tgagaattat ttgg                       944
```

<210> SEQ ID NO 51
<211> LENGTH: 74
<212> TYPE: PRT
<213> ORGANISM: Homo sapiens

<400> SEQUENCE: 51

```
Met Pro Val Ile Asn Ile Glu Asp Leu Thr Glu Lys Asp Lys Leu Lys
 1               5                  10                  15

Met Glu Val Asp Gln Leu Lys Lys Glu Val Thr Leu Glu Arg Met Leu
             20                  25                  30

Val Ser Lys Cys Cys Glu Glu Val Arg Asp Tyr Val Glu Glu Arg Ser
         35                  40                  45

Gly Glu Asp Pro Leu Val Lys Gly Ile Pro Glu Asp Lys Asn Pro Phe
     50                  55                  60

Lys Glu Leu Lys Gly Gly Cys Val Ile Ser
 65                  70
```

<210> SEQ ID NO 52
<211> LENGTH: 413
<212> TYPE: PRT
<213> ORGANISM: Homo sapiens

<400> SEQUENCE: 52

```
Met Val Glu Arg Cys Ser Arg Gln Gly Cys Thr Ile Thr Met Ala Tyr
 1               5                  10                  15

Ile Asp Tyr Asn Met Ile Val Ala Phe Met Leu Gly Asn Tyr Ile Asn
             20                  25                  30

Leu Arg Glu Ser Ser Thr Glu Pro Asn Asp Ser Leu Trp Phe Ser Leu
         35                  40                  45

Gln Lys Lys Asn Asp Thr Thr Glu Ile Glu Thr Leu Leu Asn Thr
     50                  55                  60

Ala Pro Lys Ile Ile Asp Glu Gln Leu Val Cys Arg Leu Ser Lys Thr
 65                  70                  75                  80

Asp Ile Phe Ile Ile Cys Arg Asp Asn Lys Ile Tyr Leu Asp Lys Met
                 85                  90                  95

Ile Thr Arg Asn Leu Lys Leu Arg Phe Tyr Gly His Arg Gln Tyr Leu
            100                 105                 110

Glu Cys Glu Val Phe Arg Val Glu Gly Ile Lys Asp Asn Leu Asp Asp
        115                 120                 125

Ile Lys Arg Ile Ile Lys Ala Arg Glu His Arg Asn Leu Leu Ala
    130                 135                 140

Asp Ile Arg Asp Tyr Arg Pro Tyr Ala Asp Leu Val Ser Glu Ile Arg
145                 150                 155                 160

Ile Leu Leu Val Gly Pro Val Gly Ser Gly Lys Ser Ser Phe Phe Asn
                165                 170                 175

Ser Val Lys Ser Ile Phe His Gly His Val Thr Gly Gln Ala Val Val
            180                 185                 190
```

```
Gly Ser Asp Thr Thr Ser Ile Thr Glu Arg Tyr Arg Ile Tyr Ser Val
            195                 200                 205

Lys Asp Gly Lys Asn Gly Lys Ser Leu Pro Phe Met Leu Cys Asp Thr
    210                 215                 220

Met Gly Leu Asp Gly Ala Glu Gly Ala Gly Leu Cys Met Asp Asp Ile
225                 230                 235                 240

Pro His Ile Leu Lys Gly Cys Met Pro Asp Arg Tyr Gln Phe Asn Ser
                245                 250                 255

Arg Lys Pro Ile Thr Pro Glu His Ser Thr Phe Ile Thr Ser Pro Ser
                260                 265                 270

Leu Lys Asp Arg Ile His Cys Val Ala Tyr Val Leu Asp Ile Asn Ser
            275                 280                 285

Ile Asp Asn Leu Tyr Ser Lys Met Leu Ala Lys Val Lys Gln Val His
            290                 295                 300

Lys Glu Val Leu Asn Cys Gly Ile Ala Tyr Val Ala Leu Leu Thr Lys
305                 310                 315                 320

Val Asp Asp Cys Ser Glu Val Leu Gln Asp Asn Phe Leu Asn Met Ser
                325                 330                 335

Arg Ser Met Thr Ser Gln Ser Arg Val Met Asn Val His Lys Met Leu
                340                 345                 350

Gly Ile Pro Ile Ser Asn Ile Leu Met Val Gly Asn Tyr Ala Ser Asp
                355                 360                 365

Leu Glu Leu Asp Pro Met Lys Asp Ile Leu Ile Leu Ser Ala Leu Arg
            370                 375                 380

Gln Met Leu Arg Ala Ala Asp Asp Phe Leu Glu Asp Leu Pro Leu Glu
385                 390                 395                 400

Glu Thr Gly Ala Ile Glu Arg Ala Leu Gln Pro Cys Ile
                405                 410

<210> SEQ ID NO 53
<211> LENGTH: 328
<212> TYPE: PRT
<213> ORGANISM: Homo sapiens

<400> SEQUENCE: 53

Met Ser Ser Tyr Leu Glu Tyr Val Ser Cys Ser Ser Ser Gly Gly Val
1               5                   10                  15

Gly Gly Asp Val Leu Ser Leu Ala Pro Lys Phe Cys Arg Ser Asp Ala
                20                  25                  30

Arg Pro Val Ala Leu Gln Pro Ala Phe Pro Leu Gly Asn Gly Asp Gly
            35                  40                  45

Ala Phe Val Ser Cys Leu Pro Leu Ala Ala Arg Pro Ser Pro Ser
50                  55                  60

Pro Pro Ala Ala Pro Ala Arg Pro Ser Val Pro Pro Ala Ala Pro
65                  70                  75                  80

Gln Tyr Ala Gln Cys Thr Leu Glu Gly Ala Tyr Glu Pro Gly Ala Ala
                85                  90                  95

Pro Ala Ala Ala Ala Gly Gly Ala Asp Tyr Gly Phe Leu Gly Ser Gly
                100                 105                 110

Pro Ala Tyr Asp Phe Pro Gly Val Leu Gly Arg Ala Ala Asp Asp Gly
                115                 120                 125

Gly Ser His Val His Tyr Ala Thr Ser Ala Val Phe Ser Gly Gly Gly
                130                 135                 140

Ser Phe Leu Leu Ser Gly Gln Val Asp Tyr Ala Ala Phe Gly Glu Pro
145                 150                 155                 160
```

```
Gly Pro Phe Pro Ala Cys Leu Lys Ala Ser Ala Asp Gly His Pro Gly
                165                 170                 175
Ala Phe Gln Thr Ala Ser Pro Ala Pro Gly Thr Tyr Pro Lys Ser Val
            180                 185                 190
Ser Pro Ala Ser Gly Leu Pro Ala Phe Ser Thr Phe Glu Trp Met
        195                 200                 205
Lys Val Lys Arg Asn Ala Ser Lys Lys Gly Lys Leu Ala Glu Tyr Gly
    210                 215                 220
Ala Ala Ser Pro Ser Ser Ala Ile Arg Thr Asn Phe Ser Thr Lys Gln
225                 230                 235                 240
Leu Thr Glu Leu Glu Lys Glu Phe His Phe Asn Lys Tyr Leu Thr Arg
                245                 250                 255
Ala Arg Arg Ile Glu Ile Ala Asn Cys Leu His Leu Asn Asp Thr Gln
            260                 265                 270
Val Lys Ile Trp Phe Gln Asn Arg Arg Met Lys Gln Lys Lys Arg Glu
        275                 280                 285
Arg Glu Gly Leu Leu Ala Thr Ala Ile Pro Val Ala Pro Leu Gln Leu
    290                 295                 300
Pro Leu Ser Gly Thr Thr Pro Thr Lys Phe Ile Lys Asn Pro Gly Ser
305                 310                 315                 320
Pro Ser Gln Ser Gln Glu Pro Ser
                325

<210> SEQ ID NO 54
<211> LENGTH: 107
<212> TYPE: PRT
<213> ORGANISM: Homo sapiens

<400> SEQUENCE: 54

Met Ala Asn Glu Val Gln Asp Leu Leu Ser Pro Arg Lys Gly Gly His
1               5                   10                  15
Pro Pro Ala Val Lys Ala Gly Gly Met Arg Ile Ser Lys Lys Gln Glu
            20                  25                  30
Ile Gly Thr Leu Glu Arg His Thr Lys Thr Gly Phe Glu Lys Thr
        35                  40                  45
Ser Ala Ile Ala Asn Val Ala Lys Ile Gln Thr Leu Asp Ala Leu Asn
50                  55                  60
Asp Thr Leu Glu Lys Leu Asn Tyr Lys Phe Pro Ala Thr Val His Met
65                  70                  75                  80
Ala His Gln Lys Pro Thr Pro Ala Leu Glu Lys Val Val Pro Leu Lys
                85                  90                  95
Arg Ile Tyr Ile Ile Gln Gln Pro Arg Lys Cys
            100                 105

<210> SEQ ID NO 55
<211> LENGTH: 478
<212> TYPE: PRT
<213> ORGANISM: Homo sapiens

<400> SEQUENCE: 55

Met Ser Thr Asn Gly Asp Asp His Gln Val Lys Asp Ser Leu Glu Gln
1               5                   10                  15
Leu Arg Cys His Phe Thr Trp Glu Leu Ser Ile Asp Asp Glu Met
            20                  25                  30
Pro Asp Leu Glu Asn Arg Val Leu Asp Gln Ile Glu Phe Leu Asp Thr
        35                  40                  45
```

```
Lys Tyr Ser Val Gly Ile His Asn Leu Leu Ala Tyr Val Lys His Leu
 50                  55                  60
Lys Gly Gln Asn Glu Glu Ala Leu Lys Ser Leu Lys Glu Ala Glu Asn
 65                  70                  75                  80
Leu Met Gln Glu Glu His Asp Asn Gln Ala Asn Val Arg Ser Leu Val
                     85                  90                  95
Thr Trp Gly Asn Phe Ala Trp Met Tyr Tyr His Met Gly Arg Leu Ala
                    100                 105                 110
Glu Ala Gln Thr Tyr Leu Asp Lys Val Glu Asn Ile Cys Lys Lys Leu
                115                 120                 125
Ser Asn Pro Phe Arg Tyr Arg Met Glu Cys Pro Glu Ile Asp Cys Glu
            130                 135                 140
Glu Gly Trp Ala Leu Leu Lys Cys Gly Gly Lys Asn Tyr Glu Arg Ala
145                 150                 155                 160
Lys Ala Cys Phe Glu Lys Val Leu Glu Val Asp Pro Glu Asn Pro Glu
                165                 170                 175
Ser Ser Ala Gly Tyr Ala Ile Ser Ala Tyr Arg Leu Asp Gly Phe Lys
                180                 185                 190
Leu Ala Thr Lys Asn His Lys Pro Phe Ser Leu Leu Pro Leu Arg Gln
                195                 200                 205
Ala Val Arg Leu Asn Pro Asp Asn Gly Tyr Ile Lys Val Leu Leu Ala
            210                 215                 220
Leu Lys Leu Gln Asp Glu Gly Gln Glu Ala Glu Gly Glu Lys Tyr Ile
225                 230                 235                 240
Glu Glu Ala Leu Ala Asn Met Ser Ser Gln Thr Tyr Val Phe Arg Tyr
                245                 250                 255
Ala Ala Lys Phe Tyr Arg Arg Lys Gly Ser Val Asp Lys Ala Leu Glu
                260                 265                 270
Leu Leu Lys Lys Ala Leu Gln Glu Thr Pro Thr Ser Val Leu Leu His
                275                 280                 285
His Gln Ile Gly Leu Cys Tyr Lys Ala Gln Met Ile Gln Ile Lys Glu
                290                 295                 300
Ala Thr Lys Gly Gln Pro Arg Gly Gln Asn Arg Glu Lys Leu Asp Lys
305                 310                 315                 320
Met Ile Arg Ser Ala Ile Phe His Phe Glu Ser Ala Val Glu Lys Lys
                325                 330                 335
Pro Thr Phe Glu Val Ala His Leu Asp Leu Ala Arg Met Tyr Ile Glu
                340                 345                 350
Ala Gly Asn His Arg Lys Ala Glu Glu Asn Phe Gln Lys Leu Leu Cys
                355                 360                 365
Met Lys Pro Val Val Glu Glu Thr Met Gln Asp Ile His Phe His Tyr
                370                 375                 380
Gly Arg Phe Gln Glu Phe Gln Lys Lys Ser Asp Val Asn Ala Ile Ile
385                 390                 395                 400
His Tyr Leu Lys Ala Ile Lys Ile Glu Gln Ala Ser Leu Thr Arg Asp
                405                 410                 415
Lys Ser Ile Asn Ser Leu Lys Lys Leu Val Leu Arg Lys Leu Arg Arg
                420                 425                 430
Lys Ala Leu Asp Leu Glu Ser Leu Ser Leu Leu Gly Phe Val Tyr Lys
                435                 440                 445
Leu Glu Gly Asn Met Asn Glu Ala Leu Glu Tyr Tyr Glu Arg Ala Leu
                450                 455                 460
Arg Leu Ala Ala Asp Phe Glu Asn Ser Val Arg Gln Gly Pro
465                 470                 475
```

-continued

```
<210> SEQ ID NO 56
<211> LENGTH: 1020
<212> TYPE: PRT
<213> ORGANISM: Homo sapiens

<400> SEQUENCE: 56
```

| | | | | | | | | | | | | | | | |
|---|---|---|---|---|---|---|---|---|---|---|---|---|---|---|---|
| Met | Gln | Ser | Cys | Ala | Arg | Ala | Trp | Gly | Leu | Arg | Leu | Gly | Arg | Gly | Val |
| 1 | | | | 5 | | | | | 10 | | | | | 15 | |
| Gly | Gly | Gly | Arg | Arg | Leu | Ala | Gly | Gly | Ser | Gly | Pro | Cys | Trp | Ala | Pro |
| | | | 20 | | | | | 25 | | | | | 30 | | |
| Arg | Ser | Arg | Asp | Ser | Ser | Gly | Gly | Asp | Ser | Ala | Ala | Ala | Gly |
| | | 35 | | | | | 40 | | | | | 45 | |
| Ala | Ser | Arg | Leu | Leu | Glu | Arg | Leu | Leu | Pro | Arg | His | Asp | Asp | Phe | Ala |
| | 50 | | | | | 55 | | | | | 60 | | | | |
| Arg | Arg | His | Ile | Gly | Pro | Gly | Asp | Lys | Asp | Gln | Arg | Glu | Met | Leu | Gln |
| 65 | | | | | 70 | | | | | 75 | | | | | 80 |
| Thr | Leu | Gly | Leu | Ala | Ser | Ile | Asp | Glu | Leu | Ile | Glu | Lys | Thr | Val | Pro |
| | | | | 85 | | | | | 90 | | | | | 95 | |
| Ala | Asn | Ile | Arg | Leu | Lys | Arg | Pro | Leu | Lys | Met | Glu | Asp | Pro | Val | Cys |
| | | | 100 | | | | | 105 | | | | | 110 | | |
| Glu | Asn | Glu | Ile | Leu | Ala | Thr | Leu | His | Ala | Ile | Ser | Ser | Lys | Asn | Gln |
| | | | 115 | | | | | 120 | | | | | 125 | | |
| Ile | Trp | Arg | Ser | Tyr | Ile | Gly | Met | Gly | Tyr | Tyr | Asn | Cys | Ser | Val | Pro |
| | 130 | | | | | 135 | | | | | 140 | | | | |
| Gln | Thr | Ile | Leu | Arg | Asn | Leu | Leu | Glu | Asn | Ser | Gly | Trp | Ile | Thr | Gln |
| 145 | | | | | 150 | | | | | 155 | | | | | 160 |
| Tyr | Thr | Pro | Tyr | Gln | Pro | Glu | Val | Ser | Gln | Gly | Arg | Leu | Glu | Ser | Leu |
| | | | | 165 | | | | | 170 | | | | | 175 | |
| Leu | Asn | Tyr | Gln | Thr | Met | Val | Cys | Asp | Ile | Thr | Gly | Leu | Asp | Met | Ala |
| | | | 180 | | | | | 185 | | | | | 190 | | |
| Asn | Ala | Ser | Leu | Leu | Asp | Glu | Gly | Thr | Ala | Ala | Ala | Glu | Ala | Leu | Gln |
| | | 195 | | | | | 200 | | | | | 205 | | | |
| Leu | Cys | Tyr | Arg | His | Asn | Lys | Arg | Arg | Lys | Phe | Leu | Val | Asp | Pro | Arg |
| | 210 | | | | | 215 | | | | | 220 | | | | |
| Cys | His | Pro | Gln | Thr | Ile | Ala | Val | Val | Gln | Thr | Arg | Ala | Lys | Tyr | Thr |
| 225 | | | | | 230 | | | | | 235 | | | | | 240 |
| Gly | Val | Leu | Thr | Glu | Leu | Lys | Leu | Pro | Cys | Glu | Met | Asp | Phe | Ser | Gly |
| | | | | 245 | | | | | 250 | | | | | 255 | |
| Lys | Asp | Val | Ser | Gly | Val | Leu | Phe | Gln | Tyr | Pro | Asp | Thr | Glu | Gly | Lys |
| | | | 260 | | | | | 265 | | | | | 270 | | |
| Val | Glu | Asp | Phe | Thr | Glu | Leu | Val | Glu | Arg | Ala | His | Gln | Ser | Gly | Ser |
| | | | 275 | | | | | 280 | | | | | 285 | | |
| Leu | Ala | Cys | Cys | Ala | Thr | Asp | Leu | Leu | Ala | Leu | Cys | Ile | Leu | Arg | Pro |
| | 290 | | | | | 295 | | | | | 300 | | | | |
| Pro | Gly | Glu | Phe | Gly | Val | Asp | Ile | Ala | Leu | Gly | Ser | Ser | Gln | Arg | Phe |
| 305 | | | | | 310 | | | | | 315 | | | | | 320 |
| Gly | Val | Pro | Leu | Gly | Tyr | Gly | Gly | Pro | His | Ala | Ala | Phe | Phe | Ala | Val |
| | | | | 325 | | | | | 330 | | | | | 335 | |
| Arg | Glu | Ser | Leu | Val | Arg | Met | Met | Pro | Gly | Arg | Met | Val | Gly | Val | Thr |
| | | | 340 | | | | | 345 | | | | | 350 | | |
| Arg | Asp | Ala | Thr | Gly | Lys | Glu | Val | Tyr | Arg | Leu | Ala | Leu | Gln | Thr | Arg |
| | | 355 | | | | | 360 | | | | | 365 | | | |
| Glu | Gln | His | Ile | Arg | Arg | Asp | Lys | Ala | Thr | Ser | Asn | Ile | Cys | Thr | Ala |
| | 370 | | | | | 375 | | | | | 380 | | | | |

```
Gln Ala Leu Leu Ala Asn Met Ala Ala Met Phe Arg Ile Tyr His Gly
385                 390                 395                 400

Ser His Gly Leu Glu His Ile Ala Arg Arg Val His Asn Ala Thr Leu
            405                 410                 415

Ile Leu Ser Glu Gly Leu Lys Arg Ala Gly His Gln Leu Gln His Asp
        420                 425                 430

Leu Phe Phe Asp Thr Leu Lys Ile His Cys Gly Cys Ser Val Lys Glu
    435                 440                 445

Val Leu Gly Arg Ala Ala Gln Arg Gln Ile Asn Phe Arg Leu Phe Glu
450                 455                 460

Asp Gly Thr Leu Gly Ile Ser Leu Asp Glu Thr Val Asn Glu Lys Asp
465                 470                 475                 480

Leu Asp Asp Leu Leu Trp Ile Phe Gly Cys Glu Ser Ser Ala Glu Leu
                485                 490                 495

Val Ala Glu Ser Met Gly Glu Glu Cys Arg Gly Ile Pro Gly Ser Val
            500                 505                 510

Phe Lys Arg Thr Ser Pro Phe Leu Thr His Gln Val Phe Asn Ser Tyr
        515                 520                 525

His Ser Glu Thr Asn Ile Val Arg Tyr Met Lys Lys Leu Glu Asn Lys
    530                 535                 540

Asp Ile Ser Leu Val His Ser Met Ile Pro Leu Gly Ser Cys Thr Met
545                 550                 555                 560

Lys Leu Asn Ser Ser Ser Glu Leu Ala Pro Ile Thr Trp Lys Glu Phe
                565                 570                 575

Ala Asn Ile His Pro Phe Val Pro Leu Asp Gln Ala Gln Gly Tyr Gln
            580                 585                 590

Gln Leu Phe Arg Glu Leu Glu Lys Asp Leu Cys Glu Leu Thr Gly Tyr
        595                 600                 605

Asp Gln Val Cys Phe Gln Pro Asn Ser Gly Ala Gln Gly Glu Tyr Ala
610                 615                 620

Gly Leu Ala Thr Ile Arg Ala Tyr Leu Asn Gln Lys Gly Glu Gly His
625                 630                 635                 640

Arg Thr Val Cys Leu Ile Pro Lys Ser Ala His Gly Thr Asn Pro Ala
                645                 650                 655

Ser Ala His Met Ala Gly Met Lys Ile Gln Pro Val Glu Val Asp Lys
            660                 665                 670

Tyr Gly Asn Ile Asp Ala Val His Leu Lys Ala Met Val Asp Lys His
        675                 680                 685

Lys Glu Asn Leu Ala Ala Ile Met Ile Thr Tyr Pro Ser Thr Asn Gly
    690                 695                 700

Val Phe Glu Glu Asn Ile Ser Asp Val Cys Asp Leu Ile His Gln His
705                 710                 715                 720

Gly Gly Gln Val Tyr Leu Asp Gly Ala Asn Met Asn Ala Gln Val Gly
                725                 730                 735

Ile Cys Arg Pro Gly Asp Phe Gly Ser Asp Val Ser His Leu Asn Leu
            740                 745                 750

His Lys Thr Phe Cys Ile Pro His Gly Gly Gly Pro Gly Met Gly
        755                 760                 765

Pro Ile Gly Val Lys Lys His Leu Ala Pro Phe Leu Pro Asn His Pro
    770                 775                 780

Val Ile Ser Leu Lys Arg Asn Glu Asp Ala Cys Pro Val Gly Thr Val
785                 790                 795                 800

Ser Ala Ala Pro Trp Gly Ser Ser Ser Ile Leu Pro Ile Ser Trp Ala
```

```
                    805                 810                 815
Tyr Ile Lys Met Met Gly Gly Lys Gly Leu Lys Gln Ala Thr Glu Thr
            820                 825                 830

Ala Ile Leu Asn Ala Asn Tyr Met Ala Lys Arg Leu Glu Thr His Tyr
        835                 840                 845

Arg Ile Leu Phe Arg Gly Ala Arg Gly Tyr Val Gly His Glu Phe Ile
    850                 855                 860

Leu Asp Thr Arg Pro Phe Lys Lys Ser Ala Asn Ile Glu Ala Val Asp
865                 870                 875                 880

Val Ala Lys Arg Leu Gln Asp Tyr Gly Phe His Ala Pro Thr Met Ser
            885                 890                 895

Trp Pro Val Ala Gly Thr Leu Met Val Glu Pro Thr Glu Ser Glu Asp
        900                 905                 910

Lys Ala Glu Leu Asp Arg Phe Cys Asp Ala Met Ile Ser Ile Arg Gln
    915                 920                 925

Glu Ile Ala Asp Ile Glu Glu Gly Arg Ile Asp Pro Arg Val Asn Pro
930                 935                 940

Leu Lys Met Ser Pro His Ser Leu Thr Cys Val Thr Ser Ser His Trp
945                 950                 955                 960

Asp Arg Pro Tyr Ser Arg Glu Val Ala Phe Pro Leu Pro Phe Met
            965                 970                 975

Lys Pro Glu Asn Lys Phe Trp Pro Thr Ile Ala Arg Ile Asp Asp Ile
        980                 985                 990

Tyr Gly Asp Gln His Leu Val Cys Thr Cys Pro Pro Met Glu Val Tyr
    995                 1000                1005

Glu Ser  Pro Phe Ser Glu Gln  Lys Arg Ala Ser Ser
    1010                1015                1020

<210> SEQ ID NO 57
<211> LENGTH: 513
<212> TYPE: PRT
<213> ORGANISM: Homo sapiens

<400> SEQUENCE: 57

Met Ile Arg Thr Pro Leu Ser Ala Ser Ala His Arg Leu Leu Leu Pro
1               5                   10                  15

Gly Ser Arg Gly Arg Pro Pro Arg Asn Met Gln Pro Thr Gly Arg Glu
            20                  25                  30

Gly Ser Arg Ala Leu Ser Arg Arg Tyr Leu Arg Arg Leu Leu Leu
        35                  40                  45

Leu Leu Leu Leu Leu Arg Gln Pro Val Thr Arg Ala Glu Thr Thr
    50                  55                  60

Pro Gly Ala Pro Arg Ala Leu Ser Thr Leu Gly Ser Pro Ser Leu Phe
65                  70                  75                  80

Thr Thr Pro Gly Val Pro Ser Ala Leu Thr Thr Pro Gly Leu Thr Thr
            85                  90                  95

Pro Gly Thr Pro Lys Thr Leu Asp Leu Arg Gly Arg Ala Gln Ala Leu
        100                 105                 110

Met Arg Ser Phe Pro Leu Val Asp Gly His Asn Asp Leu Pro Gln Val
    115                 120                 125

Leu Arg Gln Arg Tyr Lys Asn Val Leu Gln Asp Val Asn Leu Arg Asn
130                 135                 140

Phe Ser His Gly Gln Thr Ser Leu Asp Arg Leu Arg Asp Gly Leu Val
145                 150                 155                 160

Gly Ala Gln Phe Trp Ser Ala Ser Val Ser Cys Gln Ser Gln Asp Gln
```

```
                   165                 170                 175
Thr Ala Val Arg Leu Ala Leu Glu Gln Ile Asp Leu Ile His Arg Met
            180                 185                 190

Cys Ala Ser Tyr Ser Glu Leu Glu Leu Val Thr Ser Ala Glu Gly Leu
            195                 200                 205

Asn Ser Ser Gln Lys Leu Ala Cys Leu Ile Gly Val Glu Gly Gly His
            210                 215                 220

Ser Leu Asp Ser Ser Leu Ser Val Leu Arg Ser Phe Tyr Val Leu Gly
225                 230                 235                 240

Val Arg Tyr Leu Thr Leu Thr Phe Thr Cys Ser Thr Pro Trp Ala Glu
                245                 250                 255

Ser Ser Thr Lys Phe Arg His His Met Tyr Thr Asn Val Ser Gly Leu
                260                 265                 270

Thr Ser Phe Gly Glu Lys Val Glu Glu Leu Asn Arg Leu Gly Met
                275                 280                 285

Met Ile Asp Leu Ser Tyr Ala Ser Asp Thr Leu Ile Arg Arg Val Leu
            290                 295                 300

Glu Val Ser Gln Ala Pro Val Ile Phe Ser His Ser Ala Ala Arg Ala
305                 310                 315                 320

Val Cys Asp Asn Leu Leu Asn Val Pro Asp Asp Ile Leu Gln Leu Leu
                325                 330                 335

Lys Lys Asn Gly Gly Ile Val Met Val Thr Leu Ser Met Gly Val Leu
                340                 345                 350

Gln Cys Asn Leu Leu Ala Asn Val Ser Thr Val Ala Asp His Phe Asp
            355                 360                 365

His Ile Arg Ala Val Ile Gly Ser Glu Phe Ile Gly Ile Gly Gly Asn
            370                 375                 380

Tyr Asp Gly Thr Gly Arg Phe Pro Gln Gly Leu Glu Asp Val Ser Thr
385                 390                 395                 400

Tyr Pro Val Leu Ile Glu Glu Leu Leu Ser Arg Ser Trp Ser Glu Glu
                405                 410                 415

Glu Leu Gln Gly Val Leu Arg Gly Asn Leu Leu Arg Val Phe Arg Gln
                420                 425                 430

Val Glu Lys Val Arg Glu Glu Ser Arg Ala Gln Ser Pro Val Glu Ala
                435                 440                 445

Glu Phe Pro Tyr Gly Gln Leu Ser Thr Ser Cys His Ser His Leu Val
            450                 455                 460

Pro Gln Asn Gly His Gln Ala Thr His Leu Glu Val Thr Lys Gln Pro
465                 470                 475                 480

Thr Asn Arg Val Pro Trp Arg Ser Ser Asn Ala Ser Pro Tyr Leu Val
                485                 490                 495

Pro Gly Leu Val Ala Ala Thr Ile Pro Thr Phe Thr Gln Trp Leu
                500                 505                 510

Cys

<210> SEQ ID NO 58
<211> LENGTH: 174
<212> TYPE: PRT
<213> ORGANISM: Homo sapiens

<400> SEQUENCE: 58

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
            20                  25                  30
```

Ala Gly Ala Cys Arg Gly Ala Pro Ile Leu Pro Gln Gly Leu Gln Pro
         35                  40                  45

Glu Gln Gln Leu Gln Leu Trp Asn Glu Ile Asp Asp Thr Cys Ser Ser
 50                  55                  60

Phe Leu Ser Ile Asp Ser Gln Pro Gln Ala Ser Asn Ala Leu Glu Glu
 65                  70                  75                  80

Leu Cys Phe Met Ile Met Gly Met Leu Pro Lys Pro Gln Glu Gln Asp
                 85                  90                  95

Glu Lys Asp Asn Thr Lys Arg Phe Leu Phe His Tyr Ser Lys Thr Gln
                100                 105                 110

Lys Leu Gly Lys Ser Asn Val Val Ser Ser Val Val His Pro Leu Leu
                115                 120                 125

Gln Leu Val Pro His Leu His Glu Arg Arg Met Lys Arg Phe Arg Val
         130                 135                 140

Asp Glu Glu Phe Gln Ser Pro Phe Ala Ser Gln Ser Arg Gly Tyr Phe
145                 150                 155                 160

Leu Phe Arg Pro Arg Asn Gly Arg Arg Ser Ala Gly Phe Ile
                165                 170

<210> SEQ ID NO 59
<211> LENGTH: 431
<212> TYPE: PRT
<213> ORGANISM: Homo sapiens

<400> SEQUENCE: 59

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                 20                  25                  30

Leu Asp Asn Glu Val His Ser Ser Phe Ile His Arg Arg Leu Arg Ser
             35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
             115                 120                 125

Asp Ala Asp Met Val Met Ser Phe Val Asn Leu Val Glu His Asp Lys
         130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
             180                 185                 190

Ser Val Tyr Gln Val Leu Gln Glu His Leu Gly Arg Glu Ser Asp Leu
         195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
            245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 60
<211> LENGTH: 212
<212> TYPE: PRT
<213> ORGANISM: Homo sapiens

<400> SEQUENCE: 60

Met Lys Pro Pro Ser Ser Ile Gln Thr Ser Glu Phe Asp Ser Ser Asp
1               5                   10                  15

Glu Glu Pro Ile Glu Asp Glu Gly Thr Pro Ile His Ile Ser Trp Leu
            20                  25                  30

Ser Leu Ser Arg Val Asn Cys Ser Gln Phe Leu Gly Leu Cys Ala Leu
        35                  40                  45

Pro Gly Cys Lys Phe Lys Asp Val Arg Arg Asn Val Gln Lys Asp Thr
    50                  55                  60

Glu Glu Leu Lys Ser Cys Gly Ile Gln Asp Ile Phe Val Phe Cys Thr
65                  70                  75                  80

Arg Gly Glu Leu Ser Lys Tyr Arg Val Pro Asn Leu Leu Asp Leu Tyr
                85                  90                  95

Gln Gln Cys Gly Ile Ile Thr His His His Pro Ile Ala Asp Gly Gly
            100                 105                 110

Thr Pro Asp Ile Ala Ser Cys Cys Glu Ile Met Glu Glu Leu Thr Thr
        115                 120                 125

Cys Leu Lys Asn Tyr Arg Lys Thr Leu Ile His Cys Tyr Gly Gly Leu
    130                 135                 140

Gly Arg Ser Cys Leu Val Ala Ala Cys Leu Leu Leu Tyr Leu Ser Asp
145                 150                 155                 160

Thr Ile Ser Pro Glu Gln Ala Ile Asp Ser Leu Arg Asp Leu Arg Gly
                165                 170                 175

Ser Gly Ala Ile Gln Thr Ile Lys Gln Tyr Asn Tyr Leu His Glu Phe
            180                 185                 190

-continued

Arg Asp Lys Leu Ala Ala His Leu Ser Ser Arg Asp Ser Gln Ser Arg
        195                 200                 205

Ser Val Ser Arg
        210

<210> SEQ ID NO 61
<211> LENGTH: 79
<212> TYPE: PRT
<213> ORGANISM: Homo sapiens

<400> SEQUENCE: 61

Met Ser His Lys Gln Ile Tyr Tyr Ser Asp Lys Tyr Asp Asp Glu Glu
1               5                   10                  15

Phe Glu Tyr Arg His Val Met Leu Pro Lys Asp Ile Ala Lys Leu Val
            20                  25                  30

Pro Lys Thr His Leu Met Ser Glu Ser Glu Trp Arg Asn Leu Gly Val
        35                  40                  45

Gln Gln Ser Gln Gly Trp Val His Tyr Met Ile His Glu Pro Glu Pro
    50                  55                  60

His Ile Leu Leu Phe Arg Arg Pro Leu Pro Lys Lys Pro Lys Lys
65                  70                  75

<210> SEQ ID NO 62
<211> LENGTH: 509
<212> TYPE: PRT
<213> ORGANISM: Homo sapiens

<400> SEQUENCE: 62

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

```
Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Ser His Ile His Ala
            260                 265                 270

Ser Ser Tyr Ile Ser Pro Glu Lys Glu Gln Tyr Ile Ala Gln Phe
            275                 280                 285

Thr Ser Gln Phe Leu Ser Leu Gln Cys Leu Gln Ala Leu Tyr Val Asp
        290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
        370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 63
<211> LENGTH: 165
<212> TYPE: PRT
<213> ORGANISM: Homo sapiens

<400> SEQUENCE: 63

Met Gly Trp Asp Leu Thr Val Lys Met Leu Ala Gly Asn Glu Phe Gln
1               5                   10                  15

Val Ser Leu Ser Ser Ser Met Ser Val Ser Leu Lys Ala Gln Ile
            20                  25                  30

Thr Gln Lys Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Arg Ser Thr Tyr
                85                  90                  95
```

-continued

```
Glu Val Arg Leu Thr Gln Thr Val Ala His Leu Lys Gln Gln Val Ser
                100                 105                 110
Gly Leu Glu Gly Val Gln Asp Asp Leu Phe Trp Leu Thr Phe Glu Gly
            115                 120                 125
Lys Pro Leu Glu Asp Gln Leu Pro Leu Gly Tyr Gly Leu Lys Pro
130                 135                 140
Leu Ser Thr Val Phe Met Asn Leu Arg Leu Arg Gly Gly Thr Glu
145                 150                 155                 160
Pro Gly Gly Arg Ser
                165

<210> SEQ ID NO 64
<211> LENGTH: 363
<212> TYPE: PRT
<213> ORGANISM: Homo sapiens

<400> SEQUENCE: 64

Met Arg Trp Val Arg His Asp Ala Pro Ala Arg Gly Gln Leu Arg
1               5                   10                  15
Arg Leu Leu Glu His Val Arg Leu Pro Leu Leu Ala Pro Ala Tyr Phe
                20                  25                  30
Leu Glu Lys Val Glu Ala Asp Glu Leu Leu Gln Ala Cys Gly Glu Cys
                35                  40                  45
Arg Pro Leu Leu Leu Glu Ala Arg Ala Cys Phe Ile Leu Gly Arg Glu
            50                  55                  60
Ala Gly Ala Leu Arg Thr Arg Pro Arg Arg Phe Met Asp Leu Ala Glu
65                  70                  75                  80
Val Ile Val Val Ile Gly Gly Cys Asp Arg Lys Gly Leu Leu Lys Leu
                85                  90                  95
Pro Phe Ala Asp Ala Tyr His Pro Glu Ser Gln Arg Trp Thr Pro Leu
                100                 105                 110
Pro Ser Leu Pro Gly Tyr Thr Arg Ser Glu Phe Ala Ala Cys Ala Leu
            115                 120                 125
Arg Asn Asp Val Tyr Val Ser Gly Gly His Ile Asn Ser His Asp Val
130                 135                 140
Trp Met Phe Ser Ser His Leu His Thr Trp Ile Lys Val Ala Ser Leu
145                 150                 155                 160
His Lys Gly Arg Trp Arg His Lys Met Ala Val Val Gln Gly Gln Leu
                165                 170                 175
Phe Ala Val Gly Gly Phe Asp Gly Leu Arg Arg Leu His Ser Val Glu
            180                 185                 190
Arg Tyr Asp Pro Phe Ser Asn Thr Trp Ala Ala Ala Pro Leu Pro
            195                 200                 205
Glu Ala Val Ser Ser Ala Ala Val Ala Ser Cys Ala Gly Lys Leu Phe
210                 215                 220
Val Ile Gly Gly Ala Arg Gln Gly Val Asn Thr Asp Lys Val Gln
225                 230                 235                 240
Cys Phe Asp Pro Lys Glu Asp Arg Trp Ser Leu Arg Ser Pro Ala Pro
                245                 250                 255
Phe Ser Gln Arg Cys Leu Glu Ala Val Ser Leu Glu Asp Thr Ile Tyr
            260                 265                 270
Val Met Gly Gly Leu Met Ser Lys Ile Phe Thr Tyr Asp Pro Gly Thr
        275                 280                 285
Asp Val Trp Gly Glu Ala Ala Val Leu Pro Ser Pro Val Glu Ser Cys
290                 295                 300
```

-continued

Gly Val Thr Val Cys Asp Gly Lys Val His Ile Leu Gly Arg Asp
305                 310                 315                 320

Asp Arg Gly Glu Ser Thr Asp Lys Val Phe Thr Phe Asp Pro Ser Ser
            325                 330                 335

Gly Gln Val Glu Val Gln Pro Ser Leu Gln Arg Cys Thr Ser Ser His
        340                 345                 350

Gly Cys Val Thr Ile Ile Gln Ser Leu Gly Arg
        355                 360

<210> SEQ ID NO 65
<211> LENGTH: 282
<212> TYPE: PRT
<213> ORGANISM: Homo sapiens

<400> SEQUENCE: 65

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 66
<211> LENGTH: 890
<212> TYPE: PRT
<213> ORGANISM: Homo sapiens

<400> SEQUENCE: 66

```
Met Ser Gln Gly Ile Leu Ser Pro Pro Ala Gly Leu Leu Ser Asp Asp
1               5                   10                  15

Asp Val Val Ser Pro Met Phe Glu Ser Thr Ala Ala Asp Leu Gly
            20                  25                  30

Ser Val Val Arg Lys Asn Leu Leu Ser Asp Cys Ser Val Val Ser Thr
            35                  40                  45

Ser Leu Glu Asp Lys Gln Gln Val Pro Ser Glu Asp Ser Met Glu Lys
        50                  55                  60

Val Lys Val Tyr Leu Arg Val Arg Pro Leu Leu Pro Ser Glu Leu Glu
65              70                  75                  80

Arg Gln Glu Asp Gln Gly Cys Val Arg Ile Glu Asn Val Glu Thr Leu
                85                  90                  95

Val Leu Gln Ala Pro Lys Asp Ser Phe Ala Leu Lys Ser Asn Glu Arg
            100                 105                 110

Gly Ile Gly Gln Ala Thr His Arg Phe Thr Phe Ser Gln Ile Phe Gly
        115                 120                 125

Pro Glu Val Gly Gln Ala Ser Phe Phe Asn Leu Thr Val Lys Glu Met
130                 135                 140

Val Lys Asp Val Leu Lys Gly Gln Asn Trp Leu Ile Tyr Thr Tyr Gly
145                 150                 155                 160

Val Thr Asn Ser Gly Lys Thr His Thr Ile Gln Gly Thr Ile Lys Asp
                165                 170                 175

Gly Gly Ile Leu Pro Arg Ser Leu Ala Leu Ile Phe Asn Ser Leu Gln
            180                 185                 190

Gly Gln Leu His Pro Thr Pro Asp Leu Lys Pro Leu Leu Ser Asn Glu
        195                 200                 205

Val Ile Trp Leu Asp Ser Lys Gln Ile Arg Gln Glu Glu Met Lys Lys
210                 215                 220

Leu Ser Leu Leu Asn Gly Gly Leu Gln Glu Glu Leu Ser Thr Ser
225                 230                 235                 240

Leu Lys Arg Ser Val Tyr Ile Glu Ser Arg Ile Gly Thr Ser Thr Ser
                245                 250                 255

Phe Asp Ser Gly Ile Ala Gly Leu Ser Ser Ile Ser Gln Cys Thr Ser
            260                 265                 270

Ser Ser Gln Leu Asp Glu Thr Ser His Arg Trp Ala Gln Pro Asp Thr
        275                 280                 285

Ala Pro Leu Pro Val Pro Ala Asn Ile Arg Phe Ser Ile Trp Ile Ser
    290                 295                 300

Phe Phe Glu Ile Tyr Asn Glu Leu Leu Tyr Asp Leu Leu Glu Pro Pro
305                 310                 315                 320

Ser Gln Gln Arg Lys Arg Gln Thr Leu Arg Leu Cys Glu Asp Gln Asn
                325                 330                 335

Gly Asn Pro Tyr Val Lys Asp Leu Asn Trp Ile His Val Gln Asp Ala
            340                 345                 350

Glu Glu Ala Trp Lys Leu Leu Lys Val Gly Arg Lys Asn Gln Ser Phe
        355                 360                 365

Ala Ser Thr His Leu Asn Gln Asn Ser Ser Arg Ser His Ser Ile Phe
    370                 375                 380

Ser Ile Arg Ile Leu His Leu Gln Gly Glu Gly Asp Ile Val Pro Lys
385                 390                 395                 400

Ile Ser Glu Leu Ser Leu Cys Asp Leu Ala Gly Ser Glu Arg Cys Lys
                405                 410                 415
```

-continued

```
Asp Gln Lys Ser Gly Glu Arg Leu Lys Glu Ala Gly Asn Ile Asn Thr
            420                 425                 430

Ser Leu His Thr Leu Gly Arg Cys Ile Ala Ala Leu Arg Gln Asn Gln
            435                 440                 445

Gln Asn Arg Ser Lys Gln Asn Leu Val Pro Phe Arg Asp Ser Lys Leu
            450                 455                 460

Thr Arg Val Phe Gln Gly Phe Phe Thr Gly Arg Gly Arg Ser Cys Met
465                 470                 475                 480

Ile Val Asn Val Asn Pro Cys Ala Ser Thr Tyr Asp Glu Thr Leu His
                485                 490                 495

Val Ala Lys Phe Ser Ala Ile Ala Ser Gln Leu Val His Ala Pro Pro
            500                 505                 510

Met Gln Leu Gly Phe Pro Ser Leu His Ser Phe Ile Lys Glu His Ser
            515                 520                 525

Leu Gln Val Ser Pro Ser Leu Glu Lys Gly Ala Lys Ala Asp Thr Gly
            530                 535                 540

Leu Asp Asp Asp Ile Glu Asn Glu Ala Asp Ile Ser Met Tyr Gly Lys
545                 550                 555                 560

Glu Glu Leu Leu Gln Val Val Glu Ala Met Lys Thr Leu Leu Leu Lys
                565                 570                 575

Glu Arg Gln Glu Lys Leu Gln Leu Glu Met His Leu Arg Asp Glu Ile
            580                 585                 590

Cys Asn Glu Met Val Glu Gln Met Gln Gln Arg Glu Gln Trp Cys Ser
            595                 600                 605

Glu His Leu Asp Thr Gln Lys Glu Leu Leu Glu Glu Met Tyr Glu Glu
            610                 615                 620

Lys Leu Asn Ile Leu Lys Glu Ser Leu Thr Ser Phe Tyr Gln Glu Glu
625                 630                 635                 640

Ile Gln Glu Arg Asp Glu Lys Ile Glu Glu Leu Glu Ala Leu Leu Gln
                645                 650                 655

Glu Ala Arg Gln Gln Ser Val Ala His Gln Gln Ser Gly Ser Glu Leu
            660                 665                 670

Ala Leu Arg Arg Ser Gln Arg Leu Ala Ala Ser Ala Ser Thr Gln Gln
            675                 680                 685

Leu Gln Glu Val Lys Ala Lys Leu Gln Gln Cys Lys Ala Glu Leu Asn
            690                 695                 700

Ser Thr Thr Glu Glu Leu His Lys Tyr Gln Lys Met Leu Glu Pro Pro
705                 710                 715                 720

Pro Ser Ala Lys Pro Phe Thr Ile Asp Val Asp Lys Lys Leu Glu Glu
                725                 730                 735

Gly Gln Lys Asn Ile Arg Leu Leu Arg Thr Glu Leu Gln Lys Leu Gly
            740                 745                 750

Glu Ser Leu Gln Ser Ala Glu Arg Ala Cys Cys His Ser Thr Gly Ala
            755                 760                 765

Gly Lys Leu Arg Gln Ala Leu Thr Thr Cys Asp Asp Ile Leu Ile Lys
            770                 775                 780

Gln Asp Gln Thr Leu Ala Glu Leu Gln Asn Asn Met Val Leu Val Lys
785                 790                 795                 800

Leu Asp Leu Arg Lys Lys Ala Ala Cys Ile Ala Glu Gln Tyr His Thr
                805                 810                 815

Val Leu Lys Leu Gln Gly Gln Val Ser Ala Lys Lys Arg Leu Gly Thr
            820                 825                 830

Asn Gln Glu Asn Gln Gln Pro Asn Gln Gln Pro Pro Gly Lys Lys Pro
            835                 840                 845
```

```
Phe Leu Arg Asn Leu Leu Pro Arg Thr Pro Thr Cys Gln Ser Ser Thr
    850                 855                 860
Asp Cys Ser Pro Tyr Ala Arg Ile Leu Arg Ser Arg Ser Pro Leu
865                 870                 875                 880
Leu Lys Ser Gly Pro Phe Gly Lys Lys Tyr
            885                 890
```

<210> SEQ ID NO 67
<211> LENGTH: 235
<212> TYPE: PRT
<213> ORGANISM: Homo sapiens

<400> SEQUENCE: 67

```
Met Phe Ile Trp Thr Ser Gly Arg Thr Ser Ser Tyr Arg His Asp
1               5                   10                  15
Glu Lys Arg Asn Ile Tyr Gln Lys Ile Arg Asp His Asp Leu Leu Asp
                20                  25                  30
Lys Arg Lys Thr Val Thr Ala Leu Lys Ala Gly Glu Asp Arg Ala Ile
            35                  40                  45
Leu Leu Gly Leu Ala Met Met Val Cys Ser Ile Met Met Tyr Phe Leu
50                  55                  60
Leu Gly Ile Thr Leu Leu Arg Ser Tyr Met Gln Ser Val Trp Thr Glu
65                  70                  75                  80
Glu Ser Gln Cys Thr Leu Leu Asn Ala Ser Ile Thr Glu Thr Phe Asn
                85                  90                  95
Cys Ser Phe Ser Cys Gly Pro Asp Cys Trp Lys Leu Ser Gln Tyr Pro
            100                 105                 110
Cys Leu Gln Val Tyr Val Asn Leu Thr Ser Ser Gly Glu Lys Leu Leu
        115                 120                 125
Leu Tyr His Thr Glu Glu Thr Ile Lys Ile Asn Gln Lys Cys Ser Tyr
130                 135                 140
Ile Pro Lys Cys Gly Lys Asn Phe Glu Glu Ser Met Ser Leu Val Asn
145                 150                 155                 160
Val Val Met Glu Asn Phe Arg Lys Tyr Gln His Phe Ser Cys Tyr Ser
                165                 170                 175
Asp Pro Glu Gly Asn Gln Lys Ser Val Ile Leu Thr Lys Leu Tyr Ser
            180                 185                 190
Ser Asn Val Leu Phe His Ser Leu Phe Trp Pro Thr Cys Met Met Ala
        195                 200                 205
Gly Gly Val Ala Ile Val Ala Met Val Lys Leu Thr Gln Tyr Leu Ser
210                 215                 220
Leu Leu Cys Glu Arg Ile Gln Arg Ile Asn Arg
225                 230                 235
```

<210> SEQ ID NO 68
<211> LENGTH: 98
<212> TYPE: PRT
<213> ORGANISM: Homo sapiens

<400> SEQUENCE: 68

```
Met Asn Gln Thr Ala Ile Leu Ile Cys Cys Leu Ile Phe Leu Thr Leu
1               5                   10                  15
Ser Gly Ile Gln Gly Val Pro Leu Ser Arg Thr Val Arg Cys Thr Cys
                20                  25                  30
Ile Ser Ile Ser Asn Gln Pro Val Asn Pro Arg Ser Leu Glu Lys Leu
            35                  40                  45
```

```
Glu Ile Ile Pro Ala Ser Gln Phe Cys Pro Arg Val Glu Ile Ala
 50                  55                  60

Thr Met Lys Lys Lys Gly Glu Lys Arg Cys Leu Asn Pro Glu Ser Lys
 65                  70                  75                  80

Ala Ile Lys Asn Leu Leu Lys Ala Val Ser Lys Glu Met Ser Lys Arg
             85                  90                  95

Ser Pro

<210> SEQ ID NO 69
<211> LENGTH: 467
<212> TYPE: PRT
<213> ORGANISM: Homo sapiens

<400> SEQUENCE: 69

Met Ala Ala Leu Thr Ile Ala Thr Gly Thr Gly Asn Trp Phe Ser Ala
  1               5                  10                  15

Leu Ala Leu Gly Val Thr Leu Leu Lys Cys Leu Leu Ile Pro Thr Tyr
             20                  25                  30

His Ser Thr Asp Phe Glu Val His Arg Asn Trp Leu Ala Ile Thr His
             35                  40                  45

Ser Leu Pro Ile Ser Gln Trp Tyr Tyr Glu Ala Thr Ser Glu Trp Thr
 50                  55                  60

Leu Asp Tyr Pro Pro Phe Phe Ala Trp Phe Glu Tyr Ile Leu Ser His
 65                  70                  75                  80

Val Ala Lys Tyr Phe Asp Gln Glu Met Leu Asn Val His Asn Leu Asn
             85                  90                  95

Tyr Ser Ser Ser Arg Thr Leu Leu Phe Gln Arg Phe Ser Val Ile Phe
            100                 105                 110

Met Asp Val Leu Phe Val Tyr Ala Val Arg Glu Cys Cys Lys Cys Ile
            115                 120                 125

Asp Gly Lys Lys Val Gly Lys Glu Leu Thr Glu Lys Pro Lys Phe Ile
130                 135                 140

Leu Ser Val Leu Leu Leu Trp Asn Phe Gly Leu Leu Ile Val Asp His
145                 150                 155                 160

Ile His Phe Gln Tyr Asn Gly Phe Leu Phe Gly Leu Met Leu Leu Ser
            165                 170                 175

Ile Ala Arg Leu Phe Gln Lys Arg His Met Glu Gly Ala Phe Leu Phe
            180                 185                 190

Ala Val Leu Leu His Phe Lys His Ile Tyr Leu Tyr Val Ala Pro Ala
            195                 200                 205

Tyr Gly Val Tyr Leu Leu Arg Ser Tyr Cys Phe Thr Ala Asn Lys Pro
210                 215                 220

Asp Gly Ser Ile Arg Trp Lys Ser Phe Ser Phe Val Arg Val Ile Ser
225                 230                 235                 240

Leu Gly Leu Val Val Phe Leu Val Ser Ala Leu Ser Leu Gly Pro Phe
            245                 250                 255

Leu Ala Leu Asn Gln Leu Pro Gln Val Phe Ser Arg Leu Phe Pro Phe
            260                 265                 270

Lys Arg Gly Leu Cys His Ala Tyr Trp Ala Pro Asn Phe Trp Ala Leu
            275                 280                 285

Tyr Asn Ala Leu Asp Lys Val Leu Ser Val Ile Gly Leu Lys Leu Lys
            290                 295                 300

Phe Leu Asp Pro Asn Asn Ile Pro Lys Ala Ser Met Thr Ser Gly Leu
305                 310                 315                 320

Val Gln Gln Phe Gln His Thr Val Leu Pro Ser Val Thr Pro Leu Ala
```

```
                        325                 330                 335
Thr Leu Ile Cys Thr Leu Ile Ala Ile Leu Pro Ser Ile Phe Cys Leu
                340                 345                 350

Trp Phe Lys Pro Gln Gly Pro Arg Gly Phe Leu Arg Cys Leu Thr Leu
            355                 360                 365

Cys Ala Leu Ser Ser Phe Met Phe Gly Trp His Val His Glu Lys Ala
        370                 375                 380

Ile Leu Leu Ala Ile Leu Pro Met Ser Leu Leu Ser Val Gly Lys Ala
385                 390                 395                 400

Gly Asp Ala Ser Ile Phe Leu Ile Leu Thr Thr Thr Gly His Tyr Ser
                405                 410                 415

Leu Phe Pro Leu Leu Phe Thr Ala Pro Glu Leu Pro Ile Lys Ile Leu
            420                 425                 430

Leu Met Leu Leu Phe Thr Ile Tyr Ser Ile Ser Ser Leu Lys Thr Leu
        435                 440                 445

Phe Arg Arg Ser Phe Thr Leu Val Ala Gln Ala Gly Val Gln Trp His
    450                 455                 460

Asp Leu Ser
465

<210> SEQ ID NO 70
<211> LENGTH: 84
<212> TYPE: PRT
<213> ORGANISM: Homo sapiens

<400> SEQUENCE: 70

Met Asp Asp Asp Ala Ala Pro Arg Val Glu Gly Val Pro Val Ala Val
1               5                   10                  15

His Lys His Ala Leu His Asp Gly Leu Arg Gln Val Ala Gly Pro Gly
            20                  25                  30

Ala Ala Ala Ala His Leu Pro Arg Trp Pro Pro Gln Leu Ala Ala
        35                  40                  45

Ser Arg Arg Glu Ala Pro Pro Leu Ser Gln Arg Pro His Arg Thr Gln
    50                  55                  60

Gly Ala Gly Ser Pro Pro Glu Thr Asn Glu Lys Leu Thr Asn Pro Gln
65                  70                  75                  80

Val Lys Glu Lys

<210> SEQ ID NO 71
<211> LENGTH: 156
<212> TYPE: PRT
<213> ORGANISM: Homo sapiens

<400> SEQUENCE: 71

Met Glu Pro Ala Ala Gly Ser Ser Met Glu Pro Ser Ala Asp Trp Leu
1               5                   10                  15

Ala Thr Ala Ala Ala Arg Gly Arg Val Glu Gly Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95
```

```
Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Gly Gly Thr Arg Gly Ser Asn His Ala Arg
    130                 135                 140

Ile Asp Ala Ala Glu Gly Pro Ser Asp Ile Pro Asp
145                 150                 155

<210> SEQ ID NO 72
<211> LENGTH: 747
<212> TYPE: PRT
<213> ORGANISM: Homo sapiens

<400> SEQUENCE: 72

Met Ser Gln Val Lys Ser Ser Tyr Ser Tyr Asp Ala Pro Ser Asp Phe
1               5                   10                  15

Ile Asn Phe Ser Ser Leu Asp Asp Glu Gly Asp Thr Gln Asn Ile Asp
            20                  25                  30

Ser Trp Phe Glu Glu Lys Ala Asn Leu Glu Asn Lys Leu Leu Gly Lys
        35                  40                  45

Asn Gly Thr Gly Gly Leu Phe Gln Gly Lys Thr Pro Leu Arg Lys Ala
    50                  55                  60

Asn Leu Gln Gln Ala Ile Val Thr Pro Leu Lys Pro Val Asp Asn Thr
65                  70                  75                  80

Tyr Tyr Lys Glu Ala Glu Lys Glu Asn Leu Val Glu Gln Ser Ile Pro
                85                  90                  95

Ser Asn Ala Cys Ser Ser Leu Glu Val Glu Ala Ala Ile Ser Arg Lys
            100                 105                 110

Thr Pro Ala Gln Pro Gln Arg Arg Ser Leu Arg Leu Ser Ala Gln Lys
        115                 120                 125

Asp Leu Glu Gln Lys Glu Lys His His Val Lys Met Lys Ala Lys Arg
    130                 135                 140

Cys Ala Thr Pro Val Ile Ile Asp Glu Ile Leu Pro Ser Lys Lys Met
145                 150                 155                 160

Lys Val Ser Asn Asn Lys Lys Lys Pro Glu Glu Gly Ser Ala His
                165                 170                 175

Gln Asp Thr Ala Glu Lys Asn Ala Ser Ser Pro Glu Lys Ala Lys Gly
            180                 185                 190

Arg His Thr Val Pro Cys Met Pro Pro Ala Lys Gln Lys Phe Leu Lys
        195                 200                 205

Ser Thr Glu Glu Gln Glu Leu Glu Lys Ser Met Lys Met Gln Gln Glu
    210                 215                 220

Val Val Glu Met Arg Lys Lys Asn Glu Glu Phe Lys Lys Leu Ala Leu
225                 230                 235                 240

Ala Gly Ile Gly Gln Pro Val Lys Lys Ser Val Ser Gln Val Thr Lys
                245                 250                 255

Ser Val Asp Phe His Phe Arg Thr Asp Glu Arg Ile Lys Gln His Pro
            260                 265                 270

Lys Asn Gln Glu Glu Tyr Lys Glu Val Asn Phe Thr Ser Glu Leu Arg
        275                 280                 285

Lys His Pro Ser Ser Pro Ala Arg Val Thr Lys Gly Cys Thr Ile Val
    290                 295                 300

Lys Pro Phe Asn Leu Ser Gln Gly Lys Lys Arg Thr Phe Asp Glu Thr
305                 310                 315                 320
```

```
Val Ser Thr Tyr Val Pro Leu Ala Gln Gln Val Glu Asp Phe His Lys
            325                 330                 335

Arg Thr Pro Asn Arg Tyr His Leu Arg Ser Lys Lys Asp Asp Ile Asn
        340                 345                 350

Leu Leu Pro Ser Lys Ser Ser Val Thr Lys Ile Cys Arg Asp Pro Gln
            355                 360                 365

Thr Pro Val Leu Gln Thr Lys His Arg Ala Arg Ala Val Thr Cys Lys
        370                 375                 380

Ser Thr Ala Glu Leu Glu Ala Glu Glu Leu Glu Lys Leu Gln Gln Tyr
385                 390                 395                 400

Lys Phe Lys Ala Arg Glu Leu Asp Pro Arg Ile Leu Glu Gly Gly Pro
                405                 410                 415

Ile Leu Pro Lys Lys Pro Pro Val Lys Pro Pro Thr Glu Pro Ile Gly
            420                 425                 430

Phe Asp Leu Glu Ile Glu Lys Arg Ile Gln Glu Arg Glu Ser Lys Lys
        435                 440                 445

Lys Thr Glu Asp Glu His Phe Glu Phe His Ser Arg Pro Cys Pro Thr
        450                 455                 460

Lys Ile Leu Glu Asp Val Val Gly Val Pro Glu Lys Lys Val Leu Pro
465                 470                 475                 480

Ile Thr Val Pro Lys Ser Pro Ala Phe Ala Leu Lys Asn Arg Ile Arg
                485                 490                 495

Met Pro Thr Lys Glu Asp Glu Glu Asp Glu Pro Val Val Ile Lys
            500                 505                 510

Ala Gln Pro Val Pro His Tyr Gly Val Pro Phe Lys Pro Gln Ile Pro
        515                 520                 525

Glu Ala Arg Thr Val Glu Ile Cys Pro Phe Ser Phe Asp Ser Arg Asp
530                 535                 540

Lys Glu Arg Gln Leu Gln Lys Glu Lys Lys Ile Lys Glu Leu Gln Lys
545                 550                 555                 560

Gly Glu Val Pro Lys Phe Lys Ala Leu Pro Leu Pro His Phe Asp Thr
                565                 570                 575

Ile Asn Leu Pro Glu Lys Lys Val Lys Asn Val Thr Gln Ile Glu Pro
            580                 585                 590

Phe Cys Leu Glu Thr Asp Arg Arg Gly Ala Leu Lys Ala Gln Thr Trp
        595                 600                 605

Lys His Gln Leu Glu Glu Glu Leu Arg Gln Gln Lys Glu Ala Ala Cys
        610                 615                 620

Phe Lys Ala Arg Pro Asn Thr Val Ile Ser Gln Glu Pro Phe Val Pro
625                 630                 635                 640

Lys Lys Glu Lys Lys Ser Val Ala Glu Gly Leu Ser Gly Ser Leu Val
                645                 650                 655

Gln Glu Pro Phe Gln Leu Ala Thr Glu Lys Arg Ala Lys Glu Arg Gln
            660                 665                 670

Glu Leu Glu Lys Arg Met Ala Glu Val Glu Ala Gln Lys Ala Gln Gln
        675                 680                 685

Leu Glu Glu Ala Arg Leu Gln Glu Glu Gln Lys Leu Glu Glu Leu
        690                 695                 700

Ala Arg Leu Arg Arg Glu Leu Val His Lys Ala Asn Pro Ile Arg Lys
705                 710                 715                 720

Tyr Gln Gly Leu Glu Ile Lys Ser Ser Asp Gln Pro Leu Thr Val Pro
                725                 730                 735

Val Ser Pro Lys Phe Ser Thr Arg Phe His Cys
            740                 745
```

```
<210> SEQ ID NO 73
<211> LENGTH: 179
<212> TYPE: PRT
<213> ORGANISM: Homo sapiens

<400> SEQUENCE: 73

Met Ala Ser Gln Asn Arg Asp Pro Ala Ala Thr Ser Val Ala Ala
1               5                   10                  15

Arg Lys Gly Ala Glu Pro Ser Gly Gly Ala Ala Arg Gly Pro Val Gly
                20                  25                  30

Lys Arg Leu Gln Gln Glu Leu Met Thr Leu Met Met Ser Gly Asp Lys
                35                  40                  45

Gly Ile Ser Ala Phe Pro Glu Ser Asp Asn Leu Phe Lys Trp Val Gly
            50                  55                  60

Thr Ile His Gly Ala Ala Gly Thr Val Tyr Glu Asp Leu Arg Tyr Lys
65                  70                  75                  80

Leu Ser Leu Glu Phe Pro Ser Gly Tyr Pro Tyr Asn Ala Pro Thr Val
                    85                  90                  95

Lys Phe Leu Thr Pro Cys Tyr His Pro Asn Val Asp Thr Gln Gly Asn
                100                 105                 110

Ile Cys Leu Asp Ile Leu Lys Glu Lys Trp Ser Ala Leu Tyr Asp Val
            115                 120                 125

Arg Thr Ile Leu Leu Ser Ile Gln Ser Leu Leu Gly Glu Pro Asn Ile
130                 135                 140

Asp Ser Pro Leu Asn Thr His Ala Ala Glu Leu Trp Lys Asn Pro Thr
145                 150                 155                 160

Ala Phe Lys Lys Tyr Leu Gln Glu Thr Tyr Ser Lys Gln Val Thr Ser
                165                 170                 175

Gln Glu Pro

<210> SEQ ID NO 74
<211> LENGTH: 138
<212> TYPE: PRT
<213> ORGANISM: Homo sapiens

<400> SEQUENCE: 74

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
                20                  25                  30

Ala Val Ala Ala Ala Ser Lys Pro Ala Val Glu Ile Lys Gln Glu Gly
                35                  40                  45

Asp Thr Phe Tyr Ile Lys Thr Ser Thr Thr Val Arg Thr Thr Glu Ile
            50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Arg
                100                 105                 110

Glu Leu Thr Asn Asp Gly Glu Leu Ile Leu Thr Met Thr Ala Asp Asp
            115                 120                 125

Val Val Cys Thr Arg Val Tyr Val Arg Glu
130                 135
```

```
<210> SEQ ID NO 75
<211> LENGTH: 130
<212> TYPE: PRT
<213> ORGANISM: Homo sapiens

<400> SEQUENCE: 75

Met Ser Gly Arg Gly Lys Gln Gly Gly Lys Ala Arg Ala Lys Ala Lys
1               5                   10                  15

Ser Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 76
<211> LENGTH: 103
<212> TYPE: PRT
<213> ORGANISM: Homo sapiens

<400> SEQUENCE: 76

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 77
<211> LENGTH: 432
<212> TYPE: PRT
<213> ORGANISM: Homo sapiens

<400> SEQUENCE: 77

Met Leu Phe Glu Gln Gly Gln Gln Ala Leu Glu Leu Pro Glu Cys Thr
1               5                   10                  15

Met Gln Lys Ala Ala Tyr Tyr Glu Asn Pro Gly Leu Phe Gly Gly Tyr
            20                  25                  30

Gly Tyr Ser Lys Thr Thr Asp Thr Tyr Gly Tyr Ser Thr Pro His Gln
        35                  40                  45
```

```
Pro Tyr Pro Pro Pro Ala Ala Ala Ser Ser Leu Asp Thr Asp Tyr Pro
 50                  55                  60

Gly Ser Ala Cys Ser Ile Gln Ser Ser Ala Pro Leu Arg Ala Pro Ala
 65                  70                  75                  80

His Lys Gly Ala Glu Leu Asn Gly Ser Cys Met Arg Pro Gly Thr Gly
                 85                  90                  95

Asn Ser Gln Gly Gly Gly Gly Ser Gln Pro Pro Gly Leu Asn Ser
                100             105                 110

Glu Gln Gln Pro Pro Gln Pro Pro Pro Pro Thr Leu Pro Pro
             115                 120                 125

Ser Ser Pro Thr Asn Pro Gly Gly Val Pro Ala Lys Lys Pro Lys
130                 135                 140

Gly Gly Pro Asn Ala Ser Ser Ser Ser Ala Thr Ile Ser Lys Gln Ile
145                 150                 155                 160

Phe Pro Trp Met Lys Glu Ser Arg Gln Asn Ser Lys Gln Lys Asn Ser
                165                 170                 175

Cys Ala Thr Ala Gly Glu Ser Cys Glu Asp Lys Ser Pro Pro Gly Pro
                180                 185                 190

Ala Ser Lys Arg Val Arg Thr Ala Tyr Thr Ser Ala Gln Leu Val Glu
                195                 200                 205

Leu Glu Lys Glu Phe His Phe Asn Arg Tyr Leu Cys Arg Pro Arg Arg
210                 215                 220

Val Glu Met Ala Asn Leu Leu Asn Leu Thr Glu Arg Gln Ile Lys Ile
225                 230                 235                 240

Trp Phe Gln Asn Arg Arg Met Lys Tyr Lys Lys Asp Gln Lys Ala Lys
                245                 250                 255

Gly Ile Leu His Ser Pro Ala Ser Gln Ser Pro Glu Arg Ser Pro Pro
                260                 265                 270

Leu Gly Gly Ala Ala Gly His Val Ala Tyr Ser Gly Gln Leu Pro Pro
                275                 280                 285

Val Pro Gly Leu Ala Tyr Asp Ala Pro Ser Pro Pro Ala Phe Ala Lys
                290                 295                 300

Ser Gln Pro Asn Met Tyr Gly Leu Ala Ala Tyr Thr Ala Pro Leu Ser
305                 310                 315                 320

Ser Cys Leu Pro Gln Gln Lys Arg Tyr Ala Ala Pro Glu Phe Glu Pro
                325                 330                 335

His Pro Met Ala Ser Asn Gly Gly Phe Ala Ser Ala Asn Leu Gln
                340                 345                 350

Gly Ser Pro Val Tyr Val Gly Gly Asn Phe Val Glu Ser Met Ala Pro
                355                 360                 365

Ala Ser Gly Pro Val Phe Asn Leu Gly His Leu Ser His Pro Ser Ser
370                 375                 380

Ala Ser Val Asp Tyr Ser Cys Ala Ala Gln Ile Pro Gly Asn His His
385                 390                 395                 400

His Gly Pro Cys Asp Pro His Pro Thr Tyr Thr Asp Leu Ser Ala His
                405                 410                 415

His Ser Ser Gln Gly Arg Leu Pro Glu Ala Pro Lys Leu Thr His Leu
                420                 425                 430
```

<210> SEQ ID NO 78
<211> LENGTH: 469
<212> TYPE: PRT
<213> ORGANISM: Homo sapiens

<400> SEQUENCE: 78

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Val Val Val Gln
            20                  25                  30

Pro Gly Gly Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
50                  55                  60

Glu Trp Val Ser Leu Ile Ser Trp Asp Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Ser Leu Tyr Leu Gln Met Asn Ser Leu Arg Ala Glu Asp Thr Ala Leu
                100                 105                 110

Tyr Tyr Cys Ala Thr Arg Gly Gly Tyr Ser Thr Ala Gly Phe Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430
```

```
Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 79
<211> LENGTH: 235
<212> TYPE: PRT
<213> ORGANISM: Homo sapiens

<400> SEQUENCE: 79

```
Met Glu Thr Pro Ala Gln Leu Leu Phe Leu Leu Leu Leu Trp Leu Pro
1               5                   10                  15

Asp Ile Thr Gly Glu Ile Val Leu Thr Gln Ser Pro Gly Thr Leu Ser
            20                  25                  30

Leu Ser Pro Gly Glu Arg Ala Ala Leu Ser Cys Arg Ala Ser Gln Ser
        35                  40                  45

Val Asn Ser Lys Tyr Leu Ala Trp Tyr Gln Gln Lys Pro Gly Gln Ala
    50                  55                  60

Pro Arg Leu Leu Met Tyr Ala Ala Ser Ile Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Ser Glu Asp Phe Ala Leu Tyr Phe Cys Gln Gln Tyr
            100                 105                 110

Gly Thr Ser Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 80
<211> LENGTH: 890
<212> TYPE: PRT
<213> ORGANISM: Homo sapiens

<400> SEQUENCE: 80

```
Met Ser Arg Ser Ala Thr Leu Leu Cys Leu Leu Gly Cys His Val
1               5                   10                  15

Trp Lys Ala Val Thr Lys Thr Leu Arg Glu Pro Gly Ala Gly Ala Gln
            20                  25                  30

Glu Val Thr Leu Lys Val His Ile Ser Asp Ala Ser Thr His Gln Pro
        35                  40                  45
```

```
Val Ala Asp Ala Leu Ile Glu Ile Phe Thr Asn Gln Ala Ser Ile Ala
 50                  55                  60

Ser Gly Thr Ser Gly Thr Asp Gly Val Ala Phe Ile Lys Phe Gln Tyr
 65                  70                  75                  80

Lys Leu Gly Ser Gln Leu Ile Val Thr Ala Ser Lys His Ala Tyr Val
                 85                  90                  95

Pro Asn Ser Ala Pro Trp Lys Pro Ile Arg Leu Pro Val Phe Ser Ser
                100                 105                 110

Leu Ser Leu Gly Leu Leu Pro Glu Arg Ser Ala Thr Leu Met Val Tyr
            115                 120                 125

Glu Asp Val Val Gln Ile Val Ser Gly Phe Gln Gly Ala Arg Pro Gln
            130                 135                 140

Pro Arg Val His Phe Gln Arg Arg Ala Leu Arg Leu Pro Glu Asn Thr
145                 150                 155                 160

Ser Tyr Ser Asp Leu Thr Ala Phe Leu Thr Ala Ala Ser Ser Pro Ser
                165                 170                 175

Glu Val Asp Ser Phe Pro Tyr Leu Arg Gly Leu Asp Gly Asn Gly Thr
            180                 185                 190

Gly Asn Ser Thr Arg His Asp Leu Thr Pro Val Thr Ala Val Ser Val
            195                 200                 205

His Leu Leu Ser Ser Asn Gly Thr Pro Val Leu Val Asp Gly Pro Ile
210                 215                 220

Tyr Val Thr Val Pro Leu Ala Thr Gln Ser Ser Leu Arg His Asn Ala
225                 230                 235                 240

Tyr Val Ala Ala Trp Arg Phe Asp Gln Lys Leu Gly Thr Trp Leu Lys
                245                 250                 255

Ser Gly Leu Gly Leu Val His Gln Glu Gly Ser Gln Leu Thr Trp Thr
            260                 265                 270

Tyr Ile Ala Pro Gln Leu Gly Tyr Trp Val Ala Ala Met Ser Pro Pro
            275                 280                 285

Ile Pro Gly Pro Val Val Thr Gln Asp Ile Thr Thr Tyr His Thr Val
            290                 295                 300

Phe Leu Leu Ala Ile Leu Gly Gly Met Ala Phe Ile Leu Leu Val Leu
305                 310                 315                 320

Leu Cys Leu Leu Leu Tyr Tyr Cys Arg Arg Lys Cys Leu Lys Pro Arg
                325                 330                 335

Gln His His Arg Lys Leu Gln Leu Pro Ala Gly Leu Glu Ser Ser Lys
            340                 345                 350

Arg Asp Gln Ser Thr Ser Met Ser His Ile Asn Leu Leu Phe Ser Arg
            355                 360                 365

Arg Ala Ser Glu Phe Pro Gly Pro Leu Ser Val Thr Ser His Gly Arg
            370                 375                 380

Pro Glu Ala Pro Gly Thr Lys Glu Leu Met Ser Gly Val His Leu Glu
385                 390                 395                 400

Met Met Ser Pro Gly Gly Glu Gly Asp Leu His Thr Pro Met Leu Lys
                405                 410                 415

Leu Ser Tyr Ser Thr Ser Gln Glu Phe Ser Ser Arg Glu Glu Leu Leu
            420                 425                 430

Ser Cys Lys Glu Glu Asp Lys Ser Gln Ile Ser Phe Asp Asn Leu Thr
            435                 440                 445

Pro Ser Gly Thr Leu Gly Lys Asp Tyr His Lys Ser Val Glu Val Phe
            450                 455                 460

Pro Leu Lys Ala Arg Lys Ser Met Glu Arg Glu Gly Tyr Glu Ser Ser
465                 470                 475                 480
```

```
Gly Asn Asp Asp Tyr Arg Gly Ser Tyr Asn Thr Val Leu Ser Gln Pro
            485                 490                 495

Leu Phe Glu Lys Gln Asp Arg Glu Gly Pro Ala Ser Thr Gly Ser Lys
        500                 505                 510

Leu Thr Ile Gln Glu His Leu Tyr Pro Ala Pro Ser Ser Pro Glu Lys
        515                 520                 525

Glu Gln Leu Leu Asp Arg Arg Pro Thr Glu Cys Met Met Ser Arg Ser
        530                 535                 540

Val Asp His Leu Glu Arg Pro Thr Ser Phe Pro Arg Pro Gly Gln Leu
545                 550                 555                 560

Ile Cys Cys Ser Ser Val Asp Gln Val Asn Asp Ser Val Tyr Arg Lys
            565                 570                 575

Val Leu Pro Ala Leu Val Ile Pro Ala His Tyr Met Lys Leu Pro Gly
            580                 585                 590

Asp His Ser Tyr Val Ser Gln Pro Leu Val Val Pro Ala Asp Gln Gln
            595                 600                 605

Leu Glu Ile Glu Arg Leu Gln Ala Glu Leu Ser Asn Pro His Ala Gly
        610                 615                 620

Ile Phe Pro His Pro Ser Ser Gln Ile Gln Pro Gln Pro Leu Ser Ser
625                 630                 635                 640

Gln Ala Ile Ser Gln Gln His Leu Gln Asp Ala Gly Thr Arg Glu Trp
            645                 650                 655

Ser Pro Gln Asn Ala Ser Met Ser Glu Ser Leu Ser Ile Pro Ala Ser
            660                 665                 670

Leu Asn Asp Ala Ala Leu Ala Gln Met Asn Ser Glu Val Gln Leu Leu
        675                 680                 685

Thr Glu Lys Ala Leu Met Glu Leu Gly Gly Gly Lys Pro Leu Pro His
        690                 695                 700

Pro Arg Ala Trp Phe Val Ser Leu Asp Gly Arg Ser Asn Ala His Val
705                 710                 715                 720

Arg His Ser Tyr Ile Asp Leu Gln Arg Ala Gly Arg Asn Gly Ser Asn
            725                 730                 735

Asp Ala Ser Leu Asp Ser Gly Val Asp Met Asn Glu Pro Lys Ser Ala
            740                 745                 750

Arg Lys Gly Arg Gly Asp Ala Leu Ser Leu Gln Gln Asn Tyr Pro Pro
        755                 760                 765

Val Gln Glu His Gln Gln Lys Glu Pro Arg Ala Pro Asp Ser Thr Ala
        770                 775                 780

Tyr Thr Gln Leu Val Tyr Leu Asp Asp Val Glu Gln Ser Gly Ser Glu
785                 790                 795                 800

Cys Gly Thr Thr Val Cys Thr Pro Glu Asp Ser Ala Leu Arg Cys Leu
            805                 810                 815

Leu Glu Gly Ser Ser Arg Arg Ser Gly Gly Gln Leu Pro Ser Leu Gln
            820                 825                 830

Glu Glu Thr Thr Arg Arg Thr Ala Asp Ala Pro Ser Glu Pro Ala Ala
        835                 840                 845

Ser Pro His Gln Arg Arg Ser Ala His Glu Glu Glu Asp Asp Asp
        850                 855                 860

Asp Asp Asp Gln Gly Glu Asp Lys Lys Ser Pro Trp Gln Lys Arg Glu
865                 870                 875                 880

Glu Arg Pro Leu Met Ala Phe Asn Ile Lys
                885                 890
```

```
<210> SEQ ID NO 81
<211> LENGTH: 394
<212> TYPE: PRT
<213> ORGANISM: Homo sapiens

<400> SEQUENCE: 81

Met Asp Ser Ala Leu Ser Asp Pro His Asn Gly Ser Ala Glu Ala Gly
1               5                   10                  15

Gly Pro Thr Asn Ser Thr Thr Arg Pro Pro Ser Thr Pro Glu Gly Ile
            20                  25                  30

Ala Leu Ala Tyr Gly Ser Leu Leu Met Ala Leu Leu Pro Ile Phe
        35                  40                  45

Phe Gly Ala Leu Arg Ser Val Arg Cys Ala Arg Gly Lys Asn Ala Ser
    50                  55                  60

Asp Met Pro Glu Thr Ile Thr Ser Arg Asp Ala Ala Arg Phe Pro Ile
65                  70                  75                  80

Ile Ala Ser Cys Thr Leu Leu Gly Leu Tyr Leu Phe Phe Lys Ile Phe
                85                  90                  95

Ser Gln Glu Tyr Ile Asn Leu Leu Ser Met Tyr Phe Phe Val Leu
            100                 105                 110

Gly Ile Leu Ala Leu Ser His Thr Ile Ser Pro Phe Met Asn Lys Phe
        115                 120                 125

Phe Pro Ala Ser Phe Pro Asn Arg Gln Tyr Gln Leu Leu Phe Thr Gln
    130                 135                 140

Gly Ser Gly Glu Asn Lys Glu Ile Ile Asn Tyr Glu Phe Asp Thr
145                 150                 155                 160

Lys Asp Leu Val Cys Leu Gly Leu Ser Ser Ile Val Gly Val Trp Tyr
                165                 170                 175

Leu Leu Arg Lys His Trp Ile Ala Asn Asn Leu Phe Gly Leu Ala Phe
            180                 185                 190

Ser Leu Asn Gly Val Glu Leu Leu His Leu Asn Asn Val Ser Thr Gly
        195                 200                 205

Cys Ile Leu Leu Gly Gly Leu Phe Ile Tyr Asp Val Phe Trp Val Phe
    210                 215                 220

Gly Thr Asn Val Met Val Thr Val Ala Lys Ser Phe Glu Ala Pro Ile
225                 230                 235                 240

Lys Leu Val Phe Pro Gln Asp Leu Leu Glu Lys Gly Leu Glu Ala Asn
                245                 250                 255

Asn Phe Ala Met Leu Gly Leu Gly Asp Val Val Ile Pro Gly Ile Phe
            260                 265                 270

Ile Ala Leu Leu Leu Arg Phe Asp Ile Ser Leu Lys Lys Asn Thr His
        275                 280                 285

Thr Tyr Phe Tyr Thr Ser Phe Ala Ala Tyr Ile Phe Gly Leu Gly Leu
    290                 295                 300

Thr Ile Phe Ile Met His Ile Phe Lys His Ala Gln Pro Ala Leu Leu
305                 310                 315                 320

Tyr Leu Val Pro Ala Cys Ile Gly Phe Pro Val Leu Val Ala Leu Ala
                325                 330                 335

Lys Gly Glu Val Thr Glu Met Phe Ser Tyr Glu Ser Ser Ala Glu Ile
            340                 345                 350

Leu Pro His Thr Pro Arg Leu Thr His Phe Pro Thr Val Ser Gly Ser
        355                 360                 365

Pro Ala Ser Leu Ala Asp Ser Met Gln Gln Lys Leu Ala Gly Pro Arg
    370                 375                 380

Arg Arg Arg Pro Gln Asn Pro Ser Ala Met
```

<210> SEQ ID NO 82
<211> LENGTH: 325
<212> TYPE: PRT
<213> ORGANISM: Homo sapiens

<400> SEQUENCE: 82

Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
            20                  25                  30

Ala Ala Cys Glu Pro Val Arg Ile Pro Leu Cys Lys Ser Leu Pro Trp
        35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Asn Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
        195                 200                 205

Lys Cys His Asp Val Thr Ala Val Val Glu Val Lys Glu Ile Leu Lys
    210                 215                 220

Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Glu Arg Ser Arg Leu Leu Leu Val Glu Gly
            260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Ser Lys Ser Asp Ser Ser
    290                 295                 300

Asn Ser Asp Ser Thr Gln Ser Gln Lys Ser Gly Arg Asn Ser Asn Pro
305                 310                 315                 320

Arg Gln Ala Arg Asn
            325

<210> SEQ ID NO 83
<211> LENGTH: 748
<212> TYPE: PRT
<213> ORGANISM: Homo sapiens

<400> SEQUENCE: 83

```
Met Lys Thr Ser Pro Arg Arg Pro Leu Ile Leu Lys Arg Arg Leu
1               5                   10                  15

Pro Leu Pro Val Gln Asn Ala Pro Ser Glu Thr Ser Glu Glu Pro
                20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
            50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys
            130                 135                 140

Pro Ala Ala Arg Asp Val Asn Leu Pro Arg Pro Gly Ala Leu Cys
145                 150                 155                 160

Glu Gln Lys Arg Glu Thr Cys Ala Asp Gly Glu Ala Ala Gly Cys Thr
            165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
            195                 200                 205

Asn Cys His Leu Glu Gln Arg Gln Val Lys Val Glu Glu Pro Ser Arg
            210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
            245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
            275                 280                 285

Leu Ser Leu His Asp Met Phe Val Arg Glu Thr Ser Ala Asn Gly Lys
            290                 295                 300

Val Ser Phe Trp Thr Ile His Pro Ser Ala Asn Arg Tyr Leu Thr Leu
305                 310                 315                 320

Asp Gln Val Phe Lys Gln Lys Arg Pro Asn Pro Glu Leu Arg Arg
            325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
            370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
            405                 410                 415

Pro Leu Ser Ser Ala Gly Pro Gly Lys Glu Glu Lys Leu Leu Phe Gly
```

```
                420             425             430
Glu Gly Phe Ser Pro Leu Leu Pro Val Gln Thr Ile Lys Glu Glu
            435                 440                 445

Ile Gln Pro Gly Glu Glu Met Pro His Leu Ala Arg Pro Ile Lys Val
        450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
    530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
        595                 600                 605

Trp Arg Leu Thr Pro Pro Ala Lys Val Gly Gly Leu Asp Phe Ser Pro
    610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
        675                 680                 685

Ser Pro Glu Pro Gln Val Ser Gly Leu Ala Ala Asn Arg Ser Leu Thr
    690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745

<210> SEQ ID NO 84
<211> LENGTH: 208
<212> TYPE: PRT
<213> ORGANISM: Homo sapiens

<400> SEQUENCE: 84

Met Gly Ser Cys Ser Gly Arg Cys Ala Leu Val Val Leu Cys Ala Phe
1               5                   10                  15

Gln Leu Val Ala Ala Leu Glu Arg Gln Val Phe Asp Phe Leu Gly Tyr
            20                  25                  30

Gln Trp Ala Pro Ile Leu Ala Asn Phe Val His Ile Ile Ile Val Ile
        35                  40                  45

Leu Gly Leu Phe Gly Thr Ile Gln Tyr Arg Leu Arg Tyr Val Met Val
```

-continued

```
                 50                  55                  60
Tyr Thr Leu Trp Ala Ala Val Trp Val Thr Trp Asn Val Phe Ile Ile
 65                  70                  75                  80

Cys Phe Tyr Leu Glu Val Gly Gly Leu Leu Lys Asp Ser Glu Leu Leu
                 85                  90                  95

Thr Phe Ser Leu Ser Arg His Arg Ser Trp Arg Glu Arg Trp Pro
                100                 105                 110

Gly Cys Leu His Glu Glu Val Pro Ala Val Gly Leu Gly Ala Pro His
                115                 120                 125

Gly Gln Ala Leu Val Ser Gly Ala Gly Cys Ala Leu Glu Pro Ser Tyr
            130                 135                 140

Val Glu Ala Leu His Ser Cys Leu Gln Ile Leu Ile Ala Leu Leu Gly
145                 150                 155                 160

Phe Val Cys Gly Cys Gln Val Val Ser Val Phe Thr Asp Glu Glu Asp
                165                 170                 175

Ser Phe Asp Phe Ile Gly Gly Phe Asp Pro Phe Pro Leu Tyr His Val
                180                 185                 190

Asn Glu Lys Pro Ser Ser Leu Leu Ser Lys Gln Val Tyr Leu Pro Ala
                195                 200                 205

<210> SEQ ID NO 85
<211> LENGTH: 64
<212> TYPE: PRT
<213> ORGANISM: Homo sapiens

<400> SEQUENCE: 85

Met Cys Val Ser Ser Ser Ser Ser His Asp Glu Ala Pro Val Leu
 1               5                  10                  15

Asn Asp Lys His Leu Asp Val Pro Asp Ile Ile Thr Pro Pro Thr
                 20                  25                  30

Pro Thr Gly Met Met Leu Pro Arg Asp Leu Gly Ser Thr Val Trp Leu
                 35                  40                  45

Asp Glu Thr Gly Ser Cys Pro Asp Asp Gly Glu Ile Asp Pro Glu Ala
             50                  55                  60

<210> SEQ ID NO 86
<211> LENGTH: 632
<212> TYPE: PRT
<213> ORGANISM: Homo sapiens

<400> SEQUENCE: 86

Met Asp Thr Met Met Leu Asn Val Arg Asn Leu Phe Glu Gln Leu Val
 1               5                  10                  15

Arg Arg Val Glu Ile Leu Ser Glu Gly Asn Glu Val Gln Phe Ile Gln
                 20                  25                  30

Leu Ala Lys Asp Phe Glu Asp Phe Arg Lys Lys Trp Gln Arg Thr Asp
                 35                  40                  45

His Glu Leu Gly Lys Tyr Lys Asp Leu Leu Met Lys Ala Glu Thr Glu
             50                  55                  60

Arg Ser Ala Leu Asp Val Lys Leu Lys His Ala Arg Asn Gln Val Asp
 65                  70                  75                  80

Val Glu Ile Lys Arg Arg Gln Arg Ala Glu Ala Asp Cys Glu Lys Leu
                 85                  90                  95

Glu Arg Gln Ile Gln Leu Ile Arg Glu Met Leu Met Cys Asp Thr Ser
                100                 105                 110

Gly Ser Ile Gln Leu Ser Glu Glu Gln Lys Ser Ala Leu Ala Phe Leu
                115                 120                 125
```

```
Asn Arg Gly Gln Pro Ser Ser Ser Asn Ala Gly Asn Lys Arg Leu Ser
        130                 135                 140

Thr Ile Asp Glu Ser Gly Ser Ile Leu Ser Asp Ile Ser Phe Asp Lys
145                 150                 155                 160

Thr Asp Glu Ser Leu Asp Trp Asp Ser Ser Leu Val Lys Thr Phe Lys
                165                 170                 175

Leu Lys Lys Arg Glu Lys Arg Arg Ser Thr Ser Arg Gln Phe Val Asp
                180                 185                 190

Gly Pro Pro Gly Pro Val Lys Lys Thr Arg Ser Ile Gly Ser Ala Val
                195                 200                 205

Asp Gln Gly Asn Glu Ser Ile Val Ala Lys Thr Thr Val Thr Val Pro
        210                 215                 220

Asn Asp Gly Gly Pro Ile Glu Ala Val Ser Thr Ile Glu Thr Val Pro
225                 230                 235                 240

Tyr Trp Thr Arg Ser Arg Arg Lys Thr Gly Thr Leu Gln Pro Trp Asn
                245                 250                 255

Ser Asp Ser Thr Leu Asn Ser Arg Gln Leu Glu Pro Arg Thr Glu Thr
            260                 265                 270

Asp Ser Val Gly Thr Pro Gln Ser Asn Gly Gly Met Arg Leu His Asp
            275                 280                 285

Phe Val Ser Lys Thr Val Ile Lys Pro Glu Ser Cys Val Pro Cys Gly
        290                 295                 300

Lys Arg Ile Lys Phe Gly Lys Leu Ser Leu Lys Cys Arg Asp Cys Arg
305                 310                 315                 320

Val Val Ser His Pro Glu Cys Arg Asp Arg Cys Pro Leu Pro Cys Ile
                325                 330                 335

Pro Thr Leu Ile Gly Thr Pro Val Lys Ile Gly Glu Gly Met Leu Ala
            340                 345                 350

Asp Phe Val Ser Gln Thr Ser Pro Met Ile Pro Ser Ile Val Val His
            355                 360                 365

Cys Val Asn Glu Ile Glu Gln Arg Gly Leu Thr Glu Thr Gly Leu Tyr
        370                 375                 380

Arg Ile Ser Gly Cys Asp Arg Thr Val Lys Glu Leu Lys Glu Lys Phe
385                 390                 395                 400

Leu Arg Val Lys Thr Val Pro Leu Leu Ser Lys Val Asp Asp Ile His
                405                 410                 415

Ala Ile Cys Ser Leu Leu Lys Asp Phe Leu Arg Asn Leu Lys Glu Pro
            420                 425                 430

Leu Leu Thr Phe Arg Leu Asn Arg Ala Phe Met Glu Ala Ala Glu Ile
        435                 440                 445

Thr Asp Glu Asp Asn Ser Ile Ala Ala Met Tyr Gln Ala Val Gly Glu
        450                 455                 460

Leu Pro Gln Ala Asn Arg Asp Thr Leu Ala Phe Leu Met Ile His Leu
465                 470                 475                 480

Gln Arg Val Ala Gln Ser Pro His Thr Lys Met Asp Val Ala Asn Leu
                485                 490                 495

Ala Lys Val Phe Gly Pro Thr Ile Val Ala His Ala Val Pro Asn Pro
            500                 505                 510

Asp Pro Val Thr Met Leu Gln Asp Ile Lys Arg Gln Pro Lys Val Val
            515                 520                 525

Glu Arg Leu Leu Ser Leu Pro Leu Glu Tyr Trp Ser Gln Phe Met Met
530                 535                 540

Val Glu Gln Glu Asn Ile Asp Pro Leu His Val Ile Glu Asn Ser Asn
```

```
            545                 550                 555                 560

Ala Phe Ser Thr Pro Gln Thr Pro Asp Ile Lys Val Ser Leu Leu Gly
                    565                 570                 575

Pro Val Thr Thr Pro Glu His Gln Leu Leu Lys Thr Pro Ser Ser Ser
            580                 585                 590

Ser Leu Ser Gln Arg Val Arg Ser Thr Leu Thr Lys Asn Thr Pro Arg
        595                 600                 605

Phe Gly Ser Lys Ser Lys Ser Ala Thr Asn Leu Gly Arg Gln Gly Asn
        610                 615                 620

Phe Phe Ala Ser Pro Met Leu Lys
625                 630

<210> SEQ ID NO 87
<211> LENGTH: 336
<212> TYPE: PRT
<213> ORGANISM: Homo sapiens

<400> SEQUENCE: 87

Met Thr Asp Leu Asn Asp Asn Ile Cys Lys Arg Tyr Ile Lys Met Ile
1               5                   10                  15

Thr Asn Ile Val Ile Leu Ser Leu Ile Cys Ile Ser Leu Ala Phe
            20                  25                  30

Trp Ile Ile Ser Met Thr Ala Ser Thr Tyr Tyr Gly Asn Leu Arg Pro
        35                  40                  45

Ile Ser Pro Trp Arg Trp Leu Phe Ser Val Val Pro Val Leu Ile
    50                  55                  60

Val Ser Asn Gly Leu Lys Lys Ser Leu Asp His Ser Gly Ala Leu
65                  70                  75                  80

Gly Gly Leu Val Val Gly Phe Ile Leu Thr Ile Ala Asn Phe Ser Phe
                85                  90                  95

Phe Thr Ser Leu Leu Met Phe Phe Leu Ser Ser Ser Lys Leu Thr Lys
            100                 105                 110

Trp Lys Gly Glu Val Lys Lys Arg Leu Asp Ser Glu Tyr Lys Glu Gly
        115                 120                 125

Gly Gln Arg Asn Trp Val Gln Val Phe Cys Asn Gly Ala Val Pro Thr
    130                 135                 140

Glu Leu Ala Leu Leu Tyr Met Ile Glu Asn Gly Pro Gly Glu Ile Pro
145                 150                 155                 160

Val Asp Phe Ser Lys Gln Tyr Ser Ala Ser Trp Met Cys Leu Ser Leu
                165                 170                 175

Leu Ala Ala Leu Ala Cys Ser Ala Gly Asp Thr Trp Ala Ser Glu Val
            180                 185                 190

Gly Pro Val Leu Ser Lys Ser Ser Pro Arg Leu Ile Thr Thr Trp Glu
        195                 200                 205

Lys Val Pro Val Gly Thr Asn Gly Gly Val Thr Val Val Gly Leu Val
    210                 215                 220

Ser Ser Leu Leu Gly Gly Thr Phe Val Gly Ile Ala Tyr Phe Leu Thr
225                 230                 235                 240

Gln Leu Ile Phe Val Asn Asp Leu Asp Ile Ser Ala Pro Gln Trp Pro
                245                 250                 255

Ile Ile Ala Phe Gly Gly Leu Ala Gly Leu Gly Ser Ile Val Asp
            260                 265                 270

Ser Tyr Leu Gly Ala Thr Met Gln Tyr Thr Gly Leu Asp Glu Ser Thr
        275                 280                 285

Gly Met Val Val Asn Ser Pro Thr Asn Lys Ala Arg His Ile Ala Gly
```

```
                       290                 295                 300
Lys Pro Ile Leu Asp Asn Asn Ala Val Asn Leu Phe Ser Ser Val Leu
305                 310                 315                 320

Ile Ala Leu Leu Leu Pro Thr Ala Ala Trp Gly Phe Trp Pro Arg Gly
                325                 330                 335

<210> SEQ ID NO 88
<211> LENGTH: 347
<212> TYPE: PRT
<213> ORGANISM: Homo sapiens

<400> SEQUENCE: 88

Met Ala Gln Ser Arg Asp Gly Gly Asn Pro Phe Ala Glu Pro Ser Glu
1               5                   10                  15

Leu Asp Asn Pro Phe Gln Asp Pro Ala Val Ile Gln His Arg Pro Ser
                20                  25                  30

Arg Gln Tyr Ala Thr Leu Asp Val Tyr Asn Pro Phe Glu Thr Arg Glu
            35                  40                  45

Pro Pro Pro Ala Tyr Glu Pro Pro Ala Pro Ala Pro Leu Pro Pro Pro
        50                  55                  60

Ser Ala Pro Ser Leu Gln Pro Ser Arg Lys Leu Ser Pro Thr Glu Pro
65                  70                  75                  80

Lys Asn Tyr Gly Ser Tyr Ser Thr Gln Ala Ser Ala Ala Ala Ala Thr
                85                  90                  95

Ala Glu Leu Leu Lys Lys Gln Glu Leu Asn Arg Lys Ala Glu Glu
            100                 105                 110

Leu Asp Arg Arg Glu Arg Glu Leu Gln His Ala Ala Leu Gly Gly Thr
        115                 120                 125

Ala Thr Arg Gln Asn Asn Trp Pro Pro Leu Pro Ser Phe Cys Pro Val
130                 135                 140

Gln Pro Cys Phe Phe Gln Asp Ile Ser Met Glu Ile Pro Gln Glu Phe
145                 150                 155                 160

Gln Lys Thr Val Ser Thr Met Tyr Tyr Leu Trp Met Cys Ser Thr Leu
                165                 170                 175

Ala Leu Leu Leu Asn Phe Leu Ala Cys Leu Ala Ser Phe Cys Val Glu
            180                 185                 190

Thr Asn Asn Gly Ala Gly Phe Gly Leu Ser Ile Leu Trp Val Leu Leu
        195                 200                 205

Phe Thr Pro Cys Ser Phe Val Cys Trp Tyr Arg Pro Met Tyr Lys Ala
210                 215                 220

Phe Arg Ser Asp Ser Ser Phe Asn Phe Phe Val Phe Phe Ile Phe
225                 230                 235                 240

Phe Val Gln Asp Val Leu Phe Val Leu Gln Ala Ile Gly Ile Pro Gly
                245                 250                 255

Trp Gly Phe Ser Gly Trp Ile Ser Ala Leu Val Val Pro Lys Gly Asn
            260                 265                 270

Thr Ala Val Ser Val Leu Met Leu Leu Val Ala Leu Phe Thr Gly
        275                 280                 285

Ile Ala Val Leu Gly Ile Val Met Leu Lys Arg Ile His Ser Leu Tyr
            290                 295                 300

Arg Arg Thr Gly Ala Ser Phe Gln Lys Ala Gln Gln Glu Phe Ala Ala
305                 310                 315                 320

Gly Val Phe Ser Asn Pro Ala Val Arg Thr Ala Ala Ala Asn Ala Ala
                325                 330                 335

Ala Gly Ala Ala Glu Asn Ala Phe Arg Ala Pro
```

<210> SEQ ID NO 89
<211> LENGTH: 257
<212> TYPE: PRT
<213> ORGANISM: Homo sapiens

<400> SEQUENCE: 89

```
Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Trp Leu Leu
                245                 250                 255

Ser
```

<210> SEQ ID NO 90
<211> LENGTH: 43
<212> TYPE: DNA
<213> ORGANISM: Homo sapiens
<220> FEATURE:
<221> NAME/KEY: misc_feature
<223> OTHER INFORMATION: oligonucleotide is biotinylated
<220> FEATURE:
<221> NAME/KEY: misc_feature
<222> LOCATION: (43)..(43)
<223> OTHER INFORMATION: nucleotide is adenine, guanine or cytosine

<400> SEQUENCE: 90
actgtactaa ccctgcggcc gctttttttt ttttttttt ttv      43

<210> SEQ ID NO 91
<211> LENGTH: 47

```
<212> TYPE: DNA
<213> ORGANISM: Homo sapiens

<400> SEQUENCE: 91
ggaattctaa tacgactcac tatagggaga cgaagacagt agacagg              47

<210> SEQ ID NO 92
<211> LENGTH: 50
<212> TYPE: DNA
<213> ORGANISM: Homo sapiens

<400> SEQUENCE: 92
cgcgcctgtc tactgtcttc gtctccctat agtgagtcgt attagaattc           50

<210> SEQ ID NO 93
<211> LENGTH: 52
<212> TYPE: DNA
<213> ORGANISM: Homo sapiens

<400> SEQUENCE: 93
ggaattctaa tacgactcac tatagggaga gcctgcacca acagttaaca gg        52

<210> SEQ ID NO 94
<211> LENGTH: 55
<212> TYPE: DNA
<213> ORGANISM: Homo sapiens

<400> SEQUENCE: 94
cgcgcctgtt aactgttggt gcaggctctc cctatagtga gtcgtattag aattc     55

<210> SEQ ID NO 95
<211> LENGTH: 19
<212> TYPE: DNA
<213> ORGANISM: Homo sapiens

<400> SEQUENCE: 95
gggagacgaa gacagtaga                                              19

<210> SEQ ID NO 96
<211> LENGTH: 20
<212> TYPE: DNA
<213> ORGANISM: Homo sapiens

<400> SEQUENCE: 96
gcctgcacca acagttaaca                                             20

<210> SEQ ID NO 97
<211> LENGTH: 28
<212> TYPE: DNA
<213> ORGANISM: Homo sapiens

<400> SEQUENCE: 97
ggaattctaa tacgactcac tataggga                                    28

<210> SEQ ID NO 98
<211> LENGTH: 31
<212> TYPE: DNA
<213> ORGANISM: Homo sapiens

<400> SEQUENCE: 98
cgcgtcccta tagtgagtcg tattagaatt c                                31

<210> SEQ ID NO 99
<211> LENGTH: 2757
```

```
<212> TYPE: DNA
<213> ORGANISM: Homo sapiens

<400> SEQUENCE: 99
ttttcccagt cacgacgttg taaaacgacg gccagtgaat tctaatacga ctcactatag     60
ggagatggag aaaaaaatca ctggacgcgt ggcgcgccat taattaatgc ggccgctagc    120
tcgagtgata taagcggat gaatggctgc aggcatgcaa gcttggcgta atcatggtca     180
tagctgtttc ctgtgtgaaa ttgttatccg ctcacaattc cacacaacat acgagccgga    240
agcataaagt gtaaagcctg gggtgcctaa tgagtgagct aactcacatt aattgcgttg    300
cgctcactgc ccgctttcca gtcgggaaac ctgtcgtgcc agctgcatta atgaatcggc    360
caacgcgcgg ggagaggcgg tttgcgtatt gggcgctctt ccgcttcctc gctcactgac    420
tcgctgcgct cggtcgttcg gctgcggcga gcggtatcag ctcactcaaa ggcggtaata    480
cggttatcca cagaatcagg ggataacgca ggaaagaaca tgtgagcaaa aggccagcaa    540
aaggccagga accgtaaaaa ggccgcgttg ctggcgtttt tccataggct ccgcccccct    600
gacgagcatc acaaaaatcg acgctcaagt cagaggtggc gaaacccgac aggactataa    660
agataccagg cgtttccccc tggaagctcc ctcgtgcgct ctcctgttcc gaccctgccg    720
cttaccggat acctgtccgc ctttctccct tcgggaagcg tggcgctttc tcaatgctca    780
cgctgtaggt atctcagttc ggtgtaggtc gttcgctcca agctgggctg tgtgcacgaa    840
ccccccgttc agcccgaccg ctgcgcctta tccggtaact atcgtcttga gtccaacccg    900
gtaagacacg acttatcgcc actggcagca gccactggta acaggattag cagagcgagg    960
tatgtaggcg gtgctacaga gttcttgaag tggtggccta actacggcta cactagaagg   1020
acagtatttg gtatctgcgc tctgctgaag ccagttacct tcggaaaaag agttggtagc   1080
tcttgatccg gcaaacaaac caccgctggt agcggtggtt ttttgtttg caagcagcag   1140 attacgcgca gaaaaaaagg atctcaagaa gatcctttga tcttttctac ggggtctgac   1200
gctcagtgga acgaaaactc acgttaaggg attttggtca tgagattatc aaaaaggatc   1260
ttcacctaga tccttttaaa ttaaaaatga agttttaaat caatctaaag tatatatgag   1320
taaacttggt ctgacagtta ccaatgctta atcagtgagg cacctatctc agcgatctgt   1380
ctatttcgtt catccatagt tgcctgactc cccgtcgtgt agataactac gatacgggag   1440
ggcttaccat ctggccccag tgctgcaatg ataccgcgag acccacgctc accggctcca   1500
gatttatcag caataaacca gccagccgga agggccgagc gcagaagtgg tcctgcaact   1560
ttatccgcct ccatccagtc tattaattgt tgccgggaag ctagagtaag tagttcgcca   1620
gttaatagtt tgcgcaacgt tgttgccatt gctacaggca tcgtggtgtc acgctcgtcg   1680
tttggtatgg cttcattcag ctccggttcc caacgatcaa ggcgagttac atgatccccc   1740
atgttgtgca aaaagcggt tagctccttc ggtcctccga tcgttgtcag aagtaagttg    1800
gccgcagtgt tatcactcat ggttatggca gcactgcata attctcttac tgtcatgcca   1860
tccgtaagat gcttttctgt gactggtgag tactcaacca agtcattctg agaatagtgt   1920
atgcggcgac cgagttgctc ttgcccgcg tcaatacggg ataataccgc gccacatagc    1980
agaactttaa aagtgctcat cattggaaaa cgttcttcgg ggcgaaaact ctcaaggatc   2040
ttaccgctgt tgagatccag ttcgatgtaa cccactcgtg cacccaactg atcttcagca   2100
tcttttactt tcaccagcgt ttctgggtga gcaaaaacag gaaggcaaaa tgccgcaaaa   2160
aagggaataa gggcgacacg gaaatgttga atactcatac tcttcctttt tcaatattat   2220
tgaagcattt atcagggtta ttgtctcatg agcggataca tatttgaatg tatttagaaa   2280
```

```
aataaacaaa tagggggttcc gcgcacattt ccccgaaaag tgccacctga cgtctaagaa   2340
accattatta tcatgacatt aacctataaa aataggcgta tcacgaggcc ctttcgtctc   2400
gcgcgtttcg gtgatgacgg tgaaaacctc tgacacatgc agctcccgga cacggtcaca   2460
gcttgtctgt aagcggatgc cgggagcaga caagcccgtc agggcgcgtc agcgggtgtt   2520
ggcgggtgtc ggggctggct taactatgcg gcatcagagc agattgtact gagagtgcac   2580
catatgcggt gtgaaatacc gcacagatgc gtaaggagaa ataccgcat caggcgccat   2640 tcgccattca ggctgcgcaa ctgttgggaa gggcgatcgg tgcgggcctc ttcgctatta   2700
cgccagctgg cgaaaggggg atgtgctgca aggcgattaa gttgggtaac gccaggg     2757

<210> SEQ ID NO 100
<211> LENGTH: 2995
<212> TYPE: DNA
<213> ORGANISM: Homo sapiens

<400> SEQUENCE: 100
ttttcccagt cacgacgttg taaaacgacg gccagtgaat tcaattaacc ctcactaaag     60
ggagacttgt tccaaatgtg ttaggcgcgc cgcatgcgtc gacggatcct gagaacttca    120
ggctcctggg caacgtgctg gttattgtgc tgtctcatca ttttggcaaa gaattcactc    180
ctcaggtgca ggctgcctat cagaaggtgg tggctggtgt ggccaatgcc ctggctcaca    240
aataccactg agatcttttt ccctctgcca aaaattatgg ggacatcatg aagccccttg    300
agcatctgac ttctggctaa taaggaaat ttatttcat tgcaaaaaaa aaaagcggcc     360
gctcttctat agtgtcacct aaatggccca gcggccgagc ttggcgtaat catggtcata    420
gctgtttcct gtgtgaaatt gttatccgct cacaattcca cacaacatac gagccggaag    480
cataaagtgt aaagcctggg gtgcctaatg agtgagctaa ctcacattaa ttgcgttgcg    540
ctcactgccc gctttccagt cgggaaacct gtcgtgccag ctgcattaat gaatcggcca    600
acgcgcgggg agaggcggtt tgcgtattgg gcgctcttcc gcttcctcgc tcactgactc    660
gctgcgctcg gtcgttcggc tgcggcgagc ggtatcagct cactcaaagg cggtaatacg    720
gttatccaca gaatcagggg ataacgcagg aaagaacatg tgagcaaaag gccagcaaaa    780
ggccaggaac cgtaaaaagg ccgcgttgct ggcgtttttc cataggctcc gcccccctga    840
cgagcatcac aaaaatcgac gctcaagtca gaggtggcga aacccgacag gactataaag    900
ataccaggcg tttccccctg gaagctccct cgtgcgctct cctgttccga ccctgccgct    960
taccggatac ctgtccgcct ttctcccttc gggaagcgtg gcgctttctc aaagctcacg   1020
ctgtaggtat ctcagttcgg tgtaggtcgt tcgctccaag ctgggctgtg tgcacgaacc   1080
ccccgttcag cccgaccgct gcgccttatc cggtaactat cgtcttgagt ccaacccggt   1140
aagacacgac ttatcgccac tggcagcagc cactggtaac aggattagca gagcgaggta   1200
tgtaggcggt gctacagagt tcttgaagtg gtggcctaac tacggctaca ctagaagaac   1260
agtatttggt atctgcgctc tgctgaagcc agttaccttc ggaaaaagag ttggtagctc   1320
ttgatccggc aaacaaacca ccgctggtag cggtggtttt tttgtttgca agcagcagat   1380
tacgcgcaga aaaaaggat ctcaagaaga tcctttgatc ttttctacgg ggtctgacgc   1440
tcagtggaac gaaaactcac gttaagggat tttggtcatg agattatcaa aaggatctt   1500 cacctagatc ctttttaaatt aaaaatgaag ttttaaatca atctaaagta tatatgagta   1560
aacttggtct gacagttacc aatgcttaat cagtgaggca cctatctcag cgatctgtct   1620
atttcgttca tccatagttg cctgactccc cgtcgtgtag ataactacga tacgggaggg   1680
```

```
cttaccatct ggccccagtg ctgcaatgat accgcgagac ccacgctcac cggctccaga    1740
tttatcagca ataaaccagc cagccggaag ggccgagcgc agaagtggtc ctgcaacttt    1800
atccgcctcc atccagtcta ttaattgttg ccgggaagct agagtaagta gttcgccagt    1860
taatagtttg cgcaacgttg ttgccattgc tacaggcatc gtggtgtcac gctcgtcgtt    1920
tggtatggct tcattcagct ccggttccca acgatcaagg cgagttacat gatcccccat    1980
gttgtgcaaa aaagcggtta gctccttcgg tcctccgatc gttgtcagaa gtaagttggc    2040
cgcagtgtta tcactcatgg ttatggcagc actgcataat tctcttactg tcatgccatc    2100
cgtaagatgc ttttctgtga ctggtgagta ctcaaccaag tcattctgag aatagtgtat    2160
gcggcgaccg agttgctctt gcccggcgtc aatacgggat aataccgcgc cacatagcag    2220
aactttaaaa gtgctcatca ttggaaaacg ttcttcgggg cgaaaactct caaggatctt    2280
accgctgttg agatccagtt cgatgtaacc cactcgtgca cccaactgat cttcagcatc    2340
ttttactttc accagcgttt ctgggtgagc aaaaacagga aggcaaaatg ccgcaaaaaa    2400
gggaataagg gcgacacgga aatgttgaat actcatactc ttccttttc aatattattg    2460 aagcatttat cagggttatt gtctcatgag cggatacata tttgaatgta tttagaaaaa    2520
taaacaaata ggggttccgc gcacatttcc ccgaaaagtg ccacctgacg tctaagaaac    2580
cattattatc atgacattaa cctataaaaa taggcgtatc acgaggccct ttcgtctcgc    2640
gcgtttcggt gatgacggtg aaaacctctg acacatgcag ctcccggaga cggtcacagc    2700
ttgtctgtaa gcggatgccg ggagcagaca agcccgtcag ggcgcgtcag cgggtgttgg    2760
cgggtgtcgg ggctggctta actatgcggc atcagagcag attgtactga gagtgcacca    2820
tatgcggtgt gaaataccgc acagatgcgt aaggagaaaa taccgcatca ggcgccattc    2880
gccattcagg ctgcgcaact gttgggaagg gcgatcggtg cgggcctctt cgctattacg    2940
ccagctggcg aaaggggat gtgctgcaag gcgattaagt tgggtaacgc caggg        2995
```

<210> SEQ ID NO 101
<211> LENGTH: 4455
<212> TYPE: DNA
<213> ORGANISM: Homo sapiens

<400> SEQUENCE: 101

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aaggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttttccaa aaaactaccg    420
ttgttatagg tgtctcttga acacctataa caacggtagt ggatcccgcg tcctttccac    480
aagatatata aacccaagaa atcgaaatac tttcaagtta cggtaagcat atgatagtcc    540
attttaaaac ataattttaa aactgcaaac tacccaagaa attattactt tctacgtcac    600
gtattttgta ctaatatctt tgtgtttaca gtcaaattaa ttctaattat ctctctaaca    660
gccttgtatc gtatatgcaa atatgaagga atcatgggaa ataggccctc ttcctgcccg    720
accttggcgc gcgctcggcg cgcggtcacg ctccgtcacg tggtgcgttt tgcctgcgcg    780
tctttccact ggggaattca tgcttctcct cccttagtg agggtaatc tctctctc     840
```

```
cctatagtga gtcgtattaa ttccttctct tctatagtgt cacctaaatc gttgcaattc    900
gtaatcatgt catagctgtt tcctgtgtga aattgttatc cgctcacaat tccacacaac    960
atacgagccg gaagcataaa gtgtaaagcc tggggtgcct aatgagtgag ctaactcaca   1020
ttaattgcgt tgcgctcact gcccgctttc cagtcgggaa acctgtcgtg ccagctgcat   1080
taatgaatcg gccaacgcgc ggggagaggc ggtttgcgta ttgggcgctc ttccgcttcc   1140
tcgctcactg actcgctgcg ctcggtcgtt cggctgcggc gagcggtatc agctcactca   1200
aaggcggtaa tacggttatc cacagaatca ggggataacg caggaaagaa catgtgagca   1260
aaaggccagc aaaaggccag gaaccgtaaa aaggccgcgt tgctggcgtt tttccatagg   1320
ctccgccccc ctgacgagca tcacaaaaat cgacgctcaa gtcagaggtg gcgaaacccg   1380
acaggactat aaagatacca ggcgtttccc cctggaagct ccctcgtgcg ctctcctgtt   1440
ccgaccctgc cgcttaccgg atacctgtcc gcctttctcc cttcgggaag cgtggcgctt   1500
tctcatagct cacgctgtag gtatctcagt tcggtgtagg tcgttcgctc caagctgggc   1560
tgtgtgcacg aaccccccgt tcagcccgac cgctgcgcct tatccggtaa ctatcgtctt   1620
gagtccaacc cggtaagaca cgacttatcg ccactggcag cagccactgg taacaggatt   1680
agcagagcga ggtatgtagg cggtgctaca gagttcttga agtggtggcc taactacggc   1740
tacactagaa gaacagtatt tggtatctgc gctctgctga agccagttac cttcggaaaa   1800
agagttggta gctcttgatc cggcaaaaaa accaccgctg gtagcggtgg tttttttgtt   1860
tgcaagcagc agattacgcg cagaaaaaaa ggatctcaag aagatccttt gatcttttct   1920
acggggtctg acgctcagtg gaacgaaaac tcacgttaag ggattttggt catgagatta   1980
tcaaaaagga tcttcaccta gatccttta aattaaaaat gaagttttaa atcaatctaa   2040
agtatatatg agtaaacttg gtctgacagt taccaatgct taatcagtga ggcacctatc   2100
tcagcgatct gtctatttcg ttcatccata gttgcctgac tccccgtcgt gtagataact   2160
acgatacggg agggcttacc atctggcccc agtgctgcaa tgataccgcg agacccacgc   2220
tcaccggctc cagatttatc agcaataaac cagccagccg gaagggccga gcgcagaagt   2280
ggtcctgcaa ctttatccgc ctccatccag tctattaatt gttgccggga agctagagta   2340
agtagttcgc cagttaatag tttgcgcaac gttgttgcca ttgctacagg catcgtggtg   2400
tcacgctcgt cgtttggtat ggcttcattc agctccggtt cccaacgatc aaggcgagtt   2460
acatgatccc ccatgttgtg caaaaaagcg gttagctcct tcggtcctcc gatcgttgtc   2520
agaagtaagt tggccgcagt gttatcactc atggttatgg cagcactgca taattctctt   2580
actgtcatgc catccgtaag atgcttttct gtgactggtg agtactcaac caagtcattc   2640
tgagaatagt gtatgcggcg accgagttgc tcttgcccgg cgtcaatacg ggataatacc   2700
gcgccacata gcagaacttt aaaagtgctc atcattggaa aacgttcttc ggggcgaaaa   2760
ctctcaagga tcttaccgct gttgagatcc agttcgatgt aacccactcg tgcacccaac   2820
tgatcttcag catcttttac tttcaccagc gtttctgggt gagcaaaaac aggaaggcaa   2880
aatgccgcaa aaaagggaat aagggcgaca cggaaatgtt gaatactcat actcttcctt   2940
tttcaatatt attgaagcat ttatcagggt tattgtctca tgagcggata catatttgaa   3000
tgtatttaga aaaataaaca ataggggtt ccgcgcacat ttccccgaaa agtgccacct   3060
attggtgtgg aaagtcccca ggctccccag caggcagaag tatgcaaagc atgcatctca   3120
attagtcagc aaccaggtgt ggaaagtccc caggctcccc agcaggcaga gtatgcaaa   3180
gcatgcatct caattagtca gcaaccatag tcccgcccct aactccgccc atcccgcccc   3240
```

```
taactccgcc cagttccgcc cattctccgc cccatggctg actaattttt tttatttatg   3300
cagaggccga ggccgcctcg gcctctgagc tattccagaa gtagtgagga ggcttttttg   3360
gaggcctagg cttttgcaaa aagctagctt gcatgcctgc aggtcggccg ccacgaccgg   3420
tgccgccacc atccctgac ccacgcccct gaccctcac aaggagacga ccttccatga   3480
ccgagtacaa gcccacggtg cgcctcgcca cccgcgacga cgtccccgg gccgtacgca   3540 ccctcgccgc cgcgttcgcc gactaccccg ccacgcgcca caccgtcgac ccggaccgcc   3600
acatcgagcg ggtcaccgag ctgcaagaac tcttcctcac gcgcgtcggg ctcgacatcg   3660
gcaaggtgtg ggtcgcggac gacggcgccg cggtggcggt ctggaccacg ccggagagcg   3720
tcgaagcggg ggcggtgttc gccgagatcg gcccgcgcat ggccgagttg agcggttccc   3780
ggctggccgc gcagcaacag atggaaggcc tcctggcgcc gcaccggccc aaggagcccg   3840
cgtggttcct ggccaccgtc ggcgtctcgc ccgaccacca gggcaagggt ctgggcagcg   3900
ccgtcgtgct ccccggagtg gaggcggccg agcgcgccgg ggtgcccgcc ttcctggaga   3960
cctccgcgcc ccgcaacctc ccttctacg agcggctcgg cttcaccgtc accgccgacg   4020
tcgaggtgcc cgaaggaccg cgcacctggt gcatgacccg caagcccggt gcctgacgcc   4080
cgccccacga cccgcagcgc ccgaccgaaa ggagcgcacg accccatggc tccgaccgaa   4140
gccaccgggg gcgccccgc cgaccccgca cccgcccccg aggcccaccg actctagagg   4200
atcataatca gccataccac atttgtagag gttttacttg ctttaaaaaa cctcccacac   4260
ctccccctga acctgaaaca taaaatgaat gcaattgttg ttgttaactt gtttattgca   4320
gcttataatg gttacaaata aagcaatagc atcacaaatt tcacaaataa agcattttt   4380 tcactgcaat ctaagaaacc attattatca tgacattaac ctataaaaat aggcgtatca   4440
cgaggccctt tcgtc                                                    4455

<210> SEQ ID NO 102
<211> LENGTH: 52
<212> TYPE: RNA
<213> ORGANISM: Homo sapiens
<220> FEATURE:
<221> NAME/KEY: misc_feature
<222> LOCATION: (1)..(52)
<223> OTHER INFORMATION: control sequence undisclosed by Ambion (may
      vary in lenght)

<400> SEQUENCE: 102
nnnnnnnnnn nnnnnnnnnn nnnnnnnnnn nnnnnnnnnn nnnnnnnnnn nn           52

<210> SEQ ID NO 103
<211> LENGTH: 19
<212> TYPE: DNA
<213> ORGANISM: Homo sapiens

<400> SEQUENCE: 103
gtcaagaaac cacacttta                                                19

<210> SEQ ID NO 104
<211> LENGTH: 19
<212> TYPE: DNA
<213> ORGANISM: Homo sapiens

<400> SEQUENCE: 104
gtgacatgga acccagcga                                                19

<210> SEQ ID NO 105
```

```
<211> LENGTH: 19
<212> TYPE: DNA
<213> ORGANISM: Homo sapiens

<400> SEQUENCE: 105
accgtggctg ctcgataaa                                                  19

<210> SEQ ID NO 106
<211> LENGTH: 19
<212> TYPE: DNA
<213> ORGANISM: Homo sapiens

<400> SEQUENCE: 106
gccagagagc acagaaata                                                  19

<210> SEQ ID NO 107
<211> LENGTH: 19
<212> TYPE: DNA
<213> ORGANISM: Homo sapiens

<400> SEQUENCE: 107
gaggaatgcc tctaagaaa                                                  19

<210> SEQ ID NO 108
<211> LENGTH: 19
<212> TYPE: DNA
<213> ORGANISM: Homo sapiens

<400> SEQUENCE: 108
gggaacgaga agggcttct                                                  19

<210> SEQ ID NO 109
<211> LENGTH: 19
<212> TYPE: DNA
<213> ORGANISM: Homo sapiens

<400> SEQUENCE: 109
agctggagga atgagaatt                                                  19

<210> SEQ ID NO 110
<211> LENGTH: 19
<212> TYPE: DNA
<213> ORGANISM: Homo sapiens

<400> SEQUENCE: 110
agggccaaag ctttccata                                                  19

<210> SEQ ID NO 111
<211> LENGTH: 19
<212> TYPE: DNA
<213> ORGANISM: Homo sapiens

<400> SEQUENCE: 111
ggcaggctgt ccgcttaaa                                                  19

<210> SEQ ID NO 112
<211> LENGTH: 19
<212> TYPE: DNA
<213> ORGANISM: Homo sapiens

<400> SEQUENCE: 112
ggtccttagg cacccagat                                                  19

<210> SEQ ID NO 113
```

```
<211> LENGTH: 19
<212> TYPE: DNA
<213> ORGANISM: Homo sapiens

<400> SEQUENCE: 113
gcggagccca gggagaata                                          19

<210> SEQ ID NO 114
<211> LENGTH: 19
<212> TYPE: DNA
<213> ORGANISM: Homo sapiens

<400> SEQUENCE: 114
gcccggattg atgacatat                                          19

<210> SEQ ID NO 115
<211> LENGTH: 19
<212> TYPE: DNA
<213> ORGANISM: Homo sapiens

<400> SEQUENCE: 115
gtggaggctg agtttccat                                          19

<210> SEQ ID NO 116
<211> LENGTH: 19
<212> TYPE: DNA
<213> ORGANISM: Homo sapiens

<400> SEQUENCE: 116
ggatgttaac ctgcgaaat                                          19

<210> SEQ ID NO 117
<211> LENGTH: 19
<212> TYPE: DNA
<213> ORGANISM: Homo sapiens

<400> SEQUENCE: 117
ggtcagcagg gttcattta                                          19

<210> SEQ ID NO 118
<211> LENGTH: 19
<212> TYPE: DNA
<213> ORGANISM: Homo sapiens

<400> SEQUENCE: 118
gcctcaggaa caagatgaa                                          19

<210> SEQ ID NO 119
<211> LENGTH: 19
<212> TYPE: DNA
<213> ORGANISM: Homo sapiens

<400> SEQUENCE: 119
gcgcgagatc ctctccatt                                          19

<210> SEQ ID NO 120
<211> LENGTH: 19
<212> TYPE: DNA
<213> ORGANISM: Homo sapiens

<400> SEQUENCE: 120
gcgccagagg agcgggaag                                          19

<210> SEQ ID NO 121
```

```
<211> LENGTH: 19
<212> TYPE: DNA
<213> ORGANISM: Homo sapiens

<400> SEQUENCE: 121
gccgcccagt tcaatacaa                                                19

<210> SEQ ID NO 122
<211> LENGTH: 19
<212> TYPE: DNA
<213> ORGANISM: Homo sapiens

<400> SEQUENCE: 122
gagcttacaa cctgcctta                                                19

<210> SEQ ID NO 123
<211> LENGTH: 19
<212> TYPE: DNA
<213> ORGANISM: Homo sapiens

<400> SEQUENCE: 123
ggcgcccact acccaagaa                                                19

<210> SEQ ID NO 124
<211> LENGTH: 19
<212> TYPE: DNA
<213> ORGANISM: Homo sapiens

<400> SEQUENCE: 124
gagtcaggga tgggtccat                                                19

<210> SEQ ID NO 125
<211> LENGTH: 19
<212> TYPE: DNA
<213> ORGANISM: Homo sapiens

<400> SEQUENCE: 125
gggccagtct gtactcatt                                                19

<210> SEQ ID NO 126
<211> LENGTH: 19
<212> TYPE: DNA
<213> ORGANISM: Homo sapiens

<400> SEQUENCE: 126
gggaattcca tctccatat                                                19

<210> SEQ ID NO 127
<211> LENGTH: 19
<212> TYPE: DNA
<213> ORGANISM: Homo sapiens

<400> SEQUENCE: 127
ggcgcagatc acccagaag                                                19

<210> SEQ ID NO 128
<211> LENGTH: 19
<212> TYPE: DNA
<213> ORGANISM: Homo sapiens

<400> SEQUENCE: 128
gagcatcctg gtgaggaat                                                19

<210> SEQ ID NO 129
```

```
<211> LENGTH: 19
<212> TYPE: DNA
<213> ORGANISM: Homo sapiens

<400> SEQUENCE: 129
ggtgccacat gactaggat                                               19

<210> SEQ ID NO 130
<211> LENGTH: 19
<212> TYPE: DNA
<213> ORGANISM: Homo sapiens

<400> SEQUENCE: 130
gctgcagacg tgtatgcat                                               19

<210> SEQ ID NO 131
<211> LENGTH: 19
<212> TYPE: DNA
<213> ORGANISM: Homo sapiens

<400> SEQUENCE: 131
gcggaggcac tgggcttat                                               19

<210> SEQ ID NO 132
<211> LENGTH: 19
<212> TYPE: DNA
<213> ORGANISM: Homo sapiens

<400> SEQUENCE: 132
gcccgcttac ttcctggag                                               19

<210> SEQ ID NO 133
<211> LENGTH: 19
<212> TYPE: DNA
<213> ORGANISM: Homo sapiens

<400> SEQUENCE: 133
gctctgctca agttggata                                               19

<210> SEQ ID NO 134
<211> LENGTH: 19
<212> TYPE: DNA
<213> ORGANISM: Homo sapiens

<400> SEQUENCE: 134
gctgctgcct tgcagtttg                                               19

<210> SEQ ID NO 135
<211> LENGTH: 19
<212> TYPE: DNA
<213> ORGANISM: Homo sapiens

<400> SEQUENCE: 135
gcccttacct gatgctaaa                                               19

<210> SEQ ID NO 136
<211> LENGTH: 19
<212> TYPE: DNA
<213> ORGANISM: Homo sapiens

<400> SEQUENCE: 136
ggcacctaca aatgttata                                               19

<210> SEQ ID NO 137
```

```
<211> LENGTH: 19
<212> TYPE: DNA
<213> ORGANISM: Homo sapiens

<400> SEQUENCE: 137
gaggcctgga agctcctaa                                              19

<210> SEQ ID NO 138
<211> LENGTH: 19
<212> TYPE: DNA
<213> ORGANISM: Homo sapiens

<400> SEQUENCE: 138
gcagcttcag gaggttaaa                                              19

<210> SEQ ID NO 139
<211> LENGTH: 19
<212> TYPE: DNA
<213> ORGANISM: Homo sapiens

<400> SEQUENCE: 139
gccggacctc ttcatctta                                              19

<210> SEQ ID NO 140
<211> LENGTH: 19
<212> TYPE: DNA
<213> ORGANISM: Homo sapiens

<400> SEQUENCE: 140
gcgtccatca cggaaacat                                              19

<210> SEQ ID NO 141
<211> LENGTH: 19
<212> TYPE: DNA
<213> ORGANISM: Homo sapiens

<400> SEQUENCE: 141
gtcatcagga cgtccatta                                              19

<210> SEQ ID NO 142
<211> LENGTH: 19
<212> TYPE: DNA
<213> ORGANISM: Homo sapiens

<400> SEQUENCE: 142
gacacgatct accctcaaa                                              19

<210> SEQ ID NO 143
<211> LENGTH: 19
<212> TYPE: DNA
<213> ORGANISM: Homo sapiens

<400> SEQUENCE: 143
gggccatagg gaagcttga                                              19

<210> SEQ ID NO 144
<211> LENGTH: 19
<212> TYPE: DNA
<213> ORGANISM: Homo sapiens

<400> SEQUENCE: 144
gcccacgtgt tgagatcaa                                              19

<210> SEQ ID NO 145
```

```
<210> SEQ ID NO 145
<211> LENGTH: 19
<212> TYPE: DNA
<213> ORGANISM: Homo sapiens

<400> SEQUENCE: 145
gctcccactg attccacat                                               19

<210> SEQ ID NO 146
<211> LENGTH: 19
<212> TYPE: DNA
<213> ORGANISM: Homo sapiens

<400> SEQUENCE: 146
gccagagagt aaaagggat                                               19

<210> SEQ ID NO 147
<211> LENGTH: 19
<212> TYPE: DNA
<213> ORGANISM: Homo sapiens

<400> SEQUENCE: 147
ggcatatgga aggagcatt                                               19

<210> SEQ ID NO 148
<211> LENGTH: 19
<212> TYPE: DNA
<213> ORGANISM: Homo sapiens

<400> SEQUENCE: 148
gtggtttggt tcagcagtt                                               19

<210> SEQ ID NO 149
<211> LENGTH: 19
<212> TYPE: DNA
<213> ORGANISM: Homo sapiens

<400> SEQUENCE: 149
ggcctccagc cacgtaatt                                               19

<210> SEQ ID NO 150
<211> LENGTH: 19
<212> TYPE: DNA
<213> ORGANISM: Homo sapiens

<400> SEQUENCE: 150
ggcgctgctg ccgctcatc                                               19

<210> SEQ ID NO 151
<211> LENGTH: 19
<212> TYPE: DNA
<213> ORGANISM: Homo sapiens

<400> SEQUENCE: 151
gggctggaac tggacttca                                               19

<210> SEQ ID NO 152
<211> LENGTH: 19
<212> TYPE: DNA
<213> ORGANISM: Homo sapiens

<400> SEQUENCE: 152
gcccataagg atgtttcct                                               19

<210> SEQ ID NO 153
```

```
<211> LENGTH: 23
<212> TYPE: DNA
<213> ORGANISM: Homo sapiens

<400> SEQUENCE: 153
gcgtccgggc ctgtcttcaa cct                                              23

<210> SEQ ID NO 154
<211> LENGTH: 24
<212> TYPE: DNA
<213> ORGANISM: Homo sapiens

<400> SEQUENCE: 154
gccccaccct ctaccccacc acta                                             24

<210> SEQ ID NO 155
<211> LENGTH: 22
<212> TYPE: DNA
<213> ORGANISM: Homo sapiens

<400> SEQUENCE: 155
gagatcctga tcaaggtgca gg                                               22

<210> SEQ ID NO 156
<211> LENGTH: 21
<212> TYPE: DNA
<213> ORGANISM: Homo sapiens

<400> SEQUENCE: 156
tgcacgctca cagcagtcag g                                                21

<210> SEQ ID NO 157
<211> LENGTH: 22
<212> TYPE: DNA
<213> ORGANISM: Homo sapiens

<400> SEQUENCE: 157
aacatgacta agatgcccaa cc                                               22

<210> SEQ ID NO 158
<211> LENGTH: 23
<212> TYPE: DNA
<213> ORGANISM: Homo sapiens

<400> SEQUENCE: 158
aatctccttc acctccacta ctg                                              23

<210> SEQ ID NO 159
<211> LENGTH: 22
<212> TYPE: DNA
<213> ORGANISM: Homo sapiens

<400> SEQUENCE: 159
aagcatagcc ataggtgatt gg                                               22

<210> SEQ ID NO 160
<211> LENGTH: 23
<212> TYPE: DNA
<213> ORGANISM: Homo sapiens

<400> SEQUENCE: 160
acaggtatca gacaagggag cag                                              23

<210> SEQ ID NO 161
```

```
<211> LENGTH: 21
<212> TYPE: DNA
<213> ORGANISM: Homo sapiens

<400> SEQUENCE: 161
ttacgaccta tttctccgtg g                                              21

<210> SEQ ID NO 162
<211> LENGTH: 21
<212> TYPE: DNA
<213> ORGANISM: Homo sapiens

<400> SEQUENCE: 162
aatgcaataa ttggccactg c                                              21

<210> SEQ ID NO 163
<211> LENGTH: 23
<212> TYPE: DNA
<213> ORGANISM: Homo sapiens

<400> SEQUENCE: 163
acacatcaaa ctgcttatcc agg                                            23

<210> SEQ ID NO 164
<211> LENGTH: 22
<212> TYPE: DNA
<213> ORGANISM: Homo sapiens

<400> SEQUENCE: 164
actgatgtga aaatgcacat cc                                             22

<210> SEQ ID NO 165
<211> LENGTH: 21
<212> TYPE: DNA
<213> ORGANISM: Homo sapiens

<400> SEQUENCE: 165
atggctcata cagcactcag g                                              21

<210> SEQ ID NO 166
<211> LENGTH: 22
<212> TYPE: DNA
<213> ORGANISM: Homo sapiens

<400> SEQUENCE: 166
gaactgtcac tccggaaagc ct                                             22

<210> SEQ ID NO 167
<211> LENGTH: 26
<212> TYPE: DNA
<213> ORGANISM: Homo sapiens

<400> SEQUENCE: 167
tgaaggtcgg agtcaacgga tttggt                                         26

<210> SEQ ID NO 168
<211> LENGTH: 24
<212> TYPE: DNA
<213> ORGANISM: Homo sapiens

<400> SEQUENCE: 168
catgtgggcc atgaggtcca ccac                                           24

<210> SEQ ID NO 169
```

<211> LENGTH: 4419
<212> TYPE: DNA
<213> ORGANISM: Homo sapiens

<400> SEQUENCE: 169

| | |
|---|---|
| ccctaatgcc tccaacaata actgttgact ttttattttc agtcagagaa gcctggcaac | 60 |
| caagaactgt tttttggtg gtttacgaga acttaactga attggaaaat atttgcttta | 120 |
| atgaaacaat ttactcttgt gcaacactaa attgtgtcaa tcaagcaaat aaggaagaaa | 180 |
| gtcttattta taaaattgcc tgctcctgat tttacttcat ttcttctcag gctccaagaa | 240 |
| ggggaaaaaa atgaagattt tgatacttgg tattttctg tttttatgta gtaccccagc | 300 |
| ctgggcgaaa gaaaagcatt attacattgg aattattgaa acgacttggg attatgcctc | 360 |
| tgaccatggg gaaagaaac ttatttctgt tgacacggaa cattccaata tctatcttca | 420 |
| aaatggccca gatagaattg ggagactata taagaaggcc ctttatcttc agtacacaga | 480 |
| tgaaaccttt aggacaacta tagaaaaacc ggtctggctt gggttttag gccctattat | 540 |
| caaagctgaa actggagata agtttatgt acacttaaaa aaccttgcct ctaggcccta | 600 |
| cacctttcat tcacatggaa taacttacta taaggaacat gagggggcca tctaccctga | 660 |
| taacaccaca gattttcaaa gagcagatga caaagtatat ccaggagagc agtatacata | 720 |
| catgttgctt gccactgaag aacaaagtcc tgggaagga gatggcaatt gtgtgactag | 780 |
| gatttaccat tcccacattg atgctccaaa agatattgcc tcaggactca tcggacccttt | 840 |
| aataatctgt aaaaaagatt ctctagataa agaaaaagaa aaacatattg accgagaatt | 900 |
| tgtggtgatg ttttctgtgg tggatgaaaa tttcagctgg tacctagaag acaacattaa | 960 |
| aacctactgc tcagaaccag agaaagttga caaagacaac gaagacttcc aggagagtaa | 1020 |
| cagaatgtat tctgtgaatg gatacacttt tggaagtctc ccaggactct ccatgtgtgc | 1080 |
| tgaagacaga gtaaaatggt acctttttgg tatgggtaat gaagttgatg tgcacgcagc | 1140 |
| tttctttcac gggcaagcac tgactaacaa gaactaccgt attgacacaa tcaacctctt | 1200 |
| tcctgctacc ctgtttgatg cttatatggt ggcccagaac cctggagaat ggatgctcag | 1260 |
| ctgtcagaat ctaaaccatc tgaaagccgg tttgcaagcc ttttccagg tccaggagtg | 1320 |
| taacaagtct tcatcaaagg ataatatccg tgggaagcat gttagacact actacattgc | 1380 |
| cgctgaggaa atcatctgga actatgctcc ctctggtata gacatcttca ctaaagaaaa | 1440 |
| cttaacagca cctggaagtg actcagcggt gttttttgaa caaggtacca caagaattgg | 1500 |
| aggctcttat aaaaagctgg tttatcgtga gtacacagat gcctccttca caaatcgaaa | 1560 |
| ggagagaggc cctgaagaag agcatcttgg catcctgggt cctgtcattt gggcagaggt | 1620 |
| gggagacacc atcagagtaa ccttccataa caaaggagca tatcccctca gtattgagcc | 1680 |
| gattggggtg agattcaata agaacaacga gggcacatac tattcccca attacaaccc | 1740 |
| ccagagcaga agtgtgcctc cttcagcctc ccatgtggca cccacagaaa cattcaccta | 1800 |
| tgaatggact gtccccaaag aagtaggacc cactaatgca gatcctgtgt gtctagctaa | 1860 |
| gatgtattat tctgctgtgg atcccactaa agatatattc actgggctta ttgggccaat | 1920 |
| gaaaatatgc aagaaaggaa gtttacatgc aaatgggaga cagaaagatg tagacaagga | 1980 |
| attctatttg tttcctacag tatttgatga gaatgagagt ttactcctgg aagataatat | 2040 |
| tagaatgttt acaactgcac ctgatcaggt ggataaggaa gatgaagact tcaggaatc | 2100 |
| taataaaatg cactccatga atggattcat gtatgggaat cagccgggtc tcactatgtg | 2160 |
| caaaggagat tcggtcgtgt ggtacttatt cagcgccgga aatgaggccg atgtacatgg | 2220 |

```
aatatacttt tcaggaaaca catatctgtg gagaggagaa cggagagaca cagcaaacct    2280
cttccctcaa acaagtctta cgctccacat gtggcctgac acagagggga cttttaatgt    2340
tgaatgcctt acaactgatc attacacagg cggcatgaag caaaaatata ctgtgaacca    2400
atgcaggcgg cagtctgagg attccacctt ctacctggga gagaggacat actatatcgc    2460
agcagtggag gtggaatggg attattcccc acaagggag tgggaaaagg agctgcatca    2520
tttacaagag cagaatgttt caaatgcatt tttagataag ggagagtttt acataggctc    2580
aaagtacaag aaagttgtgt atcggcagta tactgatagc acattccgtg ttccagtgga    2640
gagaaaagct gaagaagaac atctgggaat tctaggtcca caacttcatg cagatgttgg    2700
agacaaagtc aaaattatct ttaaaaacat ggccacaagg ccctactcaa tacatgccca    2760 tgggggtacaa acagagagtt ctacagttac tccaacatta ccaggtgaaa ctctcactta    2820
cgtatggaaa atcccagaaa gatctggagc tggaacagag gattctgctt gtattccatg    2880
ggcttattat tcaactgtgg atcaagttaa ggacctctac agtggattaa ttggccccct    2940
gattgtttgt cgaagacctt acttgaaagt attcaatccc agaaggaaac tggaatttgc    3000
ccttctgttt ctagttttg atgagaatga atcttggtac ttagatgaca acatcaaaac    3060
atactctgat caccccgaga agtaaacaa agatgatgag gaattcatag aaagcaataa    3120
aatgcatgct attaatggaa gaatgttttgg aaacctacaa ggcctcacaa tgcacgtggg    3180
agatgaagtc aactggtatc tgatgggaat gggcaatgaa atagacttac acactgtaca    3240
ttttcacggc catagcttcc aatacaagca caggggagtt tatagttctg atgtctttga    3300
catttttcct ggaacatacc aaaccctaga atgttccca agaacacctg gaatttggtt    3360
actccactgc catgtgaccg accacattca tgctggaatg gaaaccactt acaccgttct    3420
acaaaatgaa gacaccaaat ctggctgaat gaaataaatt ggtgataagt ggaaaaaga    3480 gaaaaaccaa tgattcataa caatgtatgt gaaagtgtaa aatagaatgt tactttggaa    3540
tgactataaa cattaaaaga agactggaag catacaactt tgtacatttg tgggggaaaa    3600
ctattaattt tttgcaaatg gaaagatcaa cagactatat aatgatacat gactgacact    3660
tgtacactag gtaataaaac tgattcatac agtctaatga tatcaccgct gttagggttt    3720
tataaaactg catttaaaaa aagatctatg accagatatt ctcctgggtg ctcctcaaag    3780
gaacactatt aaggttcatt gaaatgttt caatcattgc cttcccattg atccttctaa    3840
catgctgttg acatcacacc taatattcag agggaatggg caaggtatga gggaaggaaa    3900
taaaaaataa aataaataaa atagaatgac acaaatttga gttttgtgaa cccctgaaca    3960
gatggtctta aggacgttat ctggaactgg agaaaagcag agttgagaga caattctata    4020
gattaaatcc tggtaaggac aaacattgcc attagaagaa aagcttcaaa atagacctgt    4080
ggcagatgtc acatgagtag aatttctgcc cagccttaac tgcattcaga ggataatatc    4140
aatgaactaa acttgaacta aaatttttt aaacaaaaag ttataaatga agacacatgg    4200
ttgtgaatac aatgatgtat ttctttattt tcacatacac tctagctaaa agagcaagag    4260
tacacatcaa caaaaatgga aacaaggctt tggctgaaaa aaacatgcat ttgacaaatc    4320
atgttaatag ctagacaaga agaaagttag ctttgtaaac ttctacttca tttgattcag    4380
agaaacagag catgagtttt cttaaaagta acaagaaaa                          4419
```

<210> SEQ ID NO 170
<211> LENGTH: 1065
<212> TYPE: PRT
<213> ORGANISM: Homo sapiens

<400> SEQUENCE: 170

```
Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
            35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140

Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
            180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
    210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
            340                 345                 350

Gln Val Gln Glu Cys Asn Lys Ser Ser Lys Asp Asn Ile Arg Gly
        355                 360                 365

Lys His Val Arg His Tyr Tyr Ile Ala Ala Glu Glu Ile Ile Trp Asn
    370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415
```

-continued

Gly Gly Ser Tyr Lys Lys Leu Val Tyr Arg Glu Tyr Thr Asp Ala Ser
            420             425             430

Phe Thr Asn Arg Lys Glu Arg Gly Pro Glu Glu His Leu Gly Ile
        435             440             445

Leu Gly Pro Val Ile Trp Ala Glu Val Gly Asp Thr Ile Arg Val Thr
450                 455                 460

Phe His Asn Lys Gly Ala Tyr Pro Leu Ser Ile Glu Pro Ile Gly Val
465             470              475             480

Arg Phe Asn Lys Asn Asn Glu Gly Thr Tyr Tyr Ser Pro Asn Tyr Asn
                485             490             495

Pro Gln Ser Arg Ser Val Pro Ser Ala Ser His Val Ala Pro Thr
            500             505             510

Glu Thr Phe Thr Tyr Glu Trp Thr Val Pro Lys Glu Val Gly Pro Thr
        515             520             525

Asn Ala Asp Pro Val Cys Leu Ala Lys Met Tyr Tyr Ser Ala Val Asp
530                 535             540

Pro Thr Lys Asp Ile Phe Thr Gly Leu Ile Gly Pro Met Lys Ile Cys
545             550             555             560

Lys Lys Gly Ser Leu His Ala Asn Gly Arg Gln Lys Asp Val Asp Lys
                565             570             575

Glu Phe Tyr Leu Phe Pro Thr Val Phe Asp Glu Asn Glu Ser Leu Leu
            580             585             590

Leu Glu Asp Asn Ile Arg Met Phe Thr Thr Ala Pro Asp Gln Val Asp
            595             600             605

Lys Glu Asp Glu Asp Phe Gln Glu Ser Asn Lys Met His Ser Met Asn
610             615             620

Gly Phe Met Tyr Gly Asn Gln Pro Gly Leu Thr Met Cys Lys Gly Asp
625             630             635             640

Ser Val Val Trp Tyr Leu Phe Ser Ala Gly Asn Glu Ala Asp Val His
                645             650             655

Gly Ile Tyr Phe Ser Gly Asn Thr Tyr Leu Trp Arg Gly Glu Arg Arg
            660             665             670

Asp Thr Ala Asn Leu Phe Pro Gln Thr Ser Leu Thr Leu His Met Trp
            675             680             685

Pro Asp Thr Glu Gly Thr Phe Asn Val Glu Cys Leu Thr Thr Asp His
690             695             700

Tyr Thr Gly Gly Met Lys Gln Lys Tyr Thr Val Asn Gln Cys Arg Arg
705             710             715             720

Gln Ser Glu Asp Ser Thr Phe Tyr Leu Gly Glu Arg Thr Tyr Tyr Ile
            725             730             735

Ala Ala Val Glu Val Glu Trp Asp Tyr Ser Pro Gln Arg Glu Trp Glu
            740             745             750

Lys Glu Leu His His Leu Gln Glu Gln Asn Val Ser Asn Ala Phe Leu
            755             760             765

Asp Lys Gly Glu Phe Tyr Ile Gly Ser Lys Tyr Lys Lys Val Val Tyr
            770             775             780

Arg Gln Tyr Thr Asp Ser Thr Phe Arg Val Pro Val Glu Arg Lys Ala
785             790             795             800

Glu Glu Glu His Leu Gly Ile Leu Gly Pro Gln Leu His Ala Asp Val
            805             810             815

Gly Asp Lys Val Lys Ile Ile Phe Lys Asn Met Ala Thr Arg Pro Tyr
            820             825             830

Ser Ile His Ala His Gly Val Gln Thr Glu Ser Ser Thr Val Thr Pro
            835             840             845

```
Thr Leu Pro Gly Glu Thr Leu Thr Tyr Val Trp Lys Ile Pro Glu Arg
    850                 855                 860
Ser Gly Ala Gly Thr Glu Asp Ser Ala Cys Ile Pro Trp Ala Tyr Tyr
865                 870                 875                 880
Ser Thr Val Asp Gln Val Lys Asp Leu Tyr Ser Gly Leu Ile Gly Pro
                885                 890                 895
Leu Ile Val Cys Arg Arg Pro Tyr Leu Lys Val Phe Asn Pro Arg Arg
            900                 905                 910
Lys Leu Glu Phe Ala Leu Leu Phe Leu Val Phe Asp Glu Asn Glu Ser
        915                 920                 925
Trp Tyr Leu Asp Asp Asn Ile Lys Thr Tyr Ser Asp His Pro Glu Lys
    930                 935                 940
Val Asn Lys Asp Asp Glu Glu Phe Ile Glu Ser Asn Lys Met His Ala
945                 950                 955                 960
Ile Asn Gly Arg Met Phe Gly Asn Leu Gln Gly Leu Thr Met His Val
                965                 970                 975
Gly Asp Glu Val Asn Trp Tyr Leu Met Gly Met Gly Asn Glu Ile Asp
            980                 985                 990
Leu His Thr Val His Phe His Gly His Ser Phe Gln Tyr Lys His Arg
        995                 1000                1005
Gly Val Tyr Ser Ser Asp Val Phe Asp Ile Phe Pro Gly Thr Tyr
    1010                1015                1020
Gln Thr Leu Glu Met Phe Pro Arg Thr Pro Gly Ile Trp Leu Leu
    1025                1030                1035
His Cys His Val Thr Asp His Ile His Ala Gly Met Glu Thr Thr
    1040                1045                1050
Tyr Thr Val Leu Gln Asn Glu Asp Thr Lys Ser Gly
    1055                1060                1065

<210> SEQ ID NO 171
<211> LENGTH: 23
<212> TYPE: DNA
<213> ORGANISM: Homo sapiens

<400> SEQUENCE: 171
gcttaaaaga gtcctcctgt ggc                                              23

<210> SEQ ID NO 172
<211> LENGTH: 23
<212> TYPE: DNA
<213> ORGANISM: Homo sapiens

<400> SEQUENCE: 172
tggacattgt tcttaaagtg tgg                                              23

<210> SEQ ID NO 173
<211> LENGTH: 21
<212> TYPE: DNA
<213> ORGANISM: Homo sapiens

<400> SEQUENCE: 173
aggttttatg gccaccgtca g                                                21

<210> SEQ ID NO 174
<211> LENGTH: 22
<212> TYPE: DNA
<213> ORGANISM: Homo sapiens

<400> SEQUENCE: 174
```
atcctatacc gctcggttat gc                                             22

<210> SEQ ID NO 175
<211> LENGTH: 22
<212> TYPE: DNA
<213> ORGANISM: Homo sapiens

<400> SEQUENCE: 175
gggcggcggc tctttcctcc tc                                             22

<210> SEQ ID NO 176
<211> LENGTH: 19
<212> TYPE: DNA
<213> ORGANISM: Homo sapiens

<400> SEQUENCE: 176
gctagcggcc ccatactcg                                                 19

<210> SEQ ID NO 177
<211> LENGTH: 24
<212> TYPE: DNA
<213> ORGANISM: Homo sapiens

<400> SEQUENCE: 177
acactggatg ccctgaatga caca                                           24

<210> SEQ ID NO 178
<211> LENGTH: 20
<212> TYPE: DNA
<213> ORGANISM: Homo sapiens

<400> SEQUENCE: 178
gctttggccc ttttgctaa                                                 20

<210> SEQ ID NO 179
<211> LENGTH: 22
<212> TYPE: DNA
<213> ORGANISM: Homo sapiens

<400> SEQUENCE: 179
cccacttctg tcttactgca tc                                             22

<210> SEQ ID NO 180
<211> LENGTH: 22
<212> TYPE: DNA
<213> ORGANISM: Homo sapiens

<400> SEQUENCE: 180
catagtactc cagggcttat tc                                             22

<210> SEQ ID NO 181
<211> LENGTH: 23
<212> TYPE: DNA
<213> ORGANISM: Homo sapiens

<400> SEQUENCE: 181
aacgattgcc cggattgatg aca                                            23

<210> SEQ ID NO 182
<211> LENGTH: 24
<212> TYPE: DNA
<213> ORGANISM: Homo sapiens

<400> SEQUENCE: 182
tacttgaggc tggggtggga gatg                                          24

<210> SEQ ID NO 183
<211> LENGTH: 22
<212> TYPE: DNA
<213> ORGANISM: Homo sapiens

<400> SEQUENCE: 183
cactacgcca ggcaccccca aa                                            22

<210> SEQ ID NO 184
<211> LENGTH: 18
<212> TYPE: DNA
<213> ORGANISM: Homo sapiens

<400> SEQUENCE: 184
cgaggcgcac ggcagtct                                                 18

<210> SEQ ID NO 185
<211> LENGTH: 24
<212> TYPE: DNA
<213> ORGANISM: Homo sapiens

<400> SEQUENCE: 185
atccgttgct gcagctcgtt cctc                                          24

<210> SEQ ID NO 186
<211> LENGTH: 24
<212> TYPE: DNA
<213> ORGANISM: Homo sapiens

<400> SEQUENCE: 186
accctgctga ccttcttcca ttcc                                          24

<210> SEQ ID NO 187
<211> LENGTH: 24
<212> TYPE: DNA
<213> ORGANISM: Homo sapiens

<400> SEQUENCE: 187
tcggaggagg gctggctggt gttt                                          24

<210> SEQ ID NO 188
<211> LENGTH: 24
<212> TYPE: DNA
<213> ORGANISM: Homo sapiens

<400> SEQUENCE: 188
cttgggcgtc ttggagcggt tctg                                          24

<210> SEQ ID NO 189
<211> LENGTH: 22
<212> TYPE: DNA
<213> ORGANISM: Homo sapiens

<400> SEQUENCE: 189
agagcctatt gaagatgaac ag                                            22

<210> SEQ ID NO 190
<211> LENGTH: 23
<212> TYPE: DNA
<213> ORGANISM: Homo sapiens

<400> SEQUENCE: 190

```
tgattgcccc ggatcctctt agg                                              23

<210> SEQ ID NO 191
<211> LENGTH: 20
<212> TYPE: DNA
<213> ORGANISM: Homo sapiens

<400> SEQUENCE: 191
ggacaaatac gacgacgagg                                                  20

<210> SEQ ID NO 192
<211> LENGTH: 19
<212> TYPE: DNA
<213> ORGANISM: Homo sapiens

<400> SEQUENCE: 192
ggtttcttgg gtagtgggc                                                   19

<210> SEQ ID NO 193
<211> LENGTH: 22
<212> TYPE: DNA
<213> ORGANISM: Homo sapiens

<400> SEQUENCE: 193
ccccggagaa ggaagagcag ta                                               22

<210> SEQ ID NO 194
<211> LENGTH: 24
<212> TYPE: DNA
<213> ORGANISM: Homo sapiens

<400> SEQUENCE: 194
cgaaagccgg cagttagtta ttga                                             24

<210> SEQ ID NO 195
<211> LENGTH: 24
<212> TYPE: DNA
<213> ORGANISM: Homo sapiens

<400> SEQUENCE: 195
ggcgggcaac gaattccagg tgtc                                             24

<210> SEQ ID NO 196
<211> LENGTH: 24
<212> TYPE: DNA
<213> ORGANISM: Homo sapiens

<400> SEQUENCE: 196
tcagaggttc gtcgcatttg tcca                                             24

<210> SEQ ID NO 197
<211> LENGTH: 22
<212> TYPE: DNA
<213> ORGANISM: Homo sapiens

<400> SEQUENCE: 197
caacagtcat gatgtgtgga tg                                               22

<210> SEQ ID NO 198
<211> LENGTH: 22
<212> TYPE: DNA
<213> ORGANISM: Homo sapiens

<400> SEQUENCE: 198
```
actgcacctt gtccgtgttg ac                                          22

<210> SEQ ID NO 199
<211> LENGTH: 20
<212> TYPE: DNA
<213> ORGANISM: Homo sapiens

<400> SEQUENCE: 199
ccggctggct gctttgttta                                             20

<210> SEQ ID NO 200
<211> LENGTH: 24
<212> TYPE: DNA
<213> ORGANISM: Homo sapiens

<400> SEQUENCE: 200
atgatcagca ggttcgttgg tagg                                        24

<210> SEQ ID NO 201
<211> LENGTH: 19
<212> TYPE: DNA
<213> ORGANISM: Homo sapiens

<400> SEQUENCE: 201
atgccggaag tgaatgtgg                                              19

<210> SEQ ID NO 202
<211> LENGTH: 19
<212> TYPE: DNA
<213> ORGANISM: Homo sapiens

<400> SEQUENCE: 202
ggtgactccg ccttttgat                                              19

<210> SEQ ID NO 203
<211> LENGTH: 20
<212> TYPE: DNA
<213> ORGANISM: Homo sapiens

<400> SEQUENCE: 203
acattcgctt ctccatctgg                                             20

<210> SEQ ID NO 204
<211> LENGTH: 20
<212> TYPE: DNA
<213> ORGANISM: Homo sapiens

<400> SEQUENCE: 204
tgtcacggaa gggaaccagg                                             20

<210> SEQ ID NO 205
<211> LENGTH: 20
<212> TYPE: DNA
<213> ORGANISM: Homo sapiens

<400> SEQUENCE: 205
acgctgcctc tgggtcactt                                             20

<210> SEQ ID NO 206
<211> LENGTH: 23
<212> TYPE: DNA
<213> ORGANISM: Homo sapiens

<400> SEQUENCE: 206

```
ttggcaaatc aatggcttgt aat                                          23

<210> SEQ ID NO 207
<211> LENGTH: 20
<212> TYPE: DNA
<213> ORGANISM: Homo sapiens

<400> SEQUENCE: 207
atggcttggg tcatcaggac                                              20

<210> SEQ ID NO 208
<211> LENGTH: 23
<212> TYPE: DNA
<213> ORGANISM: Homo sapiens

<400> SEQUENCE: 208
gtgtcactgg gcgtaagata ctg                                          23

<210> SEQ ID NO 209
<211> LENGTH: 24
<212> TYPE: DNA
<213> ORGANISM: Homo sapiens

<400> SEQUENCE: 209
caccaaatca gctgctacta ctcc                                         24

<210> SEQ ID NO 210
<211> LENGTH: 24
<212> TYPE: DNA
<213> ORGANISM: Homo sapiens

<400> SEQUENCE: 210
gataaacccc aaagcagaaa gatt                                         24

<210> SEQ ID NO 211
<211> LENGTH: 20
<212> TYPE: DNA
<213> ORGANISM: Homo sapiens

<400> SEQUENCE: 211
cgagattccg tgggcgtagg                                              20

<210> SEQ ID NO 212
<211> LENGTH: 19
<212> TYPE: DNA
<213> ORGANISM: Homo sapiens

<400> SEQUENCE: 212
tgagtgggag cttcgtagg                                               19

<210> SEQ ID NO 213
<211> LENGTH: 21
<212> TYPE: DNA
<213> ORGANISM: Homo sapiens

<400> SEQUENCE: 213
tcagagtgga cgttggatta c                                            21

<210> SEQ ID NO 214
<211> LENGTH: 21
<212> TYPE: DNA
<213> ORGANISM: Homo sapiens

<400> SEQUENCE: 214
```

-continued

```
tgcttgaaat gtaggagaac a                                      21

<210> SEQ ID NO 215
<211> LENGTH: 24
<212> TYPE: DNA
<213> ORGANISM: Homo sapiens

<400> SEQUENCE: 215 gagggggcatc aatcacaccg agaa                                  24

<210> SEQ ID NO 216
<211> LENGTH: 22
<212> TYPE: DNA
<213> ORGANISM: Homo sapiens

<400> SEQUENCE: 216
ccccaccgcc cacccattta gg                                     22

<210> SEQ ID NO 217
<211> LENGTH: 20
<212> TYPE: DNA
<213> ORGANISM: Homo sapiens

<400> SEQUENCE: 217
gggggcacca gaggcagtaa                                        20

<210> SEQ ID NO 218
<211> LENGTH: 22
<212> TYPE: DNA
<213> ORGANISM: Homo sapiens

<400> SEQUENCE: 218
ggttgtggcg ggggcagttg tg                                     22

<210> SEQ ID NO 219
<211> LENGTH: 22
<212> TYPE: DNA
<213> ORGANISM: Homo sapiens

<400> SEQUENCE: 219
acagactcct gtactgcaaa cc                                     22

<210> SEQ ID NO 220
<211> LENGTH: 21
<212> TYPE: DNA
<213> ORGANISM: Homo sapiens

<400> SEQUENCE: 220
taccggttcg tcctcttcct c                                      21

<210> SEQ ID NO 221
<211> LENGTH: 23
<212> TYPE: DNA
<213> ORGANISM: Homo sapiens

<400> SEQUENCE: 221
gaagttcctc acgccctgct atc                                    23

<210> SEQ ID NO 222
<211> LENGTH: 24
<212> TYPE: DNA
<213> ORGANISM: Homo sapiens

<400> SEQUENCE: 222
```

```
ctggctggtg acctgctttg agta                                          24

<210> SEQ ID NO 223
<211> LENGTH: 31
<212> TYPE: DNA
<213> ORGANISM: Homo sapiens

<400> SEQUENCE: 223
taggcgcgcc tgacatacag caatgccagt t                                  31

<210> SEQ ID NO 224
<211> LENGTH: 36
<212> TYPE: DNA
<213> ORGANISM: Homo sapiens

<400> SEQUENCE: 224
taagaatgcg gccgcgccac atcttgaaca ctttgc                             36

<210> SEQ ID NO 225
<211> LENGTH: 24
<212> TYPE: DNA
<213> ORGANISM: Homo sapiens

<400> SEQUENCE: 225
tggggaggag tttgaggagc agac                                          24

<210> SEQ ID NO 226
<211> LENGTH: 23
<212> TYPE: DNA
<213> ORGANISM: Homo sapiens

<400> SEQUENCE: 226
gtgggacgga ggggggcagtg aag                                          23

<210> SEQ ID NO 227
<211> LENGTH: 20
<212> TYPE: DNA
<213> ORGANISM: Homo sapiens

<400> SEQUENCE: 227
gcaactattc ggagcgcgtg                                               20

<210> SEQ ID NO 228
<211> LENGTH: 20
<212> TYPE: DNA
<213> ORGANISM: Homo sapiens

<400> SEQUENCE: 228
ccagcagctt gttgagctcc                                               20

<210> SEQ ID NO 229
<211> LENGTH: 21
<212> TYPE: DNA
<213> ORGANISM: Homo sapiens

<400> SEQUENCE: 229
ggaggagcta agcgtcatcg c                                             21

<210> SEQ ID NO 230
<211> LENGTH: 19
<212> TYPE: DNA
<213> ORGANISM: Homo sapiens

<400> SEQUENCE: 230
```

-continued

```
tcgcttcagc gcgtagacc                                              19

<210> SEQ ID NO 231
<211> LENGTH: 24
<212> TYPE: DNA
<213> ORGANISM: Homo sapiens

<400> SEQUENCE: 231
tattagttgg gatggtggta gcac                                        24

<210> SEQ ID NO 232
<211> LENGTH: 22
<212> TYPE: DNA
<213> ORGANISM: Homo sapiens

<400> SEQUENCE: 232
gagaattcga gtcgacgatg ac                                          22

<210> SEQ ID NO 233
<211> LENGTH: 23
<212> TYPE: DNA
<213> ORGANISM: Homo sapiens

<400> SEQUENCE: 233
gaaattgtgt tgacgcagtc tcc                                         23

<210> SEQ ID NO 234
<211> LENGTH: 22
<212> TYPE: DNA
<213> ORGANISM: Homo sapiens

<400> SEQUENCE: 234
aggcacacaa cagaggcagt tc                                          22

<210> SEQ ID NO 235
<211> LENGTH: 22
<212> TYPE: DNA
<213> ORGANISM: Homo sapiens

<400> SEQUENCE: 235
gtacatcaac ctcctgctgt cc                                          22

<210> SEQ ID NO 236
<211> LENGTH: 22
<212> TYPE: DNA
<213> ORGANISM: Homo sapiens

<400> SEQUENCE: 236
gacatctcca agtcccagca tg                                          22

<210> SEQ ID NO 237
<211> LENGTH: 23
<212> TYPE: DNA
<213> ORGANISM: Homo sapiens

<400> SEQUENCE: 237
agtctctcac tgtgccttat gcc                                         23

<210> SEQ ID NO 238
<211> LENGTH: 20
<212> TYPE: DNA
<213> ORGANISM: Homo sapiens

<400> SEQUENCE: 238
```

```
agtcctaaga actgtaaacg                                              20

<210> SEQ ID NO 239
<211> LENGTH: 21
<212> TYPE: DNA
<213> ORGANISM: Homo sapiens

<400> SEQUENCE: 239
catctatacg tggattgagg a                                            21

<210> SEQ ID NO 240
<211> LENGTH: 21
<212> TYPE: DNA
<213> ORGANISM: Homo sapiens

<400> SEQUENCE: 240
ataggtacca ggtatgagct g                                            21

<210> SEQ ID NO 241
<211> LENGTH: 23
<212> TYPE: DNA
<213> ORGANISM: Homo sapiens

<400> SEQUENCE: 241
tgtccacatc atcatcgtca tcc                                          23

<210> SEQ ID NO 242
<211> LENGTH: 22
<212> TYPE: DNA
<213> ORGANISM: Homo sapiens

<400> SEQUENCE: 242
tgtcactggt cggtcgctga gg                                           22

<210> SEQ ID NO 243
<211> LENGTH: 18
<212> TYPE: DNA
<213> ORGANISM: Homo sapiens

<400> SEQUENCE: 243
catggggctt aagatgtc                                                18

<210> SEQ ID NO 244
<211> LENGTH: 20
<212> TYPE: DNA
<213> ORGANISM: Homo sapiens

<400> SEQUENCE: 244
gtcgatttct ccatcatctg                                              20

<210> SEQ ID NO 245
<211> LENGTH: 20
<212> TYPE: DNA
<213> ORGANISM: Homo sapiens

<400> SEQUENCE: 245
aagaggcgct ctactagccg                                              20

<210> SEQ ID NO 246
<211> LENGTH: 20
<212> TYPE: DNA
<213> ORGANISM: Homo sapiens

<400> SEQUENCE: 246
```
ctttccacat ggaacacagg                                              20

<210> SEQ ID NO 247
<211> LENGTH: 23
<212> TYPE: DNA
<213> ORGANISM: Homo sapiens

<400> SEQUENCE: 247
cattttcctg gaatttgata cag                                          23

<210> SEQ ID NO 248
<211> LENGTH: 23
<212> TYPE: DNA
<213> ORGANISM: Homo sapiens

<400> SEQUENCE: 248
gtagagagtt tatttgggcc aag                                          23

<210> SEQ ID NO 249
<211> LENGTH: 21
<212> TYPE: DNA
<213> ORGANISM: Homo sapiens

<400> SEQUENCE: 249
catctatggt aactacaatc g                                            21

<210> SEQ ID NO 250
<211> LENGTH: 22
<212> TYPE: DNA
<213> ORGANISM: Homo sapiens

<400> SEQUENCE: 250
gtagaagtca ctgatcagac ac                                           22

<210> SEQ ID NO 251
<211> LENGTH: 24
<212> TYPE: DNA
<213> ORGANISM: Homo sapiens

<400> SEQUENCE: 251
ctgcctgcca acctttccat ttct                                         24

<210> SEQ ID NO 252
<211> LENGTH: 23
<212> TYPE: DNA
<213> ORGANISM: Homo sapiens

<400> SEQUENCE: 252
tgagcagcca cagcagcatt agg                                          23

<210> SEQ ID NO 253
<211> LENGTH: 21
<212> TYPE: DNA
<213> ORGANISM: Homo sapiens

<400> SEQUENCE: 253
cacctgatca ggtggataag g                                            21

<210> SEQ ID NO 254
<211> LENGTH: 22
<212> TYPE: DNA
<213> ORGANISM: Homo sapiens

<400> SEQUENCE: 254

-continued

| | |
|---|---|
| tcccaggtag aaggtggaat cc | 22 |

<210> SEQ ID NO 255
<211> LENGTH: 628
<212> TYPE: DNA
<213> ORGANISM: Homo sapiens

<400> SEQUENCE: 255

| | |
|---|---|
| aatcatatta gtgaagatta ggaagaagct ttaaaatccc aaggctagtg tgcattgcta | 60 |
| gaattgttaa gagagagagc tcatatgaaa ttggttatcg tgggatattt aaaataaaac | 120 |
| aaagaacagt ttactttcag gcaaaaagat gccagtaatc aatattgagg acctgacaga | 180 |
| aaaggacaaa ttgaagatgg aagttgacca gctcaagaaa gaagtgacac tggaaagaat | 240 |
| gctagtttcc aaatgttgtg aagaagtaag agattacgtt gaagaacgat ctggcgagga | 300 |
| tccactggta aagggcatcc cagaggacaa aaatcccttc aaggagctca aggaggctg | 360 |
| tgtgatttca taatacaaac aaaaagaaaa aaaattaaac aaattcttgg aaatatctca | 420 |
| aatgttaata acaatatgaa ttttctcat gcatactatt actactaagc atgtacgtga | 480 |
| atttttaaat ttatagatgt aaactttaa taaaaattgg ggtgtggtaa cccatcattc | 540 |
| tatgttttc ttaacatagc tggcacaggg tttaacacat aattgccaat aaatattgct | 600 |
| taaagttctt taaaaagaac tatgtttt | 628 |

<210> SEQ ID NO 256
<211> LENGTH: 2499
<212> TYPE: DNA
<213> ORGANISM: Homo sapiens

<400> SEQUENCE: 256

| | |
|---|---|
| gctgggcacc gttctgtttt ctttcttttc ttaatcctat ccaagtatgc agtacgctct | 60 |
| tgggtcgtct catgagaccc aggggcatgt tggaaagaac tgagagaaag agcaacaaag | 120 |
| cggcgagtgg tgtgagaggg cagcacgcgc tgtggggccc ttccagagaa atgtactgaa | 180 |
| aaagtctacg caatgtctgg gatttgctaa acaatacctg gaaagcagac aggtcttttt | 240 |
| gccattcctc caggacatcc accataagga aaggagaccc tggaccaaca ttctctaaga | 300 |
| tgtttatatg gaccagtggc cggacctctt catcttatag acatgatgaa aaagaaata | 360 |
| tttaccagaa aatcagggac catgacctcc tggacaaaag gaaaacagtc acagcactga | 420 |
| aggcaggaga ggaccgagct attctcctgg gactggctat gatggtgtgc tccatcatga | 480 |
| tgtattttct gctgggaatc acactcctgc gctcatacat gcagagcgtg tggaccgaag | 540 |
| agtctcaatg caccttgctg aatgcgtcca tcacgaaaac atttaattgc tccttcagct | 600 |
| gtggtccaga ctgctggaaa ctttctcagt accccctgcct ccaggtgtac gttaacctga | 660 |
| cttcttccgg ggaaaagctc ctcctctacc acacagaaga gacaataaaa atcaatcaga | 720 |
| agtgctccta tatacctaaa tgtggaaaaa attttgaaga atccatgtcc ctggtgaatg | 780 |
| ttgtcatgga aaacttcagg aagtatcaac acttctcctg ctattctgac ccagaaggaa | 840 |
| accagaagag tgttatccta acaaaactct acagttccaa cgtgctgttc cattcactct | 900 |
| tctggccaac ctgtatgatg gctggggtg tggcaattgt tgccatggtg aaacttacac | 960 |
| agtacctctc cctactatgt gagaggatcc aacggatcaa tagataaatg caaaaatgga | 1020 |
| taaaataatt tttgttaaag ctcaaatact gttttcttc attcttcacc aaagaacctt | 1080 |
| aagtttgtaa cgtgcagtct gttatgagtt ccctaatata ttcttatatg tagagcaata | 1140 |
| atgcaaaagc tgttctatat gcaaacatga tgtctttatt attcaggaga ataaataact | 1200 |

```
gttttgtgtt ggttggtggt tttcataatc ttatttctgt actggaacta gtactttctt    1260
ctctcattcc gccaaaacag ggctcagtta ttcatttgcc aagcttcgtg gaggaatgta    1320
ggtgacatca atgtgataaa gtctgtgttc tgagttgtca gatctcttga agacaatatt    1380
tttcatcact tattgtttac taaagctaca gccaaaaata ttttttttc ttattctaaa     1440 ctgagcccta tagcaagtga agggaccaga tttcctaatt aaaggaagtt aggtactttt    1500
cttgtatttt ttaccatatc actgtaaaga agaggggaaa cccagccagc tactttttt    1560 catcactttt tattcataac ttcagatttg taaaactaat ttccaaaata taagctgttt    1620
tcattagcca gttctataat atcttcctgt gatttatgta gaaaatgaac acaccccttt    1680
tccatttaag accctgctac tgtgtgaaga gatgatactt acaaggagtg tcattacctg    1740
tgagctgact gaatgttggt aggtgctcca ttacaatcca ggaaagtctg tgttactgat    1800
atttgtgtgg aaatctttat ttcacttcaa tttaaccatt agatggtaaa attaagatgc    1860
tacttgttgg taaaaattgg tggactggtt tcaatgggta aatgtgttgt ggcaaattaa    1920
tgtgttggaa tattgctctt tgtgaatttg tgcttaagtc aatgaatgtg tagtatctcc    1980
ttctgacaag cattccctat tgggatttta aagctatgtg cacagaatat tagtctcttc    2040
tacatgtttt attttctat ttataattcc ctttttttgtt gttatatttt atacacagaa    2100
tagatctttt ttctaacaca tatttgaact gaataacaga cttaaagaaa gcctttgttc    2160
acattgctat ttacttttgt gtttggggga aaatacgagg gattgatttt aaataaaaaa    2220
cattccatct ttcatttaat atcaatatca aagaagaag acaaacatct atctttctca    2280
tctatattta agtacctttt tgtaatgtag tatcaaagtt ttttaggtaa tgcaaaattt    2340
tacaaatcat ttgtggaatg aatggtaaaa ctaatctgat gaaatggaaa attattctgc    2400
aatattgtaa ttcatagttt gacttttcat aagcaaataa atccctagga tgtaatcagg    2460
acttcaaatg tgtaattaaa ttttttttaaa aaaaatcta                          2499
```